(12) United States Patent
Nishi et al.

(10) Patent No.: US 8,101,650 B2
(45) Date of Patent: *Jan. 24, 2012

(54) METHOD FOR TREATING A IMMUNOLOGY-RELATED DISEASE

(75) Inventors: Takahide Nishi, Tokyo (JP); Takaichi Shimozato, Miura (JP); Futoshi Nara, Yachiyo (JP); Shojiro Miyazaki, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 244 days.

This patent is subject to a terminal disclaimer.

(21) Appl. No.: 12/583,001

(22) Filed: Aug. 12, 2009

(65) Prior Publication Data

US 2009/0326038 A1   Dec. 31, 2009

Related U.S. Application Data

(63) Continuation of application No. 11/651,205, filed on Jan. 9, 2007, now Pat. No. 7,638,551, which is a continuation of application No. 10/889,657, filed on Jul. 12, 2004, now Pat. No. 7,199,150, which is a continuation-in-part of application No. PCT/JP03/00136, filed on Jan. 9, 2003.

(30) Foreign Application Priority Data

Jan. 11, 2002 (JP) ................. 2002-004456
Jan. 11, 2002 (JP) ................. 2002-004484

(51) Int. Cl.
*A61K 31/40* (2006.01)
(52) U.S. Cl. ........................................ 514/423
(58) Field of Classification Search ............ 514/423
See application file for complete search history.

(56) References Cited

U.S. PATENT DOCUMENTS

| | | |
|---|---|---|
| 3,726,948 A | 4/1973 | Botts |
| 4,363,918 A | 12/1982 | Albert et al. |
| 4,386,090 A | 5/1983 | Moinet et al. |
| 4,536,601 A | 8/1985 | Tukamoto et al. |
| 4,613,596 A | 9/1986 | Moroni |
| 4,634,689 A | 1/1987 | Witkowski et al. |
| 4,667,038 A | 5/1987 | Clark et al. |
| 4,716,155 A | 12/1987 | Karanewsky et al. |
| 4,792,568 A | 12/1988 | Auerbach |
| 4,888,338 A | 12/1989 | Godfroid et al. |
| 4,977,171 A | 12/1990 | Suzuki et al. |
| 5,002,966 A | 3/1991 | Skidmore et al. |
| 5,037,853 A | 8/1991 | Brooks et al. |
| 5,037,958 A | 8/1991 | Hashimoto et al. |
| 5,039,706 A | 8/1991 | Wilkerson |
| 5,061,704 A | 10/1991 | Wierzbicki et al. |
| 5,068,247 A | 11/1991 | Fujita et al. |
| 5,112,848 A | 5/1992 | Brooks et al. |
| 5,130,487 A | 7/1992 | Budai et al. |
| 5,135,947 A | 8/1992 | Robertson et al. |
| 5,177,085 A | 1/1993 | Naef |
| 5,219,884 A | 6/1993 | Fujita et al. |
| 5,234,934 A | 8/1993 | Budai et al. |
| 5,260,329 A | 11/1993 | Mongelli et al. |
| 5,266,599 A | 11/1993 | Aubard et al. |
| 5,276,190 A | 1/1994 | Boesten et al. |
| 5,288,751 A | 2/1994 | Brooks et al. |
| 5,433,896 A | 7/1995 | Kang et al. |
| 5,470,878 A | 11/1995 | Michnick et al. |
| 5,501,980 A | 3/1996 | Katerinopoulos et al. |
| 5,534,539 A | 7/1996 | Mongelli et al. |
| 5,573,909 A | 11/1996 | Singer et al. |
| 5,604,229 A | 2/1997 | Fujita et al. |
| 5,641,783 A | 6/1997 | Klein et al. |

(Continued)

FOREIGN PATENT DOCUMENTS

EP  0 125 315 A1  11/1984

(Continued)

OTHER PUBLICATIONS

Huang, et al. *Kidney International*, "Th1 responsiveness to nephritogenic antigens determines susceptibility to crescentic glomerulonephritis in mice," 51, pp. 94-103 (1997).

(Continued)

*Primary Examiner* — Rei-tsang Shiao
(74) *Attorney, Agent, or Firm* — Holtz, Holtz, Goodman & Chick PC

(57) ABSTRACT

A method for treating an immunology-related disease. The method involves administering to a mammal in need thereof a pharmaceutically effective amount of an amino acid compound, a pharmacologically acceptable salt thereof or a pharmacologically acceptable ester thereof. The compound has the following formula:

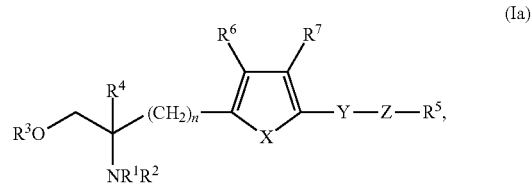

(Ia)

wherein $R^1$ and $R^2$ are each hydrogen; $R^3$ is hydrogen; $R^4$ is $C_1$-$C_2$ alkyl; n is 2; X is =N-D, wherein D is hydrogen, $C_1$-$C_4$ alkyl or phenyl; Y is ethylene, ethynylene, —CO—$CH_2$ or phenylene; Z is ethylene or trimethylene; $R^5$ is unsubstituted $C_3$-$C_{10}$ cycloalkyl, unsubstituted $C_3$-$C_{10}$ aryl, or $C_3$-$C_{10}$ cycloalkyl or $C_6$-$C_{10}$ aryl substituted with 1 to 3 substituents selected from the group consisting of halogen, lower alkyl, halogeno lower alkyl and lower alkoxy; and $R^6$ and $R^7$ are each hydrogen.

26 Claims, No Drawings

U.S. PATENT DOCUMENTS

| | | |
|---|---|---|
| 5,686,479 A | 11/1997 | Okumoto et al. |
| 5,714,605 A | 2/1998 | Vazquez et al. |
| 5,719,176 A | 2/1998 | Fujita et al. |
| 5,723,218 A | 3/1998 | Haugland et al. |
| 5,837,703 A | 11/1998 | Kumar et al. |
| 5,891,892 A | 4/1999 | Cheng et al. |
| 5,922,770 A | 7/1999 | Peschke et al. |
| 5,948,820 A | 9/1999 | Fujita et al. |
| 5,952,316 A | 9/1999 | Fujita et al. |
| 6,004,565 A | 12/1999 | Chiba et al. |
| 6,013,802 A | 1/2000 | Hoyland et al. |
| 6,028,098 A | 2/2000 | Goodman et al. |
| 6,077,954 A | 6/2000 | Cook et al. |
| 6,121,329 A | 9/2000 | Fujii et al. |
| 6,187,821 B1 | 2/2001 | Fujita et al. |
| 6,214,873 B1 | 4/2001 | Adachi et al. |
| 6,277,888 B1 | 8/2001 | Sakai et al. |
| 6,284,915 B2 | 9/2001 | Hirase et al. |
| 6,372,800 B1 | 4/2002 | Fujita et al. |
| 6,437,165 B1 | 8/2002 | Mandala et al. |
| 6,444,686 B1 | 9/2002 | Ko et al. |
| 6,455,528 B1 | 9/2002 | Adachi et al. |
| 6,462,092 B1 | 10/2002 | Sikorski et al. |
| 6,468,998 B1 | 10/2002 | Kuroita et al. |
| 6,476,004 B1 | 11/2002 | Sakai et al. |
| 6,476,075 B1 | 11/2002 | Sikorski et al. |
| 6,525,069 B1 | 2/2003 | Ko et al. |
| 6,605,744 B2 | 8/2003 | Abel et al. |
| 6,630,492 B1 | 10/2003 | Bauer et al. |
| 6,630,493 B1 | 10/2003 | Lubisch et al. |
| 6,638,950 B2 | 10/2003 | Duncia et al. |
| 6,649,611 B2 | 11/2003 | Blumberg et al. |
| 6,667,025 B2 | 12/2003 | Chiba et al. |
| 6,677,375 B2 | 1/2004 | Sikorski et al. |
| 6,683,099 B2 | 1/2004 | Sikorski et al. |
| 6,686,353 B1 | 2/2004 | Shiota et al. |
| 6,723,745 B2 | 4/2004 | Nishi et al. |
| 6,765,023 B2 | 7/2004 | Sikorski et al. |
| 6,960,692 B2 | 11/2005 | Kohno et al. |
| 6,963,012 B2 | 11/2005 | Kohno et al. |
| 6,964,976 B2 | 11/2005 | Nishi et al. |
| 7,199,150 B2 * | 4/2007 | Nishi et al. ............ 514/423 |
| 7,312,360 B2 | 12/2007 | TenBrink et al. |
| 7,638,551 B2 * | 12/2009 | Nishi et al. ............ 514/423 |
| 7,910,617 B2 * | 3/2011 | Nishi et al. ............ 514/423 |
| 2002/0052349 A1 | 5/2002 | Krauss et al. |
| 2002/0091105 A1 | 7/2002 | Mandala et al. |
| 2003/0216393 A1 | 11/2003 | Buschmann et al. |
| 2003/0220390 A1 | 11/2003 | Buschmann et al. |
| 2003/0236297 A1 | 12/2003 | Nishi et al. |
| 2004/0034063 A1 | 2/2004 | Ko et al. |
| 2004/0058894 A1 | 3/2004 | Doherty et al. |
| 2004/0082790 A1 | 4/2004 | Duncia et al. |
| 2004/0092603 A1 | 5/2004 | Chiba et al. |
| 2004/0097508 A1 | 5/2004 | Lubisch et al. |
| 2004/0132784 A1 | 7/2004 | Nishi et al. |
| 2004/0242654 A1 | 12/2004 | Kohno et al. |
| 2004/0254222 A1 | 12/2004 | Kohno et al. |
| 2007/0105933 A1 | 5/2007 | Nishi et al. |
| 2007/0142335 A1 | 6/2007 | Nishi et al. |
| 2007/0149597 A1 | 6/2007 | Nishi et al. |
| 2007/0191468 A1 | 8/2007 | Nishi et al. |
| 2008/0153882 A1 | 6/2008 | Nishi et al. |

FOREIGN PATENT DOCUMENTS

| | | | |
|---|---|---|---|
| EP | 0 167 459 | B1 | 1/1986 |
| EP | 0 297 782 | A1 | 1/1989 |
| EP | 0 300 688 | A1 | 1/1989 |
| EP | 0 480 659 | B1 | 4/1992 |
| EP | 0 492 497 | A2 | 7/1992 |
| EP | 0 520 336 | A2 | 12/1992 |
| EP | 0 627 406 | B1 | 12/1994 |
| EP | 0 778 263 | A1 | 6/1997 |
| EP | 1 002 792 | A1 | 5/2000 |
| EP | 1 050 301 | A1 | 11/2000 |
| EP | 1 176 140 | B1 | 1/2002 |
| EP | 1 201 236 | A1 | 5/2002 |
| EP | 1 319 651 | A2 | 6/2003 |
| EP | 1 431 275 | A1 | 6/2004 |
| EP | 1 431 284 | A1 | 6/2004 |
| GB | 1 134 687 | | 11/1968 |
| GB | 2 022 085 | A | 12/1979 |
| GB | 2 054 588 | A | 2/1981 |
| JP | 58-105946 | A | 6/1983 |
| JP | 59-44345 | A | 3/1984 |
| JP | 62-123126 | A | 6/1987 |
| JP | 63-139179 | A | 6/1988 |
| JP | 1-104087 | A | 4/1989 |
| JP | 2-256612 | A | 10/1990 |
| JP | 3-246264 | A | 11/1991 |
| JP | 4-104796 | A | 4/1992 |
| JP | 5-294907 | A | 11/1993 |
| JP | 6-067229 | A | 3/1994 |
| JP | 6345728 | A | 12/1994 |
| JP | 7-002665 | A | 1/1995 |
| JP | 7-138230 | A | 5/1995 |
| JP | 9-124564 | A | 5/1997 |
| JP | 10-81623 | A | 3/1998 |
| JP | 11-80026 | A | 3/1999 |
| JP | 11-310556 | A | 11/1999 |
| JP | 11-343300 | A | 12/1999 |
| JP | 2002-053575 | A | 2/2002 |
| JP | 2002-316985 | A | 10/2002 |
| JP | 2003-267974 | A | 9/2003 |
| JP | 2005-41867 | A | 2/2005 |
| WO | WO 93/09185 | A1 | 5/1993 |
| WO | WO 94/08943 | A1 | 4/1994 |
| WO | WO 96/06068 | A1 | 2/1996 |
| WO | WO 98/15278 | A1 | 4/1998 |
| WO | WO 98/22100 | A2 | 5/1998 |
| WO | WO 98/45249 | A1 | 10/1998 |
| WO | WO 00/27798 | A1 | 5/2000 |
| WO | WO 00/33836 | A1 | 6/2000 |
| WO | WO 00/53569 | A1 | 9/2000 |
| WO | WO 01/01978 | A1 | 1/2001 |
| WO | WO 01/08685 | A1 | 2/2001 |
| WO | WO 01/49663 | A2 | 7/2001 |
| WO | WO 01/49685 | A2 | 7/2001 |
| WO | WO 02/06268 | A1 | 1/2002 |
| WO | WO 02/18395 | A1 | 3/2002 |
| WO | WO 02/067915 | A1 | 9/2002 |
| WO | WO 02/076995 | A2 | 10/2002 |
| WO | WO 02/094342 | A2 | 11/2002 |
| WO | WO 03/009836 | A2 | 2/2003 |
| WO | WO 03/013509 | A1 | 2/2003 |
| WO | WO 03/029205 | A1 | 4/2003 |
| WO | WO 03/035068 | A1 | 5/2003 |
| WO | WO 03/044015 | A2 | 5/2003 |
| WO | WO 03/097028 | A1 | 11/2003 |
| WO | WO 2004/024673 | A1 | 3/2004 |
| WO | WO 2004/028521 | A2 | 4/2004 |

OTHER PUBLICATIONS

Berman et al., *J. Immunology*, "Decreased Il-4 Production in New Onset Type 1 Insulin-Dependent Diabetes Mellitus[1]". 157, pp. 4690-4696 (1996).

Cativiela et al., "Stereoselective synthesis of quaternary α-amino acids, Part 1: Acyclic compounds", *Tetrahedron: Asymmetry*, 9, pp. 3517-3599 (1998).

Gander-Coquoz et al., "Synthesis of Enantiomercially Pure, α-Alkylated Lysine, Ornithine, and Tryptophan Derivatives", *Helvetica Chimica Acta.*, 71, pp. 224-236, (1988).

Sano et al., "Lewis Acid- and Cationic Lithium-Mediated Diastereoselective Aldol-Type Reaction Based on a Double Chiral Recognition Manner for the Asymmetric Synthesis of α-Substituted Serines", *Tetrahedron Letters*, 36, No. 23, pp. 4101-4104 (1995).

Nagao et al., "Efficient Preparation of New Chiral Synthons Useful for (+)-Carbacyclin Synthesis by Utilizing Enzymatic Hydrolysis" *Chemistry Letters*, pp. 239-242 (1989).

Tamai et al., Enzymatic Hydrolyses of the σ-Symmetric Dicarboxylic Diesters Bearing a Sulfinyl Group as the Prochiral Center, *Chemistry Letters*, pp. 2381-2384 (1994).

Casarrubio et al., "On the Syntheses of Thiophene Analogs of Practolol and 'Reversed' Practolol", *J. Heterocyclic Chem.*, 20, 1557-1560 (1983).

Charette et al., "Syntheses of α, α-Disubstituted-α-Amino Acids by Double Nucleophilic Addition to Cyanohydrins", *Tetrahedron Letters*, 39, 5147-5150 (1998).

Hirose et al., "2-Aminoalcohol Immunosuppressants: Structure-Activity Relationships," *Bioorganic & Medicinal Chemistry Letters*, vol. 6, No. 22, pp. 2647-2650, 1996.

Kley et al., "Synthesis and PLA$_2$-Inhibitory Properties 2(R)-Acetamido-Alkylphosphomethanols with a Variable Aggregate Anchor," *Bioorganic & Medicinal Chemistry Letters*, 9 (1999) 261-264.

Maier et al., "Organic Phosphorus Compounds 93. Preparation, Properties and Herbicidal Activity of 2-Substituted 5-Phenoxy- and 5-Pyridyloxy-Phenylaminoalkyl-Phosphonic- and -Phosphinic Acid—as well as—Phosphine Oxide Derivatives," *Phosphorus, Sulfur and Silicon*, 56 (1-4): 5-15 (1991).

Hatakeyama et al., "Et$_2$AlCl-Catalyzed Cyclization of Epoxytrichloroacetimidates for the Synthesis of α-Substituted Serines", *J. Org. Chem.*, 62, No. 7, 2275-2279 (1997).

Hatakeyama et al., "Total Synthesis of (+)-Conagenin", *Tetrahedron Letters*, 37, No. 23, pp. 4047-4050 (1996).

Avenoza et al., "Preparation and Synthetic Applications of (S)-and (R)-N-Boc-N,O-isopropylidene-α-methylserinals: Asymmetric Synthesis of (S)- and (R)-2-Amino-2-methylbutanoic Acids (Iva)", *J. Org. Chem.*, 64, 8220-8225 (1999).

Wermuth et al., "Molecular Variations Based on Isosteric Replacements", *The Practice of Medicinal Chemistry*, 203-237 (1996).

Kiuchi et al., "Synthesis and Biological Evaluation of 2,2-Disubstituted 2-Aminoethanols: Analogues of FTY720", *Bioorganic & Medicinal Chemistry Letters*, 8, 101-106 (1998).

Kiuchi et al., "Synthesis and Immunosuppressive Activity of 2-Substituted 2-Aminopropane-1,3-diols and 2-Aminoethanols", *J. Med. Chem.*, 43, 2946-2961 (2000).

English-language International Preliminary Examination Report of International application No. PCT/JP03/00136, filed Jan. 9, 2003, Applicant: Sankyo Company, Limited.

Adachi et al., "Design, Synthesis, and Structure-Activity Relationships of 2-Substituted-2-Amino-1,3-Propanediols: Discovery of a Novel Immunosuppressant, FTY720," *Bioorganic & Medicinal Chemistry Letters*, vol. 5, No. 8, pp. 853-856, 1995.

Chiba et al., "FTY720: Immunosuppressant," *Drugs of the Future*, 22(1):18-22 (1997).

Constantinou-Kokotou et al., "Synthesis of optically active lipidic α-amino acids and lipidic 2-amino alcohols," *Amino Acids*, (1999) 16:273-285.

Constantinou-Kokotou et al., "Synthesis and biological activities of long chain 2-amino alcohols," *Letters in Peptide Science*, 9:143-152, 2002.

Dagan et al., "Synthetic, non-natural sphingolipid analogs inhibit the biosynthesis of cellular sphingolipids, elevate ceramide and induce apoptotic cell death," *Biochimica et Biophysica Acta*, 1633(3):161-169 (2003).

Fujita et al., "Simple Compounds, 2-Alkyl-2-Amino-1,3-Propanediols Have Potent Immunosuppressive Activity," *Bioorganic & Medicinal Chemistry Letters*, vol. 5, No. 8, pp. 847-852, 1995.

Fujita et al., 2-Substituted 2-Aminoethanol: Minimum Essential Structure for Immunosuppressive Activity of ISP-I (Myriocin), *Bioorganic & Medicinal Chemistry Letters*, vol. 5, No. 16, pp. 1857-1860, 1995.

Fujita et al., "2-Aminoalcohol: Minimum essential structure of immunosuppressive activity of ISP-I (myriocin)," Tennen Yuki Kagobutsu Toronkai Koen Yoshisyu, 38:7272-732 (1996).

Fujita et al., "Potent Immunosuppressants, 2-Alkyl-2-aminopropane-1,3-diols," *J. Med. Chem.*, 1996, 39, 4451-4459.

Fujita et al., "Design of Novel Immunosuppressants Based on Fungal Metabolites," *International Symposium on Natural Medicines*, PL-1, p. 3-4, 1997, Kyoto, Japan.

Hinterding et al., "Synthesis of Chiral Analogues of FTY720 and its Phosphate," *Synthesis 2003*, No. 11, 1667-1670, 2003.

Hinterding et al., "First asymmetric synthesis of chiral analogues of the novel immunosuppressant FTY720," *Tetrahedron Letters*, 43 (2002) 8095-8097.

* cited by examiner

METHOD FOR TREATING A IMMUNOLOGY-RELATED DISEASE

CROSS-REFERENCE TO RELATED APPLICATIONS

This application is a Continuation application of application Ser. No. 11/651,205 filed Jan. 9, 2007, now U.S. Pat. No. 7,638,551 which is a Continuation application of application Ser. No. 10/889,657 filed Jul. 12, 2004 (U.S. Pat. No. 7,199,150), which is a continuation-in-part application of International application PCT/JP03/00136 filed Jan. 9, 2003, the entire contents of each of Ser. No. 11/651,205, Ser. No. 10/889,657 and PCT/JP03/00136 are incorporated by reference herein.

TECHNICAL FIELD

The present invention relates to amino alcohol derivatives or phosphonic acid derivatives having excellent immunosuppressive activity, pharmacologically acceptable salts of amino alcohol derivatives or phosphonic acid derivatives, pharmacologically acceptable esters of amino alcohol derivatives or phosphonic acid derivatives, and to pharmaceutical compositions comprising said compounds as an active ingredient.

The present invention also relates to pharmaceutical compositions comprising, as active ingredients, one or more immunosuppressants and one or more compounds selected from the group consisting of amino alcohol derivatives or phosphonic acid derivatives having excellent immunosuppressive activity, pharmacologically acceptable salts thereof, and pharmacologically acceptable esters thereof. Said compositions are useful as preventive or therapeutic agents for autoimmune diseases such as rejection of transplanted tissues or cells, rheumatoid arthritis, or other immune activity-related autoimmune diseases.

BACKGROUND OF THE INVENTION

In the past, anti-inflammatory agents such as steroids have been used for inflammatory reactions arising from abnormal immune response in treatment of immune-related diseases such as rheumatoid arthritis and other autoimmune diseases. These are, however, a symptomatic therapy, but not a fundamental remedy.

Furthermore, it has been reported that immune system abnormalities are also involved in the development of diabetes and nephritis, but agents that improve these abnormalities have not yet been developed.

On the other hand, it is critical to develop an approach to suppress the immune response for avoiding rejection in transplanted tissues or cells, as well as for treating and preventing various autoimmune diseases.

However, immunosuppressants, such as cyclosporin A (CsA) and tacrolimus (TRL) that have been known in the past, are known to show toxicity against the kidney and liver. Although treatments that also use steroids are commonly used for the relief of such adverse reactions, it is presently the case that such agents have not necessarily led to producing a satisfactory immunosuppressive effect without showing any adverse reaction.

In light of this background, it has been attempted to find excellent compounds with immunosuppressive effects that are less toxic.

As to immunosuppressants, the following compounds are known.

(1) Compounds having the general formula (a) disclosed in WO 94/08943 (page 371)

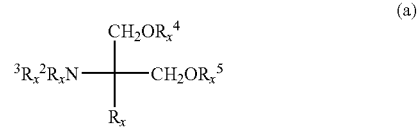

(a)

{in the above compounds (a), $R_x$, represents a straight or branched carbon chain which may optionally be substituted with one or more substituents [said chain may contain a double bond, a triple bond, an oxygen atom, a sulfur atom, a group of formula —$N(R_x^6)$— (wherein $R_x^6$ represents a hydrogen atom), an arylene group which may optionally be substituted with one or more substituents, or a heteroarylene group which may optionally be substituted with one or more substituents, and may contain, at the end of said chain, an aryl group which may optionally be substituted with one or more substituents, a cycloalkyl group which may optionally be substituted with one or more substituents, or an aromatic heterocyclic group which may optionally be substituted with one or substituents], and $R_x^2$, $R_x^3$, $R_x^4$, and $R_x^5$ are the same or different and each represents a hydrogen atom or an alkyl group] are known as immunosuppressants.

The above compounds (a) of the prior art contain two oxymethyl groups (—$CH_2OR_x^4$ and —$CH_2OR_x^5$) as essential groups substituted on the same carbon atom. The compounds of the present invention, however, contain one —$CH_2OR^3$ group and one lower alkyl group as essential groups substituted on the same carbon atom and are different from the compounds (a) in these substituents.

(2) Compounds having the general formula (b) disclosed in WO 96/06068 (page 271)

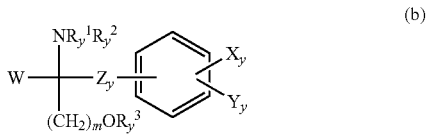

(b)

[in the above compounds (b), $R_y^1$, $R_y^2$ and $R_y^3$ each represent a hydrogen atom or the like, W represents a hydrogen atom, an alkyl group or the like, $Z_y$ represents a single bond or an alkylene group, $X_y$ represents a hydrogen atom or an alkoxy group, and $Y_y$ represents a hydrogen atom, an alkyl, alkoxy, acyl, acyloxy, amino, acylamino group or the like] are known as immunosuppressants.

The above compounds (b) contain a phenyl group as an essential group in the basic skeleton. The compounds of the present invention contain a heterocyclic group such as a furyl group, a pyrrolyl group, or a pyrrolyl group having a substituent on the nitrogen atom instead of the phenyl group of compounds (b) and are different from the compounds (b).

However, compounds having a similar chemical structure to compounds (I) of the present invention have heretofore not been disclosed concretely in that publication.

(3) Compounds having the general formula (c) disclosed in WO 98/45249

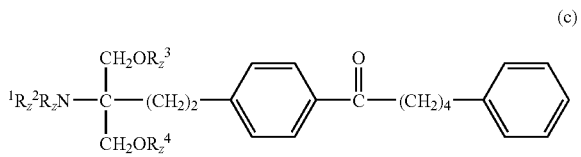

[in the above compounds (c), $R_z^1$, $R_z^2$, $R_z^3$, and $R_z^4$ are the same or different and each represents a hydrogen atom or an acyl group] are known as immunosuppressants.

The above compounds (c) contain two oxymethyl groups (—$CH_2OR_z^3$ and —$CH_2OR_z^4$) as essential groups substituted on the same carbon atom. The compounds of the present invention, however, contain one —$CH_2OR^3$ group and one lower alkyl group as essential groups substituted on the same carbon atom and are different from the compounds (c) in these substituents.

In addition, above compounds (c) contain a phenyl group between the —$(CH_2)_2$— group and the —CO—$(CH_2)_4$ group as an essential group in the basic skeleton. The compounds of the present invention contain a heterocyclic group such as a furyl group, a pyrrolyl group, or a pyrrolyl group having a substituent on the nitrogen atom instead of the phenyl group of compound (c) and are different from the compounds (c).

On the other hand, a compound having the general formula (II) of the present invention shown below wherein X represents a sulfur atom is disclosed in WO 02/06268 as a compound wherein the protecting group of the hydroxyl group is a residual group of an ester of phosphoric acid.

Furthermore, as to combinations of immunosuppressants, combinations of immunosuppressants such as FTY-720 and cyclosporin A or FTY-720 and tacrolimus are disclosed in Japanese Patent Publication (Kokai) Number Hei 11-80026.

In light of this background, it has been desired to find excellent pharmaceutical compositions with immunosuppressive effects that are less toxic.

SUMMARY OF THE INVENTION

The present inventors have eagerly studied new compounds having excellent immunosuppressive activity with low toxicity and found new compounds which are useful as preventive or therapeutic agents for autoimmune diseases or other immunology-related diseases such as rejection caused by transplantation of various organs or skin, systemic lupus erythematosus, rheumatoid arthritis, polymyositis, fibrositis, skeletal muscle inflammation, arthrosteitis, osteoarthritis, dermatomyositis, scleoderma, Behcet's syndrome, Crohn's disease, ulcerative colitis, autoimmune hepatitis, aplastic anemia, idiopathic thrombocytopenic purpura, autoimmune hemolytic anemia, multiple sclerosis, autoimmune bullosis, psoriasis vulgaris, vasculitis syndrome, Wegener's granuloma, uveitis, Sjögren's syndrome, idiopathic interstitial pneumonia, Goodpasture's syndrome, sarcoidosis, allergic granulomatous angitis, bronchial asthma, myocarditis, cardiomyopathy, aortitis syndrome, post myocardial infarction syndrome, primary pulmonary hypertension, minimal change nephrotic syndrome, membranous nephropathy, membranoproliferative glomerulonephritis, focal glomerular sclerosis, crescentic glomerulonephritis, myasthenia gravis, inflammatory neuropathy, atopic dermatitis, chronic actinic dermatitis, photosensitivity, pressure sores, Sydenham's chorea, sclerosis, adult-onset type diabetes mellitus, insulin dependent diabetes mellitus, juvenile diabetes mellitus; atherosclerosis, glomerular nephritis, IgA nephropathy, tubulointerstitial nephritis, primary biliary cirrhosis, primary sclerosing cholangitis, fulminant hepatitis, viral hepatitis, GVHD, contact dermatitis, and sepsis; diseases of infection by fungus, mycoplasma, virus, and protozoan and the like; cardiovascular diseases such as cardiac failure, cardiac hypertrophy, arrhythmia, angina pectoris, cardiac ischemia, arterial embolism, aneurysm, varix, and circulation disorders; brain diseases such as Alzheimer's disease, dementia, Parkinson's disease, stroke, brain infarction, brain ischemia, depression, manic-depressive illness, schizophrenia, Huntington's chorea, epilepsy, convulsion, attention deficit disorder, encephalitis, cerebral meningitis, loss of appetite, and hyperphagia; and various diseases such as lymphoma, leukemia, diuresis, pollakisuria, and diabetic retinopathy (particularly, autoimmune diseases such as rejection caused by transplantation of various organs or skin, systemic lupus erythematosus, rhematoid arthritis, multiple sclerosis, and atopic dermatitis), and completed the present invention.

Furthermore, the present inventors have studied eagerly pharmaceutical compositions having immunosuppressive activity and found that the pharmaceutical compositions of the present invention comprising, as active ingredients, one or more immunosuppressants and one or more compounds of the present invention exhibit excellent immunosuppressive activity with low toxicity. The pharmaceutical compositions increase activity more than that of the individual immunosuppressants and decrease adverse reactions so that they are less than that of the individual immunosuppressants. As a result, the pharmaceutical compositions of the present invention are useful as preventive or therapeutic agents for autoimmune diseases or other immunology-related diseases such as rejection caused by transplantation of various organs or skin, systemic lupus erythematosus, rheumatoid arthritis, polymyositis, fibrositis, skeletal muscle inflammation, arthrosteitis, osteoarthritis, dermatomyositis, scleoderma, Behcet's syndrome, Crohn's disease, ulcerative colitis, autoimmune hepatitis, aplastic anemia, idiopathic thrombocytopenic purpura, autoimmune hemolytic anemia, multiple sclerosis, autoimmune bullosis, psoriasis vulgaris, vasculitis syndrome, Wegener's granuloma, uveitis, Sjögren's syndrome, idiopathic interstitial pneumonia, Goodpasture's syndrome, sarcoidosis, allergic granulomatous angitis, bronchial asthma, myocarditis, cardiomyopathy, aortitis syndrome, post myocardial infarction syndrome, primary pulmonary hypertension, minimal change nephrotic syndrome, membranous nephropathy, membranoproliferative glomerulonephritis, focal glomerular sclerosis, crescentic glomerulonephritis, myasthenia gravis, inflammatory neuropathy, atopic dermatitis, chronic actinic dermatitis, photosensitivity, pressure sores, Sydenham's chorea, sclerosis, adult-onset type diabetes mellitus, insulin dependent diabetes mellitus, juvenile diabetes mellitus, atherosclerosis, glomerular nephritis, IgA nephropathy, tubulointerstitial nephritis, primary biliary cirrhosis, primary sclerosing cholangitis, fulminant hepatitis, viral hepatitis, GVHD, contact dermatitis, and sepsis; diseases of infection by fungus, mycoplasma, virus, and protozoan and the like; cardiovascular diseases such as cardiac failure, cardiac hypertrophy, arrhythmia, angina pectoris, cardiac ischemia, arterial embolism, aneurysm, varix, and circulation disorders; brain diseases such as Alzheimer's disease, dementia, Parkinson's disease, stroke, brain infarction, brain ischemia, depression, manic-depressive illness, schizophrenia, Huntington's chorea, epilepsy, convulsion, attention deficit disorder, encephalitis, cerebral meningitis, loss of appetite, and hyperphagia; and various diseases such as lymphoma, leukemia, diuresis, pollakisuria, and diabetic retinopathy (particularly, autoimmune diseases such as rejection caused by transplantation of various organs or skin, systemic lupus erythematosus, rhematoid arthritis, multiple sclerosis, and atopic dermatitis) and the present inventors completed the present invention.

The present invention is explained in detail.

(1) Amino alcohol derivatives of the present invention are compounds of the general formula (I) shown below:

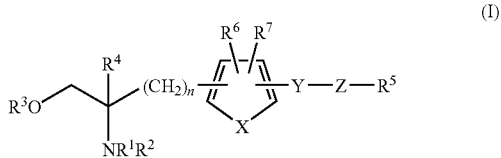

[wherein, $R^1$ and $R^2$ are the same or different and each represents a hydrogen atom, a lower alkyl group, or a protecting group of the amino group;

$R^3$ represents a hydrogen atom, a lower alkyl group, or a protecting group of the hydroxyl group;

$R^4$ represents a lower alkyl group;

n represents an integer of from 1 to 6;

X represents an oxygen atom or a group of formula =N-D (wherein D represents a hydrogen atom, a $C_6$-$C_{10}$ aryl group, a lower alkylsulfonyl group, a $C_6$-$C_{10}$ arylsulfonyl group, or a group selected from Substituent group (a));

Y represents an ethylene group, a vinylene group, an ethynylene group, a group of formula: -E-$CH_2$— (wherein E represents a carbonyl group or a group of formula: —CH(OH)—), a $C_6$-$C_{10}$ arylene group, or a $C_6$-$C_{10}$ arylene group substituted with from 1 to 3 substituents selected from Substituent group (a);

Z represents a single bond, a $C_1$-$C_{10}$ alkylene group, a $C_1$-$C_{10}$ alkylene group substituted with from 1 to 3 substituents selected from Substituent group (a) and Substituent group (b), a $C_1$-$C_{10}$ alkylene group which has an oxygen atom or a sulfur atom in said carbon chain or at the end of said carbon chain, or a $C_1$-$C_{10}$ alkylene group substituted with from 1 to 3 substituents selected from the group consisting of Substituent group (a) and Substituent group (b) which has an oxygen atom or a sulfur atom in said carbon chain or at the end of said carbon chain;

$R^5$ represents a hydrogen atom, a $C_3$-$C_{10}$ cycloalkyl group, a $C_6$-$C_{10}$ aryl group, a 5- to 7-membered heterocyclic group containing from 1 to 3 heteroatoms selected from the group consisting of a sulfur atom, an oxygen atom, and a nitrogen atom, a $C_3$-$C_{10}$ cycloalkyl group substituted with from 1 to 3 substituents selected from the group consisting of Substituent group (a) and Substituent group (b), a $C_6$-$C_{10}$ aryl group substituted with from 1 to 3 substituents selected from the group consisting of Substituent group (a) and Substituent group (b), or a 5- to 7-membered heterocyclic group containing from 1 to 3 heteroatoms selected from the group consisting of a sulfur atom, an oxygen atom, and a nitrogen atom in which said heterocyclic group is substituted with from 1 to 3 substituents selected from Substituent group (a) and Substituent group (b);

$R^6$ and $R^7$ are the same or different and each represents a hydrogen atom or a group selected from Substituent group (a);

Substituent group (a) represents the group consisting of a halogen atom, a lower alkyl group, a halogeno lower alkyl group, a lower alkoxy group, a lower alkylthio group, a carboxyl group, a lower alkoxycarbonyl group, a hydroxyl group, a lower aliphatic acyl group, an amino group, a mono-lower alkylamino group, a di-lower alkylamino group, a lower aliphatic acylamino group, a cyano group, and a nitro group; and Substituent group (b) represents the group consisting of a $C_3$-$C_{10}$ cycloalkyl group, a $C_6$-$C_{10}$ aryl group, a 5- to 7-membered heterocyclic group containing from 1 to 3 heteroatoms selected from the group consisting of a sulfur atom, an oxygen atom, and a nitrogen atom, a $C_3$-$C_{10}$ cycloalkyl group substituted with from 1 to 3 substituents selected from Substituent group (a), a $C_6$-$C_{10}$ aryl group substituted with from 1 to 3 substituents selected from Substituent group (a), and a 5- to 7-membered heterocyclic group containing from 1 to 3 heteroatoms selected from the group consisting of a sulfur atom, an oxygen atom, and a nitrogen atom in which said heterocyclic group is substituted with from 1 to 3 substituents selected from Substituent group (a);

provided that when $R^5$ represents a hydrogen atom, then Z represents a branched chain $C_1$-$C_{10}$ alkylene group, a $C_1$-$C_{10}$ alkylene group substituted with from 1 to 3 substituents selected from the group consisting of Substituent group (a) and Substituent group (b), a $C_1$-$C_{10}$ alkylene group which has an oxygen atom or a sulfur atom in said carbon chain or at the end of said carbon chain, or a $C_1$-$C_{10}$ alkylene group substituted with from 1 to 3 substituents selected from the group consisting of Substituent group (a) and Substituent group (b) which has an oxygen atom or a sulfur atom in said carbon chain or at the end of said carbon chain].

The present invention provides compounds of formula (I), pharmacologically acceptable salts thereof, and pharmacologically acceptable esters thereof.

Of these, preferred compounds are:

(2) a compound according to (1) wherein said compound of formula (I) has the formula (Ia):

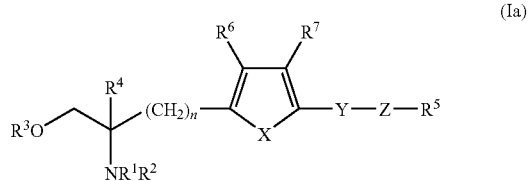

(wherein, $R^1$, $R^2$, $R^3$, $R^4$, $R^5$, $R^6$, $R^7$, X, Y, Z and n have the same meanings as those indicated hereinbefore), a pharmacologically acceptable salt thereof, or a pharmacologically acceptable ester thereof, (3) a compound according to (1) wherein said compound of formula (I) has the formula (Ib):

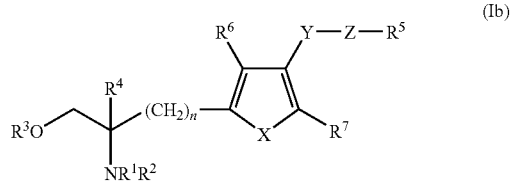

(wherein, $R^1$, $R^2$, $R^3$, $R^4$, $R^5$, $R^6$, $R^7$, X, Y, Z and n have the same meanings as those indicated hereinbefore), a pharmacologically acceptable salt thereof, or a pharmacologically acceptable ester thereof, (4) a pharmacologically acceptable ester of the compound of formula (I) according to (1) wherein said compound of formula (I) has the formula (II):

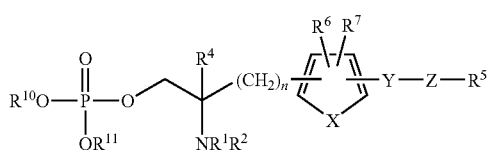

(II)

(wherein, $R^1$, $R^2$, $R^4$, $R^5$, $R^6$, $R^7$, X, Y, Z and n have the same meanings as those indicated hereinbefore; $R^{10}$ and $R^{11}$ are the same or different and each represents a hydrogen atom or a protecting group of phosphoric acid), or a pharmacologically acceptable salt thereof, (5) a pharmacologically acceptable ester of the compound of formula (II) according to (4) wherein said ester of formula (II) has the formula (IIa):

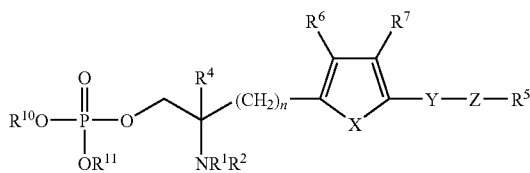

(IIa)

(wherein, $R^1$, $R^2$, $R^4$, $R^5$, $R^6$, $R^7$, X, Y, Z and n have the same meanings as those indicated hereinbefore; $R^{10}$ and $R^{11}$ are the same or different and each represents a hydrogen atom or a protecting group of phosphoric acid), or a pharmacologically acceptable salt thereof, and (6) a pharmacologically acceptable ester of the compound of formula (II) according to (4) wherein said ester of formula (II) has the formula (IIb):

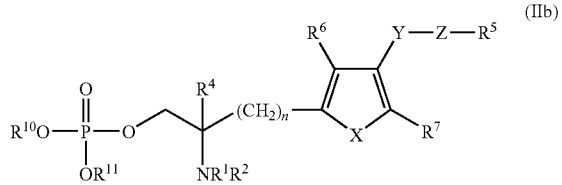

(IIb)

(wherein, $R^1$, $R^2$, $R^4$, $R^5$, $R^6$, $R^7$, X, Y, Z and n have the same meanings as those indicated hereinbefore; $R^{10}$ and $R^{11}$ are the same or different and each represents a hydrogen atom or a protecting group of phosphoric acid), or a pharmacologically acceptable salt thereof.

(7) Phosphonic acid derivatives of the present invention are compounds of the general formula (III) shown below:

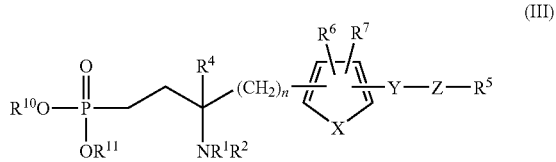

(III)

(wherein, $R^1$, $R^2$, $R^4$, $R^5$, $R^6$, $R^7$, $R^{10}$, $R^{11}$, X, Y, Z and n have the same meanings as those indicated hereinbefore).

The present invention provides compounds of formula (III), pharmacologically acceptable salts thereof, and pharmacologically acceptable esters thereof.

Of these, preferred compounds are:

(8) a compound according to (7) wherein said compound of formula (III) has the formula (IIIa):

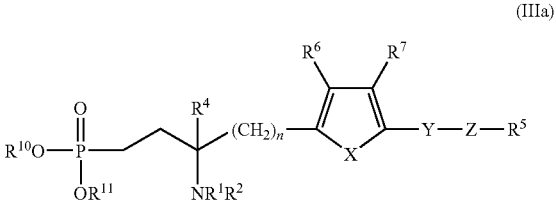

(IIIa)

(wherein, $R^1$, $R^2$, $R^4$, $R^5$, $R^6$, $R^7$, $R^{10}$, $R^{11}$, X, Y, Z and n have the same meanings as those indicated hereinbefore), a pharmacologically acceptable salt thereof, or a pharmacologically acceptable ester thereof, and (9) a compound according to (7) wherein said compound of formula (III) has the formula (IIIb):

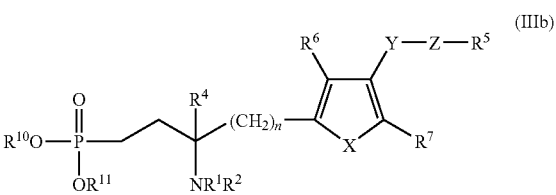

(IIIb)

(wherein, $R^1$, $R^2$, $R^4$, $R^5$, $R^6$, $R^7$, $R^{10}$, $R^{11}$, X, Y, Z and n have the same meanings as those indicated hereinbefore), a pharmacologically acceptable salt thereof, or a pharmacologically acceptable ester thereof.

DETAILED DESCRIPTION OF THE INVENTION

Of these, preferred compounds are:

(10) a compound according to any one of (1) to (9) wherein $R^1$ and $R^2$ are the same or different and each represents a hydrogen atom, a lower aliphatic acyl group, a lower alkoxycarbonyl group, an aralkyloxycarbonyl group, or an aralkyloxycarbonyl group substituted with from 1 to 3 substituents selected from Substituent group (a), or a pharmacologically acceptable salt thereof,

(11) a compound according to any one of (1) to (9) wherein $R^1$ and $R^2$ are the same or different and each represents a hydrogen atom, a lower aliphatic acyl group, or a lower alkoxycarbonyl group, or a pharmacologically acceptable salt thereof,

(12) a compound according to any one of (1) to (9) wherein $R^1$ and $R^2$ are the same or different and each represents a hydrogen atom, a $C_1$-$C_4$ aliphatic acyl group, or a $C_1$-$C_4$ alkoxycarbonyl group, or a pharmacologically acceptable salt thereof,

(13) a compound according to any one of (1) to (9) wherein $R^1$ and $R^2$ are the same or different and each represents a hydrogen atom, a $C_1$-$C_2$ aliphatic acyl group, or a $C_1$-$C_2$ alkoxycarbonyl group, or a pharmacologically acceptable salt thereof,

(14) a compound according to any one of (1) to (9) wherein $R^1$ and $R^2$ are the same or different and each represents a hydrogen atom, an acetyl group, or a methoxycarbonyl group, or a pharmacologically acceptable salt thereof,

(15) a compound according to any one of (1) to (9) wherein each of $R^1$ and $R^2$ represents a hydrogen atom, or a pharmacologically acceptable salt thereof,

(16) a compound according to any one of (1) to (3) and (10) to (15) wherein $R^3$ represents a hydrogen atom, a lower alkyl group, a lower aliphatic acyl group, an aromatic acyl group, an aromatic acyl group substituted with from 1 to 3 substituents selected from Substituent group (a), or a silyl group, or a pharmacologically acceptable salt thereof,

(17) a compound according to any one of (1) to (3) and (10) to (15) wherein $R^3$ represents a hydrogen atom or a lower alkyl group, or a pharmacologically acceptable salt thereof,

(18) a compound according to any one of (1) to (3) and (10) to (15) wherein $R^3$ represents a hydrogen atom or a $C_1$-$C_4$ alkyl group, or a pharmacologically acceptable salt thereof,

(19) a compound according to any one of (1) to (3) and (10) to (15) wherein $R^3$ represents a hydrogen atom, a methyl group, or an ethyl group, or a pharmacologically acceptable salt thereof,

(20) a compound according to any one of (1) to (3) and (10) to (15) wherein $R^3$ represents a hydrogen atom, or a pharmacologically acceptable salt thereof,

(21) a compound according to any one of (1) to (20) wherein $R^4$ represents a $C_1$-$C_4$ alkyl group, or a pharmacologically acceptable salt thereof,

(22) a compound according to any one of (1) to (20) wherein $R^4$ represents a $C_1$-$C_2$ alkyl group, or a pharmacologically acceptable salt thereof,

(23) a compound according to any one of (1) to (20) wherein $R^4$ represents a methyl group, or a pharmacologically acceptable salt thereof,

(24) a compound according to any one of (1) to (23) wherein n represents an integer 2 or 3, or a pharmacologically acceptable salt thereof,

(25) a compound according to any one of (1) to (23) wherein n represents an integer 2, or a pharmacologically acceptable salt thereof,

(26) a compound according to any one of (1) to (25) wherein X represents an oxygen atom, or a pharmacologically acceptable salt thereof,

(27) a compound according to any one of (1) to (25) wherein X represents a group of formula: =N-D (wherein D represents a hydrogen atom, a $C_1$-$C_4$ alkyl group, or a phenyl group), or a pharmacologically acceptable salt thereof,

(28) a compound according to any one of (1) to (25) wherein X represents a group of formula: =N—$CH_3$, or a pharmacologically acceptable salt thereof,

(29) a compound according to any one of (1) to (28) wherein Y represents an ethylene group, an ethynylene group, a group of formula: —CO—$CH_2$—, a group of formula: —CH(OH)—$CH_2$—, a phenylene group, or a phenylene group substituted with from 1 to 3 substituents selected from the group consisting of a halogen atom and a lower alkyl group, or a pharmacologically acceptable salt thereof,

(30) a compound according to any one of (1) to (28) wherein Y represents an ethylene group, an ethynylene group, a group of formula: —CO—$CH_2$—, or a phenylene group, or a pharmacologically acceptable salt thereof,

(31) a compound according to any one of (1) to (30) wherein Z represents a $C_1$-$C_{10}$ alkylene group or a $C_1$-$C_{10}$ alkylene group substituted with from 1 to 3 substituents selected from the group consisting of Substituent group (a) and Substituent group (b), or a pharmacologically acceptable salt thereof,

(32) a compound according to any one of (1) to (30) wherein Z represents a $C_1$-$C_6$ alkylene group or a $C_1$-$C_6$ alkylene group substituted with from 1 to 3 hydroxyl groups, or a pharmacologically acceptable salt thereof,

(33) a compound according to any one of (1) to (30) wherein Z represents a $C_1$-$C_5$ alkylene group or a $C_1$-$C_5$ alkylene group substituted with from 1 to 3 hydroxyl groups, or a pharmacologically acceptable salt thereof,

(34) a compound according to any one of (1) to (30) wherein Z represents an ethylene group, a trimethylene group, a tetramethylene group, or an ethylene, trimethylene, or tetramethylene group substituted with one hydroxyl group, or a pharmacologically acceptable salt thereof,

(35) a compound according to any one of (1) to (30) wherein Z represents an ethylene group, a trimethylene group, or a tetramethylene group, or a pharmacologically acceptable salt thereof,

(36) a compound according to any one of (1) to (30) wherein Z represents an ethylene group or a trimethylene group, or a pharmacologically acceptable salt thereof,

(37) a compound according to any one of (1) to (30) wherein Z represents a $C_1$-$C_{10}$ alkylene group which has an oxygen atom or a sulfur atom in said carbon chain or at the end of said carbon chain or a $C_1$-$C_{10}$ alkylene group substituted with one substituent which has an oxygen atom or a sulfur atom in said carbon chain or at the end of said carbon chain (said substituent is selected from the group consisting of a lower alkyl group and a hydroxyl group), or a pharmacologically acceptable salt thereof,

(38) a compound according to any one of (1) to (30) wherein Z represents a $C_1$-$C_{10}$ alkylene group which has an oxygen atom or a sulfur atom in said carbon chain or at the end of said carbon chain, or a pharmacologically acceptable salt thereof,

(39) a compound according to any one of (1) to (30) wherein Z represents a $C_1$-$C_{10}$ alkylene group which has an oxygen atom in said carbon chain or at the end of said carbon chain, or a pharmacologically acceptable salt thereof,

(40) a compound according to any one of (1) to (30) wherein Z represents a $C_1$-$C_6$ alkylene group which has an oxygen atom in said carbon chain or at the end of said carbon chain, or a pharmacologically acceptable salt thereof,

(41) a compound according to any one of (1) to (30) wherein Z represents a group of formula —O—$CH_2$—, —O—$(CH_2)_2$—, —O—$(CH_2)_3$—, —$CH_2$—O—, —$(CH_2)_2$—O—, or —$(CH_2)_3$—O—, or a pharmacologically acceptable salt thereof,

(42) a compound according to any one of (1) to (30) wherein Z represents a group of formula —$CH_2$—O— or —$(CH_2)_2$—O—, or a pharmacologically acceptable salt thereof,

(43) a compound according to any one of (1) to (42) wherein $R^5$ represents a hydrogen atom, or a pharmacologically acceptable salt thereof,

(44) a compound according to any one of (1) to (42) wherein $R^5$ represents a $C_3$-$C_{10}$ cycloalkyl group, a $C_6$-$C_{10}$ aryl group, or a $C_3$-$C_{10}$ cycloalkyl or $C_6$-$C_{10}$ aryl group substituted with from 1 to 3 substituents selected from the group consisting of a halogen atom, a lower alkyl group, a halogeno lower alkyl group, a lower alkoxy group, and a lower alkylthio group, or a pharmacologically acceptable salt thereof,

(45) a compound according to any one of (1) to (42) wherein $R^5$ represents a $C_3$-$C_{10}$ cycloalkyl group, a $C_6$-$C_{10}$ aryl group, or a $C_3$-$C_{10}$ cycloalkyl or $C_6$-$C_{10}$ aryl group substituted with from 1 to 3 substituents selected from the group consisting of a halogen atom, a lower alkyl group, a halogeno lower alkyl group, and a lower alkoxy group, or a pharmacologically acceptable salt thereof,

(46) a compound according to any one of (1) to (42) wherein $R^5$ represents a $C_5$-$C_6$ cycloalkyl group, a phenyl group, or a naphthyl group, or a pharmacologically acceptable salt thereof,

(47) a compound according to any one of (1) to (42) wherein $R^5$ represents a cyclohexyl group or a phenyl group, or a pharmacologically acceptable salt thereof,

(48) a compound according to any one of (1) to (47) wherein $R^6$ and $R^7$ are the same or different and each represents a hydrogen atom, a halogen atom, a lower alkyl group, a halogeno lower alkyl group, a lower alkoxy group, or a lower alkylthio group, or a pharmacologically acceptable salt thereof,

(49) a compound according to any one of (1) to (47) wherein each of $R^6$ and $R^7$ represents a hydrogen atom, or a pharmacologically acceptable salt thereof,

(50) a compound according to any one of (4) to (15) and (21) to (49) wherein $R^{10}$ and $R^{11}$ are the same or different and each represents a hydrogen atom or a lower alkyl group, or a pharmacologically acceptable salt thereof,

(51) a compound according to any one of (4) to (15) and (21) to (49) wherein $R^{10}$ and $R^{11}$ are the same or different and each represents a hydrogen atom or a $C_1$-$C_4$ alkyl group, or a pharmacologically acceptable salt thereof,

(52) a compound according to any one of (4) to (15) and (21) to (49) wherein $R^{10}$ and $R^{11}$ are the same or different and each represents a hydrogen atom, a methyl group, or an ethyl group, or a pharmacologically acceptable salt thereof, and

(53) a compound according to any one of (4) to (15) and (21) to (49) wherein each of $R^{10}$ and $R^{11}$ represents a hydrogen atom, or a pharmacologically acceptable salt thereof.

Compounds according to (1) above which comprise any combination selected freely from the groups consisting of (2) and (3); (10) to (15); (16) to (20); (21) to (23); (24) and (25); (26) to (28); (29) and (30); (31) to (42); (43) to (47); and (48) and (49) are preferred.

Compounds according to (4) above which comprise any combination selected freely from the groups consisting of (5) and (6); (10) to (15); (21) to (23); (24) and (25); (26) to (28); (29) and (30); (31) to (42); (43) to (47); (48) and (49); and (50) to (53) are preferred.

Compounds according to (7) above which comprise any combination selected freely from the groups consisting of (8) and (9); (10) to (15); (21) to (23); (24) and (25); (26) to (28); (29) and (30); (31) to (42); (43) to (47); (48) and (49); and (50) to (53) are preferred.

Of these, the most preferred compounds are:

(54) a compound selected from the following compounds, a pharmacologically acceptable salt thereof, or a pharmacologically acceptable ester thereof:

2-amino-2-methyl-4-[5-(5-phenylpentyl)furan-2-yl]butan-1-ol, 2-amino-2-methyl-4-[5-(5-cyclohexylpent-1-ynyl)furan-2-yl]butan-1-ol, 2-amino-2-methyl-4-[5-(5-phenylpent-1-ynyl)furan-2-yl]butan-1-ol, 2-amino-2-methyl-4-[5-(4-cyclohexyloxybut-1-ynyl)furan-2-yl]butan-1-ol, 2-amino-2-methyl-4-[5-(5-cyclohexylpentanoyl)furan-2-yl]butan-1-ol, and 2-amino-2-methyl-4-(5-[3-(3,4-dimethylphenoxy)prop-1-ynyl]furan-2-yl)butan-1-ol,

(55) a compound selected from the following compounds, a pharmacologically acceptable salt thereof, or a pharmacologically acceptable ester thereof:

2-amino-2-methyl-4-[1-methyl-5-(5-phenylpent-1-ynyl)pyrrol-2-yl]butan-1-ol, 2-amino-2-methyl-4-{1-methyl-5-[3-(4-methylphenoxy)prop-1-ynyl]pyrrol-2-yl}butan-1-ol, 2-amino-2-methyl-4-[1-methyl-5-(4-cyclohexyloxybut-1-ynyl)pyrrol-2-yl]butan-1-ol, 2-amino-2-methyl-4-{1-methyl-5-[3-(3,4-dimethylphenoxy)prop-1-ynyl]pyrrol-2-yl}butan-1-ol, 2-amino-2-methyl-4-[1-methyl-5-(5-phenylpentanoyl)pyrrol-2-yl]butan-1-ol, 2-amino-2-methyl-4-[1-methyl-5-(5-cyclohexylpentanoyl)pyrrol-2-yl]butan-1-ol, 2-amino-2-methyl-4-[1-methyl-5-(4-phenylbutanoyl)pyrrol-2-yl]butan-1-ol, 2-amino-2-methyl-4-[1-methyl-5-(4-cyclohexylbutanoyl)pyrrol-2-yl]butan-1-ol, 2-amino-2-methyl-4-{1-methyl-5-[4-(4-methylphenyl)butanoyl]pyrrol-2-yl}butan-1-ol, 2-amino-2-methyl-4-[1-ethyl-5-(5-phenylpentanoyl)pyrrol-2-yl]butan-1-ol, 2-amino-2-methyl-4-[1-ethyl-5-(5-cyclohexylpentanoyl)pyrrol-2-yl]butan-1-ol, 2-amino-2-methyl-4-[1-ethyl-5-(4-phenylbutanoyl)pyrrol-2-yl]butan-1-ol, and 2-amino-2-methyl-4-[1-ethyl-5-(4-cyclohexylbutanoyl)pyrrol-2-yl]butan-1-ol, 2-amino-2-methyl-4-{1-methyl-5-[4-(3,4-dimethylphenyl)butanoyl]pyrrol-2-yl}butan-1-ol, 2-amino-2-methyl-4-{1-methyl-5-[4-(3,5-dimethylphenyl)butanoyl]pyrrol-2-yl}butan-1-ol, 2-amino-2-methyl-4-{1-methyl-5-[4-(3-trifluoromethylphenyl)butanoyl]pyrrol-2-yl}butan-1-ol, 2-amino-2-methyl-4-{1-methyl-5-[4-(4-trifluoromethylphenyl)butanoyl]pyrrol-2-yl}butan-1-ol, 2-amino-2-methyl-4-{1-methyl-5-[4-(4-methoxyphenyl)butanoyl]pyrrol-2-yl}butan-1-ol, 2-amino-2-methyl-4-{1-methyl-5-[4-(3-methylphenyl)butyl]pyrrol-2-yl}butan-1-ol, 2-amino-2-methyl-4-{1-methyl-5-[4-(3,4-dimethylphenyl)butyl]pyrrol-2-yl}butan-1-ol, 2-amino-2-methyl-4-(1-methyl-5-[4-(3,5-dimethylphenyl)butyl]pyrrol-2-yl)butan-1-ol, 2-amino-2-methyl-4-(1-methyl-5-[4-(3-trifluoromethylphenyl)butyl]pyrrol-2-yl)butan-1-ol.

(56) a compound according to (4) wherein said compound is selected from the following compounds or a pharmacologically acceptable salt thereof:

mono 2-amino-2-methyl-4-[5-(5-phenylpentyl)furan-2-yl]-1-butyl phosphate, mono 2-amino-2-methyl-4-[5-(5-cyclohexylpent-1-ynyl)furan-2-yl]-1-butyl phosphate, mono 2-amino-2-methyl-4-[5-(5-phenylpent-1-ynyl)furan-2-yl]-1-butyl phosphate, mono 2-amino-2-methyl-4-[S-(4-cyclohexyloxybut-1-ynyl)furan-2-yl]-1-butyl phosphate, mono 2-amino-2-methyl-4-[5-(5-cyclohexylpentanoyl)furan-2-yl]-1-butyl phosphate, and mono 2-amino-2-methyl-4-{5-[3-(3,4-dimethylphenoxy)prop-1-ynyl]furan-2-yl}-1-butyl phosphate,

(57) a compound according to (4) wherein said compound is selected from the following compounds or a pharmacologically acceptable salt thereof:

mono 2-amino-2-methyl-4-[1-methyl-5-(5-phenylpent-1-ynyl)pyrrol-2-yl]-1-butyl phosphate, mono 2-amino-2-methyl-4-{(1-methyl-5-[3-(4-methylphenoxy)prop-1-ynyl]pyrrol-2-yl}-1-butyl phosphate,
mono 2-amino-2-methyl-4-[1-methyl-5-(4-cyclohexyloxybut-1-ynyl)pyrrol-2-yl]-1-butyl phosphate,
mono 2-amino-2-methyl-4-{1-methyl-5-[3-(3,4-dimethylphenoxy)prop-1-ynyl]pyrrol-2-yl}-1-butyl phosphate,
mono 2-amino-2-methyl-4-[1-methyl-5-(5-phenylpentanoyl)pyrrol-2-yl]-1-butyl phosphate,
mono 2-amino-2-methyl-4-[1-methyl-5-(5-cyclohexylpentanoyl)pyrrol-2-yl]-1-butyl phosphate,
mono 2-amino-2-methyl-4-[1-methyl-5-(4-phenylbutanoyl)pyrrol-2-yl]-1-butyl phosphate,
mono 2-amino-2-methyl-4-[1-methyl-5-(4-cyclohexylbutanoyl)pyrrol-2-yl]-1-butyl phosphate,
mono 2-amino-2-methyl-4-{(1-methyl-5-[4-(4-methylphenyl)butanoyl]pyrrol-2-yl}-1-butyl phosphate,
mono 2-amino-2-methyl-4-[1-ethyl-5-(5-phenylpentanoyl)pyrrol-2-yl]-1-butyl phosphate,
mono 2-amino-2-methyl-4-[1-ethyl-5-(5-cyclohexylpentanoyl)pyrrol-2-yl]-1-butyl phosphate,
mono 2-amino-2-methyl-4-[1-ethyl-5-(4-phenylbutanoyl)pyrrol-2-yl]-1-butyl phosphate, and
mono 2-amino-2-methyl-4-[1-ethyl-5-(4-cyclohexylbutanoyl)pyrrol-2-yl]-1-butyl phosphate,
mono 2-amino-2-methyl-4'-{1-methyl-5-[4-(3,4-dimethylphenyl)butanoyl]pyrrol-2-yl}-1-butyl phosphate,
mono 2-amino-2-methyl-4-{1-methyl-5-[4-(3,5-dimethylphenyl)butanoyl]pyrrol-2-yl}-1-butyl phosphate.
(58) a compound according to (7) wherein said compound is selected from the following compounds or a pharmacologically acceptable salt thereof:
3-amino-3-methyl-5-[5-(5-phenylpentyl) furan-2-yl]pentylphosphonic acid,
3-amino-3-methyl-5-[5-(5-cyclohexylpent-1-ynyl)furan-2-yl]pentylphosphonic acid,
3-amino-3-methyl-5-[5-(5-phenylpent-1-ynyl)furan-2-yl]pentylphosphonic acid,
3-amino-3-methyl-5-[5-(4-cyclohexyloxybut-1-ynyl)furan-2-yl]pentylphosphonic acid,
3-amino-3-methyl-5-[5-(5-cyclohexylpentanoyl)furan-2-yl]pentylphosphonic acid, and
3-amino-3-methyl-5-(5-[3-(3,4-dimethylphenoxy)prop-1-ynyl]furan-2-yl)pentylphosphonic acid, and
(59) a compound according to (7) wherein said compound is selected from the following compounds or a pharmacologically acceptable salt thereof:
3-amino-3-methyl-5-[1-methyl-5-(5-phenylpent-1-ynyl) pyrrol-2-yl]pentylphosphonic acid,
3-amino-3-methyl-5-{1-methyl-5-[3-(4-methylphenoxy)prop-1-ynyl]pyrrol-2-yl}pentylphosphonic acid,
3-amino-3-methyl-5-[1-methyl-5-(4-cyclohexyloxybut-1-ynyl)pyrrol-2-yl]pentylphosphonic acid,
3-amino-3-methyl-5-{1-methyl-5-[3-(3,4-dimethylphenoxy)prop-1-ynyl]pyrrol-2-yl}pentylphosphonic acid,
3-amino-3-methyl-5-[1-methyl-5-(5-phenylpentanoyl)pyrrol-2-yl]pentylphosphonic acid,
3-amino-3-methyl-5-[1-methyl-5-(5-cyclohexylpentanoyl) pyrrol-2-yl]pentylphosphonic acid,
3-amino-3-methyl-5-[1-methyl-5-(4-phenylbutanoyl)pyrrol-2-yl]pentylphosphonic acid,
3-amino-3-methyl-5-[1-methyl-5-(4-cyclohexylbutanoyl) pyrrol-2-yl]pentylphosphonic acid,
3-amino-3-methyl-5-[1-ethyl-5-(5-phenylpentanoyl)pyrrol-2-yl]pentylphosphonic acid,
3-amino-3-methyl-5-[1-ethyl-5-(5-cyclohexylpentanoyl) pyrrol-2-yl]pentylphosphonic acid,
3-amino-3-methyl-5-[1-ethyl-5-(4-phenylbutanoyl)pyrrol-2-yl]pentylphosphonic acid, and
3-amino-3-methyl-5-[1-ethyl-5-(4-cyclohexylbutanoyl)pyrrol-2-yl]pentylphosphonic acid.

Furthermore, the present invention provides the following pharmaceutical compositions:

(60) a pharmaceutical composition containing at least one immunosuppressant selected from the group consisting of an agent having the action of inhibiting intracellular signal transduction involved in cytokine expression of T-cells,
an agent having the action of inhibiting nucleoside synthesis in immune cells,
an agent having the action of inhibiting the action of cytokines on immune cells and having antirheumatic action,
an alkylating agent causing cell death by breakdown of DNA chains or blocking DNA synthesis,
a metabolic antagonist inhibiting the metabolism of nucleic acids by blocking folic acid production,
a protein drug having the suppression action of TNF-α,
a steroid hormone agent that binds to intracellular steroid receptors to form a complex which binds to reaction sites on chromosomes, resulting in the synthesis of proteins which show immunosuppressive activity,
a substance suppressing prostaglandin production and/or nonsteroidal anti-inflammatory drug antagonizing the action of prostaglandin, and
at least one compound selected from the group consisting of compounds of the general formula (I):

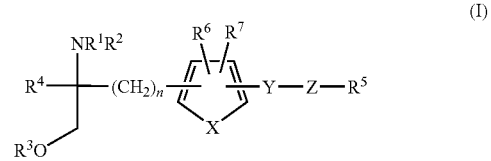

[wherein,
$R^1$ and $R^2$ are the same or different and each represents a hydrogen atom, a lower alkyl group, or a protecting group of the amino group;
$R^3$ represents a hydrogen atom, a lower alkyl group, or a protecting group of the hydroxyl group;
$R^4$ represents a lower alkyl group;
n represents an integer of from 1 to 6;
X represents a sulfur atom, an oxygen atom, or a group of formula =N-D (wherein D represents a hydrogen atom, an aryl group, a lower alkylsulfonyl group, an arylsulfonyl group, or a group selected from Substituent group (a));
Y represents an ethylene group, a vinylene group, an ethynylene group, a group of formula -E-CH$_2$— (wherein E represents a carbonyl group or a group of formula —CH (OH)—), a $C_6$-$C_{10}$ arylene group, or a $C_6$-$C_{10}$ arylene group substituted with from 1 to 3 substituents selected from Substituent group (a);
Z represents a single bond, a $C_1$-$C_{10}$ alkylene group, a $C_1$-$C_{10}$ alkylene group substituted with from 1 to 3 substituents selected from the group consisting of Substituent group (a) and Substituent group (b), a $C_1$-$C_{10}$ alkylene group which has an oxygen atom or a sulfur atom in said carbon chain or at the end of said carbon chain, or a $C_1$-$C_{10}$ alkylene group substituted with from 1 to 3 substituents selected from the group consisting of Substituent group (a) and Substituent group (b) which has an oxygen atom or a sulfur atom in said carbon chain or at the end of said carbon chain;

$R^5$ represents a hydrogen atom, a $C_3$-$C_{10}$ cycloalkyl group, a $C_6$-$C_{10}$ aryl group, a 5- to 7-membered heterocyclic group containing from 1 to 3 heteroatoms selected from the group consisting of a sulfur atom, an oxygen atom, and a nitrogen atom, a $C_3$-$C_{10}$ cycloalkyl group substituted with from 1 to 3 substituents selected from the group consisting of Substituent group (a) and Substituent group (b), a $C_6$-$C_{10}$ aryl group substituted with from 1 to 3 substituents selected from the group consisting of Substituent group (a) and Substituent group (b), or a 5- to 7-membered heterocyclic group containing from 1 to 3 heteroatoms selected from the group consisting of a sulfur atom, an oxygen atom, and a nitrogen atom in which said heterocyclic group is substituted with from 1 to 3 substituents selected from the group consisting of Substituent group (a) and Substituent group (b);

$R^6$ and $R^7$ are the same or different and each represents a hydrogen atom or a group selected from Substituent group (a);

Substituent group (a) represents the group consisting of a halogen atom, a lower alkyl group, a halogeno lower alkyl group, a lower alkoxy group, a lower alkylthio group, a carboxyl group, a lower alkoxycarbonyl group, a hydroxyl group, a lower aliphatic acyl group, an amino group, a mono-lower alkylamino group, a di-lower alkylamino group, a lower aliphatic acylamino group, a cyano group, and a nitro group; and Substituent group (b) represents the group consisting of a $C_6$-$C_{10}$ cycloalkyl group, a $C_6$-$C_{10}$ aryl group, a 5- to 7-membered heterocyclic group containing from 1 to 3 heteroatoms selected from the group consisting of a sulfur atom, an oxygen atom, and a nitrogen atom, a $C_3$-$C_{10}$ cycloalkyl group substituted with from 1 to 3 substituents selected from Substituent group (a), a $C_6$-$C_{10}$ aryl group substituted with from 1 to 3 substituents selected from Substituent group (a), and a 5- to 7-membered heterocyclic group containing from 1 to 3 heteroatoms selected from the group consisting of a sulfur atom, an oxygen atom, and a nitrogen atom in which said heterocyclic group is substituted with from 1 to 3 substituents selected from Substituent group (a);

provided that when $R^5$ represents a hydrogen atom, then Z represents a branched chain $C_1$-$C_{10}$ alkylene group, a $C_1$-$C_{10}$ alkylene group substituted with from 1 to 3 substituents selected from the group consisting of Substituent group (a) and Substituent group (b), a $C_1$-$C_{10}$ alkylene group which has an oxygen atom or a sulfur atom in said carbon chain or at the end of said carbon chain, or a $C_1$-$C_{10}$ alkylene group substituted with from 1 to 3 substituents selected from the group consisting of Substituent group (a) and Substituent group (b) which has an oxygen atom or a sulfur atom in said carbon chain or at the end of said carbon chain], a pharmacologically acceptable salt thereof, or a pharmacologically acceptable ester thereof.

Of these, preferred pharmaceutical compositions are:

(61) a pharmaceutical composition according to (60) wherein said compound of general formula (I) has the general formula (Ia) shown below:

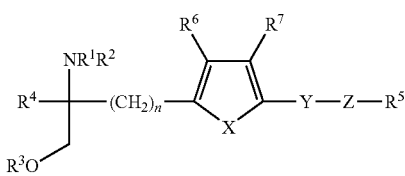

(Ia)

(wherein, $R^1$, $R^2$, $R^3$, $R^4$, $R^5$, $R^6$, $R^7$, X, Y, Z and n have the same meanings as those indicated hereinbefore),

(62) a pharmaceutical composition according to (60) wherein said compound of general formula (I) has the general formula (Ib) shown below:

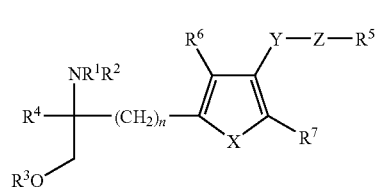

(Ib)

(wherein, $R^1$, $R^2$, $R^3$, $R^4$, $R^5$, $R^6$, $R^7$, X, Y, Z and n have the same meanings as those indicated hereinbefore),

(63) a pharmaceutical composition according to (60) wherein the pharmacologically acceptable ester of the compound of formula (I) has the formula (II):

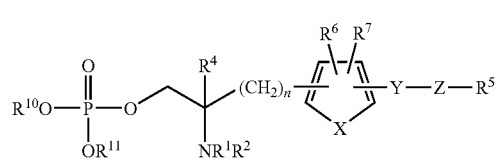

(II)

(wherein, $R^1$, $R^2$, $R^4$, $R^5$, $R^6$, $R^7$, X, Y, Z and n have the same meanings as those indicated hereinbefore; $R^{10}$ and $R^{11}$ are the same or different and each represents a hydrogen atom or a protecting group of phosphoric acid) or a pharmacologically acceptable salt thereof,

(64) a pharmaceutical composition according to (63) wherein the ester of the compound of formula (II) has the formula (IIa):

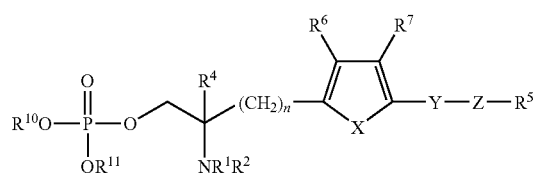

(IIa)

(wherein, $R^1$, $R^2$, $R^4$, $R^5$, $R^6$, $R^7$, $R^{10}$, $R^{11}$, X, Y, Z and n have the same meanings as those indicated hereinbefore) or a pharmacologically acceptable salt thereof, and

(65) a pharmaceutical composition according to (63) wherein the ester of the compound of formula (II) has the formula (IIb):

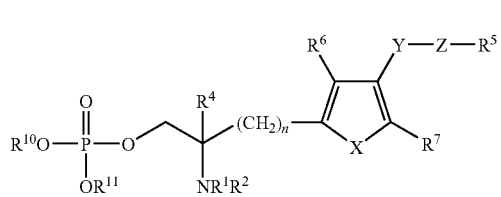

(IIIb)

(wherein, $R^1$, $R^2$, $R^4$, $R^5$, $R^6$, $R^7$, $R^{10}$, $R^{11}$, X, Y, Z and n have the same meanings as those indicated hereinbefore) or a pharmacologically acceptable salt thereof.

Furthermore, the present invention provides the following pharmaceutical compositions:

(66) a pharmaceutical composition containing at least one immunosuppressant selected from the group consisting of an agent having the action of inhibiting intracellular signal transduction involved in cytokine expression of T-cells, an agent having the action of inhibiting nucleoside synthesis in immune cells, an agent having the action of inhibiting the action of cytokines on immune cells and having antirheumatic action, an alkylating agent causing cell death by breakdown of DNA chains or blocking DNA synthesis, a metabolic antagonist inhibiting the metabolism of nucleic acids by blocking folic acid production, a protein drug having the suppression action of TNF-α, a steroid hormone agent that binds to intracellular steroid receptors to form a complex which binds to reaction sites on chromosomes, resulting in the synthesis of proteins which show immunosuppressive activity, and a substance suppressing prostaglandin production and/or nonsteroidal anti-inflammatory drug antagonizing the action of prostaglandin, and at least one compound selected from the group consisting of compounds of the general formula (III) shown below:

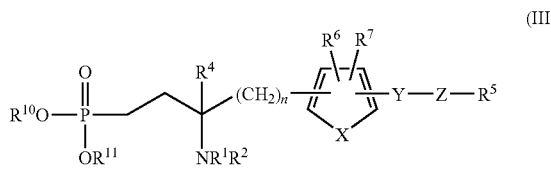

(III)

[wherein, $R^1$ and $R^2$ are the same or different and each represents a hydrogen atom, a lower alkyl group, or a protecting group of the amino group;

$R^4$ represents a lower alkyl group;

n represents an integer of from 1 to 6;

X represents a sulfur atom, an oxygen atom or a group of formula =N-D (wherein D represents a hydrogen atom, a $C_6$-$C_{10}$ aryl group, a lower alkylsulfonyl group, a $C_6$-$C_{10}$ arylsulfonyl group, or a group selected from Substituent group (a));

Y represents an ethylene group, a vinylene group, an ethynylene group, a group of formula -E-$CH_2$— (wherein E represents a carbonyl group or a group of formula —CH(OH)—), a $C_6$-$C_{10}$ arylene group, or a $C_6$-$C_{10}$ arylene group substituted with from 1 to 3 substituents selected from Substituent group (a);

Z represents a single bond, a $C_1$-$C_{10}$ alkylene group, a $C_1$-$C_{10}$ alkylene group substituted with from 1 to 3 substituents selected from the group consisting of Substituent group (a) and Substituent group (b), a $C_1$-$C_{10}$ alkylene group which has an oxygen atom or a sulfur atom in said carbon chain or at the end of said carbon chain, or a $C_1$-$C_{10}$ alkylene group substituted with from 1 to 3 substituents selected from the group consisting of Substituent group (a) and Substituent group (b) which has an oxygen atom or a sulfur atom in said carbon chain or at the end of said carbon chain;

$R^5$ represents a hydrogen atom, a $C_3$-$C_{10}$ cycloalkyl group, a $C_6$-$C_{10}$ aryl group, a 5- to 7-membered heterocyclic group containing from 1 to 3 heteroatoms selected from the group consisting of a sulfur atom, an oxygen atom, and a nitrogen atom, a $C_3$-$C_{10}$ cycloalkyl group substituted with from 1 to 3 substituents selected from the group consisting of Substituent group (a) and Substituent group (b), a $C_6$-$C_{10}$ aryl group substituted with from 1 to 3 substituents selected from the group consisting of Substituent group (a) and Substituent group (b), or a 5- to 7-membered heterocyclic group containing from 1 to 3 heteroatoms selected from the group consisting of a sulfur atom, an oxygen atom, and a nitrogen atom in which said heterocyclic group is substituted with from 1 to 3 substituents selected from the group consisting of Substituent group (a) and Substituent group (b);

$R^6$ and $R^7$ are the same or different and each represents a hydrogen atom or a group selected from Substituent group (a);

$R^{10}$ and $R^{11}$ are the same or different and each represents a hydrogen atom or a protecting group of phosphoric acid;

Substituent group (a) represents the group consisting of a halogen atom, a lower alkyl group, a halogeno lower alkyl group, a lower alkoxy group, a lower alkylthio group, a carboxyl group, a lower alkoxycarbonyl group, a hydroxyl group, a lower aliphatic acyl group, an amino group, a mono-lower alkylamino group, a di-lower alkylamino group, a lower aliphatic acylamino group, a cyano group, and a nitro group; and Substituent group (b) represents the group consisting of a $C_3$-$C_{10}$ cycloalkyl group, a $C_6$-$C_{10}$ aryl group, a 5- to 7-membered heterocyclic group containing from 1 to 3 heteroatoms selected from the group consisting of a sulfur atom, an oxygen atom, and a nitrogen atom, a $C_3$-$C_{10}$ cycloalkyl group substituted with from 1 to 3 substituents selected from Substituent group (a), a $C_6$-$C_{10}$ aryl group substituted with from 1 to 3 substituents selected from Substituent group (a), and a 5- to 7-membered heterocyclic group containing from 1 to 3 heteroatoms selected from the group consisting of a sulfur atom, an oxygen atom, and a nitrogen atom in which said heterocyclic group is substituted with from 1 to 3 substituents selected from Substituent group (a);

provided that when $R^5$ represents a hydrogen atom, then Z represents a branched chain $C_1$-$C_{10}$ alkylene group, a $C_1$-$C_{10}$ alkylene group substituted with from 1 to 3 substituents selected from the group consisting of Substituent group (a) and Substituent group (b), a $C_1$-$C_{10}$ alkylene group which has an oxygen atom or a sulfur atom in said carbon chain or at the end of said carbon chain, or a $C_1$-$C_{10}$ alkylene group substituted with from 1 to 3 substituents selected from the group consisting of Substituent group (a) and Substituent group (b) which has an oxygen atom or a sulfur atom in said carbon chain or at the end of said carbon chain], a pharmacologically acceptable salt thereof, or a pharmacologically acceptable ester thereof.

Of these, preferred pharmaceutical compositions are:

(67) a pharmaceutical composition according to (66) wherein the compound of formula (III) has the formula (IIIa):

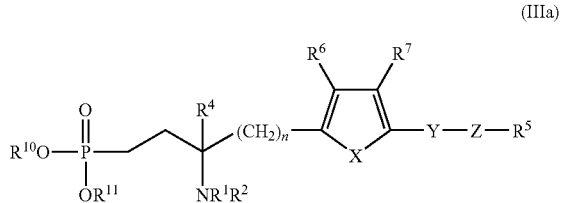

(IIIa)

(wherein, $R^1$, $R^2$, $R^4$, $R^5$, $R^6$, $R^7$, $R^{10}$, $R^{11}$, X, Y, Z and n have the same meanings as those indicated hereinbefore), and

(68) a pharmaceutical composition according to (66) wherein the compound of formula (III) has the formula (IIIb):

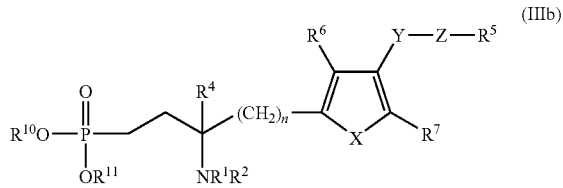

(wherein, $R^1$, $R^2$, $R^4$, $R^5$, $R^6$, $R^7$, $R^{10}$, $R^{11}$, X, Y, Z and n have the same meanings as those indicated hereinbefore)

Of these, more preferred pharmaceutical compositions are:

(69) a pharmaceutical composition according to any one of (60) to (68) containing a compound wherein $R^1$ and $R^2$ are the same or different and each represents a hydrogen atom, a lower aliphatic acyl group, a lower alkoxycarbonyl group, an aralkyloxycarbonyl group, or an aralkyloxycarbonyl group substituted with from 1 to 3 substituents selected from Substituent group (a), or a pharmacologically acceptable salt thereof,

(70) a pharmaceutical composition according to any one of (60) to (68) containing a compound wherein $R^1$ and $R^2$ are the same or different and each represents a hydrogen atom, a lower aliphatic acyl group, or a lower alkoxycarbonyl group, or a pharmacologically acceptable salt thereof,

(71) a pharmaceutical composition according to any one of (60) to (68) containing a compound wherein $R^1$ and $R^2$ are the same or different and each represents a hydrogen atom, a $C_1$-$C_4$ aliphatic acyl group, or a $C_1$-$C_4$ alkoxycarbonyl group, or a pharmacologically acceptable salt thereof,

(72) a pharmaceutical composition according to any one of (60) to (68) containing a compound wherein $R^1$ and $R^2$ are the same or different and each represents a hydrogen atom, a $C_1$-$C_2$ aliphatic acyl group, or a $C_1$-$C_2$ alkoxycarbonyl group, or a pharmacologically acceptable salt thereof,

(73) a pharmaceutical composition according to any one of (60) to (68) containing a compound wherein $R^1$ and $R^2$ are the same or different and each represents a hydrogen atom, an acetyl group, or a methoxycarbonyl group, or a pharmacologically acceptable salt thereof,

(74) a pharmaceutical composition according to any one of (60) to (68) containing a compound wherein each of $R^1$ and $R^2$ represents a hydrogen atom, or a pharmacologically acceptable salt thereof,

(75) a pharmaceutical composition according to any one of (60) to (62) and (69) to (74) containing a compound wherein $R^3$ represents a hydrogen atom, a lower alkyl group, a lower aliphatic acyl group, an aromatic acyl group, an aromatic acyl group substituted with from 1 to 3 substituents selected from Substituent group (a), or a silyl group, or a pharmacologically acceptable salt thereof,

(76) a pharmaceutical composition according to any one of (60) to (62) and (69) to (74) containing a compound wherein $R^3$ represents a hydrogen atom or a lower alkyl group, or a pharmacologically acceptable salt thereof,

(77) a pharmaceutical composition according to any one of (60) to (62) and (69) to (74) containing a compound wherein $R^3$ represents a hydrogen atom or a $C_1$-$C_4$ alkyl group, or a pharmacologically acceptable salt thereof,

(78) a pharmaceutical composition according to any one of (60) to (62) and (69) to (74) containing a compound wherein $R^3$ represents a hydrogen atom, a methyl group, or an ethyl group, or a pharmacologically acceptable salt thereof,

(79) a pharmaceutical composition according to any one of (60) to (62) and (69) to (74) containing a compound wherein $R^3$ represents a hydrogen atom, or a pharmacologically-acceptable salt thereof,

(80) a pharmaceutical composition according to any one of (60) to (79) containing a compound wherein $R^4$ represents a $C_1$-$C_4$ alkyl group, or a pharmacologically acceptable salt thereof.

(81) a pharmaceutical composition according to any one of (60) to (79) containing a compound wherein $R^4$ represents a $C_1$-$C_2$ alkyl group, or a pharmacologically acceptable salt thereof,

(82) a pharmaceutical composition according to any one of (60) to (79) containing a compound wherein $R^4$ represents a methyl group, or a pharmacologically acceptable salt thereof,

(83) a pharmaceutical composition according to any one of (60) to (82) containing a compound wherein n represents an integer 2 or 3, or a pharmacologically acceptable salt thereof,

(84) a pharmaceutical composition according to any one of (60) to (82) containing a compound wherein n represents an integer 2, or a pharmacologically acceptable salt thereof,

(85) a pharmaceutical composition according to any one of (60) to (84) containing a compound wherein X represents a sulfur atom, or a pharmacologically acceptable salt thereof,

(86) a pharmaceutical composition according to any one of (60) to (84) containing a compound wherein X represents an oxygen atom, or a pharmacologically acceptable salt thereof,

(87) a pharmaceutical composition according to any one of (60) to (84) containing a compound wherein X represents a group of formula =N-D (wherein D represents a hydrogen atom, a $C_1$-$C_4$ alkyl group, or a phenyl group), or a pharmacologically acceptable salt thereof,

(88) a pharmaceutical composition according to any one of (60) to (84) containing a compound wherein X represents a group of formula =N—$CH_3$, or a pharmacologically acceptable salt thereof,

(89) a pharmaceutical composition according to any one of (60) to (88) containing a compound wherein Y represents an ethylene group, an ethynylene group, a group of formula —CO—$CH_2$—, a group of formula —CH(OH)—$CH_2$—, a phenylene group, or a phenylene group substituted with from 1 to 3 substituents selected from the group consisting of a halogen atom and a lower alkyl group, or a pharmacologically acceptable salt thereof,

(90) a pharmaceutical composition according to any one of (60) to (88) containing a compound wherein Y represents an ethylene group, an ethynylene group, a group of formula —CO—$CH_2$—, or a phenylene group, or a pharmacologically acceptable salt thereof,

(91) a pharmaceutical composition according to any one of (60) to (90) containing a compound wherein Z represents a $C_1$-$C_{10}$ alkylene group or a $C_1$-$C_{10}$ alkylene group substituted with from 1 to 3 substituents selected from the group consisting of Substituent group (a) and Substituent group (b), or a pharmacologically acceptable salt thereof,

(92) a pharmaceutical composition according to any one of (60) to (90) containing a compound wherein Z represents a $C_1$-$C_6$ alkylene group or a $C_1$-$C_6$ alkylene group substituted with from 1 to 3 hydroxyl groups, or a pharmacologically acceptable salt thereof,

(93) a pharmaceutical composition according to any one of (60) to (90) containing a compound wherein Z represents a $C_1$-$C_5$ alkylene group or a $C_1$-$C_5$ alkylene group substituted with from 1 to 3 hydroxyl groups, or a pharmacologically acceptable salt thereof,

(94) a pharmaceutical composition according to any one of (60) to (90) containing a compound wherein Z represents an ethylene group, a trimethylene group, a tetramethylene group, or an ethylene, trimethylene, or tetramethylene group substituted with one hydroxyl group, or a pharmacologically acceptable salt thereof,
(95) a pharmaceutical composition according to any one of (60) to (90) containing a compound wherein Z represents an ethylene group, a trimethylene group, or a tetramethylene group, or a pharmacologically acceptable salt thereof,
(96) a pharmaceutical composition according to any one of (60) to (90) containing a compound wherein Z represents an ethylene group or a trimethylene group, or a pharmacologically acceptable salt thereof,
(97) a pharmaceutical composition according to any one of (60) to (90) containing a compound wherein Z represents a $C_1$-$C_{10}$ alkylene group which has an oxygen atom or a sulfur atom in said carbon chain or at the end of said carbon chain or a $C_1$-$C_{10}$ alkylene group substituted with one substituent which has an oxygen atom or a sulfur atom in said carbon chain or at the end of said carbon chain (said substituent is selected from the group consisting of lower alkyl groups and hydroxyl groups), or a pharmacologically acceptable salt thereof,
(98) a pharmaceutical composition according to any one of (60) to (90) containing a compound wherein Z represents a $C_1$-$C_{10}$ alkylene group which has an oxygen atom or a sulfur atom in said carbon chain or at the end of said carbon chain, or a pharmacologically acceptable salt thereof,
(99) a pharmaceutical composition according to any one of (60) to (90) containing a compound wherein Z represents a $C_1$-$C_{10}$ alkylene group which has an oxygen atom in said carbon chain or at the end of said carbon chain, or a pharmacologically acceptable salt thereof,
(100) a pharmaceutical composition according to any one of (60) to (90) containing a compound wherein Z represents a $C_1$-$C_6$ alkylene group which has an oxygen atom in said carbon chain or at the end of said carbon chain, or a pharmacologically acceptable salt thereof,
(101) a pharmaceutical composition according to any one of (60) to (90) containing a compound wherein Z represents a group of formula —O—CH$_2$—, —O—(CH$_2$)$_2$, —O—(CH$_2$)$_3$—, —CH$_2$—O—, —(CH$_2$)$_2$—O—, or —(CH$_2$)$_3$—O—, or a pharmacologically acceptable salt thereof,
(102) a pharmaceutical composition according to any one of (60) to (90) containing a compound wherein Z represents a group of formula —CH$_2$—O— or —(CH$_2$)$_2$—O—, or a pharmacologically acceptable salt thereof,
(103) a pharmaceutical composition according to any one of (60) to (102) containing a compound wherein $R^5$ represents a hydrogen atom, or a pharmacologically acceptable salt thereof,
(104) a pharmaceutical composition according to any one of (60) to (102) containing a compound wherein $R^5$ represents a $C_3$-$C_{10}$ cycloalkyl group, a $C_6$-$C_{10}$ aryl group, or a $C_3$-$C_{10}$ cycloalkyl or $C_6$-$C_{10}$ aryl group substituted with from 1 to 3 substituents selected from the group consisting of a halogen atom, a lower alkyl group, a halogeno lower alkyl group, a lower alkoxy group, and a lower alkylthio group, or a pharmacologically acceptable salt thereof,
(105) a pharmaceutical composition according to any one of (60) to (102) containing a compound wherein $R^5$ represents a $C_3$-$C_{10}$ cycloalkyl group, a $C_6$-$C_{10}$ aryl group, or a $C_3$-$C_{10}$ cycloalkyl or $C_6$-$C_{10}$ aryl group substituted with from 1 to 3 substituents selected from the group consisting of a halogen atom, a lower alkyl group, a halogeno lower alkyl group, and a lower alkoxy group, or a pharmacologically acceptable salt thereof,
(106) a pharmaceutical composition according to any one of (60) to (102) containing a compound wherein $R^5$ represents a $C_5$-$C_6$ cycloalkyl group, a phenyl group, or a naphthyl group, or a pharmacologically acceptable salt thereof,
(107) a pharmaceutical composition according to any one of (60) to (102) containing a compound wherein $R^5$ represents a cyclohexyl group or a phenyl group, or a pharmacologically acceptable salt thereof,
(108) a pharmaceutical composition according to any one of (60) to (107) containing a compound wherein $R^6$ and $R^7$ are the same or different and each represents a hydrogen atom, a halogen atom, a lower alkyl group, a halogeno lower-alkyl group, a lower alkoxy group, or a lower alkylthio group, or a pharmacologically acceptable salt thereof,
(109) a pharmaceutical composition according to any one of (60) to (107) containing a compound wherein each of $R^6$ and $R^7$ represents a hydrogen atom, or a pharmacologically acceptable salt thereof,
(110) a pharmaceutical composition according to any one of (63) to (74) and (80) to (109) containing a compound wherein $R^{10}$ and $R^{11}$ are the same or different and each represents a hydrogen atom or a lower alkyl group, or a pharmacologically acceptable salt thereof,
(111) a pharmaceutical composition according to any one of (63) to (74) and (80) to (109) containing a compound wherein $R^{10}$ and $R^{11}$ are the same or different and each represents a hydrogen atom or a $C_1$-$C_4$ alkyl group, or a pharmacologically acceptable salt thereof,
(112) a pharmaceutical composition according to any one of (63) to (74) and (80) to (109) containing a compound wherein $R^{10}$ and $R^{11}$ are the same or different and each represents a hydrogen atom, a methyl group or an ethyl group, or a pharmacologically acceptable salt thereof, and
(113) a pharmaceutical composition according to any one of (63) to (74) and (80) to (109) containing a compound wherein each of $R^{10}$ and $R^{11}$ represents a hydrogen atom, or a pharmacologically acceptable salt thereof.

Of these, particularly preferred pharmaceutical compositions are:
(114) a pharmaceutical composition according to (60), wherein the compound of general formula (I), or pharmacologically acceptable salt thereof, or pharmacologically acceptable ester thereof is selected from the group consisting of the compounds described below, pharmacologically acceptable salts thereof, and pharmacologically acceptable esters thereof:
2-amino-2-methyl-4-[5-(4-cyclohexylbutyl)thiophen-2-yl]butan-1-ol,
2-amino-2-methyl-4-[5-(5-cyclohexylpentyl)thiophen-2-yl]butan-1-ol,
2-amino-2-methyl-4-[5-(5-phenylpentyl)thiophen-2-yl]butan-1-ol,
2-amino-2-methyl-4-[5-(4-cyclohexyloxybutyl)thiophen-2-yl]butan-1-ol,
2-amino-2-methyl-4-{5-[4-(4-fluorophenoxy)butyl]thiophen-2-yl}butan-1-ol,
2-amino-2-methyl-4-{5-[4-(4-methoxyphenoxy)butyl]thiophen-2-yl}butan-1-ol
2-amino-2-methyl-4-[5-(4-benzyloxybutyl)thiophen-2-yl]butan-1-ol,
2-amino-2-methyl-4-[5-(4-cyclohexylbut-1-ynyl)thiophen-2-yl]butan-1-ol,
2-amino-2-methyl-4-[5-(4-phenylbut-1-ynyl)thiophen-2-yl]butan-1-ol, 2-amino-2-methyl-4-[5-(4-cyclohexylpent-1-ynyl)thiophen-2-yl]butan-1-ol,
2-amino-2-methyl-4-[5-(5-phenylpent-1-ynyl)thiophen-2-yl]butan-1-ol,
2-amino-2-methyl-4-{5-[5-(4-fluorophenyl)pent-1-ynyl]thiophen-2-yl}butan-1-ol,
2-amino-2-methyl-4-{5-[5-(4-methoxyphenyl)pent-1-ynyl]thiophen-2-yl}butan-1-ol,
2-amino-2-methyl-4-{5-[3-(4-methylphenoxy)prop-1-ynyl]thiophen-2-yl}butan-1-ol,
2-amino-2-methyl-4-{5-[3-(4-ethylphenoxy)prop-1-ynyl]thiophen-2-yl}butan-1-ol,
2-amino-2-methyl-4-{5-[3-(4-methylthiophenoxy)prop-1-ynyl]thiophen-2-yl}butan-1-ol,
2-amino-2-methyl-4-[5-(4-cyclohexyloxybut-1-ynyl)thiophen-2-yl]butan-1-ol,
2-amino-2-methyl-4-{5-[4-(4-fluorophenoxy)but-1-ynyl]thiophen-1-2-yl}butan-1-ol,
2-amino-2-methyl-4-{-5-[4-(4-methylphenoxy)but-1-ynyl]thiophen-2-yl}butan-1-ol,
2-amino-2-methyl-4-[5-(3-cyclohexylmethoxyprop-1-ynyl)thiophen-2-yl]butan-1-ol,
2-amino-2-methyl-4-[5-(4-benzyloxybut-1-ynyl)thiophen-2-yl]butan-1-ol,
2-amino-2-methyl-4-[5-(4-cyclohexylbutanoyl)thiophen-2-yl]butan-1-ol,
2-amino-2-methyl-4-[5-(4-phenylbutanoyl)thiophen-2-yl]butan-1-ol,
2-amino-2-methyl-4-[5-(5-cyclohexylpentanoyl)thiophen-2-yl]butan-1-ol,
2-amino-2-methyl-4-[5-(5-phenylpentanoyl)thiophen-2-yl]butan-1-ol,
2-amino-2-methyl-4-{5-[5-(4-fluorophenyl)pentanoyl]thiophen-2-yl}butan-1-ol,
2-amino-2-ethyl-4-[5-(5-cyclohexylpentyl)thiophen-2-yl]butan-1-ol,
2-amino-2-ethyl-4-[5-(5-cyclohexylpent-1-ynyl)thiophen-2-yl]butan-1-ol,
2-amino-2-ethyl-4-[5-(5-cyclohexylpentanoyl)thiophen-2-yl]butan-1-ol,
2-amino-2-methyl-4-{5-[3-(4-chlorophenoxy)prop-1-ynyl]thiophen-2-yl}butan-1-ol,
2-amino-2-methyl-4-{5-[3-(3-methylphenoxy)prop-1-ynyl]thiophen-2-yl}butan-1-ol,
2-amino-2-methyl-4-{5-[3-(3,4-dimethylphenoxy)prop-1-ynyl]thiophen-2-yl}butan-1-ol,
2-amino-2-methyl-4-{5-[3-(3-methoxyphenoxy)prop-1-ynyl]thiophen-2-yl}butan-1-ol,
2-amino-2-methyl-4-{5-[3-(3,4-dimethoxyphenoxy)prop-1-ynyl]thiophen-2-yl}butan-1-ol,
2-amino-2-methyl-4-{5-[3-(3,5-dimethoxyphenoxy)prop-1-ynyl]thiophen-2-yl}butan-1-ol,
2-amino-2-methyl-4-{5-[3-(3-acetylphenoxy)prop-1-ynyl]thiophen-2-yl}butan-1-ol, and
2-amino-2-methyl-4-{5-[3-(4-acetylphenoxy)prop-1-ynyl]thiophen-2-yl}butan-1-ol,
(115) a pharmaceutical composition according to (60), wherein the compound of general formula (I), or pharmacologically acceptable salt thereof, or pharmacologically acceptable ester thereof is selected from the group consisting of the compounds described below, pharmacologically acceptable salts thereof, and pharmacologically acceptable esters thereof:
2-amino-2-methyl-4-[5-(5-phenylpentyl)furan-2-yl]butan-1-ol,
2-amino-2-methyl-4-[5-(5-cyclohexylpent-1-ynyl) furan-2-yl]butan-1-ol,
2-amino-2-methyl-4-[5-(5-phenylpent-1-ynyl)furan-2-yl]butan-1-ol,
2-amino-2-methyl-4-[5-(4-cyclohexyloxybut-1-ynyl)furan-2-yl]butan-1-ol,
2-amino-2-methyl-4-[5-(5-cyclohexylpentanoyl)furan-2-yl]butan-1-ol, and
2-amino-2-methyl-4-{5-[3-(3,4-dimethylphenoxy)prop-1-ynyl]furan-2-yl}butan-1-ol,
(116) a pharmaceutical composition according to (60), wherein the compound of general formula (I), or pharmacologically acceptable salt thereof, or pharmacologically acceptable ester thereof is selected from the group consisting of the compounds described below, pharmacologically acceptable salts thereof, and pharmacologically acceptable esters thereof:
2-amino-2-methyl-4-[1-methyl-5-(5-phenylpent-1-ynyl)pyrrol-2-yl]butan-1-ol,
2-amino-2-methyl-4-{1-methyl-5-[3-(4-methylphenoxy)prop-1-ynyl]pyrrol-2-yl}butan-1-ol,
2-amino-2-methyl-4-[1-methyl-5-(4-cyclohexyloxybut-1-ynyl)pyrrol-2-yl]butan-1-ol,
2-amino-2-methyl-4-{1-methyl-5-[3-(3,4-dimethylphenoxy)prop-1-ynyl]pyrrol-2-yl}butan-1-ol,
2-amino-2-methyl-4-[1-methyl-5-(5-phenylpentanoyl)pyrrol-2-yl]butan-1-ol,
2-amino-2-methyl-4-[1-methyl-5-(5-cyclhexylpentanoyl)pyrrol-2-yl]butan-1-ol,
2-amino-2-methyl-4-[1-methyl-5-(4-phenylbutanoyl)pyrrol-2-yl]butan-1-ol,
2-amino-2-methyl-4-[1-methyl-5-(4-cyclohexylbutanoyl)pyrrol-2-yl]butan-1-ol,
2-amino-2-methyl-4-{1-methyl-5-[4-(4-methylphenyl)butanoyl]pyrrol-2-yl}butan-1-ol,
2-amino-2-methyl-4-[1-ethyl-5-(5-phenylpentanoyl)pyrrol-2-yl]butan-1-ol,
2-amino-2-methyl-4-[1-ethyl-5-(5-cyclohexylpentanoyl)pyrrol-2-yl]butan-1-ol,
2-amino-2-methyl-4-[1-ethyl-5-(4-phenylbutanoyl)pyrrol-2-yl]butan-1-ol, and
2-amino-2-methyl-4-[(1-ethyl-5-(4-cyclohexylbutanoyl)pyrrol-2-yl]butan-1-ol,
2-amino-2-methyl-4-{1-methyl-5-[4-(3,4-dimethylphenyl)butanoyl]pyrrol-2-yl}butan-1-ol,
2-amino-2-methyl-4-(1-methyl-5-[4-(3,5-dimethylphenyl)butanoyl]pyrrol-2-yl)butan-1-ol
2-amino-2-methyl-4-{1-methyl-5-[4-(3-trifluoromethylphenyl)butanoyl]pyrrol-2-yl}butan-1-ol,
2-amino-2-methyl-4-(1-methyl-5-[4-(4-trifluoromethylphenyl)butanoyl]pyrrol-2-yl)butan-1-ol,
2-amino-2-methyl-4-{1-methyl-5-[4-(4-methoxyphenyl)butanoyl]pyrrol-2-yl}butan-1-ol,
2-amino-2-methyl-4-(1-methyl-5-[4-(3-methylphenyl)butyl]pyrrol-2-yl)butan-1-ol,
2-amino-2-methyl-4-{1-methyl-5-[4-(3,4-dimethylphenyl)butyl]pyrrol-2-yl}butan-1-ol,
2-amino-2-methyl-4-(1-methyl-5-[4-(3,5-dimethylphenyl)butyl]pyrrol-2-yl)butan-1-ol,
2-amino-2-methyl-4-{1-methyl-5-[4-(3-trifluoromethylphenyl)butyl]pyrrol-2-yl}butan-1-ol.
(117) a pharmaceutical composition according to (63), wherein the compound of general formula (II), or pharmacologically acceptable salt thereof, or pharmacologically acceptable eater thereof in selected from the group consisting of the compounds described below, pharmacologically acceptable salts thereof, and pharmacologically acceptable esters thereof:

mono 2-amino-2-methyl-4-[5-(4-cyclohexylbutyl)thiophen-2-yl]-1-butyl phosphate,
mono 2-amino-2-methyl-4-[5-(5-cyclohexylpentyl)thiophen-2-yl]-1-butyl phosphate,
mono 2-amino-2-methyl-4-[5-(5-phenylpentyl)thiophen-2-yl]-1-butyl phosphate,
mono 2-amino-2-methyl-4-[5-(4-cyclohexyloxybutyl)thiophen-2-yl]-1-butyl phosphate,
mono 2-amino-2-methyl-4-{5-[4-(4-fluorophenoxy)butyl]thiophen-2-yl}-1-butyl phosphate,
mono 2-amino-2-methyl-4-{5-[4-(4-methoxyphenoxy)butyl]thiophen-2-yl}-1-butyl phosphate,
mono 2-amino-2-methyl-4-[5-(4-benzyloxybutyl)thiophen-2-yl]-1-butyl phosphate,
mono 2-amino-2-methyl-4-[5-(4-cyclohexylbut-1-ynyl)thiophen-2-yl]-1-butyl phosphate,
mono 2-amino-2-methyl-4-[5-(4-phenylbut-1-ynyl)thiophen-2-yl]-1-butyl phosphate,
mono 2-amino-2-methyl-4-[5-(5-cyclohexylpent-1-ynyl)thiophen-2-yl]-1-butyl phosphate,
mono 2-amino-2-methyl-4-[5-(5-phenylpent-1-ynyl)thiophen-2-yl]-1-butyl phosphate,
mono 2-amino-2-methyl-4-{5-[5-(4-fluorophenyl)pent-1-ynyl]thiophen-2-yl}-1-butyl phosphate,
mono 2-amino-2-methyl-4-{5-[5-(4-methoxyphenyl)pent-1-ynyl]thiophen-2-yl}-1-butyl phosphate,
mono 2-amino-2-methyl-4-{5-[3-(4-methylphenoxy)prop-1-ynyl]thiophen-2-yl}-1-butyl phosphate,
mono 2-amino-2-methyl-4-{5-[3-(4-ethylphenoxy)prop-1-ynyl]thiophen-2-yl}-1-butyl phosphate,
mono 2-amino-2-methyl-4-{5-[3-(4-methylthiophenoxy)prop-1-ynyl]thiophen-2-yl}-1-butyl phosphate,
mono 2-amino-2-methyl-4-[5-(4-cyclohexyloxybut-1-ynyl)thiophen-2-yl]-1-butyl phosphate,
mono 2-amino-2-methyl-4-{5-[4-(4-fluorophenoxy)but-1-ynyl]thiophen-2-yl}-1-butyl phosphate,
mono 2-amino-2-methyl-4-{5-[4-(4-methylphenoxy)but-1-ynyl]thiophen-2-yl}-1-butyl phosphate,
mono 2-amino-2-methyl-4-{5-(3-cyclohexylmethoxy)prop-1-ynyl]thiophen-2-yl}-1-butyl phosphate,
mono 2-amino-2-methyl-4-[5-(4-benzyloxybut-1-ynyl)thiophen-2-yl]-1-butyl phosphate,
mono 2-amino-2-methyl-4-[5-(4-cyclohexylbutanoyl)thiophen-2-yl]-1-butyl phosphate,
mono 2-amino-2-methyl-4-[5-(4-phenylbutanoyl)thiophen-2-yl]-1-butyl phosphate,
mono 2-amino-2-methyl-4-[5-(5-cyclohexylpentanoyl)thiophen-2-yl]-1-butyl phosphate,
mono 2-amino-2-methyl-4-[5-(5-phenylpentanoyl)thiophen-2-yl]-1-butyl phosphate,
mono 2-amino-2-methyl-4-{5-[5-(4-fluorophenyl)pentanoyl]thiophen-2-yl}-1-butyl phosphate,
mono 2-amino-2-ethyl-4-[5-(5-cyclohexylpentyl)thiophen-2-yl]-1-butyl phosphate,
mono 2-amino-2-ethyl-4-[5-(5-cyclohexylpent-1-ynyl)thiophen-2-yl]-1-butyl phosphate,
mono 2-amino-2-ethyl-4-[5-(5-cyclohexylpentanoyl)thiophen-2-yl]-1-butyl phosphate,
mono 2-amino-2-methyl-4-{5-[3-(4-chlorophenoxy)prop-1-ynyl]thiophen-2-yl}-1-butyl phosphate,
mono 2-amino-2-methyl-4-{5-[3-(3-methylphenoxy)prop-1-ynyl]thiophen-2-yl}-1-butyl phosphate,
mono 2-amino-2-methyl-4-{5-[3-(3,4-dimethylphenoxy)prop-1-ynyl]thiophen-2-yl}-1-butyl phosphate,
mono 2-amino-2-methyl-4-{5-[3-(3-methoxyphenoxyl)prop-1-ynyl]thiophen-2-yl}-1-butyl phosphate,
mono 2-amino-2-methyl-4-{5-[3-(3,4-dimethoxyphenoxy)prop-1-ynyl]thiophen-2-yl}-1-butyl phosphate,
mono 2-amino-2-methyl-4-{5-[3-(3,5-dimethoxyphenoxyl)prop-1-ynyl]thiophen-2-yl}-1-butyl phosphate,
mono 2-amino-2-methyl-4-{5-[3-(3-acetylphenoxy)prop-1-ynyl]thiophen-2-yl}-1-butyl phosphate, and
mono 2-amino-2-methyl-4-{5-[3-(4-acetylphenoxy)prop-1-ynyl]thiophen-2-yl}-1-butyl phosphate, (118) a pharmaceutical composition according to (63), wherein the compound of general formula (II), or pharmacologically acceptable salt thereof, or pharmacologically acceptable ester thereof is selected from the group consisting of the compounds described below, pharmacologically-acceptable salts thereof, and pharmacologically acceptable-esters thereof:
mono 2-amino-2-methyl-4-[5-(5-phenylpentyl)furan-2-yl]-1-butyl phosphate,
mono 2-amino-2-methyl-4-[5-(5-cyclohexylpent-1-ynyl)furan-2-yl]-1-butyl phosphate,
mono 2-amino-2-methyl-4-[5-(5-phenylpent-1-ynyl)furan-2-yl]-1-butyl phosphate,
mono 2-amino-2-methyl-4-[5-(4-cyclohexyloxybut-1-ynyl)furan-2-yl]-1-butyl phosphate,
mono 2-amino-2-methyl-4-[5-(5-cyclohexylpentanoyl)furan-2-yl]-1-butyl phosphate, and
mono 2-amino-2-methyl-4-{5-[3-(3,4-dimethylphenoxy)prop-1-ynyl]furan-2-yl}-1-butyl phosphate, (119) a pharmaceutical composition according to (63), wherein the compound of general formula (II), or pharmacologically acceptable salt thereof, or pharmacologically acceptable ester thereof is selected from the group consisting of the compounds described below, pharmacologically acceptable salts thereof, and pharmacologically acceptable esters thereof:
mono 2-amino-2-methyl-4-[1-methyl-5-(5-phenylpent-1-ynyl)pyrrol-2-yl]-1-butyl phosphate,
mono 2-amino-2-methyl-4-{1-methyl-5-[3-(4-methylphenoxy)prop-1-ynyl]pyrrol-2-yl}-1-butyl phosphate,
mono 2-amino-2-methyl-4-[1-methyl-5-(4-cyclohexyloxybut-1-ynyl)pyrrol-2-yl]-1-butyl phosphate,
mono 2-amino-2-methyl-4-{1-methyl-5-[3-(3,4-dimethylphenoxy)prop-1-ynyl]pyrrol-2-yl}-1-butyl phosphate,
mono 2-amino-2-methyl-4-[1-methyl-5-(5-phenylpentanoyl)pyrrol-2-yl]-1-butyl phosphate,
mono 2-amino-2-methyl-4-[1-methyl-5-(5-cyclohexylpentanoyl)pyrrol-2-yl]-1-butyl phosphate,
mono 2-amino-2-methyl-4-[1-methyl-5-(4-phenylbutanoyl)pyrrol-2-yl]-1-butyl phosphate,
mono 2-amino-2-methyl-4-[1-methyl-5-(4-cyclohexylbutanoyl)pyrrol-2-yl]-1-butyl phosphate,
mono 2-amino-2-methyl-4-{1-methyl-5-[4-(4-methylphenyl)butanoyl]pyrrol-2-yl}-1-butyl phosphate,
mono 2-amino-2-methyl-4-[1-ethyl-5-(5-phenylpentanoyl)pyrrol-2-yl]-1-butyl phosphate,
mono 2-amino-2-methyl-4-[1-ethyl-5-(5-cyclohexylpentanoyl)pyrrol-2-yl]-1-butyl phosphate,
mono 2-amino-2-methyl-4-[1-ethyl-5-(4-phenylbutanoyl)pyrrol-2-yl]-1-butyl phosphate, and
mono 2-amino-2-methyl-4-[1-ethyl-5-(4-cyclohexylbutanoyl)pyrrol-2-yl]-1-butyl phosphate,
mono 2-amino-2-methyl-4-{1-methyl-5-[4-(3,4-dimethylphenyl)butanoyl]pyrrol-2-yl}-1-butyl phosphate,
mono 2-amino-2-methyl-4-{1-methyl-5-[4-(3,5-dimethylphenyl)butanoyl]pyrrol-2-yl}-1-butyl phosphate.

(120) a pharmaceutical composition according to (66), wherein the compound of general formula (III), or pharmacologically acceptable salt thereof, or pharmacologically acceptable ester thereof is selected from the group consisting of the compounds described below, pharmacologically acceptable salts thereof, and pharmacologically acceptable esters thereof:
3-amino-3-methyl-5-[5-(4-cyclohexylbutyl)thiophen-2-yl]pentylphosphonic acid,
3-amino-3-methyl-5-[5-(5-cyclohexylpentyl)thiophen-2-yl]pentylphosphonic acid,
3-amino-3-methyl-5-[5-(5-phenylpentyl)thiophen-2-yl]pentylphosphonic acid,
3-amino-3-methyl-5-[5-(4-cyclohexyloxybutyl)thiophen-2-yl]pentylphosphonic acid,
3-amino-3-methyl-5-{5-[4-(4-fluorophenoxy)butyl]thiophen-2-yl}pentylphosphonic acid,
3-amino-3-methyl-5-{5-[4-(4-methoxyphenoxy)butyl]thiophen-2-yl}pentylphosphonic acid,
3-amino-3-methyl-5-[5-(4-benzyloxybutyl)thiophen-2-yl]pentylphosphonic acid,
3-amino-3-methyl-5-[5-(4-cyclohexylbut-1-ynyl)thiophen-2-yl]pentylphosphonic acid,
3-amino-3-methyl-5-[5-(4-phenylbut-1-ynyl) thiophen-2-yl]pentylphosphonic acid,
3-amino-3-methyl-5-[5-(5-cyclohexylpent-1-ynyl)thiophen-2-yl]pentylphosphonic acid,
3-amino-3-methyl-5-[5-(5-phenylpent-1-ynyl)thiophen-2-yl]pentylphosphonic acid,
3-amino-3-methyl-5-{5-[5-(4-fluorophenyl)pent-1-ynyl]thiophen-2-yl}pentylphosphonic acid,
3-amino-3-methyl-5-{5-[5-(4-methoxyphenyl)pent-1-ynyl]thiophen-2-yl}pentylphosphonic acid,
3-amino-3-methyl-5-{5-[3-(4-methylphenoxy)prop-1-ynyl]thiophen-2-yl}pentylphosphonic acid,
3-amino-3-methyl-5-{5-[3-(4-ethylphenoxy)prop-1-ynyl]thiophen-2-yl}pentylphosphonic acid,
3-amino-3-methyl-5-{5-[3-(4-methylthiophenoxy)prop-1-ynyl]thiophen-2-yl}pentylphosphonic acid,
3-amino-3-methyl-5-[5-(4-cyclohexyloxybut-1-ynyl)thiophen-2-yl]pentylphosphonic acid,
3-amino-3-methyl-5-{5-[4-(4-fluorophenoxy)but-1-ynyl]thiophen-2-yl}pentylphosphonic acid,
3-amino-3-methyl-5-{5-[4-(4-methylphenoxy)but-1-ynyl]thiophen-2-yl}pentylphosphonic acid,
3-amino-3-methyl-5-[5-(3-cyclohexylmethoxy)prop-1-ynyl]thiophen-2-yl]pentylphosphonic acid,
3-amino-3-methyl-5-[5-(4-benzyloxybut-1-ynyl)thiophen-2-yl]pentylphosphonic acid,
3-amino-3-methyl-5-[5-(4-cyclohexylbutanoyl)thiophen-2-yl]pentylphosphonic acid,
3-amino-3-methyl-5-[5-(4-phenylbutanoyl)thiophen-2-yl]pentylphosphonic acid,
3-amino-3-methyl-5-[5-(5-cyclohexylpentanoyl)thiophen-2-yl]pentylphosphonic acid,
3-amino-3-methyl-5-[5-(5-phenylpentanoyl)thiophen-2-yl]pentylphosphonic acid,
3-amino-3-methyl-5-{5-[5-(4-fluorophenyl)pentanoyl]thiophen-2-yl}pentylphosphonic acid,
3-amino-3-ethyl-5-[5-(5-cyclohexylpentyl)thiophen-2-yl]pentylphosphonic acid,
3-amino-3-ethyl-5-[5-(5-cyclohexylpent-1-ynyl)thiophen-2-yl]pentylphosphonic acid,
3-amino-3-ethyl-5-[5-(5-cyclohexylpentanoyl)thiophen-2-yl]pentylphosphonic acid,
3-amino-3-methyl-5-{5-[3-(4-chlorophenoxy)prop-1-ynyl]thiophen-2-yl}pentylphosphonic acid,
3-amino-3-methyl-5-{5-[3-(3-methylphenoxy)prop-1-ynyl]thiophen-2-yl}pentylphosphonic acid,
3-amino-3-methyl-5-{5-[3-(3,4-dimethylphenoxy)prop-1-ynyl]thiophen-2-yl}pentylphosphonic acid,
3-amino-3-methyl-5-{5-[3-(3-methoxyphenoxyl)prop-1-ynyl]thiophen-2-yl}pentylphosphonic acid,
3-amino-3-methyl-5-{5-[3-(3,4-dimethoxyphenoxy)prop-1-ynyl]thiophen-2-yl}pentylphosphonic acid,
3-amino-3-methyl-5-{5-[3-(3,5-dimethoxyphenoxyl)prop-1-ynyl]thiophen-2-yl}pentylphosphonic acid,
3-amino-3-methyl-5-{5-[3-(3-acetylphenoxy)prop-1-ynyl]thiophen-2-yl}pentylphosphonic acid, and
3-amino-3-methyl-5-{5-[3-(4-acetylphenoxy)prop-1-ynyl]thiophen-2-yl}pentylphosphonic acid, (121) a pharmaceutical composition according to (66), wherein the compound of general formula (III), or pharmacologically acceptable salt thereof, or pharmacologically acceptable ester thereof is selected from the group consisting of the compounds described below, pharmacologically acceptable salts thereof, and pharmacologically acceptable esters thereof:
3-amino-3-methyl-5-[5-(5-phenylpentyl)furan-2-yl]pentylphosphonic acid,
3-amino-3-methyl-5-[5-(5-cyclohexylpent-1-ynyl)furan-2-yl]pentylphosphonic acid,
3-amino-3-methyl-5-[5-(5-phenylpent-1-ynyl)furan-2-yl]pentylphosphonic acid,
3-amino-3-methyl-5-[5-(4-cyclohexyloxybut-1-ynyl)furan-2-yl]pentylphosphonic acid,
3-amino-3-methyl-5-[5-(5-cyclohexylpentanoyl)furan-2-yl]pentylphosphonic acid, and
3-amino-3-methyl-5-{5-[3-(3,4-dimethylphenoxy)prop-1-ynyl]furan-2-yl}pentylphosphonic acid, (122) a pharmaceutical composition according to (66), wherein the compound of general formula (III), or pharmacologically acceptable salt thereof, or pharmacologically acceptable ester thereof is selected from the group consisting of the compounds described below, pharmacologically acceptable salts thereof, and pharmacologically acceptable esters thereof:
3-amino-3-methyl-5-[1-methyl-5-(5-phenylpent-1-ynyl)pyrrol-2-yl]pentylphosphonic acid,
3-amino-3-methyl-5-{5-methyl-5-[3-(4-methylphenoxy)prop-1-ynyl]pyrrol-2-yl}pentylphosphonic acid,
3-amino-3-methyl-5-[1-methyl-5-(4-cyclohexyloxybut-1-ynyl)pyrrol-2-yl]pentylphosphonic acid,
3-amino-3-methyl-5-{1-methyl-5-[3-(3,4-dimethylphenoxy)prop-1-ynyl]pyrrol-2-yl}pentylphosphonic acid,
3-amino-3-methyl-5-[1-methyl-5-(5-phenylpentanoyl)pyrrol-2-yl]pentylphosphonic acid,
3-amino-3-methyl-5-[1-methyl-5-(5-cyclohexylpentanoyl)pyrrol-2-yl]pentylphosphonic acid,
3-amino-3-methyl-5-[1-methyl-5-(4-phenylbutanoyl)pyrrol-2-yl]pentylphosphonic acid,
3-amino-3-methyl-5-[1-methyl-5-(4-cyclohexylbutanoyl)pyrrol-2-yl]pentylphosphonic acid,
3-amino-3-methyl-5-[1-ethyl-5-(5-phenylpentanoyl)pyrrol-2-yl]pentylphosphonic acid,
3-amino-3-methyl-5-[1-ethyl-5-(5-cyclohexylpentanoyl)pyrrol-2-yl]pentylphosphonic acid,
3-amino-3-methyl-5-[1-ethyl-5-(4-phenylbutanoyl)pyrrol-2-yl]pentylphosphonic acid, and
3-amino-3-methyl-5-[1-ethyl-5-(4-cyclohexylbutanoyl)pyrrol-2-yl]pentylphosphonic acid, (123) a pharmaceutical composition according to any one of (60) to (122) wherein said composition contains at least one immunosuppressant selected from the group consisting of agents having the action of inhibiting intracellular signal transduction involved in cytokine expression of T-cells (said agents are cyclosporin A, tacrolimus, rapamycin, gusperimus, everolimus, tresperimus, anisperimus, SDZ-281-240, ABT-281, tigderimus, A-119435, or 17-ethyl-1,14-dihydroxy-12-[2-[4-(2-phenylhydrazinocarbonyloxy)-3-methoxycyclohexyl]-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetrone), agents having the action of inhibiting nucleoside synthesis in immune cells (said agents are mizoribine, azathioprine, mycophenolate Mofetil, leflunomide, merimempodib, HMR-1279, TSK-204, or SP-100030), agents having the action of inhibiting the action of cytokines on immune cells and having antirheumatic action (said agents are T-614, actarit, salazosulfapyridine, or CDC-801), alkylating agents causing cell death by breakdown of DNA chains or blocking DNA synthesis (said alkylating agent is cyclophosphamide), metabolic antagonists inhibiting the metabolism of nucleic acids by blocking folic acid production (said metabolic antagonist is methotrexate), protein drugs having the suppression action of TNF-α (said protein drugs are remicade, enbrel, daclizumab, basiliximab, alemtuzumab, omalizumab, BMS-188667, CDP-571, inolimomab, ATM-027, or BTI-322), steroid hormone agents that bind to intracellular steroid receptors to form a complex which binds to reaction sites on chromosomes, resulting in the synthesis of proteins which show immunosuppressive activity (said steroid hormone agent is prednisolone), and substances suppressing prostaglandin production and/or nonsteroidal anti-inflammatory drugs antagonizing the action of prostaglandin (said nonsteroidal anti-inflammatory drugs are loxoprofen sodium, diclofenac sodium, meloxicam, celecoxib, or rofecoxib), and (124) a pharmaceutical composition according to any one of (60) to (122) wherein said composition contains at least one immunosuppressant selected from the group consisting of cyclosporin A, tacrolimus, rapamycin, leflunomide, methotrexate, remicade, and enbrel.

Another object of the present invention is to provide the following pharmaceutical compositions and methods:

(125) a pharmaceutical composition comprising as an active ingredient a compound, a pharmacologically acceptable salt thereof or a pharmacologically acceptable ester thereof according to any one of (1) to (59), (126) a pharmaceutical composition according to (125) for the prevention or treatment of autoimmune diseases, (127) a pharmaceutical composition according to (126) wherein said autoimmune disease is rheumatoid arthritis, a pharmaceutical composition according to (126) wherein said autoimmune disease is Crohn's disease or ulcerative colitis, a pharmaceutical composition according to (126) wherein said autoimmune disease is multiple sclerosis, a pharmaceutical composition according to (126) wherein said autoimmune disease is psoriasis, a pharmaceutical composition according to (126) wherein said autoimmune disease is atopic dermatitis, a pharmaceutical composition according to (126) wherein said autoimmune disease is insulin dependent diabetes mellitus, a pharmaceutical composition according to (126) wherein said autoimmune disease is glomerular nephritis, (128) a pharmaceutical composition according to (125) for suppression of rejection caused by transplantation of various organs or skin, (129) a method for the prevention or treatment of autoimmune diseases in a mammal which comprises administering to said mammal an effective amount of a pharmaceutical composition according to any one of (60) to (125), (130) a method for the prevention or treatment of rheumatoid arthritis in a mammal which comprises administering to said mammal an effective amount of a pharmaceutical composition according to any one of (60) to (125), and a method for the prevention or treatment of psoriasis in a mammal which comprises administering to said mammal an effective amount of a pharmaceutical composition according to any one of (60) to (125), a method for the prevention or treatment of Crohn's disease or ulcerative colitis in a mammal which comprises administering to said mammal an effective amount of a pharmaceutical composition according to any one of (60) to (125), a method for the prevention or treatment of multiple sclerosis in a mammal which comprises administering to said mammal an effective amount of a pharmaceutical composition according to any one of (60) to (125), a method for the prevention or treatment of atopic dermatitis in a mammal which comprises administering to said mammal an effective amount of a pharmaceutical composition according to any one of claims 60 to 125.

a method for the prevention or treatment of insulin dependent diabetes mellitus in a mammal which comprises administering to said mammal an effective amount of a pharmaceutical composition according to any one of claims 60 to 125.

a method for the prevention or treatment of glomerular nephritis in a mammal which comprises administering to said mammal an effective amount of a pharmaceutical composition according to any one of claims 60 to 125.

(131) a method for the prevention or treatment of rejection caused by transplantation of various organs or skin in a mammal which comprises administering to said mammal an effective amount of a pharmaceutical composition according to any one of (60) to (125).

In the formulae (I), (II) and (III), the aryl moiety of the "$C_6$-$C_{10}$ aryl group", the "$C_6$-$C_{10}$ aryl group which is substituted with from 1 to 3 substituents selected from Substituent group (a)", or the "$C_6$-$C_{10}$ aryl group which is substituted with from 1 to 3 substituents selected from the group consisting of Substituent group (a) and Substituent group (b)" in the definition of D, $R^5$ or Substituent group (b) can be, for example, a group such as a phenyl, indenyl, or naphthyl group, and is preferably a phenylene or naphthylene group, and most preferably a phenylene group.

The arylene moiety of the "$C_6$-$C_{10}$ arylene group"; the "$C_6$-$C_{10}$ arylene group which is substituted with from 1 to 3 substituents selected from Substituent group (a)", or the "$C_6$-$C_{10}$ arylene group which is substituted with from 1 to 3 substituents selected from the group consisting of Substituent group (a) and Substituent group (b)" in the definition of Y or E can be, for example, a group such as a phenylene, indenylene, or naphthylene group, and is preferably a phenylene or naphthylene group, and most preferably a phenylene group.

The $C_1$-$C_{10}$ alkylene moiety of the "$C_1$-$C_{10}$ alkylene group" or the "$C_1$-$C_{10}$ alkylene group which is substituted with from 1 to 3 substituents selected from the group consisting of Substituent group (a) and Substituent group (b)", in the definition of Z includes straight or branched chain alkylene groups having from 1 to 10 carbon atoms, and can be, for example, a group such as a methylene, methylmethylene, ethylene, propylene, trimethylene, 1-methylethylene, tetramethylene, 1-methyltrimethylene, 2-methyltrimethylene, 3-methyltrimethylene, 1-methylpropylene, 1,1-dimethylethylene, pentamethylene, 1-methyltetramethylene, 2-methyltetramethylene, 3-methyltetramethylene, 4-methyltetramethylene, 1,1-dimethyltrimethylene, 2,2-dimethyltrimethylene, 3,3-dimethyltrimethylene, hexamethylene, 1-methylpentamethylene, 2-methylpentamethylene, 3-methylpentamethylene, 4-methylpentamethylene, 5-methylpentamethylene, 1,1-dimethyltetramethylene, 2,2-dimethyltetramethylene, 3,3-dimethyltetramethylene, 4,4-dimethyltetramethylene, heptamethylene, 1-methylhexamethylene, 2-methylhexamethylene, 5-methylhexamethylene, 3-ethylpentamethylene, octamethylene, 2-methylheptamethylene, 5-methylheptamethylene, 2-ethylhexamethylene, 2-ethyl-3-methylpentartethylene, 3-ethyl-2-methylpentamethylene, nonamethylene, 2-methyloctamethylene, 7-methyloctamethylene, 4-ethylheptamethylene, 3-ethyl-2-methylhexamethylene, 2-ethyl-1-methylhexamethylene or decamethylene group, and is preferably a $C_1$-$C_6$ alkylene group, more preferably a $C_1$-$C_5$ alkylene group, still more preferably an ethylene, trimethylene, or tetramethylene group, and most preferably an ethylene or trimethylene group.

The "$C_1$-$C_{10}$ alkylene moiety which contains an oxygen atom or a sulfur atom in the carbon chain or at the end of the carbon chain" of the "$C_1$-$C_{10}$ alkylene group which has an oxygen atom or a sulfur atom in said carbon chain or at the end of said carbon chain" or the "$C_1$-$C_{10}$ alkylene group substituted with from 1 to 3 substituents selected from the group consisting of Substituent group (a) and Substituent group (b) which has an oxygen atom or a sulfur atom in said carbon chain or at the end of said carbon chain" in the definition of Z represents a "$C_1$-$C_{10}$-alkylene group" described above which contains an oxygen atom or a sulfur atom in the carbon chain or at the end of the carbon chain, and can be, for example, a —O—CH$_2$—, —O—(CH$_2$)$_2$—, —O— (CH$_2$)$_3$—, —O—(CH$_2$)$_4$—, —O— (CH$_2$)$_5$—, —O—(CH$_2$)$_6$—, —O—(CH$_2$)$_7$—, —O— (CH$_2$)$_8$—, —O— (CH$_2$)$_9$—, —O—(CH$_2$)$_{10}$—, —CH$_2$—O—CH$_2$—, —CH$_2$—O— (CH$_2$)$_2$, —CH$_2$—O— (CH$_2$)$_3$—, —CH$_2$—O— (CH$_2$)$_4$—, —(CH$_2$)$_2$, —O—CH$_2$—, —(CH$_2$)$_2$—, —O— (CH$_2$)$_2$—, —(CH$_2$)$_2$—O— (CH$_2$)$_3$—, —(CH$_2$)$_2$—, —(CH$_2$)$_4$—, —(CH$_2$)$_3$—O—, —CH$_2$—, —(CH$_2$)$_3$—, —O— (CH$_2$)$_2$—, —(CH$_2$)$_3$—O— (CH$_2$)$_3$—, —(CH$_2$)$_4$—O—CH$_2$—, —(CH$_2$)$_4$—O— (CH$_2$)$_2$—, —(CH$_2$)$_5$—O—CH$_2$— —CH$_2$—O—, —(CH$_2$)$_2$—O—(CH$_2$)$_3$—O—, —(CH$_2$)$_4$—(CH$_2$)$_5$—O— (CH$_2$)$_6$—O, —O—, —(CH$_2$)$_7$—O— (CH$_2$)$_8$—, —(CH$_2$)$_9$—O—, —(CH$_2$)$_{10}$—O—, —S—CH$_2$—, —S— (CH$_2$)$_2$—, —S— (CH$_2$)$_3$—, —S— (CH$_2$)$_4$—, —S— (CH$_2$)$_5$—, —S— (CH$_2$)$_6$—, —S— (CH$_2$)$_7$—, —S— (CH$_2$)$_8$—, —S— (CH$_2$)$_9$—, —S—(CH$_2$)$_{10}$—, —CH$_2$—S—CH$_2$—, —CH$_2$—S— (CH$_2$)$_2$—, —CH$_2$—S— (CH$_2$)$_3$—S—CH$_2$—S— (CH$_2$)$_4$—, —(CH$_2$)$_2$—S—CH$_2$—, —(CH$_2$)$_2$—S— (CH$_2$)$_2$—, —(CH$_2$)$_2$—S— (CH$_2$)$_3$—, —(CH$_2$)$_2$—S— (CH$_2$)$_4$—, —(CH$_2$)$_3$—S—CH$_2$—, —(CH$_2$)$_3$—S— (CH$_2$)$_2$—, —(CH$_2$)$_3$—S—(CH$_2$)$_3$—, —(CH$_2$)$_4$—S—CH$_2$—, —(CH$_2$)$_4$—S— (CH$_2$)$_2$—, (CH$_2$)$_5$—S—CH$_2$—, —CH$_2$—S—, —(CH$_2$)$_2$—S—, —(CH$_2$)$_3$—S—, —(CH$_2$)$_4$—S—, —(CH$_2$)$_5$—S—, —(CH$_2$)$_6$—S—, —(CH$_2$)$_7$—S—, —(CH$_2$)$_8$—S—, —(CH$_2$)$_9$—S—, or —(CH$_2$)$_{10}$—S— group, and is preferably a $C_1$-$C_6$ alkylene group which contains an oxygen atom in the carbon chain or at the end of the carbon chain, more preferably a —O—CH$_2$—, —O—(CH$_2$)$_2$—, —O— (CH$_2$)$_3$—, —CH$_2$—O—, —(CH$_2$)$_2$—O—, or —(CH$_2$)$_3$—O— group, and most preferably a —CH$_2$—O— or —(CH$_2$)$_2$—O— group.

The $C_3$-$C_{10}$ cycloalkyl moiety of the "$C_3$-$C_{10}$ cycloalkyl group", the "$C_3$-$C_{10}$ cycloalkyl group substituted with from 1 to 3 substituents selected from Substituent group (a)", or the "$C_3$-$C_{10}$ cycloalkyl group substituted with from 1 to 3 substituents selected from the group consisting of Substituent group (a) and Substituent group (b)" in the definition of $R^5$ or Substituent group (b), may optionally be fused with other cyclic groups, and can be, for example, a group such as a cyclopropyl, cyclobutyl, cyclopentyl, cyclohexyl, cycloheptyl, norbornyl, adamantyl, or indanyl group, and is preferably a $C_5$-$C_6$ cycloalkyl group, and most preferably a cyclohexyl group.

The 5- to 7-membered heterocyclic moiety containing from 1 to 3 heteroatoms selected from the group consisting of a sulfur atom, an oxygen atom, and a nitrogen atom in the "5- to 7-membered heterocyclic group containing from 1 to 3 heteroatoms selected from the group consisting of a sulfur atom, an oxygen atom, and a nitrogen atom", the "5- to 7-membered heterocyclic group containing from 1 to 3 heteroatoms selected from the group consisting of a sulfur atom, an oxygen atom, and a nitrogen atom in which said heterocyclic group is substituted with from 1 to 3 substituents selected from Substituent group (a)", or the "5- to 7-membered heterocyclic group containing from 1 to 3 heteroatoms selected from the group consisting of a sulfur atom, an oxygen atom, and a nitrogen atom in which said heterocyclic group is substituted with from 1 to 3 substituents selected from the group consisting of Substituent group (a) and Substituent group (b) in the definition of $R^5$ or substituent group (b)" can be, for example, a 5- to 7-membered aromatic heterocyclic or partially or fully hydrogenated saturated heterocyclic group containing from 1 to 3 heteroatoms selected from the group consisting of a sulfur atom, an oxygen atom, and a nitrogen atom.

The heterocyclic group can be a furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl, pyrazinyl, tetrahydropyranyl, morpholinyl, thiomorpholinyl, pyrrolidinyl, pyrrolinyl, imidazolidinyl, pyrazolidinyl, piperidinyl, piperadinyl, oxazolidinyl, isoxazolidinyl, thiazolidinyl, or pyrazolidinyl group, and is preferably a 5- or 6-membered aromatic heterocyclic group, more preferably a furyl, thienyl, or pyrrolyl group, still more preferably a furyl or thienyl group, and most preferably a thienyl group.

The "aromatic heterocyclic group" described above may optionally be fused with other cyclic groups, and can be, for example, a benzothienyl, isobenzofuranyl, chromenyl, xanthenyl, phenoxathiinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, carbazolyl, carbolinyl, acridinyl, or isoindolinyl group, and is preferably a benzothienyl group.

The "halogen atom" in the definition of Substituent group (a) can be a fluorine, chlorine, bromine or iodine atom, of which a fluorine or chlorine atom is preferred.

The "lower alkyl group" in the definition of $R^1$, $R^2$, $R^3$, $R^4$, or Substituent group (a) can be, for example, a straight or branched chain alkyl group having from 1 to 6 carbon atoms. Said lower alkyl group can be, for example, a methyl, ethyl, propyl, isopropyl, butyl, isobutyl, s-butyl, tert-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 1-ethylbutyl or 2-ethylbutyl group, and is preferably a $C_1$-$C_4$ alkyl group, more preferably a $C_1$-$C_2$ alkyl group, and most preferably a methyl group.

The "halogeno lower alkyl group" in the definition of Substituent group (a) is a group wherein said "lower alkyl group"

is substituted with a halogen atom. Said halogeno lower alkyl group can be, for example, a halogeno $C_1$-$C_6$ alkyl group such as a trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, 4-fluorobutyl, 6-iodohexyl, or 2,2-dibromoethyl group, and is preferably a halogeno $C_1$-$C_4$ alkyl group, more preferably a trifluoromethyl, trichloromethyl, 2,2,2-trifluoroethyl, or 2,2,2-trichloroethyl group, and most preferably a trifluoromethyl group.

The "lower alkoxy group" in the definition of Substituent group (a) is a group wherein said "lower alkyl group" is bonded to an oxygen atom. Said lower alkoxy group can be, for example, a straight or branched chain alkoxy group having from 1 to 6 carbon atoms such as a methoxy, ethoxy, propoxy, isopropoxy, butoxy, isobutoxy, s-butoxy, tert-butoxy, pentoxy, isopentoxy, 2-methylbutoxy, 1-ethylpropoxy, 2-ethylpropoxy, neopentoxy, hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy, or 2,3-dimethylbutoxy group, and is preferably a $C_1$-$C_4$ alkoxy group, more preferably a $C_1$-$C_2$ alkoxy group, and most preferably a methoxy group.

The "lower alkylthio group" in the definition of Substituent group (a) is a group wherein said "lower alkyl group" is bonded to a sulfur atom. Said lower alkylthio group can be, for example, a straight or branched chain alkylthio group having from 1 to 6 carbon atoms such as a methylthio, ethylthio, propylthio, isopropylthio, butylthio, isobutylthio, s-butylthio, tert-butylthio, pentylthio, isopentylthio, 2-methylbutylthio, neopentylthio, hexylthio, 4-methylpentylthio, 3-methylpentylthio, 2-methylpentylthio, 3,3-dimethylbutylthio, 2,2-dimethylbutylthio, 1,1-dimethylbutylthio, 1,2-dimethylbutylthio, 1,3-dimethylbutylthio, or 2,3-dimethylbutylthio group, and is preferably a $C_1$-$C_4$ alkylthio group, more preferably a $C_1$-$C_2$ alkylthio group, and most preferably a methylthio group.

The "lower alkoxycarbonyl group" in the definition of Substituent group (a) is a group wherein said "lower alkoxy group" is bonded to a carbonyl group. Said lower alkoxycarbonyl group can be, for example, a straight or branched chain alkoxycarbonyl group having from 1 to 6 carbon atoms such as a methoxycarbonyl, ethoxycarbonyl, propoxycarbonyl, isopropoxycarbonyl, butoxycarbonyl, isobutoxycarbonyl, s-butoxycarbonyl, tert-butoxycarbonyl, pentoxycarbonyl, isopentoxycarbonyl, 2-methylbutoxycarbonyl, neopentoxycarbonyl, hexyloxycarbonyl, 4-methylpentoxycarbonyl, 3-methylpentoxycarbonyl, 2-methylpentoxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl, or 2,3-dimethylbutoxycarbonyl group, and is preferably a $C_1$-$C_4$ alkoxycarbonyl group, more preferably a $C_1$-$C_2$ alkoxycarbonyl group, and most preferably a methoxycarbonyl group.

The "lower aliphatic acyl group" in the definition of Substituent group (a) is a group wherein a hydrogen atom or a saturated or unsaturated aliphatic hydrocarbon group is bonded to a carbonyl group. Said lower aliphatic hydrocarbon group can be, for example, a straight or branched chain lower aliphatic acyl group having from 1 to 8 carbon atoms such as a formyl, acetyl, propionyl, butyryl, isobutyryl, valeryl, isovaleryl, pivaloyl, hexanoyl, acryloyl, methacryloyl, or crotonoyl group, and is preferably a $C_1$-$C_4$ lower aliphatic acyl group, more preferably an acetyl or propionyl group, and most preferably an acetyl group.

The "mono lower alkylamino group" in the definition of Substituent group (a) is a group wherein said "lower alkyl group" is bonded to one amino group. Said mono lower alkylamino group can be, for example, a mono-$C_1$-$C_4$ alkylamino group such as a methylamino, ethylamino, propylamino, isopropylamino, butylamino, isobutylamino, s-butylamino, tert-butylamino, pentylamino, isopentylamino, 2-methylbutylamino, neopentylamino, 1-ethylpropylamino, hexylamino, isohexylamino, 4-methylpentylamino, 3-methylpentylamino, 2-methylpentylamino, 1-methylpentylamino, 3,3-dimethylbutylamino, 2,2-dimethylbutylamino, 1,1-dimethylbutylamino, 1,2-dimethylbutylamino, 1,3-dimethylbutylamino, 2,3-dimethylbutylamino, or 2-ethylbutylamino group, and is preferably a mono-$C_1$-$C_4$ alkylamino group, more preferably a mono-$C_1$-$C_2$ alkylamino group, and most preferably a methylamino group.

The "di-lower alkylamino group" in the definition of Substituent group (a) is a group-wherein two said "lower alkyl groups" are bonded to an amino group. Said di-lower alkylamino group can be, for example, a di-$C_1$-$C_6$ alkylamino group such as a dimethylamino, diethylamino, N-ethyl-N-methylamino, dipropylamino, dibutylamino, dipentylamino, or dihexylamino group, and is preferably a di-$C_1$-$C_4$ alkylamino group, more preferably a di-$C_1$-$C_2$ alkylamino group, and most preferably a dimethylamino group.

The "lower aliphatic acylamino group" in the definition of Substituent group (a) is a group wherein said "lower aliphatic acyl group" is bonded to an amino group. Said lower aliphatic acylamino group can be, for example, a straight or branched chain lower aliphatic acylamino group having from 1 to 7 carbon atoms such as a formylamino, acetylamino, propionylamino, butyrylamino, isobutyrylamino, valerylamino, isovalerylamino, pivaloylamino, hexanoylamino, acryloylamino, methacryloylamino, or crotonoylamino group, and is preferably a $C_1$-$C_4$ lower aliphatic acylamino group, more preferably an acetylamino or propionylamino group, and most preferably an acetylamino group.

The "lower alkylsulfonyl group" in the definition of D is a group wherein said "lower alkyl group" is bonded to a sulfonyl group. Said lower alkylsulfonyl group can be, for example, a straight or branched chain alkylsulfonyl group having from 1 to 6 carbon atoms such as a methanesulfonyl, ethanesulfonyl, propanesulfonyl, isopropanesulfonyl, butanesulfonyl, isobutanesulfonyl, s-butanesulfonyl, tert-butanesulfonyl, pentanesulfonyl, isopentanesulfonyl, 2-methylbutanesulfonyl, neopentanesulfonyl, hexanesulfonyl, 4-methylpentanesulfonyl, 3-methylpentanesulfonyl, 2-methylpentanesulfonyl, 3,3-dimethylbutanesulfonyl, 2,2-dimethylbutanesulfonyl, 1,1-dimethylbutanesulfonyl, 1,2-dimethylbutanesulfonyl, 1,3-dimethylbutanesulfonyl, or 2,3-dimethylbutanesulfonyl group, and is preferably a $C_1$-$C_4$ alkylsulfonyl group, more preferably a $C_1$-$C_2$ alkylsulfonyl group, and most preferably a methanesulfonyl group.

The "arylsulfonyl group" in the definition of D is a group wherein said "aryl group" is bonded to a sulfonyl group. Said arylsulfonyl group can be, for example, an arylsulfonyl group having from 6 to 10 carbon atoms such as a benzenesulfonyl, p-toluenesulfonyl, o-xylene-4-sulfonyl, m-xylene-4-sulfonyl, p-xylenesulfonyl, or naphthalenesulfonyl group, and is preferably a benzenesulfonyl group.

The "protecting group of the amino group" in the definitions of $R^1$ and $R^2$ is a protecting group for an amino group which is generally used in the field of synthetic organic chemistry, and can be:

an "aliphatic acyl group", for example, a "lower aliphatic acyl group" described above, a halogeno lower aliphatic acyl group such as a chloroacetyl, dichloroacetyl, trichloroacetyl, or trifluoroacetyl group, or a lower aliphatic acyl group substituted with a lower alkoxy such as a methoxyacetyl group;

an "aromatic acyl group", for example, an aromatic acyl group such as a benzoyl, 1-indanecarbonyl, 2-indanecarbonyl, or 1- or 2-naphthoyl group, or n aromatic acyl group substituted with from 1 to 3 substituents selected from Substituent group (a) described above such as a 4-chlorobenzoyl, 4-fluorobenzoyl, 2,4,6-trimethylbenzoyl, 4-toluoyl, 4-anisoyl, 4-nitrobenzoyl, 2-nitrobenzoyl, 2-(methoxycarbonyl)benzoyl, or 4-phenylbenzoyl group;

an "alkoxycarbonyl group", for example, a "lower alkoxycarbonyl group" described above, or a lower alkoxycarbonyl group substituted with one or more halogen atoms or one or more tri-lower alkylsilyl groups such as a 2,2,2-trichloroethoxycarbonyl or 2-trimethylsilylethoxycarbonyl group;

an "alkenyloxycarbonyl group" such as a vinyloxycarbonyl or allyloxycarbonyl group;

an "aralkyloxycarbonyl group", for example, an aralkyloxycarbonyl group such as a benzyloxycarbonyl group, or an aralkyloxycarbonyl group substituted with 1 to 3 substituents selected from Substituent group (a) described above such as a 4-methoxybenzyloxycarbonyl, 3,4-dimethoxybenzyloxycarbonyl, 2-nitrobenzyloxycarbonyl, or 4-nitrobenzyloxycarbonyl group;

a "silyl group", for example, a tri-lower alkylsilyl group such as a trimethylsilyl, triethylsilyl, isopropyldimethylsilyl, tert-butyldimethylsilyl, methyldiisopropylsilyl, methyldi(tert-butyl)silyl, or triisopropylsilyl group, or a silyl group substituted with 3 substituents selected from aryl groups or aryl groups and lower alkyl groups such as a diphenylmethylsilyl, diphenylbutylsilyl, diphenylisopropylsilyl, or phenyldiisopropylsilyl group;

an "aralkyl group", for example, a lower alkyl group substituted with from 1 to 3 aryl groups such as a benzyl, phenethyl, 3-phenylpropyl, α-naphthylmethyl, β-naphthylmethyl, diphenylmethyl, triphenylmethyl, α-naphthyldiphenylmethyl, or 9-anthrylmethyl group, or a lower alkyl group substituted with from 1 to 3 aryl groups, wherein said aryl group is substituted with a lower alkyl group, a lower alkoxy group, a nitro group, a halogen atom, or a cyano group, such as a 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, 4-cyanobenzyldiphenylmethyl, bis(2-nitrophenyl)methyl, or piperonyl group; or a "substituted methylene group forming a Schiff base" such as a N,N-dimethylaminomethylene, benzylidene, 4-methoxybenzylidene, 4-nitrobenzylidene, salicylidene, 5-chlorosalicylidene, diphenylmethylene, or (5-chloro-2-hydroxyphenyl)phenylmethylene group.

The "protecting group of the amino group" is preferably a lower aliphatic acyl group, a lower alkoxycarbonyl group, an aralkyloxycarbonyl group, or an aralkyloxycarbonyl group substituted with from 1 to 3 substituents selected from Substituent group (a), particularly preferably an acetyl or tert-butoxycarbonyl group.

The "protecting group of the hydroxyl group" in the definition of $R^3$ represents a "general protecting group in chemical reactions" which can be cleaved by a chemical process such as hydrogenolysis, hydrolysis, electrolysis, and photolysis, or a "protecting group which can be cleaved by a biological process such as hydrolysis in vivo".

The "general protecting group in chemical reactions" can be, for example, an "aliphatic acyl group" described above;

an "aromatic acyl group" described above;

a "tetrahydropyranyl or tetrahydrothiopyranyl group" such as a tetrahydropyran-2-yl, 3-bromotetrahydropyran-2-yl, 4-methoxytetrahydropyran-4-yl, tetrahydrothiopyran-2-yl, or 4-methoxytetrahydrothiopyran-4-yl-group;

a "tetrahydrofuranyl or tetrahydrothiofuranyl group" such as a tetrahydrofuran-2-yl or tetrahydrothiofuran-2-yl group;

a "silyl group" described above;

an "alkoxymethyl group", for example, a lower alkoxymethyl group such as a methoxymethyl, 1,1-dimethyl-1-methoxymethyl, ethoxymethyl, propoxymethyl, isopropoxymethyl, butoxymethyl, or tert-butoxymethyl group, a lower alkoxylated lower alkoxymethyl group such as a 2-methoxyethoxymethyl group, or a halogeno lower alkoxymethyl group such as a 2,2,2-trichloroethoxymethyl or bis(2-chloroethoxy)methyl group;

a "substituted ethyl group", for example, a lower alkoxylated ethyl group such as a 1-ethoxyethyl or 1-(isopropoxy)ethyl group, or a halogenated ethyl group such as a 2,2,2-trichloroethyl group;

an "aralkyl group" described above;

an "alkoxycarbonyl group" described above;

an "alkenyloxycarbonyl group" described above; or an "aralkyloxycarbonyl group" described above.

On the other hand, the "protecting group which can be cleaved by a biological process such as hydrolysis in vivo" can be, for example, a "carbonyloxyalkyl group", for example, an acyloxyalkyl group such as an ethylcarbonyloxymethyl, pivaloyloxymethyl, dimethylaminoacetoxymethyl, or 1-acetoxyethyl group;

a 1-(alkoxycarbonyloxy)alkyl group such a 1-(methoxycarbonyloxy)ethyl, 1-(ethoxycarbonyloxy)ethyl, ethoxycarbonyloxymethyl, 1-(isopropoxycarbonyloxy)ethyl, 1-(tert-butoxycarbonyloxy)ethyl, 1-(ethoxycarbonyloxy)propyl, or 1-(cyclohexyloxycarbonyloxy)ethyl group;

a phthalidyl group; or an oxodioxolenylmethyl group such as a 4-methyl-oxodioxolenylmethyl, 4-phenyl-oxodioxolenylmethyl, or oxodioxolenylmethyl group;

an "aliphatic acyl group" described above;

an "aromatic acyl group" described above;

a "residual group of a succinic acid half-ester";

a "residual group of a phosphoric acid ester";

a "residual group forming an amino acid ester or the like";

a carbamoyl group;

a "protecting group of two hydroxyl groups", for example, an aralkylidene group such as a benzylidene group, an alkoxyethylidene group such as amethoxyethylidene or ethoxyethylidene group, an oxomethylene group, or a thioxomethylene group; or a "carbonyloxyalkyloxycarbonyl group" such as a pivaloyloxymethyloxycarbonyl group.

The suitability of such a derivative can be determined by administering it to an experimental animal such as a rat or a mouse by an intravenous injection, measuring a body fluid of the animal thereafter and detecting the original compound or a pharmacologically acceptable salt thereof.

The "protecting group of the hydroxyl group" is preferably a lower aliphatic acyl group, an aromatic acyl group, an aromatic acyl group substituted with from 1 to 3 substituents selected from Substituent group (a), or a silyl group, particularly preferably an acetyl group or a tert-butyldimethylsilyl group.

The "protecting group of phosphoric acid" in the definition of $R^{10}$ or $R^{11}$ can be, for example, a lower alkyl group such as a methyl, ethyl, isopropyl, or butyl group, a lower alkyl group substituted with one or more cyano groups such as a 2-cyanoethyl or 2-cyano-1,1-dimethylethyl group, a lower alkyl group substituted with one or more silyl groups wherein said silyl group is substituted with 3 substituents selected from the group consisting of lower alkyl groups or aryl groups and lower alkyl groups such as a 2-(methyldiphenylsilyl)ethyl or 2-trimethylsilylethyl group, a lower alkyl group substituted with one or more heterocyclyl groups such as a 2-(2'-pyridyl)ethyl or 2-(4'-pyridyl)ethyl group, a lower alkyl group substituted with one or more arylthio groups such as a 2-phenylthioethyl, 2-(4'-nitrophenylthio)ethyl, or 2-(4'-triphenylmethylphenylthio)ethyl group, a lower alkyl group substituted with one or more alkylsulfonyl groups, arylsulfonyl groups, or arylalkylsulfonyl groups such as a 2-(tert-butylsulfonyl)ethyl, 2-(phenylsulfonyl)ethyl, or 2-(benzylsulfonyl)ethyl group, or a halogeno lower alkyl group such as a 2,2,2-trichloroethyl, 2,2,2-trichloroethyl-1,1-dimethylethyl, 2,2,2-tribromoethyl, 2,3-dibromopropyl, or 2,2,2-trifluoroethyl group;

an aralkyl group, for example, a lower alkyl group substituted with from 1 to 3 aryl groups, such as a benzyl, phenethyl, 3-phenylpropyl, α-naphthylmethyl, β-naphthylmethyl, diphenylmethyl, triphenylmethyl, α-naphthyldiphenylmethyl, or 9-anthrylmethyl group, a lower alkyl group substituted with one or more aryl groups wherein said aryl moiety is substituted with one or more nitro groups, halogen atoms, or lower aliphatic acyl groups, such as an o-nitrobenzyl, 4-nitrobenzyl, 2,4-dinitrobenzyl, 4-chlorobenzyl, 4-chloro-2-nitrobenzyl, or 4-acyloxybenzyl group, a lower alkyl group substituted with one or more aryl groups having one or more substituents such as a 2-nitrophenylethyl group, or a lower alkyl group substituted with one or more fluorenyl groups such as a 9-fluorenylmethyl group;

a lower alkenyl group such as an allyl or propenyl group;

a lower alkenyl group substituted with one or more cyano groups such as a 4-cyano-2-butenyl group;

an aryl group such as a phenyl group;

an aryl group substituted with one or more substituents selected from the group consisting of a lower alkyl group, a lower alkyl group substituted with 3 aryl groups, a lower alkoxy group, a nitro group, and a halogen atom, such as a 2-methylphenyl, 2,6-dimethylphenyl, 2-chlorophenyl, 4-chlorophenyl, 2,4-dichlorophenyl, 2,5-dichlorophenyl, 2,6-dichlorophenyl, 2-bromophenyl, 4-nitrophenyl, 3,5-dinitrophenyl, 4-chloro-2-nitrophenyl, or 2-methoxy-5-nitrophenyl group; or an amide such as an anilidate, 4-triphenylmethylanilidate, [N-(2-trityloxy)ethyl]anilidate, p-(N,N-dimethylamino)anilidate, or 3-(N,N-diethylaminomethyl)anilidate.

The "protecting group of phosphoric acid" is preferably a lower alkyl group, a lower alkenyl group, or a methyl group substituted with from 1 to 3 substituents selected from the group consisting of a phenyl group and a naphthyl group, more preferably a methyl group, an ethyl group, an allyl group, or a benzyl group, and most preferably a methyl group or an ethyl group.

The "$C_3$-$C_{10}$ cycloalkyl group substituted with from 1 to 3 substituents selected from the group consisting of Substituent group (a) and Substituent group (b)" in the definition of $R^5$ can be, for example, a 2-fluorocyclopropyl, 2-chlorocyclopropyl, 2- or 3-fluorocyclopentyl, 2- or 3-chlorocyclopentyl, 2-,3- or 4-fluorocyclohexyl, 2-,3- or 4-chlorocyclohexyl, 2-,3- or 4-bromocyclohexyl, 2-,3- or 4-iodocyclohexyl, 2-methylcyclopropyl, 2-ethylcyclopropyl, 2- or 3-methylcyclopentyl, 2- or 3-ethylcyclopentyl, 2-,3- or 4-methylcyclohexyl, 2-,3- or 4-ethylcyclohexyl, 2-trifluoromethylcyclopropyl, 2- or 3-trifluoromethylcyclobutyl, 2- or 3-trifluoromethylcyclopentyl, 2-,3- or 4-trifluoromethylcyclohexyl, 2-methoxycyclopropyl, 2- or 3-methoxycyclobutyl, 2- or 3-methoxycyclopentyl, 2-, 3- or 4-methoxycyclohexyl, 2-, 3- or 4-ethoxycyclohexyl, 2-, 3- or 4-propoxycyclohexyl, 2-,3- or 4-isopropoxycyclohexyl, 2-, 3- or 4-(1-ethylpropoxy)cyclohexyl, 2-, 3- or 4-(2-ethylpropoxy)cyclohexyl, 2-carboxycyclopropyl, 2- or 3-carboxycyclopentyl, 2-,3- or 4-carboxycyclohexyl, 2-methoxycarbonylcyclopropyl, 2- or 3-methoxycarbonylcyclopentyl, 2-,3- or 4-methoxycarbonylcyclohexyl, 2-hydroxycyclopropyl, 2- or 3-hydroxycyclopentyl, 2-,3- or 4-hydroxycyclohexyl, 2-formylcyclopropyl, 2- or 3-formylcyclopentyl, 2-,3- or 4-formylcyclohexyl, 2-acetylcyclopropyl, 2- or 3-acetylcyclopentyl, 2-,3- or 4-acetylcyclohexyl, 2-aminocyclopropyl, 2- or 3-aminocyclopentyl, 2-,3- or 4-aminocyclohexyl, 2-methylaminocyclopropyl, 2- or 3-methylaminocyclobutyl, 2- or 3-methylaminocyclopentyl, 2-,3- or 4-methylaminocyclohexyl, 2-dimethylaminocyclopropyl, 2- or 3-dimethylaminocyclobutyl, 2- or 3-dimethylaminocyclopentyl, 2-,3- or 4-dimethylaminocyclohexyl, 2-cyanocyclopropyl, 2- or 3-cyanocyclopentyl, 2-,3- or 4-cyanocyclohexyl, 2- or 3-cyclohexylcyclopentyl, 2-,3- or 4-cyclohexylcyclohexyl, 2-phenylcyclopropyl, 2- or 3-phenylcyclopentyl, 2-, 3- or 4-phenylcyclohexyl, 3,4-difluorocyclohexyl, 3,4-dichlorocyclohexyl, 2,3-dimethoxycyclohexyl, 3,4-dimethoxycyclohexyl, 3,5-dimethoxycyclohexyl, or 3,4,5-trimethoxycyclohexyl group, and is preferably a $C_3$-$C_{10}$ cycloalkyl group substituted with from 1 to 3 substituents (said substituent(s) being selected from the group consisting of halogen atoms, lower alkyl groups, halogeno lower alkyl groups, lower alkoxy groups, lower alkylthio groups, and lower aliphatic acyl groups), more preferably a $C_3$-$C_{10}$ cycloalkyl group substituted with from 1 to 3 substituents (said substituent(s) being selected from the group consisting of halogen atoms, lower alkyl groups, halogeno lower alkyl groups, lower alkoxy groups, and lower aliphatic acyl groups), still more preferably a $C_3$-$C_{10}$ cycloalkyl group substituted with from 1 to 3 substituents (said substituent(s) being selected from the group consisting of halogen atoms, lower alkyl groups, halogeno lower alkyl groups, lower alkoxy groups, and lower aliphatic acyl groups), and most-preferably a cyclohexyl group substituted with one substituent (said substituent is selected from the group consisting of a fluorine atom, a chlorine atom, methyl, trifluoromethyl, methoxy and acetyl groups).

The "$C_6$-$C_{10}$ aryl group substituted with from 1 to 3 substituents selected from the group consisting of Substituent group (a) and Substituent group (b)" in the definition of $R^5$ can be, for example, a 2-,3- or 4-fluorophenyl, 2-,3- or 4-chlorophenyl, 2-,3- or 4-bromophenyl, 2-,3- or 4-iodophenyl, 2-,3- or 4-methylphenyl, 2-,3- or 4-ethylphenyl, 2-,3- or 4-propylphenyl, 2-,3- or 4-butylphenyl, 2-,3- or 4-pentylphenyl, 2-,3- or 4-trifluoromethylphenyl, 2-, 3- or 4-methoxyphenyl, 2-, 3- or 4-ethoxyphenyl, 2-, 3- or 4-propoxyphenyl, 2-, 3- or 4-isopropoxyphenyl, 2-, 3- or 4-butoxyphenyl, 2-, 3- or 4-(1-ethylpropoxy)phenyl, 2-, 3- or 4-(2-ethylpropoxy) phenyl, 2-,3- or 4-methylthiophenyl, 2-,3- or 4-ethylthiophenyl, 2-,3- or 4-carboxyphenyl, 2-,3- or 4-methoxycarbonylphenyl, 2-,3- or 4-ethoxycarbonylphenyl, 2-,3- or 4-hydroxyphenyl, 2-,3- or 4-formylphenyl, 2-,3- or 4-acetylphenyl, 2-,3- or 4-aminophenyl, 2-,3- or 4-methylaminophenyl, 2-,3- or 4-dimethylaminophenyl, 2-,3- or 4-cyanophenyl, 2-,3- or 4-cyclopentylphenyl, 2-,3- or 4-cyclohexylphenyl, 2-,3- or 4-biphenyl, 2,4-difluorophenyl, 3,4-difluorophenyl, 3,5-difluorophenyl, 2,4-dichlorophenyl, 3,4-dichlorophenyl, 3,5-dichlorophenyl, 3,4-dibromophenyl, 2,3-dimethylphenyl, 3,4-dimethylphenyl, 3,5-dimethylphenyl, 2,3-dimethoxyphenyl, 3,4-dimethoxyphenyl, 3,5-dimethoxyphenyl, 3,4,5-trimethoxyphenyl, 3-fluoro-4-methoxyphenyl, 4-methyl-2-methoxyphenyl, 6-fluoro-4-methyl-2-methoxyphenyl, 5-fluoroinden-3-yl, 5-methylinden-3-yl, 5-methoxyinden-3-yl, 5-fluoroinden-2-yl, 5-chloroinden-2-yl, 5-methylinden-2-yl, 5-methoxyinden-2-yl, 5-hydroxyinden-3-yl, 5-nitroinden-3-yl, 5-cyclohexylinden-3-yl, 5-phenylinden-3-yl, 5-phenoxyinden-3-yl, 5-benzyloxyinden-3-yl, 5-phenylthioinden-3-yl, 5-hydroxyinden-2-yl, 5-nitroinden-2-yl, 5-cyclohexylinden-2-yl, 5-phenylinden-2-yl, 5-fluoronaphthalen-2-yl, 5-methylnaphthalen-2-yl, 5-methoxynaphthalen-2-yl, 5-fluoronaphthalen-1-yl, 5-methylnaphthalen-1-yl, 5-methoxynaphthalen-1-yl, 5-hydroxynaphthalen-2-yl, 5-nitronaphthalen-2-yl, 5-cyclohexylnaphthalen-2-yl, 5-phenylnaphthalen-2-yl, 5-phenoxynaphthalen-2-yl, 5-benzyloxynaphthalen-2-yl, 5-phenylthionaphthalen-2-yl, 5-hydroxynaphthalen-1-yl, 5-nitronaphthalen-1-yl, 5-cyclohexylnaphthalen-1-yl, or 5-phenylnaphthalen-1-yl group, and is preferably a $C_6$-$C_{10}$ aryl group substituted with from 1 to 3 substituents (said substituent(s) being selected from the group consisting of halogen atoms, lower alkyl groups, halogeno lower alkyl groups, lower alkoxy groups, a lower alkylthio groups, and lower aliphatic acyl groups), more preferably a $C_6$-$C_{10}$ aryl group substituted with from 1 to 3 substituents (said substituent(s) being selected from the group consisting of halogen atoms, lower alkyl groups, halogeno lower alkyl groups, lower alkoxy groups, and lower aliphatic acyl groups), still more preferably a phenyl group substituted with from 1 to 3 substituents (said substituent(s) being selected from the group consisting of halogen atoms, lower alkyl groups, halogeno lower alkyl groups, lower alkoxy groups, and lower aliphatic acyl groups), particularly preferably a phenyl group substituted with 1 or 2 substituents (said substituent(s) being selected from the group consisting of fluorine atoms, chlorine atoms, methyl, trifluoromethyl, methoxy and acetyl groups; but, in the case of methoxy group, a phenyl group substituted with from 1 to 3 methoxy groups is preferred), and most preferably a 3-fluorophenyl, 4-fluorophenyl, 3,4-difluorophenyl, 3,5-difluorophenyl, 3-chlorophenyl, 4-chlorophenyl, 3,4-dichlorophenyl, 3,5-dichlorophenyl, 3-methylphenyl, 4-methylphenyl, 3,4-dimethylphenyl, 3,5-dimethylphenyl, 3-trifluoromethylphenyl, 4-trifluoromethylphenyl, 3,4-ditrifluoromethylphenyl, 3,5-ditrifluoromethylphenyl, 3-methoxyphenyl, 4-methoxyphenyl, 3,4-dimethoxyphenyl, 3,5-dimethoxyphenyl, 3,4,5-trimethoxyphenyl, 3-acetylphenyl, or 4-acetylphenyl group.

The "5- to 7-membered heterocyclic group containing from 1 to 3 heteroatoms selected from the group consisting of a sulfur atom, an oxygen atom, and a nitrogen atom in which said heterocyclic group is substituted with from 1 to 3 substituents selected from the group consisting of Substituent group (a) and Substituent group (b)" in the definition of $R^5$ can be, for example, a 3-,4- or 5-methylfuran-2-yl, 2-,4- or 5-methylfuran-3-yl, 3-,4- or 5-fluorothiophen-2-yl, 2-,4- or 5-fluorofuran-3-yl, 3-,4- or 5-bromothiophen-2-yl, 2-,4- or 5-bromofuran-3-yl, 3-,4- or 5-methylthiophen-2-yl, 2-,4- or 5-methylthiophen-3-yl, 3-,4- or 5-ethylthiophen-2-yl, 2-,4- or 5-ethylthiophen-3-yl, 3-,4- or 5-methoxythiophen-2-yl, 2-,4- or 5-methoxythiophen-3-yl, 3- or 4-methylthiazol-5-yl, 3-,4- or 5-fluorobenzothiophen-2-yl, 3-,4- or 5-bromobenzothiophen-2-yl, 3-,4- or 5-methylbenzothiophen-2-yl, 3-,4- or 5-methoxybenzothiophen-2-yl, 2-,4- or 5-fluorobenzothiophen-3-yl, 2-,4- or 5-bromobenzothiophen-3-yl, 2-,4- or 5-methylbenzothiophen-3-yl, 2-,4- or 5-methoxybenzothiophen-3-yl, 4-,5-,6- or 7-methylbenzothiophen-2-yl, 3-,4- or 5-hydroxyfuran-2-yl, 2-,4- or 5-hydroxyfuran-3-yl, 3-,4- or 5-hydroxythiophen-2-yl, 3-,4- or 5-nitrothiophen-2-yl, 3-,4- or 5-phenylthiophen-2-yl, 2-,4- or 5-hydroxythiophen-3-yl, 2-,4- or 5-cyanothiophen-3-yl, 1-,2- or 3-hydroxypyridin-4-yl, 1-,2- or 3-cyanopyridin-4-yl, or 1-,2- or 3-phenylpyridin-4-yl group, and is preferably a 3-,4- or 5-fluorothiophen-2-yl or 2-,4- or 5-fluorofuran-3-yl group.

The "pharmacologically acceptable salt thereof." means a salt which, when the compounds of general formula (I), (II), or (III) of the present invention have a basic group such as an amino group, can be prepared by reacting the compounds with an acid, and when the compounds of general formula (I), (II), or (III) of the present invention have an acidic group such as a carboxyl group or a phosphate group, can be prepared by reacting the compounds with a base. Such salts are included in the present invention.

The salt, when the compounds of general formula (I), (II), or (III) have a basic group, can be an inorganic acid salt, for example, a hydrohalide such as hydrofluoride, hydrochloride, hydrobromide, or hydroiodide, a nitrate, a perchlorate, a sulfate, a phosphate or the like; an organic acid salt, for example, a lower alkanesulfonate such as methanesulfonate, trifluoromethanesulfonate, or ethanesulfonate, an arylsulfonate such as benzenesulfonate or p-toluenesulfonate, an acetate, a malate, a fumarate, a succinate, a citrate, an ascorbate, a tartrate, an oxalate, a maleate, or the like; or an amino acid salt such as glycine salt, lysine salt, arginine salt, ornithine salt, glutamic acid salt, or aspartic acid salt. The salt is preferably an organic acid salt (particularly fumarate, oxalate or maleate) or a hydrohalide (particularly hydrochloride).

The salt, when the compounds of general formula (I), (II), or (III) have an acidic group, can be a metal salt, for example, an alkali metal salt such as sodium salt, potassium salt, or lithium salt, an alkaline earth metal salt such as calcium salt or magnesium salt, an aluminum salt, an iron salt, or the like; an amine salt, for example, an inorganic amine salt such as ammonium salt, an organic amine salt such as t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt, tris(hydroxymethyl) aminomethane salt, or the like; or an amino acid salt such as glycine salt, lysine salt, arginine salt, ornithine salt, glutamic acid salt, or aspartic acid salt. The salt preferably is an alkali metal salt (particularly sodium salt).

When the compounds of general formula (I), (II), or (III), pharmacologically acceptable salts thereof, or pharmacologically acceptable esters thereof of the present invention are allowed to stand in contact with the atmosphere or to recrystallize, they may absorb water or water may attach to them to form a hydrate. The present invention encompasses such hydrates.

The compounds of general formula (I), (II), or (III), pharmacologically acceptable salts, or pharmacologically acceptable esters thereof of the present invention have one or more asymmetric carbon atoms in their structures, and can exist as optical isomers due to such asymmetric carbon atoms. In the present invention, a single optical isomer and mixtures of optical isomers are represented as a single chemical formula (I), (II), or (III) individually. The present invention encompasses both individual optical isomers and mixtures thereof in any ratio.

In the compounds as shown in formulas (I), (II) and (III), preferred compounds are compounds in which the asymmetric carbon to which the formula —$NR^1R^2$ attaches, is the R configuration.

The "ester thereof" described above indicates an ester of compounds of general formula (I), (II), or (III) of the present invention which have a group capable of being esterified. The ester can be an "ester of a hydroxyl group" or an "ester of a carboxyl group". Each ester residual group belongs to a "general protecting group in chemical reactions" or a "protecting group which can be cleaved by a biological process such as hydrolysis in vivo".

The "general protecting group in chemical reactions" is a protecting group which can be cleaved by a chemical process such as hydrogenolysis, hydrolysis, electrolysis, and photolysis.

The "general protecting group in chemical reactions" and the "protecting group which can be cleaved by a biological process such as hydrolysis in vivo" related to the "ester of a hydroxyl group" have the same meanings as those described above for the "protecting group of the hydroxyl group".

The "general protecting group in chemical reactions" related to the "ester of a carboxyl group" is preferably a "lower alkyl group" described above; a lower alkenyl group such as ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl, or 5-hexenyl; a lower alkynyl group such as ethynyl, 2-propynyl, 1-methyl-2-propynyl, 2-butynyl, 1-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl, or 5-hexynyl; a "halogeno lower alkyl group" described above; a hydroxy "lower alkyl group" such as 2-hydroxyethyl, 2,3-dihydroxypropyl, 3-hydroxypropyl, 3,4-dihydroxybutyl, or 4-hydroxybutyl; a "lower aliphatic acyl"-"lower alkyl group" such as acetylmethyl; an "aralkyl group" described above; or a "silyl group" described above.

The "protecting group which can be cleaved by a biological process such as hydrolysis in vivo" related to the "ester of a carboxyl group" is preferably an "alkoxyalkyl group" such as a lower alkoxy lower alkyl group, e.g., methoxyethyl, 1-ethoxyethyl, 1-methyl-1-methoxyethyl, 1-(isopropoxy) ethyl, 2-methoxyethyl, 2-ethoxyethyl, ethoxymethyl, n-propoxymethyl, isopropoxymethyl, n-butoxymethyl, or t-butoxymethyl, a lower alkoxylated lower alkoxy lower alkyl group, e.g., 2-methoxyethoxymethyl, an "aryl" oxy "lower alkyl group", e.g., phenoxymethyl, or a halogenated lower alkoxy lower alkyl group, e.g., 2,2,2-trichloroethoxymethyl or bis(2-chloroethoxy)methyl; a "lower alkoxy" carbonyl "lower alkyl group" such as methoxycarbonylmethyl; a cyano "lower alkyl group" such as cyanomethyl or 2-cyanoethyl; a "lower alkyl" thiomethyl group such as methylthiomethyl or ethylthiomethyl; an "aryl" thiomethyl group such as phenylthiomethyl or naphthylthiomethyl; a "lower alkyl" sulfonyl "lower alkyl group" which may be substituted with one or more halogen atoms such as 2-methanesulfonylethyl or 2-trifluoromethanesulfonylethyl; an "aryl" sulfonyl "lower alkyl group" such as 2-benzenesulfonylethyl or 2-toluenesulfonylethyl; a 1-(acyloxy) "lower alkyl group" described above; a "phthalidyl group" described above; an "aryl group" described above; a "lower alkyl group" described above; a "carboxyalkyl group" such as carboxymethyl; or an "amide forming residual group of an amino acid" such as phenylalanine.

The more preferred "general protecting group in chemical reactions" and "protecting group which can be cleaved by a biological process such as hydrolysis in vivo" related to the "ester of a carboxyl group" described above is a lower alkyl or aralkyl group.

"Immunosuppressants", which are an active ingredient of pharmaceutical compositions of the present invention, are agents preventing or inhibiting the progression of immune responses as well as compounds with immunosuppressive activity, and are classified into the following groups on the basis of mechanism of action:

(1) agents which have the action of inhibiting intracellular signal transduction involved in cytokine expression of T-cells, include those blocking cytokine production as well as those preventing cytokine signaling from acting on immune cells by inhibiting the intracellular signal transduction. Such agents, which have the action of inhibiting the intracellular signal transduction involved in cytokine expression of T-cells, include, for example, S7481/F-1 or a pharmacologically acceptable salt thereof disclosed in the specification of U.S. Pat. No. 4,117,118 [preferably cyclosporin A, of which the chemical name is cyclo [3-hydroxy-4-methyl-2-(methylamino)-6-octenoyl]-2-aminobutyryl-methylglycyl-methyl-leucyl-valyl-methyl-leucyl-alanyl-alanyl-methyl-leucyl-methyl-leucyl-methyl-valyl.], a compound having the general formula (I) or a pharmacologically acceptable salt thereof disclosed in the specification of E.P. Publication Number 184,162 {preferably tacrolimus, of which the chemical name is 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetrone.}, rapamycin disclosed in the specification of U.S. Pat. No. 3,929,992 [of which the chemical name is 9,10,12,13,14,21,22,23,24,25,26,27,32,33,34,34a-hexadecahydro-9,27-dihydroxy-3-[2-(4-hydroxy-3-methoxycyclohexyl)-1-methylethyl]-10,21-dimethoxy-6,8,12,14,20,26-hexamethyl-23,27-epoxy-3H-pyrido[2,1-c][1,4]oxaazacyclohentriacontine-1,5,11,28,29(4H,6H,31H)-pentone.], a compound having the general formula (II) or a pharmacologically acceptable salt thereof disclosed in the specification of E.P. Publication Number 94,632 (Japanese Patent Publication (Kokai) Number Sho 58-62152) [preferably gusperimus, of which the chemical name is N-[4-(3-aminopropyl)aminobutyl]carbamoylhydroxymethyl-7-guanidinoheptanamide, and in the present invention gusperimus includes a pharmacologically-acceptable salt (trihydrochloride) thereof.], a compound having the general formula (I) or a pharmacologically acceptable salt thereof disclosed in the specification of U.S. Pat. No. 5,912,253 {preferably everolimus, of which the chemical name is 9,10,12,13,14,21,22,23,24,25,26,27,32,33,34,34a-hexadecahydro-9,27-dihydroxy-3-[2-[4-hydroxyethoxy-3-methoxycyclohexyl]-1-methylethyl]-10,21-dimethoxy-6,8,12,14,20,26-hexamethyl-23,27-epoxy-3H-pyrido[2,1-c][1,4]azacyclohentriacontine-1,5,11,28,29(4H,6H,31H)-pentone.}, a compound having the general formula (I) or a pharmacologically acceptable salt thereof disclosed in the specification of E.P. Publication Number 600,762 {preferably tresperimus, of which the chemical name is 2-[4-(3-aminopropylamino)butyl]aminocarbonyloxy-N-[6-(aminoiminomethyl)aminohexyl]acetamide, and in the present invention tresperimus includes a pharmacologically acceptable salt thereof.}, LF15-0195 disclosed in Int. J. Immunopharmacol., vol. 21 (5), 349-358 (1999) {anisperimus, of which the chemical name is [(6-guanidinohexyl)carbamoyl]methyl[4-(3-aminobutyl)aminobutyl]carbamate.}, a compound having the general formula (I) or a pharmacologically acceptable salt thereof disclosed in the specification of E.P. Publication Number 626,385 (Japanese Patent Number 3076724 or U.S. Pat. No. 5,493,019) {preferably SDZ-281-240, of which the chemical name is 17-ethyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetrone, and in the present invention SDZ-281-240 includes a pharmacologically acceptable salt thereof.}, a compound having the general formula (VII) or a pharmacologically acceptable salt thereof disclosed in the specification of WO Publication Number 93/04680 (E.P. Publication Number 642,516) {preferably ABT-281, of which the chemical name is 17-ethyl-1,14-dihydroxy-12-[2-(4-tetrazolyl-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetrone.}, a compound having the general formula (A) or a pharmacologically acceptable salt thereof disclosed in the specification of E.P. Publication Number 414,632 {preferably tigderimus, of which the chemical name is cyclo[[3-hydroxy-4-methyl-2-(methylamino)-6-octenoyl]-L-2-aminobutyryl-N-methylglycyl-N-methyl-L-leucyl-L-valyl-N-methyl-L-leucyl-L-alanyl-[3-O-(2-hydroxyethyl)-D-seryl]-N-methyl-L-leucyl-N-methyl-L-leucyl-N-methyl-L-valyl.], a compound having the general formula (I) or a pharmacologically acceptable salt thereof disclosed in the specification of WO Publication Number 97/11080 {preferably A-119435, of which the chemical name is 17-ethyl-1,14-dihydroxy-12-[2-[4-(acetylaminoacetylthio)-3-methoxycyclohexyl]-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetrone.}, and 17-ethyl-1,14-dihydroxy-12-[2-[4-(2-phenylhydrazinocarbonyloxy)-3-methoxycyclohexyl]-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetrone disclosed in Bioorg. Med. Chem. Lett., vol. 9 (2), 227-232 (1999).

The planar chemical structures of the typical compounds are shown below.

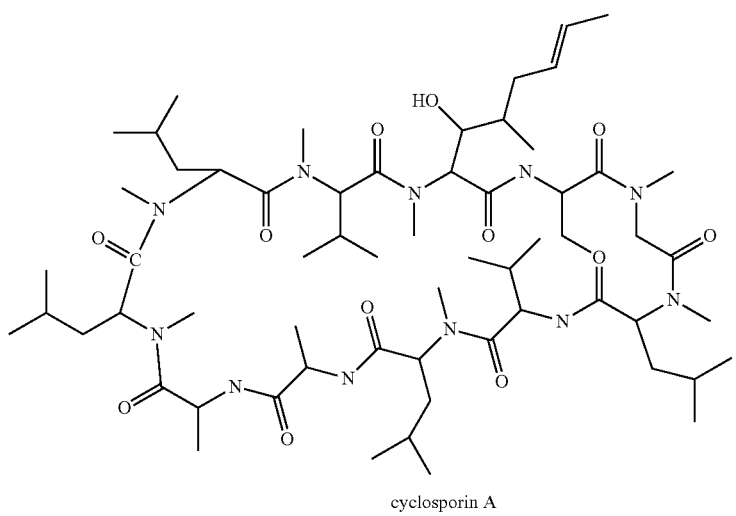

cyclosporin A

-continued
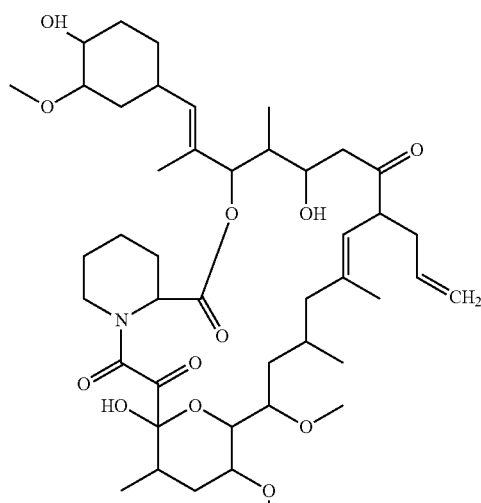
tacrolimus
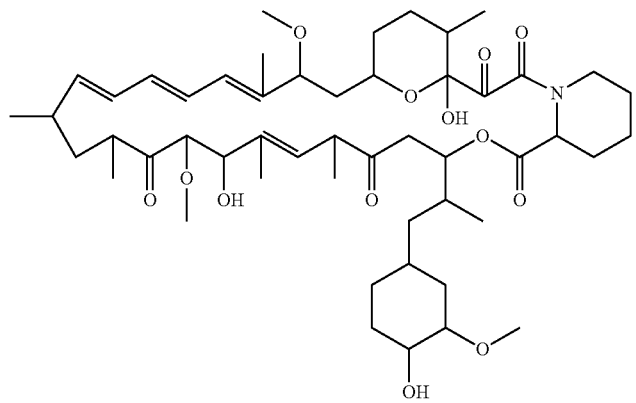
rapamycin
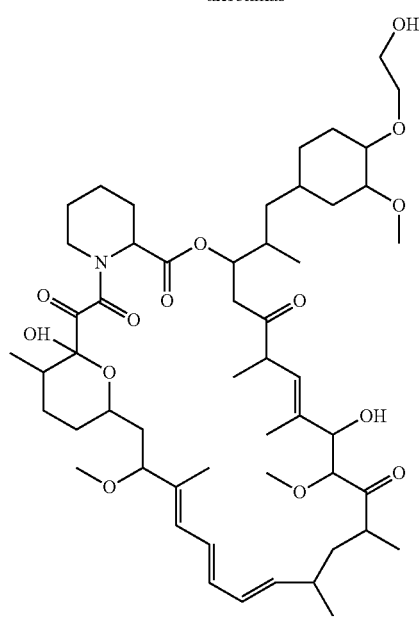
everolimus
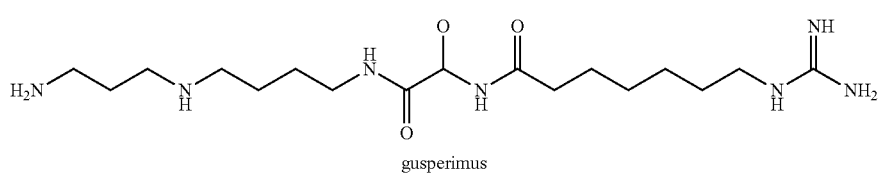
gusperimus
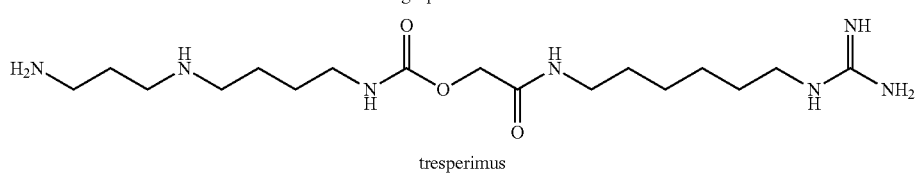
tresperimus
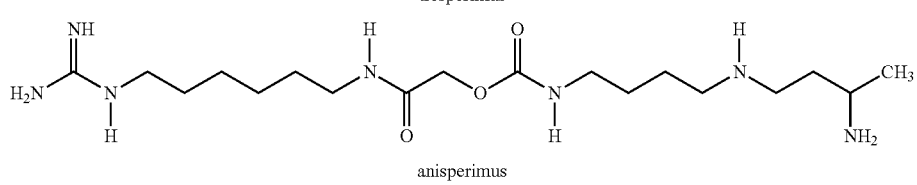
anisperimus -continued
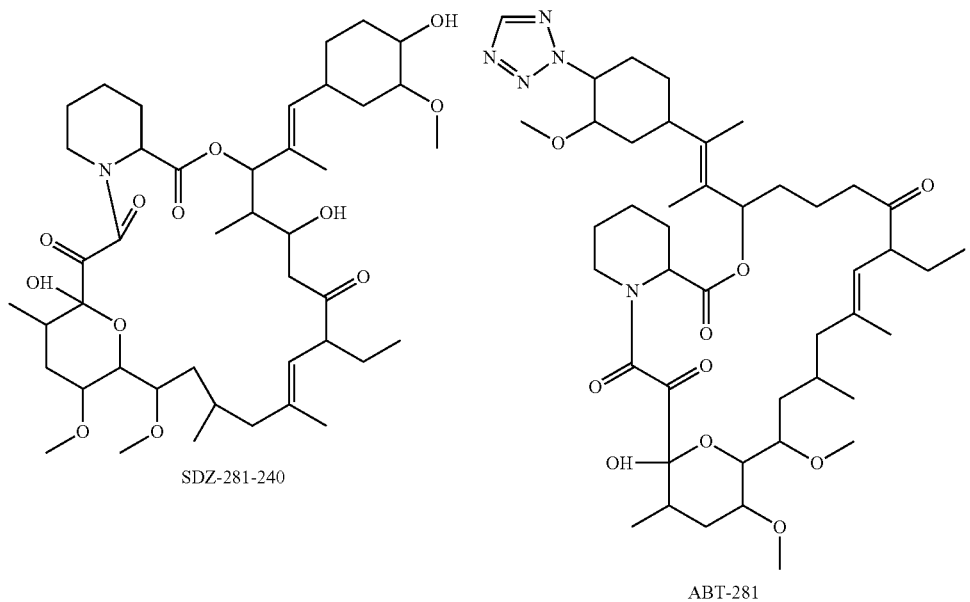
SDZ-281-240
ABT-281
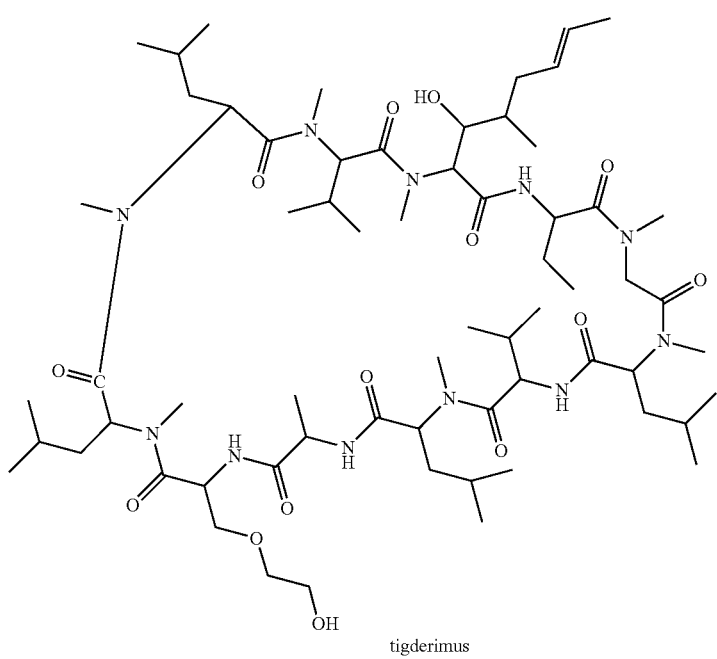
tigderimus -continued

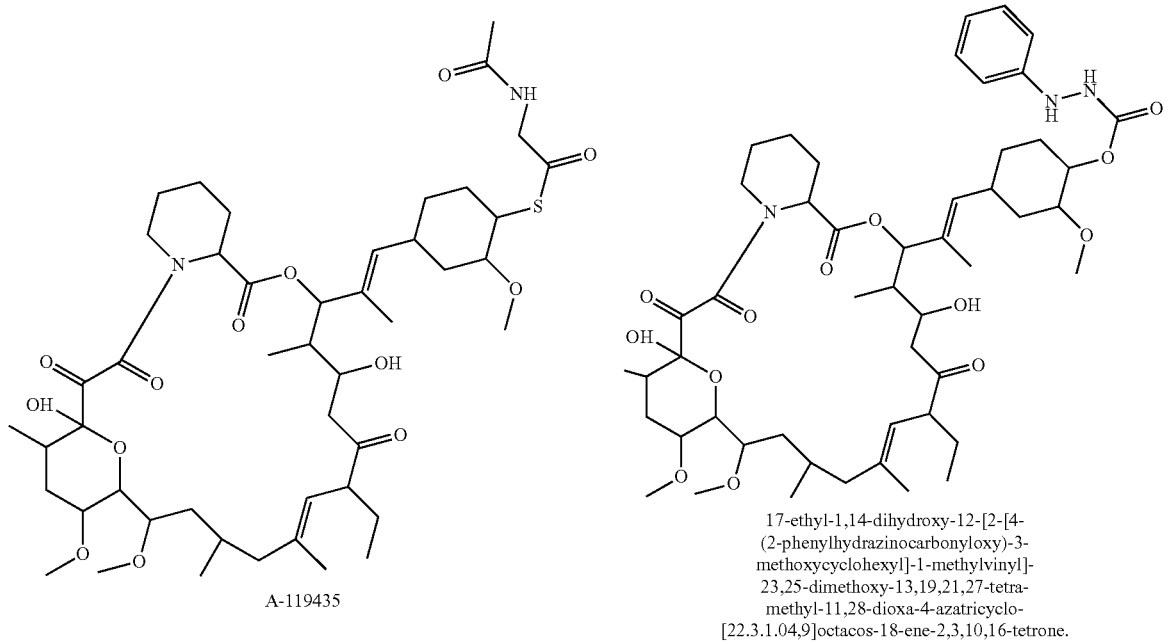

A-119435

17-ethyl-1,14-dihydroxy-12-[2-[4-(2-phenylhydrazinocarbonyloxy)-3-methoxycyclohexyl]-1-methylvinyl]-23,25-dimethoxy-13,19,21,27-tetra-methyl-11,28-dioxa-4-azatricyclo-[22.3.1.0 4,9]octacos-18-ene-2,3,10,16-tetrone.

(2) Agents which have the action of inhibiting nucleoside synthesis in immune cells, depress lymphocytic proliferation by inhibiting nucleoside synthesis in the immune cells and show nonspecific immunosuppressive activity. Such agents, which have the action of inhibiting nucleoside synthesis in the immune cells, include, for example, a compound having the chemical structure disclosed in claim 1 of U.S. Pat. No. 3,888,843 (mizoribine, of which the chemical name is 5-hydroxy-1-β-D-ribofuranosyl-1H-imidazole-4-carboxamide), a compound having the general formula disclosed in claim 7 of U.S. Pat. No. 3,056,785 or a pharmacologically acceptable salt thereof [preferably azathioprine, of which the chemical name is 6-[(1-methyl-4-nitro-1H-imidazol-5-yl)thio]-1H-purine, and in the present invention azathioprine includes a pharmacologically acceptable salt (hydrochloride) thereof], a compound having the general formula (A) or a pharmacologically acceptable salt thereof disclosed in the specification of E.P. Publication Number 281,713 (U.S. Pat. No. 4,753,935) [preferably mycophenolate Mofetil, of which the chemical name is 2-(4-morpholinyl)ethyl 6-(1,3-dihydro-4-hydroxy-6-methoxy-7-methyl-3-oxo-5-isobenzofuranyl)-4-methyl-(4E)-hexenoate.], a compound having the general formula (I) or a pharmacologically acceptable salt thereof disclosed in the specification of E.P. Publication Number 13376 (Japanese Patent Publication (Kokai) Number Sho 62-72614 or U.S. Pat. No. 4,284,786) [preferably leflunomide, of which the chemical name is 5-methyl-N-[4-(trifluoromethyl)phenyl]-4-isoxazolecarboxamide.], a compound having the general formula (I) or a pharmacologically acceptable salt thereof disclosed in the specification of WO Publication Number 97/40028 {preferably merimempodib, of which the chemical name is (3s)-tetrahydro-3-furanyl [[3-[[[[3-methoxy-4-(5-oxazolyl)phenyl]amino]carbonyl]amino]phenyl]methyl]carbamate.}, a compound having the general formula (I) or a pharmacologically acceptable salt thereof disclosed in the specification of FR Patent Publication Number 2,727,628 [preferably HMR-1279, of which the chemical name is α-cyano-N-(4-cyanophenyl)-β-oxo-cyclopropanepropaneamide.], a compound having the general formula (I) or a pharmacologically acceptable salt thereof disclosed in the specification of WO Publication Number 93/22286 (Japanese Patent Number 2,928,385, E.P. Publication Number 601,191 or U.S. Pat. No. 5,371,225) {preferably TSK-204, of which the chemical name is 6,7-dihydro-10-fluoro-3-(2-fluorophenyl)-5H-benzo[6,7]cyclohepta[1,2-b]quinoline-8-carboxylic acid.}, and a compound having the general formula (I) or a pharmacologically acceptable salt thereof disclosed in the specification of E.P. Publication Number 569,912 (Japanese Patent Publication (Kokai) Number Hei 6-32784) (preferably SP-100030, of which the chemical name is 2-chloro-N-[3,5-di(trifluoromethyl)phenyl]-4-(trifluoromethyl)pyrimidine-5-carboxyamide.}.

The planar chemical structures of the typical compounds are shown below.

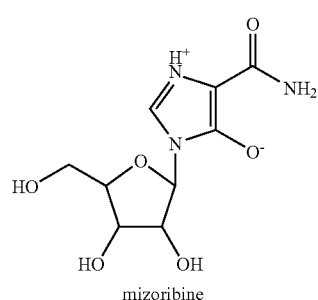

mizoribine

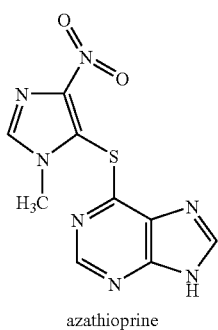
azathioprine

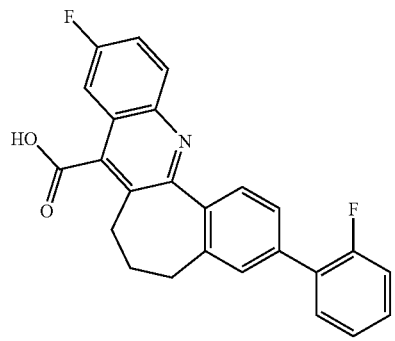
TSK-204

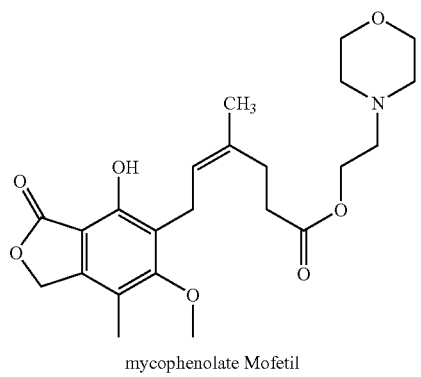
mycophenolate Mofetil

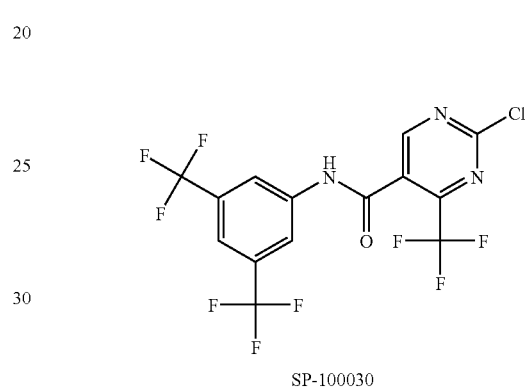
SP-100030

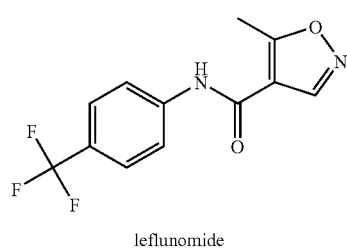
leflunomide

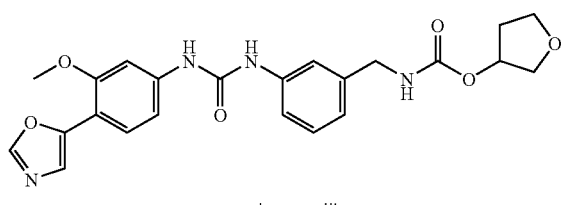
merimempodib

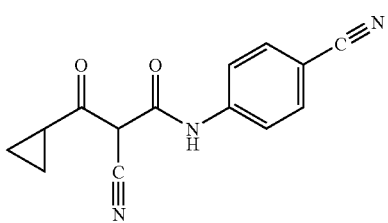
HMR-1279

(3) Agents which inhibit the action of cytokines on immune cells and have antirheumatic action, have the combination of suppression of cytokine production, suppression of lymphocytic proliferation, and suppression of immunoglobulin production. Furthermore, the agents include compounds having suppressive action on T-cell proliferation, suppression of NK cell activity, TNF-receptor antagonistic action, and the like. Such agents, which inhibit the action of cytokine on immune cells and have antirheumatic action, include, for example, a compound having the general formula disclosed in claim (1) of Japanese Patent, Publication (Kokai) Number Hei 2-49778 or a pharmacologically acceptable salt thereof (preferably T-614, of which the chemical name is N-[3-formylamino-4-oxo-6-phenoxy-4H-1-benzopyran-7-yl]methanesulfonamide.), a compound having the general formula (I) disclosed in the specification of U.S. Pat. No. 4,720,506 or a pharmacologically acceptable salt thereof [preferably actarit, of which the chemical name is 4-(acetylamino)phenylacetic acid.], a compound having the general formula disclosed in claim 1 of U.S. Pat. No. 2,396,145 or a pharmacologically acceptable salt thereof {preferably salazosulfapyridine, of which the chemical name is 5-[[p-(2-pyridylsulfamoyl)-phenyl]azo]salicylic acid.}, and a compound having the general formula (I) disclosed in the specification of WO Publication Number 97/23457 {preferably CDC-801, of which the chemical name is 3-phthalimido-3-(3-cyclopentyloxy-4-methoxyphenyl)propionamide.}.

The planar chemical structures of the typical compounds are shown below.

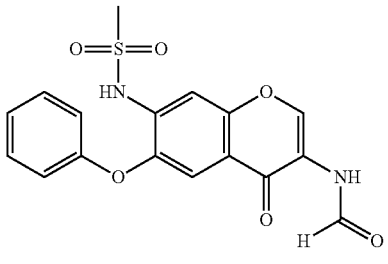

T-614

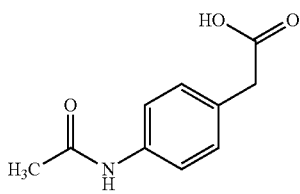

actarit

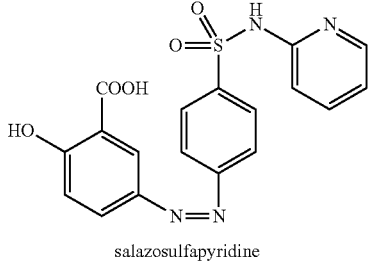

salazosulfapyridine

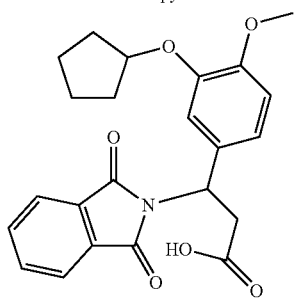

CDC-801

(4) Agents which are alkylating agents causing cell death by breakdown of DNA chains or blocking DNA synthesis, include, for example, a compound having the general formula (IIIa) or a pharmacologically acceptable salt thereof disclosed in the specification of U.S. Pat. No. 3,018,302 [preferably cyclophosphamide, of which the chemical name is N,N'-bis-(2-chloroethyl) tetrahydro-2H-1,3,2-oxazaphosphorin-2-amine 2-oxide.].

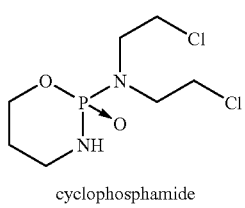

cyclophosphamide (5) Metabolic antagonists, which inhibit the metabolism of nucleic acids by blocking folic acid production, have the action of inhibiting the metabolism of nucleic acids by binding to dihydrofolate reductases and blocking the production of tetrahydrofolic acids that are essential to the synthesis of components of nucleic acids. Such metabolic antagonists, which inhibit the metabolism of nucleic acids by blocking folic acid production, include, for example, a compound having the general formula disclosed in claim 1 of U.S. Pat. No. 2,512,572 or a pharmacologically acceptable salt thereof {preferably methotrexate, of which the chemical name is N-[4-[[2,4-diamino-6-pteridinyl]methyl]methylamino]benzoyl-L-glutamic acid.}.

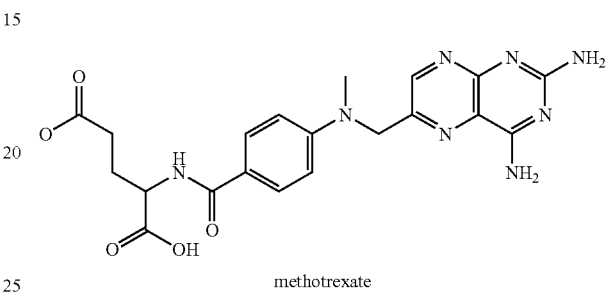

methotrexate (6) The group of protein drugs, which have the suppression action of TNF-alpha, includes compounds such as IL-1 receptor antagonists, soluble IL-1 receptors, and anti-IL-6 receptor antibodies, which suppress the action of TNF-alpha by inhibiting the neutralizing action of circulating TNF-alpha and its receptor-mediated intracellular TNF-alpha signaling. Such protein drugs, which have the inhibitory action of TNF-alpha, include, for example, remicade (infliximab) disclosed in the specification of U.S. Pat. No. 5,656,272 and Drugs, vol. 59(6), 1341-1359 (2000), enbrel (etanercept) disclosed in the specification of WO Publication Number 94/06,476, U.S. Pat. No. 5,605,690, and Expert. Opin. Pharmacother., July vol. 2(7), 1137-1148 (2000), dacliziumab disclosed in the specification of WO Publication Number 92/11,018, U.S. Pat. No. 5,530,101, and N. Engl. J. Med., vol. 338(3), 161-165 (1997), basiliximab disclosed in the specification of E.P. Publication Number 449,769 and Clin. Pharmacol. Ther., Vol. 64(1), 66-72 (1998), alemtuzumab disclosed in the specification of WO Publication Number 89/07,452, U.S. Pat. No. 5,846,534; and J. Clin. Oncol., vol. 15(4), 1567-1574 (1997), omalizumab disclosed in the specification of U.S. Pat. No. 5,965,709 and Drugs vol. 61(2), 253-260 (2001), BMS-188667 disclosed in the specification of E.P. Publication Number 613,944 and J. Pharm. Sci., vol. 84(12), 1488-1489 (1995), CDP-571 disclosed in Arthritis-Rheum., vol. 37(9), Suppl., S295 (1994), inolimomab and ATM-027 disclosed in Transplant., June, vol. 55, 1320-1327 (1993), and BTI-322 disclosed in Blood, December 1, vol. 92(11), 4066-4071 (1998).

(7). Agents which are steroid hormone agents that bind to intracellular steroid receptors to form a complex which binds to reaction sites on chromosomes, resulting in the synthesis of proteins which show immunosuppressive activity, include, for example, prednisolone (of which the chemical name is 1,4-pregnadiene-3,20-dione-11β,17α-21-triol.).

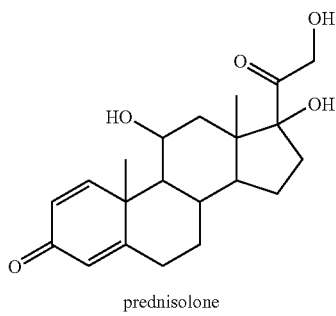

prednisolone (8) Agents which are substances suppressing prostaglandin production and/or nonsteroidal anti-inflammatory drugs antagonizing the action of prostaglandin, include, for example, a compound having the general formula disclosed in claim 1 of Japanese Patent Publication (Kokoku) Number Sho 58-4699 or a pharmacologically acceptable salt thereof {preferably loxoprofen sodium, of which the chemical name is sodium 2-[4-(2-oxocyclopentan-1-ylmethyl)phenyl]propionate.}, a compound having the general formula I(A) or a pharmacologically acceptable salt thereof disclosed in the specification of U.S. Pat. No. 3,558,690 {preferably diclofenac sodium, of which the chemical name is sodium [o-(2,6-dichloroanilino)phenyl]acetate.}, a compound having the general formula (I) or a pharmacologically acceptable salt thereof disclosed in the specification of U.S. Pat. No. 4,233,299 (E.P. Publication Number 0,002,482 or Japanese Patent Publication (Kokai) Number Sho 58-92976) [preferably meloxicam, of which the chemical name is 4-hydroxy-2-methyl-N-(5-methyl-2-thiazolyl)-2H-1,2-benzothiazine-3-carboxamide 1,1-dioxide.], a compound having the general formula (II) or a pharmacologically acceptable salt thereof disclosed in the specification of WO Publication Number 95/15316 (U.S. Pat. No. 5,521,207 or Japanese Patent Publication (Kokai) Number 2000-109466) {preferably celecoxib, of which the chemical name is 4-[5-(4-methylphenyl)-3-(trifluoromethyl)pyrazol-1-yl]benzenesulfonamide.}, and a compound having the general formula (I) or a pharmacologically acceptable salt thereof disclosed in the specification of WO Publication Number 95/00501 (U.S. Pat. No. 5,474,995) {preferably rofecoxib, of which the chemical name is 4-[4-(methylsulfonyl)phenyl]-3-phenyl-2(5H)-furanone.}.

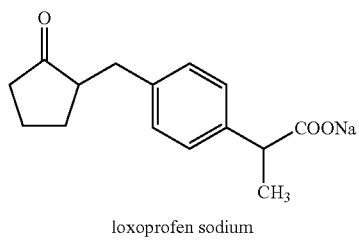

loxoprofen sodium

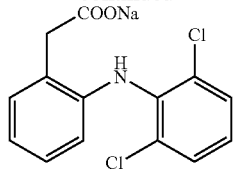

diclofenac sodium

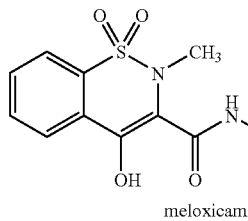

meloxicam

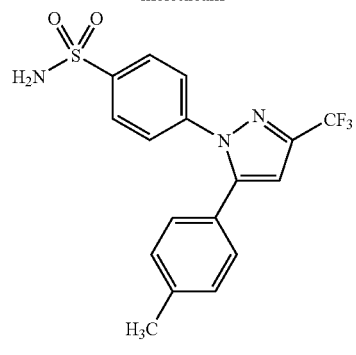

celecoxib

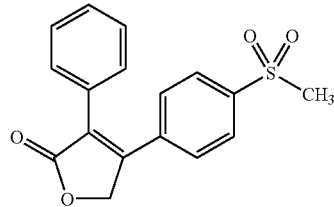

rofecoxib

Of the above immunosuppressants, more preferred are cyclosporin A, tacrolimus, rapamycin, leflunomide, methotrexate, remicade and enbrel.

The "pharmacologically acceptable salt thereof" described above means a salt into which the above immunosuppressants can be converted, by reacting a compound having a basic group such as an amino group with an acid or by reacting a compound having an acidic group such as a carboxyl group with a base. Such salts are included in the present invention.

The salt formed with a basic group of the above immunosuppressants is preferably an inorganic acid salt, for example, a hydrohalide such as hydrofluoride, hydrochloride, hydrobromide, or hydroiodide, a nitrate, a perchlorate, a sulfate, a phosphate or the like; an organic acid salt, for example, a lower alkanesulfonate such as methanesulfonate, trifluoromethanesulfonate, or ethanesulfonate, an arylsulfonate such as benzenesulfonate or p-toluenesulfonate, an acetate, a malate, a fumarate, a succinate, a citrate, an ascorbate, a tartrate, a oxalate, a maleate, or the like; or an amino acid salt such as glycine salt, lysine salt, arginine salt, ornithine salt, glutamate, or aspartic acid salt. The salt is more preferably hydrochloride, acetate, fumarate, succinate, or maleate.

The salt formed with an acidic group of the above immunosuppressants is preferably a metal salt, for example, an alkali metal salt such as sodium salt, potassium salt, or lithium salt, an alkaline earth metal salt such as calcium salt or magnesium salt, an aluminum salt, an iron salt, or the like; an amine salt, for example, an inorganic salt such as ammonium salt, an organic acid salt such as t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt, tris(hydroxymethyl)aminomethane salt, or the like; or an amino acid salt such as glycine salt, lysine salt, arginine salt, ornithine salt, glutamic acid salt, or aspartic acid salt. The salt is more preferably sodium salt, potassium salt, calcium salt, magnesium salt, or aluminum salt.

When the immunosuppressants, the active ingredients of the pharmaceutical compositions of the present invention, are allowed to stand in contact with the atmosphere or to recrystallize, they may absorb water or water may attach to them to form a hydrate. The present invention encompasses such hydrates.

When the immunosuppressants, the active ingredients of the pharmaceutical compositions of the present invention, have asymmetric carbons in their structures, these compounds can exist as various stereoisomers due to such asymmetric carbons. In the present invention these compounds are represented as a single chemical formula individually. The present invention encompasses both individual stereoisomers and mixtures of two or more stereoisomers in any ratio.

Compounds shown in the following Table 1, Table 2, Table 3, Table 4, Table 5 and Table 6 are specifically illustrated as preferred compounds of general formula (I), (II), or (III) of the present invention. However, the compounds of the present invention are not limited to these.

The compounds represented by the same compound number in Table 1 and Table 2 include compounds wherein X is a sulfur atom (S), an oxygen atom (O), or a group of formula =N—CH$_3$.

The compounds represented by the same compound number in Table 5 and Table 6 include the six types of compounds wherein X is a sulfur atom (S), an oxygen atom (O), or a group of formula =N—CH$_3$, and the phosphate group is linked to an oxygen atom (O) or a —CH$_2$— group.

The meaning of the abbreviations in the following Tables is shown below.
Bu represents a butyl group,
iBu represents a isobutyl group,
Bz represents a benzyl group,
Et represents an ethyl group,
cHx represents a cyclohexyl group,
Me represents a methyl group,
Np(1) represents a naphthalen-1-yl group,
Np(2) represents a naphthalen-2-yl group,
Ph represents a phenyl group,
cPn represents a cyclopentyl group,
Pr represents a propyl group, and
iPr represents an isopropyl-group.

TABLE 1

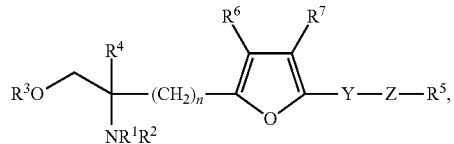

(Ia-1)

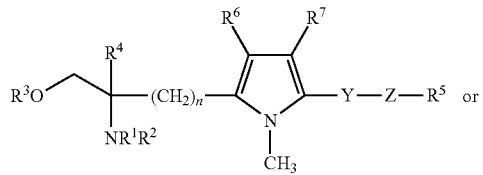

(Ia-2)

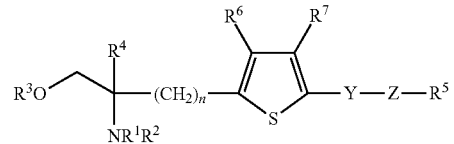

(Ia-3)

| Compd. | R$^1$ | R$^2$ | R$^3$ | R$^4$ | n | —Y—Z—R$^5$ | R$^6$ | R$^7$ |
|---|---|---|---|---|---|---|---|---|
| 1-1 | H | H | H | Me | 2 | —(CH$_2$)$_3$-cHx | H | H |
| 1-2 | H | H | H | Me | 2 | —(CH$_2$)$_3$-(4-F-cHx) | H | H |
| 1-3 | H | H | H | Me | 2 | —(CH$_2$)$_3$-(4-Me-cHx) | H | H |
| 1-4 | H | H | H | Me | 2 | —(CH$_2$)$_3$-(4-Et-cHx) | H | H |
| 1-5 | H | H | H | Me | 2 | —(CH$_2$)$_3$-(4-CF$_3$-cHx) | H | H |
| 1-6 | H | H | H | Me | 2 | —(CH$_2$)$_3$-(4-MeO-cHx) | H | H |
| 1-7 | H | H | H | Me | 2 | —(CH$_2$)$_3$-(4-EtO-cHx) | H | H |
| 1-8 | H | H | H | Me | 2 | —(CH$_2$)$_3$-(4-MeS-cHx) | H | H |
| 1-9 | H | H | H | Me | 2 | —(CH$_2$)$_3$-(4-cHx-cHx) | H | H |
| 1-10 | H | H | H | Me | 2 | —(CH$_2$)$_3$-(4-Ph-cHx) | H | H |
| 1-11 | H | H | H | Me | 2 | —(CH$_2$)$_3$-Ph | H | H |
| 1-12 | H | H | H | Me | 2 | —(CH$_2$)$_3$-(4-F-Ph) | H | H |
| 1-13 | H | H | H | Me | 2 | —(CH$_2$)$_3$-(4-Me-Ph) | H | H |
| 1-14 | H | H | H | Me | 2 | —(CH$_2$)$_3$-(4-Et-Ph) | H | H |
| 1-15 | H | H | H | Me | 2 | —(CH$_2$)$_3$-(4-CF$_3$-Ph) | H | H |

TABLE 1-continued

| | | | | | | | | |
|---|---|---|---|---|---|---|---|---|
| 1-16 | H | H | H | Me | 2 | —(CH$_2$)$_3$-(4-MeO-Ph) | H | H |
| 1-17 | H | H | H | Me | 2 | —(CH$_2$)$_3$-(4-EtO-Ph) | H | H |
| 1-18 | H | H | H | Me | 2 | —(CH$_2$)$_3$-(4-MeS-Ph) | H | H |
| 1-19 | H | H | H | Me | 2 | —(CH$_2$)$_3$-(4-cHx-Ph) | H | H |
| 1-20 | H | H | H | Me | 2 | —(CH$_2$)$_3$-(4-Ph-Ph) | H | H |
| 1-21 | H | H | H | Me | 2 | —(CH$_2$)$_4$-cHx | H | H |
| 1-22 | H | H | H | Me | 2 | —(CH$_2$)$_4$-(4-F-cHx) | H | H |
| 1-23 | H | H | H | Me | 2 | —(CH$_2$)$_4$-(4-Me-cHx) | H | H |
| 1-24 | H | H | H | Me | 2 | —(CH$_2$)$_4$-(4-Et-cHx) | H | H |
| 1-25 | H | H | H | Me | 2 | —(CH$_2$)$_4$-(4-CF$_3$-cHx) | H | H |
| 1-26 | H | H | H | Me | 2 | —(CH$_2$)$_4$-(4-MeO-cHx) | H | H |
| 1-27 | H | H | H | Me | 2 | —(CH$_2$)$_4$-(4-EtO-cHx) | H | H |
| 1-28 | H | H | H | Me | 2 | —(CH$_2$)$_4$-(4-MeS-cHx) | H | H |
| 1-29 | H | H | H | Me | 2 | —(CH$_2$)$_4$-(4-cHx-cHx) | H | H |
| 1-30 | H | H | H | Me | 2 | —(CH$_2$)$_4$-(4-Ph-cHx) | H | H |
| 1-31 | H | H | H | Me | 2 | —(CH$_2$)$_4$-Ph | H | H |
| 1-32 | H | H | H | Me | 2 | —(CH$_2$)$_4$-(4-F-Ph) | H | H |
| 1-33 | H | H | H | Me | 2 | —(CH$_2$)$_4$-(4Me-Ph) | H | H |
| 1-34 | H | H | H | Me | 2 | —(CH$_2$)$_4$-(4-Et-Ph) | H | H |
| 1-35 | H | H | H | Me | 2 | —(CH$_2$)$_4$-(4-CF$_3$-Ph) | H | H |
| 1-36 | H | H | H | Me | 2 | —(CH$_2$)$_4$-(4-MeO-Ph) | H | H |
| 1-37 | H | H | H | Me | 2 | —(CH$_2$)$_4$-(4-EtO-Ph) | H | H |
| 1-38 | H | H | H | Me | 2 | —(CH$_2$)$_4$-(4-MeS-Ph) | H | H |
| 1-39 | H | H | H | Me | 2 | —(CH$_2$)$_4$-(4-cHx-Ph) | H | H |
| 1-40 | H | H | H | Me | 2 | —(CH$_2$)$_4$-(4-Ph-Ph) | H | H |
| 1-41 | H | H | H | Me | 2 | —(CH$_2$)$_5$-cPn | H | H |
| 1-42 | H | H | H | Me | 2 | —(CH$_2$)$_5$-cHx | H | H |
| 1-43 | H | H | H | Me | 2 | —(CH$_2$)$_5$-cHx | Me | H |
| 1-44 | H | H | H | Me | 2 | —(CH$_2$)$_5$-cHx | H | Me |
| 1-45 | H | H | H | Me | 2 | —(CH$_2$)$_5$-cHx | F | H |
| 1-46 | H | H | H | Me | 2 | —(CH$_2$)$_5$-cHx | H | F |
| 1-47 | H | H | H | Me | 2 | —(CH$_2$)$_5$-(3-F-cHx) | H | H |
| 1-48 | H | H | H | Me | 2 | —(CH$_2$)$_5$-(4-F-cHx) | H | H |
| 1-49 | H | H | H | Me | 2 | —(CH$_2$)$_5$-(4-Cl-cRx) | H | H |
| 1-50 | H | H | H | Me | 2 | —(CH$_2$)$_5$-(4-Br-cHx) | H | H |
| 1-51 | H | H | H | Me | 2 | —(CH$_2$)$_5$-(3-Me-cHx) | H | H |
| 1-52 | H | H | H | Me | 2 | —(CH$_2$)$_5$-(4-Me-cHx) | H | H |
| 1-53 | H | H | H | Me | 2 | —(CH$_2$)$_5$-(3-Et-cHx) | H | H |
| 1-54 | H | H | H | Me | 2 | —(CH$_2$)$_5$-(4-Et-cHx) | H | H |
| 1-55 | H | H | H | Me | 2 | —(CH$_2$)$_5$-(3-Pr-cHx) | H | H |
| 1-56 | H | H | H | Me | 2 | —(CH$_2$)$_5$-(4-Pr-cHx) | H | H |
| 1-57 | H | H | H | Me | 2 | —(CH$_2$)$_5$-(4-iPr-cHx) | H | H |
| 1-58 | H | H | H | Me | 2 | —(CH$_2$)$_5$-(3-Bu-cHx) | H | H |
| 1-59 | H | H | H | Me | 2 | —(CH$_2$)$_5$-(4-Bu-cHx) | H | H |
| 1-60 | H | H | H | Me | 2 | —(CH$_2$)$_5$-(3-CF$_3$-cHx) | H | H |
| 1-61 | H | H | H | Me | 2 | —(CH$_2$)$_5$-(4-CF$_3$-cHx) | H | H |
| 1-62 | H | H | H | Me | 2 | —(CH$_2$)$_5$-(3-MeO-cHx) | H | H |
| 1-63 | H | H | H | Me | 2 | —(CH$_2$)$_5$-(4-MeO-cHx) | H | H |
| 1-64 | H | H | H | Me | 2 | —(CH$_2$)$_5$-(3-EtO-cHx) | H | H |
| 1-65 | H | H | H | Me | 2 | —(CH$_2$)$_5$-(4-EtO-cHx) | H | H |
| 1-66 | H | H | H | Me | 2 | —(CH$_2$)$_5$-(3-PrO-cHx) | H | H |
| 1-67 | H | H | H | Me | 2 | —(CH$_2$)$_5$-(4-PrO-cHx) | H | H |
| 1-68 | H | H | H | Me | 2 | —(CH$_2$)$_5$-(3-iPrO-cHx) | H | H |
| 1-69 | H | H | H | Me | 2 | —(CH$_2$)$_5$-(4-iPrO-cHx) | H | H |
| 1-70 | H | H | H | Me | 2 | —(CH$_2$)$_5$-[3-(2-Et-PrO)-cHx] | H | H |
| 1-71 | H | H | H | Me | 2 | —(CH$_2$)$_5$-[4-(2-Et-PrO)-cHx] | H | H |
| 1-72 | H | H | H | Me | 2 | —(CH$_2$)$_5$-(3-iBuO-cHx) | H | H |
| 1-73 | H | H | H | Me | 2 | —(CH$_2$)$_5$-(4-iBuO-cHx) | H | H |
| 1-74 | H | H | H | Me | 2 | —(CH$_2$)$_5$-(3-MeS-cHx) | H | H |
| 1-75 | H | H | H | Me | 2 | —(CH$_2$)$_5$-(4-MeS-cHx) | H | H |
| 1-76 | H | H | H | Me | 2 | —(CH$_2$)$_5$-(3-EtS-cHx) | H | H |
| 1-77 | H | H | H | Me | 2 | —(CH$_2$)$_5$-(4-EtS-cHx) | H | H |
| 1-78 | H | H | H | Me | 2 | —(CH$_2$)$_5$-(3-PrS-cHx) | H | H |
| 1-79 | H | H | H | Me | 2 | —(CH$_2$)$_5$-(4-PrS-cHx) | H | H |
| 1-80 | H | H | H | Me | 2 | —(CH$_2$)$_5$-(3-iPrS-cHx) | H | H |
| 1-81 | H | H | H | Me | 2 | —(CH$_2$)$_5$-(4-iPrS-cHx) | H | H |
| 1-82 | H | H | H | Me | 2 | —(CH$_2$)$_5$-[3-(2-Et-PrS)-cHx] | H | H |
| 1-83 | H | H | H | Me | 2 | —(CH$_2$)$_5$-[4-(2-Et-PrS)-cHx] | H | H |
| 1-84 | H | H | H | Me | 2 | —(CH$_2$)$_5$-(3-iBuS-cHx) | H | H |
| 1-85 | H | H | H | Me | 2 | —(CH$_2$)$_5$-(4-iBuS-cHx) | H | H |
| 1-86 | H | H | H | Me | 2 | —(CH$_2$)$_5$-(3-cHx-cHx) | H | H |
| 1-87 | H | H | H | Me | 2 | —(CH$_2$)$_5$-(4-cHx-cHx) | H | H |
| 1-88 | H | H | H | Me | 2 | —(CH$_2$)$_5$-(3-Ph-cHx) | H | H |
| 1-89 | H | H | H | Me | 2 | —(CH$_2$)$_5$-(4-Ph-cHx) | H | H |
| 1-90 | H | H | H | Me | 2 | —(CH$_2$)$_5$-(2,4-diMe-cHx) | H | H |
| 1-91 | H | H | H | Me | 2 | —(CH$_2$)$_5$-(3,4-diMe-cHx) | H | H |
| 1-92 | H | H | H | Me | 2 | —(CH$_2$)$_5$-(3,5-diMe-cHx) | H | H |
| 1-93 | H | H | H | Me | 2 | —(CH$_2$)$_5$-Ph | H | H |
| 1-94 | H | H | H | Me | 2 | —(CH$_2$)$_5$-Ph | Me | H |
| 1-95 | H | H | H | Me | 2 | —(CH$_2$)$_5$-Ph | H | Me |

TABLE 1-continued

| | | | | | | | | |
|---|---|---|---|---|---|---|---|---|
| 1-96  | H | H | H | Me | 2 | —(CH$_2$)$_5$-Ph | F | H |
| 1-97  | H | H | H | Me | 2 | —(CH$_2$)$_5$-Ph | H | F |
| 1-98  | H | H | H | Me | 2 | —(CH$_2$)$_5$-(3-F-Ph) | H | H |
| 1-99  | H | H | H | Me | 2 | —(CH$_2$)$_5$-(4-F-Ph) | H | H |
| 1-100 | H | H | H | Me | 2 | —(CH$_2$)$_5$-(4-Cl-Ph) | H | H |
| 1-101 | H | H | H | Me | 2 | —(CH$_2$)$_5$-(4-Br-Ph) | H | H |
| 1-102 | H | H | H | Me | 2 | —(CH$_2$)$_5$-(3-Me-Ph) | H | H |
| 1-103 | H | H | H | Me | 2 | —(CH$_2$)$_5$-(4-Me-Ph) | H | H |
| 1-104 | H | H | H | Me | 2 | —(CH$_2$)$_5$-(3-Et-Ph) | H | H |
| 1-105 | H | H | H | Me | 2 | —(CH$_2$)$_5$-(4-Et-Ph) | H | H |
| 1-106 | H | H | H | Me | 2 | —(CH$_2$)$_5$-(3-Pr-Ph) | H | H |
| 1-107 | H | H | H | Me | 2 | —(CH$_2$)$_5$-(4-Pr-Ph) | H | H |
| 1-108 | H | H | H | Me | 2 | —(CH$_2$)$_5$-(3-iPr-Ph) | H | H |
| 1-109 | H | H | H | Me | 2 | —(CH$_2$)$_5$-(4-iPr-Ph) | H | H |
| 1-110 | H | H | H | Me | 2 | —(CH$_2$)$_5$-(3-Bu-Ph) | H | H |
| 1-111 | H | H | H | Me | 2 | —(CH$_2$)$_5$-(4-Bu-Ph) | H | H |
| 1-112 | H | H | H | Me | 2 | —(CH$_2$)$_5$-(3-CF$_3$-Ph) | H | H |
| 1-113 | H | H | H | Me | 2 | —(CH$_2$)$_5$-(4-CF$_3$-Ph) | H | H |
| 1-114 | H | H | H | Me | 2 | —(CH$_2$)$_5$-(3-MeO-Ph) | H | H |
| 1-115 | H | H | H | Me | 2 | —(CH$_2$)$_5$-(4-MeO-Ph) | H | H |
| 1-116 | H | H | H | Me | 2 | —(CH$_2$)$_5$-(3-EtO-Ph) | H | H |
| 1-117 | H | H | H | Me | 2 | —(CH$_2$)$_5$-(4-EtO-Ph) | H | H |
| 1-118 | H | H | H | Me | 2 | —(CH$_2$)$_5$-(3-PrO-Ph) | H | H |
| 1-119 | H | H | H | Me | 2 | —(CH$_2$)$_5$-(4-PrO-Ph) | H | H |
| 1-120 | H | H | H | Me | 2 | —(CH$_2$)$_5$-(3-iPrO-Ph) | H | H |
| 1-121 | H | H | H | Me | 2 | —(CH$_2$)$_5$-(4-iPrO-Ph) | H | H |
| 1-122 | H | H | H | Me | 2 | —(CH$_2$)$_5$-[3-(2-Et-PrO)-Ph] | H | H |
| 1-123 | H | H | H | Me | 2 | —(CH$_2$)$_5$-[4-(2-Et-PrO)-Ph] | H | H |
| 1-124 | H | H | H | Me | 2 | —(CH$_2$)$_5$-(3-iBuO-Ph) | H | H |
| 1-125 | H | H | H | Me | 2 | —(CH$_2$)$_5$-(4-iBuO-Ph) | H | H |
| 1-126 | H | H | H | Me | 2 | —(CH$_2$)$_5$-(3-MeS-Ph) | H | H |
| 1-127 | H | H | H | Me | 2 | —(CH$_2$)$_5$-(4-MeS-Ph) | H | H |
| 1-128 | H | H | H | Me | 2 | —(CH$_2$)$_5$-(3-EtS-Ph) | H | H |
| 1-129 | H | H | H | Me | 2 | —(CH$_2$)$_5$-(4-EtS-Ph) | H | H |
| 1-130 | H | H | H | Me | 2 | —(CH$_2$)$_5$-(3-PrS-Ph) | H | H |
| 1-131 | H | H | H | Me | 2 | —(CH$_2$)$_5$-(4-PrS-Ph) | H | H |
| 1-132 | H | H | H | Me | 2 | —(CH$_2$)$_5$-(3-iPrS-Ph) | H | H |
| 1-133 | H | H | H | Me | 2 | —(CH$_2$)$_5$-(4-iPrS-Ph) | H | H |
| 1-134 | H | H | H | Me | 2 | —(CH$_2$)$_5$-[3-(2-Et-PrS)-Ph] | H | H |
| 1-135 | H | H | H | Me | 2 | —(CH$_2$)$_5$-[4-(2-Et-PrS)-Ph] | H | H |
| 1-136 | H | H | H | Me | 2 | —(CH$_2$)$_5$-(3-iBuS-Ph) | H | H |
| 1-137 | H | H | H | Me | 2 | —(CH$_2$)$_5$-(4-iBuS-Ph) | H | H |
| 1-138 | H | H | H | Me | 2 | —(CH$_2$)$_5$-(3-cHx-Ph) | H | H |
| 1-139 | H | H | H | Me | 2 | —(CH$_2$)$_5$-(4-cHx-Ph) | H | H |
| 1-140 | H | H | H | Me | 2 | —(CH$_2$)$_5$-(3-Ph-Ph) | H | H |
| 1-141 | H | H | H | Me | 2 | —(CH$_2$)$_5$-(4-Ph-Ph) | H | H |
| 1-142 | H | H | H | Me | 2 | —(CH$_2$)$_5$-(2,4-diMe-Ph) | H | H |
| 1-143 | H | H | H | Me | 2 | —(CH$_2$)$_5$-(3,4-diMe-Ph) | H | H |
| 1-144 | H | H | H | Me | 2 | —(CH$_2$)$_5$-(3,5-diMe-Ph) | H | H |
| 1-145 | H | H | H | Me | 2 | —(CH$_2$)$_5$-Np (1) | H | H |
| 1-146 | H | H | H | Me | 2 | —(CH$_2$)$_5$-Np (2) | H | H |
| 1-147 | H | H | H | Me | 2 | —(CH$_2$)$_6$-cPn | H | H |
| 1-148 | H | H | H | Me | 2 | —(CH$_2$)$_6$-cHx | H | H |
| 1-149 | H | H | H | Me | 2 | —(CH$_2$)$_6$-cHx | Me | H |
| 1-150 | H | H | H | Me | 2 | —(CH$_2$)$_6$-cHx | H | Me |
| 1-151 | H | H | H | Me | 2 | —(CH$_2$)$_6$-cHx | F | H |
| 1-152 | H | H | H | Me | 2 | —(CH$_2$)$_6$-cHx | H | F |
| 1-153 | H | H | H | Me | 2 | —(CH$_2$)$_6$-(3-F-cHx) | H | H |
| 1-154 | H | H | H | Me | 2 | —(CH$_2$)$_6$-(4-F-cHx) | H | H |
| 1-155 | H | H | H | Me | 2 | —(CH$_2$)$_6$-(4-Cl-cHx) | H | H |
| 1-156 | H | H | H | Me | 2 | —(CH$_2$)$_6$-(4-Br-cHx) | H | H |
| 1-157 | H | H | H | Me | 2 | —(CH$_2$)$_6$-(3-Me-cHx) | H | H |
| 1-158 | H | H | H | Me | 2 | —(CH$_2$)$_6$-(4-Me-cHx) | H | H |
| 1-159 | H | H | H | Me | 2 | —(CH$_2$)$_6$-(3-Et-cHx) | H | H |
| 1-160 | H | H | H | Me | 2 | —(CH$_2$)$_6$-(4-Et-cHx) | H | H |
| 1-161 | H | H | H | Me | 2 | —(CH$_2$)$_6$-(3-Pr-cHx) | H | H |
| 1-162 | H | H | H | Me | 2 | —(CH$_2$)$_6$-(4-Pr-cHx) | H | H |
| 1-163 | H | H | H | Me | 2 | —(CH$_2$)$_6$-(4-iPr-cHx) | H | H |
| 1-164 | H | H | H | Me | 2 | —(CH$_2$)$_6$-(3-Bu-cHx) | H | H |
| 1-165 | H | H | H | Me | 2 | —(CH$_2$)$_6$-(4-Bu-cHx) | H | H |
| 1-166 | H | H | H | Me | 2 | —(CH$_2$)$_6$-(3-CF$_3$-cHx) | H | H |
| 1-167 | H | H | H | Me | 2 | —(CH$_2$)$_6$-(4-CF$_3$-cHx) | H | H |
| 1-168 | H | H | H | Me | 2 | —(CH$_2$)$_6$-(3-MeO-cHx) | H | H |
| 1-169 | H | H | H | Me | 2 | —(CH$_2$)$_6$-(4-MeO-cHx) | H | H |
| 1-170 | H | H | H | Me | 2 | —(CH$_2$)$_6$-(3-EtO-cHx) | H | H |
| 1-171 | H | H | H | Me | 2 | —(CH$_2$)$_6$-(4-EtO-cHx) | H | H |
| 1-172 | H | H | H | Me | 2 | —(CH$_2$)$_6$-(3-PrO-cHx) | H | H |
| 1-173 | H | H | H | Me | 2 | —(CH$_2$)$_6$-(4-PrO-cHx) | H | H |
| 1-174 | H | H | H | Me | 2 | —(CH$_2$)$_6$-(3-iPrO-cHx) | H | H |
| 1-175 | H | H | H | Me | 2 | —(CH$_2$)$_6$-(4-iPrO-cHx) | H | H |

TABLE 1-continued

| | | | | | | | | |
|---|---|---|---|---|---|---|---|---|
| 1-176 | H | H | H | Me | 2 | —(CH$_2$)$_6$-[3-(2-Et-PrO)-cHx] | H | H |
| 1-177 | H | H | H | Me | 2 | —(CH$_2$)$_6$-[4-(2-Et-PrO)-cHx] | H | H |
| 1-178 | H | H | H | Me | 2 | —(CH$_2$)$_6$-(3-iBuO-cHx) | H | H |
| 1-179 | H | H | H | Me | 2 | —(CH$_2$)$_6$-(4-iBuO-cHx) | H | H |
| 1-180 | H | H | H | Me | 2 | —(CH$_2$)$_6$-(3-MeS-cHx) | H | H |
| 1-181 | H | H | H | Me | 2 | —(CH$_2$)$_6$-(4-MeS-cHx) | H | H |
| 1-182 | H | H | H | Me | 2 | —(CH$_2$)$_6$-(3-EtS-cHx) | H | H |
| 1-183 | H | H | H | Me | 2 | —(CH$_2$)$_6$-(4-EtS-cHx) | H | H |
| 1-184 | H | H | H | Me | 2 | —(CH$_2$)$_6$-(3-PrS-cHx) | H | H |
| 1-185 | H | H | H | Me | 2 | —(CH$_2$)$_6$-(4-PrS-cHx) | H | H |
| 1-186 | H | H | H | Me | 2 | —(CH$_2$)$_6$-(3-iPrS-cHx) | H | H |
| 1-187 | H | H | H | Me | 2 | —(CH$_2$)$_6$-(4-iPrS-cHx) | H | H |
| 1-188 | H | H | H | Me | 2 | —(CH$_2$)$_6$-[3-(2-Et-PrS)-cHx] | H | H |
| 1-189 | H | H | H | Me | 2 | —(CH$_2$)$_6$-[4-(2-Et-PrS)-cHx] | H | H |
| 1-190 | H | H | H | Me | 2 | —(CH$_2$)$_6$-(3-iBuS-cHx) | H | H |
| 1-191 | H | H | H | Me | 2 | —(CH$_2$)$_6$-(4-iBuS-cHx) | H | H |
| 1-192 | H | H | H | Me | 2 | —(CH$_2$)$_6$-(3-cHx-cHx) | H | H |
| 1-193 | H | H | H | Me | 2 | —(CH$_2$)$_6$-(4-cHx-cHx) | H | H |
| 1-194 | H | H | H | Me | 2 | —(CH$_2$)$_6$-(3-Ph-cHx) | H | H |
| 1-195 | H | H | H | Me | 2 | —(CH$_2$)$_6$-(4-Ph-cHx) | H | H |
| 1-196 | H | H | H | Me | 2 | —(CH$_2$)$_6$-(2,4-diMe-cHx) | H | H |
| 1-197 | H | H | H | Me | 2 | —(CH$_2$)$_6$-(3,4-diMe-cHx) | H | H |
| 1-198 | H | H | H | Me | 2 | —(CH$_2$)$_6$-(3,5-diMe-cHx) | H | H |
| 1-199 | H | H | H | Me | 2 | —(CH$_2$)$_6$-Ph | H | H |
| 1-200 | H | H | H | Me | 2 | —(CH$_2$)$_6$-Ph | Me | H |
| 1-201 | H | H | H | Me | 2 | —(CH$_2$)$_6$-Ph | H | Me |
| 1-202 | H | H | H | Me | 2 | —(CH$_2$)$_6$-Ph | F | H |
| 1-203 | H | H | H | Me | 2 | —(CH$_2$)$_6$-Ph | H | F |
| 1-204 | H | H | H | Me | 2 | —(CH$_2$)$_6$-(3-F-Ph) | H | H |
| 1-205 | H | H | H | Me | 2 | —(CH$_2$)$_6$-(4-F-Ph) | H | H |
| 1-206 | H | H | H | Me | 2 | —(CH$_2$)$_6$-(4-Cl-Ph) | H | H |
| 1-207 | H | H | H | Me | 2 | —(CH$_2$)$_6$-(4-Br-Ph) | H | H |
| 1-208 | H | H | H | Me | 2 | —(CH$_2$)$_6$-(3-Me-Ph) | H | H |
| 1-209 | H | H | H | Me | 2 | —(CH$_2$)$_6$-(4-Me-Ph) | H | H |
| 1-210 | H | H | H | Me | 2 | —(CH$_2$)$_6$-(3-Et-Ph) | H | H |
| 1-211 | H | H | H | Me | 2 | —(CH$_2$)$_6$-(4-Et-Ph) | H | H |
| 1-212 | H | H | H | Me | 2 | —(CH$_2$)$_6$-(3-Pr-Ph) | H | H |
| 1-213 | H | H | H | Me | 2 | —(CH$_2$)$_6$-(4-Pr-Ph) | H | H |
| 1-214 | H | H | H | Me | 2 | —(CH$_2$)$_6$-(3-iPr-Ph) | H | H |
| 1-215 | H | H | H | Me | 2 | —(CH$_2$)$_6$-(4-iPr-Ph) | H | H |
| 1-216 | H | H | H | Me | 2 | —(CH$_2$)$_6$-(3-Bu-Ph) | H | H |
| 1-217 | H | H | H | Me | 2 | —(CH$_2$)$_6$-(4-Bu-Ph) | H | H |
| 1-218 | H | H | H | Me | 2 | —(CH$_2$)$_6$-(3-CF$_3$-Ph) | H | H |
| 1-219 | H | H | H | Me | 2 | —(CH$_2$)$_6$-(4-CF$_3$-Ph) | H | H |
| 1-220 | H | H | H | Me | 2 | —(CH$_2$)$_6$-(3-MeO-Ph) | H | H |
| 1-221 | H | H | H | Me | 2 | —(CH$_2$)$_6$-(4-MeO-Ph) | H | H |
| 1-222 | H | H | H | Me | 2 | —(CH$_2$)$_6$-(3-EtO-Ph) | H | H |
| 1-223 | H | H | H | Me | 2 | —(CH$_2$)$_6$-(4-EtO-Ph) | H | H |
| 1-224 | H | H | H | Me | 2 | —(CH$_2$)$_6$-(3-PrO-Ph) | H | H |
| 1-225 | H | H | H | Me | 2 | —(CH$_2$)$_6$-(4-PrO-Ph) | H | H |
| 1-226 | H | H | H | Me | 2 | —(CH$_2$)$_6$-(3-iPrO-Ph) | H | H |
| 1-227 | H | H | H | Me | 2 | —(CH$_2$)$_6$-(4-iPrO-Ph) | H | H |
| 1-228 | H | H | H | Me | 2 | —(CH$_2$)$_6$-[3-(2-Et-PrO)-Ph] | H | H |
| 1-229 | H | H | H | Me | 2 | —(CH$_2$)$_6$-[4-(2-Et-PrO)-Ph] | H | H |
| 1-230 | H | H | H | Me | 2 | —(CH$_2$)$_6$-(3-iBuO-Ph) | H | H |
| 1-231 | H | H | H | Me | 2 | —(CH$_2$)$_6$-(4-iBuO-Ph) | H | H |
| 1-232 | H | H | H | Me | 2 | —(CH$_2$)$_6$-(3-MeS-Ph) | H | H |
| 1-233 | H | H | H | Me | 2 | —(CH$_2$)$_6$-(4-MeS-Ph) | H | H |
| 1-234 | H | H | H | Me | 2 | —(CH$_2$)$_6$-(3-EtS-Ph) | H | H |
| 1-235 | H | H | H | Me | 2 | —(CH$_2$)$_6$-(4-EtS-Ph) | H | H |
| 1-236 | H | H | H | Me | 2 | —(CH$_2$)$_6$-(3-PrS-Ph) | H | H |
| 1-237 | H | H | H | Me | 2 | —(CH$_2$)$_6$-(4-PrS-Ph) | H | H |
| 1-238 | H | H | H | Me | 2 | —(CH$_2$)$_6$-(3-iPrS-Ph) | H | H |
| 1-239 | H | H | H | Me | 2 | —(CH$_2$)$_6$-(4-iPrS-Ph) | H | H |
| 1-240 | H | H | H | Me | 2 | —(CH$_2$)$_6$-[3-(2-Et-PrS)-Ph] | H | H |
| 1-241 | H | H | H | Me | 2 | —(CH$_2$)$_6$-[4-(2-Et-PrS)-Ph] | H | H |
| 1-242 | H | H | H | Me | 2 | —(CH$_2$)$_6$-(3-iBuS-Ph) | H | H |
| 1-243 | H | H | H | Me | 2 | —(CH$_2$)$_6$-(4-iBuS-Ph) | H | H |
| 1-244 | H | H | H | Me | 2 | —(CH$_2$)$_6$-(3-cHx-Ph) | H | H |
| 1-245 | H | H | H | Me | 2 | —(CH$_2$)$_6$-(4-cHx-Ph) | H | H |
| 1-246 | H | H | H | Me | 2 | —(CH$_2$)$_6$-(3-Ph-Ph) | H | H |
| 1-247 | H | H | H | Me | 2 | —(CH$_2$)$_6$-(4-Ph-Ph) | H | H |
| 1-248 | H | H | H | Me | 2 | —(CH$_2$)$_6$-(2,4-diMe-Ph) | H | H |
| 1-249 | H | H | H | Me | 2 | —(CH$_2$)$_6$-(3,4-diMe-Ph) | H | H |
| 1-250 | H | H | H | Me | 2 | —(CH$_2$)$_6$-(3,5-diMe-Ph) | H | H |
| 1-251 | H | H | H | Me | 2 | —(CH$_2$)$_6$-Np (1) | H | H |
| 1-252 | H | H | H | Me | 2 | —(CH$_2$)$_6$-Np (2) | H | H |
| 1-253 | H | H | H | Me | 2 | —(CH$_2$)$_7$-cHx | H | H |
| 1-254 | H | H | H | Me | 2 | —(CH$_2$)$_7$-(4-F-cHx) | H | H |
| 1-255 | H | H | H | Me | 2 | —(CH$_2$)$_7$-(4-Me-cHx) | H | H |

TABLE 1-continued

| | | | | | | | |
|---|---|---|---|---|---|---|---|
| 1-256 | H | H | H | Me 2 | —(CH$_2$)$_7$-(4-Et-cHx) | H | H |
| 1-257 | H | H | H | Me 2 | —(CH$_2$)$_7$-(4-CF$_3$-cHx) | H | H |
| 1-258 | H | H | H | Me 2 | —(CH$_2$)$_7$-(4-MeO-cHx) | H | H |
| 1-259 | H | H | H | Me 2 | —(CH$_2$)$_7$-(4-EtO-cHx) | H | H |
| 1-260 | H | H | H | Me 2 | —(CH$_2$)$_7$-(4-MeS-cHx) | H | H |
| 1-261 | H | H | H | Me 2 | —(CH$_2$)$_7$-(4-cHx-cHx) | H | H |
| 1-262 | H | H | H | Me 2 | —(CH$_2$)$_7$-(4-Ph-cHx) | H | H |
| 1-263 | H | H | H | Me 2 | —(CH$_2$)$_7$-Ph | H | H |
| 1-264 | H | H | H | Me 2 | —(CH$_2$)$_7$-(4-F-Ph) | H | H |
| 1-265 | H | H | H | Me 2 | —(CH$_2$)$_7$-(4-Me-Ph) | H | H |
| 1-266 | H | H | H | Me 2 | —(CH$_2$)$_7$-(4-Et-Ph) | H | H |
| 1-267 | H | H | H | Me 2 | —(CH$_2$)$_7$-(4-CF$_3$-Ph) | H | H |
| 1-268 | H | H | H | Me 2 | —(CH$_2$)$_7$-(4-MeO-Ph) | H | H |
| 1-269 | H | H | H | Me 2 | —(CH$_2$)$_7$-(4-EtO-Ph) | H | H |
| 1-270 | H | H | H | Me 2 | —(CH$_2$)$_7$-(4-MeS-Ph) | H | H |
| 1-271 | H | H | H | Me 2 | —(CH$_2$)$_7$-(4-cHx-Ph) | H | H |
| 1-272 | H | H | H | Me 2 | —(CH$_2$)$_7$-(4-Ph-Ph) | H | H |
| 1-273 | H | H | H | Me 2 | —(CH$_2$)$_3$—O-cHx | H | H |
| 1-274 | H | H | H | Me 2 | —(CH$_2$)$_3$—O-(4-F-cHx) | H | H |
| 1-275 | H | H | H | Me 2 | —(CH$_2$)$_3$—O-(4-Me-cHx) | H | H |
| 1-276 | H | H | H | Me 2 | —(CH$_2$)$_3$—O-(4-Et-cHx) | H | H |
| 1-277 | H | H | H | Me 2 | —(CH$_2$)$_3$—O-(4-CF$_3$-cHx) | H | H |
| 1-278 | H | H | H | Me 2 | —(CH$_2$)$_3$—O-(4-MeO-cHx) | H | H |
| 1-279 | H | H | H | Me 2 | —(CH$_2$)$_3$—O-(4-EtO-cHx) | H | H |
| 1-280 | H | H | H | Me 2 | —(CH$_2$)$_3$—O-(4-MeS-cHx) | H | H |
| 1-281 | H | H | H | Me 2 | —(CH$_2$)$_3$—O-(4-cHx-cHx) | H | H |
| 1-282 | H | H | H | Me 2 | —(CH$_2$)$_3$—O-(4-Ph-cHx) | H | H |
| 1-283 | H | H | H | Me 2 | —(CH$_2$)$_3$—O-Ph | H | H |
| 1-284 | H | H | H | Me 2 | —(CH$_2$)$_3$—O-(4-F-Ph) | H | H |
| 1-285 | H | H | H | Me 2 | —(CH$_2$)$_3$—O-(4-Me-Ph) | H | H |
| 1-286 | H | H | H | Me 2 | —(CH$_2$)$_3$—O-(4-Et-Ph) | H | H |
| 1-287 | H | H | H | Me 2 | —(CH$_2$)$_3$—O-(4-CF$_3$-Ph) | H | H |
| 1-288 | H | H | H | Me 2 | —(CH$_2$)$_3$—O-(4-MeO-Ph) | H | H |
| 1-289 | H | H | H | Me 2 | —(CH$_2$)$_3$—O-(4-EtO-Ph) | H | H |
| 1-290 | H | H | H | Me 2 | —(CH$_2$)$_3$—O-(4-MeS-Ph) | H | H |
| 1-291 | H | H | H | Me 2 | —(CH$_2$)$_3$—O-(4-cHx-Ph) | H | H |
| 1-292 | H | H | H | Me 2 | —(CH$_2$)$_3$—O-(4-Ph-Ph) | H | H |
| 1-293 | H | H | H | Me 2 | —(CH$_2$)$_4$—O-cPn | H | H |
| 1-294 | H | H | H | Me 2 | —(CH$_2$)$_4$—O-cHx | H | H |
| 1-295 | H | H | H | Me 2 | —(CH$_2$)$_4$—O-cHx | Me | H |
| 1-296 | H | H | H | Me 2 | —(CH$_2$)$_4$—O-cHx | H | Me |
| 1-297 | H | H | H | Me 2 | —(CH$_2$)$_4$—O-cHx | F | H |
| 1-298 | H | H | H | Me 2 | —(CH$_2$)$_4$—O-cHx | H | F |
| 1-299 | H | H | H | Me 2 | —(CH$_2$)$_4$—O-(3-F-cHx) | H | H |
| 1-300 | H | H | H | Me 2 | —(CH$_2$)$_4$—O-(4-F-cHx) | H | H |
| 1-301 | H | H | H | Me 2 | —(CH$_2$)$_4$—O-(4-Cl-cHx) | H | H |
| 1-302 | H | H | H | Me 2 | —(CH$_2$)$_4$—O-(4-Br-cHx) | H | H |
| 1-303 | H | H | H | Me 2 | —(CH$_2$)$_4$—O-(3-Me-cHx) | H | H |
| 1-304 | H | H | H | Me 2 | —(CH$_2$)$_4$—O-(4-Me-cHx) | H | H |
| 1-305 | H | H | H | Me 2 | —(CH$_2$)$_4$—O-(3-Et-cHx) | H | H |
| 1-306 | H | H | H | Me 2 | —(CH$_2$)$_4$—O-(4-Et-cHx) | H | H |
| 1-307 | H | H | H | Me 2 | —(CH$_2$)$_4$—O-(3-Pr-cHx) | H | H |
| 1-308 | H | H | H | Me 2 | —(CH$_2$)$_4$—O-(4-Pr-cHx) | H | H |
| 1-309 | H | H | H | Me 2 | —(CH$_2$)$_4$—O-(4-iPr-cHx) | H | H |
| 1-310 | H | H | H | Me 2 | —(CH$_2$)$_4$—O-(3-Bu-cHx) | H | H |
| 1-311 | H | H | H | Me 2 | —(CH$_2$)$_4$—O-(4-Bu-cHx) | H | H |
| 1-312 | H | H | H | Me 2 | —(CH$_2$)$_4$—O-(3-CF$_3$-cHx) | H | H |
| 1-313 | H | H | H | Me 2 | —(CH$_2$)$_4$—O-(4-CF$_3$-cHx) | H | H |
| 1-314 | H | H | H | Me 2 | —(CH$_2$)$_4$—O-(3-MeO-cHx) | H | H |
| 1-315 | H | H | H | Me 2 | —(CH$_2$)$_4$—O-(4-MeO-cHx) | H | H |
| 1-316 | H | H | H | Me 2 | —(CH$_2$)$_4$—O-(3-EtO-cHx) | H | H |
| 1-317 | H | H | H | Me 2 | —(CH$_2$)$_4$—O-(4-EtO-cHx) | H | H |
| 1-318 | H | H | H | Me 2 | —(CH$_2$)$_4$—O-(3-PrO-cHx) | H | H |
| 1-319 | H | H | H | Me 2 | —(CH$_2$)$_4$—O-(4-PrO-cHx) | H | H |
| 1-320 | H | H | H | Me 2 | —(CH$_2$)$_4$—O-(3-iPrO-cHx) | H | H |
| 1-321 | H | H | H | Me 2 | —(CH$_2$)$_4$—O-(4-iPrO-cHx) | H | H |
| 1-322 | H | H | H | Me 2 | —(CH$_2$)$_4$—O-[3-(2-Et-PrO)-cHx] | H | H |
| 1-323 | H | H | H | Me 2 | —(CH$_2$)$_4$—O-[4-(2-Et-PrO)-cHx] | H | H |
| 1-324 | H | H | H | Me 2 | —(CH$_2$)$_4$—O-(3-iBuO-cHx) | H | H |
| 1-325 | H | H | H | Me 2 | —(CH$_2$)$_4$—O-(4-iBuO-cHx) | H | H |
| 1-326 | H | H | H | Me 2 | —(CH$_2$)$_4$—O-(3-MeS-cHx) | H | H |
| 1-327 | H | H | H | Me 2 | —(CH$_2$)$_4$—O-(4-MeS-cHx) | H | H |
| 1-328 | H | H | H | Me 2 | —(CH$_2$)$_4$—O-(3-EtS-cHx) | H | H |
| 1-329 | H | H | H | Me 2 | —(CH$_2$)$_4$—O-(4-EtS-cHx) | H | H |
| 1-330 | H | H | H | Me 2 | —(CH$_2$)$_4$—O-(3-PrS-cHx) | H | H |
| 1-331 | H | H | H | Me 2 | —(CH$_2$)$_4$—O-(4-PrS-cHx) | H | H |
| 1-332 | H | H | H | Me 2 | —(CH$_2$)$_4$—O-(3-iPrS-cHx) | H | H |
| 1-333 | H | H | H | Me 2 | —(CH$_2$)$_4$—O-(4-iPrS-cHx) | H | H |
| 1-334 | H | H | H | Me 2 | —(CH$_2$)$_4$—O-[3-(2-Et-PrS)-cHx] | H | H |
| 1-335 | H | H | H | Me 2 | —(CH$_2$)$_4$—O-[4-(2-Et-PrS)-cHx] | H | H |

TABLE 1-continued

| | | | | | | | |
|---|---|---|---|---|---|---|---|
| 1-336 | H | H | H | Me 2 | —(CH$_2$)$_4$—O-(3-iBuS-cHx) | H | H |
| 1-337 | H | H | H | Me 2 | —(CH$_2$)$_4$—O-(4-iBuS-cHx) | H | H |
| 1-338 | H | H | H | Me 2 | —(CH$_2$)$_4$—O-(3-cHx-cHx) | H | H |
| 1-339 | H | H | H | Me 2 | —(CH$_2$)$_4$—O-(4-cHx-cHx) | H | H |
| 1-340 | H | H | H | Me 2 | —(CH$_2$)$_4$—O-(3-Ph-cHx) | H | H |
| 1-341 | H | H | H | Me 2 | —(CH$_2$)$_4$—O-(4-Ph-cHx) | H | H |
| 1-342 | H | H | H | Me 2 | —(CH$_2$)$_4$—O-(2,4-diMe-cHx) | H | H |
| 1-343 | H | H | H | Me 2 | —(CH$_2$)$_4$—O-(3,4-diMe-cHx) | H | H |
| 1-344 | H | H | H | Me 2 | —(CH$_2$)$_4$—O-(3,5-diMe-cHx) | H | H |
| 1-345 | H | H | H | Me 2 | —(CH$_2$)$_4$—O-Ph | H | H |
| 1-346 | H | H | H | Me 2 | —(CH$_2$)$_4$—O-Ph | Me | H |
| 1-347 | H | H | H | Me 2 | —(CH$_2$)$_4$—O-Ph | H | Me |
| 1-348 | H | H | H | Me 2 | —(CH$_2$)$_4$—O-Ph | F | H |
| 1-349 | H | H | H | Me 2 | —(CH$_2$)$_4$—O-Ph | H | F |
| 1-350 | H | H | H | Me 2 | —(CH$_2$)$_4$—O-(3-F-Ph) | H | H |
| 1-351 | H | H | H | Me 2 | —(CH$_2$)$_4$—O-(4-F-Ph) | H | H |
| 1-352 | H | H | H | Me 2 | —(CH$_2$)$_4$—O-(4-Cl-Ph) | H | H |
| 1-353 | H | H | H | Me 2 | —(CH$_2$)$_4$—O-(4-Br-Ph) | H | H |
| 1-354 | H | H | H | Me 2 | —(CH$_2$)$_4$—O-(3-Me-Ph) | H | H |
| 1-355 | H | H | H | Me 2 | —(CH$_2$)$_4$—O-(4-Me-Ph) | H | H |
| 1-356 | H | H | H | Me 2 | —(CH$_2$)$_4$—O-(3-Et-Ph) | H | H |
| 1-357 | H | H | H | Me 2 | —(CH$_2$)$_4$—O-(4-Et-Ph) | H | H |
| 1-358 | H | H | H | Me 2 | —(CH$_2$)$_4$—O-(3-Pr-Ph) | H | H |
| 1-359 | H | H | H | Me 2 | —(CH$_2$)$_4$—O-(4-Pr-Ph) | H | H |
| 1-360 | H | H | H | Me 2 | —(CH$_2$)$_4$—O-(3-iPr-Ph) | H | H |
| 1-361 | H | H | H | Me 2 | —(CH$_2$)$_4$—O-(4-iPr-Ph) | H | H |
| 1-362 | H | H | H | Me 2 | —(CH$_2$)$_4$—O-(3-Bu-Ph) | H | H |
| 1-363 | H | H | H | Me 2 | —(CH$_2$)$_4$—O-(4-Bu-Ph) | H | H |
| 1-364 | H | H | H | Me 2 | —(CH$_2$)$_4$—O-(3-CF$_3$-Ph) | H | H |
| 1-365 | H | H | H | Me 2 | —(CH$_2$)$_4$—O-(4-CF$_3$-Ph) | H | H |
| 1-366 | H | H | H | Me 2 | —(CH$_2$)$_4$—O-(3-MeO-Ph) | H | H |
| 1-367 | H | H | H | Me 2 | —(CH$_2$)$_4$—O-(4-MeO-Ph) | H | H |
| 1-368 | H | H | H | Me 2 | —(CH$_2$)$_4$—O-(3-EtO-Ph) | H | H |
| 1-369 | H | H | H | Me 2 | —(CH$_2$)$_4$—O-(4-EtO-Ph) | H | H |
| 1-370 | H | H | H | Me 2 | —(CH$_2$)$_4$—O-(3-PrO-Ph) | H | H |
| 1-371 | H | H | H | Me 2 | —(CH$_2$)$_4$—O-(4-PrO-Ph) | H | H |
| 1-372 | H | H | H | Me 2 | —(CH$_2$)$_4$—O-(3-iPrO-Ph) | H | H |
| 1-373 | H | H | H | Me 2 | —(CH$_2$)$_4$—O-(4-iPrO-Ph) | H | H |
| 1-374 | H | H | H | Me 2 | —(CH$_2$)$_4$—O-[3-(2-Et-PrO)-Ph] | H | H |
| 1-375 | H | H | H | Me 2 | —(CH$_2$)$_4$—O-[4-(2-Et-PrO)-Ph] | H | H |
| 1-376 | H | H | H | Me 2 | —(CH$_2$)$_4$—O-(3-iBuO-Ph) | H | H |
| 1-377 | H | H | H | Me 2 | —(CH$_2$)$_4$—O-(4-iBuO-Ph) | H | H |
| 1-378 | H | H | H | Me 2 | —(CH$_2$)$_4$—O-(3-MeS-Ph) | H | H |
| 1-379 | H | H | H | Me 2 | —(CH$_2$)$_4$—O-(4-MeS-Ph) | H | H |
| 1-380 | H | H | H | Me 2 | —(CH$_2$)$_4$—O-(3-EtS-Ph) | H | H |
| 1-381 | H | H | H | Me 2 | —(CH$_2$)$_4$—O-(4-EtS-Ph) | H | H |
| 1-382 | H | H | H | Me 2 | —(CH$_2$)$_4$—O-(3-PrS-Ph) | H | H |
| 1-383 | H | H | H | Me 2 | —(CH$_2$)$_4$—O-(4-PrS-Ph) | H | H |
| 1-384 | H | H | H | Me 2 | —(CH$_2$)$_4$—O-(3-iPrS-Ph) | H | H |
| 1-385 | H | H | H | Me 2 | —(CH$_2$)$_4$—O-(4-iPrS-Ph) | H | H |
| 1-386 | H | H | H | Me 2 | —(CH$_2$)$_4$—O-[3-(2-Et-PrS)-Ph] | H | H |
| 1-387 | H | H | H | Me 2 | —(CH$_2$)$_4$—O-[4-(2-Et-PrS)-Ph] | H | H |
| 1-388 | H | H | H | Me 2 | —(CH$_2$)$_4$—O-(3-iBuS-Ph) | H | H |
| 1-389 | H | H | H | Me 2 | —(CH$_2$)$_4$—O-(4-iBuS-Ph) | H | H |
| 1-390 | H | H | H | Me 2 | —(CH$_2$)$_4$—O-(3-cHx-Ph) | H | H |
| 1-391 | H | H | H | Me 2 | —(CH$_2$)$_4$—O-(4-cHx-Ph) | H | H |
| 1-392 | H | H | H | Me 2 | —(CH$_2$)$_4$—O-(3-Ph-Ph) | H | H |
| 1-393 | H | H | H | Me 2 | —(CH$_2$)$_4$—O-(4-Ph-Ph) | H | H |
| 1-394 | H | H | H | Me 2 | —(CH$_2$)$_4$—O-(2,4-diMe-Ph) | H | H |
| 1-395 | H | H | H | Me 2 | —(CH$_2$)$_4$—O-(3,4-diMe-Ph) | H | H |
| 1-396 | H | H | H | Me 2 | —(CH$_2$)$_4$—O-(3,5-diMe-Ph) | H | H |
| 1-397 | H | H | H | Me 2 | —(CH$_2$)$_5$—O-cHx | H | H |
| 1-398 | H | H | H | Me 2 | —(CH$_2$)$_5$—O-Ph | H | H |
| 1-399 | H | H | H | Me 2 | —(CH$_2$)$_6$—O-cHx | H | H |
| 1-400 | H | H | H | Me 2 | —(CH$_2$)$_6$—O-Ph | H | H |
| 1-401 | H | H | H | Me 2 | —(CH$_2$)$_3$—OCH$_2$-cHx | H | H |
| 1-402 | H | H | H | Me 2 | —(CH$_2$)$_3$—OCH$_2$-(4-F-cHx) | H | H |
| 1-403 | H | H | H | Me 2 | —(CH$_2$)$_3$—OCH$_2$-(4-Me-cHx) | H | H |
| 1-404 | H | H | H | Me 2 | —(CH$_2$)$_3$—OCH$_2$-(4-Et-cHx) | H | H |
| 1-405 | H | H | H | Me 2 | —(CH$_2$)$_3$—OCH$_2$-(4-CF$_3$-cHx) | H | H |
| 1-406 | H | H | H | Me 2 | —(CH$_2$)$_3$—OCH$_2$-(4-MeO-cHx) | H | H |
| 1-407 | H | H | H | Me 2 | —(CH$_2$)$_3$—OCH$_2$-(4-EtO-cHx) | H | H |
| 1-408 | H | H | H | Me 2 | —(CH$_2$)$_3$—OCH$_2$-(4-MeS-cHx) | H | H |
| 1-409 | H | H | H | Me 2 | —(CH$_2$)$_3$—OCH$_2$-(4-cHx-cHx) | H | H |
| 1-410 | H | H | H | Me 2 | —(CH$_2$)$_3$—OCH$_2$-(4-Ph-cHx) | H | H |
| 1-411 | H | H | H | Me 2 | —(CH$_2$)$_3$—OCH$_2$-Ph | H | H |
| 1-412 | H | H | H | Me 2 | —(CH$_2$)$_3$—OCH$_2$-(4-F-Ph) | H | H |
| 1-413 | H | H | H | Me 2 | —(CH$_2$)$_3$—OCH$_2$-(4-Me-Ph) | H | H |
| 1-414 | H | H | H | Me 2 | —(CH$_2$)$_3$—OCH$_2$-(4-Et-Ph) | H | H |
| 1-415 | H | H | H | Me 2 | —(CH$_2$)$_3$—OCH$_2$-(4-CF$_3$-Ph) | H | H |

TABLE 1-continued

| | | | | | | | |
|---|---|---|---|---|---|---|---|
| 1-416 | H | H | H | Me 2 | —(CH$_2$)$_3$—OCH$_2$-(4-MeO-Ph) | H | H |
| 1-417 | H | H | H | Me 2 | —(CH$_2$)$_3$—OCH$_2$-(4-EtO-Ph) | H | H |
| 1-418 | H | H | H | Me 2 | —(CH$_2$)$_3$—OCH$_2$-(4-MeS-Ph) | H | H |
| 1-419 | H | H | H | Me 2 | —(CH$_2$)$_3$—OCH$_2$-(4-cHx-Ph) | H | H |
| 1-420 | H | H | H | Me 2 | —(CH$_2$)$_3$—OCH$_2$-(4-Ph-Ph) | H | H |
| 1-421 | H | H | H | Me 2 | —(CH$_2$)$_4$—OCH$_2$-cPn | H | H |
| 1-422 | H | H | H | Me 2 | —(CH$_2$)$_4$—OCH$_2$-cHx | H | H |
| 1-423 | H | H | H | Me 2 | —(CH$_2$)$_4$—OCH$_2$-cRx | Me | H |
| 1-424 | H | H | H | Me 2 | —(CH$_2$)$_4$—OCH$_2$-cHx | H | Me |
| 1-425 | H | H | H | Me 2 | —(CH$_2$)$_4$—OCH$_2$-cRx | F | H |
| 1-426 | H | H | H | Me 2 | —(CH$_2$)$_4$—OCH$_2$-cHx | H | F |
| 1-427 | H | H | H | Me 2 | —(CH$_2$)$_4$—OCH$_2$-(3-F-cHx) | H | H |
| 1-428 | H | H | H | Me 2 | —(CH$_2$)$_4$—OCH$_2$-(4-F-cHx) | H | H |
| 1-429 | H | H | H | Me 2 | —(CH$_2$)$_4$—OCH$_2$-(4-Cl-cHx) | H | H |
| 1-430 | H | H | H | Me 2 | —(CH$_2$)$_4$—OCH$_2$-(4-Br-cHx) | H | H |
| 1-431 | H | H | H | Me 2 | —(CH$_2$)$_4$—OCH$_2$-(3-Me-cHx) | H | H |
| 1-432 | H | H | H | Me 2 | —(CH$_2$)$_4$—OCH$_2$-(4-Me-cHx) | H | H |
| 1-433 | H | H | H | Me 2 | —(CH$_2$)$_4$—OCH$_2$-(3-Et-cHx) | H | H |
| 1-434 | H | H | H | Me 2 | —(CH$_2$)$_4$—OCH$_2$-(4-Et-cHx) | H | H |
| 1-435 | H | H | H | Me 2 | —(CH$_2$)$_4$—OCH$_2$-(3-Pr-cHx) | H | H |
| 1-436 | H | H | H | Me 2 | —(CH$_2$)$_4$—OCH$_2$-(4-Pr-cHx) | H | H |
| 1-437 | H | H | H | Me 2 | —(CH$_2$)$_4$—OCH$_2$-(4-iPr-cHx) | H | H |
| 1-438 | H | H | H | Me 2 | —(CH$_2$)$_4$—OCH$_2$-(3-Bu-cHx) | H | H |
| 1-439 | H | H | H | Me 2 | —(CH$_2$)$_4$—OCH$_2$-(4-Bu-cHx) | H | H |
| 1-440 | H | H | H | Me 2 | —(CH$_2$)$_4$—OCH$_2$-(3-CF$_3$-cHx) | H | H |
| 1-441 | H | H | H | Me 2 | —(CH$_2$)$_4$—OCH$_2$-(4-CF$_3$-cHx) | H | H |
| 1-442 | H | H | H | Me 2 | —(CH$_2$)$_4$—OCH$_2$-(3-MeO-cHx) | H | H |
| 1-443 | H | H | H | Me 2 | —(CH$_2$)$_4$—OCH$_2$-(4-MeO-cHx) | H | H |
| 1-444 | H | H | H | Me 2 | —(CH$_2$)$_4$—OCH$_2$-(3-EtO-cHx) | H | H |
| 1-445 | H | H | H | Me 2 | —(CH$_2$)$_4$—OCH$_2$-(4-EtO-cHx) | H | H |
| 1-446 | H | H | H | Me 2 | —(CH$_2$)$_4$—OCH$_2$-(3-PrO-cHx) | H | H |
| 1-447 | H | H | H | Me 2 | —(CH$_2$)$_4$—OCH$_2$-(4-PrO-cHx) | H | H |
| 1-448 | H | H | H | Me 2 | —(CH$_2$)$_4$—OCH$_2$-(3-iPrO-cHx) | H | H |
| 1-449 | H | H | H | Me 2 | —(CH$_2$)$_4$—OCH$_2$-(4-iPrO-cHx) | H | H |
| 1-450 | H | H | H | Me 2 | —(CH$_2$)$_4$—OCH$_2$-[3-(2-Et-PrO)-cHx] | H | H |
| 1-451 | H | H | H | Me 2 | —(CH$_2$)$_4$—OCH$_2$-[4-(2-Et-PrO)-cHx] | H | H |
| 1-452 | H | H | H | Me 2 | —(CH$_2$)$_4$—OCH$_2$-(3-iBuO-cHx) | H | H |
| 1-453 | H | H | H | Me 2 | —(CH$_2$)$_4$—OCH$_2$-(4-iBuO-cHx) | H | H |
| 1-454 | H | H | H | Me 2 | —(CH$_2$)$_4$—OCH$_2$-(3-MeS-cHx) | H | H |
| 1-455 | H | H | H | Me 2 | —(CH$_2$)$_4$—OCH$_2$-(4-MeS-cHx) | H | H |
| 1-456 | H | H | H | Me 2 | —(CH$_2$)$_4$—OCH$_2$-(3-EtS-cHx) | H | H |
| 1-457 | H | H | H | Me 2 | —(CH$_2$)$_4$—OCH$_2$-(4-EtS-cHx) | H | H |
| 1-458 | H | H | H | Me 2 | —(CH$_2$)$_4$—OCH$_2$-(3-PrS-cHx) | H | H |
| 1-459 | H | H | H | Me 2 | —(CH$_2$)$_4$—OCH$_2$-(4-PrS-cHx) | H | H |
| 1-460 | H | H | H | Me 2 | —(CH$_2$)$_4$—OCH$_2$-(3-iPrS-cHx) | H | H |
| 1-461 | H | H | H | Me 2 | —(CH$_2$)$_4$—OCH$_2$-(4-iPrS-cHx) | H | H |
| 1-462 | H | H | H | Me 2 | —(CH$_2$)$_4$—OCH$_2$-[3-(2-Et-PrS)-cHx] | H | H |
| 1-463 | H | H | H | Me 2 | —(CH$_2$)$_4$—OCH$_2$-[4-(2-Et-PrS)-cHx] | H | H |
| 1-464 | H | H | H | Me 2 | —(CH$_2$)$_4$—OCH$_2$-(3-iBuS-cHx) | H | H |
| 1-465 | H | H | H | Me 2 | —(CH$_2$)$_4$—OCH$_2$-(4-iBuS-cHx) | H | H |
| 1-466 | H | H | H | Me 2 | —(CH$_2$)$_4$—OCH$_2$-(3-cHx-cHx) | H | H |
| 1-467 | H | H | H | Me 2 | —(CH$_2$)$_4$—OCH$_2$-(4-cHx-cHx) | H | H |
| 1-468 | H | H | H | Me 2 | —(CH$_2$)$_4$—OCH$_2$-(3-Ph-cHx) | H | H |
| 1-469 | H | H | H | Me 2 | —(CH$_2$)$_4$—OCH$_2$-(4-Ph-cHx) | H | H |
| 1-470 | H | H | H | Me 2 | —(CH$_2$)$_4$—OCH$_2$-(2,4-diMe-cHx) | H | H |
| 1-471 | H | H | H | Me 2 | —(CH$_2$)$_4$—OCH$_2$-(3,4-diMe-cHx) | H | H |
| 1-472 | H | H | H | Me 2 | —(CH$_2$)$_4$—OCH$_2$-(3,5-diMe-cHx) | H | H |
| 1-473 | H | H | H | Me 2 | —(CH$_2$)$_4$—OCH$_2$-Ph | H | H |
| 1-474 | H | H | H | Me 2 | —(CH$_2$)$_4$—OCH$_2$-Ph | Me | H |
| 1-475 | H | H | H | Me 2 | —(CH$_2$)$_4$—OCH$_2$-Ph | H | Me |
| 1-476 | H | H | H | Me 2 | —(CH$_2$)$_4$—OCH$_2$-Ph | F | H |
| 1-477 | H | H | H | Me 2 | —(CH$_2$)$_4$—OCH$_2$-Ph | H | F |
| 1-478 | H | H | H | Me 2 | —(CH$_2$)$_4$—OCH$_2$-(3-F-Ph) | H | H |
| 1-479 | H | H | H | Me 2 | —(CH$_2$)$_4$—OCH$_2$-(4-F-Ph) | H | H |
| 1-480 | H | H | H | Me 2 | —(CH$_2$)$_4$—OCH$_2$-(4-Cl-Ph) | H | H |
| 1-481 | H | H | H | Me 2 | —(CH$_2$)$_4$—OCH$_2$-(4-Br-Ph) | H | H |
| 1-482 | H | H | H | Me 2 | —(CH$_2$)$_4$—OCH$_2$-(3-Me-Ph) | H | H |
| 1-483 | H | H | H | Me 2 | —(CH$_2$)$_4$—OCH$_2$-(4-Me-Ph) | H | H |
| 1-484 | H | H | H | Me 2 | —(CH$_2$)$_4$—OCH$_2$-(3-Et-Ph) | H | H |
| 1-485 | H | H | H | Me 2 | —(CH$_2$)$_4$—OCH$_2$-(4-Et-Ph) | H | H |
| 1-486 | H | H | H | Me 2 | —(CH$_2$)$_4$—OCH$_2$-(3-Pr-Ph) | H | H |
| 1-487 | H | H | H | Me 2 | —(CH$_2$)$_4$—OCH$_2$-(4-Pr-Ph) | H | H |
| 1-488 | H | H | H | Me 2 | —(CH$_2$)$_4$—OCH$_2$-(3-iPr-Ph) | H | H |
| 1-489 | H | H | H | Me 2 | —(CH$_2$)$_4$—OCH$_2$-(4-iPr-Ph) | H | H |
| 1-490 | H | H | H | Me 2 | —(CH$_2$)$_4$—OCH$_2$-(3-Bu-Ph) | H | H |
| 1-491 | H | H | H | Me 2 | —(CH$_2$)$_4$—OCH$_2$-(4-Bu-Ph) | H | H |
| 1-492 | H | H | H | Me 2 | —(CH$_2$)$_4$—OCH$_2$-(3-CF$_3$-Ph) | H | H |
| 1-493 | H | H | H | Me 2 | —(CH$_2$)$_4$—OCH$_2$-(4-CF$_3$-Ph) | H | H |
| 1-494 | H | H | H | Me 2 | —(CH$_2$)$_4$—OCH$_2$-(3-MeO-Ph) | H | H |
| 1-495 | H | H | H | Me 2 | —(CH$_2$)$_4$—OCH$_2$-(4-MeO-Ph) | H | H |

TABLE 1-continued

| | | | | | | | |
|---|---|---|---|---|---|---|---|
| 1-496 | H | H | H | Me 2 | —(CH$_2$)$_4$—OCH$_2$-(3-EtO-Ph) | H | H |
| 1-497 | H | H | H | Me 2 | —(CH$_2$)$_4$—OCH$_2$-(4-EtO-Ph) | H | H |
| 1-498 | H | H | H | Me 2 | —(CH$_2$)$_4$—OCH$_2$-(3-PrO-Ph) | H | H |
| 1-499 | H | H | H | Me 2 | —(CH$_2$)$_4$—OCH$_2$-(4-PrO-Ph) | H | H |
| 1-500 | H | H | H | Me 2 | —(CH$_2$)$_4$—OCH$_2$-(3-iPrO-Ph) | H | H |
| 1-501 | H | H | H | Me 2 | —(CH$_2$)$_4$—OCH$_2$-(4-iPrO-Ph) | H | H |
| 1-502 | H | H | H | Me 2 | —(CH$_2$)$_4$—OCH$_2$-[3-(2-Et-PrO)-Ph] | H | H |
| 1-503 | H | H | H | Me 2 | —(CH$_2$)$_4$—OCH$_2$-[4-(2-Et-PrO)-Ph] | H | H |
| 1-504 | H | H | H | Me 2 | —(CH$_2$)$_4$—OCH$_2$-(3-iBuO-Ph) | H | H |
| 1-505 | H | H | H | Me 2 | —(CH$_2$)$_4$—OCH$_2$-(4-iBuO-Ph) | H | H |
| 1-506 | H | H | H | Me 2 | —(CH$_2$)$_4$—OCH$_2$-(3-MeS-Ph) | H | H |
| 1-507 | H | H | H | Me 2 | —(CH$_2$)$_4$—OCH$_2$-(4-MeS-Ph) | H | H |
| 1-508 | H | H | H | Me 2 | —(CH$_2$)$_4$—OCH$_2$-(3-EtS-Ph) | H | H |
| 1-509 | H | H | H | Me 2 | —(CH$_2$)$_4$—OCH$_2$-(4-EtS-Ph) | H | H |
| 1-510 | H | H | H | Me 2 | —(CH$_2$)$_4$—OCH$_2$-(3-PrS-Ph) | H | H |
| 1-511 | H | H | H | Me 2 | —(CH$_2$)$_4$—OCH$_2$-(4-PrS-Ph) | H | H |
| 1-512 | H | H | H | Me 2 | —(CH$_2$)$_4$—OCH$_2$-(3-iPrS-Ph) | H | H |
| 1-513 | H | H | H | Me 2 | —(CH$_2$)$_4$—OCH$_2$-(4-iPrS-Ph) | H | H |
| 1-514 | H | H | H | Me 2 | —(CH$_2$)$_4$—OCH$_2$-[3-(2-Et-PrS)-Ph] | H | H |
| 1-515 | H | H | H | Me 2 | —(CH$_2$)$_4$—OCH$_2$-[4-(2-Et-PrS)-Ph] | H | H |
| 1-516 | H | H | H | Me 2 | —(CH$_2$)$_4$—OCH$_2$-(3-iBuS-Ph) | H | H |
| 1-517 | H | H | H | Me 2 | —(CH$_2$)$_4$—OCH$_2$-(4-iBuS-Ph) | H | H |
| 1-518 | H | H | H | Me 2 | —(CH$_2$)$_4$—OCH$_2$-(3-cHx-Ph) | H | H |
| 1-519 | H | H | H | Me 2 | —(CH$_2$)$_4$—OCH$_2$-(4-cHx-Ph) | H | H |
| 1-520 | H | H | H | Me 2 | —(CH$_2$)$_4$—OCH$_2$-(3-Ph-Ph) | H | H |
| 1-521 | H | H | H | Me 2 | —(CH$_2$)$_4$—OCH$_2$-(4-Ph-Ph) | H | H |
| 1-522 | H | H | H | Me 2 | —(CH$_2$)$_4$—OCH$_2$-(2,4-diMe-Ph) | H | H |
| 1-523 | H | H | H | Me 2 | —(CH$_2$)$_4$—OCH$_2$-(3,4-diMe-Ph) | H | H |
| 1-524 | H | H | H | Me 2 | —(CH$_2$)$_4$—OCH$_2$-(3,5-diMe-Ph) | H | H |
| 1-525 | H | H | H | Me 2 | —(CH$_2$)$_5$—OCH$_2$-cHx | H | H |
| 1-526 | H | H | H | Me 2 | —(CH$_2$)$_5$—OCH$_2$-Ph | H | H |
| 1-527 | H | H | H | Me 2 | —(CH$_2$)$_6$—OCH$_2$-cHx | H | H |
| 1-528 | H | H | H | Me 2 | —(CH$_2$)$_6$—OCH$_2$-Ph | H | H |
| 1-529 | H | H | H | Me 2 | —C≡C-cHx | H | H |
| 1-530 | H | H | H | Me 2 | —C≡C-(4-F-cHx) | H | H |
| 1-531 | H | H | H | Me 2 | —C≡C-(4-Me-cHx) | H | H |
| 1-532 | H | H | H | Me 2 | —C≡C-(4-Et-cHx) | H | H |
| 1-533 | H | H | H | Me 2 | —C≡C-(4-CF$_3$-cHx) | H | H |
| 1-534 | H | H | H | Me 2 | —C≡C-(4-MeO-cHx) | H | H |
| 1-535 | H | H | H | Me 2 | —C≡C-(4-EtO-cHx) | H | H |
| 1-536 | H | H | H | Me 2 | —C≡C-(4-MeS-cHx) | H | H |
| 1-537 | H | H | H | Me 2 | —C≡C-(4-cHx-cHx) | H | H |
| 1-538 | H | H | H | Me 2 | —C≡C-(4-Ph-cHx) | H | H |
| 1-539 | H | H | H | Me 2 | —C≡C-Ph | H | H |
| 1-540 | H | H | H | Me 2 | —C≡C-(4-F-Ph) | H | H |
| 1-541 | H | H | H | Me 2 | —C≡C-(4-Me-Ph) | H | H |
| 1-542 | H | H | H | Me 2 | —C≡C-(4-Pr-Ph) | H | H |
| 1-543 | H | H | H | Me 2 | —C≡C-(4-Bu-Ph) | H | H |
| 1-544 | H | H | H | Me 2 | —C≡C-(4-MeO-Ph) | H | H |
| 1-545 | H | H | H | Me 2 | —C≡C-(4-EtO-Ph) | H | H |
| 1-546 | H | H | H | Me 2 | —C≡C-(4-PrO-Ph) | H | H |
| 1-547 | H | H | H | Me 2 | —C≡C-(4-cHx-Ph) | H | H |
| 1-548 | H | H | H | Me 2 | —C≡C-(4-Ph-Ph) | H | H |
| 1-549 | H | H | H | Me 2 | —C≡C—(CH$_2$)$_2$-cHx | H | H |
| 1-550 | H | H | H | Me 2 | —C≡C—(CH$_2$)$_2$-(4-F-cHx) | H | H |
| 1-551 | H | H | H | Me 2 | —C≡C—(CH$_2$)$_2$-(4-Me-cHx) | H | H |
| 1-552 | H | H | H | Me 2 | —C≡C—(CH$_2$)$_2$-(4-Et-cHx) | H | H |
| 1-553 | H | H | H | Me 2 | —C≡C—(CH$_2$)$_2$-(4-CF$_3$-cHx) | H | H |
| 1-554 | H | H | H | Me 2 | —C≡C—(CH$_2$)$_2$-(4-MeO-cHx) | H | H |
| 1-555 | H | H | H | Me 2 | —C≡C—(CH$_2$)$_2$-(4-EtO-cHx) | H | H |
| 1-556 | H | H | H | Me 2 | —C≡C—(CH$_2$)$_2$-(4-MeS-cHx) | H | H |
| 1-557 | H | H | H | Me 2 | —C≡C—(CH$_2$)$_2$-(4-cHx-cHx) | H | H |
| 1-558 | H | H | H | Me 2 | —C≡C—(CH$_2$)$_2$-(4-Ph-cHx) | H | H |
| 1-559 | H | H | H | Me 2 | —C≡C—(CH$_2$)$_2$-Ph | H | H |
| 1-560 | H | H | H | Me 2 | —C≡C—(CH$_2$)$_2$-(4-F-Ph) | H | H |
| 1-561 | H | H | H | Me 2 | —C≡C—(CH$_2$)$_2$-(4-Me-Ph) | H | H |
| 1-562 | H | H | H | Me 2 | —C≡C—(CH$_2$)$_2$-(4-Et-Ph) | H | H |
| 1-563 | H | H | H | Me 2 | —C≡C—(CH$_2$)$_2$-(4-CF$_3$-Ph) | H | H |
| 1-564 | H | H | H | Me 2 | —C≡C—(CH$_2$)$_2$-(4-MeO-Ph) | H | H |
| 1-565 | H | H | H | Me 2 | —C≡C—(CH$_2$)$_2$-(4-EtO-Ph) | H | H |
| 1-566 | H | H | H | Me 2 | —C≡C—(CH$_2$)$_2$-(4-MeS-Ph) | H | H |
| 1-567 | H | H | H | Me 2 | —C≡C—(CH$_2$)$_2$-(4-cHx-Ph) | H | H |
| 1-568 | H | H | H | Me 2 | —C≡C—(CH$_2$)$_2$-(4-Ph-Ph) | H | H |
| 1-569 | H | H | H | Me 2 | —C≡C—(CH$_2$)$_3$-cPn | H | H |
| 1-570 | H | H | H | Me 2 | —C≡C—(CH$_2$)$_3$-cHx | H | H |
| 1-571 | H | H | H | Me 2 | —C≡C—(CH$_2$)$_3$-cHx | Me | H |
| 1-572 | H | H | H | Me 2 | —C≡C—(CH$_2$)$_3$-cHx | H | Me |
| 1-573 | H | H | H | Me 2 | —C≡C—(CH$_2$)$_3$-cHx | F | H |
| 1-574 | H | H | H | Me 2 | —C≡C—(CH$_2$)$_3$-cHx | H | F |
| 1-575 | H | H | H | Me 2 | —C≡C—(CH$_2$)$_3$-(3-F-cHx) | H | H |

TABLE 1-continued

| | | | | | | | | |
|---|---|---|---|---|---|---|---|---|
| 1-576 | H | H | H | Me | 2 | —C≡C—(CH$_2$)$_3$-(4-F-cHx) | H | H |
| 1-577 | H | H | H | Me | 2 | —C≡C—(CH$_2$)$_3$-(4-Cl-cHx) | H | H |
| 1-578 | H | H | H | Me | 2 | —C≡C—(CH$_2$)$_3$-(4-Br-cHx) | H | H |
| 1-579 | H | H | H | Me | 2 | —C≡C—(CH$_2$)$_3$-(3-Me-cHx) | H | H |
| 1-580 | H | H | H | Me | 2 | —C≡C—(CH$_2$)$_3$-(4-Me-cHx) | H | H |
| 1-581 | H | H | H | Me | 2 | —C≡C—(CH$_2$)$_3$-(3-Et-cHx) | H | H |
| 1-582 | H | H | H | Me | 2 | —C≡C—(CH$_2$)$_3$-(4-Et-cHx) | H | H |
| 1-583 | H | H | H | Me | 2 | —C≡C—(CH$_2$)$_3$-(3-Pr-cHx) | H | H |
| 1-584 | H | H | H | Me | 2 | —C≡C—(CH$_2$)$_3$-(4-Pr-cHx) | H | H |
| 1-585 | H | H | H | Me | 2 | —C≡C—(CH$_2$)$_3$-(4-iPr-cHx) | H | H |
| 1-586 | H | H | H | Me | 2 | —C≡C—(CH$_2$)$_3$-(3-Bu-cHx) | H | H |
| 1-587 | H | H | H | Me | 2 | —C≡C—(CH$_2$)$_3$-(4-Bu-cHx) | H | H |
| 1-588 | H | H | H | Me | 2 | —C≡C—(CH$_2$)$_3$-(3-CF$_3$-cHx) | H | H |
| 1-589 | H | H | H | Me | 2 | —C≡C—(CH$_2$)$_3$-(4-CF$_3$-cHx) | H | H |
| 1-590 | H | H | H | Me | 2 | —C≡C—(CH$_2$)$_3$-(3-MeO-cHx) | H | H |
| 1-591 | H | H | H | Me | 2 | —C≡C—(CH$_2$)$_3$-(4-MeO-cHx) | H | H |
| 1-592 | H | H | H | Me | 2 | —C≡C—(CH$_2$)$_3$-(3-EtO-cHx) | H | H |
| 1-593 | H | H | H | Me | 2 | —C≡C—(CH$_2$)$_3$-(4-EtO-cHx) | H | H |
| 1-594 | H | H | H | Me | 2 | —C≡C—(CH$_2$)$_3$-(3-PrO-cHx) | H | H |
| 1-595 | H | H | H | Me | 2 | —C≡C—(CH$_2$)$_3$-(4-PrO-cHx) | H | H |
| 1-596 | H | H | H | Me | 2 | —C≡C—(CH$_2$)$_3$-(3-iPrO-cHx) | H | H |
| 1-597 | H | H | H | Me | 2 | —C≡C—(CH$_2$)$_3$-(4-iPrO-cHx) | H | H |
| 1-598 | H | H | H | Me | 2 | —C≡C—(CH$_2$)$_3$-[3-(2-Et-PrO)-cHx] | H | H |
| 1-599 | H | H | H | Me | 2 | —C≡C—(CH$_2$)$_3$-[4-(2-Et-PrO)-cHx] | H | H |
| 1-600 | H | H | H | Me | 2 | —C≡C—(CH$_2$)$_3$-(3-iBuO-cHx) | H | H |
| 1-601 | H | H | H | Me | 2 | —C≡C—(CH$_2$)$_3$-(4-iBuO-cHx) | H | H |
| 1-602 | H | H | H | Me | 2 | —C≡C—(CH$_2$)$_3$-(3-MeS-cHx) | H | H |
| 1-603 | H | H | H | Me | 2 | —C≡C—(CH$_2$)$_3$-(4-MeS-cHx) | H | H |
| 1-604 | H | H | H | Me | 2 | —C≡C—(CH$_2$)$_3$-(3-EtS-cHx) | H | H |
| 1-605 | H | H | H | Me | 2 | —C≡C—(CH$_2$)$_3$-(4-EtS-cHx) | H | H |
| 1-606 | H | H | H | Me | 2 | —C≡C—(CH$_2$)$_3$-(3-PrS-cHx) | H | H |
| 1-607 | H | H | H | Me | 2 | —C≡C—(CH$_2$)$_3$-(4-PrS-cHx) | H | H |
| 1-608 | H | H | H | Me | 2 | —C≡C—(CH$_2$)$_3$-(3-iPrS-cHx) | H | H |
| 1-609 | H | H | H | Me | 2 | —C≡C—(CH$_2$)$_3$-(4-iPrS-cHx) | H | H |
| 1-610 | H | H | H | Me | 2 | —C≡C—(CH$_2$)$_3$-[3-(2-Et-PrS)-cHx] | H | H |
| 1-611 | H | H | H | Me | 2 | —C≡C—(CH$_2$)$_3$-[4-(2-Et-PrS)-cHx] | H | H |
| 1-612 | H | H | H | Me | 2 | —C≡C—(CH$_2$)$_3$-(3-iBuS-cHx) | H | H |
| 1-613 | H | H | H | Me | 2 | —C≡C—(CH$_2$)$_3$-(4-iBuS-cHx) | H | H |
| 1-614 | H | H | H | Me | 2 | —C≡C—(CH$_2$)$_3$-(3-cHx-cHx) | H | H |
| 1-615 | H | H | H | Me | 2 | —C≡C—(CH$_2$)$_3$-(4-cHx-cHx) | H | H |
| 1-616 | H | H | H | Me | 2 | —C≡C—(CH$_2$)$_3$-(3-Ph-cHx) | H | H |
| 1-617 | H | H | H | Me | 2 | —C≡C—(CH$_2$)$_3$-(4-Ph-cHx) | H | H |
| 1-618 | H | H | H | Me | 2 | —C≡C—(CH$_2$)$_3$-(2,4-diMe-cHx) | H | H |
| 1-619 | H | H | H | Me | 2 | —C≡C—(CH$_2$)$_3$-(3,4-diMe-cHx) | H | H |
| 1-620 | H | H | H | Me | 2 | —C≡C—(CH$_2$)$_3$-(3,5-diMe-cHx) | H | H |
| 1-621 | H | H | H | Me | 2 | —C≡C—(CH$_2$)$_3$-Ph | H | H |
| 1-622 | H | H | H | Me | 2 | —C≡C—(CH$_2$)$_3$-Ph | Me | H |
| 1-623 | H | H | H | Me | 2 | —C≡C—(CH$_2$)$_3$-Ph | H | Me |
| 1-624 | H | H | H | Me | 2 | —C≡C—(CH$_2$)$_3$-Ph | F | H |
| 1-625 | H | H | H | Me | 2 | —C≡C—(CH$_2$)$_3$-Ph | H | F |
| 1-626 | H | H | H | Me | 2 | —C≡C—(CH$_2$)$_3$-(3-F-Ph) | H | H |
| 1-627 | H | H | H | Me | 2 | —C≡C—(CH$_2$)$_3$-(4-F-Ph) | H | H |
| 1-628 | H | H | H | Me | 2 | —C≡C—(CH$_2$)$_3$-(4-Cl-Ph) | H | H |
| 1-629 | H | H | H | Me | 2 | —C≡C—(CH$_2$)$_3$-(4-Br-Ph) | H | H |
| 1-630 | H | H | H | Me | 2 | —C≡C—(CH$_2$)$_3$-(3-Me-Ph) | H | H |
| 1-631 | H | H | H | Me | 2 | —C≡C—(CH$_2$)$_3$-(4-Me-Ph) | H | H |
| 1-632 | H | H | H | Me | 2 | —C≡C—(CH$_2$)$_3$-(3-Et-Ph) | H | H |
| 1-633 | H | H | H | Me | 2 | —C≡C—(CH$_2$)$_3$-(4-Et-Ph) | H | H |
| 1-634 | H | H | H | Me | 2 | —C≡C—(CH$_2$)$_3$-(3-Pr-Ph) | H | H |
| 1-635 | H | H | H | Me | 2 | —C≡C—(CH$_2$)$_3$-(4-Pr-Ph) | H | H |
| 1-636 | H | H | H | Me | 2 | —C≡C—(CH$_2$)$_3$-(3-iPr-Ph) | H | H |
| 1-637 | H | H | H | Me | 2 | —C≡C—(CH$_2$)$_3$-(4-iPr-Ph) | H | H |
| 1-638 | H | H | H | Me | 2 | —C≡C—(CH$_2$)$_3$-(3-Bu-Ph) | H | H |
| 1-639 | H | H | H | Me | 2 | —C≡C—(CH$_2$)$_3$-(4-Bu-Ph) | H | H |
| 1-640 | H | H | H | Me | 2 | —C≡C—(CH$_2$)$_3$-(3-CF$_3$-Ph) | H | H |
| 1-641 | H | H | H | Me | 2 | —C≡C—(CH$_2$)$_3$-(4-CF$_3$-Ph) | H | H |
| 1-642 | H | H | H | Me | 2 | —C≡C—(CH$_2$)$_3$-(3-MeO-Ph) | H | H |
| 1-643 | H | H | H | Me | 2 | —C≡C—(CH$_2$)$_3$-(4-MeO-Ph) | H | H |
| 1-644 | H | H | H | Me | 2 | —C≡C—(CH$_2$)$_3$-(3-EtO-Ph) | H | H |
| 1-645 | H | H | H | Me | 2 | —C≡C—(CH$_2$)$_3$-(4-EtO-Ph) | H | H |
| 1-646 | H | H | H | Me | 2 | —C≡C—(CH$_2$)$_3$-(3-PrO-Ph) | H | H |
| 1-647 | H | H | H | Me | 2 | —C≡C—(CH$_2$)$_3$-(4-PrO-Ph) | H | H |
| 1-648 | H | H | H | Me | 2 | —C≡C—(CH$_2$)$_3$-(3-iPrO-Ph) | H | H |
| 1-649 | H | H | H | Me | 2 | —C≡C—(CH$_2$)$_3$-(4-iPrO-Ph) | H | H |
| 1-650 | H | H | H | Me | 2 | —C≡C—(CH$_2$)$_3$-[3-(2-Et-PrO)-Ph] | H | H |
| 1-651 | H | H | H | Me | 2 | —C≡C—(CH$_2$)$_3$-[4-(2-Et-PrO)-Ph] | H | H |
| 1-652 | H | H | H | Me | 2 | —C≡C—(CH$_2$)$_3$-(3-iBuO-Ph) | H | H |
| 1-653 | H | H | H | Me | 2 | —C≡C—(CH$_2$)$_3$-(4-iBuO-Ph) | H | H |
| 1-654 | H | H | H | Me | 2 | —C≡C—(CH$_2$)$_3$-(3-MeS-Ph) | H | H |
| 1-655 | H | H | H | Me | 2 | —C≡C—(CH$_2$)$_3$-(4-MeS-Ph) | H | H |

TABLE 1-continued

| | | | | | | | |
|---|---|---|---|---|---|---|---|
| 1-656 | H | H | H | Me | 2 | —C≡C—(CH$_2$)$_3$-(3-EtS-Ph) | H | H |
| 1-657 | H | H | H | Me | 2 | —C≡C—(CH$_2$)$_3$-(4-EtS-Ph) | H | H |
| 1-658 | H | H | H | Me | 2 | —C≡C—(CH$_2$)$_3$-(3-PrS-Ph) | H | H |
| 1-659 | H | H | H | Me | 2 | —C≡C—(CH$_2$)$_3$-(4-PrS-Ph) | H | H |
| 1-660 | H | H | H | Me | 2 | —C≡C—(CH$_2$)$_3$-(3-iPrS-Ph) | H | H |
| 1-661 | H | H | H | Me | 2 | —C≡C—(CH$_2$)$_3$-(4-iPrS-Ph) | H | H |
| 1-662 | H | H | H | Me | 2 | —C≡C—(CH$_2$)$_3$-[3-(2-Et-PrS)-Ph] | H | H |
| 1-663 | H | H | H | Me | 2 | —C≡C—(CH$_2$)$_3$-[4-(2-Et-PrS)-Ph] | H | H |
| 1-664 | H | H | H | Me | 2 | —C≡C—(CH$_2$)$_3$-(3-iBuS-Ph) | H | H |
| 1-665 | H | H | H | Me | 2 | —C≡C—(CH$_2$)$_3$-(4-iBuS-Ph) | H | H |
| 1-666 | H | H | H | Me | 2 | —C≡C—(CH$_2$)$_3$-(3-cHx-Ph) | H | H |
| 1-667 | H | H | H | Me | 2 | —C≡C—(CH$_2$)$_3$-(4-cHx-Ph) | H | H |
| 1-668 | H | H | H | Me | 2 | —C≡C—(CH$_2$)$_3$-(3-Ph-Ph) | H | H |
| 1-669 | H | H | H | Me | 2 | —C≡C—(CH$_2$)$_3$-(4-Ph-Ph) | H | H |
| 1-670 | H | H | H | Me | 2 | —C≡C—(CH$_2$)$_3$-(2,4-diMe-Ph) | H | H |
| 1-671 | H | H | H | Me | 2 | —C≡C—(CH$_2$)$_3$-(3,4-diMe-Ph) | H | H |
| 1-672 | H | H | H | Me | 2 | —C≡C—(CH$_2$)$_3$-(3,5-diMe-Ph) | H | H |
| 1-673 | H | H | H | Me | 2 | —C≡C—(CH$_2$)$_3$-Np (1) | H | H |
| 1-674 | H | H | H | Me | 2 | —C≡C—(CH$_2$)$_3$-Np (2) | H | H |
| 1-675 | H | H | H | Me | 2 | —C≡C—(CH$_2$)$_4$-cPn | H | H |
| 1-676 | H | H | H | Me | 2 | —C≡C—(CH$_2$)$_4$-cHx | H | H |
| 1-677 | H | H | H | Me | 2 | —C≡C—(CH$_2$)$_4$-cHx | Me | H |
| 1-678 | H | H | H | Me | 2 | —C≡C—(CH$_2$)$_4$-cHx | H | Me |
| 1-679 | H | H | H | Me | 2 | —C≡C—(CH$_2$)$_4$-cHx | F | H |
| 1-680 | H | H | H | Me | 2 | —C≡C—(CH$_2$)$_4$-cHx | H | F |
| 1-681 | H | H | H | Me | 2 | —C≡C—(CH$_2$)$_4$-(3-F-cHx) | H | H |
| 1-682 | H | H | H | Me | 2 | —C≡C—(CH$_2$)$_4$-(4-F-cHx) | H | H |
| 1-683 | H | H | H | Me | 2 | —C≡C—(CH$_2$)$_4$-(4-Cl-cHx) | H | H |
| 1-684 | H | H | H | Me | 2 | —C≡C—(CH$_2$)$_4$-(4-Br-cHx) | H | H |
| 1-685 | H | H | H | Me | 2 | —C≡C—(CH$_2$)$_4$-(3-Me-cHx) | H | H |
| 1-686 | H | H | H | Me | 2 | —C≡C—(CH$_2$)$_4$-(4-Me-cHx) | H | H |
| 1-687 | H | H | H | Me | 2 | —C≡C—(CH$_2$)$_4$-(3-Et-cHx) | H | H |
| 1-688 | H | H | H | Me | 2 | —C≡C—(CH$_2$)$_4$-(4-Et-cHx) | H | H |
| 1-689 | H | H | H | Me | 2 | —C≡C—(CH$_2$)$_4$-(3-Pr-cHx) | H | H |
| 1-690 | H | H | H | Me | 2 | —C≡C—(CH$_2$)$_4$-(4-Pr-cHx) | H | H |
| 1-691 | H | H | H | Me | 2 | —C≡C—(CH$_2$)$_4$-(4-iPr-cHx) | H | H |
| 1-692 | H | H | H | Me | 2 | —C≡C—(CH$_2$)$_4$-(3-Bu-cHx) | H | H |
| 1-693 | H | H | H | Me | 2 | —C≡C—(CH$_2$)$_4$-(4-Bu-cHx) | H | H |
| 1-694 | H | H | H | Me | 2 | —C≡C—(CH$_2$)$_4$-(3-CF$_3$-cHx) | H | H |
| 1-695 | H | H | H | Me | 2 | —C≡C—(CH$_2$)$_4$-(4-CF$_3$-cHx) | H | H |
| 1-696 | H | H | H | Me | 2 | —C≡C—(CH$_2$)$_4$-(3-MeO-cHx) | H | H |
| 1-697 | H | H | H | Me | 2 | —C≡C—(CH$_2$)$_4$-(4-MeO-cHx) | H | H |
| 1-698 | H | H | H | Me | 2 | —C≡C—(CH$_2$)$_4$-(3-EtO-cHx) | H | H |
| 1-699 | H | H | H | Me | 2 | —C≡C—(CH$_2$)$_4$-(4-EtO-cHx) | H | H |
| 1-700 | H | H | H | Me | 2 | —C≡C—(CH$_2$)$_4$-(3-PrO-cHx) | H | H |
| 1-701 | H | H | H | Me | 2 | —C≡C—(CH$_2$)$_4$-(4-PrO-cHx) | H | H |
| 1-702 | H | H | H | Me | 2 | —C≡C—(CH$_2$)$_4$-(3-iPrO-cHx) | H | H |
| 1-703 | H | H | H | Me | 2 | —C≡C—(CH$_2$)$_4$-(4-iPrO-cHx) | H | H |
| 1-704 | H | H | H | Me | 2 | —C≡C—(CH$_2$)$_4$-[3-(2-Et-PrO)-cHx] | H | H |
| 1-705 | H | H | H | Me | 2 | —C≡C—(CH$_2$)$_4$-[4-(2-Et-PrO)-cHx] | H | H |
| 1-706 | H | H | H | Me | 2 | —C≡C—(CH$_2$)$_4$-(3-iBuO-cHx) | H | H |
| 1-707 | H | H | H | Me | 2 | —C≡C—(CH$_2$)$_4$-(4-iBuO-cHx) | H | H |
| 1-708 | H | H | H | Me | 2 | —C≡C—(CH$_2$)$_4$-(3-MeS-cHx) | H | H |
| 1-709 | H | H | H | Me | 2 | —C≡C—(CH$_2$)$_4$-(4-MeS-cHx) | H | H |
| 1-710 | H | H | H | Me | 2 | —C≡C—(CH$_2$)$_4$-(3-EtS-cHx) | H | H |
| 1-711 | H | H | H | Me | 2 | —C≡C—(CH$_2$)$_4$-(4-EtS-cHx) | H | H |
| 1-712 | H | H | H | Me | 2 | —C≡C—(CH$_2$)$_4$-(3-PrS-cHx) | H | H |
| 1-713 | H | H | H | Me | 2 | —C≡C—(CH$_2$)$_4$-(4-PrS-cHx) | H | H |
| 1-714 | H | H | H | Me | 2 | —C≡C—(CH$_2$)$_4$-(3-iPrS-cHx) | H | H |
| 1-715 | H | H | H | Me | 2 | —C≡C—(CH$_2$)$_4$-(4-iPrS-cHx) | H | H |
| 1-716 | H | H | H | Me | 2 | —C≡C—(CH$_2$)$_4$-[3-(2-Et-PrS)-cHx] | H | H |
| 1-717 | H | H | H | Me | 2 | —C≡C—(CH$_2$)$_4$-[4-(2-Et-PrS)-cHx] | H | H |
| 1-718 | H | H | H | Me | 2 | —C≡C—(CH$_2$)$_4$-(3-iBuS-cHx) | H | H |
| 1-719 | H | H | H | Me | 2 | —C≡C—(CH$_2$)$_4$-(4-iBuS-cHx) | H | H |
| 1-720 | H | H | H | Me | 2 | —C≡C—(CH$_2$)$_4$-(3-cHx-cHx) | H | H |
| 1-721 | H | H | H | Me | 2 | —C≡C—(CH$_2$)$_4$-(4-cHx-cHx) | H | H |
| 1-722 | H | H | H | Me | 2 | —C≡C—(CH$_2$)$_4$-(3-Ph-cHx) | H | H |
| 1-723 | H | H | H | Me | 2 | —C≡C—(CH$_2$)$_4$-(4-Ph-cHx) | H | H |
| 1-724 | H | H | H | Me | 2 | —C≡C—(CH$_2$)$_4$-(2,4-diMe-cHx) | H | H |
| 1-725 | H | H | H | Me | 2 | —C≡C—(CH$_2$)$_4$-(3,4-diMe-cHx) | H | H |
| 1-726 | H | H | H | Me | 2 | —C≡C—(CH$_2$)$_4$-(3,5-diMe-cHx) | H | H |
| 1-727 | H | H | H | Me | 2 | —C≡C—(CH$_2$)$_4$-Ph | H | H |
| 1-728 | H | H | H | Me | 2 | —C≡C—(CH$_2$)$_4$-Ph | Me | H |
| 1-729 | H | H | H | Me | 2 | —C≡C—(CH$_2$)$_4$-Ph | H | Me |
| 1-730 | H | H | H | Me | 2 | —C≡C—(CH$_2$)$_4$-Ph | F | H |
| 1-731 | H | H | H | Me | 2 | —C≡C—(CH$_2$)$_4$-Ph | H | F |
| 1-732 | H | H | H | Me | 2 | —C≡C—(CH$_2$)$_4$-(3-F-Ph) | H | H |
| 1-733 | H | H | H | Me | 2 | —C≡C—(CH$_2$)$_4$-(4-F-Ph) | H | H |
| 1-734 | H | H | H | Me | 2 | —C≡C—(CH$_2$)$_4$-(4-Cl-Ph) | H | H |
| 1-735 | H | H | H | Me | 2 | —C≡C—(CH$_2$)$_4$-(4-Br-Ph) | H | H |

TABLE 1-continued

| | | | | | | | |
|---|---|---|---|---|---|---|---|
| 1-736 | H | H | H | Me | 2 | —C≡C—(CH$_2$)$_4$-(3-Me-Ph) | H | H |
| 1-737 | H | H | H | Me | 2 | —C≡C—(CH$_2$)$_4$-(4-Me-Ph) | H | H |
| 1-738 | H | H | H | Me | 2 | —C≡C—(CH$_2$)$_4$-(3-Et-Ph) | H | H |
| 1-739 | H | H | H | Me | 2 | —C≡C—(CH$_2$)$_4$-(4-Et-Ph) | H | H |
| 1-740 | H | H | H | Me | 2 | —C≡C—(CH$_2$)$_4$-(3-Pr-Ph) | H | H |
| 1-741 | H | H | H | Me | 2 | —C≡C—(CH$_2$)$_4$-(4-Pr-Ph) | H | H |
| 1-742 | H | H | H | Me | 2 | —C≡C—(CH$_2$)$_4$-(3-iPr-Ph) | H | H |
| 1-743 | H | H | H | Me | 2 | —C≡C—(CH$_2$)$_4$-(4-iPr-Ph) | H | H |
| 1-744 | H | H | H | Me | 2 | —C≡C—(CH$_2$)$_4$-(3-Bu-Ph) | H | H |
| 1-745 | H | H | H | Me | 2 | —C≡C—(CH$_2$)$_4$-(4-Bu-Ph) | H | H |
| 1-746 | H | H | H | Me | 2 | —C≡C—(CH$_2$)$_4$-(3-CF$_3$-Ph) | H | H |
| 1-747 | H | H | H | Me | 2 | —C≡C—(CH$_2$)$_4$-(4-CF$_3$-Ph) | H | H |
| 1-748 | H | H | H | Me | 2 | —C≡C—(CH$_2$)$_4$-(3-MeO-Ph) | H | H |
| 1-749 | H | H | H | Me | 2 | —C≡C—(CH$_2$)$_4$-(4-MeO-Ph) | H | H |
| 1-750 | H | H | H | Me | 2 | —C≡C—(CH$_2$)$_4$-(3-EtO-Ph) | H | H |
| 1-751 | H | H | H | Me | 2 | —C≡C—(CH$_2$)$_4$-(4-EtO-Ph) | H | H |
| 1-752 | H | H | H | Me | 2 | —C≡C—(CH$_2$)$_4$-(3-PrO-Ph) | H | H |
| 1-753 | H | H | H | Me | 2 | —C≡C—(CH$_2$)$_4$-(4-PrO-Ph) | H | H |
| 1-754 | H | H | H | Me | 2 | —C≡C—(CH$_2$)$_4$-(3-iPrO-Ph) | H | H |
| 1-755 | H | H | H | Me | 2 | —C≡C—(CH$_2$)$_4$-(4-iPrO-Ph) | H | H |
| 1-756 | H | H | H | Me | 2 | —C≡C—(CH$_2$)$_4$-[3-(2-Et-PrO)-Ph] | H | H |
| 1-757 | H | H | H | Me | 2 | —C≡C—(CH$_2$)$_4$-[4-(2-Et-PrO)-Ph] | H | H |
| 1-758 | H | H | H | Me | 2 | —C≡C—(CH$_2$)$_4$-(3-iBuO-Ph) | H | H |
| 1-759 | H | H | H | Me | 2 | —C≡C—(CH$_2$)$_4$-(4-iBuO-Ph) | H | H |
| 1-760 | H | H | H | Me | 2 | —C≡C—(CH$_2$)$_4$-(3-MeS-Ph) | H | H |
| 1-761 | H | H | H | Me | 2 | —C≡C—(CH$_2$)$_4$-(4-MeS-Ph) | H | H |
| 1-762 | H | H | H | Me | 2 | —C≡C—(CH$_2$)$_4$-(3-EtS-Ph) | H | H |
| 1-763 | H | H | H | Me | 2 | —C≡C—(CH$_2$)$_4$-(4-EtS-Ph) | H | H |
| 1-764 | H | H | H | Me | 2 | —C≡C—(CH$_2$)$_4$-(3-PrS-Ph) | H | H |
| 1-765 | H | H | H | Me | 2 | —C≡C—(CH$_2$)$_4$-(4-PrS-Ph) | H | H |
| 1-766 | H | H | H | Me | 2 | —C≡C—(CH$_2$)$_4$-(3-iPrS-Ph) | H | H |
| 1-767 | H | H | H | Me | 2 | —C≡C—(CH$_2$)$_4$-(4-iPrS-Ph) | H | H |
| 1-768 | H | H | H | Me | 2 | —C≡C—(CH$_2$)$_4$-[3-(2-Et-PrS)-Ph] | H | H |
| 1-769 | H | H | H | Me | 2 | —C≡C—(CH$_2$)$_4$-[4-(2-Et-PrS)-Ph] | H | H |
| 1-770 | H | H | H | Me | 2 | —C≡C—(CH$_2$)$_4$-(3-iBuS-Ph) | H | H |
| 1-771 | H | H | H | Me | 2 | —C≡C—(CH$_2$)$_4$-(4-iBuS-Ph) | H | H |
| 1-772 | H | H | H | Me | 2 | —C≡C—(CH$_2$)$_4$-(3-cHx-Ph) | H | H |
| 1-773 | H | H | H | Me | 2 | —C≡C—(CH$_2$)$_4$-(4-cHx-Ph) | H | H |
| 1-774 | H | H | H | Me | 2 | —C≡C—(CH$_2$)$_4$-(3-Ph-Ph) | H | H |
| 1-775 | H | H | H | Me | 2 | —C≡C—(CH$_2$)$_4$-(4-Ph-Ph) | H | H |
| 1-776 | H | H | H | Me | 2 | —C≡C—(CH$_2$)$_4$-(2,4-diMe-Ph) | H | H |
| 1-777 | H | H | H | Me | 2 | —C≡C—(CH$_2$)$_4$-(3,4-diMe-Ph) | H | H |
| 1-778 | H | H | H | Me | 2 | —C≡C—(CH$_2$)$_4$-(3,5-diMe-Ph) | H | H |
| 1-779 | H | H | H | Me | 2 | —C≡C—(CH$_2$)$_4$-Np (1) | H | H |
| 1-780 | H | H | H | Me | 2 | —C≡C—(CH$_2$)$_4$-Np (2) | H | H |
| 1-781 | H | H | H | Me | 2 | —C≡C—(CH$_2$)$_5$-cHx | H | H |
| 1-782 | H | H | H | Me | 2 | —C≡C—(CH$_2$)$_5$-(4-F-cHx) | H | H |
| 1-783 | H | H | H | Me | 2 | —C≡C—(CH$_2$)$_5$-(4-Me-cHx) | H | H |
| 1-784 | H | H | H | Me | 2 | —C≡C—(CH$_2$)$_5$-(4-Et-cHx) | H | H |
| 1-785 | H | H | H | Me | 2 | —C≡C—(CH$_2$)$_5$-(4-CF$_3$-cHx) | H | H |
| 1-786 | H | H | H | Me | 2 | —C≡C—(CH$_2$)$_5$-(4-MeO-cHx) | H | H |
| 1-787 | H | H | H | Me | 2 | —C≡C—(CH$_2$)$_5$-(4-EtO-cHx) | H | H |
| 1-788 | H | H | H | Me | 2 | —C≡C—(CH$_2$)$_5$-(4-MeS-cHx) | H | H |
| 1-789 | H | H | H | Me | 2 | —C≡C—(CH$_2$)$_5$-(4-cHx-cHx) | H | H |
| 1-790 | H | H | H | Me | 2 | —C≡C—(CH$_2$)$_5$-(4-Ph-cHx) | H | H |
| 1-791 | H | H | H | Me | 2 | —C≡C—(CH$_2$)$_5$-Ph | H | H |
| 1-792 | H | H | H | Me | 2 | —C≡C—(CH$_2$)$_5$-(4-F-Ph) | H | H |
| 1-793 | H | H | H | Me | 2 | —C≡C—(CH$_2$)$_5$-(4-Me-Ph) | H | H |
| 1-794 | H | H | H | Me | 2 | —C≡C—(CH$_2$)$_5$-(4-Et-Ph) | H | H |
| 1-795 | H | H | H | Me | 2 | —C≡C—(CH$_2$)$_5$-(4-CF$_3$-Ph) | H | H |
| 1-796 | H | H | H | Me | 2 | —C≡C—(CH$_2$)$_5$-(4-MeO-Ph) | H | H |
| 1-797 | H | H | H | Me | 2 | —C≡C—(CH$_2$)$_5$-(4-EtO-Ph) | H | H |
| 1-798 | H | H | H | Me | 2 | —C≡C—(CH$_2$)$_5$-(4-MeS-Ph) | H | H |
| 1-799 | H | H | H | Me | 2 | —C≡C—(CH$_2$)$_5$-(4-cHx-Ph) | H | H |
| 1-800 | H | H | H | Me | 2 | —C≡C—(CH$_2$)$_5$-(4-Ph-Ph) | H | H |
| 1-801 | H | H | H | Me | 2 | —C≡C—(CH$_2$)$_6$-cHx | H | H |
| 1-802 | H | H | H | Me | 2 | —C≡C—(CH$_2$)$_6$-(4-F-cHx) | H | H |
| 1-803 | H | H | H | Me | 2 | —C≡C—(CH$_2$)$_6$-(4-Me-cHx) | H | H |
| 1-804 | H | H | H | Me | 2 | —C≡C—(CH$_2$)$_6$-(4-Et-cHx) | H | H |
| 1-805 | H | H | H | Me | 2 | —C≡C—(CH$_2$)$_6$-(4-CF$_3$-cHx) | H | H |
| 1-806 | H | H | H | Me | 2 | —C≡C—(CH$_2$)$_6$-(4-MeO-cHx) | H | H |
| 1-807 | H | H | H | Me | 2 | —C≡C—(CH$_2$)$_6$-(4-EtO-cHx) | H | H |
| 1-808 | H | H | H | Me | 2 | —C≡C—(CH$_2$)$_6$-(4-MeS-cHx) | H | H |
| 1-809 | H | H | H | Me | 2 | —C≡C—(CH$_2$)$_6$-(4-cHx-cHx) | H | H |
| 1-810 | H | H | H | Me | 2 | —C≡C—(CH$_2$)$_6$-(4-Ph-cHx) | H | H |
| 1-811 | H | H | H | Me | 2 | —C≡C—(CH$_2$)$_6$-Ph | H | H |
| 1-812 | H | H | H | Me | 2 | —C≡C—(CH$_2$)$_6$-(4-F-Ph) | H | H |
| 1-813 | H | H | H | Me | 2 | —C≡C—(CH$_2$)$_6$-(4-Me-Ph) | H | H |
| 1-814 | H | H | H | Me | 2 | —C≡C—(CH$_2$)$_6$-(4-Et-Ph) | H | H |
| 1-815 | H | H | H | Me | 2 | —C≡C—(CH$_2$)$_6$-(4-CF$_3$-Ph) | H | H |

TABLE 1-continued

| | | | | | | | |
|---|---|---|---|---|---|---|---|
| 1-816 | H | H | H | Me | 2 | —C≡C—(CH$_2$)$_6$-(4-MeO-Ph) | H | H |
| 1-817 | H | H | H | Me | 2 | —C≡C—(CH$_2$)$_6$-(4-EtO-Ph) | H | H |
| 1-818 | H | H | H | Me | 2 | —C≡C—(CH$_2$)$_6$-(4-MeS-Ph) | H | H |
| 1-819 | H | H | H | Me | 2 | —C≡C—(CH$_2$)$_6$-(4-cHx-Ph) | H | H |
| 1-820 | H | H | H | Me | 2 | —C≡C—(CH$_2$)$_6$-(4-Ph-Ph) | H | H |
| 1-821 | H | H | H | Me | 2 | —C≡C—CH$_2$—O-cHx | H | H |
| 1-822 | H | H | H | Me | 2 | —C≡C—CH$_2$—O-(4-F-cHx) | H | H |
| 1-823 | H | H | H | Me | 2 | —C≡C—CH$_2$—O-(4-Me-cHx) | H | H |
| 1-824 | H | H | H | Me | 2 | —C≡C—CH$_2$—O-(4-Et-cHx) | H | H |
| 1-825 | H | H | H | Me | 2 | —C≡C—CH$_2$—O-(4-CF$_3$-cHx) | H | H |
| 1-826 | H | H | H | Me | 2 | —C≡C—CH$_2$—O-(4-MeO-cHx) | H | H |
| 1-827 | H | H | H | Me | 2 | —C≡C—CH$_2$—O-(4-EtO-cHx) | H | H |
| 1-828 | H | H | H | Me | 2 | —C≡C—CH$_2$—O-(4-MeS-cHx) | H | H |
| 1-829 | H | H | H | Me | 2 | —C≡C—CH$_2$—O-(4-cHx-cHx) | H | H |
| 1-830 | H | H | H | Me | 2 | —C≡C—CH$_2$—O-(4-Ph-cHx) | H | H |
| 1-831 | H | H | H | Me | 2 | —C≡C—CH$_2$—O-Ph | H | H |
| 1-832 | H | H | H | Me | 2 | —C≡C—CH$_2$—O-(4-F-Ph) | H | H |
| 1-833 | H | H | H | Me | 2 | —C≡C—CH$_2$—O-(4-Me-Ph) | H | H |
| 1-834 | H | H | H | Me | 2 | —C≡C—CH$_2$—O-(4-Et-Ph) | H | H |
| 1-835 | H | H | H | Me | 2 | —C≡C—CH$_2$—O-(4-CF$_3$-Ph) | H | H |
| 1-836 | H | H | H | Me | 2 | —C≡C—CH$_2$—O-(4-MeO-Ph) | H | H |
| 1-837 | H | H | H | Me | 2 | —C≡C—CH$_2$—O-(4-EtO-Ph) | H | H |
| 1-838 | H | H | H | Me | 2 | —C≡C—CH$_2$—O-(4-MeS-Ph) | H | H |
| 1-839 | H | H | H | Me | 2 | —C≡C—CH$_2$—O-(4-cHx-Ph) | H | H |
| 1-840 | H | H | H | Me | 2 | —C≡C—CH$_2$—O-(4-Ph-Ph) | H | H |
| 1-841 | H | H | H | Me | 2 | —C≡C—(CH$_2$)$_2$O-cPn | H | H |
| 1-842 | H | H | H | Me | 2 | —C≡C—(CH$_2$)$_2$O-cHx | H | H |
| 1-843 | H | H | H | Me | 2 | —C≡C—(CH$_2$)$_2$O-cHx | Me | H |
| 1-844 | H | H | H | Me | 2 | —C≡C—(CH$_2$)$_2$O-cHx | H | Me |
| 1-845 | H | H | H | Me | 2 | —C≡C—(CH$_2$)$_2$O-cHx | F | H |
| 1-846 | H | H | H | Me | 2 | —C≡C—(CH$_2$)$_2$O-cHx | H | F |
| 1-847 | H | H | H | Me | 2 | —C≡C—(CH$_2$)$_2$O-(3-F-cHx) | H | H |
| 1-848 | H | H | H | Me | 2 | —C≡C—(CH$_2$)$_2$O-(4-F-cHx) | H | H |
| 1-849 | H | H | H | Me | 2 | —C≡C—(CH$_2$)$_2$O-(4-Cl-cHx) | H | H |
| 1-850 | H | H | H | Me | 2 | —C≡C—(CH$_2$)$_2$O-(4-Br-cHx) | H | H |
| 1-851 | H | H | H | Me | 2 | —C≡C—(CH$_2$)$_2$O-(3-Me-cHx) | H | H |
| 1-852 | H | H | H | Me | 2 | —C≡C—(CH$_2$)$_2$O-(4-Me-cHx) | H | H |
| 1-853 | H | H | H | Me | 2 | —C≡C—(CH$_2$)$_2$O-(3-Et-cHx) | H | H |
| 1-854 | H | H | H | Me | 2 | —C≡C—(CH$_2$)$_2$O-(4-Et-cHx) | H | H |
| 1-855 | H | H | H | Me | 2 | —C≡C—(CH$_2$)$_2$O-(3-Pr-cHx) | H | H |
| 1-856 | H | H | H | Me | 2 | —C≡C—(CH$_2$)$_2$O-(4-Pr-cHx) | H | H |
| 1-857 | H | H | H | Me | 2 | —C≡C—(CH$_2$)$_2$O-(4-iPr-cHx) | H | H |
| 1-858 | H | H | H | Me | 2 | —C≡C—(CH$_2$)$_2$O-(3-Bu-cHx) | H | H |
| 1-859 | H | H | H | Me | 2 | —C≡C—(CH$_2$)$_2$O-(4-Bu-cHx) | H | H |
| 1-860 | H | H | H | Me | 2 | —C≡C—(CH$_2$)$_2$O-(3-CF$_3$-cHx) | H | H |
| 1-861 | H | H | H | Me | 2 | —C≡C—(CH$_2$)$_2$O-(4-CF$_3$-cHx) | H | H |
| 1-862 | H | H | H | Me | 2 | —C≡C—(CH$_2$)$_2$O-(3-MeO-cHx) | H | H |
| 1-863 | H | H | H | Me | 2 | —C≡C—(CH$_2$)$_2$O-(4-MeO-cHx) | H | H |
| 1-864 | H | H | H | Me | 2 | —C≡C—(CH$_2$)$_2$O-(3-EtO-cHx) | H | H |
| 1-865 | H | H | H | Me | 2 | —C≡C—(CH$_2$)$_2$O-(4-EtO-cHx) | H | H |
| 1-866 | H | H | H | Me | 2 | —C≡C—(CH$_2$)$_2$O-(3-PrO-cHx) | H | H |
| 1-867 | H | H | H | Me | 2 | —C≡C—(CH$_2$)$_2$O-(4-PrO-cHx) | H | H |
| 1-868 | H | H | H | Me | 2 | —C≡C—(CH$_2$)$_2$O-(3-iPrO-cHx) | H | H |
| 1-869 | H | H | H | Me | 2 | —C≡C—(CH$_2$)$_2$O-(4-iPrO-cHx) | H | H |
| 1-870 | H | H | H | Me | 2 | —C≡C—(CH$_2$)$_2$O-[3-(2-Et-PrO)-cHx] | H | H |
| 1-871 | H | H | H | Me | 2 | —C≡C—(CH$_2$)$_2$O-[4-(2-Et-PrO)-cHx] | H | H |
| 1-872 | H | H | H | Me | 2 | —C≡C—(CH$_2$)$_2$O-(3-iBuO-cHx) | H | H |
| 1-873 | H | H | H | Me | 2 | —C≡C—(CH$_2$)$_2$O-(4-iBuO-cHx) | H | H |
| 1-874 | H | H | H | Me | 2 | —C≡C—(CH$_2$)$_2$O-(3-MeS-cHx) | H | H |
| 1-875 | H | H | H | Me | 2 | —C≡C—(CH$_2$)$_2$O-(4-MeS-cHx) | H | H |
| 1-876 | H | H | H | Me | 2 | —C≡C—(CH$_2$)$_2$O-(3-EtS-cHx) | H | H |
| 1-877 | H | H | H | Me | 2 | —C≡C—(CH$_2$)$_2$O-(4-EtS-cHx) | H | H |
| 1-878 | H | H | H | Me | 2 | —C≡C—(CH$_2$)$_2$O-(3-PrS-cHx) | H | H |
| 1-879 | H | H | H | Me | 2 | —C≡C—(CH$_2$)$_2$O-(4-PrS-cHx) | H | H |
| 1-880 | H | H | H | Me | 2 | —C≡C—(CH$_2$)$_2$O-(3-iPrS-cHx) | H | H |
| 1-881 | H | H | H | Me | 2 | —C≡C—(CH$_2$)$_2$O-(4-iPrS-cHx) | H | H |
| 1-882 | H | H | H | Me | 2 | —C≡C—(CH$_2$)$_2$O-[3-(2-Et-PrS)-cHx] | H | H |
| 1-883 | H | H | H | Me | 2 | —C≡C—(CH$_2$)$_2$O-[4-(2-Et-PrS)-cHx] | H | H |
| 1-884 | H | H | H | Me | 2 | —C≡C—(CH$_2$)$_2$O-(3-iBuS-cHx) | H | H |
| 1-885 | H | H | H | Me | 2 | —C≡C—(CH$_2$)$_2$O-(4-iBuS-cHx) | H | H |
| 1-886 | H | H | H | Me | 2 | —C≡C—(CH$_2$)$_2$O-(3-cHx-cHx) | H | H |
| 1-887 | H | H | H | Me | 2 | —C≡C—(CH$_2$)$_2$O-(4-cHx-cHx) | H | H |
| 1-888 | H | H | H | Me | 2 | —C≡C—(CH$_2$)$_2$O-(3-Ph-cHx) | H | H |
| 1-889 | H | H | H | Me | 2 | —C≡C—(CH$_2$)$_2$O-(4-Ph-cHx) | H | H |
| 1-890 | H | H | H | Me | 2 | —C≡C—(CH$_2$)$_2$O-(2,4-diMe-cHx) | H | H |
| 1-891 | H | H | H | Me | 2 | —C≡C—(CH$_2$)$_2$O-(3,4-diMe-cHx) | H | H |
| 1-892 | H | H | H | Me | 2 | —C≡C—(CH$_2$)$_2$O-(3,5-diMe-cHx) | H | H |
| 1-893 | H | H | H | Me | 2 | —C≡C—(CH$_2$)$_2$O-Ph | H | H |
| 1-894 | H | H | H | Me | 2 | —C≡C—(CH$_2$)$_2$O-Ph | Me | H |
| 1-895 | H | H | H | Me | 2 | —C≡C—(CH$_2$)$_2$O-Ph | H | Me |

TABLE 1-continued

| ID | | | | | | | | |
|---|---|---|---|---|---|---|---|---|
| 1-896 | H | H | H | Me | 2 | —C≡C—(CH$_2$)$_2$O-Ph | F | H |
| 1-897 | H | H | H | Me | 2 | —C≡C—(CH$_2$)$_2$O-Ph | H | F |
| 1-898 | H | H | H | Me | 2 | —C≡C—(CH$_2$)$_2$O-(3-F-Ph) | H | H |
| 1-899 | H | H | H | Me | 2 | —C≡C—(CH$_2$)$_2$O-(4-F-Ph) | H | H |
| 1-900 | H | H | H | Me | 2 | —C≡C—(CH$_2$)$_2$O-(4-Cl-Ph) | H | H |
| 1-901 | H | H | H | Me | 2 | —C≡C—(CH$_2$)$_2$O-(4-Br-Ph) | H | H |
| 1-902 | H | H | H | Me | 2 | —C≡C—(CH$_2$)$_2$O-(3-Me-Ph) | H | H |
| 1-903 | H | H | H | Me | 2 | —C≡C—(CH$_2$)$_2$O-(4-Me-Ph) | H | H |
| 1-904 | H | H | H | Me | 2 | —C≡C—(CH$_2$)$_2$O-(3-Et-Ph) | H | H |
| 1-905 | H | H | H | Me | 2 | —C≡C—(CH$_2$)$_2$O-(4-Et-Ph) | H | H |
| 1-906 | H | H | H | Me | 2 | —C≡C—(CH$_2$)$_2$O-(3-Pr-Ph) | H | H |
| 1-907 | H | H | H | Me | 2 | —C≡C—(CH$_2$)$_2$O-(4-Pr-Ph) | H | H |
| 1-908 | H | H | H | Me | 2 | —C≡C—(CH$_2$)$_2$O-(3-iPr-Ph) | H | H |
| 1-909 | H | H | H | Me | 2 | —C≡C—(CH$_2$)$_2$O-(4-iPr-Ph) | H | H |
| 1-910 | H | H | H | Me | 2 | —C≡C—(CH$_2$)$_2$O-(3-Bu-Ph) | H | H |
| 1-911 | H | H | H | Me | 2 | —C≡C—(CH$_2$)$_2$O-(4-Bu-Ph) | H | H |
| 1-912 | H | H | H | Me | 2 | —C≡C—(CH$_2$)$_2$O-(3-CF$_3$-Ph) | H | H |
| 1-913 | H | H | H | Me | 2 | —C≡C—(CH$_2$)$_2$O-(4-CF$_3$-Ph) | H | H |
| 1-914 | H | H | H | Me | 2 | —C≡C—(CH$_2$)$_2$O-(3-MeO-Ph) | H | H |
| 1-915 | H | H | H | Me | 2 | —C≡C—(CH$_2$)$_2$O-(4-MeO-Ph) | H | H |
| 1-916 | H | H | H | Me | 2 | —C≡C—(CH$_2$)$_2$O-(3-EtO-Ph) | H | H |
| 1-917 | H | H | H | Me | 2 | —C≡C—(CH$_2$)$_2$O-(4-EtO-Ph) | H | H |
| 1-918 | H | H | H | Me | 2 | —C≡C—(CH$_2$)$_2$O-(3-PrO-Ph) | H | H |
| 1-919 | H | H | H | Me | 2 | —C≡C—(CH$_2$)$_2$O-(4-PrO-Ph) | H | H |
| 1-920 | H | H | H | Me | 2 | —C≡C—(CH$_2$)$_2$O-(3-iPrO-Ph) | H | H |
| 1-921 | H | H | H | Me | 2 | —C≡C—(CH$_2$)$_2$O-(4-iPrO-Ph) | H | H |
| 1-922 | H | H | H | Me | 2 | —C≡C—(CH$_2$)$_2$O-[3-(2-Et-PrO)-Ph] | H | H |
| 1-923 | H | H | H | Me | 2 | —C≡C—(CH$_2$)$_2$O-[4-(2-Et-PrO)-Ph] | H | H |
| 1-924 | H | H | H | Me | 2 | —C≡C—(CH$_2$)$_2$O-(3-iBuO-Ph) | H | H |
| 1-925 | H | H | H | Me | 2 | —C≡C—(CH$_2$)$_2$O-(4-iBuO-Ph) | H | H |
| 1-926 | H | H | H | Me | 2 | —C≡C—(CH$_2$)$_2$O-(3-MeS-Ph) | H | H |
| 1-927 | H | H | H | Me | 2 | —C≡C—(CH$_2$)$_2$O-(4-MeS-Ph) | H | H |
| 1-928 | H | H | H | Me | 2 | —C≡C—(CH$_2$)$_2$O-(3-EtS-Ph) | H | H |
| 1-929 | H | H | H | Me | 2 | —C≡C—(CH$_2$)$_2$O-(4-EtS-Ph) | H | H |
| 1-930 | H | H | H | Me | 2 | —C≡C—(CH$_2$)$_2$O-(3-PrS-Ph) | H | H |
| 1-931 | H | H | H | Me | 2 | —C≡C—(CH$_2$)$_2$O-(4-PrS-Ph) | H | H |
| 1-932 | H | H | H | Me | 2 | —C≡C—(CH$_2$)$_2$O-(3-iPrS-Ph) | H | H |
| 1-933 | H | H | H | Me | 2 | —C≡C—(CH$_2$)$_2$O-(4-iPrS-Ph) | H | H |
| 1-934 | H | H | H | Me | 2 | —C≡C—(CH$_2$)$_2$O-[3-(2-Et-PrS)-Ph] | H | H |
| 1-935 | H | H | H | Me | 2 | —C≡C—(CH$_2$)$_2$O-[4-(2-Et-PrS)-Ph] | H | H |
| 1-936 | H | H | H | Me | 2 | —C≡C—(CH$_2$)$_2$O-(3-iBuS-Ph) | H | H |
| 1-937 | H | H | H | Me | 2 | —C≡C—(CH$_2$)$_2$O-(4-iBuS-Ph) | H | H |
| 1-938 | H | H | H | Me | 2 | —C≡C—(CH$_2$)$_2$O-(3-cHx-Ph) | H | H |
| 1-939 | H | H | H | Me | 2 | —C≡C—(CH$_2$)$_2$O-(4-cHx-Ph) | H | H |
| 1-940 | H | H | H | Me | 2 | —C≡C—(CH$_2$)$_2$O-(3-Ph-Ph) | H | H |
| 1-941 | H | H | H | Me | 2 | —C≡C—(CH$_2$)$_2$O-(4-Ph-Ph) | H | H |
| 1-942 | H | H | H | Me | 2 | —C≡C—(CH$_2$)$_2$O-(2,4-diMe-Ph) | H | H |
| 1-943 | H | H | H | Me | 2 | —C≡C—(CH$_2$)$_2$O-(3,4-diMe-Ph) | H | H |
| 1-944 | H | H | H | Me | 2 | —C≡C—(CH$_2$)$_2$O-(3,5-diMe-Ph) | H | H |
| 1-945 | H | H | H | Me | 2 | —C≡C—(CH$_2$)$_3$O-cHx | H | H |
| 1-946 | H | H | H | Me | 2 | —C≡C—(CH$_2$)$_3$O-Ph | H | H |
| 1-947 | H | H | H | Me | 2 | —C≡C—(CH$_2$)$_4$O-cHx | H | H |
| 1-948 | H | H | H | Me | 2 | —C≡C—(CH$_2$)$_4$O-Ph | H | H |
| 1-949 | H | H | H | Me | 2 | —C≡C—CH$_2$—OCH$_2$-cHx | H | H |
| 1-950 | H | H | H | Me | 2 | —C≡C—CH$_2$—OCH$_2$-(4-F-cHx) | H | H |
| 1-951 | H | H | H | Me | 2 | —C≡C—CH$_2$—OCH$_2$-(4-Me-cHx) | H | H |
| 1-952 | H | H | H | Me | 2 | —C≡C—CH$_2$—OCH$_2$-(4-Et-cHx) | H | H |
| 1-953 | H | H | H | Me | 2 | —C≡C—CH$_2$—OCH$_2$-(4-CF$_3$-cHx) | H | H |
| 1-954 | H | H | H | Me | 2 | —C≡C—CH$_2$—OCH$_2$-(4-MeO-cHx) | H | H |
| 1-955 | H | H | H | Me | 2 | —C≡C—CH$_2$—OCH$_2$-(4-EtO-cHx) | H | H |
| 1-956 | H | H | H | Me | 2 | —C≡C—CH$_2$—OCH$_2$-(4-MeS-cHx) | H | H |
| 1-957 | H | H | H | Me | 2 | —C≡C—CH$_2$—OCH$_2$-(4-cHx-cHx) | H | H |
| 1-958 | H | H | H | Me | 2 | —C≡C—CH$_2$—OCH$_2$-(4-Ph-cHx) | H | H |
| 1-959 | H | H | H | Me | 2 | —C≡C—CH$_2$—OCH$_2$-Ph | H | H |
| 1-960 | H | H | H | Me | 2 | —C≡C—CH$_2$—OCH$_2$-(4-F-Ph) | H | H |
| 1-961 | H | H | H | Me | 2 | —C≡C—CH$_2$—OCH$_2$-(4-Me-Ph) | H | H |
| 1-962 | H | H | H | Me | 2 | —C≡C—CH$_2$—OCH$_2$-(4-Et-Ph) | H | H |
| 1-963 | H | H | H | Me | 2 | —C≡C—CH$_2$—OCH$_2$-(4-CF$_3$-Ph) | H | H |
| 1-964 | H | H | H | Me | 2 | —C≡C—CH$_2$—OCH$_2$-(4-MeO-Ph) | H | H |
| 1-965 | H | H | H | Me | 2 | —C≡C—CH$_2$—OCH$_2$-(4-EtO-Ph) | H | H |
| 1-966 | H | H | H | Me | 2 | —C≡C—CH$_2$—OCH$_2$-(4-MeS-Ph) | H | H |
| 1-967 | H | H | H | Me | 2 | —C≡C—CH$_2$—OCH$_2$-(4-cHx-Ph) | H | H |
| 1-968 | H | H | H | Me | 2 | —C≡C—CH$_2$—OCH$_2$-(4-Ph-Ph) | H | H |
| 1-969 | H | H | H | Me | 2 | —C≡C—(CH$_2$)$_2$—OCH$_2$-cPn | H | H |
| 1-970 | H | H | H | Me | 2 | —C≡C—(CH$_2$)$_2$—OCH$_2$-cHx | H | H |
| 1-971 | H | H | H | Me | 2 | —C≡C—(CH$_2$)$_2$—OCH$_2$-cHx | Me | H |
| 1-972 | H | H | H | Me | 2 | —C≡C—(CH$_2$)$_2$—OCH$_2$-cHx | H | Me |
| 1-973 | H | H | H | Me | 2 | —C≡C—(CH$_2$)$_2$—OCH$_2$-cHx | F | H |
| 1-974 | H | H | H | Me | 2 | —C≡C—(CH$_2$)$_2$—OCH$_2$-cHx | H | F |
| 1-975 | H | H | H | Me | 2 | —C≡C—(CH$_2$)$_2$—OCH$_2$-(3-F-cHx) | H | H |

TABLE 1-continued

| | | | | | | | | |
|---|---|---|---|---|---|---|---|---|
| 1-976 | H | H | H | Me | 2 | —C≡C—(CH$_2$)$_2$—OCH$_2$-(4-F-cHx) | H | H |
| 1-977 | H | H | H | Me | 2 | —C≡C—(CH$_2$)$_2$—OCH$_2$-(4-Cl-cHx) | H | H |
| 1-978 | H | H | H | Me | 2 | —C≡C—(CH$_2$)$_2$—OCH$_2$-(4-Br-cHx) | H | H |
| 1-979 | H | H | H | Me | 2 | —C≡C—(CH$_2$)$_2$—OCH$_2$-(3-Me-cHx) | H | H |
| 1-980 | H | H | H | Me | 2 | —C≡C—(CH$_2$)$_2$—OCH$_2$-(4-Me-cHx) | H | H |
| 1-981 | H | H | H | Me | 2 | —C≡C—(CH$_2$)$_2$—OCH$_2$-(3-Et-cHx) | H | H |
| 1-982 | H | H | H | Me | 2 | —C≡C—(CH$_2$)$_2$—OCH$_2$-(4-Et-cHx) | H | H |
| 1-983 | H | H | H | Me | 2 | —C≡C—(CH$_2$)$_2$—OCH$_2$-(3-Pr-cHx) | H | H |
| 1-984 | H | H | H | Me | 2 | —C≡C—(CH$_2$)$_2$—OCH$_2$-(4-Pr-cHx) | H | H |
| 1-985 | H | H | H | Me | 2 | —C≡C—(CH$_2$)$_2$—OCH$_2$-(4-iPr-cHx) | H | H |
| 1-986 | H | H | H | Me | 2 | —C≡C—(CH$_2$)$_2$—OCH$_2$-(3-Bu-cHx) | H | H |
| 1-987 | H | H | H | Me | 2 | —C≡C—(CH$_2$)$_2$—OCH$_2$-(4-Bu-cHx) | H | H |
| 1-988 | H | H | H | Me | 2 | —C≡C—(CH$_2$)$_2$—OCH$_2$-(3-CF$_3$-cHx) | H | H |
| 1-989 | H | H | H | Me | 2 | —C≡C—(CH$_2$)$_2$—OCH$_2$-(4-CF$_3$-cHx) | H | H |
| 1-990 | H | H | H | Me | 2 | —C≡C—(CH$_2$)$_2$—OCH$_2$-(3-MeO-cHx) | H | H |
| 1-991 | H | H | H | Me | 2 | —C≡C—(CH$_2$)$_2$—OCH$_2$-(4-MeO-cHx) | H | H |
| 1-992 | H | H | H | Me | 2 | —C≡C—(CH$_2$)$_2$—OCH$_2$-(3-EtO-cHx) | H | H |
| 1-993 | H | H | H | Me | 2 | —C≡C—(CH$_2$)$_2$—OCH$_2$-(4-EtO-cHx) | H | H |
| 1-994 | H | H | H | Me | 2 | —C≡C—(CH$_2$)$_2$—OCH$_2$-(3-PrO-cHx) | H | H |
| 1-995 | H | H | H | Me | 2 | —C≡C—(CH$_2$)$_2$—OCH$_2$-(4-PrO-cHx) | H | H |
| 1-996 | H | H | H | Me | 2 | —C≡C—(CH$_2$)$_2$—OCH$_2$-(3-iPrO-cHx) | H | H |
| 1-997 | H | H | H | Me | 2 | —C≡C—(CH$_2$)$_2$—OCH$_2$-(4-iPrO-cHx) | H | H |
| 1-998 | H | H | H | Me | 2 | —C≡C—(CH$_2$)$_2$—OCH$_2$-[3-(2-Et-PrO)cHx] | H | H |
| 1-999 | H | H | H | Me | 2 | —C≡C—(CH$_2$)$_2$—OCH$_2$-[4-(2-Et-PrO)cHx] | H | H |
| 1-1000 | H | H | H | Me | 2 | —C≡C—(CH$_2$)$_2$—OCH$_2$-(3-iBuO-cHx) | H | H |
| 1-1001 | H | H | H | Me | 2 | —C≡C—(CH$_2$)$_2$—OCH$_2$-(4-iBuO-cHx) | H | H |
| 1-1002 | H | H | H | Me | 2 | —C≡C—(CH$_2$)$_2$—OCH$_2$-(3-MeS-cHx) | H | H |
| 1-1003 | H | H | H | Me | 2 | —C≡C—(CH$_2$)$_2$—OCH$_2$-(4-MeS-cHx) | H | H |
| 1-1004 | H | H | H | Me | 2 | —C≡C—(CH$_2$)$_2$—OCH$_2$-(3-EtS-cHx) | H | H |
| 1-1005 | H | H | H | Me | 2 | —C≡C—(CH$_2$)$_2$—OCH$_2$-(4-EtS-cHx) | H | H |
| 1-1006 | H | H | H | Me | 2 | —C≡C—(CH$_2$)$_2$—OCH$_2$-(3-PrS-cHx) | H | H |
| 1-1007 | H | H | H | Me | 2 | —C≡C—(CH$_2$)$_2$—OCH$_2$-(4-PrS-cHx) | H | H |
| 1-1008 | H | H | H | Me | 2 | —C≡C—(CH$_2$)$_2$—OCH$_2$-(3-iPrS-cHx) | H | H |
| 1-1009 | H | H | H | Me | 2 | —C≡C—(CH$_2$)$_2$—OCH$_2$-(4-iPrS-cHx) | H | H |
| 1-1010 | H | H | H | Me | 2 | —C≡C—(CH$_2$)$_2$—OCH$_2$-[3-(2-Et-PrS)cHx] | H | H |
| 1-1011 | H | H | H | Me | 2 | —C≡C—(CH$_2$)$_2$—OCH$_2$-[4-(2-Et-PrS)cHx] | H | H |
| 1-1012 | H | H | H | Me | 2 | —C≡C—(CH$_2$)$_2$—OCH$_2$-(3-iBuS-cHx) | H | H |
| 1-1013 | H | H | H | Me | 2 | —C≡C—(CH$_2$)$_2$—OCH$_2$-(4-iBuS-cHx) | H | H |
| 1-1014 | H | H | H | Me | 2 | —C≡C—(CH$_2$)$_2$—OCH$_2$-(3-cHx-cHx) | H | H |
| 1-1015 | H | H | H | Me | 2 | —C≡C—(CH$_2$)$_2$—OCH$_2$-(4-cHx-cHx) | H | H |
| 1-1016 | H | H | H | Me | 2 | —C≡C—(CH$_2$)$_2$—OCH$_2$-(3-Ph-cHx) | H | H |
| 1-1017 | H | H | H | Me | 2 | —C≡C—(CH$_2$)$_2$—OCH$_2$-(4-Ph-cHx) | H | H |
| 1-1018 | H | H | H | Me | 2 | —C≡C—(CH$_2$)$_2$—OCH$_2$-(2,4-diMe-cHx) | H | H |
| 1-1019 | H | H | H | Me | 2 | —C≡C—(CH$_2$)$_2$—OCH$_2$-(3,4-diMe-cHx) | H | H |
| 1-1020 | H | H | H | Me | 2 | —C≡C—(CH$_2$)$_2$—OCH$_2$-(3,5-diMe-cHx) | H | H |
| 1-1021 | H | H | H | Me | 2 | —C≡C—(CH$_2$)$_2$—OCH$_2$-Ph | H | H |
| 1-1022 | H | H | H | Me | 2 | —C≡C—(CH$_2$)$_2$—OCH$_2$-Ph | Me | H |
| 1-1023 | H | H | H | Me | 2 | —C≡C—(CH$_2$)$_2$—OCH$_2$-Ph | H | Me |
| 1-1924 | H | H | H | Me | 2 | —C≡C—(CH$_2$)$_2$—OCH$_2$-Ph | F | H |
| 1-1025 | H | H | H | Me | 2 | —C≡C—(CH$_2$)$_2$—OCH$_2$-Ph | H | F |
| 1-1026 | H | H | H | Me | 2 | —C≡C—(CH$_2$)$_2$—OCH$_2$-(3-F-Ph) | H | H |
| 1-1027 | H | H | H | Me | 2 | —C≡C—(CH$_2$)$_2$—OCH$_2$-(4-F-Ph) | H | H |
| 1-1028 | H | H | H | Me | 2 | —C≡C—(CH$_2$)$_2$—OCH$_2$-(4-Cl-Ph) | H | H |
| 1-1029 | H | H | H | Me | 2 | —C≡C—(CH$_2$)$_2$—OCH$_2$-(4-Br-Ph) | H | H |
| 1-1030 | H | H | H | Me | 2 | —C≡C—(CH$_2$)$_2$—OCH$_2$-(3-Me-Ph) | H | H |
| 1-1031 | H | H | H | Me | 2 | —C≡C—(CH$_2$)$_2$—OCH$_2$-(4-Me-Ph) | H | H |
| 1-1032 | H | H | H | Me | 2 | —C≡C—(CH$_2$)$_2$—OCH$_2$-(3-Et-Ph) | H | H |
| 1-1033 | H | H | H | Me | 2 | —C≡C—(CH$_2$)$_2$—OCH$_2$-(4-Et-Ph) | H | H |
| 1-1034 | H | H | H | Me | 2 | —C≡C—(CH$_2$)$_2$—OCH$_2$-(3-Pr-Ph) | H | H |
| 1-1035 | H | H | H | Me | 2 | —C≡C—(CH$_2$)$_2$—OCH$_2$-(4-Pr-Ph) | H | H |
| 1-1036 | H | H | H | Me | 2 | —C≡C—(CH$_2$)$_2$—OCH$_2$-(3-iPr-Ph) | H | H |
| 1-1037 | H | H | H | Me | 2 | —C≡C—(CH$_2$)$_2$—OCH$_2$-(4-iPr-Ph) | H | H |
| 1-1038 | H | H | H | Me | 2 | —C≡C—(CH$_2$)$_2$—OCH$_2$-(3-Bu-Ph) | H | H |
| 1-1039 | H | H | H | Me | 2 | —C≡C—(CH$_2$)$_2$—OCH$_2$-(4-Bu-Ph) | H | H |
| 1-1040 | H | H | H | Me | 2 | —C≡C—(CH$_2$)$_2$—OCH$_2$-(3-CF$_3$-Ph) | H | H |
| 1-1041 | H | H | H | Me | 2 | —C≡C—(CH$_2$)$_2$—OCH$_2$-(4-CF$_3$-Ph) | H | H |
| 1-1042 | H | H | H | Me | 2 | —C≡C—(CH$_2$)$_2$—OCH$_2$-(3-MeO-Ph) | H | H |
| 1-1043 | H | H | H | Me | 2 | —C≡C—(CH$_2$)$_2$—OCH$_2$-(4-MeO-Ph) | H | H |
| 1-1044 | H | H | H | Me | 2 | —C≡C—(CH$_2$)$_2$—OCH$_2$-(3-EtO-Ph) | H | H |
| 1-1045 | H | H | H | Me | 2 | —C≡C—(CH$_2$)$_2$—OCH$_2$-(4-EtO-Ph) | H | H |
| 1-1046 | H | H | H | Me | 2 | —C≡C—(CH$_2$)$_2$—OCH$_2$-(3-PrO-Ph) | H | H |
| 1-1047 | H | H | H | Me | 2 | —C≡C—(CH$_2$)$_2$—OCH$_2$-(4-PrO-Ph) | H | H |
| 1-1048 | H | H | H | Me | 2 | —C≡C—(CH$_2$)$_2$—OCH$_2$-(3-iPrO-Ph) | H | H |
| 1-1049 | H | H | H | Me | 2 | —C≡C—(CH$_2$)$_2$—OCH$_2$-(4-iPrO-Ph) | H | H |
| 1-1050 | H | H | H | Me | 2 | —C≡C—(CH$_2$)$_2$—OCH$_2$-[3-(2-Et-PrO)Ph] | H | H |
| 1-1051 | H | H | H | Me | 2 | —C≡C—(CH$_2$)$_2$—OCH$_2$-[4-(2-Et-PrO)Ph] | H | H |
| 1-1052 | H | H | H | Me | 2 | —C≡C—(CH$_2$)$_2$—OCH$_2$-(3-iBuO-Ph) | H | H |
| 1-1053 | H | H | H | Me | 2 | —C≡C—(CH$_2$)$_2$—OCH$_2$-(4-iBuO-Ph) | H | H |
| 1-1054 | H | H | H | Me | 2 | —C≡C—(CH$_2$)$_2$—OCH$_2$-(3-MeS-Ph) | H | H |
| 1-1055 | H | H | H | Me | 2 | —C≡C—(CH$_2$)$_2$—OCH$_2$-(4-MeS-Ph) | H | H |

TABLE 1-continued

| | | | | | | | | |
|---|---|---|---|---|---|---|---|---|
| 1-1056 | H | H | H | Me | 2 | —C≡C—(CH$_2$)$_2$—OCH$_2$-(3-EtS-Ph) | H | H |
| 1-1057 | H | H | H | Me | 2 | —C≡C—(CH$_2$)$_2$—OCH$_2$-(4-EtS-Ph) | H | H |
| 1-1058 | H | H | H | Me | 2 | —C≡C—(CH$_2$)$_2$—OCH$_2$-(3-PrS-Ph) | H | H |
| 1-1059 | H | H | H | Me | 2 | —C≡C—(CH$_2$)$_2$—OCH$_2$-(4-PrS-Ph) | H | H |
| 1-1060 | H | H | H | Me | 2 | —C≡C—(CH$_2$)$_2$—OCH$_2$-(3-iPrS-Ph) | H | H |
| 1-1061 | H | H | H | Me | 2 | —C≡C—(CH$_2$)$_2$—OCH$_2$-(4-iPrS-Ph) | H | H |
| 1-1062 | H | H | H | Me | 2 | —C≡C—(CH$_2$)$_2$—OCH$_2$-[3-(2-Et-PrS)Ph] | H | H |
| 1-1063 | H | H | H | Me | 2 | —C≡C—(CH$_2$)$_2$—OCH$_2$-[4-(2-Et-PrS)Ph] | H | H |
| 1-1064 | H | H | H | Me | 2 | —C≡C—(CH$_2$)$_2$—OCH$_2$-(3-iBuS-Ph) | H | H |
| 1-1065 | H | H | H | Me | 2 | —C≡C—(CH$_2$)$_2$—OCH$_2$-(4-iBuS-Ph) | H | H |
| 1-1066 | H | H | H | Me | 2 | —C≡C—(CH$_2$)$_2$—OCH$_2$-(3-cHx-Ph) | H | H |
| 1-1067 | H | H | H | Me | 2 | —C≡C—(CH$_2$)$_2$—OCH$_2$-(4-cHx-Ph) | H | H |
| 1-1068 | H | H | H | Me | 2 | —C≡C—(CH$_2$)$_2$—OCH$_2$-(3-Ph-Ph) | H | H |
| 1-1069 | H | H | H | Me | 2 | —C≡C—(CH$_2$)$_2$—OCH$_2$-(4-Ph-Ph) | H | H |
| 1-1070 | H | H | H | Me | 2 | —C≡C—(CH$_2$)$_2$—OCH$_2$-(2,4-diMe-Ph) | H | H |
| 1-1071 | H | H | H | Me | 2 | —C≡C—(CH$_2$)$_2$—OCH$_2$-(3,4-diMe-Ph) | H | H |
| 1-1072 | H | H | H | Me | 2 | —C≡C—(CH$_2$)$_2$—OCH$_2$-(3,5-diMe-Ph) | H | H |
| 1-1073 | H | H | H | Me | 2 | —C≡C—(CH$_2$)$_3$—OCH$_2$-cHx | H | H |
| 1-1074 | H | H | H | Me | 2 | —C≡C—(CH$_2$)$_3$—OCH$_2$-Ph | H | H |
| 1-1075 | H | H | H | Me | 2 | —C≡C—(CH$_2$)$_4$—OCH$_2$-cHx | H | H |
| 1-1076 | H | H | H | Me | 2 | —C≡C—(CH$_2$)$_4$—OCH$_2$-Ph | H | H |
| 1-1077 | H | H | H | Me | 2 | —CO—CH$_2$-(4-cHx-Ph) | H | H |
| 1-1078 | H | H | H | Me | 2 | —CO—CH$_2$-(4-Ph-Ph) | H | H |
| 1-1079 | H | H | H | Me | 2 | —CO—(CH$_2$)$_2$-cHx | H | H |
| 1-1080 | H | H | H | Me | 2 | —CO—(CH$_2$)$_2$-Ph | H | H |
| 1-1081 | H | H | H | Me | 2 | —CO—(CH$_2$)$_3$-cHx | H | H |
| 1-1082 | H | H | H | Me | 2 | —CO—(CH$_2$)$_3$-Ph | H | H |
| 1-1083 | H | H | H | Me | 2 | —CO—(CH$_2$)$_4$-cHx | H | H |
| 1-1084 | H | H | H | Me | 2 | —CO—(CH$_2$)$_4$-(4-F-cHx) | H | H |
| 1-1085 | H | H | H | Me | 2 | —CO—(CH$_2$)$_4$-(4-Me-cHx) | H | H |
| 1-1086 | H | H | H | Me | 2 | —CO—(CH$_2$)$_4$-(4-Et-cHx) | H | H |
| 1-1087 | H | H | H | Me | 2 | —CO—(CH$_2$)$_4$-(4-CF$_3$-cHx) | H | H |
| 1-1088 | H | H | H | Me | 2 | —CO—(CH$_2$)$_4$-(4-MeO-cHx) | H | H |
| 1-1089 | H | H | H | Me | 2 | —CO—(CH$_2$)$_4$-(4-EtO-cHx) | H | H |
| 1-1090 | H | H | H | Me | 2 | —CO—(CH$_2$)$_4$-(4-MeS-cHx) | H | H |
| 1-1091 | H | H | H | Me | 2 | —CO—(CH$_2$)$_4$-(4-cHx-cHx) | H | H |
| 1-1092 | H | H | H | Me | 2 | —CO—(CH$_2$)$_4$-(4-Ph-cHx) | H | H |
| 1-1093 | H | H | H | Me | 2 | —CO—(CH$_2$)$_4$-Ph | H | H |
| 1-1094 | H | H | H | Me | 2 | —CO—(CH$_2$)$_4$-(4-F-Ph) | H | H |
| 1-1095 | H | H | H | Me | 2 | —CO—(CH$_2$)$_4$-(4-Me-Ph) | H | H |
| 1-1096 | H | H | H | Me | 2 | —CO—(CH$_2$)$_4$-(4-Et-Ph) | H | H |
| 1-1097 | H | H | H | Me | 2 | —CO—(CH$_2$)$_4$-(4-CF$_3$-Ph) | H | H |
| 1-1098 | H | H | H | Me | 2 | —CO—(CH$_2$)$_4$-(4-MeO-Ph) | H | H |
| 1-1099 | H | H | H | Me | 2 | —CO—(CH$_2$)$_4$-(4-EtO-Ph) | H | H |
| 1-1100 | H | H | H | Me | 2 | —CO—(CH$_2$)$_4$-(4-MeS-Ph) | H | H |
| 1-1101 | H | H | H | Me | 2 | —CO—(CH$_2$)$_4$-(4-cHx-Ph) | H | H |
| 1-1102 | H | H | H | Me | 2 | —CO—(CH$_2$)$_4$-(4-Ph-Ph) | H | H |
| 1-1103 | H | H | H | Me | 2 | —CO—(CH$_2$)$_5$-cHx | H | H |
| 1-1104 | H | H | H | Me | 2 | —CO—(CH$_2$)$_5$-(4-F-cHx) | H | H |
| 1-1105 | H | H | H | Me | 2 | —CO—(CH$_2$)$_5$-(4-Me-cHx) | H | H |
| 1-1106 | H | H | H | Me | 2 | —CO—(CH$_2$)$_5$-(4-Et-cHx) | H | H |
| 1-1107 | H | H | H | Me | 2 | —CO—(CH$_2$)$_5$-(4-CF$_3$-cHx) | H | H |
| 1-1108 | H | H | H | Me | 2 | —CO—(CH$_2$)$_5$-(4-MeO-cHx) | H | H |
| 1-1109 | H | H | H | Me | 2 | —CO—(CH$_2$)$_5$-(4-EtO-cHx) | H | H |
| 1-1110 | H | H | H | Me | 2 | —CO—(CH$_2$)$_5$-(4-MeS-cHx) | H | H |
| 1-1111 | H | H | H | Me | 2 | —CO—(CH$_2$)$_5$-(4-cHx-cHx) | H | H |
| 1-1112 | H | H | H | Me | 2 | —CO—(CH$_2$)$_5$-(4-Ph-cHx) | H | H |
| 1-1113 | H | H | H | Me | 2 | —CO—(CH$_2$)$_5$-Ph | H | H |
| 1-1114 | H | H | H | Me | 2 | —CO—(CH$_2$)$_5$-(4-F-Ph) | H | H |
| 1-1115 | H | H | H | Me | 2 | —CO—(CH$_2$)$_5$-(4-Me-Ph) | H | H |
| 1-1116 | H | H | H | Me | 2 | —CO—(CH$_2$)$_5$-(4-Et-Ph) | H | H |
| 1-1117 | H | H | H | Me | 2 | —CO—(CH$_2$)$_5$-(4-CF$_3$-Ph) | H | H |
| 1-1118 | H | H | H | Me | 2 | —CO—(CH$_2$)$_5$-(4-MeO-Ph) | H | H |
| 1-1119 | H | H | H | Me | 2 | —CO—(CH$_2$)$_5$-(4-EtO-Ph) | H | H |
| 1-1120 | H | H | H | Me | 2 | —CO—(CH$_2$)$_5$-(4-MeS-Ph) | H | H |
| 1-1121 | H | H | H | Me | 2 | —CO—(CH$_2$)$_5$-(4-cHx-Ph) | H | H |
| 1-1122 | H | H | H | Me | 2 | —CO—(CH$_2$)$_5$-(4-Ph-Ph) | H | H |
| 1-1123 | H | H | H | Me | 2 | —CO—(CH$_2$)$_6$-cHx | H | H |
| 1-1124 | H | H | H | Me | 2 | —CO—(CH$_2$)$_6$-Ph | H | H |
| 1-1125 | H | H | H | Me | 2 | —CO—(CH$_2$)$_7$-cHx | H | H |
| 1-1126 | H | H | H | Me | 2 | —CO—(CH$_2$)$_7$-Ph | H | H |
| 1-1127 | H | H | H | Me | 2 | —CO—(CH$_2$)$_2$—O-cHx | H | H |
| 1-1128 | H | H | H | Me | 2 | —CO—(CH$_2$)$_2$—O-(4-F-cHx) | H | H |
| 1-1129 | H | H | H | Me | 2 | —CO—(CH$_2$)$_2$—O-(4-Me-cHx) | H | H |
| 1-1130 | H | H | H | Me | 2 | —CO—(CH$_2$)$_2$—O-(4-Et-cHx) | H | H |
| 1-1131 | H | H | H | Me | 2 | —CO—(CH$_2$)$_2$—O-(4-CF$_3$-cHx) | H | H |
| 1-1132 | H | H | H | Me | 2 | —CO—(CH$_2$)$_2$—O-(4-MeO-cHx) | H | H |
| 1-1133 | H | H | H | Me | 2 | —CO—(CH$_2$)$_2$—O-(4-EtO-cHx) | H | H |
| 1-1134 | H | H | H | Me | 2 | —CO—(CH$_2$)$_2$—O-(4-MeS-cHx) | H | H |
| 1-1135 | H | H | H | Me | 2 | —CO—(CH$_2$)$_2$—O-(4-cHx-cHx) | H | H |

TABLE 1-continued

| | | | | | | | | |
|---|---|---|---|---|---|---|---|---|
| 1-1136 | H | H | H | Me | 2 | —CO—(CH$_2$)$_2$—O-(4-Ph-cHx) | H | H |
| 1-1137 | H | H | H | Me | 2 | —CO—(CH$_2$)$_2$—O-Ph | H | H |
| 1-1138 | H | H | H | Me | 2 | —CO—(CH$_2$)$_2$—O-(4-F-Ph) | H | H |
| 1-1139 | H | H | H | Me | 2 | —CO—(CH$_2$)$_2$—O-(4-Me-Ph) | H | H |
| 1-1140 | H | H | H | Me | 2 | —CO—(CH$_2$)$_2$—O-(4-Et-Ph) | H | H |
| 1-1141 | H | H | H | Me | 2 | —CO—(CH$_2$)$_2$—O-(4-CF$_3$-Ph) | H | H |
| 1-1142 | H | H | H | Me | 2 | —CO—(CH$_2$)$_2$—O-(4-MeO-Ph) | H | H |
| 1-1143 | H | H | H | Me | 2 | —CO—(CH$_2$)$_2$—O-(4-EtO-Ph) | H | H |
| 1-1144 | H | H | H | Me | 2 | —CO—(CH$_2$)$_2$—O-(4-MeS-Ph) | H | H |
| 1-1145 | H | H | H | Me | 2 | —CO—(CH$_2$)$_2$—O-(4-cHx-Ph) | H | H |
| 1-1146 | H | H | H | Me | 2 | —CO—(CH$_2$)$_2$—O-(4-Ph-Ph) | H | H |
| 1-1147 | H | H | H | Me | 2 | —CO—(CH$_2$)$_3$—O-cPn | H | H |
| 1-1148 | H | H | H | Me | 2 | —CO—(CH$_2$)$_3$—O-cHx | H | H |
| 1-1149 | H | H | H | Me | 2 | —CO—(CH$_2$)$_3$—O-cHx | Me | H |
| 1-1150 | H | H | H | Me | 2 | —CO—(CH$_2$)$_3$—O-cHx | H | Me |
| 1-1151 | H | H | H | Me | 2 | —CO—(CH$_2$)$_3$—O-cHx | F | H |
| 1-1152 | H | H | H | Me | 2 | —CO—(CH$_2$)$_3$—O-cHx | H | F |
| 1-1153 | H | H | H | Me | 2 | —CO—(CH$_2$)$_3$—O-(3-F-cHx) | H | H |
| 1-1154 | H | H | H | Me | 2 | —CO—(CH$_2$)$_3$—O-(4-F-cHx) | H | H |
| 1-1155 | H | H | H | Me | 2 | —CO—(CH$_2$)$_3$—O-(4-Cl-cHx) | H | H |
| 1-1156 | H | H | H | Me | 2 | —CO—(CH$_2$)$_3$—O-(4-Br-cHx) | H | H |
| 1-1157 | H | H | H | Me | 2 | —CO—(CH$_2$)$_3$—O-(3-Me-cHx) | H | H |
| 1-1158 | H | H | H | Me | 2 | —CO—(CH$_2$)$_3$—O-(4-Me-cHx) | H | H |
| 1-1159 | H | H | H | Me | 2 | —CO—(CH$_2$)$_3$—O-(3-Et-cHx) | H | H |
| 1-1160 | H | H | H | Me | 2 | —CO—(CH$_2$)$_3$—O-(4-Et-cHx) | H | H |
| 1-1161 | H | H | H | Me | 2 | —CO—(CH$_2$)$_3$—O-(3-Pr-cHx) | H | H |
| 1-1162 | H | H | H | Me | 2 | —CO—(CH$_2$)$_3$—O-(4-Pr-cHx) | H | H |
| 1-1163 | H | H | H | Me | 2 | —CO—(CH$_2$)$_3$—O-(4-iPr-cHx) | H | H |
| 1-1164 | H | H | H | Me | 2 | —CO—(CH$_2$)$_3$—O-(3-Bu-cHx) | H | H |
| 1-1165 | H | H | H | Me | 2 | —CO—(CH$_2$)$_3$—O-(4-Bu-cHx) | H | H |
| 1-1166 | H | H | H | Me | 2 | —CO—(CH$_2$)$_3$—O-(3-CF$_3$-cHx) | H | H |
| 1-1167 | H | H | H | Me | 2 | —CO—(CH$_2$)$_3$—O-(4-CF$_3$-cHx) | H | H |
| 1-1168 | H | H | H | Me | 2 | —CO—(CH$_2$)$_3$—O-(3-MeO-cHx) | H | H |
| 1-1169 | H | H | H | Me | 2 | —CO—(CH$_2$)$_3$—O-(4-MeO-cHx) | H | H |
| 1-1170 | H | H | H | Me | 2 | —CO—(CH$_2$)$_3$—O-(3-EtO-cHx) | H | H |
| 1-1171 | H | H | H | Me | 2 | —CO—(CH$_2$)$_3$—O-(4-EtO-cHx) | H | H |
| 1-1172 | H | H | H | Me | 2 | —CO—(CH$_2$)$_3$—O-(3-PrO-cHx) | H | H |
| 1-1173 | H | H | H | Me | 2 | —CO—(CH$_2$)$_3$—O-(4-PrO-cHx) | H | H |
| 1-1174 | H | H | H | Me | 2 | —CO—(CH$_2$)$_3$—O-(3-iPrO-cHx) | H | H |
| 1-1175 | H | H | H | Me | 2 | —CO—(CH$_2$)$_3$—O-(4-iPrO-cHx) | H | H |
| 1-1176 | H | H | H | Me | 2 | —CO—(CH$_2$)$_3$—O-[3-(2-Et-PrO)cHx] | H | H |
| 1-1177 | H | H | H | Me | 2 | —CO—(CH$_2$)$_3$—O-[4-(2-Et-PrO)cHx] | H | H |
| 1-1178 | H | H | H | Me | 2 | —CO—(CH$_2$)$_3$—O-(3-iBuO-cHx) | H | H |
| 1-1179 | H | H | H | Me | 2 | —CO—(CH$_2$)$_3$—O-(4-iBuO-cHx) | H | H |
| 1-1180 | H | H | H | Me | 2 | —CO—(CH$_2$)$_3$—O-(3-MeS-cHx) | H | H |
| 1-1181 | H | H | H | Me | 2 | —CO—(CH$_2$)$_3$—O-(4-MeS-cHx) | H | H |
| 1-1182 | H | H | H | Me | 2 | —CO—(CH$_2$)$_3$—O-(3-EtS-cHx) | H | H |
| 1-1183 | H | H | H | Me | 2 | —CO—(CH$_2$)$_3$—O-(4-EtS-cHx) | H | H |
| 1-1184 | H | H | H | Me | 2 | —CO—(CH$_2$)$_3$—O-(3-PrS-cHx) | H | H |
| 1-1185 | H | H | H | Me | 2 | —CO—(CH$_2$)$_3$—O-(4-PrS-cHx) | H | H |
| 1-1186 | H | H | H | Me | 2 | —CO—(CH$_2$)$_3$—O-(3-iPrS-cHx) | H | H |
| 1-1187 | H | H | H | Me | 2 | —CO—(CH$_2$)$_3$—O-(4-iPrS-cHx) | H | H |
| 1-1188 | H | H | H | Me | 2 | —CO—(CH$_2$)$_3$—O-[3-(2-Et-PrS)cHx] | H | H |
| 1-1189 | H | H | H | Me | 2 | —CO—(CH$_2$)$_3$—O-[4-(2-Et-PrS)cHx] | H | H |
| 1-1190 | H | H | H | Me | 2 | —CO—(CH$_2$)$_3$—O-(3-iBuS-cHx) | H | H |
| 1-1191 | H | H | H | Me | 2 | —CO—(CH$_2$)$_3$—O-(4-iBuS-cHx) | H | H |
| 1-1192 | H | H | H | Me | 2 | —CO—(CH$_2$)$_3$—O-(3-cHx-cHx) | H | H |
| 1-1193 | H | H | H | Me | 2 | —CO—(CH$_2$)$_3$—O-(4-cHx-cHx) | H | H |
| 1-1194 | H | H | H | Me | 2 | —CO—(CH$_2$)$_3$—O-(3-Ph-cHx) | H | H |
| 1-1195 | H | H | H | Me | 2 | —CO—(CH$_2$)$_3$—O-(4-Ph-cHx) | H | H |
| 1-1196 | H | H | H | Me | 2 | —CO—(CH$_2$)$_3$—O-(2,4-diMe-cHx) | H | H |
| 1-1197 | H | H | H | Me | 2 | —CO—(CH$_2$)$_3$—O-(3,4-diMe-cHx) | H | H |
| 1-1198 | H | H | H | Me | 2 | —CO—(CH$_2$)$_3$—O-(3,5-diMe-cHx) | H | H |
| 1-1199 | H | H | H | Me | 2 | —CO—(CH$_2$)$_3$—O-Ph | H | H |
| 1-1200 | H | H | H | Me | 2 | —CO—(CH$_2$)$_3$—O-Ph | Me | H |
| 1-1201 | H | H | H | Me | 2 | —CO—(CH$_2$)$_3$—O-Ph | H | Me |
| 1-1202 | H | H | H | Me | 2 | —CO—(CH$_2$)$_3$—O-Ph | F | H |
| 1-1203 | H | H | H | Me | 2 | —CO—(CH$_2$)$_3$—O-Ph | H | F |
| 1-1204 | H | H | H | Me | 2 | —CO—(CH$_2$)$_3$—O-(3-F-Ph) | H | H |
| 1-1205 | H | H | H | Me | 2 | —CO—(CH$_2$)$_3$—O-(4-F-Ph) | H | H |
| 1-1206 | H | H | H | Me | 2 | —CO—(CH$_2$)$_3$—O-(4-Cl-Ph) | H | H |
| 1-1207 | H | H | H | Me | 2 | —CO—(CH$_2$)$_3$—O-(4-Br-Ph) | H | H |
| 1-1208 | H | H | H | Me | 2 | —CO—(CH$_2$)$_3$—O-(3-Me-Ph) | H | H |
| 1-1209 | H | H | H | Me | 2 | —CO—(CH$_2$)$_3$—O-(4-Me-Ph) | H | H |
| 1-1210 | H | H | H | Me | 2 | —CO—(CH$_2$)$_3$—O-(3-Et-Ph) | H | H |
| 1-1211 | H | H | H | Me | 2 | —CO—(CH$_2$)$_3$—O-(4-Et-Ph) | H | H |
| 1-1212 | H | H | H | Me | 2 | —CO—(CH$_2$)$_3$—O-(3-Pr-Ph) | H | H |
| 1-1213 | H | H | H | Me | 2 | —CO—(CH$_2$)$_3$—O-(4-Pr-Ph) | H | H |
| 1-1214 | H | H | H | Me | 2 | —CO—(CH$_2$)$_3$—O-(3-iPr-Ph) | H | H |
| 1-1215 | H | H | H | Me | 2 | —CO—(CH$_2$)$_3$—O-(4-iPr-Ph) | H | H |

TABLE 1-continued

| | | | | | | | | |
|---|---|---|---|---|---|---|---|---|
| 1-1216 | H | H | H | Me | 2 | —CO—(CH$_2$)$_3$—O-(3-Bu-Ph) | H | H |
| 1-1217 | H | H | H | Me | 2 | —CO—(CH$_2$)$_3$—O-(4-Bu-Ph) | H | H |
| 1-1218 | H | H | H | Me | 2 | —CO—(CH$_2$)$_3$—O-(3-CF$_3$-Ph) | H | H |
| 1-1219 | H | H | H | Me | 2 | —CO—(CH$_2$)$_3$—O-(4-CF$_3$-PPh) | H | H |
| 1-1220 | H | H | H | Me | 2 | —CO—(CH$_2$)$_3$—O-(3-MeO-Ph) | H | H |
| 1-1221 | H | H | H | Me | 2 | —CO—(CH$_2$)$_3$—O-(4-MeO-Ph) | H | H |
| 1-1222 | H | H | H | Me | 2 | —CO—(CH$_2$)$_3$—O-(3-EtO-Ph) | H | H |
| 1-1223 | H | H | H | Me | 2 | —CO—(CH$_2$)$_3$—O-(4-EtO-Ph) | H | H |
| 1-1224 | H | H | H | Me | 2 | —CO—(CH$_2$)$_3$—O-(3-PrO-Ph) | H | H |
| 1-1225 | H | H | H | Me | 2 | —CO—(CH$_2$)$_3$—O-(4-PrO-Ph) | H | H |
| 1-1226 | H | H | H | Me | 2 | —CO—(CH$_2$)$_3$—O-(3-iPrO-Ph) | H | H |
| 1-1227 | H | H | H | Me | 2 | —CO—(CH$_2$)$_3$—O-(4-iPrO-Ph) | H | H |
| 1-1228 | H | H | H | Me | 2 | —CO—(CH$_2$)$_3$—O-[3-(2-Et-PrO)-Ph] | H | H |
| 1-1229 | H | H | H | Me | 2 | —CO—(CH$_2$)$_3$—O-[4-(2-Et-PrO)-Ph] | H | H |
| 1-1230 | H | H | H | Me | 2 | —CO—(CH$_2$)$_3$—O-(3-iBuO-Ph) | H | H |
| 1-1231 | H | H | H | Me | 2 | —CO—(CH$_2$)$_3$—O-(4-iBuO-Ph) | H | H |
| 1-1232 | H | H | H | Me | 2 | —CO—(CH$_2$)$_3$—O-(3-MeS-Ph) | H | H |
| 1-1233 | H | H | H | Me | 2 | —CO—(CH$_2$)$_3$—O-(4-MeS-Ph) | H | H |
| 1-1234 | H | H | H | Me | 2 | —CO—(CH$_2$)$_3$—O-(3-EtS-Ph) | H | H |
| 1-1235 | H | H | H | Me | 2 | —CO—(CH$_2$)$_3$—O-(4-EtS-Ph) | H | H |
| 1-1236 | H | H | H | Me | 2 | —CO—(CH$_2$)$_3$—O-(3-PrS-Ph) | H | H |
| 1-1237 | H | H | H | Me | 2 | —CO—(CH$_2$)$_3$—O-(4-PrS-Ph) | H | H |
| 1-1238 | H | H | H | Me | 2 | —CO—(CH$_2$)$_3$—O-(3-iPrS-Ph) | H | H |
| 1-1239 | H | H | H | Me | 2 | —CO—(CH$_2$)$_3$—O-(4-iPrS-Ph) | H | H |
| 1-1240 | H | H | H | Me | 2 | —CO—(CH$_2$)$_3$—O-[3-(2-Et-PrS)-Ph] | H | H |
| 1-1241 | H | H | H | Me | 2 | —CO—(CH$_2$)$_3$—O-[4-(2-Et-PrS)-Ph] | H | H |
| 1-1242 | H | H | H | Me | 2 | —CO—(CH$_2$)$_3$—O-(3-iBuS-Ph) | H | H |
| 1-1243 | H | H | H | Me | 2 | —CO—(CH$_2$)$_3$—O-(4-iBuS-Ph) | H | H |
| 1-1244 | H | H | H | Me | 2 | —CO—(CH$_2$)$_3$—O-(3-cHx-Ph) | H | H |
| 1-1245 | H | H | H | Me | 2 | —CO—(CH$_2$)$_3$—O-(4-cHx-Ph) | H | H |
| 1-1246 | H | H | H | Me | 2 | —CO—(CH$_2$)$_3$—O-(3-Ph-Ph) | H | H |
| 1-1247 | H | H | H | Me | 2 | —CO—(CH$_2$)$_3$—O-(4-Ph-Ph) | H | H |
| 1-1248 | H | H | H | Me | 2 | —CO—(CH$_2$)$_3$—O-(2,4-diMe-Ph) | H | H |
| 1-1249 | H | H | H | Me | 2 | —CO—(CH$_2$)$_3$—O-(3,4-diMe-Ph) | H | H |
| 1-1250 | H | H | H | Me | 2 | —CO—(CH$_2$)$_3$—O-(3,5-diMe-Ph) | H | H |
| 1-1251 | H | H | H | Me | 2 | —CO—(CH$_2$)$_4$—O-cHx | H | H |
| 1-1252 | H | H | H | Me | 2 | —CO—(CH$_2$)$_4$—O-Ph | H | H |
| 1-1253 | H | H | H | Me | 2 | —CO—(CH$_2$)$_5$—O-cHx | H | H |
| 1-1254 | H | H | H | Me | 2 | —CO—(CH$_2$)$_5$—O-Ph | H | H |
| 1-1255 | H | H | H | Me | 2 | —CO—(CH$_2$)$_2$—OCH$_2$-cHx | H | H |
| 1-1256 | H | H | H | Me | 2 | —CO—(CH$_2$)$_2$—OCH$_2$-(4-F-cHx) | H | H |
| 1-1257 | H | H | H | Me | 2 | —CO—(CH$_2$)$_2$—OCH$_2$-(4-Me-cHx) | H | H |
| 1-1258 | H | H | H | Me | 2 | —CO—(CH$_2$)$_2$—OCH$_2$-(4-Et-cHx) | H | H |
| 1-1259 | H | H | H | Me | 2 | —CO—(CH$_2$)$_2$—OCH$_2$-(4-CF$_3$-cHx) | H | H |
| 1-1260 | H | H | H | Me | 2 | —CO—(CH$_2$)$_2$—OCH$_2$-(4-MeO-cHx) | H | H |
| 1-1261 | H | H | H | Me | 2 | —CO—(CH$_2$)$_2$—OCH$_2$-(4-EtO-cHx) | H | H |
| 1-1262 | H | H | H | Me | 2 | —CO—(CH$_2$)$_2$—OCH$_2$-(4-MeS-cHx) | H | H |
| 1-1263 | H | H | H | Me | 2 | —CO—(CH$_2$)$_2$—OCH$_2$-(4-cHx-cHx) | H | H |
| 1-1264 | H | H | H | Me | 2 | —CO—(CH$_2$)$_2$—OCH$_2$-(4-Ph-cHx) | H | H |
| 1-1265 | H | H | H | Me | 2 | —CO—(CH$_2$)$_2$—OCH$_2$-Ph | H | H |
| 1-1266 | H | H | H | Me | 2 | —CO—(CH$_2$)$_2$—OCH$_2$-(4-F-Ph) | H | H |
| 1-1267 | H | H | H | Me | 2 | —CO—(CH$_2$)$_2$—OCH$_2$-(4-Me-Ph) | H | H |
| 1-1268 | H | H | H | Me | 2 | —CO—(CH$_2$)$_2$—OCH$_2$-(4-Et-Ph) | H | H |
| 1-1269 | H | H | H | Me | 2 | —CO—(CH$_2$)$_2$—OCH$_2$-(4-CF$_3$-Ph) | H | H |
| 1-1270 | H | H | H | Me | 2 | —CO—(CH$_2$)$_2$—OCH$_2$-(4-MeO-Ph) | H | H |
| 1-1271 | H | H | H | Me | 2 | —CO—(CH$_2$)$_2$—OCH$_2$-(4-EtO-Ph) | H | H |
| 1-1272 | H | H | H | Me | 2 | —CO—(CH$_2$)$_2$—OCH$_2$-(4-MeS-Ph) | H | H |
| 1-1273 | H | H | H | Me | 2 | —CO—(CH$_2$)$_2$—OCH$_2$-(4-cHx-Ph) | H | H |
| 1-1274 | H | H | H | Me | 2 | —CO—(CH$_2$)$_2$—OCH$_2$-(4-Ph-Ph) | H | H |
| 1-1275 | H | H | H | Me | 2 | —CO—(CH$_2$)$_3$—OCH$_2$—CH$_2$-cPn | H | H |
| 1-1276 | H | H | H | Me | 2 | —CO—(CH$_2$)$_3$—OCH$_2$-cHx | H | H |
| 1-1277 | H | H | H | Me | 2 | —CO—(CH$_2$)$_3$—OCH$_2$-cHx | Me | H |
| 1-1278 | H | H | H | Me | 2 | —CO—(CH$_2$)$_3$—OCH$_2$-cHx | H | Me |
| 1-1279 | H | H | H | Me | 2 | —CO—(CH$_2$)$_3$—OCH$_2$-cHx | F | H |
| 1-1280 | H | H | H | Me | 2 | —CO—(CH$_2$)$_3$—OCH$_2$-cHx | H | F |
| 1-1281 | H | H | H | Me | 2 | —CO—(CH$_2$)$_3$—OCH$_2$-(3-F-cHx) | H | H |
| 1-1282 | H | H | H | Me | 2 | —CO—(CH$_2$)$_3$—OCH$_2$-(4-F-cHx) | H | H |
| 1-1283 | H | H | H | Me | 2 | —CO—(CH$_2$)$_3$—OCH$_2$-(4-Cl-cHx) | H | H |
| 1-1284 | H | H | H | Me | 2 | —CO—(CH$_2$)$_3$—OCH$_2$-(4-Br-cHx) | H | H |
| 1-1285 | H | H | H | Me | 2 | —CO—(CH$_2$)$_3$—OCH$_2$-(3-Me-cHx) | H | H |
| 1-1286 | H | H | H | Me | 2 | —CO—(CH$_2$)$_3$—OCH$_2$-(4-Me-cHx) | H | H |
| 1-1287 | H | H | H | Me | 2 | —CO—(CH$_2$)$_3$—OCH$_2$-(3-Et-cHx) | H | H |
| 1-1288 | H | H | H | Me | 2 | —CO—(CH$_2$)$_3$—OCH$_2$-(4-Et-cHx) | H | H |
| 1-1289 | H | H | H | Me | 2 | —CO—(CH$_2$)$_3$—OCH$_2$-(3-Pr-cHx) | H | H |
| 1-1290 | H | H | H | Me | 2 | —CO—(CH$_2$)$_3$—OCH$_2$-(4-Pr-cHx) | H | H |
| 1-1291 | H | H | H | Me | 2 | —CO—(CH$_2$)$_3$—OCH$_2$-(4-iPr-cHx) | H | H |
| 1-1292 | H | H | H | Me | 2 | —CO—(CH$_2$)$_3$—OCH$_2$-(3-Bu-cHx) | H | H |
| 1-1293 | H | H | H | Me | 2 | —CO—(CH$_2$)$_3$—OCH$_2$-(4-Bu-cHx) | H | H |
| 1-1294 | H | H | H | Me | 2 | —CO—(CH$_2$)$_3$—OCH$_2$-(3-CF$_3$-cHx) | H | H |
| 1-1295 | H | H | H | Me | 2 | —CO—(CH$_2$)$_3$—OCH$_2$-(4-CF$_3$-cHx) | H | H |

TABLE 1-continued

| | | | | | | | | |
|---|---|---|---|---|---|---|---|---|
| 1-1296 | H | H | H | Me | 2 | —CO—(CH$_2$)$_3$—OCH$_2$-(3-MeO-cHx) | H | H |
| 1-1297 | H | H | H | Me | 2 | —CO—(CH$_2$)$_3$—OCH$_2$-(4-MeO-cHx) | H | H |
| 1-1298 | H | H | H | Me | 2 | —CO—(CH$_2$)$_3$—OCH$_2$-(3-EtO-cHx) | H | H |
| 1-1299 | H | H | H | Me | 2 | —CO—(CH$_2$)$_3$—OCH$_2$-(4-EtO-cHx) | H | H |
| 1-1300 | H | H | H | Me | 2 | —CO—(CH$_2$)$_3$—OCH$_2$-(3-PrO-cHx) | H | H |
| 1-1301 | H | H | H | Me | 2 | —CO—(CH$_2$)$_3$—OCH$_2$-(4-PrO-cHx) | H | H |
| 1-1302 | H | H | H | Me | 2 | —CO—(CH$_2$)$_3$—OCH$_2$-(3-iPrO-cHx) | H | H |
| 1-1303 | H | H | H | Me | 2 | —CO—(CH$_2$)$_3$—OCH$_2$-(4-iPrO-cHx) | H | H |
| 1-1304 | H | H | H | Me | 2 | —CO—(CH$_2$)$_3$—OCH$_2$-[3-(2-Et-PrO)cHx] | H | H |
| 1-1305 | H | H | H | Me | 2 | —CO—(CH$_2$)$_3$—OCH$_2$-[4-(2-Et-PrO)cHx] | H | H |
| 1-1306 | H | H | H | Me | 2 | —CO—(CH$_2$)$_3$—OCH$_2$-(3-iBuO-cHx) | H | H |
| 1-1307 | H | H | H | Me | 2 | —CO—(CH$_2$)$_3$—OCH$_2$-(4-iBuO-cHx) | H | H |
| 1-1308 | H | H | H | Me | 2 | —CO—(CH$_2$)$_3$—OCH$_2$-(3-MeS-cHx) | H | H |
| 1-1309 | H | H | H | Me | 2 | —CO—(CH$_2$)$_3$—OCH$_2$-(4-MeS-cHx) | H | H |
| 1-1310 | H | H | H | Me | 2 | —CO—(CH$_2$)$_3$—OCH$_2$-(3-EtS-cHx) | H | H |
| 1-1311 | H | H | H | Me | 2 | —CO—(CH$_2$)$_3$—OCH$_2$-(4-EtS-cHx) | H | H |
| 1-1312 | H | H | H | Me | 2 | —CO—(CH$_2$)$_3$—OCH$_2$-(3-PrS-cHx) | H | H |
| 1-1313 | H | H | H | Me | 2 | —CO—(CH$_2$)$_3$—OCH$_2$-(4-PrS-cHx) | H | H |
| 1-1314 | H | H | H | Me | 2 | —CO—(CH$_2$)$_3$—OCH$_2$-(3-iPrS-cHx) | H | H |
| 1-1315 | H | H | H | Me | 2 | —CO—(CH$_2$)$_3$—OCH$_2$-(4-iPrS-cHx) | H | H |
| 1-1316 | H | H | H | Me | 2 | —CO—(CH$_2$)$_3$—OCH$_2$-[3-(2-Et-PrS)cHx] | H | H |
| 1-1317 | H | H | H | Me | 2 | —CO—(CH$_2$)$_3$—OCH$_2$-[4-(2-Et-PrS)cHx] | H | H |
| 1-1318 | H | H | H | Me | 2 | —CO—(CH$_2$)$_3$—OCH$_2$-(3-iBuS-cHx) | H | H |
| 1-1319 | H | H | H | Me | 2 | —CO—(CH$_2$)$_3$—OCH$_2$-(4-iBuS-cHx) | H | H |
| 1-1320 | H | H | H | Me | 2 | —CO—(CH$_2$)$_3$—OCH$_2$-(3-cHx-cHx) | H | H |
| 1-1321 | H | H | H | Me | 2 | —CO—(CH$_2$)$_3$—OCH$_2$-(4-cHx-cHx) | H | H |
| 1-1322 | H | H | H | Me | 2 | —CO—(CH$_2$)$_3$—OCH$_2$-(3-Ph-cHx) | H | H |
| 1-1323 | H | H | H | Me | 2 | —CO—(CH$_2$)$_3$—OCH$_2$-(4-Ph-cHx) | H | H |
| 1-1324 | H | H | H | Me | 2 | —CO—(CH$_2$)$_3$—OCH$_2$-(2,4-diMe-cHx) | H | H |
| 1-1325 | H | H | H | Me | 2 | —CO—(CH$_2$)$_3$—OCH$_2$-(3,4-diMe-cHx) | H | H |
| 1-1326 | H | H | H | Me | 2 | —CO—(CH$_2$)$_3$—OCH$_2$-(3,5-diMe-cHx) | H | H |
| 1-1327 | H | H | H | Me | 2 | —CO—(CH$_2$)$_3$—OCH$_2$-Ph | H | H |
| 1-1328 | H | H | H | Me | 2 | —CO—(CH$_2$)$_3$—OCH$_2$-Ph | Me | H |
| 1-1329 | H | H | H | Me | 2 | —CO—(CH$_2$)$_3$—OCH$_2$-Ph | H | Me |
| 1-1330 | H | H | H | Me | 2 | —CO—(CH$_2$)$_3$—OCH$_2$-Ph | F | H |
| 1-1331 | H | H | H | Me | 2 | —CO—(CH$_2$)$_3$—OCH$_2$-Ph | H | F |
| 1-1332 | H | H | H | Me | 2 | —CO—(CH$_2$)$_3$—OCH$_2$-(3-F-Ph) | H | H |
| 1-1333 | H | H | H | Me | 2 | —CO—(CH$_2$)$_3$—OCH$_2$-(4-F-Ph) | H | H |
| 1-1334 | H | H | H | Me | 2 | —CO—(CH$_2$)$_3$—OCH$_2$-(4-Cl-Ph) | H | H |
| 1-1335 | H | H | H | Me | 2 | —CO—(CH$_2$)$_3$—OCH$_2$-(4-Br-Ph) | H | H |
| 1-1336 | H | H | H | Me | 2 | —CO—(CH$_2$)$_3$—OCH$_2$-(3-Me-Ph) | H | H |
| 1-1337 | H | H | H | Me | 2 | —CO—(CH$_2$)$_3$—OCH$_2$-(4-Me-Ph) | H | H |
| 1-1338 | H | H | H | Me | 2 | —CO—(CH$_2$)$_3$—OCH$_2$-(3-Et-Ph) | H | H |
| 1-1339 | H | H | H | Me | 2 | —CO—(CH$_2$)$_3$—OCH$_2$-(4-Et-Ph) | H | H |
| 1-1340 | H | H | H | Me | 2 | —CO—(CH$_2$)$_3$—OCH$_2$-(3-Pr-Ph) | H | H |
| 1-1341 | H | H | H | Me | 2 | —CO—(CH$_2$)$_3$—OCH$_2$-(4-Pr-Ph) | H | H |
| 1-1342 | H | H | H | Me | 2 | —CO—(CH$_2$)$_3$—OCH$_2$-(3-iPr-Ph) | H | H |
| 1-1343 | H | H | H | Me | 2 | —CO—(CH$_2$)$_3$—OCH$_2$-(4-iPr-Ph) | H | H |
| 1-1344 | H | H | H | Me | 2 | —CO—(CH$_2$)$_3$—OCH$_2$-(3-Bu-Ph) | H | H |
| 1-1345 | H | H | H | Me | 2 | —CO—(CH$_2$)$_3$—OCH$_2$-(4-Bu-Ph) | H | H |
| 1-1346 | H | H | H | Me | 2 | —CO—(CH$_2$)$_3$—OCH$_2$-(3-CF$_3$-Ph) | H | H |
| 1-1347 | H | H | H | Me | 2 | —CO—(CH$_2$)$_3$—OCH$_2$-(4-CF$_3$-Ph) | H | H |
| 1-1348 | H | H | H | Me | 2 | —CO—(CH$_2$)$_3$—OCH$_2$-(3-MeO-Ph) | H | H |
| 1-1349 | H | H | H | Me | 2 | —CO—(CH$_2$)$_3$—OCH$_2$-(4-MeO-Ph) | H | H |
| 1-1350 | H | H | H | Me | 2 | —CO—(CH$_2$)$_3$—OCH$_2$-(3-EtO-Ph) | H | H |
| 1-1351 | H | H | H | Me | 2 | —CO—(CH$_2$)$_3$—OCH$_2$-(4-EtO-Ph) | H | H |
| 1-1352 | H | H | H | Me | 2 | —CO—(CH$_2$)$_3$—OCH$_2$-(3-PrO-Ph) | H | H |
| 1-1353 | H | H | H | Me | 2 | —CO—(CH$_2$)$_3$—OCH$_2$-(4-PrO-Ph) | H | H |
| 1-1354 | H | H | H | Me | 2 | —CO—(CH$_2$)$_3$—OCH$_2$-(3-iPrO-Ph) | H | H |
| 1-1355 | H | H | H | Me | 2 | —CO—(CH$_2$)$_3$—OCH$_2$-(4-iPrO-Ph) | H | H |
| 1-1356 | H | H | H | Me | 2 | —CO—(CH$_2$)$_3$—OCH$_2$-[3-(2-Et-PrO)Ph] | H | H |
| 1-1357 | H | H | H | Me | 2 | —CO—(CH$_2$)$_3$—OCH$_2$-[4-(2-Et-PrO)Ph] | H | H |
| 1-1358 | H | H | H | Me | 2 | —CO—(CH$_2$)$_3$—OCH$_2$-(3-iBuO-Ph) | H | H |
| 1-1359 | H | H | H | Me | 2 | —CO—(CH$_2$)$_3$—OCH$_2$-(4-iBuO-Ph) | H | H |
| 1-1360 | H | H | H | Me | 2 | —CO—(CH$_2$)$_3$—OCH$_2$-(3-MeS-Ph) | H | H |
| 1-1361 | H | H | H | Me | 2 | —CO—(CH$_2$)$_3$—OCH$_2$-(4-MeS-Ph) | H | H |
| 1-1362 | H | H | H | Me | 2 | —CO—(CH$_2$)$_3$—OCH$_2$-(3-EtS-Ph) | H | H |
| 1-1363 | H | H | H | Me | 2 | —CO—(CH$_2$)$_3$—OCH$_2$-(4-EtS-Ph) | H | H |
| 1-1364 | H | H | H | Me | 2 | —CO—(CH$_2$)$_3$—OCH$_2$-(3-PrS-Ph) | H | H |
| 1-1365 | H | H | H | Me | 2 | —CO—(CH$_2$)$_3$—OCH$_2$-(4-PrS-Ph) | H | H |
| 1-1366 | H | H | H | Me | 2 | —CO—(CH$_2$)$_3$—OCH$_2$-(3-iPrS-Ph) | H | H |
| 1-1367 | H | H | H | Me | 2 | —CO—(CH$_2$)$_3$—OCH$_2$-(4-iPrS-Ph) | H | H |
| 1-1368 | H | H | H | Me | 2 | —CO—(CH$_2$)$_3$—OCH$_2$-[3-(2-Et-PrS)Ph] | H | H |
| 1-1369 | H | H | H | Me | 2 | —CO—(CH$_2$)$_3$—OCH$_2$-[4-(2-Et-PrS)Ph] | H | H |
| 1-1370 | H | H | H | Me | 2 | —CO—(CH$_2$)$_3$—OCH$_2$-(3-iBuS-Ph) | H | H |
| 1-1371 | H | H | H | Me | 2 | —CO—(CH$_2$)$_3$—OCH$_2$-(4-iBuS-Ph) | H | H |
| 1-1372 | H | H | H | Me | 2 | —CO—(CH$_2$)$_3$—OCH$_2$-(3-cHx-Ph) | H | H |
| 1-1373 | H | H | H | Me | 2 | —CO—(CH$_2$)$_3$—OCH$_2$-(4-cHx-Ph) | H | H |
| 1-1374 | H | H | H | Me | 2 | —CO—(CH$_2$)$_3$—OCH$_2$-(3-Ph-Ph) | H | H |
| 1-1375 | H | H | H | Me | 2 | —CO—(CH$_2$)$_3$—OCH$_2$-(4-Ph-Ph) | H | H |

TABLE 1-continued

| | | | | | | | | |
|---|---|---|---|---|---|---|---|---|
| 1-1376 | H | H | H | Me | 2 | —CO—(CH$_2$)$_3$—OCH$_2$-(2,4-diMe-Ph) | H | H |
| 1-1377 | H | H | H | Me | 2 | —CO—(CH$_2$)$_3$—OCH$_2$-(3,4-diMe-Ph) | H | H |
| 1-1378 | H | H | H | Me | 2 | —CO—(CH$_2$)$_3$—OCH$_2$-(3,5-diMe-Ph) | H | H |
| 1-1379 | H | H | H | Me | 2 | —CO—(CH$_2$)$_4$—OCH$_2$-cHx | H | H |
| 1-1380 | H | H | H | Me | 2 | —CO—(CH$_2$)$_4$—OCH$_2$-Ph | H | H |
| 1-1381 | H | H | H | Me | 2 | —CO—(CH$_2$)$_5$—OCH$_2$-cHx | H | H |
| 1-1382 | H | H | H | Me | 2 | —CO—(CH$_2$)$_5$—OCH$_2$-Ph | H | H |
| 1-1383 | H | H | H | Me | 2 | —CH(OH)—CH$_2$-cHx | H | H |
| 1-1384 | H | H | H | Me | 2 | —CH(OH)—CH$_2$-Ph | H | H |
| 1-1385 | H | H | H | Me | 2 | —CH(OH)—(CH$_2$)$_2$-cHx | H | H |
| 1-1386 | H | H | H | Me | 2 | —CH(OH)—(CH$_2$)$_2$-Ph | H | H |
| 1-1387 | H | H | H | Me | 2 | —CH(OH)—(CH$_2$)$_3$-cHx | H | H |
| 1-1388 | H | H | H | Me | 2 | —CH(OH)—(CH$_2$)$_3$-Ph | H | H |
| 1-1389 | H | H | H | Me | 2 | —CH(OH)—(CH$_2$)$_4$-cHx | H | H |
| 1-1390 | H | H | H | Me | 2 | —CH(OH)—(CH$_2$)$_4$-(4-F-cHx) | H | H |
| 1-1391 | H | H | H | Me | 2 | —CH(OH)—(CH$_2$)$_4$-(4-Me-cHx) | H | H |
| 1-1392 | H | H | H | Me | 2 | —CH(OH)—(CH$_2$)$_4$-(4-Et-cHx) | H | H |
| 1-1393 | H | H | H | Me | 2 | —CH(OH)—(CH$_2$)$_4$-(4-CF$_3$-cHx) | H | H |
| 1-1394 | H | H | H | Me | 2 | —CH(OH)—(CH$_2$)$_4$-(4-MeO-cHx) | H | H |
| 1-1395 | H | H | H | Me | 2 | —CH(OH)—(CH$_2$)$_4$-(4-EtO-cHx) | H | H |
| 1-1396 | H | H | H | Me | 2 | —CH(OH)—(CH$_2$)$_4$-(4-MeS-cHx) | H | H |
| 1-1397 | H | H | H | Me | 2 | —CH(OH)—(CH$_2$)$_4$-(4-cHx-cHx) | H | H |
| 1-1398 | H | H | H | Me | 2 | —CH(OH)—(CH$_2$)$_4$-(4-Ph-cHx) | H | H |
| 1-1399 | H | H | H | Me | 2 | —CH(OH)—(CH$_2$)$_4$-Ph | H | H |
| 1-1400 | H | H | H | Me | 2 | —CH(OH)—(CH$_2$)$_4$-(4-F-Ph) | H | H |
| 1-1401 | H | H | H | Me | 2 | —CH(OH)—(CH$_2$)$_4$-(4-Me-Ph) | H | H |
| 1-1402 | H | H | H | Me | 2 | —CH(OH)—(CH$_2$)$_4$-(4-Et-Ph) | H | H |
| 1-1403 | H | H | H | Me | 2 | —CH(OH)—(CH$_2$)$_4$-(4-CF$_3$-Ph) | H | H |
| 1-1404 | H | H | H | Me | 2 | —CH(OH)—(CH$_2$)$_4$-(4-MeO-Ph) | H | H |
| 1-1405 | H | H | H | Me | 2 | —CH(OH)—(CH$_2$)$_4$-(4-EtO-Ph) | H | H |
| 1-1406 | H | H | H | Me | 2 | —CH(OH)—(CH$_2$)$_4$-(4-MeS-Ph) | H | H |
| 1-1407 | H | H | H | Me | 2 | —CH(OH)—(CH$_2$)$_4$-(4-cHx-Ph) | H | H |
| 1-1408 | H | H | H | Me | 2 | —CH(OH)—(CH$_2$)$_4$-(4-Ph-Ph) | H | H |
| 1-1409 | H | H | H | Me | 2 | —CH(OH)—(CH$_2$)$_5$-cHx | H | H |
| 1-1410 | H | H | H | Me | 2 | —CH(OH)—(CH$_2$)$_5$-(4-F-cHx) | H | H |
| 1-1411 | H | H | H | Me | 2 | —CH(OH)—(CH$_2$)$_5$-(4-Me-cHx) | H | H |
| 1-1412 | H | H | H | Me | 2 | —CH(OH)—(CH$_2$)$_5$-(4-Et-cHx) | H | H |
| 1-1413 | H | H | H | Me | 2 | —CH(OH)—(CH$_2$)$_5$-(4-CF$_3$-cHx) | H | H |
| 1-1414 | H | H | H | Me | 2 | —CH(OH)—(CH$_2$)$_5$-(4-MeO-cHx) | H | H |
| 1-1415 | H | H | H | Me | 2 | —CH(OH)—(CH$_2$)$_5$-(4-EtO-cHx) | H | H |
| 1-1416 | H | H | H | Me | 2 | —CH(OH)—(CH$_2$)$_5$-(4-MeS-cHx) | H | H |
| 1-1417 | H | H | H | Me | 2 | —CH(OH)—(CH$_2$)$_5$-(4-cHx-cHx) | H | H |
| 1-1418 | H | H | H | Me | 2 | —CH(OH)—(CH$_2$)$_5$-(4-Ph-cHx) | H | H |
| 1-1419 | H | H | H | Me | 2 | —CH(OH)—(CH$_2$)$_5$-Ph | H | H |
| 1-1420 | H | H | H | Me | 2 | —CH(OH)—(CH$_2$)$_5$-(4-F-Ph) | H | H |
| 1-1421 | H | H | H | Me | 2 | —CH(OH)—(CH$_2$)$_5$-(4-Me-Ph) | H | H |
| 1-1422 | H | H | H | Me | 2 | —CH(OH)—(CH$_2$)$_5$-(4-Et-Ph) | H | H |
| 1-1423 | H | H | H | Me | 2 | —CH(OH)—(CH$_2$)$_5$-(4-CF$_3$-Ph) | H | H |
| 1-1424 | H | H | H | Me | 2 | —CH(OH)—(CH$_2$)$_5$-(4-MeO-Ph) | H | H |
| 1-1425 | H | H | H | Me | 2 | —CH(OH)—(CH$_2$)$_5$-(4-EtO-Ph) | H | H |
| 1-1426 | H | H | H | Me | 2 | —CH(OH)—(CH$_2$)$_5$-(4-MeS-Ph) | H | H |
| 1-1427 | H | H | H | Me | 2 | —CH(OH)—(CH$_2$)$_5$-(4-cHx-Ph) | H | H |
| 1-1428 | H | H | H | Me | 2 | —CH(OH)—(CH$_2$)$_5$-(4-Ph-Ph) | H | H |
| 1-1429 | H | H | H | Me | 2 | —CH(OH)—(CH$_2$)$_6$-cHx | H | H |
| 1-1430 | H | H | H | Me | 2 | —CH(OH)—(CH$_2$)$_6$-Ph | H | H |
| 1-1431 | H | H | H | Me | 2 | —CH(OH)—(CH$_2$)$_7$-cHx | H | H |
| 1-1432 | H | H | H | Me | 2 | —CH(OH)—(CH$_2$)$_7$-Ph | H | H |
| 1-1433 | H | H | H | Me | 2 | -4-(cHx-CH$_2$O)Ph | H | H |
| 1-1434 | H | H | H | Me | 2 | -4-(cHx-CH$_2$O)-2-F-Ph | H | H |
| 1-1435 | H | H | H | Me | 2 | -4-(cHx-CH$_2$O)-3-F-Ph | H | H |
| 1-1436 | H | H | H | Me | 2 | -4-(cHx-CH$_2$O)-2,3-diF-Ph | H | H |
| 1-1437 | H | H | H | Me | 2 | -4-(cHx-CH$_2$O)-2-Cl-Ph | H | H |
| 1-1438 | H | H | H | Me | 2 | -4-(cHx-CH$_2$O)-3-Cl-Ph | H | H |
| 1-1439 | H | H | H | Me | 2 | -4-(cHx-CH$_2$O)-2,3-diCl-Ph | H | H |
| 1-1440 | H | H | H | Me | 2 | -4-(cHx-CH$_2$O)-2-Me-Ph | H | H |
| 1-1441 | H | H | H | Me | 2 | -4-(cHx-CH$_2$O)-3-Me-Ph | H | H |
| 1-1442 | H | H | H | Me | 2 | -4-(cHx-CH$_2$O)-2,3-diMe-Ph | H | H |
| 1-1443 | H | H | H | Me | 2 | -4-[cHx-(CH$_2$)$_2$O]Ph | H | H |
| 1-1444 | H | H | H | Me | 2 | -3-[cHx-(CH$_2$)$_2$O]Ph | H | H |
| 1-1445 | H | H | H | Me | 2 | -(4-BzO-Ph) | H | H |
| 1-1446 | H | H | H | Me | 2 | -(4-BzO-2-F-Ph) | H | H |
| 1-1447 | H | H | H | Me | 2 | -(4-BzO-3-F-Ph) | H | H |
| 1-1448 | H | H | H | Me | 2 | -(4-BzO-2,3-diF-Ph) | H | H |
| 1-1449 | H | H | H | Me | 2 | -(4-BzO-2-Cl-Ph) | H | H |
| 1-1450 | H | H | H | Me | 2 | -(4-BzO-3-Cl-Ph) | H | H |
| 1-1451 | H | H | H | Me | 2 | -(4-BzO-2,3-diCl-Ph) | H | H |
| 1-1452 | H | H | H | Me | 2 | -(4-BzO-2-Me-Ph) | H | H |
| 1-1453 | H | H | H | Me | 2 | -(4-BzO-3-Me-Ph) | H | H |
| 1-1454 | H | H | H | Me | 2 | -(4-BzO-2,3-diMe-Ph) | H | H |
| 1-1455 | H | H | H | Me | 2 | -4-[Ph-(CH$_2$)$_2$O]-Ph | H | H |

TABLE 1-continued

| | | | | | | | | |
|---|---|---|---|---|---|---|---|---|
| 1-1456 | H | H | H | Me | 2 | -4-[Ph-(CH$_2$)$_3$O]-Ph | H | H |
| 1-1457 | H | H | H | Et | 2 | —(CH$_2$)$_3$-cHx | H | H |
| 1-1458 | H | H | H | Et | 2 | —(CH$_2$)$_3$-Ph | H | H |
| 1-1459 | H | H | H | Et | 2 | —(CH$_2$)$_4$-cHx | H | H |
| 1-1460 | H | H | H | Et | 2 | —(CH$_2$)$_4$-Ph | H | H |
| 1-1461 | H | H | H | Et | 2 | —(CH$_2$)$_5$-cPn | H | H |
| 1-1462 | H | H | H | Et | 2 | —(CH$_2$)$_5$-cHx | H | H |
| 1-1463 | H | H | H | Et | 2 | —(CH$_2$)$_5$-cHx | Me | H |
| 1-1464 | H | H | H | Et | 2 | —(CH$_2$)$_5$-cHx | H | Me |
| 1-1465 | H | H | H | Et | 2 | —(CH$_2$)$_5$-cHx | F | H |
| 1-1466 | H | H | H | Et | 2 | —(CH$_2$)$_5$-cHx | H | F |
| 1-1467 | H | H | H | Et | 2 | —(CH$_2$)$_5$-(4-F-cHx) | H | H |
| 1-1468 | H | H | H | Et | 2 | —(CH$_2$)$_5$-(4-Cl-cHx) | H | H |
| 1-1469 | H | H | H | Et | 2 | —(CH$_2$)$_5$-(4-Br-cHx) | H | H |
| 1-1470 | H | H | H | Et | 2 | —(CH$_2$)$_5$-(4-Me-cHx) | H | H |
| 1-1471 | H | H | H | Et | 2 | —(CH$_2$)$_5$-(4-Et-cHx) | H | H |
| 1-1472 | H | H | H | Et | 2 | —(CH$_2$)$_5$-(4-Pr-cHx) | H | H |
| 1-1473 | H | H | H | Et | 2 | —(CH$_2$)$_5$-(4-iPr-cHx) | H | H |
| 1-1474 | H | H | H | Et | 2 | —(CH$_2$)$_5$-(4-CF$_3$-cHx) | H | H |
| 1-1475 | H | H | H | Et | 2 | —(CH$_2$)$_5$-(4-MeO-cHx) | H | H |
| 1-1476 | H | H | H | Et | 2 | —(CH$_2$)$_5$-(4-EtO-cHx) | H | H |
| 1-1477 | H | H | H | Et | 2 | —(CH$_2$)$_5$-(4-PrO-cHx) | H | H |
| 1-1478 | H | H | H | Et | 2 | —(CH$_2$)$_5$-(4-iPrO-cHx) | H | H |
| 1-1479 | H | H | H | Et | 2 | —(CH$_2$)$_5$-(3-MeS-cHx) | H | H |
| 1-1480 | H | H | H | Et | 2 | —(CH$_2$)$_5$-(4-MeS-cHx) | H | H |
| 1-1481 | H | H | H | Et | 2 | —(CH$_2$)$_5$-(2,4-diMe-cHx) | H | H |
| 1-1482 | H | H | H | Et | 2 | —(CH$_2$)$_5$-(3,4-diMe-cHx) | H | H |
| 1-1483 | H | H | H | Et | 2 | —(CH$_2$)$_5$-(3,5-diMe-cHx) | H | H |
| 1-1484 | H | H | H | Et | 2 | —(CH$_2$)$_5$-Ph | H | H |
| 1-1485 | H | H | H | Et | 2 | —(CH$_2$)$_5$-Ph | Me | H |
| 1-1486 | H | H | H | Et | 2 | —(CH$_2$)$_5$-Ph | H | Me |
| 1-1487 | H | H | H | Et | 2 | —(CH$_2$)$_5$-Ph | F | H |
| 1-1488 | H | H | H | Et | 2 | —(CH$_2$)$_5$-Ph | H | F |
| 1-1489 | H | H | H | Et | 2 | —(CH$_2$)$_5$-(4-F-Ph) | H | H |
| 1-1490 | H | H | H | Et | 2 | —(CH$_2$)$_5$-(4-Cl-Ph) | H | H |
| 1-1491 | H | H | H | Et | 2 | —(CH$_2$)$_5$-(4-Br-Ph) | H | H |
| 1-1492 | H | H | H | Et | 2 | —(CH$_2$)$_5$-(4-Me-Ph) | H | H |
| 1-1493 | H | H | H | Et | 2 | —(CH$_2$)$_5$-(4-Et-Ph) | H | H |
| 1-1494 | H | H | H | Et | 2 | —(CH$_2$)$_5$-(4-Pr-Ph) | H | H |
| 1-1495 | H | H | H | Et | 2 | —(CH$_2$)$_5$-(4-iPr-Ph) | H | H |
| 1-1496 | H | H | H | Et | 2 | —(CH$_2$)$_5$-(4-Bu-Ph) | H | H |
| 1-1497 | H | H | H | Et | 2 | —(CH$_2$)$_5$-(4-CF$_3$-Ph) | H | H |
| 1-1498 | H | H | H | Et | 2 | —(CH$_2$)$_5$-(4-MeO-Ph) | H | H |
| 1-1499 | H | H | H | Et | 2 | —(CH$_2$)$_5$-(4-EtO-Ph) | H | H |
| 1-1500 | H | H | H | Et | 2 | —(CH$_2$)$_5$-(4-PrO-Ph) | H | H |
| 1-1501 | H | H | H | Et | 2 | —(CH$_2$)$_5$-(4-iPrO-Ph) | H | H |
| 1-1502 | H | H | H | Et | 2 | —(CH$_2$)$_5$-(3-MeS-Ph) | H | H |
| 1-1503 | H | H | H | Et | 2 | —(CH$_2$)$_5$-(4-MeS-Ph) | H | H |
| 1-1504 | H | H | H | Et | 2 | —(CH$_2$)$_5$-(2,4-diMe-Ph) | H | H |
| 1-1505 | H | H | H | Et | 2 | —(CH$_2$)$_5$-(3,4-diMe-Ph) | H | H |
| 1-1506 | H | H | H | Et | 2 | —(CH$_2$)$_5$-(3,5-diMe-Ph) | H | H |
| 1-1507 | H | H | H | Et | 2 | —(CH$_2$)$_6$-cPn | H | H |
| 1-1508 | H | H | H | Et | 2 | —(CH$_2$)$_6$-cHx | H | H |
| 1-1509 | H | H | H | Et | 2 | —(CH$_2$)$_6$-cHx | Me | H |
| 1-1510 | H | H | H | Et | 2 | —(CH$_2$)$_6$-cHx | H | Me |
| 1-1511 | H | H | H | Et | 2 | —(CH$_2$)$_6$-cHx | F | H |
| 1-1512 | H | H | H | Et | 2 | —(CH$_2$)$_6$-cHx | H | F |
| 1-1513 | H | H | H | Et | 2 | —(CH$_2$)$_6$-(4-F-cHx) | H | H |
| 1-1514 | H | H | H | Et | 2 | —(CH$_2$)$_6$-(4-Cl-cHx) | H | H |
| 1-1515 | H | H | H | Et | 2 | —(CH$_2$)$_6$-(4-Br-cHx) | H | H |
| 1-1516 | H | H | H | Et | 2 | —(CH$_2$)$_6$-(4-Me-cHx) | H | H |
| 1-1517 | H | H | H | Et | 2 | —(CH$_2$)$_6$-(4-Et-cHx) | H | H |
| 1-1518 | H | H | H | Et | 2 | —(CH$_2$)$_6$-(4-Pr-cHx) | H | H |
| 1-1519 | H | H | H | Et | 2 | —(CH$_2$)$_6$-(4-iPr-cHx) | H | H |
| 1-1520 | H | H | H | Et | 2 | —(CH$_2$)$_6$-(4-Bu-cHx) | H | H |
| 1-1521 | H | H | H | Et | 2 | —(CH$_2$)$_6$-(4-CF$_3$-cHx) | H | H |
| 1-1522 | H | H | H | Et | 2 | —(CH$_2$)$_6$-(4-MeO-cHx) | H | H |
| 1-1523 | H | H | H | Et | 2 | —(CH$_2$)$_6$-(4-EtO-cHx) | H | H |
| 1-1524 | H | H | H | Et | 2 | —(CH$_2$)$_6$-(4-PrO-cHx) | H | H |
| 1-1525 | H | H | H | Et | 2 | —(CH$_2$)$_6$-(4-iPrO-cHx) | H | H |
| 1-1526 | H | H | H | Et | 2 | —(CH$_2$)$_6$-(3-MeS-cHx) | H | H |
| 1-1527 | H | H | H | Et | 2 | —(CH$_2$)$_6$-(4-MeS-cHx) | H | H |
| 1-1528 | H | H | H | Et | 2 | —(CH$_2$)$_6$-(2,4-diMe-cHx) | H | H |
| 1-1529 | H | H | H | Et | 2 | —(CH$_2$)$_6$-(3,4-diMe-cHx) | H | H |
| 1-1530 | H | H | H | Et | 2 | —(CH$_2$)$_6$-(3,5-diMe-cHx) | H | H |
| 1-1531 | H | H | H | Et | 2 | —(CH$_2$)$_6$-Ph | H | H |
| 1-1532 | H | H | H | Et | 2 | —(CH$_2$)$_6$-Ph | Me | H |
| 1-1533 | H | H | H | Et | 2 | —(CH$_2$)$_6$-Ph | H | Me |
| 1-1534 | H | H | H | Et | 2 | —(CH$_2$)$_6$-Ph | F | H |
| 1-1535 | H | H | H | Et | 2 | —(CH$_2$)$_6$-Ph | H | F |

TABLE 1-continued

| | | | | | | | | |
|---|---|---|---|---|---|---|---|---|
| 1-1536 | H | H | H | Et | 2 | —(CH$_2$)$_6$-(4-F-Ph) | H | H |
| 1-1537 | H | H | H | Et | 2 | —(CH$_2$)$_6$-(4-Cl-Ph) | H | H |
| 1-1538 | H | H | H | Et | 2 | —(CH$_2$)$_6$-(4-Br-Ph) | H | H |
| 1-1539 | H | H | H | Et | 2 | —(CH$_2$)$_6$-(4-Me-Ph) | H | H |
| 1-1540 | H | H | H | Et | 2 | —(CH$_2$)$_6$-(4-Et-Ph) | H | H |
| 1-1541 | H | H | H | Et | 2 | —(CH$_2$)$_6$-(4-Pr-Ph) | H | H |
| 1-1542 | H | H | H | Et | 2 | —(CH$_2$)$_6$-(4-iPr-Ph) | H | H |
| 1-1543 | H | H | H | Et | 2 | —(CH$_2$)$_6$-(4-Bu-Ph) | H | H |
| 1-1544 | H | H | H | Et | 2 | —(CH$_2$)$_6$-(4-CF$_3$-Ph) | H | H |
| 1-1545 | H | H | H | Et | 2 | —(CH$_2$)$_6$-(4-MeO-Ph) | H | H |
| 1-1546 | H | H | H | Et | 2 | —(CH$_2$)$_6$-(4-EtO-Ph) | H | H |
| 1-1547 | H | H | H | Et | 2 | —(CH$_2$)$_6$-(4-PrO-Ph) | H | H |
| 1-1548 | H | H | H | Et | 2 | —(CH$_2$)$_6$-(4-iPrO-Ph) | H | H |
| 1-1549 | H | H | H | Et | 2 | —(CH$_2$)$_6$-(3-MeS-Ph) | H | H |
| 1-1550 | H | H | H | Et | 2 | —(CH$_2$)$_6$-(4-MeS-Ph) | H | H |
| 1-1551 | H | H | H | Et | 2 | —(CH$_2$)$_6$-(2,4-diMe-Ph) | H | H |
| 1-1552 | H | H | H | Et | 2 | —(CH$_2$)$_6$-(3,4-diMe-Ph) | H | H |
| 1-1553 | H | H | H | Et | 2 | —(CH$_2$)$_6$-(3,5-diMe-Ph) | H | H |
| 1-1554 | H | H | H | Et | 2 | —(CH$_2$)$_7$-cHx | H | H |
| 1-1555 | H | H | H | Et | 2 | —(CH$_2$)$_7$-Ph | H | H |
| 1-1556 | H | H | H | Et | 2 | —C≡C—CH$_2$-cHx | H | H |
| 1-1557 | H | H | H | Et | 2 | —C≡C—CH$_2$-Ph | H | H |
| 1-1558 | H | H | H | Et | 2 | —C≡C—(CH$_2$)$_2$-cHx | H | H |
| 1-1559 | H | H | H | Et | 2 | —C≡C—(CH$_2$)$_2$-Ph | H | H |
| 1-1560 | H | H | H | Et | 2 | —C≡C—(CH$_2$)$_3$-cPn | H | H |
| 1-1561 | H | H | H | Et | 2 | —C≡C—(CH$_2$)$_3$-cHx | H | H |
| 1-1562 | H | H | H | Et | 2 | —C≡C—(CH$_2$)$_3$-cHx | Me | H |
| 1-1563 | H | H | H | Et | 2 | —C≡C—(CH$_2$)$_3$-cHx | H | Me |
| 1-1564 | H | H | H | Et | 2 | —C≡C—(CH$_2$)$_3$-cHx | F | H |
| 1-1565 | H | H | H | Et | 2 | —C≡C—(CH$_2$)$_3$-cHx | H | F |
| 1-1566 | H | H | H | Et | 2 | —C≡C—(CH$_2$)$_3$-(4-F-cHx) | H | H |
| 1-1567 | H | H | H | Et | 2 | —C≡C—(CH$_2$)$_3$-(4-Cl-cHx) | H | H |
| 1-1568 | H | H | H | Et | 2 | —C≡C—(CH$_2$)$_3$-(4-Br-cHx) | H | H |
| 1-1569 | H | H | H | Et | 2 | —C≡C—(CH$_2$)$_3$-(4-Me-cHx) | H | H |
| 1-1570 | H | H | H | Et | 2 | —C≡C—(CH$_2$)$_3$-(4-Et-cHx) | H | H |
| 1-1571 | H | H | H | Et | 2 | —C≡C—(CH$_2$)$_3$-(4-Pr-cHx) | H | H |
| 1-1572 | H | H | H | Et | 2 | —C≡C—(CH$_2$)$_3$-(4-iPr-cHx) | H | H |
| 1-1573 | H | H | H | Et | 2 | —C≡C—(CH$_2$)$_3$-(4-Bu-cHx) | H | H |
| 1-1574 | H | H | H | Et | 2 | —C≡C—(CH$_2$)$_3$-(4-CF$_3$-cHx) | H | H |
| 1-1575 | H | H | H | Et | 2 | —C≡C—(CH$_2$)$_3$-(4-MeO-cHx) | H | H |
| 1-1576 | H | H | H | Et | 2 | —C≡C—(CH$_2$)$_3$-(4-EtO-cHx) | H | H |
| 1-1577 | H | H | H | Et | 2 | —C≡C—(CH$_2$)$_3$-(4-PrO-cHx) | H | H |
| 1-1578 | H | H | H | Et | 2 | —C≡C—(CH$_2$)$_3$-(4-iPrO-cHx) | H | H |
| 1-1579 | H | H | H | Et | 2 | —C≡C—(CH$_2$)$_3$-(3-MeS-cHx) | H | H |
| 1-1580 | H | H | H | Et | 2 | —C≡C—(CH$_2$)$_3$-(4-MeS-cHx) | H | H |
| 1-1581 | H | H | H | Et | 2 | —C≡C—(CH$_2$)$_3$-(2,4-diMe-cHx) | H | H |
| 1-1582 | H | H | H | Et | 2 | —C≡C—(CH$_2$)$_3$-(3,4-diMe-cHx) | H | H |
| 1-1583 | H | H | H | Et | 2 | —C≡C—(CH$_2$)$_3$-(3,5-diMe-cHx) | H | H |
| 1-1584 | H | H | H | Et | 2 | —C≡C—(CH$_2$)$_3$-Ph | H | H |
| 1-1585 | H | H | H | Et | 2 | —C≡C—(CH$_2$)$_3$-Ph | Me | H |
| 1-1586 | H | H | H | Et | 2 | —C≡C—(CH$_2$)$_3$-Ph | H | Me |
| 1-1587 | H | H | H | Et | 2 | —C≡C—(CH$_2$)$_3$-Ph | F | H |
| 1-1588 | H | H | H | Et | 2 | —C≡C—(CH$_2$)$_3$-Ph | H | F |
| 1-1589 | H | H | H | Et | 2 | —C≡C—(CH$_2$)$_3$-(4-F-Ph) | H | H |
| 1-1590 | H | H | H | Et | 2 | —C≡C—(CH$_2$)$_3$-(4-Cl-Ph) | H | H |
| 1-1591 | H | H | H | Et | 2 | —C≡C—(CH$_2$)$_3$-(4-Br-Ph) | H | H |
| 1-1592 | H | H | H | Et | 2 | —C≡C—(CH$_2$)$_3$-(4-Me-Ph) | H | H |
| 1-1593 | H | H | H | Et | 2 | —C≡C—(CH$_2$)$_3$-(4-Et-Ph) | H | H |
| 1-1594 | H | H | H | Et | 2 | —C≡C—(CH$_2$)$_3$-(4-Pr-Ph) | H | H |
| 1-1595 | H | H | H | Et | 2 | —C≡C—(CH$_2$)$_3$-(4-iPr-Ph) | H | H |
| 1-1596 | H | H | H | Et | 2 | —C≡C—(CH$_2$)$_3$-(4-Bu-Ph) | H | H |
| 1-1597 | H | H | H | Et | 2 | —C≡C—(CH$_2$)$_3$-(4-CF$_3$-Ph) | H | H |
| 1-1598 | H | H | H | Et | 2 | —C≡C—(CH$_2$)$_3$-(4-MeO-Ph) | H | H |
| 1-1599 | H | H | H | Et | 2 | —C≡C—(CH$_2$)$_3$-(4-EtO-Ph) | H | H |
| 1-1600 | H | H | H | Et | 2 | —C≡C—(CH$_2$)$_3$-(4-PrO-Ph) | H | H |
| 1-1601 | H | H | H | Et | 2 | —C≡C—(CH$_2$)$_3$-(4-iPrO-Ph) | H | H |
| 1-1602 | H | H | H | Et | 2 | —C≡C—(CH$_2$)$_3$-(3-MeS-Ph) | H | H |
| 1-1603 | H | H | H | Et | 2 | —C≡C—(CH$_2$)$_3$-(4-MeS-Ph) | H | H |
| 1-1604 | H | H | H | Et | 2 | —C≡C—(CH$_2$)$_3$-(2,4-diMe-Ph) | H | H |
| 1-1605 | H | H | H | Et | 2 | —C≡C—(CH$_2$)$_3$-(3,4-diMe-Ph) | H | H |
| 1-1606 | H | H | H | Et | 2 | —C≡C—(CH$_2$)$_3$-(3,5-diMe-Ph) | H | H |
| 1-1607 | H | H | H | Et | 2 | —C≡C—(CH$_2$)$_4$-cPn | H | H |
| 1-1608 | H | H | H | Et | 2 | —C≡C—(CH$_2$)$_4$-cHx | H | H |
| 1-1609 | H | H | H | Et | 2 | —C≡C—(CH$_2$)$_4$-cHx | Me | H |
| 1-1610 | H | H | H | Et | 2 | —C≡C—(CH$_2$)$_4$-cHx | H | Me |
| 1-1611 | H | H | H | Et | 2 | —C≡C—(CH$_2$)$_4$-cHx | F | H |
| 1-1612 | H | H | H | Et | 2 | —C≡C—(CH$_2$)$_4$-cHx | H | F |
| 1-1613 | H | H | H | Et | 2 | —C≡C—(CH$_2$)$_4$-(4-F-cHx) | H | H |
| 1-1614 | H | H | H | Et | 2 | —C≡C—(CH$_2$)$_4$-(4-Cl-cHx) | H | H |
| 1-1615 | H | H | H | Et | 2 | —C≡C—(CH$_2$)$_4$-(4-Br-cHx) | H | H |

TABLE 1-continued

| | | | | | | | | |
|---|---|---|---|---|---|---|---|---|
| 1-1616 | H | H | H | Et | 2 | —C≡C—(CH$_2$)$_4$-(4-Me-cHx) | H | H |
| 1-1617 | H | H | H | Et | 2 | —C≡C—(CH$_2$)$_4$-(4-Et-cHx) | H | H |
| 1-1618 | H | H | H | Et | 2 | —C≡C—(CH$_2$)$_4$-(4-Pr-cHx) | H | H |
| 1-1619 | H | H | H | Et | 2 | —C≡C—(CH$_2$)$_4$-(4-iPr-cHx) | H | H |
| 1-1620 | H | H | H | Et | 2 | —C≡C—(CH$_2$)$_4$-(4-Bu-cHx) | H | H |
| 1-1621 | H | H | H | Et | 2 | —C≡C—(CH$_2$)$_4$-(4-CF$_3$-cHx) | H | H |
| 1-1622 | H | H | H | Et | 2 | —C≡C—(CH$_2$)$_4$-(4-MeO-cHx) | H | H |
| 1-1623 | H | H | H | Et | 2 | —C≡C—(CH$_2$)$_4$-(4-EtO-cHx) | H | H |
| 1-1624 | H | H | H | Et | 2 | —C≡C—(CH$_2$)$_4$-(4-PrO-cHx) | H | H |
| 1-1625 | H | H | H | Et | 2 | —C≡C—(CH$_2$)$_4$-(4-iPrO-cHx) | H | H |
| 1-1626 | H | H | H | Et | 2 | —C≡C—(CH$_2$)$_4$-(4-MeS-cHx) | H | H |
| 1-1627 | H | H | H | Et | 2 | —C≡C—(CH$_2$)$_4$-(2,4-diMe-cHx) | H | H |
| 1-1628 | H | H | H | Et | 2 | —C≡C—(CH$_2$)$_4$-(3,4-diMe-cHx) | H | H |
| 1-1629 | H | H | H | Et | 2 | —C≡C—(CH$_2$)$_4$-(3,5-diMe-cHx) | H | H |
| 1-1630 | H | H | H | Et | 2 | —C≡C—(CH$_2$)$_4$-Ph | H | H |
| 1-1631 | H | H | H | Et | 2 | —C≡C—(CH$_2$)$_4$-Ph | Me | H |
| 1-1632 | H | H | H | Et | 2 | —C≡C—(CH$_2$)$_4$-Ph | H | Me |
| 1-1633 | H | H | H | Et | 2 | —C≡C—(CH$_2$)$_4$-Ph | F | H |
| 1-1634 | H | H | H | Et | 2 | —C≡C—(CH$_2$)$_4$-Ph | H | F |
| 1-1635 | H | H | H | Et | 2 | —C≡C—(CH$_2$)$_4$-(4-F-Ph) | H | H |
| 1-1636 | H | H | H | Et | 2 | —C≡C—(CH$_2$)$_4$-(4-Cl-Ph) | H | H |
| 1-1637 | H | H | H | Et | 2 | —C≡C—(CH$_2$)$_4$-(4-Br-Ph) | H | H |
| 1-1638 | H | H | H | Et | 2 | —C≡C—(CH$_2$)$_4$-(4-Me-Ph) | H | H |
| 1-1639 | H | H | H | Et | 2 | —C≡C—(CH$_2$)$_4$-(4-Et-Ph) | H | H |
| 1-1640 | H | H | H | Et | 2 | —C≡C—(CH$_2$)$_4$-(4-Pr-Ph) | H | H |
| 1-1641 | H | H | H | Et | 2 | —C≡C—(CH$_2$)$_4$-(4-iPr-Ph) | H | H |
| 1-1642 | H | H | H | Et | 2 | —C≡C—(CH$_2$)$_4$-(4-Bu-Ph) | H | H |
| 1-1643 | H | H | H | Et | 2 | —C≡C—(CH$_2$)$_4$-(4-CF$_3$-Ph) | H | H |
| 1-1644 | H | H | H | Et | 2 | —C≡C—(CH$_2$)$_4$-(4-MeO-Ph) | H | H |
| 1-1645 | H | H | H | Et | 2 | —C≡C—(CH$_2$)$_4$-(4-EtO-Ph) | H | H |
| 1-1646 | H | H | H | Et | 2 | —C≡C—(CH$_2$)$_4$-(4-PrO-Ph) | H | H |
| 1-1647 | H | H | H | Et | 2 | —C≡C—(CH$_2$)$_4$-(4-iPrO-Ph) | H | H |
| 1-1648 | H | H | H | Et | 2 | —C≡C—(CH$_2$)$_4$-(3-MeS-Ph) | H | H |
| 1-1649 | H | H | H | Et | 2 | —C≡C—(CH$_2$)$_4$-(4-MeS-Ph) | H | H |
| 1-1650 | H | H | H | Et | 2 | —C≡C—(CH$_2$)$_4$-(2,4-diMe-Ph) | H | H |
| 1-1651 | H | H | H | Et | 2 | —C≡C—(CH$_2$)$_4$-(3,4-diMe-Ph) | H | H |
| 1-1652 | H | H | H | Et | 2 | —C≡C—(CH$_2$)$_4$-(3,5-diMe-Ph) | H | H |
| 1-1653 | H | H | H | Et | 2 | —C≡C—(CH$_2$)$_5$-cHx | H | H |
| 1-1654 | H | H | H | Et | 2 | —C≡C—(CH$_2$)$_5$-Ph | H | H |
| 1-1655 | H | H | H | Et | 2 | —C≡C—(CH$_2$)$_6$-cHx | H | H |
| 1-1656 | H | H | H | Et | 2 | —C≡C—(CH$_2$)$_6$-Ph | H | H |
| 1-1657 | H | H | H | Et | 2 | —C≡C—CH$_2$O-cHx | H | H |
| 1-1658 | H | H | H | Et | 2 | —C≡C—CH$_2$O-Ph | H | H |
| 1-1659 | H | H | H | Et | 2 | —C≡C—(CH$_2$)$_2$O-cPn | H | H |
| 1-1660 | H | H | H | Et | 2 | —C≡C—(CH$_2$)$_2$O-cHx | H | H |
| 1-1661 | H | H | H | Et | 2 | —C≡C—(CH$_2$)$_2$O-cHx | Me | H |
| 1-1662 | H | H | H | Et | 2 | —C≡C—(CH$_2$)$_2$O-cHx | H | Me |
| 1-1663 | H | H | H | Et | 2 | —C≡C—(CH$_2$)$_2$O-cHx | F | H |
| 1-1664 | H | H | H | Et | 2 | —C≡C—(CH$_2$)$_2$O-cHx | H | F |
| 1-1665 | H | H | H | Et | 2 | —C≡C—(CH$_2$)$_2$O-(4-F-cHx) | H | H |
| 1-1666 | H | H | H | Et | 2 | —C≡C—(CH$_2$)$_2$O-(4-Cl-cHx) | H | H |
| 1-1667 | H | H | H | Et | 2 | —C≡C—(CH$_2$)$_2$O-(4-Br-cHx) | H | H |
| 1-1668 | H | H | H | Et | 2 | —C≡C—(CH$_2$)$_2$O-(4-Me-cHx) | H | H |
| 1-1669 | H | H | H | Et | 2 | —C≡C—(CH$_2$)$_2$O-(4-Et-cHx) | H | H |
| 1-1670 | H | H | H | Et | 2 | —C≡C—(CH$_2$)$_2$O-(4-Pr-cHx) | H | H |
| 1-1671 | H | H | H | Et | 2 | —C≡C—(CH$_2$)$_2$O-(4-iPr-cHx) | H | H |
| 1-1672 | H | H | H | Et | 2 | —C≡C—(CH$_2$)$_2$O-(4-Bu-cHx) | H | H |
| 1-1673 | H | H | H | Et | 2 | —C≡C—(CH$_2$)$_2$O-(4-CF$_3$-cHx) | H | H |
| 1-1674 | H | H | H | Et | 2 | —C≡C—(CH$_2$)$_2$O-(4-MeO-cHx) | H | H |
| 1-1675 | H | H | H | Et | 2 | —C≡C—(CH$_2$)$_2$O-(4-EtO-cHx) | H | H |
| 1-1676 | H | H | H | Et | 2 | —C≡C—(CH$_2$)$_2$O-(4-PrO-cHx) | H | H |
| 1-1677 | H | H | H | Et | 2 | —C≡C—(CH$_2$)$_2$O-(4-iPrO-cHx) | H | H |
| 1-1678 | H | H | H | Et | 2 | —C≡C—(CH$_2$)$_2$O-(3-MeS-cHx) | H | H |
| 1-1679 | H | H | H | Et | 2 | —C≡C—(CH$_2$)$_2$O-(4-MeS-cHx) | H | H |
| 1-1680 | H | H | H | Et | 2 | —C≡C—(CH$_2$)$_2$O-(2,4-diMe-cHx) | H | H |
| 1-1681 | H | H | H | Et | 2 | —C≡C—(CH$_2$)$_2$O-(3,4-diMe-cHx) | H | H |
| 1-1682 | H | H | H | Et | 2 | —C≡C—(CH$_2$)$_2$O-(3,5-diMe-cHx) | H | H |
| 1-1683 | H | H | H | Et | 2 | —C≡C—(CH$_2$)$_2$O-Ph | H | H |
| 1-1684 | H | H | H | Et | 2 | —C≡C—(CH$_2$)$_2$O-Ph | Me | H |
| 1-1685 | H | H | H | Et | 2 | —C≡C—(CH$_2$)$_2$O-Ph | H | Me |
| 1-1686 | H | H | H | Et | 2 | —C≡C—(CH$_2$)$_2$O-Ph | F | H |
| 1-1687 | H | H | H | Et | 2 | —C≡C—(CH$_2$)$_2$O-Ph | H | F |
| 1-1688 | H | H | H | Et | 2 | —C≡C—(CH$_2$)$_2$O-(4-F-Ph) | H | H |
| 1-1689 | H | H | H | Et | 2 | —C≡C—(CH$_2$)$_2$O-(4-Cl-Ph) | H | H |
| 1-1690 | H | H | H | Et | 2 | —C≡C—(CH$_2$)$_2$O-(4-Br-Ph) | H | H |
| 1-1691 | H | H | H | Et | 2 | —C≡C—(CH$_2$)$_2$O-(4-Me-Ph) | H | H |
| 1-1692 | H | H | H | Et | 2 | —C≡C—(CH$_2$)$_2$O-(4-Et-Ph) | H | H |
| 1-1693 | H | H | H | Et | 2 | —C≡C—(CH$_2$)$_2$O-(4-Pr-Ph) | H | H |
| 1-1694 | H | H | H | Et | 2 | —C≡C—(CH$_2$)$_2$O-(4-iPr-Ph) | H | H |
| 1-1695 | H | H | H | Et | 2 | —C≡C—(CH$_2$)$_2$O-(4-Bu-Ph) | H | H |

TABLE 1-continued

| | | | | | | | |
|---|---|---|---|---|---|---|---|
| 1-1696 | H | H | H | Et | 2 | —C≡C—(CH$_2$)$_2$O-(4-CF$_3$-Ph) | H | H |
| 1-1697 | H | H | H | Et | 2 | —C≡C—(CH$_2$)$_2$O-(4-MeO-Ph) | H | H |
| 1-1698 | H | H | H | Et | 2 | —C≡C—(CH$_2$)$_2$O-(4-EtO-Ph) | H | H |
| 1-1699 | H | H | H | Et | 2 | —C≡C—(CH$_2$)$_2$O-(4-PrO-Ph) | H | H |
| 1-1700 | H | H | H | Et | 2 | —C≡C—(CH$_2$)$_2$O-(4-iPrO-Ph) | H | H |
| 1-1701 | H | H | H | Et | 2 | —C≡C—(CH$_2$)$_2$O-(4-MeS-Ph) | H | H |
| 1-1702 | H | H | H | Et | 2 | —C≡C—(CH$_2$)$_2$O-(2,4-diMe-Ph) | H | H |
| 1-1703 | H | H | H | Et | 2 | —C≡C—(CH$_2$)$_2$O-(3,4-diMe-Ph) | H | H |
| 1-1704 | H | H | H | Et | 2 | —C≡C—(CH$_2$)$_2$O-(3,5-diMe-Ph) | H | H |
| 1-1705 | H | H | H | Et | 2 | —CO—(CH$_2$)$_3$-cHx | H | H |
| 1-1706 | H | H | H | Et | 2 | —CO—(CH$_2$)$_3$-Ph | H | H |
| 1-1707 | H | H | H | Et | 2 | —CO—(CH$_2$)$_4$-cHx | H | H |
| 1-1708 | H | H | H | Et | 2 | —CO—(CH$_2$)$_4$-Ph | H | H |
| 1-1709 | H | H | H | Et | 2 | —CO—(CH$_2$)$_5$-cHx | H | H |
| 1-1710 | H | H | H | Et | 2 | —CO—(CH$_2$)$_5$-Ph | H | H |
| 1-1711 | H | H | H | Et | 2 | —CH(OH)—(CH$_2$)$_4$-cHx | H | H |
| 1-1712 | H | H | H | Et | 2 | —CH(OH)—(CH$_2$)$_4$-Ph | H | H |
| 1-1713 | H | H | H | Et | 2 | —CH(OH)—(CH$_2$)$_5$-cHx | H | H |
| 1-1714 | H | H | H | Et | 2 | —CH(OH)—(CH$_2$)$_5$-Ph | H | H |
| 1-1715 | H | H | H | Et | 2 | -4-(cHx-CH$_2$O)Ph | H | H |
| 1-1716 | H | H | H | Et | 2 | -4-[cHx-(CH$_2$)$_2$O]Ph | H | H |
| 1-1717 | H | H | H | Et | 2 | -4-[cHx-(CH$_2$)$_3$O]Ph | H | H |
| 1-1718 | H | H | H | Et | 2 | -(4-BzO-Ph) | H | H |
| 1-1719 | H | H | H | Et | 2 | -(4-BzO-2-F-Ph) | H | H |
| 1-1720 | H | H | H | Et | 2 | -(4-BzO-3-F-Ph) | H | H |
| 1-1721 | H | H | H | Et | 2 | -(4-BzO-2,3-diF-Ph) | H | H |
| 1-1722 | H | H | H | Et | 2 | -(4-BzO-2-Cl-Ph) | H | H |
| 1-1723 | H | H | H | Et | 2 | -(4-BzO-3-Cl-Ph) | H | H |
| 1-1724 | H | H | H | Et | 2 | -(4-BzO-2,3-diCl-Ph) | H | H |
| 1-1725 | H | H | H | Et | 2 | -(4-BzO-2-Me-Ph) | H | H |
| 1-1726 | H | H | H | Et | 2 | -(4-BzO-3-Me-Ph) | H | H |
| 1-1727 | H | H | H | Et | 2 | -(4-BzO-2,3-diMe-Ph) | H | H |
| 1-1728 | H | H | H | Et | 2 | -4-[Ph-(CH$_2$)$_2$O]-Ph | H | H |
| 1-1729 | H | H | H | Et | 2 | -4-[Ph-(CH$_2$)$_3$O]-Ph | H | H |
| 1-1730 | H | H | H | Pr | 2 | —(CH$_2$)$_5$-cHx | H | H |
| 1-1731 | H | H | H | Pr | 2 | —(CH$_2$)$_5$-Ph | H | H |
| 1-1732 | H | H | H | Pr | 2 | —(CH$_2$)$_6$-cHx | H | H |
| 1-1733 | H | H | H | Pr | 2 | —(CH$_2$)$_6$-Ph | H | H |
| 1-1734 | H | H | H | Pr | 2 | —C≡C—CH$_2$-cHx | H | H |
| 1-1735 | H | H | H | Pr | 2 | —C≡C—(CH$_2$)$_3$-cHx | H | H |
| 1-1736 | H | H | H | Pr | 2 | —C≡C—(CH$_2$)$_3$-Ph | H | H |
| 1-1737 | H | H | H | Pr | 2 | —C≡C—(CH$_2$)$_4$-cHx | H | H |
| 1-1738 | H | H | H | Pr | 2 | —C≡C—(CH$_2$)$_4$-Ph | H | H |
| 1-1739 | H | H | H | Pr | 2 | —C≡C—(CH$_2$)$_2$O-cHx | H | H |
| 1-1740 | H | H | H | Pr | 2 | —C≡C—(CH$_2$)$_2$O-Ph | H | H |
| 1-1741 | H | H | H | Pr | 2 | -4-(cHx-CH$_2$O)Ph | H | H |
| 1-1742 | H | H | H | Pr | 2 | -(4-BzO-Ph) | H | H |
| 1-1743 | H | H | H | Me | 2 | —(CH$_2$)$_4$-(3-F-Ph) | H | H |
| 1-1744 | H | H | H | Me | 2 | —(CH$_2$)$_4$-(3,4-diF-Ph) | H | H |
| 1-1745 | H | H | H | Me | 2 | —(CH$_2$)$_4$-(3,5-diF-Ph) | H | H |
| 1-1746 | H | H | H | Me | 2 | —(CH$_2$)$_4$-(3-Cl-Ph) | H | H |
| 1-1747 | H | H | H | Me | 2 | —(CH$_2$)$_4$-(4-Cl-Ph) | H | H |
| 1-1748 | H | H | H | Me | 2 | —(CH$_2$)$_4$-(3,4-diCl-Ph) | H | H |
| 1-1749 | H | H | H | Me | 2 | —(CH$_2$)$_4$-(3,5-diCl-Ph) | H | H |
| 1-1750 | H | H | H | Me | 2 | —(CH$_2$)$_4$-(3-Me-Ph) | H | H |
| 1-1751 | H | H | H | Me | 2 | —(CH$_2$)$_4$-(3,4-diMe-Ph) | H | H |
| 1-1752 | H | H | H | Me | 2 | —(CH$_2$)$_4$-(3,5-diMe-Ph) | H | H |
| 1-1753 | H | H | H | Me | 2 | —(CH$_2$)$_4$-(3-CF$_3$-Ph) | H | H |
| 1-1754 | H | H | H | Me | 2 | —(CH$_2$)$_4$-(3,4-diCF$_3$-Ph) | H | H |
| 1-1755 | H | H | H | Me | 2 | —(CH$_2$)$_4$-(3,5-diCF$_3$-Ph) | H | H |
| 1-1756 | H | H | H | Me | 2 | —(CH$_2$)$_4$-(3-MeO-Ph) | H | H |
| 1-1757 | H | H | H | Me | 2 | —(CH$_2$)$_4$-(3,4-diMeO-Ph) | H | H |
| 1-1758 | H | H | H | Me | 2 | —(CH$_2$)$_4$-(3,5-diMeO-Ph) | H | H |
| 1-1759 | H | H | H | Me | 2 | —(CH$_2$)$_4$-(3,4,5-triMeO-Ph) | H | H |
| 1-1760 | H | H | H | Me | 2 | —(CH$_2$)$_4$-(3-Ac-Ph) | H | H |
| 1-1761 | H | H | H | Me | 2 | —(CH$_2$)$_4$-(4-Ac-Ph) | H | H |
| 1-1762 | H | H | H | Me | 2 | —(CH$_2$)$_5$-(3,4-diF-Ph) | H | H |
| 1-1763 | H | H | H | Me | 2 | —(CH$_2$)$_5$-(3,5-diF-Ph) | H | H |
| 1-1764 | H | H | H | Me | 2 | —(CH$_2$)$_5$-(3-Cl-Ph) | H | H |
| 1-1765 | H | H | H | Me | 2 | —(CH$_2$)$_5$-(3,4-diCl-Ph) | H | H |
| 1-1766 | H | H | H | Me | 2 | —(CH$_2$)$_5$-(3,5-diCl-Ph) | H | H |
| 1-1767 | H | H | H | Me | 2 | —(CH$_2$)$_5$-(3,4-di-CF$_3$-Ph) | H | H |
| 1-1768 | H | H | H | Me | 2 | —(CH$_2$)$_5$-(3,5-di-CF$_3$-Ph) | H | H |
| 1-1769 | H | H | H | Me | 2 | —(CH$_2$)$_5$-(3,4-diMeO-Ph) | H | H |
| 1-1770 | H | H | H | Me | 2 | —(CH$_2$)$_5$-(3,5-diMeO-Ph) | H | H |
| 1-1771 | H | H | H | Me | 2 | —(CH$_2$)$_5$-(3,4,5-triMeO-Ph) | H | H |
| 1-1772 | H | H | H | Me | 2 | —(CH$_2$)$_5$-(3-Ac-Ph) | H | H |
| 1-1773 | H | H | H | Me | 2 | —(CH$_2$)$_5$-(4-Ac-Ph) | H | H |
| 1-1774 | H | H | H | Me | 2 | —(CH$_2$)$_3$—O-(3-F-Ph) | H | H |
| 1-1775 | H | H | H | Me | 2 | —(CH$_2$)$_3$—O-(3,4-diF-Ph) | H | H |

TABLE 1-continued

| | | | | | | | | |
|---|---|---|---|---|---|---|---|---|
| 1-1776 | H | H | H | Me | 2 | —(CH$_2$)$_3$—O-(3,5-diF-Ph) | H | H |
| 1-1777 | H | H | H | Me | 2 | —(CH$_2$)$_3$—O-(3-Me-Ph) | H | H |
| 1-1778 | H | H | H | Me | 2 | —(CH$_2$)$_3$—O-(3,4-diMe-Ph) | H | H |
| 1-1779 | H | H | H | Me | 2 | —(CH$_2$)$_3$—O-(3,5-diMe-Ph) | H | H |
| 1-1780 | H | H | H | Me | 2 | —(CH$_2$)$_3$—O-(3-CF$_3$-Ph) | H | H |
| 1-1781 | H | H | H | Me | 2 | —(CH$_2$)$_3$—O-(3,4-diCF$_3$-Ph) | H | H |
| 1-1782 | H | H | H | Me | 2 | —(CH$_2$)$_3$—O-(3,5-diCF$_3$-Ph) | H | H |
| 1-1783 | H | H | H | Me | 2 | —(CH$_2$)$_3$—O-(3-MeO-Ph) | H | H |
| 1-1784 | H | H | H | Me | 2 | —(CH$_2$)$_3$—O-(3,4-diMeO-Ph) | H | H |
| 1-1785 | H | H | H | Me | 2 | —(CH$_2$)$_3$—O-(3,5-diMeO-Ph) | H | H |
| 1-1786 | H | H | H | Me | 2 | —(CH$_2$)$_3$—O-(3,4,5-triMeO-Ph) | H | H |
| 1-1787 | H | H | H | Me | 2 | —(CH$_2$)$_3$—O-(3-Ac-Ph) | H | H |
| 1-1788 | H | H | H | Me | 2 | —(CH$_2$)$_3$—O-(4-Ac-Ph) | H | H |
| 1-1789 | H | H | H | Me | 2 | —(CH$_2$)$_4$—O-(3,4-diF-Ph) | H | H |
| 1-1790 | H | H | H | Me | 2 | —(CH$_2$)$_4$—O-(3,5-diF-Ph) | H | H |
| 1-1791 | H | H | H | Me | 2 | —(CH$_2$)$_4$—O-(3,4-diMeO-Ph) | H | H |
| 1-1792 | H | H | H | Me | 2 | —(CH$_2$)$_4$—O-(3,5-diMeO-Ph) | H | H |
| 1-1793 | H | H | H | Me | 2 | —(CH$_2$)$_4$—O-(3,4,5-triMeO-Ph) | H | H |
| 1-1794 | H | H | H | Me | 2 | —(CH$_2$)$_4$—O-(3-Ac-Ph) | H | H |
| 1-1795 | H | H | H | Me | 2 | —(CH$_2$)$_4$—O-(4-Ac-Ph) | H | H |
| 1-1796 | H | H | H | Me | 2 | —C≡C—(CH$_2$)$_2$-(3-F-Ph) | H | H |
| 1-1797 | H | H | H | Me | 2 | —C≡C—(CH$_2$)$_2$-(3,4-diF-Ph) | H | H |
| 1-1798 | H | H | H | Me | 2 | —C≡C—(CH$_2$)$_2$-(3,5-diF-Ph) | H | H |
| 1-1799 | H | H | H | Me | 2 | —C≡C—(CH$_2$)$_2$-(3-Cl-Ph) | H | H |
| 1-1800 | H | H | H | Me | 2 | —C≡C—(CH$_2$)$_2$-(4-Cl-Ph) | H | H |
| 1-1801 | H | H | H | Me | 2 | —C≡C—(CH$_2$)$_2$-(3,4-diCl-Ph) | H | H |
| 1-1802 | H | H | H | Me | 2 | —C≡C—(CH$_2$)$_2$-(3,5-diCl-Ph) | H | H |
| 1-1803 | H | H | H | Me | 2 | —C≡C—(CH$_2$)$_2$-(3-Me-Ph) | H | H |
| 1-1804 | H | H | H | Me | 2 | —C≡C—(CH$_2$)$_2$-(3,4-diMe-Ph) | H | H |
| 1-1805 | H | H | H | Me | 2 | —C≡C—(CH$_2$)$_2$-(3,5-diMe-Ph) | H | H |
| 1-1806 | H | H | H | Me | 2 | —C≡C—(CH$_2$)$_2$-(3-CF$_3$-Ph) | H | H |
| 1-1807 | H | H | H | Me | 2 | —C≡C—(CH$_2$)$_2$-(3,4-diCF$_3$-Ph) | H | H |
| 1-1808 | H | H | H | Me | 2 | —C≡C—(CH$_2$)$_2$-(3,5-diCF$_3$-Ph) | H | H |
| 1 1809 | H | H | H | Me | 2 | —C≡C—(CH$_2$)$_2$-(3-MeO-Ph) | H | H |
| 1-1810 | H | H | H | Me | 2 | —C≡C—(CH$_2$)$_2$-(3,4-diMeO-Ph) | H | H |
| 1-1811 | H | H | H | Me | 2 | —C≡C—(CH$_2$)$_2$-(3,5-diMeO-Ph) | H | H |
| 1-1812 | H | H | H | Me | 2 | —C≡C—(CH$_2$)$_2$-(3,4,5-triMeO-Ph) | H | H |
| 1-1813 | H | H | H | Me | 2 | —C≡C—(CH$_2$)$_2$-(3-Ac-Ph) | H | H |
| 1-1814 | H | H | H | Me | 2 | —C≡C—(CH$_2$)$_2$-(4-Ac-Ph) | H | H |
| 1-1815 | H | H | H | Me | 2 | —C≡C—(CH$_2$)$_3$-(3,4-diF-Ph) | H | H |
| 1-1816 | H | H | H | Me | 2 | —C≡C—(CH$_2$)$_3$-(3,5-diF-Ph) | H | H |
| 1-1817 | H | H | H | Me | 2 | —C≡C—(CH$_2$)$_3$-(3-Cl-Ph) | H | H |
| 1-1818 | H | H | H | Me | 2 | —C≡C—(CH$_2$)$_3$-(3,4-diCl-Ph) | H | H |
| 1-1819 | H | H | H | Me | 2 | —C≡C—(CH$_2$)$_3$-(3,5-diCl-Ph) | H | H |
| 1 1820 | H | H | H | Me | 2 | —C≡C—(CH$_2$)$_3$-(3,4-diCF$_3$-Ph) | H | H |
| 1-1821 | H | H | H | Me | 2 | —C≡C—(CH$_2$)$_3$-(3,5-diCF$_3$-Ph) | H | H |
| 1-1822 | H | H | H | Me | 2 | —C≡C—(CH$_2$)$_3$-(3,4-diMeO-Ph) | H | H |
| 1-1823 | H | H | H | Me | 2 | —C≡C—(CH$_2$)$_2$-(3,5-diMeO-Ph) | H | H |
| 1-1824 | H | H | H | Me | 2 | —C≡C—(CH$_2$)$_3$-(3,4,5-triMeO-Ph) | H | H |
| 1-1825 | H | H | H | Me | 2 | —C≡C—(CH$_2$)$_3$-(3-Ac-Ph) | H | H |
| 1-1826 | H | H | H | Me | 2 | —C≡C—(CH$_2$)$_3$-(4-Ac-Ph) | H | H |
| 1-1827 | H | H | H | Me | 2 | —C≡C—CH$_2$—O-(3-F-Ph) | H | H |
| 1-1828 | H | H | H | Me | 2 | —C≡C—CH$_2$—O-(3,4-diF-Ph) | H | H |
| 1-1829 | H | H | H | Me | 2 | —C≡C—CH$_2$—O-(3,5-diF-Ph) | H | H |
| 1-1830 | H | H | H | Me | 2 | —C≡C—CH$_2$—O-(3-Cl-Ph) | H | H |
| 1-1831 | H | H | H | Me | 2 | —C≡C—CH$_2$—O-(4-Cl-Ph) | H | H |
| 1-1832 | H | H | H | Me | 2 | —C≡C—CH$_2$—O-(3,4-diCl-Ph) | H | H |
| 1-1833 | H | H | H | Me | 2 | —C≡C—CH$_2$—O-(3,5-diCl-Ph) | H | H |
| 1-1834 | H | H | H | Me | 2 | —C≡C—CH$_2$—O-(3-Me-Ph) | H | H |
| 1-1835 | H | H | H | Me | 2 | —C≡C—CH$_2$—O-(2,4-diMe-Ph) | H | H |
| 1-1836 | H | H | H | Me | 2 | —C≡C—CH$_2$—O-(3,4-diMe-Ph) | H | H |
| 1-1837 | H | H | H | Me | 2 | —C≡C—CH$_2$—O-(3,5-diMe-Ph) | H | H |
| 1-1838 | H | H | H | Me | 2 | —C≡C—CH$_2$—O-(3-CF$_3$-Ph) | H | H |
| 1-1839 | H | H | H | Me | 2 | —C≡C—CH$_2$—O-(3,4-diCF$_3$-Ph) | H | H |
| 1-1840 | H | H | H | Me | 2 | —C≡C—CH$_2$—O (3,5-diCF$_3$-Ph) | H | H |
| 1-1841 | H | H | H | Me | 2 | —C≡C—CH$_2$—O-(3-MeO-Ph) | H | H |
| 1-1842 | H | H | H | Me | 2 | —C≡C—CH$_2$—O-(3,4-diMeO-Ph) | H | H |
| 1-1843 | H | H | H | Me | 2 | —C≡C—CH$_2$—O-(3,5-diMeO-Ph) | H | H |
| 1-1844 | H | H | H | Me | 2 | —C≡C—CH$_2$—O-(3,4,5-triMeO-Ph) | H | H |
| 1-1845 | H | H | H | Me | 2 | —C≡C—CH$_2$—O-(3-Ac-Ph) | H | H |
| 1-1846 | H | H | H | Me | 2 | —C≡C—CH$_2$—O-(4-Ac-Ph) | H | H |
| 1-1847 | H | H | H | Me | 2 | —C≡C—CH$_2$—O-(4-CO$_2$H-Ph) | H | H |
| 1-1848 | H | H | H | Me | 2 | —C≡C—(CH$_2$)$_2$—O-(3,4-diF-Ph) | H | H |
| 1-1849 | H | H | H | Me | 2 | —C≡C—(CH$_2$)$_2$—O-(3,5-diF-Ph) | H | H |
| 1-1850 | H | H | H | Me | 2 | —C≡C—(CH$_2$)$_2$—O-(3-Cl-Ph) | H | H |
| 1-1851 | H | H | H | Me | 2 | —C≡C—(CH$_2$)$_2$—O-(3,4-diCl-Ph) | H | H |
| 1-1852 | H | H | H | Me | 2 | —C≡C—(CH$_2$)$_2$—O-(3,5-diCl-Ph) | H | H |
| 1-1853 | H | H | H | Me | 2 | —C≡C—(CH$_2$)$_2$—O-(3,4-diCF$_3$-Ph) | H | H |
| 1-1854 | H | H | H | Me | 2 | —C≡C—(CH$_2$)$_2$—O-(3,5-diCF$_3$-Ph) | H | H |
| 1-1855 | H | H | H | Me | 2 | —C≡C—(CH$_2$)$_2$—O-(3,4-diMeO-Ph) | H | H |

TABLE 1-continued

| | | | | | | | | |
|---|---|---|---|---|---|---|---|---|
| 1-1856 | H | H | H | Me | 2 | —C≡C—(CH₂)₂—O-(3,5-diMeO-Ph) | H | H |
| 1-1857 | H | H | H | Me | 2 | —C≡C—(CH₂)₂—O-(3,4,5-triMeO-Ph) | H | H |
| 1-1858 | H | H | H | Me | 2 | —C≡C—(CH₂)₂—O-(3-Ac-Ph) | H | H |
| 1-1859 | H | H | H | Me | 2 | —C≡C—(CH₂)₂—O-(4-Ac-Ph) | H | H |
| 1-1860 | H | H | H | Me | 2 | —CO—(CH₂)₃-(3-F-Ph) | H | H |
| 1-1861 | H | H | H | Me | 2 | —CO—(CH₂)₃-(4-F-Ph) | H | H |
| 1-1862 | H | H | H | Me | 2 | —CO—(CH₂)₃-(3,4-diF-Ph) | H | H |
| 1-1863 | H | H | H | Me | 2 | —CO—(CH₂)₃-(3,5-diF-Ph) | H | H |
| 1-1864 | H | H | H | Me | 2 | —CO—(CH₂)₃-(3-Cl-Ph) | H | H |
| 1-1865 | H | H | H | Me | 2 | —CO—(CH₂)₃-(4-Cl-Ph) | H | H |
| 1-1866 | H | H | H | Me | 2 | —CO—(CH₂)₃-(3,4-diCl-Ph) | H | H |
| 1-1867 | H | H | H | Me | 2 | —CO—(CH₂)₃-(3,5-diCl-Ph) | H | H |
| 1-1868 | H | H | H | Me | 2 | —CO—(CH₂)₃-(3-Me-Ph) | H | H |
| 1-1869 | H | H | H | Me | 2 | —CO—(CH₂)₃-(4-Me-Ph) | H | H |
| 1-1870 | H | H | H | Me | 2 | —CO—(CH₂)₃-(3,4-diMe-Ph) | H | H |
| 1-1871 | H | H | H | Me | 2 | —CO—(CH₂)₃-(3,5-diMe-Ph) | H | H |
| 1-1872 | H | H | H | Me | 2 | —CO—(CH₂)₃-(3-Et-Ph) | H | H |
| 1-1873 | H | H | H | Me | 2 | —CO—(CH₂)₃-(4-Et-Ph) | H | H |
| 1-1874 | H | H | H | Me | 2 | —CO—(CH₂)₃-(3-CF₃-Ph) | H | H |
| 1-1875 | H | H | H | Me | 2 | —CO—(CH₂)₃-(4-CF₃-Ph) | H | H |
| 1-1876 | H | H | H | Me | 2 | —CO—(CH₂)₃-(3,4-diCF₃-Ph) | H | H |
| 1-1877 | H | H | H | Me | 2 | —CO—(CH₂)₃-(3,5-diCF₃-Ph) | H | H |
| 1-1878 | H | H | H | Me | 2 | —CO—(CH₂)₃-(3-MeO-Ph) | H | H |
| 1-1879 | H | H | H | Me | 2 | —CO—(CH₂)₃-(4-MeO-Ph) | H | H |
| 1-1880 | H | H | H | Me | 2 | —CO—(CH₂)₃-(3,4-diMeO-Ph) | H | H |
| 1-1881 | H | H | H | Me | 2 | —CO—(CH₂)₃-(3,5-diMeO-Ph) | H | H |
| 1-1882 | H | H | H | Me | 2 | —CO—(CH₂)₃-(3,4,5-triMeO-Ph) | H | H |
| 1-1883 | H | H | H | Me | 2 | —CO—(CH₂)₃-(4-MeS-Ph) | H | H |
| 1-1884 | H | H | H | Me | 2 | —CO—(CH₂)₃-(3-Ac-Ph) | H | H |
| 1-1885 | H | H | H | Me | 2 | —CO—(CH₂)₃-(4-Ac-Ph) | H | H |
| 1-1886 | H | H | H | Me | 2 | —CO—(CH₂)₄-(3-F-Ph) | H | H |
| 1-1887 | H | H | H | Me | 2 | —CO—(CH₂)₄-(3,4-diF-Ph) | H | H |
| 1-1888 | H | H | H | Me | 2 | —CO—(CH₂)₄-(3,5-diF-Ph) | H | H |
| 1-1889 | H | H | H | Me | 2 | —CO—(CH₂)₄-(3-Cl-Ph) | H | H |
| 1-1890 | H | H | H | Me | 2 | —CO—(CH₂)₄-(4-Cl-Ph) | H | H |
| 1-1891 | H | H | H | Me | 2 | —CO—(CH₂)₄-(3,4-diCl-Ph) | H | H |
| 1-1892 | H | H | H | Me | 2 | —CO—(CH₂)₄-(3,5-diCl-Ph) | H | H |
| 1-1893 | H | H | H | Me | 2 | —CO—(CH₂)₄-(3-Me-Ph) | H | H |
| 1-1894 | H | H | H | Me | 2 | —CO—(CH₂)₄-(3,4-diMe-Ph) | H | H |
| 1-1895 | H | H | H | Me | 2 | —CO—(CH₂)₄-(3,5-diMe-Ph) | H | H |
| 1-1896 | H | H | H | Me | 2 | —CO—(CH₂)₄-(3-CF₃-Ph) | H | H |
| 1-1897 | H | H | H | Me | 2 | —CO—(CH₂)₄-(3,4-diCF₃-Ph) | H | H |
| 1-1898 | H | H | H | Me | 2 | —CO—(CH₂)₄-(3,5-diCF₃-Ph) | H | H |
| 1-1899 | H | H | H | Me | 2 | —CO—(CH₂)₄-(3-MeO-Ph) | H | H |
| 1-1900 | H | H | H | Me | 2 | —CO—(CH₂)₄-(3,4-diMeO-Ph) | H | H |
| 1-1901 | H | H | H | Me | 2 | —CO—(CH₂)₄-(3,5-diMeO-Ph) | H | H |
| 1-1902 | H | H | H | Me | 2 | —CO—(CH₂)₄-(3,4,5-triMeO-Ph) | H | H |
| 1-1903 | H | H | H | Me | 2 | —CO—(CH₂)₄-(3-Ac-Ph) | H | H |
| 1-1904 | H | H | H | Me | 2 | —CO—(CH₂)₄-(4-Ac-Ph) | H | H |
| 1-1905 | H | H | H | Me | 2 | —CH(OH)—(CH₂)₃-(3-F-Ph) | H | H |
| 1-1906 | H | H | H | Me | 2 | —CH(OH)—(CH₂)₃-(4-F-Ph) | H | H |
| 1-1907 | H | H | H | Me | 2 | —CH(OH)—(CH₂)₃-(3,4-diF-Ph) | H | H |
| 1-1908 | H | H | H | Me | 2 | —CH(OH)—(CH₂)₃-(3,5-diF-Ph) | H | H |
| 1-1909 | H | H | H | Me | 2 | —CH(OH)—(CH₂)₃-(3-Cl-Ph) | H | H |
| 1-1910 | H | H | H | Me | 2 | —CH(OH)—(CH₂)₃-(4-Cl-Ph) | H | H |
| 1-1911 | H | H | H | Me | 2 | —CH(OH)—(CH₂)₃-(3,4-diCl-Ph) | H | H |
| 1-1912 | H | H | H | Me | 2 | —CH(OH)—(CH₂)₃-(3,5-diCl-Ph) | H | H |
| 1-1913 | H | H | H | Me | 2 | —CH(OH)—(CH₂)₃-(3-Me-Ph) | H | H |
| 1-1914 | H | H | H | Me | 2 | —CH(OH)—(CH₂)₃-(4-Me-Ph) | H | H |
| 1-1915 | H | H | H | Me | 2 | —CH(OH)—(CH₂)₃-(3,4-diMe-Ph) | H | H |
| 1-1916 | H | H | H | Me | 2 | —CH(OH)—(CH₂)₃-(3,5-diMe-Ph) | H | H |
| 1-1917 | H | H | H | Me | 2 | —CH(OH)—(CH₂)₃-(3-Et-Ph) | H | H |
| 1-1918 | H | H | H | Me | 2 | —CH(OH)—(CH₂)₃-(4-Et-Ph) | H | H |
| 1-1919 | H | H | H | Me | 2 | —CH(OH)—(CH₂)₃-(3-CF₃-Ph) | H | H |
| 1-1920 | H | H | H | Me | 2 | —CH(OH)—(CH₂)₃-(4-CF₃-Ph) | H | H |
| 1-1921 | H | H | H | Me | 2 | —CH(OH)—(CH₂)₃-(3,4-diCF₃-Ph) | H | H |
| 1-1922 | H | H | H | Me | 2 | —CH(OH)—(CH₂)₃-(3,5-diCF₃-Ph) | H | H |
| 1-1923 | H | H | H | Me | 2 | —CH(OH)—(CH₂)₃-(3-MeO-Ph) | H | H |
| 1-1924 | H | H | H | Me | 2 | —CH(OH)—(CH₂)₃-(4-MeO-Ph) | H | H |
| 1-1925 | H | H | H | Me | 2 | —CH(OH)—(CH₂)₃-(3,4-diMeO-Ph) | H | H |
| 1-1926 | H | H | H | Me | 2 | —CH(OH)—(CH₂)₃-(3,5-diMeO-Ph) | H | H |
| 1-1927 | H | H | H | Me | 2 | —CH(OH)—(CH₂)₃-(3,4,5-triMeO-Ph) | H | H |
| 1-1928 | H | H | H | Me | 2 | —CH(OH)—(CH₂)₃-(4-MeS-Ph) | H | H |
| 1-1929 | H | H | H | Me | 2 | —CH(OH)—(CH₂)₃-(3-Ac-Ph) | H | H |
| 1-1930 | H | H | H | Me | 2 | —CH(OH)—(CH₂)₃-(4-Ac-Ph) | H | H |
| 1-1931 | H | H | H | Me | 2 | —CH(OH)—(CH₂)₄-(3-F-Ph) | H | H |
| 1-1932 | H | H | H | Me | 2 | —CH(OH)—(CH₂)₄-(3,4-diF-Ph) | H | H |
| 1-1933 | H | H | H | Me | 2 | —CH(OH)—(CH₂)₄-(3,5-diF-Ph) | H | H |
| 1-1934 | H | H | H | Me | 2 | —CH(OH)—(CH₂)₄-(3-Cl-Ph) | H | H |
| 1-1935 | H | H | H | Me | 2 | —CH(OH)—(CH₂)₄-(4-Cl-Ph) | H | H |

TABLE 1-continued

| | | | | | | | | |
|---|---|---|---|---|---|---|---|---|
| 1-1936 | H | H | H | Me | 2 | —CH(OH)—(CH$_2$)$_4$-(3,4-diCl-Ph) | H | H |
| 1-1937 | H | H | H | Me | 2 | —CH(OH)—(CH$_2$)$_4$-(3,5-diCl-Ph) | H | H |
| 1-1938 | H | H | H | Me | 2 | —CH(OH)—(CH$_2$)$_4$-(3-Me-Ph) | H | H |
| 1-1939 | H | H | H | Me | 2 | —CH(OH)—(CH$_2$)$_4$-(3,4-diMe-Ph) | H | H |
| 1-1940 | H | H | H | Me | 2 | —CH(OH)—(CH$_2$)$_4$-(3,5-diMe-Ph) | H | H |
| 1-1941 | H | H | H | Me | 2 | —CH(OH)—(CH$_2$)$_4$-(3-CF$_3$-Ph) | H | H |
| 1-1942 | H | H | H | Me | 2 | —CH(OH)—(CH$_2$)$_4$-(3,4-diCF$_3$-Ph) | H | H |
| 1-1943 | H | H | H | Me | 2 | —CH(OH)—(CH$_2$)$_4$-(3,5-diCF$_3$-Ph) | H | H |
| 1-1944 | H | H | H | Me | 2 | —CH(OH)—(CH$_2$)$_4$-(3-MeO-Ph) | H | H |
| 1-1945 | H | H | H | Me | 2 | —CH(OH)—(CH$_2$)$_4$-(3,4-diMeO-Ph) | H | H |
| 1-1946 | H | H | H | Me | 2 | —CH(OH)—(CH$_2$)$_4$-(3,5-diMeO-Ph) | H | H |
| 1-1947 | H | H | H | Me | 2 | —CH(OH)—(CH$_2$)$_4$-(3,4,5-triMeO-Ph) | H | H |
| 1-1948 | H | H | H | Me | 2 | —CH(OH)—(CH$_2$)$_4$-(3-Ac-Ph) | H | H |
| 1-1949 | H | H | H | Me | 2 | —CH(OH)—(CH$_2$)$_4$-(4-Ac-Ph) | H | H |

TABLE 2

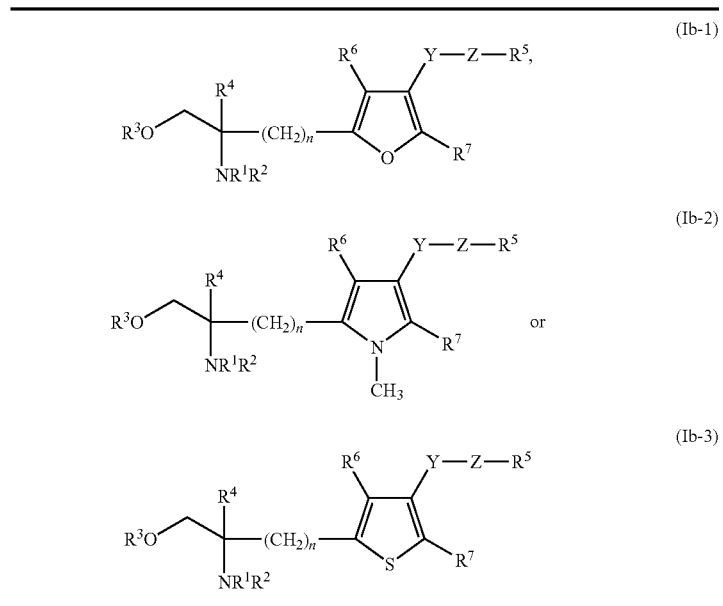

| Compd. | R$^1$ | R$^2$ | R$^3$ | R$^4$ | n | —Y—Z—R$^5$ | R$^6$ | R$^7$ |
|---|---|---|---|---|---|---|---|---|
| 2-1 | H | H | H | Me | 2 | —(CH$_2$)$_3$-cHx | H | H |
| 2-2 | H | H | H | Me | 2 | —(CH$_2$)$_3$-Ph | H | H |
| 2-3 | H | H | H | Me | 2 | —(CH$_2$)$_4$-cHx | H | H |
| 2-4 | H | H | H | Me | 2 | —(CH$_2$)$_4$-Ph | H | H |
| 2-5 | H | H | H | Me | 2 | —(CH$_2$)$_5$-cPn | H | H |
| 2-6 | H | H | H | Me | 2 | —(CH$_2$)$_5$-cHx | H | H |
| 2-7 | H | H | H | Me | 2 | —(CH$_2$)$_5$-cHx | Me | H |
| 2-8 | H | H | H | Me | 2 | —(CH$_2$)$_5$-cHx | H | Me |
| 2-9 | H | H | H | Me | 2 | —(CH$_2$)$_5$-cHx | F | H |
| 2-10 | H | H | H | Me | 2 | —(CH$_2$)$_5$-cHx | H | F |
| 2-11 | H | H | H | Me | 2 | —(CH$_2$)$_5$-(4-F-cHx) | H | H |
| 2-12 | H | H | H | Me | 2 | —(CH$_2$)$_5$-(4-Cl-cHx) | H | H |
| 2-13 | H | H | H | Me | 2 | —(CH$_2$)$_5$-(4-Br-cHx) | H | H |
| 2-14 | H | H | H | Me | 2 | —(CH$_2$)$_5$-(4-Me-cHx) | H | H |
| 2-15 | H | H | H | Me | 2 | —(CH$_2$)$_5$-(4-Et-cHx) | H | H |
| 2-16 | H | H | H | Me | 2 | —(CH$_2$)$_5$-(4-Pr-cHx) | H | H |
| 2-17 | H | H | H | Me | 2 | —(CH$_2$)$_5$-(4-iPr-cHx) | H | H |
| 2-18 | H | H | H | Me | 2 | —(CH$_2$)$_5$-(4-CF$_3$-cHx) | H | H |
| 2-19 | H | H | H | Me | 2 | —(CH$_2$)$_5$-(4-MeO-cHx) | H | H |
| 2-20 | H | H | H | Me | 2 | —(CH$_2$)$_5$-(4-EtO-cHx) | H | H |
| 2-21 | H | H | H | Me | 2 | —(CH$_2$)$_5$-(4-PrO-cHx) | H | H |
| 2-22 | H | H | H | Me | 2 | —(CH$_2$)$_5$-(4-iPrO-cHx) | H | H |
| 2-23 | H | H | H | Me | 2 | —(CH$_2$)$_5$-(3-MeS-cHx) | H | H |
| 2-24 | H | H | H | Me | 2 | —(CH$_2$)$_5$-(4-MeS-cHx) | H | H |
| 2-25 | H | H | H | Me | 2 | —(CH$_2$)$_5$-(2,4-diMe-cHx) | H | H |
| 2-26 | H | H | H | Me | 2 | —(CH$_2$)$_5$-(3,4-diMe-cHx) | H | H |
| 2-27 | H | H | H | Me | 2 | —(CH$_2$)$_5$-(3,5-diMe-cHx) | H | H |
| 2-28 | H | H | H | Me | 2 | —(CH$_2$)$_5$-Ph | H | H |
| 2-29 | H | H | H | Me | 2 | —(CH$_2$)$_5$-Ph | Me | H |
| 2-30 | H | H | H | Me | 2 | —(CH$_2$)$_5$-Ph | H | Me |

TABLE 2-continued

| | | | | | | | | |
|---|---|---|---|---|---|---|---|---|
| 2-31 | H | H | H | Me | 2 | —(CH$_2$)$_5$-Ph | F | H |
| 2-32 | H | H | H | Me | 2 | —(CH$_2$)$_5$-Ph | H | F |
| 2-33 | H | H | H | Me | 2 | —(CH$_2$)$_5$-(4-F-Ph) | H | H |
| 2-34 | H | H | H | Me | 2 | —(CH$_2$)$_5$-(4-Cl-Ph) | H | H |
| 2-35 | H | H | H | Me | 2 | —(CH$_2$)$_5$-(4-Br-Ph) | H | H |
| 2-36 | H | H | H | Me | 2 | —(CH$_2$)$_5$-(4-Me-Ph) | H | H |
| 2-37 | H | H | H | Me | 2 | —(CH$_2$)$_5$-(4-Et-Ph) | H | H |
| 2-38 | H | H | H | Me | 2 | —(CH$_2$)$_5$-(4-Pr-Ph) | H | H |
| 2-39 | H | H | H | Me | 2 | —(CH$_2$)$_5$-(4-iPr-Ph) | H | H |
| 2-40 | H | H | H | Me | 2 | —(CH$_2$)$_5$-(4-Bu-Ph) | H | H |
| 2-41 | H | H | H | Me | 2 | —(CH$_2$)$_5$-(4-CF$_3$-Ph) | H | H |
| 2-42 | H | H | H | Me | 2 | —(CH$_2$)$_5$-(4-MeO-Ph) | H | H |
| 2-43 | H | H | H | Me | 2 | —(CH$_2$)$_5$-(4-EtO-Ph) | H | H |
| 2-44 | H | H | H | Me | 2 | —(CH$_2$)$_5$-(4-PrO-Ph) | H | H |
| 2-45 | H | H | H | Me | 2 | —(CH$_2$)$_5$-(4-iPrO-Ph) | H | H |
| 2-46 | H | H | H | Me | 2 | —(CH$_2$)$_5$-(3-MeS-Ph) | H | H |
| 2-47 | H | H | H | Me | 2 | —(CH$_2$)$_5$-(4-MeS-Ph) | H | H |
| 2-48 | H | H | H | Me | 2 | —(CH$_2$)$_5$-(2,4-diMe-Ph) | H | H |
| 2-49 | H | H | H | Me | 2 | —(CH$_2$)$_5$-(3,4-diMe-Ph) | H | H |
| 2-50 | H | H | H | Me | 2 | —(CH$_2$)$_5$-(3,5-diMe-Ph) | H | H |
| 2-51 | H | H | H | Me | 2 | —(CH$_2$)$_6$-cPn | H | H |
| 2-52 | H | H | H | Me | 2 | —(CH$_2$)$_6$-cHx | H | H |
| 2-53 | H | H | H | Me | 2 | —(CH$_2$)$_6$-cHx | Me | H |
| 2-54 | H | H | H | Me | 2 | —(CH$_2$)$_6$-cHx | H | Me |
| 2-55 | H | H | H | Me | 2 | —(CH$_2$)$_6$-cHx | F | H |
| 2-56 | H | H | H | Me | 2 | —(CH$_2$)$_6$-cHx | H | F |
| 2-57 | H | H | H | Me | 2 | —(CH$_2$)$_6$-(4-F-cHx) | H | H |
| 2-58 | H | H | H | Me | 2 | —(CH$_2$)$_6$-(4-Cl-cHx) | H | H |
| 2-59 | H | H | H | Me | 2 | —(CH$_2$)$_6$-(4-Br-cHx) | H | H |
| 2-60 | H | H | H | Me | 2 | —(CH$_2$)$_6$-(4-Me-cHx) | H | H |
| 2-61 | H | H | H | Me | 2 | —(CH$_2$)$_6$-(4-Et-cHx) | H | H |
| 2-62 | H | H | H | Me | 2 | —(CH$_2$)$_6$-(4-Pr-cHx) | H | H |
| 2-63 | H | H | H | Me | 2 | —(CH$_2$)$_6$-(4-iPr-cHx) | H | H |
| 2-64 | H | H | H | Me | 2 | —(CH$_2$)$_6$-(4-Bu-cHx) | H | H |
| 2-65 | H | H | H | Me | 2 | —(CH$_2$)$_6$-(4-CF$_3$-cHx) | H | H |
| 2-66 | H | H | H | Me | 2 | —(CH$_2$)$_6$-(4-MeO-cHx) | H | H |
| 2-67 | H | H | H | Me | 2 | —(CH$_2$)$_6$-(4-EtO-cHx) | H | H |
| 2-68 | H | H | H | Me | 2 | —(CH$_2$)$_6$-(4-PrO-cHx) | H | H |
| 2-69 | H | H | H | Me | 2 | —(CH$_2$)$_6$-(4-iPrO-cHx) | H | H |
| 2-70 | H | H | H | Me | 2 | —(CH$_2$)$_6$-(3-MeS-cHx) | H | H |
| 2-71 | H | H | H | Me | 2 | —(CH$_2$)$_6$-(4-MeS-cHx) | H | H |
| 2-72 | H | H | H | Me | 2 | —(CH$_2$)$_6$-(2,4-diMe-cHx) | H | H |
| 2-73 | H | H | H | Me | 2 | —(CH$_2$)$_6$-(3,4-diMe-cHx) | H | H |
| 2-74 | H | H | H | Me | 2 | —(CH$_2$)$_6$-(3,5-diMe-cHx) | H | H |
| 2-75 | H | H | H | Me | 2 | —(CH$_2$)$_6$-Ph | H | H |
| 2-76 | H | H | H | Me | 2 | —(CH$_2$)$_6$-Ph | Me | H |
| 2-77 | H | H | H | Me | 2 | —(CH$_2$)$_6$-Ph | H | Me |
| 2-78 | H | H | H | Me | 2 | —(CH$_2$)$_6$-Ph | F | H |
| 2-79 | H | H | H | Me | 2 | —(CH$_2$)$_6$-Ph | H | F |
| 2-80 | H | H | H | Me | 2 | —(CH$_2$)$_6$-(4-F-Ph) | H | H |
| 2-81 | H | H | H | Me | 2 | —(CH$_2$)$_6$-(4-Cl-Ph) | H | H |
| 2-82 | H | H | H | Me | 2 | —(CH$_2$)$_6$-(4-Br-Ph) | H | H |
| 2-83 | H | H | H | Me | 2 | —(CH$_2$)$_6$-(4-Me-Ph) | H | H |
| 2-84 | H | H | H | Me | 2 | —(CH$_2$)$_6$-(4-Et-Ph) | H | H |
| 2-85 | H | H | H | Me | 2 | —(CH$_2$)$_6$-(4-Pr-Ph) | H | H |
| 2-86 | H | H | H | Me | 2 | —(CH$_2$)$_6$-(4-iPr-Ph) | H | H |
| 2-87 | H | H | H | Me | 2 | —(CH$_2$)$_6$-(4-Bu-Ph) | H | H |
| 2-88 | H | H | H | Me | 2 | —(CH$_2$)$_6$-(4-CF$_3$-Ph) | H | H |
| 2-89 | H | H | H | Me | 2 | —(CH$_2$)$_6$-(4-MeO-Ph) | H | H |
| 2-90 | H | H | H | Me | 2 | —(CH$_2$)$_6$-(4-EtO-Ph) | H | H |
| 2-91 | H | H | H | Me | 2 | —(CH$_2$)$_6$-(4-PrO-Ph) | H | H |
| 2-92 | H | H | H | Me | 2 | —(CH$_2$)$_6$-(4-iPrO-Ph) | H | H |
| 2-93 | H | H | H | Me | 2 | —(CH$_2$)$_6$-(3-MeS-Ph) | H | H |
| 2-94 | H | H | H | Me | 2 | —(CH$_2$)$_6$-(4-MeS-Ph) | H | H |
| 2-95 | H | H | H | Me | 2 | —(CH$_2$)$_6$-(2,4-diMe-Ph) | H | H |
| 2-96 | H | H | H | Me | 2 | —(CH$_2$)$_6$-(3,4-diMe-Ph) | H | H |
| 2-97 | H | H | H | Me | 2 | —(CH$_2$)$_6$-(3,5-diMe-Ph) | H | H |
| 2-98 | H | H | H | Me | 2 | —(CH$_2$)$_7$-cHx | H | H |
| 2-99 | H | H | H | Me | 2 | —(CH$_2$)$_7$-Ph | H | H |
| 2-100 | H | H | H | Me | 2 | —(CH$_2$)$_8$-cHx | H | H |
| 2-101 | H | H | H | Me | 2 | —(CH$_2$)$_8$-Ph | H | H |
| 2-102 | H | H | H | Me | 2 | —C≡C—CH$_2$-cHx | H | H |
| 2-103 | H | H | H | Me | 2 | —C≡C—CH$_2$-Ph | H | H |
| 2-104 | H | H | H | Me | 2 | —C≡C—(CH$_2$)$_2$-cHx | H | H |
| 2-105 | H | H | H | Me | 2 | —C≡C—(CH$_2$)$_2$-Ph | H | H |
| 2-106 | H | H | H | Me | 2 | —C≡C—(CH$_2$)$_3$-cPn | H | H |
| 2-107 | H | H | H | Me | 2 | —C≡C—(CH$_2$)$_3$-cHx | H | H |
| 2-108 | H | H | H | Me | 2 | —C≡C—(CH$_2$)$_3$-cHx | Me | H |
| 2-109 | H | H | H | Me | 2 | —C≡C—(CH$_2$)$_3$-cHx | H | Me |
| 2-110 | H | H | H | Me | 2 | —C≡C—(CH$_2$)$_3$-cHx | F | H |

TABLE 2-continued

| | | | | | | | | |
|---|---|---|---|---|---|---|---|---|
| 2-111 | H | H | H | Me | 2 | —C≡C—(CH$_2$)$_3$-cHx | H | F |
| 2-112 | H | H | H | Me | 2 | —C≡C—(CH$_2$)$_3$-(4-F-cHx) | H | H |
| 2-113 | H | H | H | Me | 2 | —C≡C—(CH$_2$)$_3$-(4-Cl-cHx) | H | H |
| 2-114 | H | H | H | Me | 2 | —C≡C—(CH$_2$)$_3$-(4-Br-cHx) | H | H |
| 2-115 | H | H | H | Me | 2 | —C≡C—(CH$_2$)$_3$-(4-Me-cHx) | H | H |
| 2-116 | H | H | H | Me | 2 | —C≡C—(CH$_2$)$_3$-(4-Et-cHx) | H | H |
| 2-117 | H | H | H | Me | 2 | —C≡C—(CH$_2$)$_3$-(4-Pr-cHx) | H | H |
| 2-118 | H | H | H | Me | 2 | —C≡C—(CH$_2$)$_3$-(4-iPr-cHx) | H | H |
| 2-119 | H | H | H | Me | 2 | —C≡C—(CH$_2$)$_3$-(4-Bu-cHx) | H | H |
| 2-120 | H | H | H | Me | 2 | —C≡C—(CH$_2$)$_3$-(4-CF$_3$-cHx) | H | H |
| 2-121 | H | H | H | Me | 2 | —C≡C—(CH$_2$)$_3$-(4-MeO-cHx) | H | H |
| 2-122 | H | H | H | Me | 2 | —C≡C—(CH$_2$)$_3$-(4-EtO-cHx) | H | H |
| 2-123 | H | H | H | Me | 2 | —C≡C—(CH$_2$)$_3$-(4-PrO-cHx) | H | H |
| 2-124 | H | H | H | Me | 2 | —C≡C—(CH$_2$)$_3$-(4-iPrO-cHx) | H | H |
| 2-125 | H | H | H | Me | 2 | —C≡C—(CH$_2$)$_3$-(3-MeS-cHx) | H | H |
| 2-126 | H | H | H | Me | 2 | —C≡C—(CH$_2$)$_3$-(4-MeS-cHx) | H | H |
| 2-127 | H | H | H | Me | 2 | —C≡C—(CH$_2$)$_3$-(2,4-diMe-cHx) | H | H |
| 2-128 | H | H | H | Me | 2 | —C≡C—(CH$_2$)$_3$-(3,4-diMe-cHx) | H | H |
| 2-129 | H | H | H | Me | 2 | —C≡C—(CH$_2$)$_3$-(3,5-diMe-cHx) | H | H |
| 2-130 | H | H | H | Me | 2 | —C≡C—(CH$_2$)$_3$-Ph | H | H |
| 2-131 | H | H | H | Me | 2 | —C≡C—(CH$_2$)$_3$-Ph | Me | H |
| 2-132 | H | H | H | Me | 2 | —C≡C—(CH$_2$)$_3$-Ph | H | Me |
| 2-133 | H | H | H | Me | 2 | —C≡C—(CH$_2$)$_3$-Ph | F | H |
| 2-134 | H | H | H | Me | 2 | —C≡C—(CH$_2$)$_3$-Ph | H | F |
| 2-135 | H | H | H | Me | 2 | —C≡C—(CH$_2$)$_3$-(4-F-Ph) | H | H |
| 2-136 | H | H | H | Me | 2 | —C≡C—(CH$_2$)$_3$-(4-Cl-Ph) | H | H |
| 2-137 | H | H | H | Me | 2 | —C≡C—(CH$_2$)$_3$-(4-Br-Ph) | H | H |
| 2-138 | H | H | H | Me | 2 | —C≡C—(CH$_2$)$_3$-(4-Me-Ph) | H | H |
| 2-139 | H | H | H | Me | 2 | —C≡C—(CH$_2$)$_3$-(4-Et-Ph) | H | H |
| 2-140 | H | H | H | Me | 2 | —C≡C—(CH$_2$)$_3$-(4-Pr-Ph) | H | H |
| 2-141 | H | H | H | Me | 2 | —C≡C—(CH$_2$)$_3$-(4-iPr-Ph) | H | H |
| 2-142 | H | H | H | Me | 2 | —C≡C—(CH$_2$)$_3$-(4-Bu-Ph) | H | H |
| 2-143 | H | H | H | Me | 2 | —C≡C—(CH$_2$)$_3$-(4-CF$_3$-Ph) | H | H |
| 2-144 | H | H | H | Me | 2 | —C≡C—(CH$_2$)$_3$-(4-MeO-Ph) | H | H |
| 2-145 | H | H | H | Me | 2 | —C≡C—(CH$_2$)$_3$-(4-EtO-Ph) | H | H |
| 2-146 | H | H | H | Me | 2 | —C≡C—(CH$_2$)$_3$-(4-PrO-Ph) | H | H |
| 2-147 | H | H | H | Me | 2 | —C≡C—(CH$_2$)$_3$-(4-iPrO-Ph) | H | H |
| 2-148 | H | H | H | Me | 2 | —C≡C—(CH$_2$)$_3$-(3-MeS-Ph) | H | H |
| 2-149 | H | H | H | Me | 2 | —C≡C—(CH$_2$)$_3$-(4-MeS-Ph) | H | H |
| 2-150 | H | H | H | Me | 2 | —C≡C—(CH$_2$)$_3$-(2,4-diMe-Ph) | H | H |
| 2-151 | H | H | H | Me | 2 | —C≡C—(CH$_2$)$_3$-(3,4-diMe-Ph) | H | H |
| 2-152 | H | H | H | Me | 2 | —C≡C—(CH$_2$)$_3$-(3,5-diMe-Ph) | H | H |
| 2-153 | H | H | H | Me | 2 | —C≡C—(CH$_2$)$_4$-cPn | H | H |
| 2-154 | H | H | H | Me | 2 | —C≡C—(CH$_2$)$_4$-cHx | H | H |
| 2-155 | H | H | H | Me | 2 | —C≡C—(CH$_2$)$_4$-cHx | Me | H |
| 2-156 | H | H | H | Me | 2 | —C≡C—(CH$_2$)$_4$-cHx | H | Me |
| 2-157 | H | H | H | Me | 2 | —C≡C—(CH$_2$)$_4$-cHx | F | H |
| 2-158 | H | H | H | Me | 2 | —C≡C—(CH$_2$)$_4$-cHx | H | F |
| 2-159 | H | H | H | Me | 2 | —C≡C—(CH$_2$)$_4$-(4-F-cHx) | H | H |
| 2-160 | H | H | H | Me | 2 | —C≡C—(CH$_2$)$_4$-(4-Cl-cHx) | H | H |
| 2-161 | H | H | H | Me | 2 | —C≡C—(CH$_2$)$_4$-(4-Br-cHx) | H | H |
| 2-162 | H | H | H | Me | 2 | —C≡C—(CH$_2$)$_4$-(4-Me-cHx) | H | H |
| 2-163 | H | H | H | Me | 2 | —C≡C—(CH$_2$)$_4$-(4-Et-cHx) | H | H |
| 2-164 | H | H | H | Me | 2 | —C≡C—(CH$_2$)$_4$-(4-Pr-cHx) | H | H |
| 2-165 | H | H | H | Me | 2 | —C≡C—(CH$_2$)$_4$-(4-iPr-cHx) | H | H |
| 2-166 | H | H | H | Me | 2 | —C≡C—(CH$_2$)$_4$-(4-Bu-cHx) | H | H |
| 2-167 | H | H | H | Me | 2 | —C≡C—(CH$_2$)$_4$-(4-CF$_3$-cHx) | H | H |
| 2-168 | H | H | H | Me | 2 | —C≡C—(CH$_2$)$_4$-(4-MeO-cHx) | H | H |
| 2-169 | H | H | H | Me | 2 | —C≡C—(CH$_2$)$_4$-(4-EtO-cHx) | H | H |
| 2-170 | H | H | H | Me | 2 | —C≡C—(CH$_2$)$_4$-(4-PrO-cHx) | H | H |
| 2-171 | H | H | H | Me | 2 | —C≡C—(CH$_2$)$_4$-(4-iPrO-cHx) | H | H |
| 2-172 | H | H | H | Me | 2 | —C≡C—(CH$_2$)$_4$-(4-MeS-cHx) | H | H |
| 2-173 | H | H | H | Me | 2 | —C≡C—(CH$_2$)$_4$-(2,4-diMe-cHx) | H | H |
| 2-174 | H | H | H | Me | 2 | —C≡C—(CH$_2$)$_4$-(3,4-diMe-cHx) | H | H |
| 2-175 | H | H | H | Me | 2 | —C≡C—(CH$_2$)$_4$-(3,5-diMe-cHx) | H | H |
| 2-176 | H | H | H | Me | 2 | —C≡C—(CH$_2$)$_4$-Ph | H | H |
| 2-177 | H | H | H | Me | 2 | —C≡C—(CH$_2$)$_4$-Ph | Me | H |
| 2-178 | H | H | H | Me | 2 | —C≡C—(CH$_2$)$_4$-Ph | H | Me |
| 2-179 | H | H | H | Me | 2 | —C≡C—(CH$_2$)$_4$-Ph | F | H |
| 2-180 | H | H | H | Me | 2 | —C≡C—(CH$_2$)$_4$-Ph | H | F |
| 2-181 | H | H | H | Me | 2 | —C≡C—(CH$_2$)$_4$-(4-F-Ph) | H | H |
| 2-182 | H | H | H | Me | 2 | —C≡C—(CH$_2$)$_4$-(4-Cl-Ph) | H | H |
| 2-183 | H | H | H | Me | 2 | —C≡C—(CH$_2$)$_4$-(4-Br-Ph) | H | H |
| 2-184 | H | H | H | Me | 2 | —C≡C—(CH$_2$)$_4$-(4-Me-Ph) | H | H |
| 2-185 | H | H | H | Me | 2 | —C≡C—(CH$_2$)$_4$-(4-Et-Ph) | H | H |
| 2-186 | H | H | H | Me | 2 | —C≡C—(CH$_2$)$_4$-(4-Pr-Ph) | H | H |
| 2-187 | H | H | H | Me | 2 | —C≡C—(CH$_2$)$_4$-(4-iPr-Ph) | H | H |
| 2-188 | H | H | H | Me | 2 | —C≡C—(CH$_2$)$_4$-(4-Bu-Ph) | H | H |
| 2-189 | H | H | H | Me | 2 | —C≡C—(CH$_2$)$_4$-(4-CF$_3$-Ph) | H | H |
| 2-190 | H | H | H | Me | 2 | —C≡C—(CH$_2$)$_4$-(4-MeO-Ph) | H | H |

TABLE 2-continued

| | | | | | | | | |
|---|---|---|---|---|---|---|---|---|
| 2-191 | H | H | H | Me | 2 | —C≡C—(CH$_2$)$_4$-(4-EtO-Ph) | H | H |
| 2-192 | H | H | H | Me | 2 | —C≡C—(CH$_2$)$_4$-(4-PrO-Ph) | H | H |
| 2-193 | H | H | H | Me | 2 | —C≡C—(CH$_2$)$_4$-(4-iPrO-Ph) | H | H |
| 2-194 | H | H | H | Me | 2 | —C≡C—(CH$_2$)$_4$-(3-MeS-Ph) | H | H |
| 2-195 | H | H | H | Me | 2 | —C≡C—(CH$_2$)$_4$-(4-MeS-Ph) | H | H |
| 2-196 | H | H | H | Me | 2 | —C≡C—(CH$_2$)$_4$-(2,4-diMe-Ph) | H | H |
| 2-197 | H | H | H | Me | 2 | —C≡C—(CH$_2$)$_4$-(3,4-diMe-Ph) | H | H |
| 2-198 | H | H | H | Me | 2 | —C≡C—(CH$_2$)$_4$-(3,5-diMe-Ph) | H | H |
| 2-199 | H | H | H | Me | 2 | —C≡C—(CH$_2$)$_5$-cHx | H | H |
| 2-200 | H | H | H | Me | 2 | —C≡C—(CH$_2$)$_5$-Ph | H | H |
| 2-201 | H | H | H | Me | 2 | —C≡C—(CH$_2$)$_6$-cHx | H | H |
| 2-202 | H | H | H | Me | 2 | —C≡C—(CH$_2$)$_6$-Ph | H | H |
| 2-203 | H | H | H | Me | 2 | —C≡C—CH$_2$O-cHx | H | H |
| 2-204 | H | H | H | Me | 2 | —C≡C—CH$_2$O-Ph | H | H |
| 2-205 | H | H | H | Me | 2 | —C≡C—(CH$_2$)$_2$O-cPn | H | H |
| 2-206 | H | H | H | Me | 2 | —C≡C—(CH$_2$)$_2$O-cHx | H | H |
| 2-207 | H | H | H | Me | 2 | —C≡C—(CH$_2$)$_2$O-cHx | Me | H |
| 2-208 | H | H | H | Me | 2 | —C≡C—(CH$_2$)$_2$O-cHx | H | Me |
| 2-209 | H | H | H | Me | 2 | —C≡C—(CH$_2$)$_2$O-cHx | F | H |
| 2-210 | H | H | H | Me | 2 | —C≡C—(CH$_2$)$_2$O-cHx | H | F |
| 2-211 | H | H | H | Me | 2 | —C≡C—(CH$_2$)$_2$O-(4-F-cHx) | H | H |
| 2-212 | H | H | H | Me | 2 | —C≡C—(CH$_2$)$_2$O-(4-Cl-cHx) | H | H |
| 2-213 | H | H | H | Me | 2 | —C≡C—(CH$_2$)$_2$O-(4-Br-cHx) | H | H |
| 2-214 | H | H | H | Me | 2 | —C≡C—(CH$_2$)$_2$O-(4-Me-cHx) | H | H |
| 2-215 | H | H | H | Me | 2 | —C≡C—(CH$_2$)$_2$O-(4-Et-cHx) | H | H |
| 2-216 | H | H | H | Me | 2 | —C≡C—(CH$_2$)$_2$O-(4-Pr-cHx) | H | H |
| 2-217 | H | H | H | Me | 2 | —C≡C—(CH$_2$)$_2$O-(4-iPr-cHx) | H | H |
| 2-218 | H | H | H | Me | 2 | —C≡C—(CH$_2$)$_2$O-(4-Bu-cHx) | H | H |
| 2-219 | H | H | H | Me | 2 | —C≡C—(CH$_2$)$_2$O-(4-CF$_3$-cHx) | H | H |
| 2-220 | H | H | H | Me | 2 | —C≡C—(CH$_2$)$_2$O-(4-MeO-cHx) | H | H |
| 2-221 | H | H | H | Me | 2 | —C≡C—(CH$_2$)$_2$O-(4-EtO-cHx) | H | H |
| 2-222 | H | H | H | Me | 2 | —C≡C—(CH$_2$)$_2$O-(4-PrO-cHx) | H | H |
| 2-223 | H | H | H | Me | 2 | —C≡C—(CH$_2$)$_2$O-(4-iPrO-cHx) | H | H |
| 2-224 | H | H | H | Me | 2 | —C≡C—(CH$_2$)$_2$O-(3-MeS-cHx) | H | H |
| 2-225 | H | H | H | Me | 2 | —C≡C—(CH$_2$)$_2$O-(4-MeS-cHx) | H | H |
| 2-226 | H | H | H | Me | 2 | —C≡C—(CH$_2$)$_2$O-(2,4-diMe-cHx) | H | H |
| 2-227 | H | H | H | Me | 2 | —C≡C—(CH$_2$)$_2$O-(3,4-diMe-cHx) | H | H |
| 2-228 | H | H | H | Me | 2 | —C≡C—(CH$_2$)$_2$O-(3,5-diMe-cHx) | H | H |
| 2-229 | H | H | H | Me | 2 | —C≡C—(CH$_2$)$_2$O-Ph | H | H |
| 2-230 | H | H | H | Me | 2 | —C≡C—(CH$_2$)$_2$O-Ph | Me | H |
| 2-231 | H | H | H | Me | 2 | —C≡C—(CH$_2$)$_2$O-Ph | H | Me |
| 2-232 | H | H | H | Me | 2 | —C≡C—(CH$_2$)$_2$O-Ph | F | H |
| 2-233 | H | H | H | Me | 2 | —C≡C—(CH$_2$)$_2$O-Ph | H | F |
| 2-234 | H | H | H | Me | 2 | —C≡C—(CH$_2$)$_2$O-(4-F-Ph) | H | H |
| 2-235 | H | H | H | Me | 2 | —C≡C—(CH$_2$)$_2$O-(4-Cl-Ph) | H | H |
| 2-236 | H | H | H | Me | 2 | —C≡C—(CH$_2$)$_2$O-(4-Br-Ph) | H | H |
| 2-237 | H | H | H | Me | 2 | —C≡C—(CH$_2$)$_2$O-(4-Me-Ph) | H | H |
| 2-238 | H | H | H | Me | 2 | —C≡C—(CH$_2$)$_2$O-(4-Et-Ph) | H | H |
| 2-239 | H | H | H | Me | 2 | —C≡C—(CH$_2$)$_2$O-(4-Pr-Ph) | H | H |
| 2-240 | H | H | H | Me | 2 | —C≡C—(CH$_2$)$_2$O-(4-iPr-Ph) | H | H |
| 2-241 | H | H | H | Me | 2 | —C≡C—(CH$_2$)$_2$O-(4-Bu-Ph) | H | H |
| 2-242 | H | H | H | Me | 2 | —C≡C—(CH$_2$)$_2$O-(4-CF$_3$-Ph) | H | H |
| 2-243 | H | H | H | Me | 2 | —C≡C—(CH$_2$)$_2$O-(4-MeO-Ph) | H | H |
| 2-244 | H | H | H | Me | 2 | —C≡C—(CH$_2$)$_2$O-(4-EtO-Ph) | H | H |
| 2-245 | H | H | H | Me | 2 | —C≡C—(CH$_2$)$_2$O-(4-PrO-Ph) | H | H |
| 2-246 | H | H | H | Me | 2 | —C≡C—(CH$_2$)$_2$O-(4-iPrO-Ph) | H | H |
| 2-247 | H | H | H | Me | 2 | —C≡C—(CH$_2$)$_2$O-(4-MeS-Ph) | H | H |
| 2-248 | H | H | H | Me | 2 | —C≡C—(CH$_2$)$_2$O-(2,4-diMe-Ph) | H | H |
| 2-249 | H | H | H | Me | 2 | —C≡C—(CH$_2$)$_2$O-(3,4-diMe-Ph) | H | H |
| 2-250 | H | H | H | Me | 2 | —C≡C—(CH$_2$)$_2$O-(3,5-diMe-Ph) | H | H |
| 2-251 | H | H | H | Me | 2 | —CO—(CH$_2$)$_4$-cHx | H | H |
| 2-252 | H | H | H | Me | 2 | —CO—(CH$_2$)$_4$-Ph | H | H |
| 2-253 | H | H | H | Me | 2 | —CO—(CH$_2$)$_5$-cHx | H | H |
| 2-254 | H | H | H | Me | 2 | —CO—(CH$_2$)$_5$-Ph | H | H |
| 2-255 | H | H | H | Me | 2 | —CH(OH)—(CH$_2$)$_4$-cHx | H | H |
| 2-257 | H | H | H | Me | 2 | —CH(OH)—(CH$_2$)$_5$-cHx | H | H |
| 2-258 | H | H | H | Me | 2 | —CH(OH)—(CH$_2$)$_5$-Ph | H | H |
| 2-259 | H | H | H | Me | 2 | 4-(cHx-CH$_2$O)Ph | H | H |
| 2-260 | H | H | H | Me | 2 | 4-[cHx-(CH$_2$)$_2$O]Ph | H | H |
| 2-261 | H | H | H | Me | 2 | 4-[cHx-(CH$_2$)$_3$O]Ph | H | H |
| 2-262 | H | H | H | Me | 2 | -(4-BzO-Ph) | H | H |
| 2-263 | H | H | H | Me | 2 | -(4-BzO-2-F-Ph) | H | H |
| 2-264 | H | H | H | Me | 2 | -(4-BzO-3-F-Ph) | H | H |
| 2-265 | H | H | H | Me | 2 | -(4-BzO-2,3-diF-Ph) | H | H |
| 2-266 | H | H | H | Me | 2 | -(4-BzO-2-Cl-Ph) | H | H |
| 2-267 | H | H | H | Me | 2 | -(4-BzO-3-Cl-Ph) | H | H |
| 2-268 | H | H | H | Me | 2 | -(4-BzO-2,3-diCl-Ph) | H | H |
| 2-269 | H | H | H | Me | 2 | -(4-BzO-2-Me-Ph) | H | H |
| 2-270 | H | H | H | Me | 2 | -(4-BzO-3-Me-Ph) | H | H |
| 2-271 | H | H | H | Me | 2 | -(4-BzO-2,3-diMe-Ph) | H | H |

TABLE 2-continued

| | | | | | | | | |
|---|---|---|---|---|---|---|---|---|
| 2-272 | H | H | H | Me | 2 | -4-[Ph-(CH$_2$)$_2$O]-Ph | H | H |
| 2-273 | H | H | H | Me | 2 | -3-[cHx-(CH$_2$)$_2$O]-Ph | H | H |
| 2-274 | H | H | H | Et | 2 | —(CH$_2$)$_5$-cHx | H | H |
| 2-275 | H | H | H | Et | 2 | —(CH$_2$)$_6$-cHx | H | H |
| 2-276 | H | H | H | Et | 2 | —C≡C—(CH$_2$)$_3$-cHx | H | H |
| 2-277 | H | H | H | Et | 2 | —C≡C—(CH$_2$)$_4$-cHx | H | H |
| 2-278 | H | H | H | Et | 2 | -4-(cHx-CH$_2$O)Ph | H | H |
| 2-279 | H | H | H | Et | 2 | -(4-BzO-Ph) | H | H |
| 2-280 | H | H | H | Et | 2 | —C≡C—(CH$_2$)$_2$O-cHx | H | H |
| 2-281 | H | H | H | Et | 2 | —C≡C—(CH$_2$)$_2$O-Ph | H | H |
| 2-282 | H | H | H | Pr | 2 | —(CH$_2$)$_5$cHx | H | H |
| 2-283 | H | H | H | Pr | 2 | —(CH$_2$)$_6$-cHx | H | H |
| 2-284 | H | H | H | Pr | 2 | —C≡C—(CH$_2$)$_3$-cHx | H | H |
| 2-285 | H | H | H | Pr | 2 | —C≡C—(CH$_2$)$_4$cHx | H | H |
| 2-286 | H | H | H | Pr | 2 | -4-(cHx-CH$_2$O)Ph | H | H |
| 2-287 | H | H | H | Pr | 2 | -(4-BzO-Ph) | H | H |
| 2-288 | H | H | H | Pr | 2 | —C≡C—(CH$_2$)$_2$O-cHx | H | H |
| 2-289 | H | H | H | Pr | 2 | —C≡C—(CH$_2$)$_2$O-Ph | H | H |

TABLE 3

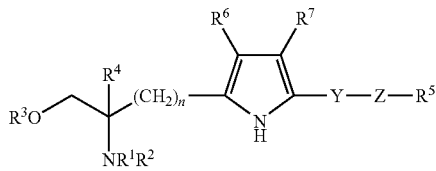

(Ia-4)

| Compd. | R$^1$ | R$^2$ | R$^3$ | R$^4$ | n | —Y—Z—R$^5$ | R$^6$ | R$^7$ |
|---|---|---|---|---|---|---|---|---|
| 3-1 | H | H | H | Me | 2 | —(CH$_2$)$_4$-cHx | H | H |
| 3-2 | H | H | H | Me | 2 | —(CH$_2$)$_4$-Ph | H | H |
| 3-3 | H | H | H | Me | 2 | —(CH$_2$)$_5$-cHx | H | H |
| 3-4 | H | H | H | Me | 2 | —(CH$_2$)$_5$-Ph | H | H |
| 3-5 | H | H | H | Me | 2 | —C≡C—(CH$_2$)$_2$-cHx | H | H |
| 3-6 | H | H | H | Me | 2 | —C≡C—(CH$_2$)$_2$-Ph | H | H |
| 3-7 | H | H | H | Me | 2 | —C≡C—(CH$_2$)$_3$-cHx | H | H |
| 3-8 | H | H | H | Me | 2 | —C≡C—(CH$_2$)$_3$-Ph | H | H |
| 3-9 | H | H | H | Me | 2 | —CO—(CH$_2$)$_3$-cHx | H | H |
| 3-10 | H | H | H | Me | 2 | —CO—(CH$_2$)$_3$-Ph | H | H |
| 3-11 | H | H | H | Me | 2 | —CO—(CH$_2$)$_4$-cHx | H | H |
| 3-12 | H | H | H | Me | 2 | —CO—(CH$_2$)$_4$-Ph | H | H |

TABLE 4

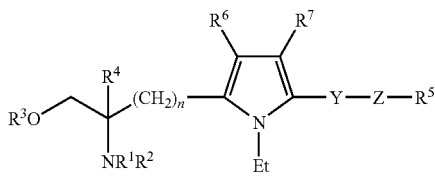

(Ia-5)

| Compd. | R$^1$ | R$^2$ | R$^3$ | R$^4$ | n | —Y—Z—R$^5$ | R$^6$ | R$^7$ |
|---|---|---|---|---|---|---|---|---|
| 4-1 | H | H | H | Me | 2 | —(CH$_2$)$_4$-cHx | H | H |
| 4-2 | H | H | H | Me | 2 | —(CH$_2$)$_4$-Ph | H | H |
| 4-3 | H | H | H | Me | 2 | —(CH$_2$)$_5$-cHx | H | H |
| 4-4 | H | H | H | Me | 2 | —(CH$_2$)$_5$-Ph | H | H |
| 4-5 | H | H | H | Me | 2 | —C≡C—(CH$_2$)$_2$-cHx | H | H |
| 4-6 | H | H | H | Me | 2 | —C≡C—(CH$_2$)$_2$-Ph | H | H |
| 4-7 | H | H | H | Me | 2 | —C≡C—(CH$_2$)$_3$-cHx | H | H |
| 4-8 | H | H | H | Me | 2 | —C≡C—(CH$_2$)$_3$-Ph | H | H |
| 4-9 | H | H | H | Me | 2 | —CO—(CH$_2$)$_3$cHx | H | H |
| 4-10 | H | H | H | Me | 2 | —CO—(CH$_2$)$_3$-Ph | H | H |
| 4-11 | H | H | H | Me | 2 | —CO—(CH$_2$)$_4$-cHx | H | H |
| 4-12 | H | H | H | Me | 2 | —CO—(CH$_2$)$_4$-Ph | H | H |

TABLE 5

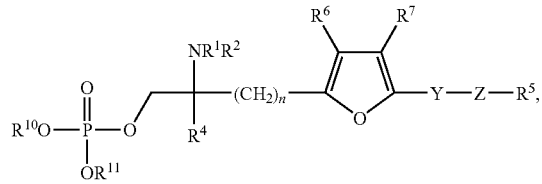

(IIa-1)

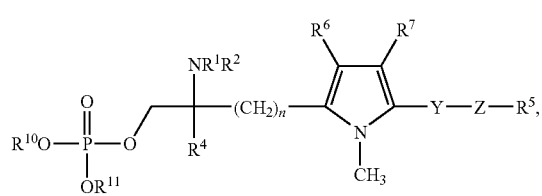

(IIa-2)

TABLE 5-continued

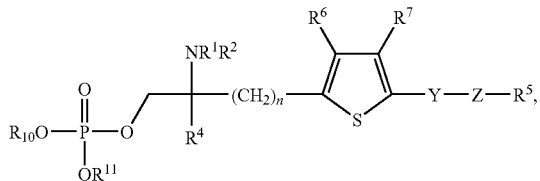
(IIIa-3)

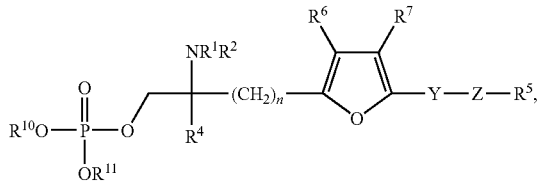
(IIIa-1)

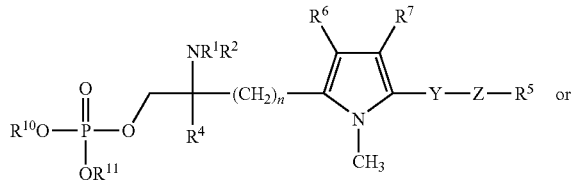
(IIIa-2) or

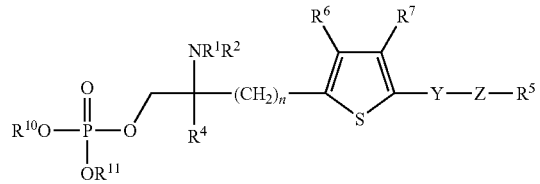
(IIIa-3)

| Compd. | $R^1$ | $R^2$ | $R^4$ | n | —Y—Z—$R^5$ | $R^6$ | $R^7$ | $R^{10}$ | $R^{11}$ |
|---|---|---|---|---|---|---|---|---|---|
| 5-1 | H | H | Me | 1 | —$(CH_2)_5$cHx | H | H | H | H |
| 5-2 | H | H | Me | 1 | —$(CH_2)_6$cHx | H | H | H | H |
| 5-3 | H | H | Me | 1 | —CH=CH—$(CH_2)_3$-cHx | H | H | H | H |
| 5-4 | H | H | Me | 1 | —CH=CH—$(CH_2)_4$-cHx | H | H | H | H |
| 5-5 | H | H | Me | 1 | —C≡C—$(CH_2)_3$-cHx | H | H | H | H |
| 5-6 | H | H | Me | 1 | —C≡C—$(CH_2)_4$-cHx | H | H | H | H |
| 5-7 | H | H | Me | 1 | —CO—$(CH_2)_4$-cHx | H | H | H | H |
| 5-8 | H | H | Me | 1 | —CO—$(CH_2)_5$-cHx | H | H | H | H |
| 5-9 | H | H | Me | 1 | —CH(OH)—$(CH_2)_4$-cHx | H | H | H | H |
| 5-10 | H | H | Me | 1 | —CH(OH)—$(CH_2)_5$cHx | H | H | H | H |
| 5-11 | H | H | Me | 1 | -4-(cHx-$CH_2$O)Ph | H | H | H | H |
| 5-12 | H | H | Me | 1 | -(4-BzO-Ph) | H | H | H | H |
| 5-13 | H | H | Me | 1 | —C≡C—$CH_2$O-cPn | H | H | H | H |
| 5-14 | H | H | Me | 1 | —C≡C—$(CH_2)_2$O-cPn | H | H | H | H |
| 5-15 | H | H | Me | 1 | —C≡C—$CH_2$O-cHx | H | H | H | H |
| 5-16 | H | H | Me | 1 | —C≡C—$(CH_2)_2$O-cHx | H | H | H | H |
| 5-17 | H | H | Me | 1 | —C≡C—$CH_2$O-Ph | H | H | H | H |
| 5-18 | H | H | Me | 1 | —C≡C—$(CH_2)_2$O-Ph | H | H | H | H |
| 5-19 | H | H | Me | 2 | —$(CH_2)_2$-cHx | H | H | H | H |
| 5-20 | H | Me | Me | 2 | —$(CH_2)_2$-cHx | H | H | H | H |
| 5-21 | $CO_2$Me | H | Me | 2 | —$(CH_2)_2$-cHx | H | H | H | H |
| 5-22 | $CO_2$Et | H | Me | 2 | —$(CH_2)_2$-cHx | H | H | H | H |
| 5-23 | H | H | Me | 2 | —$(CH_2)_2$-(4-F-cHx) | H | H | H | H |
| 5-24 | H | H | Me | 2 | —$(CH_2)_2$-(4-Me-cHx) | H | H | H | H |
| 5-25 | H | H | Me | 2 | —$(CH_2)_2$-(4-Et-cHx) | H | H | H | H |
| 5-26 | H | H | Me | 2 | —$(CH_2)_2$-(4-$CF_3$-cHx) | H | H | H | H |
| 5-27 | H | H | Me | 2 | —$(CH_2)_2$-(4-MeO-cHx) | H | H | H | H |
| 5-28 | H | H | Me | 2 | —$(CH_2)_2$-(4-EtO-cHx) | H | H | H | H |
| 5-29 | H | H | Me | 2 | —$(CH_2)_2$-(4-MeS-cHx) | H | H | H | H |
| 5-30 | H | H | Me | 2 | —$(CH_2)_2$-(4-cHx-cHx) | H | H | H | H |
| 5-31 | H | H | Me | 2 | —$(CH_2)_2$-(4-Ph-cHx) | H | H | H | H |
| 5-32 | H | H | Me | 2 | —$(CH_2)_2$-Ph | H | H | H | H |
| 5-33 | H | Me | Me | 2 | —$(CH_2)_2$-Ph | H | H | H | H |
| 5-34 | $CO_2$Me | H | Me | 2 | —$(CH_2)_2$-Ph | H | H | H | H |
| 5-35 | $CO_2$Et | H | Me | 2 | —$(CH_2)_2$-Ph | H | H | H | H |

TABLE 5-continued

| | | | | | | | | | |
|---|---|---|---|---|---|---|---|---|---|
| 5-36 | H | H | Me | 2 | —(CH$_2$)$_2$-(4-F-Ph) | H | H | H | H |
| 5-37 | H | H | Me | 2 | —(CH$_2$)$_2$-(4-Me-Ph) | H | H | H | H |
| 5-38 | H | H | Me | 2 | —(CH$_2$)$_2$-(4-Et-Ph) | H | H | H | H |
| 5-39 | H | H | Me | 2 | —(CH$_2$)$_2$-(4-CF$_3$-Ph) | H | H | H | H |
| 5-40 | H | H | Me | 2 | —(CH$_2$)$_2$-(4-MeO-Ph) | H | H | H | H |
| 5-41 | H | H | Me | 2 | —(CH$_2$)$_2$-(4-EtO-Ph) | H | H | H | H |
| 5-42 | H | H | Me | 2 | —(CH$_2$)$_2$-(4-MeS-Ph) | H | H | H | H |
| 5-43 | H | H | Me | 2 | —(CH$_2$)$_2$-(4-cHx-Ph) | H | H | H | H |
| 5-44 | H | H | Me | 2 | —(CH$_2$)$_2$-(4-Ph-Ph) | H | H | H | H |
| 5-45 | H | H | Me | 2 | —(CH$_2$)$_3$-cHx | H | H | H | H |
| 5-46 | H | Me | Me | 2 | —(CH$_2$)$_3$-cHx | H | H | H | H |
| 5-47 | CO$_2$Me | H | Me | 2 | —(CH$_2$)$_3$-cHx | H | H | H | H |
| 5-48 | CO$_2$Et | H | Me | 2 | —(CH$_2$)$_3$-cHx | H | H | H | H |
| 5-49 | H | H | Me | 2 | —(CH$_2$)$_3$-(4-F-cHx) | H | H | H | H |
| 5-50 | H | H | Me | 2 | —(CH$_2$)$_3$-(4-Me-cHx) | H | H | H | H |
| 5-51 | H | H | Me | 2 | —(CH$_2$)$_3$-(4-Et-cHx) | H | H | H | H |
| 5-52 | H | H | Me | 2 | —(CH$_2$)$_3$-(4-CF$_3$-cHx) | H | H | H | H |
| 5-53 | H | H | Me | 2 | —(CH$_2$)$_3$-(4-MeO-cHx) | H | H | H | H |
| 5-54 | H | H | Me | 2 | —(CH$_2$)$_3$-(4-EtO-cHx) | H | H | H | H |
| 5-55 | H | H | Me | 2 | —(CH$_2$)$_3$-(4-MeS-cHx) | H | H | H | H |
| 5-56 | H | H | Me | 2 | —(CH$_2$)$_3$-(4-cHx-cHx) | H | H | H | H |
| 5-57 | H | H | Me | 2 | —(CH$_2$)$_3$-(4-Ph-cHx) | H | H | H | H |
| 5-58 | H | H | Me | 2 | —(CH$_2$)$_3$-Ph | H | H | H | H |
| 5-59 | H | Me | Me | 2 | —(CH$_2$)$_3$-Ph | H | H | H | H |
| 5-60 | CO$_2$Me | H | Me | 2 | —(CH$_2$)$_3$-Ph | H | H | H | H |
| 5-61 | CO$_2$Et | H | Me | 2 | —(CH$_2$)$_3$-Ph | H | H | H | H |
| 5-62 | H | H | Me | 2 | —(CH$_2$)$_3$-(4-F-Ph) | H | H | H | H |
| 5-63 | H | H | Me | 2 | —(CH$_2$)$_3$-(4-Me-Ph) | H | H | H | H |
| 5-64 | H | H | Me | 2 | —(CH$_2$)$_3$-(4-Et-Ph) | H | H | H | H |
| 5-65 | H | H | Me | 2 | —(CH$_2$)$_3$-(4-CF$_3$-Ph) | H | H | H | H |
| 5-66 | H | H | Me | 2 | —(CH$_2$)$_3$-(4-MeO-Ph) | H | H | H | H |
| 5-67 | H | H | Me | 2 | —(CH$_2$)$_3$-(4-EtO-Ph) | H | H | H | H |
| 5-68 | H | H | Me | 2 | —(CH$_2$)$_3$-(4-MeS-Ph) | H | H | H | H |
| 5-69 | H | H | Me | 2 | —(CH$_2$)$_3$-(4-cHx-Ph) | H | H | H | H |
| 5-70 | H | H | Me | 2 | —(CH$_2$)$_3$-(4-Ph-Ph) | H | H | H | H |
| 5-71 | H | H | Me | 2 | —(CH$_2$)$_4$-cHx | H | H | H | H |
| 5-72 | H | Me | Me | 2 | —(CH$_2$)$_4$-cHx | H | H | H | H |
| 5-73 | CO$_2$Me | H | Me | 2 | —(CH$_2$)$_4$-cHx | H | H | H | H |
| 5-74 | CO$_2$Et | H | Me | 2 | —(CH$_2$)$_4$-cHx | H | H | H | H |
| 5-75 | H | H | Me | 2 | —(CH$_2$)$_4$-(4-F-cHx) | H | H | H | H |
| 5-76 | H | H | Me | 2 | —(CH$_2$)$_4$-(4-Me-cHx) | H | H | H | H |
| 5-77 | H | H | Me | 2 | —(CH$_2$)$_4$-(4-Et-cHx) | H | H | H | H |
| 5-78 | H | H | Me | 2 | —(CH$_2$)$_4$-(4-CF$_3$-cHx) | H | H | H | H |
| 5-79 | H | H | Me | 2 | —(CH$_2$)$_4$-(4-MeO-cHx) | H | H | H | H |
| 5-80 | H | H | Me | 2 | —(CH$_2$)$_4$-(4-EtO-cHx) | H | H | H | H |
| 5-81 | H | H | Me | 2 | —(CH$_2$)$_4$-(4-MeS-cHx) | H | H | H | H |
| 5-82 | H | H | Me | 2 | —(CH$_2$)$_4$-(4-cHx-cHx) | H | H | H | H |
| 5-83 | H | H | Me | 2 | —(CH$_2$)$_4$-(4-Ph-cHx) | H | H | H | H |
| 5-84 | H | H | Me | 2 | —(CH$_2$)$_4$-Ph | H | H | H | H |
| 5-85 | H | Me | Me | 2 | —(CH$_2$)$_4$-Ph | H | H | H | H |
| 5-86 | CO$_2$Me | H | Me | 2 | —(CH$_2$)$_4$-Ph | H | H | H | H |
| 5-87 | CO$_2$Et | H | Me | 2 | —(CH$_2$)$_4$-Ph | H | H | H | H |
| 5-88 | H | H | Me | 2 | —(CH$_2$)$_4$-(4-F-Ph) | H | H | H | H |
| 5-89 | H | H | Me | 2 | —(CH$_2$)$_4$-(4-Me-Ph) | H | H | H | H |
| 5-90 | H | H | Me | 2 | —(CH$_2$)$_4$-(4-Et-Ph) | H | H | H | H |
| 5-91 | H | H | Me | 2 | —(CH$_2$)$_4$-(4-CF$_3$-Ph) | H | H | H | H |
| 5-92 | H | H | Me | 2 | —(CH$_2$)$_4$-(4-MeO-Ph) | H | H | H | H |
| 5-93 | H | H | Me | 2 | —(CH$_2$)$_4$-(4-EtO-Ph) | H | H | H | H |
| 5-94 | H | H | Me | 2 | —(CH$_2$)$_4$-(4-MeS-Ph) | H | H | H | H |
| 5-95 | H | H | Me | 2 | —(CH$_2$)$_4$-(4-cHx-Ph) | H | H | H | H |
| 5-96 | H | H | Me | 2 | —(CH$_2$)$_4$-(4-Ph-Ph) | H | H | H | H |
| 5-97 | H | H | Me | 2 | —(CH$_2$)$_5$-cPn | H | H | H | H |
| 5-98 | H | H | Me | 2 | —(CH$_2$)$_5$-cHx | H | H | H | H |
| 5-99 | H | H | Me | 2 | —(CH$_2$)$_5$-cHx | Me | H | H | H |
| 5-100 | H | H | Me | 2 | —(CH$_2$)$_5$-cHx | H | Me | H | H |
| 5-101 | H | H | Me | 2 | —(CH$_2$)$_5$-cHx | F | H | H | H |
| 5-102 | H | H | Me | 2 | —(CH$_2$)$_5$-cHx | H | F | H | H |
| 5-103 | H | Me | Me | 2 | —(CH$_2$)$_5$-cHx | H | H | H | H |
| 5-104 | CO$_2$Me | H | Me | 2 | —(CH$_2$)$_5$-cHx | H | H | H | H |
| 5-105 | CO$_2$Et | H | Me | 2 | —(CH$_2$)$_5$-cHx | H | H | H | H |
| 5-106 | H | H | Me | 2 | —(CH$_2$)$_5$-(3-F-cHx) | H | H | H | H |
| 5-107 | H | H | Me | 2 | —(CH$_2$)$_5$-(4-F-cHx) | H | H | H | H |
| 5-108 | H | H | Me | 2 | —(CH$_2$)$_5$-(4-Cl-cHx) | H | H | H | H |
| 5-109 | H | H | Me | 2 | —(CH$_2$)$_5$-(4-Br-cHx) | H | H | H | H |
| 5-110 | H | H | Me | 2 | —(CH$_2$)$_5$-(3-Me-cHx) | H | H | H | H |
| 5-111 | H | H | Me | 2 | —(CH$_2$)$_5$-(4-Me-cHx) | H | H | H | H |
| 5-112 | H | H | Me | 2 | —(CH$_2$)$_5$-(3-Et-cHx) | H | H | H | H |
| 5-113 | H | H | Me | 2 | —(CH$_2$)$_5$-(4-Et-cHx) | H | H | H | H |
| 5-114 | H | H | Me | 2 | —(CH$_2$)$_5$-(3-Pr-cHx) | H | H | H | H |
| 5-115 | H | H | Me | 2 | —(CH$_2$)$_5$-(4-Pr-cHx) | H | H | H | H |

TABLE 5-continued

| | | | | | | | | | |
|---|---|---|---|---|---|---|---|---|---|
| 5-116 | H | H | Me | 2 | —(CH$_2$)$_5$-(4-iPr-cHx) | H | H | H | H |
| 5-117 | H | H | Me | 2 | —(CH$_2$)$_5$-(3-Bu-cHx) | H | H | H | H |
| 5-118 | H | H | Me | 2 | —(CH$_2$)$_5$-(4-Bu-cHx) | H | H | H | H |
| 5-119 | H | H | Me | 2 | —(CH$_2$)$_5$-(3-CF$_3$-cHx) | H | H | H | H |
| 5-120 | H | H | Me | 2 | —(CH$_2$)$_5$-(4-CF$_3$-cHx) | H | H | H | H |
| 5-121 | H | H | Me | 2 | —(CH$_2$)$_5$-(3-MeO-cHx) | H | H | H | H |
| 5-122 | H | H | Me | 2 | —(CH$_2$)$_5$-(4-MeO-cHx) | H | H | H | H |
| 5-123 | H | H | Me | 2 | —(CH$_2$)$_5$-(3-EtO-cHx) | H | H | H | H |
| 5-124 | H | H | Me | 2 | —(CH$_2$)$_5$-(4-EtO-cHx) | H | H | H | H |
| 5-125 | H | H | Me | 2 | —(CH$_2$)$_5$-(3-PrO-cHx) | H | H | H | H |
| 5-126 | H | H | Me | 2 | —(CH$_2$)$_5$-(4-PrO-cHx) | H | H | H | H |
| 5-127 | H | H | Me | 2 | —(CH$_2$)$_5$-(3-iPrO-cHx) | H | H | H | H |
| 5-128 | H | H | Me | 2 | —(CH$_2$)$_5$-(4-iPrO-cHx) | H | H | H | H |
| 5-129 | H | H | Me | 2 | —(CH$_2$)$_5$-[3-(2-Et-PrO)-cHx] | H | H | H | H |
| 5-130 | H | H | Me | 2 | —(CH$_2$)$_5$-[4-(2-Et-PrO)-cHx] | H | H | H | H |
| 5-131 | H | H | Me | 2 | —(CH$_2$)$_5$-(3-iBuO-cHx) | H | H | H | H |
| 5-132 | H | H | Me | 2 | —(CH$_2$)$_5$-(4-iBuO-cHx) | H | H | H | H |
| 5-133 | H | H | Me | 2 | —(CH$_2$)$_5$-(3-MeS-cHx) | H | H | H | H |
| 5-134 | H | H | Me | 2 | —(CH$_2$)$_5$-(4-MeS-cHx) | H | H | H | H |
| 5-135 | H | H | Me | 2 | —(CH$_2$)$_5$-(3-EtS-cHx) | H | H | H | H |
| 5-136 | H | H | Me | 2 | —(CH$_2$)$_5$-(4-EtS-cHx) | H | H | H | H |
| 5-137 | H | H | Me | 2 | —(CH$_2$)$_5$-(3-PrS-cHx) | H | H | H | H |
| 5-138 | H | H | Me | 2 | —(CH$_2$)$_5$-(4-PrS-cHx) | H | H | H | H |
| 5-139 | H | H | Me | 2 | —(CH$_2$)$_5$-(3-iPrS-cHx) | H | H | H | H |
| 5-140 | H | H | Me | 2 | —(CH$_2$)$_5$-(4-iPrS-cHx) | H | H | H | H |
| 5-141 | H | H | Me | 2 | —(CH$_2$)$_5$-[3-(2-Et-PrS)-cHx] | H | H | H | H |
| 5-142 | H | H | Me | 2 | —(CH$_2$)$_5$-[4-(2-Et-PrS)-cHx] | H | H | H | H |
| 5-143 | H | H | Me | 2 | —(CH$_2$)$_5$-(3-iBuS-cHx) | H | H | H | H |
| 5-144 | H | H | Me | 2 | —(CH$_2$)$_5$-(4-iBuS-cHx) | H | H | H | H |
| 5-145 | H | H | Me | 2 | —(CH$_2$)$_5$-(3-cHx-cHx) | H | H | H | H |
| 5-146 | H | H | Me | 2 | —(CH$_2$)$_5$-(4-cHx-cHx) | H | H | H | H |
| 5-147 | H | H | Me | 2 | —(CH$_2$)$_5$-(3-Ph-cHx) | H | H | H | H |
| 5-148 | H | H | Me | 2 | —(CH$_2$)$_5$-(4-Ph-cHx) | H | H | H | H |
| 5-149 | H | H | Me | 2 | —(CH$_2$)$_5$-(2,4-diMe-cHx) | H | H | H | H |
| 5-150 | H | H | Me | 2 | —(CH$_2$)$_5$-(3,4-diMe-cHx) | H | H | H | H |
| 5-151 | H | H | Me | 2 | —(CH$_2$)$_5$-(3,5-diMe-cHx) | H | H | H | H |
| 5-152 | H | H | Me | 2 | —(CH$_2$)$_5$-Ph | H | H | H | H |
| 5-153 | H | H | Me | 2 | —(CH$_2$)$_5$-Ph | Me | H | H | H |
| 5-154 | H | H | Me | 2 | —(CH$_2$)$_5$-Ph | H | Me | H | H |
| 5-155 | H | H | Me | 2 | —(CH$_2$)$_5$-Ph | F | H | H | H |
| 5-156 | H | H | Me | 2 | —(CH$_2$)$_5$-Ph | H | F | H | H |
| 5-157 | H | Me | Me | 2 | —(CH$_2$)$_5$-Ph | H | H | H | H |
| 5-158 | CO$_2$Me | H | Me | 2 | —(CH$_2$)$_5$-Ph | H | H | H | H |
| 5-159 | CO$_2$Et | H | Me | 2 | —(CH$_2$)$_5$-Ph | H | H | H | H |
| 5-160 | H | H | Me | 2 | —(CH$_2$)$_5$-(3-F-Ph) | H | H | H | H |
| 5-161 | H | H | Me | 2 | —(CH$_2$)$_5$-(4-F-Ph) | H | H | H | H |
| 5-162 | H | H | Me | 2 | —(CH$_2$)$_5$-(4-Cl-Ph) | H | H | H | H |
| 5-163 | H | H | Me | 2 | —(CH$_2$)$_5$-(4-Br-Ph) | H | H | H | H |
| 5-164 | H | H | Me | 2 | —(CH$_2$)$_5$-(3-Me-Ph) | H | H | H | H |
| 5-165 | H | H | Me | 2 | —(CH$_2$)$_5$-(4-Me-Ph) | H | H | H | H |
| 5-166 | H | H | Me | 2 | —(CH$_2$)$_5$-(3-Et-Ph) | H | H | H | H |
| 5-167 | H | H | Me | 2 | —(CH$_2$)$_5$-(4-Et-Ph) | H | H | H | H |
| 5-168 | H | H | Me | 2 | —(CH$_2$)$_5$-(3-Pr-Ph) | H | H | H | H |
| 5-169 | H | H | Me | 2 | —(CH$_2$)$_5$-(4-Pr-Ph) | H | H | H | H |
| 5-170 | H | H | Me | 2 | —(CH$_2$)$_5$-(3-iPr-Ph) | H | H | H | H |
| 5-171 | H | H | Me | 2 | —(CH$_2$)$_5$-(4-iPr-Ph) | H | H | H | H |
| 5-172 | H | H | Me | 2 | —(CH$_2$)$_5$-(3-Bu-Ph) | H | H | H | H |
| 5-173 | H | H | Me | 2 | —(CH$_2$)$_5$-(4-Bu-Ph) | H | H | H | H |
| 5-174 | H | H | Me | 2 | —(CH$_2$)$_5$-(3-CF$_3$-Ph) | H | H | H | H |
| 5-175 | H | H | Me | 2 | —(CH$_2$)$_5$-(4-CF$_3$-Ph) | H | H | H | H |
| 5-176 | H | H | Me | 2 | —(CH$_2$)$_5$-(3-MeO-Ph) | H | H | H | H |
| 5-177 | H | H | Me | 2 | —(CH$_2$)$_5$-(4-MeO-Ph) | H | H | H | H |
| 5-178 | H | H | Me | 2 | —(CH$_2$)$_5$-(3-EtO-Ph) | H | H | H | H |
| 5-179 | H | H | Me | 2 | —(CH$_2$)$_5$-(4-EtO-Ph) | H | H | H | H |
| 5-180 | H | H | Me | 2 | —(CH$_2$)$_5$-(3-PrO-Ph) | H | H | H | H |
| 5-181 | H | H | Me | 2 | —(CH$_2$)$_5$-(4-PrO-Ph) | H | H | H | H |
| 5-182 | H | H | Me | 2 | —(CH$_2$)$_5$-(3-iPrO-Ph) | H | H | H | H |
| 5-183 | H | H | Me | 2 | —(CH$_2$)$_5$-(4-iPrO-Ph) | H | H | H | H |
| 5-184 | H | H | Me | 2 | —(CH$_2$)$_5$-[3-(2-Et-PrO)-Ph] | H | H | H | H |
| 5-185 | H | H | Me | 2 | —(CH$_2$)$_5$-[4-(2-Et-PrO)-Ph] | H | H | H | H |
| 5-186 | H | H | Me | 2 | —(CH$_2$)$_5$-(3-iBuO-Ph) | H | H | H | H |
| 5-187 | H | H | Me | 2 | —(CH$_2$)$_5$-(4-iBuO-Ph) | H | H | H | H |
| 5-188 | H | H | Me | 2 | —(CH$_2$)$_5$-(3-MeS-Ph) | H | H | H | H |
| 5-189 | H | H | Me | 2 | —(CH$_2$)$_5$-(4-MeS-Ph) | H | H | H | H |
| 5-190 | H | H | Me | 2 | —(CH$_2$)$_5$-(3-EtS-Ph) | H | H | H | H |
| 5-191 | H | H | Me | 2 | —(CH$_2$)$_5$-(4-EtS-Ph) | H | H | H | H |
| 5-192 | H | H | Me | 2 | —(CH$_2$)$_5$-(3-PrS-Ph) | H | H | H | H |
| 5-193 | H | H | Me | 2 | —(CH$_2$)$_5$-(4-PrS-Ph) | H | H | H | H |
| 5-194 | H | H | Me | 2 | —(CH$_2$)$_5$-(3-iPrS-Ph) | H | H | H | H |
| 5-195 | H | H | Me | 2 | —(CH$_2$)$_5$-(4-iPrS-Ph) | H | H | H | H |

TABLE 5-continued

| | | | | | | | | | |
|---|---|---|---|---|---|---|---|---|---|
| 5-196 | H | H | Me | 2 | —(CH$_2$)$_5$-[3-(2-Et-PrS)-Ph] | H | H | H | H |
| 5-197 | H | H | Me | 2 | —(CH$_2$)$_5$-[4-(2-Et-PrS)-Ph] | H | H | H | H |
| 5-198 | H | H | Me | 2 | —(CH$_2$)$_5$-(3-iBuS-Ph) | H | H | H | H |
| 5-199 | H | H | Me | 2 | —(CH$_2$)$_5$-(4-iBuS-Ph) | H | H | H | H |
| 5-200 | H | H | Me | 2 | —(CH$_2$)$_5$-(3-cHx-Ph) | H | H | H | H |
| 5-201 | H | H | Me | 2 | —(CH$_2$)$_5$-(4-cHx-Ph) | H | H | H | H |
| 5-202 | H | H | Me | 2 | —(CH$_2$)$_5$-(3-Ph-Ph) | H | H | H | H |
| 5-203 | H | H | Me | 2 | —(CH$_2$)$_5$-(4-Ph-Ph) | H | H | H | H |
| 5-204 | H | H | Me | 2 | —(CH$_2$)$_5$-(2,4-diMe-Ph) | H | H | H | H |
| 5-205 | H | H | Me | 2 | —(CH$_2$)$_5$-(3,4-diMe-Ph) | H | H | H | H |
| 5-206 | H | H | Me | 2 | —(CH$_2$)$_5$-(3,5-diMe-Ph) | H | H | H | H |
| 5-207 | H | H | Me | 2 | —(CH$_2$)$_5$-Np (1) | H | H | H | H |
| 5-208 | H | H | Me | 2 | —(CH$_2$)$_5$-Np (2) | H | H | H | H |
| 5-209 | H | H | Me | 2 | —(CH$_2$)$_6$-cPn | H | H | H | H |
| 5-210 | H | H | Me | 2 | —(CH$_2$)$_6$-cHx | H | H | H | H |
| 5-211 | H | H | Me | 2 | —(CH$_2$)$_6$-cHx | Me | H | H | H |
| 5-212 | H | H | Me | 2 | —(CH$_2$)$_6$-cHx | H | Me | H | H |
| 5-213 | H | H | Me | 2 | —(CH$_2$)$_6$-cHx | F | H | H | H |
| 5-214 | H | H | Me | 2 | —(CH$_2$)$_6$-cHx | H | F | H | H |
| 5-215 | H | Me | Me | 2 | —(CH$_2$)$_6$-cHx | H | H | H | H |
| 5-216 | CO$_2$Me | H | Me | 2 | —(CH$_2$)$_6$-cHx | H | H | H | H |
| 5-217 | CO$_2$Et | H | Me | 2 | —(CH$_2$)$_6$-cHx | H | H | H | H |
| 5-218 | H | H | Me | 2 | —(CH$_2$)$_6$-(3-F-cHx) | H | H | H | H |
| 5-219 | H | H | Me | 2 | —(CH$_2$)$_6$-(4-F-cHx) | H | H | H | H |
| 5-220 | H | H | Me | 2 | —(CH$_2$)$_6$-(4-Cl-cHx) | H | H | H | H |
| 5-221 | H | H | Me | 2 | —(CH$_2$)$_6$-(4-Br-cHx) | H | H | H | H |
| 5-222 | H | H | Me | 2 | —(CH$_2$)$_6$-(3-Me-cHx) | H | H | H | H |
| 5-223 | H | H | Me | 2 | —(CH$_2$)$_6$-(4-Me-cHx) | H | H | H | H |
| 5-224 | H | H | Me | 2 | —(CH$_2$)$_6$-(3-Et-cHx) | H | H | H | H |
| 5-225 | H | H | Me | 2 | —(CH$_2$)$_6$-(4-Et-cHx) | H | H | H | H |
| 5-226 | H | H | Me | 2 | —(CH$_2$)$_6$-(3-Pr-cHx) | H | H | H | H |
| 5-227 | H | H | Me | 2 | —(CH$_2$)$_6$-(4-Pr-cHx) | H | H | H | H |
| 5-228 | H | H | Me | 2 | —(CH$_2$)$_6$-(4-iPr-cHx) | H | H | H | H |
| 5-229 | H | H | Me | 2 | —(CH$_2$)$_6$-(3-Bu-cHx) | H | H | H | H |
| 5-230 | H | H | Me | 2 | —(CH$_2$)$_6$-(4-Bu-cHx) | H | H | H | H |
| 5-231 | H | H | Me | 2 | —(CH$_2$)$_6$-(3-CF$_3$-cHx) | H | H | H | H |
| 5-232 | H | H | Me | 2 | —(CH$_2$)$_6$-(4-CF$_3$-cHx) | H | H | H | H |
| 5-233 | H | H | Me | 2 | —(CH$_2$)$_6$-(3-MeO-cHx) | H | H | H | H |
| 5-234 | H | H | Me | 2 | —(CH$_2$)$_6$-(4-MeO-cHx) | H | H | H | H |
| 5-235 | H | H | Me | 2 | —(CH$_2$)$_6$-(3-EtO-cHx) | H | H | H | H |
| 5-236 | H | H | Me | 2 | —(CH$_2$)$_6$-(4-EtO-cHx) | H | H | H | H |
| 5-237 | H | H | Me | 2 | —(CH$_2$)$_6$-(3-PrO-cHx) | H | H | H | H |
| 5-238 | H | H | Me | 2 | —(CH$_2$)$_6$-(4-PrO-cHx) | H | H | H | H |
| 5-239 | H | H | Me | 2 | —(CH$_2$)$_6$-(3-iPrO-cHx) | H | H | H | H |
| 5-240 | H | H | Me | 2 | —(CH$_2$)$_6$-(4-iPrO-cHx) | H | H | H | H |
| 5-241 | H | H | Me | 2 | —(CH$_2$)$_6$-[3-(2-Et-PrO)-cHx] | H | H | H | H |
| 5-242 | H | H | Me | 2 | —(CH$_2$)$_6$-[4-(2-Et-PrO)-cHx] | H | H | H | H |
| 5-243 | H | H | Me | 2 | —(CH$_2$)$_6$-(3-iBuO-cHx) | H | H | H | H |
| 5-244 | H | H | Me | 2 | —(CH$_2$)$_6$-(4-iBuO-cHx) | H | H | H | H |
| 5-245 | H | H | Me | 2 | —(CH$_2$)$_6$-(3-MeS-cHx) | H | H | H | H |
| 5-246 | H | H | Me | 2 | —(CH$_2$)$_6$-(4-MeS-cHx) | H | H | H | H |
| 5-247 | H | H | Me | 2 | —(CH$_2$)$_6$-(3-EtS-cHx) | H | H | H | H |
| 5-248 | H | H | Me | 2 | —(CH$_2$)$_6$-(4-EtS-cHx) | H | H | H | H |
| 5-249 | H | H | Me | 2 | —(CH$_2$)$_6$-(3-PrS-cHx) | H | H | H | H |
| 5-250 | H | H | Me | 2 | —(CH$_2$)$_6$-(4-PrS-cHx) | H | H | H | H |
| 5-251 | H | H | Me | 2 | —(CH$_2$)$_6$-(3-iPrS-cHx) | H | H | H | H |
| 5-252 | H | H | Me | 2 | —(CH$_2$)$_6$-(4-iPrS-cHx) | H | H | H | H |
| 5-253 | H | H | Me | 2 | —(CH$_2$)$_6$-[3-(2-Et-PrS)-cHx] | H | H | H | H |
| 5-254 | H | H | Me | 2 | —(CH$_2$)$_6$-[4-(2-Et-PrS)-cHx] | H | H | H | H |
| 5-255 | H | H | Me | 2 | —(CH$_2$)$_6$-(3-iBuS-cHx) | H | H | H | H |
| 5-256 | H | H | Me | 2 | —(CH$_2$)$_6$-(4-iBuS-cHx) | H | H | H | H |
| 5-257 | H | H | Me | 2 | —(CH$_2$)$_6$-(3-cHx-cHx) | H | H | H | H |
| 5-258 | H | H | Me | 2 | —(CH$_2$)$_6$-(4-cHx-cHx) | H | H | H | H |
| 5-259 | H | H | Me | 2 | —(CH$_2$)$_6$-(3-Ph-cHx) | H | H | H | H |
| 5-260 | H | H | Me | 2 | —(CH$_2$)$_6$-(4-Ph-cHx) | H | H | H | H |
| 5-261 | H | H | Me | 2 | —(CH$_2$)$_6$-(2,4-diMe-cHx) | H | H | H | H |
| 5-262 | H | H | Me | 2 | —(CH$_2$)$_6$-(3,4-diMe-cHx) | H | H | H | H |
| 5-263 | H | H | Me | 2 | —(CH$_2$)$_6$-(3,5-diMe-cHx) | H | H | H | H |
| 5-264 | H | H | Me | 2 | —(CH$_2$)$_6$-Ph | H | H | H | H |
| 5-265 | H | H | Me | 2 | —(CH$_2$)$_6$-Ph | Me | H | H | H |
| 5-266 | H | H | Me | 2 | —(CH$_2$)$_6$-Ph | H | Me | H | H |
| 5-267 | H | H | Me | 2 | —(CH$_2$)$_6$-Ph | F | H | H | H |
| 5-268 | H | H | Me | 2 | —(CH$_2$)$_6$-Ph | H | F | H | H |
| 5-269 | H | Me | Me | 2 | —(CH$_2$)$_6$-Ph | H | H | H | H |
| 5-270 | CO$_2$Me | H | Me | 2 | —(CH$_2$)$_6$-Ph | H | H | H | H |
| 5-271 | CO$_2$Et | H | Me | 2 | —(CH$_2$)$_6$-Ph | H | H | H | H |
| 5-272 | H | H | Me | 2 | —(CH$_2$)$_6$-(3-F-Ph) | H | H | H | H |
| 5-273 | H | H | Me | 2 | —(CH$_2$)$_6$-(4-F-Ph) | H | H | H | H |
| 5-274 | H | H | Me | 2 | —(CH$_2$)$_6$-(4-Cl-Ph) | H | H | H | H |
| 5-275 | H | H | Me | 2 | —(CH$_2$)$_6$-(4-Br-Ph) | H | H | H | H |

TABLE 5-continued

| | | | | | | | | | |
|---|---|---|---|---|---|---|---|---|---|
| 5-276 | H | H | Me | 2 | —(CH$_2$)$_6$-(3-Me-Ph) | H | H | H | H |
| 5-277 | H | H | Me | 2 | —(CH$_2$)$_6$-(4-Me-Ph) | H | H | H | H |
| 5-278 | H | H | Me | 2 | —(CH$_2$)$_6$-(3-Et-Ph) | H | H | H | H |
| 5-279 | H | H | Me | 2 | —(CH$_2$)$_6$-(4-Et-Ph) | H | H | H | H |
| 5-280 | H | H | Me | 2 | —(CH$_2$)$_6$-(3-Pr-Ph) | H | H | H | H |
| 5-281 | H | H | Me | 2 | —(CH$_2$)$_6$-(4-Pr-Ph) | H | H | H | H |
| 5-282 | H | H | Me | 2 | —(CH$_2$)$_6$-(3-iPr-Ph) | H | H | H | H |
| 5-283 | H | H | Me | 2 | —(CH$_2$)$_6$-(4-iPr-Ph) | H | H | H | H |
| 5-284 | H | H | Me | 2 | —(CH$_2$)$_6$-(3-Bu-Ph) | H | H | H | H |
| 5-285 | H | H | Me | 2 | —(CH$_2$)$_6$-(4-Bu-Ph) | H | H | H | H |
| 5-286 | H | H | Me | 2 | —(CH$_2$)$_6$-(3-CF$_3$-Ph) | H | H | H | H |
| 5-287 | H | H | Me | 2 | —(CH$_2$)$_6$-(4-CF$_3$-Ph) | H | H | H | H |
| 5-288 | H | H | Me | 2 | —(CH$_2$)$_6$-(3-MeO-Ph) | H | H | H | H |
| 5-289 | H | H | Me | 2 | —(CH$_2$)$_6$-(4-MeO-Ph) | H | H | H | H |
| 5-290 | H | H | Me | 2 | —(CH$_2$)$_6$-(3-EtO-Ph) | H | H | H | H |
| 5-291 | H | H | Me | 2 | —(CH$_2$)$_6$-(4-EtO-Ph) | H | H | H | H |
| 5-292 | H | H | Me | 2 | —(CH$_2$)$_6$-(3-PrO-Ph) | H | H | H | H |
| 5-293 | H | H | Me | 2 | —(CH$_2$)$_6$-(4-PrO-Ph) | H | H | H | H |
| 5-294 | H | H | Me | 2 | —(CH$_2$)$_6$-(3-iPrO-Ph) | H | H | H | H |
| 5-295 | H | H | Me | 2 | —(CH$_2$)$_6$-(4-iPrO-Ph) | H | H | H | H |
| 5-296 | H | H | Me | 2 | —(CH$_2$)$_6$-[3-(2-Et-PrO)-Ph] | H | H | H | H |
| 5-297 | H | H | Me | 2 | —(CH$_2$)$_6$-[4-(2-Et-PrO)-Ph] | H | H | H | H |
| 5-298 | H | H | Me | 2 | —(CH$_2$)$_6$-(3-iBuO-Ph) | H | H | H | H |
| 5-299 | H | H | Me | 2 | —(CH$_2$)$_6$-(4-iBuO-Ph) | H | H | H | H |
| 5-300 | H | H | Me | 2 | —(CH$_2$)$_6$-(3-MeS-Ph) | H | H | H | H |
| 5-301 | H | H | Me | 2 | —(CH$_2$)$_6$-(4-MeS-Ph) | H | H | H | H |
| 5-302 | H | H | Me | 2 | —(CH$_2$)$_6$-(3-EtS-Ph) | H | H | H | H |
| 5-303 | H | H | Me | 2 | —(CH$_2$)$_6$-(4-EtS-Ph) | H | H | H | H |
| 5-304 | H | H | Me | 2 | —(CH$_2$)$_6$-(3-PrS-Ph) | H | H | H | H |
| 5-305 | H | H | Me | 2 | —(CH$_2$)$_6$-(4-PrS-Ph) | H | H | H | H |
| 5-306 | H | H | Me | 2 | —(CH$_2$)$_6$-(3-iPrS-Ph) | H | H | H | H |
| 5-307 | H | H | Me | 2 | —(CH$_2$)$_6$-(4-iPrS-Ph) | H | H | H | H |
| 5-308 | H | H | Me | 2 | —(CH$_2$)$_6$-[3-(2-Et-PrS)-Ph] | H | H | H | H |
| 5-309 | H | H | Me | 2 | —(CH$_2$)$_6$-[4-(2-Et-PrS)-Ph] | H | H | H | H |
| 5-310 | H | H | Me | 2 | —(CH$_2$)$_6$-(3-iBuS-Ph) | H | H | H | H |
| 5-311 | H | H | Me | 2 | —(CH$_2$)$_6$-(4-iBuS-Ph) | H | H | H | H |
| 5-312 | H | H | Me | 2 | —(CH$_2$)$_6$-(3-cHx-Ph) | H | H | H | H |
| 5-313 | H | H | Me | 2 | —(CH$_2$)$_6$-(4-cHx-Ph) | H | H | H | H |
| 5-314 | H | H | Me | 2 | —(CH$_2$)$_6$-(3-Ph-Ph) | H | H | H | H |
| 5-315 | H | H | Me | 2 | —(CH$_2$)$_6$-(4-Ph-Ph) | H | H | H | H |
| 5-316 | H | H | Me | 2 | —(CH$_2$)$_6$-(2,4-diMe-Ph) | H | H | H | H |
| 5-317 | H | H | Me | 2 | —(CH$_2$)$_6$-(3,4-diMe-Ph) | H | H | H | H |
| 5-318 | H | H | Me | 2 | —(CH$_2$)$_6$-(3,5-diMe-Ph) | H | H | H | H |
| 5-319 | H | H | Me | 2 | —(CH$_2$)$_6$-Np (1) | H | H | H | H |
| 5-320 | H | H | Me | 2 | —(CH$_2$)$_6$-Np (2) | H | H | H | H |
| 5-321 | H | H | Me | 2 | —(CH$_2$)$_7$-cHx | H | H | H | H |
| 5-322 | H | H | Me | 2 | —(CH$_2$)$_7$-cHx | H | H | H | H |
| 5-323 | CO$_2$Me | H | Me | 2 | —(CH$_2$)$_7$-cHx | H | H | H | H |
| 5-324 | CO$_2$Et | H | Me | 2 | —(CH$_2$)$_7$-cHx | H | H | H | H |
| 5-325 | H | H | Me | 2 | —(CH$_2$)$_7$-(4-F-cHx) | H | H | H | H |
| 5-326 | H | H | Me | 2 | —(CH$_2$)$_7$-(4-Me-cHx) | H | H | H | H |
| 5-327 | H | H | Me | 2 | —(CH$_2$)$_7$-(4-Et-cHx) | H | H | H | H |
| 5-328 | H | H | Me | 2 | —(CH$_2$)$_7$-(4-CF$_3$cHx) | H | H | H | H |
| 5-329 | H | H | Me | 2 | —(CH$_2$)$_7$-(4-MeO-cHx) | H | H | H | H |
| 5-330 | H | H | Me | 2 | —(CH$_2$)$_7$-(4-EtO-cHx) | H | H | H | H |
| 5-331 | H | H | Me | 2 | —(CH$_2$)$_7$-(4-MeS-cHx) | H | H | H | H |
| 5-332 | H | H | Me | 2 | —(CH$_2$)$_7$-(4-cHx-cHx) | H | H | H | H |
| 5-333 | H | H | Me | 2 | —(CH$_2$)$_7$-(4-Ph-cHx) | H | H | H | H |
| 5-334 | H | H | Me | 2 | —(CH$_2$)$_7$-Ph | H | H | H | H |
| 5-335 | H | Me | Me | 2 | —(CH$_2$)$_7$-Ph | H | H | H | H |
| 5-336 | CO$_2$Me | H | Me | 2 | —(CH$_2$)$_7$-Ph | H | H | H | H |
| 5-337 | CO$_2$Et | H | Me | 2 | —(CH$_2$)$_7$-Ph | H | H | H | H |
| 5-338 | H | H | Me | 2 | —(CH$_2$)$_7$-(4-F-Ph) | H | H | H | H |
| 5-339 | H | H | Me | 2 | —(CH$_2$)$_7$-(4-Me-Ph) | H | H | H | H |
| 5-340 | H | H | Me | 2 | —(CH$_2$)$_7$-(4-Et-Ph) | H | H | H | H |
| 5-341 | H | H | Me | 2 | —(CH$_2$)$_7$-(4-CF$_3$Ph) | H | H | H | H |
| 5-342 | H | H | Me | 2 | —(CH$_2$)$_7$-(4-MeO-Ph) | H | H | H | H |
| 5-343 | H | H | Me | 2 | —(CH$_2$)$_7$-(4-EtO-Ph) | H | H | H | H |
| 5-344 | H | H | Me | 2 | —(CH$_2$)$_7$-(4-MeS-Ph) | H | H | H | H |
| 5-345 | H | H | Me | 2 | —(CH$_2$)$_7$-(4-cHx-Ph) | H | H | H | H |
| 5-346 | H | H | Me | 2 | —(CH$_2$)$_7$-(4-Ph-Ph) | H | H | H | H |
| 5-347 | H | H | Me | 2 | —(CH$_2$)$_8$-cHx | H | H | H | H |
| 5-348 | H | Me | Me | 2 | —(CH$_2$)$_8$-cHx | H | H | H | H |
| 5-349 | CO$_2$Me | H | Me | 2 | —(CH$_2$)$_8$-cHx | H | H | H | H |
| 5-350 | CO$_2$Et | H | Me | 2 | —(CH$_2$)$_8$-cHx | H | H | H | H |
| 5-351 | H | H | Me | 2 | —(CH$_2$)$_8$-(4-F-cHx) | H | H | H | H |
| 5-352 | H | H | Me | 2 | —(CH$_2$)$_8$-(4-Me-cHx) | H | H | H | H |
| 5-353 | H | H | Me | 2 | —(CH$_2$)$_8$-(4-Et-cHx) | H | H | H | H |
| 5-354 | H | H | Me | 2 | —(CH$_2$)$_8$-(4-CF$_3$-cHx) | H | H | H | H |
| 5-355 | H | H | Me | 2 | —(CH$_2$)$_8$-(4-MeO-cHx) | H | H | H | H |

TABLE 5-continued

| | | | | | | | | | |
|---|---|---|---|---|---|---|---|---|---|
| 5-356 | H | H | Me | 2 | —(CH$_2$)$_8$-(4-EtO-cHx) | H | H | H | H |
| 5-357 | H | H | Me | 2 | —(CH$_2$)$_8$-(4-MeS-cHx) | H | H | H | H |
| 5-358 | H | H | Me | 2 | —(CH$_2$)$_8$-(4-cHx-cHx) | H | H | H | H |
| 5-359 | H | H | Me | 2 | —(CH$_2$)$_8$-(4-Ph-cHx) | H | H | H | H |
| 5-360 | H | H | Me | 2 | —(CH$_2$)$_8$-Ph | H | H | H | H |
| 5-361 | H | Me | Me | 2 | —(CH$_2$)$_8$-Ph | H | H | H | H |
| 5-362 | CO$_2$Me | H | Me | 2 | —(CH$_2$)$_8$-Ph | H | H | H | H |
| 5-363 | CO$_2$Et | H | Me | 2 | —(CH$_2$)$_8$-Ph | H | H | H | H |
| 5-364 | H | H | Me | 2 | —(CH$_2$)$_8$-(4-F-Ph) | H | H | H | H |
| 5-365 | H | H | Me | 2 | —(CH$_2$)$_8$-(4-Me-Ph) | H | H | H | H |
| 5-366 | H | H | Me | 2 | —(CH$_2$)$_8$-(4-Et-Ph) | H | H | H | H |
| 5-367 | H | H | Me | 2 | —(CH$_2$)$_8$-(4-CF$_3$Ph) | H | H | H | H |
| 5-368 | H | H | Me | 2 | —(CH$_2$)$_8$-(4-MeO-Ph) | H | H | H | H |
| 5-369 | H | H | Me | 2 | —(CH$_2$)$_8$-(4-EtO-Ph) | H | H | H | H |
| 5-370 | H | H | Me | 2 | —(CH$_2$)$_8$-(4-MeS-Ph) | H | H | H | H |
| 5-371 | H | H | Me | 2 | —(CH$_2$)$_8$-(4-cHx-Ph) | H | H | H | H |
| 5-372 | H | H | Me | 2 | —(CH$_2$)$_8$-(4-Ph-Ph) | H | H | H | H |
| 5-373 | H | H | Me | 2 | —(CH$_2$)$_3$-O-cHx | H | H | H | H |
| 5-374 | H | Me | Me | 2 | —(CH$_2$)$_3$-O-cHx | H | H | H | H |
| 5-375 | CO$_2$Me | H | Me | 2 | —(CH$_2$)$_3$-O-cHx | H | H | H | H |
| 5-376 | CO$_2$Et | H | Me | 2 | —(CH$_2$)$_3$-O-cHx | H | H | H | H |
| 5-377 | H | H | Me | 2 | —(CH$_2$)$_3$-O-(4-F-cHx) | H | H | H | H |
| 5-378 | H | H | Me | 2 | —(CH$_2$)$_3$-O-(4-Me-cHx) | H | H | H | H |
| 5-379 | H | H | Me | 2 | —(CH$_2$)$_3$-O-(4-Et-cHx) | H | H | H | H |
| 5-380 | H | H | Me | 2 | —(CH$_2$)$_3$-O-(4-CF$_3$-cHx) | H | H | H | H |
| 5-381 | H | H | Me | 2 | —(CH$_2$)$_3$-O-(4-MeO-cHx) | H | H | H | H |
| 5-382 | H | H | Me | 2 | —(CH$_2$)$_3$-O-(4-EtO-cHx) | H | H | H | H |
| 5-383 | H | H | Me | 2 | —(CH$_2$)$_3$-O-(4-MeS-cHx) | H | H | H | H |
| 5-384 | H | H | Me | 2 | —(CH$_2$)$_3$-O-(4-cHx-cHx) | H | H | H | H |
| 5-385 | H | H | Me | 2 | —(CH$_2$)$_3$-O-(4-Ph-cHx) | H | H | H | H |
| 5-386 | H | H | Me | 2 | —(CH$_2$)$_3$-O-Ph | H | H | H | H |
| 5-387 | H | Me | Me | 2 | —(CH$_2$)$_3$-O-Ph | H | H | H | H |
| 5-388 | CO$_2$Me | H | Me | 2 | —(CH$_2$)$_3$-O-Ph | H | H | H | H |
| 5-389 | CO$_2$Et | H | Me | 2 | —(CH$_2$)$_3$-O-Ph | H | H | H | H |
| 5-390 | H | H | Me | 2 | —(CH$_2$)$_3$-(4-F-Ph) | H | H | H | H |
| 5-391 | H | H | Me | 2 | —(CH$_2$)$_3$-O-(4-Me-Ph) | H | H | H | H |
| 5-392 | H | H | Me | 2 | —(CH$_2$)$_3$-O-(4-Et-Ph) | H | H | H | H |
| 5-393 | H | H | Me | 2 | —(CH$_2$)$_3$-O-(4-CF$_3$Ph) | H | H | H | H |
| 5-394 | H | H | Me | 2 | —(CH$_2$)$_3$-O-(4-MeO-Ph) | H | H | H | H |
| 5-395 | H | H | Me | 2 | —(CH$_2$)$_3$-O-(4-EtO-Ph) | H | H | H | H |
| 5-396 | H | H | Me | 2 | —(CH$_2$)$_3$-O-(4-MeS-Ph) | H | H | H | H |
| 5-397 | H | H | Me | 2 | —(CH$_2$)$_3$-O-(4-cHx-Ph) | H | H | H | H |
| 5-398 | H | H | Me | 2 | —(CH$_2$)$_3$-O-(4-Ph-Ph) | H | H | H | H |
| 5-399 | H | H | Me | 2 | —(CH$_2$)$_4$-O-cPn | H | H | H | H |
| 5-400 | H | H | Me | 2 | —(CH$_2$)$_4$-O-cHx | H | H | H | H |
| 5-401 | H | H | Me | 2 | —(CH$_2$)$_4$-O-cHx | Me | H | H | H |
| 5-402 | H | H | Me | 2 | —(CH$_2$)$_4$-O-cHx | H | Me | H | H |
| 5-403 | H | H | Me | 2 | —(CH$_2$)$_4$-O-cHx | F | H | H | H |
| 5-404 | H | H | Me | 2 | —(CH$_2$)$_4$-O-cHx | H | F | H | H |
| 5-405 | H | Me | Me | 2 | —(CH$_2$)$_4$-O-cHx | H | H | H | H |
| 5-406 | CO$_2$Me | H | Me | 2 | —(CH$_2$)$_4$-O-cHx | H | H | H | H |
| 5-407 | CO$_2$Et | H | Me | 2 | —(CH$_2$)$_4$-O-cHx | H | H | H | H |
| 5-408 | H | H | Me | 2 | —(CH$_2$)$_4$-O-(3-F-cHx) | H | H | H | H |
| 5-409 | H | H | Me | 2 | —(CH$_2$)$_4$-O-(4-F-cHx) | H | H | H | H |
| 5-410 | H | H | Me | 2 | —(CH$_2$)$_4$-O-(4-Cl-cHx) | H | H | H | H |
| 5-411 | H | H | Me | 2 | —(CH$_2$)$_4$-O-(4-Br-cHx) | H | H | H | H |
| 5-412 | H | H | Me | 2 | —(CH$_2$)$_4$-O-(3-Me-cHx) | H | H | H | H |
| 5-413 | H | H | Me | 2 | —(CH$_2$)$_4$-O-(4-Me-cHx) | H | H | H | H |
| 5-414 | H | H | Me | 2 | —(CH$_2$)$_4$-O-(3-Et-cHx) | H | H | H | H |
| 5-415 | H | H | Me | 2 | —(CH$_2$)$_4$-O-(4-Et-cHx) | H | H | H | H |
| 5-416 | H | H | Me | 2 | —(CH$_2$)$_4$-O-(3-Pr-cHx) | H | H | H | H |
| 5-417 | H | H | Me | 2 | —(CH$_2$)$_4$-O-(4-Pr-cHx) | H | H | H | H |
| 5-418 | H | H | Me | 2 | —(CH$_2$)$_4$-O-(4-iPr-cHx) | H | H | H | H |
| 5-419 | H | H | Me | 2 | —(CH$_2$)$_4$-O-(3-Bu-cHx) | H | H | H | H |
| 5-420 | H | H | Me | 2 | —(CH$_2$)$_4$-O-(4-Bu-cHx) | H | H | H | H |
| 5-421 | H | H | Me | 2 | —(CH$_2$)$_4$-O-(3-CF$_3$-cHx) | H | H | H | H |
| 5-422 | H | H | Me | 2 | —(CH$_2$)$_4$-O-(4-CF$_3$-cHx) | H | H | H | H |
| 5-423 | H | H | Me | 2 | —(CH$_2$)$_4$-O-(3-MeO-cHx) | H | H | H | H |
| 5-424 | H | H | Me | 2 | —(CH$_2$)$_4$-O-(4-MeO-cHx) | H | H | H | H |
| 5-425 | H | H | Me | 2 | —(CH$_2$)$_4$-O-(3-EtO-cHx) | H | H | H | H |
| 5-426 | H | H | Me | 2 | —(CH$_2$)$_4$-O-(4-EtO-cHx) | H | H | H | H |
| 5-427 | H | H | Me | 2 | —(CH$_2$)$_4$-O-(3-PrO-cHx) | H | H | H | H |
| 5-428 | H | H | Me | 2 | —(CH$_2$)$_4$-O-(4-PrO-cHx) | H | H | H | H |
| 5-429 | H | H | Me | 2 | —(CH$_2$)$_4$-O-(3-iPrO-cHx) | H | H | H | H |
| 5-430 | H | H | Me | 2 | —(CH$_2$)$_4$-O-(4-iPrO-cHx) | H | H | H | H |
| 5-431 | H | H | Me | 2 | —(CH$_2$)$_4$-O-[3-(2-Et-PrO)-cHx] | H | H | H | H |
| 5-432 | H | H | Me | 2 | —(CH$_2$)$_4$-O-[4-(2-Et-PrO)-cHx] | H | H | H | H |
| 5-433 | H | H | Me | 2 | —(CH$_2$)$_4$-O-(3-iBuO-cHx) | H | H | H | H |
| 5-434 | H | H | Me | 2 | —(CH$_2$)$_4$-O-(4-iBuO-cHx) | H | H | H | H |
| 5-435 | H | H | Me | 2 | —(CH$_2$)$_4$-O-(3-MeS-cHx) | H | H | H | H |

TABLE 5-continued

| | | | | | | | | | |
|---|---|---|---|---|---|---|---|---|---|
| 5-436 | H | H | Me | 2 | —(CH$_2$)$_4$-O-(4-MeS-cHx) | H | H | H | H |
| 5-437 | H | H | Me | 2 | —(CH$_2$)$_4$-O-(3-EtS-cHx) | H | H | H | H |
| 5-438 | H | H | Me | 2 | —(CH$_2$)$_4$-O-(4-EtS-cHx) | H | H | H | H |
| 5-439 | H | H | Me | 2 | —(CH$_2$)$_4$-O-(3-PrS-cHx) | H | H | H | H |
| 5-440 | H | H | Me | 2 | —(CH$_2$)$_4$-O-(4-PrS-cHx) | H | H | H | H |
| 5-441 | H | H | Me | 2 | —(CH$_2$)$_4$-O-(3-iPrS-cHx) | H | H | H | H |
| 5-442 | H | H | Me | 2 | —(CH$_2$)$_4$-O-(4-iPrS-cHx) | H | H | H | H |
| 5-443 | H | H | Me | 2 | —(CH$_2$)$_4$-O-[3-(2-Et-PrS)-cHx] | H | H | H | H |
| 5-444 | H | H | Me | 2 | —(CH$_2$)$_4$-O-[4-(2-Et-PrS)-cHx] | H | H | H | H |
| 5-445 | H | H | Me | 2 | —(CH$_2$)$_4$-O-(3-iBuS-cHx) | H | H | H | H |
| 5-446 | H | H | Me | 2 | —(CH$_2$)$_4$-O-(4-iBuS-cHx) | H | H | H | H |
| 5-447 | H | H | Me | 2 | —(CH$_2$)$_4$-O-(3-cHx-cHx) | H | H | H | H |
| 5-448 | H | H | Me | 2 | —(CH$_2$)$_4$-O-(4-cHx-cHx) | H | H | H | H |
| 5-449 | H | H | Me | 2 | —(CH$_2$)$_4$-O-(3-Ph-cHx) | H | H | H | H |
| 5-450 | H | H | Me | 2 | —(CH$_2$)$_4$-O-(4-Ph-cHx) | H | H | H | H |
| 5-451 | H | H | Me | 2 | —(CH$_2$)$_4$-O-(2,4-diMe-cHx) | H | H | H | H |
| 5-452 | H | H | Me | 2 | —(CH$_2$)$_4$-O-(3,4-diMe-cHx) | H | H | H | H |
| 5-453 | H | H | Me | 2 | —(CH$_2$)$_4$-O-(3,5-diMe-cHx) | H | H | H | H |
| 5-454 | H | H | Me | 2 | —(CH$_2$)$_4$-O-Ph | H | H | H | H |
| 5-455 | H | H | Me | 2 | —(CH$_2$)$_4$-O-Ph | Me | H | H | H |
| 5-456 | H | H | Me | 2 | —(CH$_2$)$_4$-O-Ph | H | Me | H | H |
| 5-457 | H | H | Me | 2 | —(CH$_2$)$_4$-O-Ph | F | H | H | H |
| 5-458 | H | H | Me | 2 | —(CH$_2$)$_4$-O-Ph | H | F | H | H |
| 5-459 | H | Me | Me | 2 | —(CH$_2$)$_4$-O-Ph | H | H | H | H |
| 5-460 | CO$_2$Me | H | Me | 2 | —(CH$_2$)$_4$-O-Ph | H | H | H | H |
| 5-461 | CO$_2$Et | H | Me | 2 | —(CH$_2$)$_4$-O-Ph | H | H | H | H |
| 5-462 | H | H | Me | 2 | —(CH$_2$)$_4$-O-(3-F-Ph) | H | H | H | H |
| 5-463 | H | H | Me | 2 | —(CH$_2$)$_4$-O-(4-F-Ph) | H | H | H | H |
| 5-464 | H | H | Me | 2 | —(CH$_2$)$_4$-O-(4-Cl-Ph) | H | H | H | H |
| 5-465 | H | H | Me | 2 | —(CH$_2$)$_4$-O-(4-Br-Ph) | H | H | H | H |
| 5-466 | H | H | Me | 2 | —(CH$_2$)$_4$-O-(3-Me-Ph) | H | H | H | H |
| 5-467 | H | H | Me | 2 | —(CH$_2$)$_4$-O-(4-Me-Ph) | H | H | H | H |
| 5-468 | H | H | Me | 2 | —(CH$_2$)$_4$-O-(3-Et-Ph) | H | H | H | H |
| 5-469 | H | H | Me | 2 | —(CH$_2$)$_4$-O-(4-Et-Ph) | H | H | H | H |
| 5-470 | H | H | Me | 2 | —(CH$_2$)$_4$-O-(3-Pr-Ph) | H | H | H | H |
| 5-471 | H | H | Me | 2 | —(CH$_2$)$_4$-O-(4-Pr-Ph) | H | H | H | H |
| 5-472 | H | H | Me | 2 | —(CH$_2$)$_4$-O-(3-iPr-Ph) | H | H | H | H |
| 5-473 | H | H | Me | 2 | —(CH$_2$)$_4$-O-(4-iPr-Ph) | H | H | H | H |
| 5-474 | H | H | Me | 2 | —(CH$_2$)$_4$-O-(3-Bu-Ph) | H | H | H | H |
| 5-475 | H | H | Me | 2 | —(CH$_2$)$_4$-O-(4-Bu-Ph) | H | H | H | H |
| 5-476 | H | H | Me | 2 | —(CH$_2$)$_4$-O-(3-CF$_3$-Ph) | H | H | H | H |
| 5-477 | H | H | Me | 2 | —(CH$_2$)$_4$-O-(4-CF$_3$-Ph) | H | H | H | H |
| 5-478 | H | H | Me | 2 | —(CH$_2$)$_4$-O-(3-MeO-Ph) | H | H | H | H |
| 5-479 | H | H | Me | 2 | —(CH$_2$)$_4$-O-(4-MeO-Ph) | H | H | H | H |
| 5-480 | H | H | Me | 2 | —(CH$_2$)$_4$-O-(3-EtO-Ph) | H | H | H | H |
| 5-481 | H | H | Me | 2 | —(CH$_2$)$_4$-O-(4-EtO-Ph) | H | H | H | H |
| 5-482 | H | H | Me | 2 | —(CH$_2$)$_4$-O-(3-PrO-Ph) | H | H | H | H |
| 5-483 | H | H | Me | 2 | —(CH$_2$)$_4$-O-(4-PrO-Ph) | H | H | H | H |
| 5-484 | H | H | Me | 2 | —(CH$_2$)$_4$-O-(3-iPrO-Ph) | H | H | H | H |
| 5-485 | H | H | Me | 2 | —(CH$_2$)$_4$-O-(4-iPrO-Ph) | H | H | H | H |
| 5-486 | H | H | Me | 2 | —(CH$_2$)$_4$-O-[3-(2-Et-PrO)-Ph] | H | H | H | H |
| 5-487 | H | H | Me | 2 | —(CH$_2$)$_4$-O-[4-(2-Et-PrO)-Ph] | H | H | H | H |
| 5-488 | H | H | Me | 2 | —(CH$_2$)$_4$-O-(3-iBuO-Ph) | H | H | H | H |
| 5-489 | H | H | Me | 2 | —(CH$_2$)$_4$-O-(4-iBuO-Ph) | H | H | H | H |
| 5-490 | H | H | Me | 2 | —(CH$_2$)$_4$-O-(3-MeS-Ph) | H | H | H | H |
| 5-491 | H | H | Me | 2 | —(CH$_2$)$_4$-O-(4-MeS-Ph) | H | H | H | H |
| 5-492 | H | H | Me | 2 | —(CH$_2$)$_4$-O-(3-EtS-Ph) | H | H | H | H |
| 5-493 | H | H | Me | 2 | —(CH$_2$)$_4$-O-(4-EtS-Ph) | H | H | H | H |
| 5-494 | H | H | Me | 2 | —(CH$_2$)$_4$-O-(3-PrS-Ph) | H | H | H | H |
| 5-495 | H | H | Me | 2 | —(CH$_2$)$_4$-O-(4-PrS-Ph) | H | H | H | H |
| 5-496 | H | H | Me | 2 | —(CH$_2$)$_4$-O-(3-iPrS-Ph) | H | H | H | H |
| 5-497 | H | H | Me | 2 | —(CH$_2$)$_4$-O-(4-iPrS-Ph) | H | H | H | H |
| 5-498 | H | H | Me | 2 | —(CH$_2$)$_4$-O-[3-(2-Et-PrS)-Ph] | H | H | H | H |
| 5-499 | H | H | Me | 2 | —(CH$_2$)$_4$-O-[4-(2-Et-PrS)-Ph] | H | H | H | H |
| 5-500 | H | H | Me | 2 | —(CH$_2$)$_4$-O-(3-iBuS-Ph) | H | H | H | H |
| 5-501 | H | H | Me | 2 | —(CH$_2$)$_4$-O-(4-iBuS-Ph) | H | H | H | H |
| 5-502 | H | H | Me | 2 | —(CH$_2$)$_4$-O-(3-cHx-Ph) | H | H | H | H |
| 5-503 | H | H | Me | 2 | —(CH$_2$)$_4$-O-(4-cHx-Ph) | H | H | H | H |
| 5-504 | H | H | Me | 2 | —(CH$_2$)$_4$-O-(3-Ph-Ph) | H | H | H | H |
| 5-505 | H | H | Me | 2 | —(CH$_2$)$_4$-O-(4-Ph-Ph) | H | H | H | H |
| 5-506 | H | H | Me | 2 | —(CH$_2$)$_4$-O-(2,4-diMe-Ph) | H | H | H | H |
| 5-507 | H | H | Me | 2 | —(CH$_2$)$_4$-O-(3,4-diMe-Ph) | H | H | H | H |
| 5-508 | H | H | Me | 2 | —(CH$_2$)$_4$-O-(3,5-diMe-Ph) | H | H | H | H |
| 5-509 | H | H | Me | 2 | —(CH$_2$)$_5$-O-cHx | H | H | H | H |
| 5-510 | H | H | Me | 2 | —(CH$_2$)$_5$-O-Ph | H | H | H | H |
| 5-511 | H | H | Me | 2 | —(CH$_2$)$_6$-O-cHx | H | H | H | H |
| 5-512 | H | H | Me | 2 | —(CH$_2$)$_6$-O-Ph | H | H | H | H |
| 5-513 | H | H | Me | 2 | —(CH$_2$)$_3$-OCH$_2$-cHx | H | H | H | H |
| 5-514 | H | Me | Me | 2 | —(CH$_2$)$_3$-OCH$_2$-cHx | H | H | H | H |
| 5-515 | CO$_2$Me | H | Me | 2 | —(CH$_2$)$_3$-OCH$_2$-cHx | H | H | H | H |

TABLE 5-continued

| | | | | | | | | | |
|---|---|---|---|---|---|---|---|---|---|
| 5-516 | CO$_2$Et | H | Me | 2 | —(CH$_2$)$_3$-OCH$_2$-cHx | H | H | H | H |
| 5-517 | H | H | Me | 2 | —(CH$_2$)$_3$-OCH$_2$-(4-F-cHx) | H | H | H | H |
| 5-518 | H | H | Me | 2 | —(CH$_2$)$_3$-OCH$_2$-(4-Me-cHx) | H | H | H | H |
| 5-519 | H | H | Me | 2 | —(CH$_2$)$_3$-OCH$_2$-(4-Et-cHx) | H | H | H | H |
| 5-520 | H | H | Me | 2 | —(CH$_2$)$_3$-OCH$_2$-(4-CF$_3$-cHx) | H | H | H | H |
| 5-521 | H | H | Me | 2 | —(CH$_2$)$_3$-OCH$_2$-(4-MeO-cHx) | H | H | H | H |
| 5-522 | H | H | Me | 2 | —(CH$_2$)$_3$-OCH$_2$-(4-EtO-cHx) | H | H | H | H |
| 5-523 | H | H | Me | 2 | —(CH$_2$)$_3$-OCH$_2$-(4-MeS-cHx) | H | H | H | H |
| 5-524 | H | H | Me | 2 | —(CH$_2$)$_3$-OCH$_2$-(4-cHx-cHx) | H | H | H | H |
| 5-525 | H | H | Me | 2 | —(CH$_2$)$_3$-OCH$_2$-(4-Ph-cHx) | H | H | H | H |
| 5-526 | H | H | Me | 2 | —(CH$_2$)$_3$-OCH$_2$-Ph | H | H | H | H |
| 5-527 | H | Me | Me | 2 | —(CH$_2$)$_3$-OCH$_2$-Ph | H | H | H | H |
| 5-528 | CO$_2$Me | H | Me | 2 | —(CH$_2$)$_3$-OCH$_2$-Ph | H | H | H | H |
| 5-529 | CO$_2$Et | H | Me | 2 | —(CH$_2$)$_3$-OCH$_2$-Ph | H | H | H | H |
| 5-530 | H | H | Me | 2 | —(CH$_2$)$_3$-OCH$_2$-(4-F-Ph) | H | H | H | H |
| 5-531 | H | H | Me | 2 | —(CH$_2$)$_3$-OCH$_2$-(4-Me-Ph) | H | H | H | H |
| 5-532 | H | H | Me | 2 | —(CH$_2$)$_3$-OCH$_2$-(4-Et-Ph) | H | H | H | H |
| 5-533 | H | H | Me | 2 | —(CH$_2$)$_3$-OCH$_2$-(4-CF$_3$Ph) | H | H | H | H |
| 5-534 | H | H | Me | 2 | —(CH$_2$)$_3$-OCH$_2$-(4-MeO-Ph) | H | H | H | H |
| 5-535 | H | H | Me | 2 | —(CH$_2$)$_3$-OCH$_2$-(4-EtO-Ph) | H | H | H | H |
| 5-536 | H | H | Me | 2 | —(CH$_2$)$_3$-OCH$_2$-(4-MeS-Ph) | H | H | H | H |
| 5-537 | H | H | Me | 2 | —(CH$_2$)$_3$-OCH$_2$-(4-cHx-Ph) | H | H | H | H |
| 5-538 | H | H | Me | 2 | —(CH$_2$)$_3$-OCH$_2$-(4-Ph-Ph) | H | H | H | H |
| 5-539 | H | H | Me | 2 | —(CH$_2$)$_4$-OCH$_2$-cPn | H | H | H | H |
| 5-540 | H | H | Me | 2 | —(CH$_2$)$_4$-OCH$_2$-cHx | H | H | H | H |
| 5-541 | H | H | Me | 2 | —(CH$_2$)$_4$-OCH$_2$-cHx | Me | H | H | H |
| 5-542 | H | H | Me | 2 | —(CH$_2$)$_4$-OCH$_2$-cHx | H | Me | H | H |
| 5-543 | H | H | Me | 2 | —(CH$_2$)$_4$-OCH$_2$-cHx | F | H | H | H |
| 5-544 | H | H | Me | 2 | —(CH$_2$)$_4$-OCH$_2$-cHx | H | F | H | H |
| 5-545 | H | Me | Me | 2 | —(CH$_2$)$_4$-OCH$_2$-cHx | H | H | H | H |
| 5-546 | CO$_2$Me | H | Me | 2 | —(CH$_2$)$_4$-OCH$_2$-cHx | H | H | H | H |
| 5-547 | CO$_2$Et | H | Me | 2 | —(CH$_2$)$_4$-OCH$_2$-cHx | H | H | H | H |
| 5-548 | H | H | Me | 2 | —(CH$_2$)$_4$-OCH$_2$-(3-F-cHx) | H | H | H | H |
| 5-549 | H | H | Me | 2 | —(CH$_2$)$_4$-OCH$_2$-(4-F-cHx) | H | H | H | H |
| 5-550 | H | H | Me | 2 | —(CH$_2$)$_4$-OCH$_2$-(4-Cl-cHx) | H | H | H | H |
| 5-551 | H | H | Me | 2 | —(CH$_2$)$_4$-OCH$_2$-(4-Br-cHx) | H | H | H | H |
| 5-552 | H | H | Me | 2 | —(CH$_2$)$_4$-OCH$_2$-(3-Me-cHx) | H | H | H | H |
| 5-553 | H | H | Me | 2 | —(CH$_2$)$_4$-OCH$_2$-(4-Me-cHx) | H | H | H | H |
| 5-554 | H | H | Me | 2 | —(CH$_2$)$_4$-OCH$_2$-(3-Et-cHx) | H | H | H | H |
| 5-555 | H | H | Me | 2 | —(CH$_2$)$_4$-OCH$_2$-(4-Et-cHx) | H | H | H | H |
| 5-556 | H | H | Me | 2 | —(CH$_2$)$_4$-OCH$_2$-(3-Pr-cHx) | H | H | H | H |
| 5-557 | H | H | Me | 2 | —(CH$_2$)$_4$-OCH$_2$-(4-Pr-cHx) | H | H | H | H |
| 5-558 | H | H | Me | 2 | —(CH$_2$)$_4$-OCH$_2$-(4-iPr-cHx) | H | H | H | H |
| 5-559 | H | H | Me | 2 | —(CH$_2$)$_4$-OCH$_2$-(3-Bu-cHx) | H | H | H | H |
| 5-560 | H | H | Me | 2 | —(CH$_2$)$_4$-OCH$_2$-(4-Bu-cHx) | H | H | H | H |
| 5-561 | H | H | Me | 2 | —(CH$_2$)$_4$-OCH$_2$-(3-CF$_3$-cHx) | H | H | H | H |
| 5-562 | H | H | Me | 2 | —(CH$_2$)$_4$-OCH$_2$-(4-CF$_3$-cHx) | H | H | H | H |
| 5-563 | H | H | Me | 2 | —(CH$_2$)$_4$-OCH$_2$-(3-MeO-cHx) | H | H | H | H |
| 5-564 | H | H | Me | 2 | —(CH$_2$)$_4$-OCH$_2$-(4-MeO-cHx) | H | H | H | H |
| 5-565 | H | H | Me | 2 | —(CH$_2$)$_4$-OCH$_2$-(3-EtO-cHx) | H | H | H | H |
| 5-566 | H | H | Me | 2 | —(CH$_2$)$_4$-OCH$_2$-(4-EtO-cHx) | H | H | H | H |
| 5-567 | H | H | Me | 2 | —(CH$_2$)$_4$-OCH$_2$-(3-PrO-cHx) | H | H | H | H |
| 5-568 | H | H | Me | 2 | —(CH$_2$)$_4$-OCH$_2$-(4-PrO-cHx) | H | H | H | H |
| 5-569 | H | H | Me | 2 | —(CH$_2$)$_4$-OCH$_2$-(3-iPrO-cHx) | H | H | H | H |
| 5-570 | H | H | Me | 2 | —(CH$_2$)$_4$-OCH$_2$-(4-iPrO-cHx) | H | H | H | H |
| 5-571 | H | H | Me | 2 | —(CH$_2$)$_4$-OCH$_2$-[3-(2-Et-PrO)-cHx] | H | H | H | H |
| 5-572 | H | H | Me | 2 | —(CH$_2$)$_4$-OCH$_2$-[4-(2-Et-PrO)-cHx] | H | H | H | H |
| 5-573 | H | H | Me | 2 | —(CH$_2$)$_4$-OCH$_2$-(3-iBuO-cHx) | H | H | H | H |
| 5-574 | H | H | Me | 2 | —(CH$_2$)$_4$-OCH$_2$-(4-iBuO-cHx) | H | H | H | H |
| 5-575 | H | H | Me | 2 | —(CH$_2$)$_4$-OCH$_2$-(3-MeS-cHx) | H | H | H | H |
| 5-576 | H | H | Me | 2 | —(CH$_2$)$_4$-OCH$_2$-(4-MeS-cHx) | H | H | H | H |
| 5-577 | H | H | Me | 2 | —(CH$_2$)$_4$-OCH$_2$-(3-EtS-cHx) | H | H | H | H |
| 5-578 | H | H | Me | 2 | —(CH$_2$)$_4$-OCH$_2$-(4-EtS-cHx) | H | H | H | H |
| 5-579 | H | H | Me | 2 | —(CH$_2$)$_4$-OCH$_2$-(3-PrS-cHx) | H | H | H | H |
| 5-580 | H | H | Me | 2 | —(CH$_2$)$_4$-OCH$_2$-(4-PrS-cHx) | H | H | H | H |
| 5-581 | H | H | Me | 2 | —(CH$_2$)$_4$-OCH$_2$-(3-iPrS-cHx) | H | H | H | H |
| 5-582 | H | H | Me | 2 | —(CH$_2$)$_4$-OCH$_2$-(4-iPrS-cHx) | H | H | H | H |
| 5-583 | H | H | Me | 2 | —(CH$_2$)$_4$-OCH$_2$-[3-(2-Et-PrS)-cHx] | H | H | H | H |
| 5-584 | H | H | Me | 2 | —(CH$_2$)$_4$-OCH$_2$-[4-(2-Et-PrS)-cHx] | H | H | H | H |
| 5-585 | H | H | Me | 2 | —(CH$_2$)$_4$-OCH$_2$-(3-iBuS-cHx) | H | H | H | H |
| 5-586 | H | H | Me | 2 | —(CH$_2$)$_4$-OCH$_2$-(4-iBuS-cHx) | H | H | H | H |
| 5-587 | H | H | Me | 2 | —(CH$_2$)$_4$-OCH$_2$-(3-cHx-cHx) | H | H | H | H |
| 5-588 | H | H | Me | 2 | —(CH$_2$)$_4$-OCH$_2$-(4-cHx-cHx) | H | H | H | H |
| 5-589 | H | H | Me | 2 | —(CH$_2$)$_4$-OCH$_2$-(3-Ph-cHx) | H | H | H | H |
| 5-590 | H | H | Me | 2 | —(CH$_2$)$_4$-OCH$_2$-(4-Ph-cHx) | H | H | H | H |
| 5-591 | H | H | Me | 2 | —(CH$_2$)$_4$-OCH$_2$-(2,4-diMe-cHx) | H | H | H | H |
| 5-592 | H | H | Me | 2 | —(CH$_2$)$_4$-OCH$_2$-(3,4-diMe-cHx) | H | H | H | H |
| 5-593 | H | H | Me | 2 | —(CH$_2$)$_4$-OCH$_2$-(3,5-diMe-cHx) | H | H | H | H |
| 5-594 | H | H | Me | 2 | —(CH$_2$)$_4$-OCH$_2$-Ph | Me | H | H | H |
| 5-595 | H | H | Me | 2 | —(CH$_2$)$_4$-OCH$_2$-Ph | Me | H | H | H |

TABLE 5-continued

| | | | | | | | | | |
|---|---|---|---|---|---|---|---|---|---|
| 5-596 | H | H | Me | 2 | —(CH$_2$)$_4$-OCH$_2$-Ph | H | Me | H | H |
| 5-597 | H | H | Me | 2 | —(CH$_2$)$_4$-OCH$_2$-Ph | F | H | H | H |
| 5-598 | H | H | Me | 2 | —(CH$_2$)$_4$-OCH$_2$-Ph | H | F | H | H |
| 5-599 | H | Me | Me | 2 | —(CH$_2$)$_4$-OCH$_2$-Ph | H | H | H | H |
| 5-600 | CO$_2$Me | H | Me | 2 | —(CH$_2$)$_4$-OCH$_2$-Ph | H | H | H | H |
| 5-601 | CO$_2$Et | H | Me | 2 | —(CH$_2$)$_4$-OCH$_2$-Ph | H | H | H | H |
| 5-602 | H | H | Me | 2 | —(CH$_2$)$_4$-OCH$_2$-(3-F-Ph) | H | H | H | H |
| 5-603 | H | H | Me | 2 | —(CH$_2$)$_4$-OCH$_2$-(4-F-Ph) | H | H | H | H |
| 5-604 | H | H | Me | 2 | —(CH$_2$)$_4$-OCH$_2$-(4-Cl-Ph) | H | H | H | H |
| 5-605 | H | H | Me | 2 | —(CH$_2$)$_4$-OCH$_2$-(4-Br-Ph) | H | H | H | H |
| 5-606 | H | H | Me | 2 | —(CH$_2$)$_4$-OCH$_2$-(3-Me-Ph) | H | H | H | H |
| 5-607 | H | H | Me | 2 | —(CH$_2$)$_4$-OCH$_2$-(4-Me-Ph) | H | H | H | H |
| 5-608 | H | H | Me | 2 | —(CH$_2$)$_4$-OCH$_2$-(3-Et-Ph) | H | H | H | H |
| 5-609 | H | H | Me | 2 | —(CH$_2$)$_4$-OCH$_2$-(4-Et-Ph) | H | H | H | H |
| 5-610 | H | H | Me | 2 | —(CH$_2$)$_4$-OCH$_2$-(3-Pr-Ph) | H | H | H | H |
| 5-611 | H | H | Me | 2 | —(CH$_2$)$_4$-OCH$_2$-(4-Pr-Ph) | H | H | H | H |
| 5-612 | H | H | Me | 2 | —(CH$_2$)$_4$-OCH$_2$-(3-iPr-Ph) | H | H | H | H |
| 5-613 | H | H | Me | 2 | —(CH$_2$)$_4$-OCH$_2$-(4-iPr-Ph) | H | H | H | H |
| 5-614 | H | H | Me | 2 | —(CH$_2$)$_4$-OCH$_2$-(3-Bu-Ph) | H | H | H | H |
| 5-615 | H | H | Me | 2 | —(CH$_2$)$_4$-OCH$_2$-(4-Bu-Ph) | H | H | H | H |
| 5-616 | H | H | Me | 2 | —(CH$_2$)$_4$-OCH$_2$-(3-CF$_3$-Ph) | H | H | H | H |
| 5-617 | H | H | Me | 2 | —(CH$_2$)$_4$-OCH$_2$-(4-CF$_3$-Ph) | H | H | H | H |
| 5-618 | H | H | Me | 2 | —(CH$_2$)$_4$-OCH$_2$-(3-MeO-Ph) | H | H | H | H |
| 5-619 | H | H | Me | 2 | —(CH$_2$)$_4$-OCH$_2$-(4-MeO-Ph) | H | H | H | H |
| 5-620 | H | H | Me | 2 | —(CH$_2$)$_4$-OCH$_2$-(3-EtO-Ph) | H | H | H | H |
| 5-621 | H | H | Me | 2 | —(CH$_2$)$_4$-OCH$_2$-(4-EtO-Ph) | H | H | H | H |
| 5-622 | H | H | Me | 2 | —(CH$_2$)$_4$-OCH$_2$-(3-PrO-Ph) | H | H | H | H |
| 5-623 | H | H | Me | 2 | —(CH$_2$)$_4$-OCH$_2$-(4-PrO-Ph) | H | H | H | H |
| 5-624 | H | H | Me | 2 | —(CH$_2$)$_4$-OCH$_2$-(3-iPrO-Ph) | H | H | H | H |
| 5-625 | H | H | Me | 2 | —(CH$_2$)$_4$-OCH$_2$-(4-iPrO-Ph) | H | H | H | H |
| 5-626 | H | H | Me | 2 | —(CH$_2$)$_4$-OCH$_2$-[3-(2-Et-PrO)-Ph] | H | H | H | H |
| 5-627 | H | H | Me | 2 | —(CH$_2$)$_4$-OCH$_2$-[4-(2-Et-PrO)-Ph] | H | H | H | H |
| 5-628 | H | H | Me | 2 | —(CH$_2$)$_4$-OCH$_2$-(3-iBuO-Ph) | H | H | H | H |
| 5-629 | H | H | Me | 2 | —(CH$_2$)$_4$-OCH$_2$-(4-iBuO-Ph) | H | H | H | H |
| 5-630 | H | H | Me | 2 | —(CH$_2$)$_4$-OCH$_2$-(3-MeS-Ph) | H | H | H | H |
| 5-631 | H | H | Me | 2 | —(CH$_2$)$_4$-OCH$_2$-(4-MeS-Ph) | H | H | H | H |
| 5-632 | H | H | Me | 2 | —(CH$_2$)$_4$-OCH$_2$-(3-EtS-Ph) | H | H | H | H |
| 5-633 | H | H | Me | 2 | —(CH$_2$)$_4$-OCH$_2$-(4-EtS-Ph) | H | H | H | H |
| 5-634 | H | H | Me | 2 | —(CH$_2$)$_4$-OCH$_2$-(3-PrS-Ph) | H | H | H | H |
| 5-635 | H | H | Me | 2 | —(CH$_2$)$_4$-OCH$_2$-(4-PrS-Ph) | H | H | H | H |
| 5-636 | H | H | Me | 2 | —(CH$_2$)$_4$-OCH$_2$-(3-iPrS-Ph) | H | H | H | H |
| 5-637 | H | H | Me | 2 | —(CH$_2$)$_4$-OCH$_2$-(4-iPrS-Ph) | H | H | H | H |
| 5-638 | H | H | Me | 2 | —(CH$_2$)$_4$-OCH$_2$-[3-(2-Et-PrS)-Ph] | H | H | H | H |
| 5-639 | H | H | Me | 2 | —(CH$_2$)$_4$-OCH$_2$-[4-(2-Et-PrS)-Ph] | H | H | H | H |
| 5-640 | H | H | Me | 2 | —(CH$_2$)$_4$-OCH$_2$-(3-iBuS-Ph) | H | H | H | H |
| 5-641 | H | H | Me | 2 | —(CH$_2$)$_4$-OCH$_2$-(4-iBuS-Ph) | H | H | H | H |
| 5-642 | H | H | Me | 2 | —(CH$_2$)$_4$-OCH$_2$-(3-cHx-Ph) | H | H | H | H |
| 5-643 | H | H | Me | 2 | —(CH$_2$)$_4$-OCH$_2$-(4-cHx-Ph) | H | H | H | H |
| 5-644 | H | H | Me | 2 | —(CH$_2$)$_4$-OCH$_2$-(3-Ph-Ph) | H | H | H | H |
| 5-645 | H | H | Me | 2 | —(CH$_2$)$_4$-OCH$_2$-(4-Ph-Ph) | H | H | H | H |
| 5-646 | H | H | Me | 2 | —(CH$_2$)$_4$-OCH$_2$-(2,4-diMe-Ph) | H | H | H | H |
| 5-647 | H | H | Me | 2 | —(CH$_2$)$_4$-OCH$_2$-(3,4-diMe-Ph) | H | H | H | H |
| 5-648 | H | H | Me | 2 | —(CH$_2$)$_4$-OCH$_2$-(3,5-diMe-Ph) | H | H | H | H |
| 5-649 | H | H | Me | 2 | —(CH$_2$)$_5$-OCH$_2$-cHx | H | H | H | H |
| 5-650 | H | H | Me | 2 | —(CH$_2$)$_5$-OCH$_2$-Ph | H | H | H | H |
| 5-651 | H | H | Me | 2 | —(CH$_2$)$_6$-OCH$_2$-cHx | H | H | H | H |
| 5-652 | H | H | Me | 2 | —(CH$_2$)$_6$-OCH$_2$-Ph | H | H | H | H |
| 5-653 | H | H | Me | 2 | —CH=CH-cHx | H | H | H | H |
| 5-654 | H | H | Me | 2 | —CH=CH-Ph | H | H | H | H |
| 5-655 | H | H | Me | 2 | —CH=CH—(CH$_2$)$_2$-cHx | H | H | H | H |
| 5-656 | H | H | Me | 2 | —CH=CH—(CH$_2$)$_2$-Ph | H | H | H | H |
| 5-657 | H | H | Me | 2 | —CH=CH—(CH$_2$)$_3$-cHx | H | H | H | H |
| 5-658 | H | Me | Me | 2 | —CH=CH—(CH$_2$)$_3$-cHx | H | H | H | H |
| 5-659 | CO$_2$Me | H | Me | 2 | —CH=CH—(CH$_2$)$_3$-cHx | H | H | H | H |
| 5-660 | CO$_2$Et | H | Me | 2 | —CH=CH—(CH$_2$)$_3$-cHx | H | H | H | H |
| 5-661 | H | H | Me | 2 | —CH=CH—(CH$_2$)$_3$-(4-F-cHx) | H | H | H | H |
| 5-662 | H | H | Me | 2 | —CH=CH—(CH$_2$)$_3$-(4-Me-cHx) | H | H | H | H |
| 5-663 | H | H | Me | 2 | —CH=CH—(CH$_2$)$_3$-(4-Et-cHx) | H | H | H | H |
| 5-664 | H | H | Me | 2 | —CH=CH—(CH$_2$)$_3$-(4-CF$_3$-cHx) | H | H | H | H |
| 5-665 | H | H | Me | 2 | —CH=CH—(CH$_2$)$_3$-(4-MeO-cHx) | H | H | H | H |
| 5-666 | H | H | Me | 2 | —CH=CH—(CH$_2$)$_3$-(4-EtO-cHx) | H | H | H | H |
| 5-667 | H | H | Me | 2 | —CH=CH—(CH$_2$)$_3$-(4-MeS-cHx) | H | H | H | H |
| 5-668 | H | H | Me | 2 | —CH=CH—(CH$_2$)$_3$-(4-cHx-cHx) | H | H | H | H |
| 5-669 | H | H | Me | 2 | —CH=CH—(CH$_2$)$_3$-(4-Ph-cHx) | H | H | H | H |
| 5-670 | H | H | Me | 2 | —CH=CH—(CH$_2$)$_3$-Ph | H | H | H | H |
| 5-671 | H | Me | Me | 2 | —CH=CH—(CH$_2$)$_3$-Ph | H | H | H | H |
| 5-672 | CO$_2$Me | H | Me | 2 | —CH=CH—(CH$_2$)$_3$-Ph | H | H | H | H |
| 5-673 | CO$_2$Et | H | Me | 2 | —CH=CH—(CH$_2$)$_3$-Ph | H | H | H | H |
| 5-674 | H | H | Me | 2 | —CH=CH—(CH$_2$)$_3$-(4-F-Ph) | H | H | H | H |
| 5-675 | H | H | Me | 2 | —CH=CH—(CH$_2$)$_3$-(4-Me-Ph) | H | H | H | H |

TABLE 5-continued

| | | | | | | | | | |
|---|---|---|---|---|---|---|---|---|---|
| 5-676 | H | H | Me | 2 | —CH=CH—(CH$_2$)$_3$-(4-Et-Ph) | H | H | H | H |
| 5-677 | H | H | Me | 2 | —CH=CH—(CH$_2$)$_3$-(4-CF$_3$-Ph) | H | H | H | H |
| 5-678 | H | H | Me | 2 | —CH=CH—(CH$_2$)$_3$-(4-MeO-Ph) | H | H | H | H |
| 5-679 | H | H | Me | 2 | —CH=CH—(CH$_2$)$_3$-(4-EtO-Ph) | H | H | H | H |
| 5-680 | H | H | Me | 2 | —CH=CH—(CH$_2$)$_3$-(4-MeS-Ph) | H | H | H | H |
| 5-681 | H | H | Me | 2 | —CH=CH—(CH$_2$)$_3$-(4-cHx-Ph) | H | H | H | H |
| 5-682 | H | H | Me | 2 | —CH=CH—(CH$_2$)$_3$-(4-Ph-Ph) | H | H | H | H |
| 5-683 | H | H | Me | 2 | —CH=CH—(CH$_2$)$_4$-cHx | H | H | H | H |
| 5-684 | H | Me | Me | 2 | —CH=CH—(CH$_2$)$_4$-cHx | H | H | H | H |
| 5-685 | CO$_2$Me | H | Me | 2 | —CH=CH—(CH$_2$)$_4$-cHx | H | H | H | H |
| 5-686 | CO$_2$Et | H | Me | 2 | —CH=CH—(CH$_2$)$_4$-cHx | H | H | H | H |
| 5-687 | H | H | Me | 2 | —CH=CH—(CH$_2$)$_4$-(4-F-cHx) | H | H | H | H |
| 5-688 | H | H | Me | 2 | —CH=CH—(CH$_2$)$_4$-(4-Me-cHx) | H | H | H | H |
| 5-689 | H | H | Me | 2 | —CH=CH—(CH$_2$)$_4$-(4-Et-cHx) | H | H | H | H |
| 5-690 | H | H | Me | 2 | —CH=CH—(CH$_2$)$_4$-(4-CF$_3$-cHx) | H | H | H | H |
| 5-691 | H | H | Me | 2 | —CH=CH—(CH$_2$)$_4$-(4-MeO-cHx) | H | H | H | H |
| 5-692 | H | H | Me | 2 | —CH=CH—(CH$_2$)$_4$-(4-EtO-cHx) | H | H | H | H |
| 5-693 | H | H | Me | 2 | —CH=CH—(CH$_2$)$_4$-(4-MeS-cHx) | H | H | H | H |
| 5-694 | H | H | Me | 2 | —CH=CH—(CH$_2$)$_4$-(4-cHx-cHx) | H | H | H | H |
| 5-695 | H | H | Me | 2 | —CH=CH—(CH$_2$)$_4$-(4-Ph-cHx) | H | H | H | H |
| 5-696 | H | H | Me | 2 | —CH=CH—(CH$_2$)$_4$-Ph | H | H | H | H |
| 5-697 | H | Me | Me | 2 | —CH=CH—(CH$_2$)$_4$-Ph | H | H | H | H |
| 5-698 | CO$_2$Me | H | Me | 2 | —CH=CH—(CH$_2$)$_4$-Ph | H | H | H | H |
| 5-699 | CO$_2$Et | H | Me | 2 | —CH=CH—(CH$_2$)$_4$-Ph | H | H | H | H |
| 5-700 | H | H | Me | 2 | —CH=CH—(CH$_2$)$_4$-(4-F-Ph) | H | H | H | H |
| 5-701 | H | H | Me | 2 | —CH=CH—(CH$_2$)$_4$-(4-Me-Ph) | H | H | H | H |
| 5-702 | H | H | Me | 2 | —CH=CH—(CH$_2$)$_4$-(4-Et-Ph) | H | H | H | H |
| 5-703 | H | H | Me | 2 | —CH=CH—(CH$_2$)$_4$-(4-CF$_3$-Ph) | H | H | H | H |
| 5-704 | H | H | Me | 2 | —CH=CH—(CH$_2$)$_4$-(4-MeO-Ph) | H | H | H | H |
| 5-705 | H | H | Me | 2 | —CH=CH—(CH$_2$)$_4$-(4-EtO-Ph) | H | H | H | H |
| 5-706 | H | H | Me | 2 | —CH=CH—(CH$_2$)$_4$-(4-MeS-Ph) | H | H | H | H |
| 5-707 | H | H | Me | 2 | —CH=CH—(CH$_2$)$_4$-(4-cHx-Ph) | H | H | H | H |
| 5-708 | H | H | Me | 2 | —CH=CH—(CH$_2$)$_4$-(4-Ph-Ph) | H | H | H | H |
| 5-709 | H | H | Me | 2 | —CH=CH—(CH$_2$)$_5$-cHx | H | H | H | H |
| 5-710 | H | H | Me | 2 | —CH=CH—(CH$_2$)$_5$-Ph | H | H | H | H |
| 5-711 | H | H | Me | 2 | —CH=CH—(CH$_2$)$_6$-cHx | H | H | H | H |
| 5-712 | H | H | Me | 2 | —CH=CH—(CH$_2$)$_6$-Ph | H | H | H | H |
| 5-713 | H | H | Me | 2 | —C≡C—CH$_2$O-cHx | H | H | H | H |
| 5-714 | H | H | Me | 2 | —C≡C—CH$_2$O-Ph | H | H | H | H |
| 5-715 | H | H | Me | 2 | —C≡C—CH$_2$O-(CH$_2$)$_2$O-cHx | H | H | H | H |
| 5-716 | H | H | Me | 2 | —C≡C—CH$_2$O-(CH$_2$)$_2$O-Ph | H | H | H | H |
| 5-717 | H | H | Me | 2 | —C≡C-cHx | H | H | H | H |
| 5-718 | H | Me | Me | 2 | —C≡C-cHx | H | H | H | H |
| 5-719 | CO$_2$Me | H | Me | 2 | —C≡C-cHx | H | H | H | H |
| 5-720 | CO$_2$Et | H | Me | 2 | —C≡C-cHx | H | H | H | H |
| 5-721 | H | H | Me | 2 | —C≡C-(4-F-cHx) | H | H | H | H |
| 5-722 | H | H | Me | 2 | —C≡C-(4-Me-cHx) | H | H | H | H |
| 5-723 | H | H | Me | 2 | —C≡C-(4-Et-cHx) | H | H | H | H |
| 5-724 | H | H | Me | 2 | —C≡C-(4-CF$_3$-cHx) | H | H | H | H |
| 5-725 | H | H | Me | 2 | —C≡C-(4-MeO-cHx) | H | H | H | H |
| 5-726 | H | H | Me | 2 | —C≡C-(4-EtO-cHx) | H | H | H | H |
| 5-727 | H | H | Me | 2 | —C≡C-(4-MeS-cHx) | H | H | H | H |
| 5-728 | H | H | Me | 2 | —C≡C-(4-cHx-cHx) | H | H | H | H |
| 5-729 | H | H | Me | 2 | —C≡C-(4-Ph-cHx) | H | H | H | H |
| 5-730 | H | H | Me | 2 | —C≡C-Ph | H | H | H | H |
| 5-731 | H | Me | Me | 2 | —C≡C-Ph | H | H | H | H |
| 5-732 | CO$_2$Me | H | Me | 2 | —C≡C-Ph | H | H | H | H |
| 5-733 | CO$_2$Et | H | Me | 2 | —C≡C-Ph | H | H | H | H |
| 5-734 | H | H | Me | 2 | —C≡C-(4-F-Ph) | H | H | H | H |
| 5-735 | H | H | Me | 2 | —C≡C-(4-Me-Ph) | H | H | H | H |
| 5-736 | H | H | Me | 2 | —C≡C-(4-Pr-Ph) | H | H | H | H |
| 5-737 | H | H | Me | 2 | —C≡C-(4-Bu-Ph) | H | H | H | H |
| 5-738 | H | H | Me | 2 | —C≡C-(4-MeO-Ph) | H | H | H | H |
| 5-739 | H | H | Me | 2 | —C≡C-(4-EtO-Ph) | H | H | H | H |
| 5-740 | H | H | Me | 2 | —C≡C-(4-PrO-Ph) | H | H | H | H |
| 5-741 | H | H | Me | 2 | —C≡C-(4-cHx-Ph) | H | H | H | H |
| 5-742 | H | H | Me | 2 | —C≡C-(4-Ph-Ph) | H | H | H | H |
| 5-743 | H | H | Me | 2 | —C≡C—(CH$_2$)$_2$-cHx | H | H | H | H |
| 5-744 | H | Me | Me | 2 | —C≡C—(CH$_2$)$_2$-cHx | H | H | H | H |
| 5-745 | CO$_2$Me | H | Me | 2 | —C≡C—(CH$_2$)$_2$-cHx | H | H | H | H |
| 5-746 | CO$_2$Et | H | Me | 2 | —C≡C—(CH$_2$)$_2$-cHx | H | H | H | H |
| 5-747 | H | H | Me | 2 | —C≡C—(CH$_2$)$_2$-(4-F-cHx) | H | H | H | H |
| 5-748 | H | H | Me | 2 | —C≡C—(CH$_2$)$_2$-(4-Me-cHx) | H | H | H | H |
| 5-749 | H | H | Me | 2 | —C≡C—(CH$_2$)$_2$-(4-Et-cHx) | H | H | H | H |
| 5-750 | H | H | Me | 2 | —C≡C—(CH$_2$)$_2$-(4-CF$_3$-cHx) | H | H | H | H |
| 5-751 | H | H | Me | 2 | —C≡C—(CH$_2$)$_2$-(4-MeO-cHx) | H | H | H | H |
| 5-752 | H | H | Me | 2 | —C≡C—(CH$_2$)$_2$-(4-EtO-cHx) | H | H | H | H |
| 5-753 | H | H | Me | 2 | —C≡C—(CH$_2$)$_2$-(4-MeS-cHx) | H | H | H | H |
| 5-754 | H | H | Me | 2 | —C≡C—(CH$_2$)$_2$-(4-cHx-cHx) | H | H | H | H |
| 5-755 | H | H | Me | 2 | —C≡C—(CH$_2$)$_2$-(4-Ph-cHx) | H | H | H | H |

TABLE 5-continued

| | | | | | | | | | |
|---|---|---|---|---|---|---|---|---|---|
| 5-756 | H | H | Me | 2 | —C≡C—(CH$_2$)$_2$-Ph | H | H | H | H |
| 5-757 | H | Me | Me | 2 | —C≡C—(CH$_2$)$_2$-Ph | H | H | H | H |
| 5-758 | CO$_2$Me | H | Me | 2 | —C≡C—(CH$_2$)$_2$-Ph | H | H | H | H |
| 5-759 | CO$_2$Et | H | Me | 2 | —C≡C—(CH$_2$)$_2$-Ph | H | H | H | H |
| 5-760 | H | H | Me | 2 | —C≡C—(CH$_2$)$_2$-(4-F-Ph) | H | H | H | H |
| 5-761 | H | H | Me | 2 | —C≡C—(CH$_2$)$_2$-(4-Me-Ph) | H | H | H | H |
| 5-762 | H | H | Me | 2 | —C≡C—(CH$_2$)$_2$-(4-Et-Ph) | H | H | H | H |
| 5-763 | H | H | Me | 2 | —C≡C—(CH$_2$)$_2$-(4-CF$_3$-Ph) | H | H | H | H |
| 5-764 | H | H | Me | 2 | —C≡C—(CH$_2$)$_2$-(4-MeO-Ph) | H | H | H | H |
| 5-765 | H | H | Me | 2 | —C≡C—(CH$_2$)$_2$-(4-EtO-Ph) | H | H | H | H |
| 5-766 | H | H | Me | 2 | —C≡C—(CH$_2$)$_2$-(4-MeS-Ph) | H | H | H | H |
| 5-767 | H | H | Me | 2 | —C≡C—(CH$_2$)$_2$-(4-cHx-Ph) | H | H | H | H |
| 5-768 | H | H | Me | 2 | —C≡C—(CH$_2$)$_2$-(4-Ph-Ph) | H | H | H | H |
| 5-769 | H | H | Me | 2 | —C≡C—(CH$_2$)$_3$-cPn | H | H | H | H |
| 5-770 | H | H | Me | 2 | —C≡C—(CH$_2$)$_3$-cHx | H | H | H | H |
| 5-771 | H | H | Me | 2 | —C≡C—(CH$_2$)$_3$-cHx | Me | H | H | H |
| 5-772 | H | H | Me | 2 | —C≡C—(CH$_2$)$_3$-cHx | H | Me | H | H |
| 5-773 | H | H | Me | 2 | —C≡C—(CH$_2$)$_3$-cHx | F | H | H | H |
| 5-774 | H | H | Me | 2 | —C≡C—(CH$_2$)$_3$-cHx | H | F | H | H |
| 5-775 | H | Me | Me | 2 | —C≡C—(CH$_2$)$_3$-cHx | H | H | H | H |
| 5-776 | CO$_2$Me | H | Me | 2 | —C≡C—(CH$_2$)$_3$-cHx | H | H | H | H |
| 5-777 | CO$_2$Et | H | Me | 2 | —C≡C—(CH$_2$)$_3$-cHx | H | H | H | H |
| 5-778 | H | H | Me | 2 | —C≡C—(CH$_2$)$_3$-(3-F-cHx) | H | H | H | H |
| 5-779 | H | H | Me | 2 | —C≡C—(CH$_2$)$_3$-(4-F-cHx) | H | H | H | H |
| 5-780 | H | H | Me | 2 | —C≡C—(CH$_2$)$_3$-(4-Cl-cHx) | H | H | H | H |
| 5-781 | H | H | Me | 2 | —C≡C—(CH$_2$)$_3$-(4-Br-cHx) | H | H | H | H |
| 5-782 | H | H | Me | 2 | —C≡C—(CH$_2$)$_3$-(3-Me-cHx) | H | H | H | H |
| 5-783 | H | H | Me | 2 | —C≡C—(CH$_2$)$_3$-(4-Me-cHx) | H | H | H | H |
| 5-784 | H | H | Me | 2 | —C≡C—(CH$_2$)$_3$-(3-Et-cHx) | H | H | H | H |
| 5-785 | H | H | Me | 2 | —C≡C—(CH$_2$)$_3$-(4-Et-cHx) | H | H | H | H |
| 5-786 | H | H | Me | 2 | —C≡C—(CH$_2$)$_3$-(3-Pr-cHx) | H | H | H | H |
| 5-787 | H | H | Me | 2 | —C≡C—(CH$_2$)$_3$-(4-Pr-cHx) | H | H | H | H |
| 5-788 | H | H | Me | 2 | —C≡C—(CH$_2$)$_3$-(4-iPr-cHx) | H | H | H | H |
| 5-789 | H | H | Me | 2 | —C≡C—(CH$_2$)$_3$-(3-Bu-cHx) | H | H | H | H |
| 5-790 | H | H | Me | 2 | —C≡C—(CH$_2$)$_3$-(4-Bu-cHx) | H | H | H | H |
| 5-791 | H | H | Me | 2 | —C≡C—(CH$_2$)$_3$-(3-CF$_3$-cHx) | H | H | H | H |
| 5-792 | H | H | Me | 2 | —C≡C—(CH$_2$)$_3$-(4-CF$_3$-cHx) | H | H | H | H |
| 5-793 | H | H | Me | 2 | —C≡C—(CH$_2$)$_3$-(3-MeO-cHx) | H | H | H | H |
| 5-794 | H | H | Me | 2 | —C≡C—(CH$_2$)$_3$-(4-MeO-cHx) | H | H | H | H |
| 5-795 | H | H | Me | 2 | —C≡C—(CH$_2$)$_3$-(3-EtO-cHx) | H | H | H | H |
| 5-796 | H | H | Me | 2 | —C≡C—(CH$_2$)$_3$-(4-EtO-cHx) | H | H | H | H |
| 5-797 | H | H | Me | 2 | —C≡C—(CH$_2$)$_3$-(3-PrO-cHx) | H | H | H | H |
| 5-798 | H | H | Me | 2 | —C≡C—(CH$_2$)$_3$-(4-PrO-cHx) | H | H | H | H |
| 5-799 | H | H | Me | 2 | —C≡C—(CH$_2$)$_3$-(3-iPrO-cHx) | H | H | H | H |
| 5-800 | H | H | Me | 2 | —C≡C—(CH$_2$)$_3$-(4-iPrO-cHx) | H | H | H | H |
| 5-801 | H | H | Me | 2 | —C≡C—(CH$_2$)$_3$-[3-(2-Et-PrO)-cHx] | H | H | H | H |
| 5-802 | H | H | Me | 2 | —C≡C—(CH$_2$)$_3$-[4-(2-Et-PrO)-cHx] | H | H | H | H |
| 5-803 | H | H | Me | 2 | —C≡C—(CH$_2$)$_3$-(3-iBuO-cHx) | H | H | H | H |
| 5-804 | H | H | Me | 2 | —C≡C—(CH$_2$)$_3$-(4-iBuO-cHx) | H | H | H | H |
| 5-805 | H | H | Me | 2 | —C≡C—(CH$_2$)$_3$-(3-MeS-cHx) | H | H | H | H |
| 5-806 | H | H | Me | 2 | —C≡C—(CH$_2$)$_3$-(4-MeS-cHx) | H | H | H | H |
| 5-807 | H | H | Me | 2 | —C≡C—(CH$_2$)$_3$-(3-EtS-cHx) | H | H | H | H |
| 5-808 | H | H | Me | 2 | —C≡C—(CH$_2$)$_3$-(4-EtS-cHx) | H | H | H | H |
| 5-809 | H | H | Me | 2 | —C≡C—(CH$_2$)$_3$-(3-PrS-cHx) | H | H | H | H |
| 5-810 | H | H | Me | 2 | —C≡C—(CH$_2$)$_3$-(4-PrS-cHx) | H | H | H | H |
| 5-811 | H | H | Me | 2 | —C≡C—(CH$_2$)$_3$-(3-iPrS-cHx) | H | H | H | H |
| 5-812 | H | H | Me | 2 | —C≡C—(CH$_2$)$_3$-(4-iPrS-cHx) | H | H | H | H |
| 5-813 | H | H | Me | 2 | —C≡C—(CH$_2$)$_3$-[3-(2-Et-PrS)-cHx] | H | H | H | H |
| 5-814 | H | H | Me | 2 | —C≡C—(CH$_2$)$_3$-[4-(2-Et-PrS)-cHx] | H | H | H | H |
| 5-815 | H | H | Me | 2 | —C≡C—(CH$_2$)$_3$-(3-iBuS-cHx) | H | H | H | H |
| 5-816 | H | H | Me | 2 | —C≡C—(CH$_2$)$_3$-(4-iBuS-cHx) | H | H | H | H |
| 5-817 | H | H | Me | 2 | —C≡C—(CH$_2$)$_3$-(3-cHx-cHx) | H | H | H | H |
| 5-818 | H | H | Me | 2 | —C≡C—(CH$_2$)$_3$-(4-cHx-cHx) | H | H | H | H |
| 5-819 | H | H | Me | 2 | —C≡C—(CH$_2$)$_3$-(3-Ph-cHx) | H | H | H | H |
| 5-820 | H | H | Me | 2 | —C≡C—(CH$_2$)$_3$-(4-Ph-cHx) | H | H | H | H |
| 5-821 | H | H | Me | 2 | —C≡C—(CH$_2$)$_3$-(2,4-diMe-cHx) | H | H | H | H |
| 5-822 | H | H | Me | 2 | —C≡C—(CH$_2$)$_3$-(3,4-diMe-cHx) | H | H | H | H |
| 5-823 | H | H | Me | 2 | —C≡C—(CH$_2$)$_3$-(3,5-diMe-cHx) | H | H | H | H |
| 5-824 | H | H | Me | 2 | —C≡C—(CH$_2$)$_3$-Ph | H | H | H | H |
| 5-825 | H | H | Me | 2 | —C≡C—(CH$_2$)$_3$-Ph | Me | H | H | H |
| 5-826 | H | H | Me | 2 | —C≡C—(CH$_2$)$_3$-Ph | H | Me | H | H |
| 5-827 | H | H | Me | 2 | —C≡C—(CH$_2$)$_3$-Ph | F | H | H | H |
| 5-828 | H | H | Me | 2 | —C≡C—(CH$_2$)$_3$-Ph | H | F | H | H |
| 5-829 | H | Me | Me | 2 | —C≡C—(CH$_2$)$_3$-Ph | H | H | H | H |
| 5-830 | CO$_2$Me | H | Me | 2 | —C≡C—(CH$_2$)$_3$-Ph | H | H | H | H |
| 5-831 | CO$_2$Et | H | Me | 2 | —C≡C—(CH$_2$)$_3$-Ph | H | H | H | H |
| 5-832 | H | H | Me | 2 | —C≡C—(CH$_2$)$_3$-(3-F-Ph) | H | H | H | H |
| 5-833 | H | H | Me | 2 | —C≡C—(CH$_2$)$_3$-(4-F-Ph) | H | H | H | H |
| 5-834 | H | H | Me | 2 | —C≡C—(CH$_2$)$_3$-(4-Cl-Ph) | H | H | H | H |
| 5-835 | H | H | Me | 2 | —C≡C—(CH$_2$)$_3$-(4-Br-Ph) | H | H | H | H |

TABLE 5-continued

| | | | | | | | | | |
|---|---|---|---|---|---|---|---|---|---|
| 5-836 | H | H | Me | 2 | —C≡C—(CH$_2$)$_3$-(3-Me-Ph) | H | H | H | H |
| 5-837 | H | H | Me | 2 | —C≡C—(CH$_2$)$_3$-(4-Me-Ph) | H | H | H | H |
| 5-838 | H | H | Me | 2 | —C≡C—(CH$_2$)$_3$-(3-Et-Ph) | H | H | H | H |
| 5-839 | H | H | Me | 2 | —C≡C—(CH$_2$)$_3$-(4-Et-Ph) | H | H | H | H |
| 5-840 | H | H | Me | 2 | —C≡C—(CH$_2$)$_3$-(3-Pr-Ph) | H | H | H | H |
| 5-841 | H | H | Me | 2 | —C≡C—(CH$_2$)$_3$-(4-Pr-Ph) | H | H | H | H |
| 5-842 | H | H | Me | 2 | —C≡C—(CH$_2$)$_3$-(3-iPr-Ph) | H | H | H | H |
| 5-843 | H | H | Me | 2 | —C≡C—(CH$_2$)$_3$-(4-iPr-Ph) | H | H | H | H |
| 5-844 | H | H | Me | 2 | —C≡C—(CH$_2$)$_3$-(3-Bu-Ph) | H | H | H | H |
| 5-845 | H | H | Me | 2 | —C≡C—(CH$_2$)$_3$-(4-Bu-Ph) | H | H | H | H |
| 5-846 | H | H | Me | 2 | —C≡C—(CH$_2$)$_3$-(3-CF$_3$-Ph) | H | H | H | H |
| 5-847 | H | H | Me | 2 | —C≡C—(CH$_2$)$_3$-(4-CF$_3$-Ph) | H | H | H | H |
| 5-848 | H | H | Me | 2 | —C≡C—(CH$_2$)$_3$-(3-MeO-Ph) | H | H | H | H |
| 5-849 | H | H | Me | 2 | —C≡C—(CH$_2$)$_3$-(4-MeO-Ph) | H | H | H | H |
| 5-850 | H | H | Me | 2 | —C≡C—(CH$_2$)$_3$-(3-EtO-Ph) | H | H | H | H |
| 5-851 | H | H | Me | 2 | —C≡C—(CH$_2$)$_3$-(4-EtO-Ph) | H | H | H | H |
| 5-852 | H | H | Me | 2 | —C≡C—(CH$_2$)$_3$-(3-PrO-Ph) | H | H | H | H |
| 5-853 | H | H | Me | 2 | —C≡C—(CH$_2$)$_3$-(4-PrO-Ph) | H | H | H | H |
| 5-854 | H | H | Me | 2 | —C≡C—(CH$_2$)$_3$-(3-iPrO-Ph) | H | H | H | H |
| 5-855 | H | H | Me | 2 | —C≡C—(CH$_2$)$_3$-(4-iPrO-Ph) | H | H | H | H |
| 5-856 | H | H | Me | 2 | —C≡C—(CH$_2$)$_3$-[3-(2-Et-PrO)-Ph] | H | H | H | H |
| 5-857 | H | H | Me | 2 | —C≡C—(CH$_2$)$_3$-[4-(2-Et-PrO)-Ph] | H | H | H | H |
| 5-858 | H | H | Me | 2 | —C≡C—(CH$_2$)$_3$-(3-iBuO-Ph) | H | H | H | H |
| 5-859 | H | H | Me | 2 | —C≡C—(CH$_2$)$_3$-(4-iBuO-Ph) | H | H | H | H |
| 5-860 | H | H | Me | 2 | —C≡C—(CH$_2$)$_3$-(3-MeS-Ph) | H | H | H | H |
| 5-861 | H | H | Me | 2 | —C≡C—(CH$_2$)$_3$-(4-MeS-Ph) | H | H | H | H |
| 5-862 | H | H | Me | 2 | —C≡C—(CH$_2$)$_3$-(3-EtS-Ph) | H | H | H | H |
| 5-863 | H | H | Me | 2 | —C≡C—(CH$_2$)$_3$-(4-EtS-Ph) | H | H | H | H |
| 5-864 | H | H | Me | 2 | —C≡C—(CH$_2$)$_3$-(3-PrS-Ph) | H | H | H | H |
| 5-865 | H | H | Me | 2 | —C≡C—(CH$_2$)$_3$-(4-PrS-Ph) | H | H | H | H |
| 5-866 | H | H | Me | 2 | —C≡C—(CH$_2$)$_3$-(3-iPrS-Ph) | H | H | H | H |
| 5-867 | H | H | Me | 2 | —C≡C—(CH$_2$)$_3$-(4-iPrS-Ph) | H | H | H | H |
| 5-868 | H | H | Me | 2 | —C≡C—(CH$_2$)$_3$-[3-(2-Et-PrS)-Ph] | H | H | H | H |
| 5-869 | H | H | Me | 2 | —C≡C—(CH$_2$)$_3$-[4-(2-Et-PrS)-Ph] | H | H | H | H |
| 5-870 | H | H | Me | 2 | —C≡C—(CH$_2$)$_3$-(3-iBuS-Ph) | H | H | H | H |
| 5-871 | H | H | Me | 2 | —C≡C—(CH$_2$)$_3$-(4-iBuS-Ph) | H | H | H | H |
| 5-872 | H | H | Me | 2 | —C≡C—(CH$_2$)$_3$-(3-cHx-Ph) | H | H | H | H |
| 5-873 | H | H | Me | 2 | —C≡C—(CH$_2$)$_3$-(4-cHx-Ph) | H | H | H | H |
| 5-874 | H | H | Me | 2 | —C≡C—(CH$_2$)$_3$-(3-Ph-Ph) | H | H | H | H |
| 5-875 | H | H | Me | 2 | —C≡C—(CH$_2$)$_3$-(4-Ph-Ph) | H | H | H | H |
| 5-876 | H | H | Me | 2 | —C≡C—(CH$_2$)$_3$-(2,4-diMe-Ph) | H | H | H | H |
| 5-877 | H | H | Me | 2 | —C≡C—(CH$_2$)$_3$-(3,4-diMe-Ph) | H | H | H | H |
| 5-878 | H | H | Me | 2 | —C≡C—(CH$_2$)$_3$-(3,5-diMe-Ph) | H | H | H | H |
| 5-879 | H | H | Me | 2 | —C≡C—(CH$_2$)$_3$-Np (1) | H | H | H | H |
| 5-880 | H | H | Me | 2 | —C≡C—(CH$_2$)$_3$-Np (2) | H | H | H | H |
| 5-881 | H | H | Me | 2 | —C≡C—(CH$_2$)$_4$-cPn | H | H | H | H |
| 5-882 | H | H | Me | 2 | —C≡C—(CH$_2$)$_4$-cHx | H | H | H | H |
| 5-883 | H | H | Me | 2 | —C≡C—(CH$_2$)$_4$-cHx | Me | H | H | H |
| 5-884 | H | H | Me | 2 | —C≡C—(CH$_2$)$_4$-cHx | H | Me | H | H |
| 5-885 | H | H | Me | 2 | —C≡C—(CH$_2$)$_4$-cHx | F | H | H | H |
| 5-886 | H | H | Me | 2 | —C≡C—(CH$_2$)$_4$-cHx | H | F | H | H |
| 5-887 | H | Me | Me | 2 | —C≡C—(CH$_2$)$_4$-cHx | H | H | H | H |
| 5-888 | CO$_2$Me | H | Me | 2 | —C≡C—(CH$_2$)$_4$-cHx | H | H | H | H |
| 5-889 | CO$_2$Et | H | Me | 2 | —C≡C—(CH$_2$)$_4$-cHx | H | H | H | H |
| 5-890 | H | H | Me | 2 | —C≡C—(CH$_2$)$_4$-(3-F-cHx) | H | H | H | H |
| 5-891 | H | H | Me | 2 | —C≡C—(CH$_2$)$_4$-(4-F-cHx) | H | H | H | H |
| 5-892 | H | H | Me | 2 | —C≡C—(CH$_2$)$_4$-(4-Cl-cHx) | H | H | H | H |
| 5-893 | H | H | Me | 2 | —C≡C—(CH$_2$)$_4$-(4-Br-cHx) | H | H | H | H |
| 5-894 | H | H | Me | 2 | —C≡C—(CH$_2$)$_4$-(3-Me-cHx) | H | H | H | H |
| 5-895 | H | H | Me | 2 | —C≡C—(CH$_2$)$_4$-(4-Me-cHx) | H | H | H | H |
| 5-896 | H | H | Me | 2 | —C≡C—(CH$_2$)$_4$-(3-Et-cHx) | H | H | H | H |
| 5-897 | H | H | Me | 2 | —C≡C—(CH$_2$)$_4$-(4-Et-cHx) | H | H | H | H |
| 5-898 | H | H | Me | 2 | —C≡C—(CH$_2$)$_4$-(3-Pr-cHx) | H | H | H | H |
| 5-899 | H | H | Me | 2 | —C≡C—(CH$_2$)$_4$-(4-Pr-cHx) | H | H | H | H |
| 5-900 | H | H | Me | 2 | —C≡C—(CH$_2$)$_4$-(4-iPr-cHx) | H | H | H | H |
| 5-901 | H | H | Me | 2 | —C≡C—(CH$_2$)$_4$-(3-Bu-cHx) | H | H | H | H |
| 5-902 | H | H | Me | 2 | —C≡C—(CH$_2$)$_4$-(4-Bu-cHx) | H | H | H | H |
| 5-903 | H | H | Me | 2 | —C≡C—(CH$_2$)$_4$-(3-CF$_3$-cHx) | H | H | H | H |
| 5-904 | H | H | Me | 2 | —C≡C—(CH$_2$)$_4$-(4-CF$_3$-cHx) | H | H | H | H |
| 5-905 | H | H | Me | 2 | —C≡C—(CH$_2$)$_4$-(3-MeO-cHx) | H | H | H | H |
| 5-906 | H | H | Me | 2 | —C≡C—(CH$_2$)$_4$-(4-MeO-cHx) | H | H | H | H |
| 5-907 | H | H | Me | 2 | —C≡C—(CH$_2$)$_4$-(3-EtO-cHx) | H | H | H | H |
| 5-908 | H | H | Me | 2 | —C≡C—(CH$_2$)$_4$-(4-EtO-cHx) | H | H | H | H |
| 5-909 | H | H | Me | 2 | —C≡C—(CH$_2$)$_4$-(3-PrO-cHx) | H | H | H | H |
| 5-910 | H | H | Me | 2 | —C≡C—(CH$_2$)$_4$-(4-PrO-cHx) | H | H | H | H |
| 5-911 | H | H | Me | 2 | —C≡C—(CH$_2$)$_4$-(3-iPrO-cHx) | H | H | H | H |
| 5-912 | H | H | Me | 2 | —C≡C—(CH$_2$)$_4$-(4-iPrO-cHx) | H | H | H | H |
| 5-913 | H | H | Me | 2 | —C≡C—(CH$_2$)$_4$-[3-(2-Et-PrO)-cHx] | H | H | H | H |
| 5-914 | H | H | Me | 2 | —C≡C—(CH$_2$)$_4$-[4-(2-Et-PrO)-cHx] | H | H | H | H |
| 5-915 | H | H | Me | 2 | —C≡C—(CH$_2$)$_4$-(3-iBuO-cHx) | H | H | H | H |

TABLE 5-continued

| | | | | | | | | | |
|---|---|---|---|---|---|---|---|---|---|
| 5-916 | H | H | Me | 2 | —C≡C—(CH$_2$)$_4$-(4-iBuO-cHx) | H | H | H | H |
| 5-917 | H | H | Me | 2 | —C≡C—(CH$_2$)$_4$-(3-MeS-cHx) | H | H | H | H |
| 5-918 | H | H | Me | 2 | —C≡C—(CH$_2$)$_4$-(4-MeS-cHx) | H | H | H | H |
| 5-919 | H | H | Me | 2 | —C≡C—(CH$_2$)$_4$-(3-EtS-cHx) | H | H | H | H |
| 5-920 | H | H | Me | 2 | —C≡C—(CH$_2$)$_4$-(4-EtS-cHx) | H | H | H | H |
| 5-921 | H | H | Me | 2 | —C≡C—(CH$_2$)$_4$-(3-PrS-cHx) | H | H | H | H |
| 5-922 | H | H | Me | 2 | —C≡C—(CH$_2$)$_4$-(4-PrS-cHx) | H | H | H | H |
| 5-923 | H | H | Me | 2 | —C≡C—(CH$_2$)$_4$-(3-iPrS-cHx) | H | H | H | H |
| 5-924 | H | H | Me | 2 | —C≡C—(CH$_2$)$_4$-(4-iPrS-cHx) | H | H | H | H |
| 5-925 | H | H | Me | 2 | —C≡C—(CH$_2$)$_4$-[3-(2-Et-PrS)-cHx] | H | H | H | H |
| 5-926 | H | H | Me | 2 | —C≡C—(CH$_2$)$_4$-[4-(2-Et-PrS)-cHx] | H | H | H | H |
| 5-927 | H | H | Me | 2 | —C≡C—(CH$_2$)$_4$-(3-iBuS-cHx) | H | H | H | H |
| 5-928 | H | H | Me | 2 | —C≡C—(CH$_2$)$_4$-(4-iBuS-cHx) | H | H | H | H |
| 5-929 | H | H | Me | 2 | —C≡C—(CH$_2$)$_4$-(3-cHx-cHx) | H | H | H | H |
| 5-930 | H | H | Me | 2 | —C≡C—(CH$_2$)$_4$-(4-cHx-cHx) | H | H | H | H |
| 5-931 | H | H | Me | 2 | —C≡C—(CH$_2$)$_4$-(3-Ph-cHx) | H | H | H | H |
| 5-932 | H | H | Me | 2 | —C≡C—(CH$_2$)$_4$-(4-Ph-cHx) | H | H | H | H |
| 5-933 | H | H | Me | 2 | —C≡C—(CH$_2$)$_4$-(2,4-diMe-cHx) | H | H | H | H |
| 5-934 | H | H | Me | 2 | —C≡C—(CH$_2$)$_4$-(3,4-diMe-cHx) | H | H | H | H |
| 5-935 | H | H | Me | 2 | —C≡C—(CH$_2$)$_4$-(3,5-diMe-cHx) | H | H | H | H |
| 5-936 | H | H | Me | 2 | —C≡C—(CH$_2$)$_4$-Ph | H | H | H | H |
| 5-937 | H | H | Me | 2 | —C≡C—(CH$_2$)$_4$-Ph | Me | H | H | H |
| 5-938 | H | H | Me | 2 | —C≡C—(CH$_2$)$_4$-Ph | H | Me | H | H |
| 5-939 | H | H | Me | 2 | —C≡C—(CH$_2$)$_4$-Ph | F | H | H | H |
| 5-940 | H | H | Me | 2 | —C≡C—(CH$_2$)$_4$-Ph | H | F | H | H |
| 5-941 | H | Me | Me | 2 | —C≡C—(CH$_2$)$_4$-Ph | H | H | H | H |
| 5-942 | CO$_2$Me | H | Me | 2 | —C≡C—(CH$_2$)$_4$-Ph | H | H | H | H |
| 5-943 | CO$_2$Et | H | Me | 2 | —C≡C—(CH$_2$)$_4$-Ph | H | H | H | H |
| 5-944 | H | H | Me | 2 | —C≡C—(CH$_2$)$_4$-(3-F-Ph) | H | H | H | H |
| 5-945 | H | H | Me | 2 | —C≡C—(CH$_2$)$_4$-(4-F-Ph) | H | H | H | H |
| 5-946 | H | H | Me | 2 | —C≡C—(CH$_2$)$_4$-(4-Cl-Ph) | H | H | H | H |
| 5-947 | H | H | Me | 2 | —C≡C—(CH$_2$)$_4$-(4-Br-Ph) | H | H | H | H |
| 5-948 | H | H | Me | 2 | —C≡C—(CH$_2$)$_4$-(3-Me-Ph) | H | H | H | H |
| 5-949 | H | H | Me | 2 | —C≡C—(CH$_2$)$_4$-(4-Me-Ph) | H | H | H | H |
| 5-950 | H | H | Me | 2 | —C≡C—(CH$_2$)$_4$-(3-Et-Ph) | H | H | H | H |
| 5-951 | H | H | Me | 2 | —C≡C—(CH$_2$)$_4$-(4-Et-Ph) | H | H | H | H |
| 5-952 | H | H | Me | 2 | —C≡C—(CH$_2$)$_4$-(3-Pr-Ph) | H | H | H | H |
| 5-953 | H | H | Me | 2 | —C≡C—(CH$_2$)$_4$-(4-Pr-Ph) | H | H | H | H |
| 5-954 | H | H | Me | 2 | —C≡C—(CH$_2$)$_4$-(3-iPr-Ph) | H | H | H | H |
| 5-955 | H | H | Me | 2 | —C≡C—(CH$_2$)$_4$-(4-iPr-Ph) | H | H | H | H |
| 5-956 | H | H | Me | 2 | —C≡C—(CH$_2$)$_4$-(3-Bu-Ph) | H | H | H | H |
| 5-957 | H | H | Me | 2 | —C≡C—(CH$_2$)$_4$-(4-Bu-Ph) | H | H | H | H |
| 5-958 | H | H | Me | 2 | —C≡C—(CH$_2$)$_4$-(3-CF$_3$-Ph) | H | H | H | H |
| 5-959 | H | H | Me | 2 | —C≡C—(CH$_2$)$_4$-(4-CF$_3$-Ph) | H | H | H | H |
| 5-960 | H | H | Me | 2 | —C≡C—(CH$_2$)$_4$-(3-MeO-Ph) | H | H | H | H |
| 5-961 | H | H | Me | 2 | —C≡C—(CH$_2$)$_4$-(4-MeO-Ph) | H | H | H | H |
| 5-962 | H | H | Me | 2 | —C≡C—(CH$_2$)$_4$-(3-EtO-Ph) | H | H | H | H |
| 5-963 | H | H | Me | 2 | —C≡C—(CH$_2$)$_4$-(4-EtO-Ph) | H | H | H | H |
| 5-964 | H | H | Me | 2 | —C≡C—(CH$_2$)$_4$-(3-PrO-Ph) | H | H | H | H |
| 5-965 | H | H | Me | 2 | —C≡C—(CH$_2$)$_4$-(4-PrO-Ph) | H | H | H | H |
| 5-966 | H | H | Me | 2 | —C≡C—(CH$_2$)$_4$-(3-iPrO-Ph) | H | H | H | H |
| 5-967 | H | H | Me | 2 | —C≡C—(CH$_2$)$_4$-(4-iPrO-Ph) | H | H | H | H |
| 5-968 | H | H | Me | 2 | —C≡C—(CH$_2$)$_4$-[3-(2-Et-PrO)-Ph] | H | H | H | H |
| 5-969 | H | H | Me | 2 | —C≡C—(CH$_2$)$_4$-[4-(2-Et-PrO)-Ph] | H | H | H | H |
| 5-970 | H | H | Me | 2 | —C≡C—(CH$_2$)$_4$-(3-iBuO-Ph) | H | H | H | H |
| 5-971 | H | H | Me | 2 | —C≡C—(CH$_2$)$_4$-(4-iBuO-Ph) | H | H | H | H |
| 5-972 | H | H | Me | 2 | —C≡C—(CH$_2$)$_4$-(3-MeS-Ph) | H | H | H | H |
| 5-973 | H | H | Me | 2 | —C≡C—(CH$_2$)$_4$-(4-MeS-Ph) | H | H | H | H |
| 5-974 | H | H | Me | 2 | —C≡C—(CH$_2$)$_4$-(3-EtS-Ph) | H | H | H | H |
| 5-975 | H | H | Me | 2 | —C≡C—(CH$_2$)$_4$-(4-EtS-Ph) | H | H | H | H |
| 5-976 | H | H | Me | 2 | —C≡C—(CH$_2$)$_4$-(3-PrS-Ph) | H | H | H | H |
| 5-977 | H | H | Me | 2 | —C≡C—(CH$_2$)$_4$-(4-PrS-Ph) | H | H | H | H |
| 5-978 | H | H | Me | 2 | —C≡C—(CH$_2$)$_4$-(3-iPrS-Ph) | H | H | H | H |
| 5-979 | H | H | Me | 2 | —C≡C—(CH$_2$)$_4$-(4-iPrS-Ph) | H | H | H | H |
| 5-980 | H | H | Me | 2 | —C≡C—(CH$_2$)$_4$-[3-(2-Et-PrS)-Ph] | H | H | H | H |
| 5-981 | H | H | Me | 2 | —C≡C—(CH$_2$)$_4$-[4-(2-Et-PrS)-Ph] | H | H | H | H |
| 5-982 | H | H | Me | 2 | —C≡C—(CH$_2$)$_4$-(3-iBuS-Ph) | H | H | H | H |
| 5-983 | H | H | Me | 2 | —C≡C—(CH$_2$)$_4$-(4-iBuS-Ph) | H | H | H | H |
| 5-984 | H | H | Me | 2 | —C≡C—(CH$_2$)$_4$-(3-cHx-Ph) | H | H | H | H |
| 5-985 | H | H | Me | 2 | —C≡C—(CH$_2$)$_4$-(4-cHx-Ph) | H | H | H | H |
| 5-986 | H | H | Me | 2 | —C≡C—(CH$_2$)$_4$-(3-Ph-Ph) | H | H | H | H |
| 5-987 | H | H | Me | 2 | —C≡C—(CH$_2$)$_4$-(4-Ph-Ph) | H | H | H | H |
| 5-988 | H | H | Me | 2 | —C≡C—(CH$_2$)$_4$-(2,4-diMe-Ph) | H | H | H | H |
| 5-989 | H | H | Me | 2 | —C≡C—(CH$_2$)$_4$-(3,4-diMe-Ph) | H | H | H | H |
| 5-990 | H | H | Me | 2 | —C≡C—(CH$_2$)$_4$-(3,5-diMe-Ph) | H | H | H | H |
| 5-991 | H | H | Me | 2 | —C≡C—(CH$_2$)$_4$-Np (1) | H | H | H | H |
| 5-992 | H | H | Me | 2 | —C≡C—(CH$_2$)$_4$-Np (2) | H | H | H | H |
| 5-993 | H | H | Me | 2 | —C≡C—(CH$_2$)$_5$-cHx | H | H | H | H |
| 5-994 | H | Me | Me | 2 | —C≡C—(CH$_2$)$_5$-cHx | H | H | H | H |
| 5-995 | CO$_2$Me | H | Me | 2 | —C≡C—(CH$_2$)$_5$-cHx | H | H | H | H |

TABLE 5-continued

| | | | | | | | | | | |
|---|---|---|---|---|---|---|---|---|---|---|
| 5-996 | CO$_2$Et | H | Me | 2 | —C≡C—(CH$_2$)$_5$-cHx | H | H | H | H |
| 5-997 | H | H | Me | 2 | —C≡C—(CH$_2$)$_5$-(4-F-cHx) | H | H | H | H |
| 5-998 | H | H | Me | 2 | —C≡C—(CH$_2$)$_5$-(4-Me-cHx) | H | H | H | H |
| 5-999 | H | H | Me | 2 | —C≡C—(CH$_2$)$_5$-(4-Et-cHx) | H | H | H | H |
| 5-1000 | H | H | Me | 2 | —C≡C—(CH$_2$)$_5$-(4-CF$_3$-cHx) | H | H | H | H |
| 5-1001 | H | H | Me | 2 | —C≡C—(CH$_2$)$_5$-(4-MeO-cHx) | H | H | H | H |
| 5-1002 | H | H | Me | 2 | —C≡C—(CH$_2$)$_5$-(4-EtO-cHx) | H | H | H | H |
| 5-1003 | H | H | Me | 2 | —C≡C—(CH$_2$)$_5$-(4-MeS-cHx) | H | H | H | H |
| 5-1004 | H | H | Me | 2 | —C≡C—(CH$_2$)$_5$-(4-cHx-cHx) | H | H | H | H |
| 5-1005 | H | H | Me | 2 | —C≡C—(CH$_2$)$_5$-(4-Ph-cHx) | H | H | H | H |
| 5-1006 | H | H | Me | 2 | —C≡C—(CH$_2$)$_5$-Ph | H | H | H | H |
| 5-1007 | H | Me | Me | 2 | —C≡C—(CH$_2$)$_5$-Ph | H | H | H | H |
| 5-1008 | CO$_2$Me | H | Me | 2 | —C≡C—(CH$_2$)$_5$-Ph | H | H | H | H |
| 5-1009 | CO$_2$Et | H | Me | 2 | —C≡C—(CH$_2$)$_5$-Ph | H | H | H | H |
| 5-1010 | H | H | Me | 2 | —C≡C—(CH$_2$)$_5$-(4-F-Ph) | H | H | H | H |
| 5-1011 | H | H | Me | 2 | —C≡C—(CH$_2$)$_5$-(4-Me-Ph) | H | H | H | H |
| 5-1012 | H | H | Me | 2 | —C≡C—(CH$_2$)$_5$-(4-Et-Ph) | H | H | H | H |
| 5-1013 | H | H | Me | 2 | —C≡C—(CH$_2$)$_5$-(4-CF$_3$-Ph) | H | H | H | H |
| 5-1014 | H | H | Me | 2 | —C≡C—(CH$_2$)$_5$-(4-MeO-Ph) | H | H | H | H |
| 5-1015 | H | H | Me | 2 | —C≡C—(CH$_2$)$_5$-(4-EtO-Ph) | H | H | H | H |
| 5-1016 | H | H | Me | 2 | —C≡C—(CH$_2$)$_5$-(4-MeS-Ph) | H | H | H | H |
| 5-1017 | H | H | Me | 2 | —C≡C—(CH$_2$)$_5$-(4-cHx-Ph) | H | H | H | H |
| 5-1018 | H | H | Me | 2 | —C≡C—(CH$_2$)$_5$-(4-Ph-Ph) | H | H | H | H |
| 5-1019 | H | H | Me | 2 | —C≡C—(CH$_2$)$_6$-cHx | H | H | H | H |
| 5-1020 | H | Me | Me | 2 | —C≡C—(CH$_2$)$_6$-cHx | H | H | H | H |
| 5-1021 | CO$_2$Me | H | Me | 2 | —C≡C—(CH$_2$)$_6$-cHx | H | H | H | H |
| 5-1022 | CO$_2$Et | H | Me | 2 | —C≡C—(CH$_2$)$_6$-cHx | H | H | H | H |
| 5-1023 | H | H | Me | 2 | —C≡C—(CH$_2$)$_6$-(4-F-cHx) | H | H | H | H |
| 5-1024 | H | H | Me | 2 | —C≡C—(CH$_2$)$_6$-(4-Me-cHx) | H | H | H | H |
| 5-1025 | H | H | Me | 2 | —C≡C—(CH$_2$)$_6$-(4-Et-cHx) | H | H | H | H |
| 5-1026 | H | H | Me | 2 | —C≡C—(CH$_2$)$_6$-(4-CF$_3$-cHx) | H | H | H | H |
| 5-1027 | H | H | Me | 2 | —C≡C—(CH$_2$)$_6$-(4-MeO-cHx) | H | H | H | H |
| 5-1028 | H | H | Me | 2 | —C≡C—(CH$_2$)$_6$-(4-EtO-cHx) | H | H | H | H |
| 5-1029 | H | H | Me | 2 | —C≡C—(CH$_2$)$_6$-(4-MeS-cHx) | H | H | H | H |
| 5-1030 | H | H | Me | 2 | —C≡C—(CH$_2$)$_6$-(4-cHx-cHx) | H | H | H | H |
| 5-1031 | H | H | Me | 2 | —C≡C—(CH$_2$)$_6$-(4-Ph-cHx) | H | H | H | H |
| 5-1032 | H | H | Me | 2 | —C≡C—(CH$_2$)$_6$-Ph | H | H | H | H |
| 5-1033 | H | Me | Me | 2 | —C≡C—(CH$_2$)$_6$-Ph | H | H | H | H |
| 5-1034 | CO$_2$Me | H | Me | 2 | —C≡C—(CH$_2$)$_6$-Ph | H | H | H | H |
| 5-1035 | CO$_2$Et | H | Me | 2 | —C≡C—(CH$_2$)$_6$-Ph | H | H | H | H |
| 5-1036 | H | H | Me | 2 | —C≡C—(CH$_2$)$_6$-(4-F-Ph) | H | H | H | H |
| 5-1037 | H | H | Me | 2 | —C≡C—(CH$_2$)$_6$-(4-Me-Ph) | H | H | H | H |
| 5-1038 | H | H | Me | 2 | —C≡C—(CH$_2$)$_6$-(4-Et-Ph) | H | H | H | H |
| 5-1039 | H | H | Me | 2 | —C≡C—(CH$_2$)$_6$-(4-CF$_3$-Ph) | H | H | H | H |
| 5-1040 | H | H | Me | 2 | —C≡C—(CH$_2$)$_6$-(4-MeO-Ph) | H | H | H | H |
| 5-1041 | H | H | Me | 2 | —C≡C—(CH$_2$)$_6$-(4-Et0-Ph) | H | H | H | H |
| 5-1042 | H | H | Me | 2 | —C≡C—(CH$_2$)$_6$-(4-MeS-Ph) | H | H | H | H |
| 5-1043 | H | H | Me | 2 | —C≡C—(CH$_2$)$_6$-(4-cHx-Ph) | H | H | H | H |
| 5-1044 | H | H | Me | 2 | —C≡C—(CH$_2$)$_6$-(4-Ph-Ph) | H | H | H | H |
| 5-1045 | H | H | Me | 2 | —C≡C—CH$_2$—O-cHx | H | H | H | H |
| 5-1046 | H | Me | Me | 2 | —C≡C—CH$_2$—O-cHx | H | H | H | H |
| 5-1047 | CO$_2$Me | H | Me | 2 | —C≡C—CH$_2$—O-cHx | H | H | H | H |
| 5-1048 | CO$_2$Et | H | Me | 2 | —C≡C—CH$_2$—O-cHx | H | H | H | H |
| 5-1049 | H | H | Me | 2 | —C≡C—CH$_2$—O-(4-F-cHx) | H | H | H | H |
| 5-1050 | H | H | Me | 2 | —C≡C—CH$_2$—O-(4-Me-cHx) | H | H | H | H |
| 5-1051 | H | H | Me | 2 | —C≡C—CH$_2$—O-(4-Et-cHx) | H | H | H | H |
| 5-1052 | H | H | Me | 2 | —C≡C—CH$_2$—O-(4-CF$_3$-cHx) | H | H | H | H |
| 5-1053 | H | H | Me | 2 | —C≡C—CH$_2$—O-(4-MeO-cHx) | H | H | H | H |
| 5-1054 | H | H | Me | 2 | —C≡C—CH$_2$—O-(4-EtO-cHx) | H | H | H | H |
| 5-1055 | H | H | Me | 2 | —C≡C—CH$_2$—O-(4-MeS-cHx) | H | H | H | H |
| 5-1056 | H | H | Me | 2 | —C≡C—CH$_2$—O-(4-cHx-cHx) | H | H | H | H |
| 5-1057 | H | H | Me | 2 | —C≡C—CH$_2$—O-(4-Ph-cHx) | H | H | H | H |
| 5-1058 | H | H | Me | 2 | —C≡C—CH$_2$—O-Ph | H | H | H | H |
| 5-1059 | H | Me | Me | 2 | —C≡C—CH$_2$—O-Ph | H | H | H | H |
| 5-1060 | CO$_2$Me | H | Me | 2 | —C≡C—CH$_2$—O-Ph | H | H | H | H |
| 5-1061 | CO$_2$Et | H | Me | 2 | —C≡C—CH$_2$—O-Ph | H | H | H | H |
| 5-1062 | H | H | Me | 2 | —C≡C—CH$_2$—O-(4-F-Ph) | H | H | H | H |
| 5-1063 | H | H | Me | 2 | —C≡C—CH$_2$—O-(4-Me-Ph) | H | H | H | H |
| 5-1064 | H | H | Me | 2 | —C≡C—CH$_2$—O-(4-Et-Ph) | H | H | H | H |
| 5-1065 | H | H | Me | 2 | —C≡C—CH$_2$—O-(4-CF$_3$-Ph) | H | H | H | H |
| 5-1066 | H | H | Me | 2 | —C≡C—CH$_2$—O-(4-MeO-Ph) | H | H | H | H |
| 5-1067 | H | H | Me | 2 | —C≡C—CH$_2$—O-(4-EtO-Ph) | H | H | H | H |
| 5-1068 | H | H | Me | 2 | —C≡C—CH$_2$—O-(4-MeS-Ph) | H | H | H | H |
| 5-1069 | H | H | Me | 2 | —C≡C—CH$_2$—O-(4-cHx-Ph) | H | H | H | H |
| 5-1070 | H | H | Me | 2 | —C≡C—CH$_2$—O-(4-Ph-Ph) | H | H | H | H |
| 5-1071 | H | H | Me | 2 | —C≡C—(CH$_2$)$_2$O-cPn | H | H | H | H |
| 5-1072 | H | H | Me | 2 | —C≡C—(CH$_2$)$_2$O-cHx | H | H | H | H |
| 5-1073 | H | H | Me | 2 | —C≡C—(CH$_2$)$_2$O-cHx | Me | H | H | H |
| 5-1074 | H | H | Me | 2 | —C≡C—(CH$_2$)$_2$O-cHx | H | Me | H | H |
| 5-1075 | H | H | Me | 2 | —C≡C—(CH$_2$)$_2$O-cHx | F | H | H | H |

TABLE 5-continued

| | | | | | | | | | |
|---|---|---|---|---|---|---|---|---|---|
| 5-1076 | H | H | Me | 2 | —C≡C—(CH$_2$)$_2$O-cHx | H | F | H | H |
| 5-1077 | H | Me | Me | 2 | —C≡C—(CH$_2$)$_2$O-cHx | H | H | H | H |
| 5-1078 | CO$_2$Me | H | Me | 2 | —C≡C—(CH$_2$)$_2$O-cHx | H | H | H | H |
| 5-1079 | CO$_2$Et | H | Me | 2 | —C≡C—(CH$_2$)$_2$O-cHx | H | H | H | H |
| 5-1080 | H | H | Me | 2 | —C≡C—(CH$_2$)$_2$O-(3-F-cHx) | H | H | H | H |
| 5-1081 | H | H | Me | 2 | —C≡C—(CH$_2$)$_2$O-(4-F-cHx) | H | H | H | H |
| 5-1082 | H | H | Me | 2 | —C≡C—(CH$_2$)$_2$O-(4-Cl-cHx) | H | H | H | H |
| 5-1083 | H | H | Me | 2 | —C≡C—(CH$_2$)$_2$O-(4-Br-cHx) | H | H | H | H |
| 5-1084 | H | H | Me | 2 | —C≡C—(CH$_2$)$_2$O-(3-Me-cHx) | H | H | H | H |
| 5-1085 | H | H | Me | 2 | —C≡C—(CH$_2$)$_2$O-(4-Me-cHx) | H | H | H | H |
| 5-1086 | H | H | Me | 2 | —C≡C—(CH$_2$)$_2$O-(3-Et-cHx) | H | H | H | H |
| 5-1087 | H | H | Me | 2 | —C≡C—(CH$_2$)$_2$O-(4-Et-cHx) | H | H | H | H |
| 5-1088 | H | H | Me | 2 | —C≡C—(CH$_2$)$_2$O-(3-Pr-cHx) | H | H | H | H |
| 5-1089 | H | H | Me | 2 | —C≡C—(CH$_2$)$_2$O-(4-Pr-cHx) | H | H | H | H |
| 5-1090 | H | H | Me | 2 | —C≡C—(CH$_2$)$_2$O-(4-iPr-cHx) | H | H | H | H |
| 5-1091 | H | H | Me | 2 | —C≡C—(CH$_2$)$_2$O-(3-Bu-cHx) | H | H | H | H |
| 5-1092 | H | H | Me | 2 | —C≡C—(CH$_2$)$_2$O-(4-Bu-cHx) | H | H | H | H |
| 5-1093 | H | H | Me | 2 | —C≡C—(CH$_2$)$_2$O-(3-CF$_3$-cHx) | H | H | H | H |
| 5-1094 | H | H | Me | 2 | —C≡C—(CH$_2$)$_2$O-(4-CF$_3$-cHx) | H | H | H | H |
| 5-1095 | H | H | Me | 2 | —C≡C—(CH$_2$)$_2$O-(3-MeO-cHx) | H | H | H | H |
| 5-1096 | H | H | Me | 2 | —C≡C—(CH$_2$)$_2$O-(4-MeO-cHx) | H | H | H | H |
| 5-1097 | H | H | Me | 2 | —C≡C—(CH$_2$)$_2$O-(3-EtO-cHx) | H | H | H | H |
| 5-1098 | H | H | Me | 2 | —C≡C—(CH$_2$)$_2$O-(4-EtO-cHx) | H | H | H | H |
| 5-1099 | H | H | Me | 2 | —C≡C—(CH$_2$)$_2$O-(3-PrO-cHx) | H | H | H | H |
| 5-1100 | H | H | Me | 2 | —C≡C—(CH$_2$)$_2$O-(4-PrO-cHx) | H | H | H | H |
| 5-1101 | H | H | Me | 2 | —C≡C—(CH$_2$)$_2$O-(3-iPrO-cHx) | H | H | H | H |
| 5-1102 | H | H | Me | 2 | —C≡C—(CH$_2$)$_2$O-(4-iPrO-cHx) | H | H | H | H |
| 5-1103 | H | H | Me | 2 | —C≡C—(CH$_2$)$_2$O-[3-(2-Et-PrO)-cHx] | H | H | H | H |
| 5-1104 | H | H | Me | 2 | —C≡C—(CH$_2$)$_2$O-[4-(2-Et-PrO)-cHx] | H | H | H | H |
| 5-1105 | H | H | Me | 2 | —C≡C—(CH$_2$)$_2$O-(3-iBuO-cHx) | H | H | H | H |
| 5-1106 | H | H | Me | 2 | —C≡C—(CH$_2$)$_2$O-(4-iBuO-cHx) | H | H | H | H |
| 5-1107 | H | H | Me | 2 | —C≡C—(CH$_2$)$_2$O-(3-MeS-cHx) | H | H | H | H |
| 5-1108 | H | H | Me | 2 | —C≡C—(CH$_2$)$_2$O-(4-MeS-cHx) | H | H | H | H |
| 5-1109 | H | H | Me | 2 | —C≡C—(CH$_2$)$_2$O-(3-EtS-cHx) | H | H | H | H |
| 5-1110 | H | H | Me | 2 | —C≡C—(CH$_2$)$_2$O-(4-EtS-cHx) | H | H | H | H |
| 5-1111 | H | H | Me | 2 | —C≡C—(CH$_2$)$_2$O-(3-PrS-cHx) | H | H | H | H |
| 5-1112 | H | H | Me | 2 | —C≡C—(CH$_2$)$_2$O-(4-PrS-cHx) | H | H | H | H |
| 5-1113 | H | H | Me | 2 | —C≡C—(CH$_2$)$_2$O-(3-iPrS-cHx) | H | H | H | H |
| 5-1114 | H | H | Me | 2 | —C≡C—(CH$_2$)$_2$O-(4-iPrS-cHx) | H | H | H | H |
| 5-1115 | H | H | Me | 2 | —C≡C—(CH$_2$)$_2$O-[3-(2-Et-PrS)-cHx] | H | H | H | H |
| 5-1116 | H | H | Me | 2 | —C≡C—(CH$_2$)$_2$O-[4-(2-Et-PrS)-cHx] | H | H | H | H |
| 5-1117 | H | H | Me | 2 | —C≡C—(CH$_2$)$_2$O-(3-iBuS-cHx) | H | H | H | H |
| 5-1118 | H | H | Me | 2 | —C≡C—(CH$_2$)$_2$O-(4-iBuS-cHx) | H | H | H | H |
| 5-1119 | H | H | Me | 2 | —C≡C—(CH$_2$)$_2$O-(3-cHx-cHx) | H | H | H | H |
| 5-1120 | H | H | Me | 2 | —C≡C—(CH$_2$)$_2$O-(4-cHx-cHx) | H | H | H | H |
| 5-1121 | H | H | Me | 2 | —C≡C—(CH$_2$)$_2$O-(3-Ph-cHx) | H | H | H | H |
| 5-1122 | H | H | Me | 2 | —C≡C—(CH$_2$)$_2$O-(4-Ph-cHx) | H | H | H | H |
| 5-1123 | H | H | Me | 2 | —C≡C—(CH$_2$)$_2$O-(2,4-diMe-cHx) | H | H | H | H |
| 5-1124 | H | H | Me | 2 | —C≡C—(CH$_2$)$_2$O-(3,4-diMe-cHx) | H | H | H | H |
| 5-1125 | H | H | Me | 2 | —C≡C—(CH$_2$)$_2$O-(3,5-diMe-cHx) | H | H | H | H |
| 5-1126 | H | H | Me | 2 | —C≡C—(CH$_2$)$_2$O-Ph | H | H | H | H |
| 5-1127 | H | H | Me | 2 | —C≡C—(CH$_2$)$_2$O-Ph | Me | H | H | H |
| 5-1128 | H | H | Me | 2 | —C≡C—(CH$_2$)$_2$O-Ph | H | Me | H | H |
| 5-1129 | H | H | Me | 2 | —C≡C—(CH$_2$)$_2$O-Ph | F | H | H | H |
| 5-1130 | H | H | Me | 2 | —C≡C—(CH$_2$)$_2$O-Ph | H | F | H | H |
| 5-1131 | H | Me | Me | 2 | —C≡C—(CH$_2$)$_2$O-Ph | H | H | H | H |
| 5-1132 | CO$_2$Me | H | Me | 2 | —C≡C—(CH$_2$)$_2$O-Ph | H | H | H | H |
| 5-1133 | CO$_2$Et | H | Me | 2 | —C≡C—(CH$_2$)$_2$O-Ph | H | H | H | H |
| 5-1134 | H | H | Me | 2 | —C≡C—(CH$_2$)$_2$O-(3-F-Ph) | H | H | H | H |
| 5-1135 | H | H | Me | 2 | —C≡C—(CH$_2$)$_2$O-(4-F-Ph) | H | H | H | H |
| 5-1136 | H | H | Me | 2 | —C≡C—(CH$_2$)$_2$O-(4-Cl-Ph) | H | H | H | H |
| 5-1137 | H | H | Me | 2 | —C≡C—(CH$_2$)$_2$O-(4-Br-Ph) | H | H | H | H |
| 5-1138 | H | H | Me | 2 | —C≡C—(CH$_2$)$_2$O-(3-Me-Ph) | H | H | H | H |
| 5-1139 | H | H | Me | 2 | —C≡C—(CH$_2$)$_2$O-(4-Me-Ph) | H | H | H | H |
| 5-1140 | H | H | Me | 2 | —C≡C—(CH$_2$)$_2$O-(3-Et-Ph) | H | H | H | H |
| 5-1141 | H | H | Me | 2 | —C≡C—(CH$_2$)$_2$O-(4-Et-Ph) | H | H | H | H |
| 5-1142 | H | H | Me | 2 | —C≡C—(CH$_2$)$_2$O-(3-Pr-Ph) | H | H | H | H |
| 5-1143 | H | H | Me | 2 | —C≡C—(CH$_2$)$_2$O-(4-Pr-Ph) | H | H | H | H |
| 5-1144 | H | H | Me | 2 | —C≡C—(CH$_2$)$_2$O-(3-iPr-Ph) | H | H | H | H |
| 5-1145 | H | H | Me | 2 | —C≡C—(CH$_2$)$_2$O-(4-iPr-Ph) | H | H | H | H |
| 5-1146 | H | H | Me | 2 | —C≡C—(CH$_2$)$_2$O-(3-Bu-Ph) | H | H | H | H |
| 5-1147 | H | H | Me | 2 | —C≡C—(CH$_2$)$_2$O-(4-Bu-Ph) | H | H | H | H |
| 5-1148 | H | H | Me | 2 | —C≡C—(CH$_2$)$_2$O-(3-CF$_3$-Ph) | H | H | H | H |
| 5-1149 | H | H | Me | 2 | —C≡C—(CH$_2$)$_2$O-(4-CF$_3$-Ph) | H | H | H | H |
| 5-1150 | H | H | Me | 2 | —C≡C—(CH$_2$)$_2$O-(3-MeO-Ph) | H | H | H | H |
| 5-1151 | H | H | Me | 2 | —C≡C—(CH$_2$)$_2$O-(4-MeO-Ph) | H | H | H | H |
| 5-1152 | H | H | Me | 2 | —C≡C—(CH$_2$)$_2$O-(3-EtO-Ph) | H | H | H | H |
| 5-1153 | H | H | Me | 2 | —C≡C—(CH$_2$)$_2$O-(4-EtO-Ph) | H | H | H | H |
| 5-1154 | H | H | Me | 2 | —C≡C—(CH$_2$)$_2$O-(3-PrO-Ph) | H | H | H | H |
| 5-1155 | H | H | Me | 2 | —C≡C—(CH$_2$)$_2$O-(4-PrO-Ph) | H | H | H | H |

TABLE 5-continued

| | | | | | | | | | |
|---|---|---|---|---|---|---|---|---|---|
| 5-1156 | H | H | Me | 2 | —C≡C—(CH$_2$)$_2$O-(3-iPrO-Ph) | H | H | H | H |
| 5-1157 | H | H | Me | 2 | —C≡C—(CH$_2$)$_2$O-(4-iPrO-Ph) | H | H | H | H |
| 5-1158 | H | H | Me | 2 | —C≡C—(CH$_2$)$_2$O-[3-(2-Et-PrO)-Ph] | H | H | H | H |
| 5-1159 | H | H | Me | 2 | —C≡C—(CH$_2$)$_2$O-[4-(2-Et-PrO)-Ph] | H | H | H | H |
| 5-1160 | H | H | Me | 2 | —C≡C—(CH$_2$)$_2$O-(3-iBuO-Ph) | H | H | H | H |
| 5-1161 | H | H | Me | 2 | —C≡C—(CH$_2$)$_2$O-(4-iBuO-Ph) | H | H | H | H |
| 5-1162 | H | H | Me | 2 | —C≡C—(CH$_2$)$_2$O-(3-MeS-Ph) | H | H | H | H |
| 5-1163 | H | H | Me | 2 | —C≡C—(CH$_2$)$_2$O-(4-MeS-Ph) | H | H | H | H |
| 5-1164 | H | H | Me | 2 | —C≡C—(CH$_2$)$_2$O-(3-EtS-Ph) | H | H | H | H |
| 5-1165 | H | H | Me | 2 | —C≡C—(CH$_2$)$_2$O-(4-EtS-Ph) | H | H | H | H |
| 5-1166 | H | H | Me | 2 | —C≡C—(CH$_2$)$_2$O-(3-PrS-Ph) | H | H | H | H |
| 5-1167 | H | H | Me | 2 | —C≡C—(CH$_2$)$_2$O-(4-PrS-Ph) | H | H | H | H |
| 5-1168 | H | H | Me | 2 | —C≡C—(CH$_2$)$_2$O-(3-iPrS-Ph) | H | H | H | H |
| 5-1169 | H | H | Me | 2 | —C≡C—(CH$_2$)$_2$O-(4-iPrS-Ph) | H | H | H | H |
| 5-1170 | H | H | Me | 2 | —C≡C—(CH$_2$)$_2$O-[3-(2-Et-PrS)-Ph] | H | H | H | H |
| 5-1171 | H | H | Me | 2 | —C≡C—(CH$_2$)$_2$O-[4-(2-Et-PrS)-Ph] | H | H | H | H |
| 5-1172 | H | H | Me | 2 | —C≡C—(CH$_2$)$_2$O-(3-iBuS-Ph) | H | H | H | H |
| 5-1173 | H | H | Me | 2 | —C≡C—(CH$_2$)$_2$O-(4-iBuS-Ph) | H | H | H | H |
| 5-1174 | H | H | Me | 2 | —C≡C—(CH$_2$)$_2$O-(3-cHx-Ph) | H | H | H | H |
| 5-1175 | H | H | Me | 2 | —C≡C—(CH$_2$)$_2$O-(4-cHx-Ph) | H | H | H | H |
| 5-1176 | H | H | Me | 2 | —C≡C—(CH$_2$)$_2$O-(3-Ph-Ph) | H | H | H | H |
| 5-1177 | H | H | Me | 2 | —C≡C—(CH$_2$)$_2$O-(4-Ph-Ph) | H | H | H | H |
| 5-1178 | H | H | Me | 2 | —C≡C—(CH$_2$)$_2$O-(2,4-diMe-Ph) | H | H | H | H |
| 5-1179 | H | H | Me | 2 | —C≡C—(CH$_2$)$_2$O-(3,4-diMe-Ph) | H | H | H | H |
| 5-1180 | H | H | Me | 2 | —C≡C—(CH$_2$)$_2$O-(3,5-diMe-Ph) | H | H | H | H |
| 5-1181 | H | H | Me | 2 | —C≡C—(CH$_2$)$_3$O-cHx | H | H | H | H |
| 5-1182 | H | H | Me | 2 | —C≡C—(CH$_2$)$_3$O-Ph | H | H | H | H |
| 5-1183 | H | H | Me | 2 | —C≡C—(CH$_2$)$_4$O-cHx | H | H | H | H |
| 5-1184 | H | H | Me | 2 | —C≡C—(CH$_2$)$_4$O-Ph | H | H | H | H |
| 5-1185 | H | H | Me | 2 | —C≡C—CH$_2$—OCH$_2$-cHx | H | H | H | H |
| 5-1186 | H | Me | Me | 2 | —C≡C—CH$_2$—OCH$_2$-cHx | H | H | H | H |
| 5-1187 | CO$_2$Me | H | Me | 2 | —C≡C—CH$_2$—OCH$_2$-cHx | H | H | H | H |
| 5-1188 | CO$_2$Et | H | Me | 2 | —C≡C—CH$_2$—OCH$_2$-cHx | H | H | H | H |
| 5-1189 | H | H | Me | 2 | —C≡C—CH$_2$—OCH$_2$-(4-F-cHx) | H | H | H | H |
| 5-1190 | H | H | Me | 2 | —C≡C—CH$_2$—OCH$_2$-(4-Me-cHx) | H | H | H | H |
| 5-1191 | H | H | Me | 2 | —C≡C—CH$_2$—OCH$_2$-(4-Et-cHx) | H | H | H | H |
| 5-1192 | H | H | Me | 2 | —C≡C—CH$_2$—OCH$_2$-(4-CF$_3$-cHx) | H | H | H | H |
| 5-1193 | H | H | Me | 2 | —C≡C—CH$_2$—OCH$_2$-(4-MeO-cHx) | H | H | H | H |
| 5-1194 | H | H | Me | 2 | —C≡C—CH$_2$—OCH$_2$-(4-EtO-cHx) | H | H | H | H |
| 5-1195 | H | H | Me | 2 | —C≡C—CH$_2$—OCH$_2$-(4-MeS-cHx) | H | H | H | H |
| 5-1196 | H | H | Me | 2 | —C≡C—CH$_2$—OCH$_2$-(4-cHx-cHx) | H | H | H | H |
| 5-1197 | H | H | Me | 2 | —C≡C—CH$_2$—OCH$_2$-(4-Ph-cHx) | H | H | H | H |
| 5-1198 | H | H | Me | 2 | —C≡C—CH$_2$—OCH$_2$-Ph | H | H | H | H |
| 5-1199 | H | Me | Me | 2 | —C≡C—CH$_2$—OCH$_2$-Ph | H | H | H | H |
| 5-1200 | CO$_2$Me | H | Me | 2 | —C≡C—CH$_2$—OCH$_2$-Ph | H | H | H | H |
| 5-1201 | CO$_2$Et | H | Me | 2 | —C≡C—CH$_2$—OCH$_2$-Ph | H | H | H | H |
| 5-1202 | H | H | Me | 2 | —C≡C—CH$_2$—OCH$_2$-(4-F-Ph) | H | H | H | H |
| 5-1203 | H | H | Me | 2 | —C≡C—CH$_2$—OCH$_2$-(4-Me-Ph) | H | H | H | H |
| 5-1204 | H | H | Me | 2 | —C≡C—CH$_2$—OCH$_2$-(4-Et-Ph) | H | H | H | H |
| 5-1205 | H | H | Me | 2 | —C≡C—CH$_2$—OCH$_2$-(4-CF$_3$-Ph) | H | H | H | H |
| 5-1206 | H | H | Me | 2 | —C≡C—CH$_2$—OCH$_2$-(4-MeO-Ph) | H | H | H | H |
| 5-1207 | H | H | Me | 2 | —C≡C—CH$_2$—OCH$_2$-(4-EtO-Ph) | H | H | H | H |
| 5-1208 | H | H | Me | 2 | —C≡C—CH$_2$—OCH$_2$-(4-MeS-Ph) | H | H | H | H |
| 5-1209 | H | H | Me | 2 | —C≡C—CH$_2$—OCH$_2$-(4-cHx-Ph) | H | H | H | H |
| 5-1210 | H | H | Me | 2 | —C≡C—CH$_2$—OCH$_2$-(4-Ph-Ph) | H | H | H | H |
| 5-1211 | H | H | Me | 2 | —C≡C—(CH$_2$)$_2$—OCH$_2$-cPn | H | H | H | H |
| 5-1212 | H | H | Me | 2 | —C≡C—(CH$_2$)$_2$—OCH$_2$-cHx | H | H | H | H |
| 5-1213 | H | H | Me | 2 | —C≡C—(CH$_2$)$_2$—OCH$_2$-cHx | Me | H | H | H |
| 5-1214 | H | H | Me | 2 | —C≡C—(CH$_2$)$_2$—OCH$_2$-cHx | H | Me | H | H |
| 5-1215 | H | H | Me | 2 | —C≡C—(CH$_2$)$_2$—OCH$_2$-cHx | F | H | H | H |
| 5-1216 | H | H | Me | 2 | —C≡C—(CH$_2$)$_2$—OCH$_2$-cHx | H | F | H | H |
| 5-1217 | H | Me | Me | 2 | —C≡C—(CH$_2$)$_2$—OCH$_2$—CH$_2$-cHx | H | H | H | H |
| 5-1218 | CO$_2$Me | H | Me | 2 | —C≡C—(CH$_2$)$_2$—OCH$_2$-cHx | H | H | H | H |
| 5-1219 | CO$_2$Et | H | Me | 2 | —C≡C—(CH$_2$)$_2$—OCH$_2$-cHx | H | H | H | H |
| 5-1220 | H | H | Me | 2 | —C≡C—(CH$_2$)$_2$—OCH$_2$-(3-F-cHx) | H | H | H | H |
| 5-1221 | H | H | Me | 2 | —C≡C—(CH$_2$)$_2$—OCH$_2$-(4-F-cHx) | H | H | H | H |
| 5-1222 | H | H | Me | 2 | —C≡C—(CH$_2$)$_2$—OCH$_2$-(4-Cl-cHx) | H | H | H | H |
| 5-1223 | H | H | Me | 2 | —C≡C—(CH$_2$)$_2$—OCH$_2$-(4-Br-cHx) | H | H | H | H |
| 5-1224 | H | H | Me | 2 | —C≡C—(CH$_2$)$_2$—OCH$_2$-(3-Me-cHx) | H | H | H | H |
| 5-1225 | H | H | Me | 2 | —C≡C—(CH$_2$)$_2$—OCH$_2$-(4-Me-cHx) | H | H | H | H |
| 5-1226 | H | H | Me | 2 | —C≡C—(CH$_2$)$_2$—OCH$_2$-(3-Et-cHx) | H | H | H | H |
| 5-1227 | H | H | Me | 2 | —C≡C—(CH$_2$)$_2$—OCH$_2$-(4-Et-cHx) | H | H | H | H |
| 5-1228 | H | H | Me | 2 | —C≡C—(CH$_2$)$_2$—OCH$_2$-(3-Pr-cHx) | H | H | H | H |
| 5-1229 | H | H | Me | 2 | —C≡C—(CH$_2$)$_2$—OCH$_2$-(4-Pr-cHx) | H | H | H | H |
| 5-1230 | H | H | Me | 2 | —C≡C—(CH$_2$)$_2$—OCH$_2$-(4-iPr-cHx) | H | H | H | H |
| 5-1231 | H | H | Me | 2 | —C≡C—(CH$_2$)$_2$—OCH$_2$-(3-Bu-cHx) | H | H | H | H |
| 5-1232 | H | H | Me | 2 | —C≡C—(CH$_2$)$_2$—OCH$_2$-(4-Bu-cHx) | H | H | H | H |
| 5-1233 | H | H | Me | 2 | —C≡C—(CH$_2$)$_2$—OCH$_2$-(3-CF$_3$-cHx) | H | H | H | H |
| 5-1234 | H | H | Me | 2 | —C≡C—(CH$_2$)$_2$—OCH$_2$-(4-CF$_3$-cHx) | H | H | H | H |
| 5-1235 | H | H | Me | 2 | —C≡C—(CH$_2$)$_2$—OCH$_2$-(3-MeO-cHx) | H | H | H | H |

TABLE 5-continued

| | | | | | | | | | |
|---|---|---|---|---|---|---|---|---|---|
| 5-1236 | H | H | Me | 2 | —C≡C—(CH$_2$)$_2$—OCH$_2$-(4-MeO-cHx) | H | H | H | H |
| 5-1237 | H | H | Me | 2 | —C≡C—(CH$_2$)$_2$—OCH$_2$-(3-EtO-cHx) | H | H | H | H |
| 5-1238 | H | H | Me | 2 | —C≡C—(CH$_2$)$_2$—OCH$_2$-(4-EtO-cHx) | H | H | H | H |
| 5-1239 | H | H | Me | 2 | —C≡C—(CH$_2$)$_2$—OCH$_2$-(3-PrO-cHx) | H | H | H | H |
| 5-1240 | H | H | Me | 2 | —C≡C—(CH$_2$)$_2$—OCH$_2$-(4-PrO-cHx) | H | H | H | H |
| 5-1241 | H | H | Me | 2 | —C≡C—(CH$_2$)$_2$—OCH$_2$-(3-iPrO-cHx) | H | H | H | H |
| 5-1242 | H | H | Me | 2 | —C≡C—(CH$_2$)$_2$—OCH$_2$-(4-iPrO-cHx) | H | H | H | H |
| 5-1243 | H | H | Me | 2 | —C≡C—(CH$_2$)$_2$—OCH$_2$-[3-(2-Et-PrO)cHx] | H | H | H | H |
| 5-1244 | H | H | Me | 2 | —C≡C—(CH$_2$)$_2$—OCH$_2$-[4-(2-Et-PrO)cHx] | H | H | H | H |
| 5-1245 | H | H | Me | 2 | —C≡C—(CH$_2$)$_2$—OCH$_2$-(3-iBuO-cHx) | H | H | H | H |
| 5-1246 | H | H | Me | 2 | —C≡C—(CH$_2$)$_2$—OCH$_2$-(4-iBuO-cHx) | H | H | H | H |
| 5-1247 | H | H | Me | 2 | —C≡C—(CH$_2$)$_2$—OCH$_2$-(3-MeS-cHx) | H | H | H | H |
| 5-1248 | H | H | Me | 2 | —C≡C—(CH$_2$)$_2$—OCH$_2$-(4-MeS-cHx) | H | H | H | H |
| 5-1249 | H | H | Me | 2 | —C≡C—(CH$_2$)$_2$—OCH$_2$-(3-EtS-cHx) | H | H | H | H |
| 5-1250 | H | H | Me | 2 | —C≡C—(CH$_2$)$_2$—OCH$_2$-(4-EtS-cHx) | H | H | H | H |
| 5-1251 | H | H | Me | 2 | —C≡C—(CH$_2$)$_2$—OCH$_2$-(3-PrS-cHx) | H | H | H | H |
| 5-1252 | H | H | Me | 2 | —C≡C—(CH$_2$)$_2$—OCH$_2$-(4-PrS-cHx) | H | H | H | H |
| 5-1253 | H | H | Me | 2 | —C≡C—(CH$_2$)$_2$—OCH$_2$-(3-iPrS-cHx) | H | H | H | H |
| 5-1254 | H | H | Me | 2 | —C≡C—(CH$_2$)$_2$—OCH$_2$-(4-iPrS-cHx) | H | H | H | H |
| 5-1255 | H | H | Me | 2 | —C≡C—(CH$_2$)$_2$—OCH$_2$-[3-(2-Et-PrS)cHx] | H | H | H | H |
| 5-1256 | H | H | Me | 2 | —C≡C—(CH$_2$)$_2$—OCH$_2$-[4-(2-Et-PrS)cHx] | H | H | H | H |
| 5-1257 | H | H | Me | 2 | —C≡C—(CH$_2$)$_2$—OCH$_2$-(3-iBuS-cHx) | H | H | H | H |
| 5-1258 | H | H | Me | 2 | —C≡C—(CH$_2$)$_2$—OCH$_2$-(4-iBuS-cHx) | H | H | H | H |
| 5-1259 | H | H | Me | 2 | —C≡C—(CH$_2$)$_2$—OCH$_2$-(3-cHx-cHx) | H | H | H | H |
| 5-1260 | H | H | Me | 2 | —C≡C—(CH$_2$)$_2$—OCH$_2$-(4-cHx-cHx) | H | H | H | H |
| 5-1261 | H | H | Me | 2 | —C≡C—(CH$_2$)$_2$—OCH$_2$-(3-Ph-cHx) | H | H | H | H |
| 5-1262 | H | H | Me | 2 | —C≡C—(CH$_2$)$_2$—OCH$_2$-(4-Ph-cHx) | H | H | H | H |
| 5-1263 | H | H | Me | 2 | —C≡C—(CH$_2$)$_2$—OCH$_2$-(2,4-diMe-cHx) | H | H | H | H |
| 5-1264 | H | H | Me | 2 | —C≡C—(CH$_2$)$_2$—OCH$_2$-(3,4-diMe-cHx) | H | H | H | H |
| 5-1265 | H | H | Me | 2 | —C≡C—(CH$_2$)$_2$—OCH$_2$-(3,5-diMe-chx) | H | H | H | H |
| 5-1266 | H | H | Me | 2 | —C≡C—(CH$_2$)$_2$—OCH$_2$-Ph | H | H | H | H |
| 5-1267 | H | H | Me | 2 | —C≡C—(CH$_2$)$_2$—OCH$_2$-Ph | Me | H | H | H |
| 5-1268 | H | H | Me | 2 | —C≡C—(CH$_2$)$_2$—OCH$_2$-Ph | H | Me | H | H |
| 5-1269 | H | H | Me | 2 | —C≡C—(CH$_2$)$_2$—OCH$_2$-Ph | F | H | H | H |
| 5-1270 | H | H | Me | 2 | —C≡C—(CH$_2$)$_2$—OCH$_2$-Ph | H | F | H | H |
| 5-1271 | H | Me | Me | 2 | —C≡C—(CH$_2$)$_2$—OCH$_2$—CH$_2$-Ph | H | H | H | H |
| 5-1272 | CO$_2$Me | H | Me | 2 | —C≡C—(CH$_2$)$_2$—OCH$_2$-Ph | H | H | H | H |
| 5-1273 | CO$_2$Et | H | Me | 2 | —C≡C—(CH$_2$)$_2$—OCH$_2$-Ph | H | H | H | H |
| 5-1274 | H | H | Me | 2 | —C≡C—(CH$_2$)$_2$—OCH$_2$-(3-F-Ph) | H | H | H | H |
| 5-1275 | H | H | Me | 2 | —C≡C—(CH$_2$)$_2$—OCH$_2$-(4-F-Ph) | H | H | H | H |
| 5-1276 | H | H | Me | 2 | —C≡C—(CH$_2$)$_2$—OCH$_2$-(4-Cl-Ph) | H | H | H | H |
| 5-1277 | H | H | Me | 2 | —C≡C—(CH$_2$)$_2$—OCH$_2$-(4-Br-Ph) | H | H | H | H |
| 5-1278 | H | H | Me | 2 | —C≡C—(CH$_2$)$_2$—OCH$_2$-(3-Me-Ph) | H | H | H | H |
| 5-1279 | H | H | Me | 2 | —C≡C—(CH$_2$)$_2$—OCH$_2$-(4-Me-Ph) | H | H | H | H |
| 5-1280 | H | H | Me | 2 | —C≡C—(CH$_2$)$_2$—OCH$_2$-(3-Et-Ph) | H | H | H | H |
| 5-1281 | H | H | Me | 2 | —C≡C—(CH$_2$)$_2$—OCH$_2$-(4-Et-Ph) | H | H | H | H |
| 5-1282 | H | H | Me | 2 | —C≡C—(CH$_2$)$_2$—OCH$_2$-(3-Pr-Ph) | H | H | H | H |
| 5-1283 | H | H | Me | 2 | —C≡C—(CH$_2$)$_2$—OCH$_2$-(4-Pr-Ph) | H | H | H | H |
| 5-1284 | H | H | Me | 2 | —C≡C—(CH$_2$)$_2$—OCH$_2$-(3-iPr-Ph) | H | H | H | H |
| 5-1285 | H | H | Me | 2 | —C≡C—(CH$_2$)$_2$—OCH$_2$-(4-iPr-Ph) | H | H | H | H |
| 5-1286 | H | H | Me | 2 | —C≡C—(CH$_2$)$_2$—OCH$_2$-(3-Bu-Ph) | H | H | H | H |
| 5-1287 | H | H | Me | 2 | —C≡C—(CH$_2$)$_2$—OCH$_2$-(4-Bu-Ph) | H | H | H | H |
| 5-1288 | H | H | Me | 2 | —C≡C—(CH$_2$)$_2$—OCH$_2$-(3-CF$_3$-Ph) | H | H | H | H |
| 5-1289 | H | H | Me | 2 | —C≡C—(CH$_2$)$_2$—OCH$_2$-(4-CF$_3$-Ph) | H | H | H | H |
| 5-1290 | H | H | Me | 2 | —C≡C—(CH$_2$)$_2$—OCH$_2$-(3-MeO-Ph) | H | H | H | H |
| 5-1291 | H | H | Me | 2 | —C≡C—(CH$_2$)$_2$—OCH$_2$-(4-MeO-Ph) | H | H | H | H |
| 5-1292 | H | H | Me | 2 | —C≡C—(CH$_2$)$_2$—OCH$_2$-(3-EtO-Ph) | H | H | H | H |
| 5-1293 | H | H | Me | 2 | —C≡C—(CH$_2$)$_2$—OCH$_2$-(4-EtO-Ph) | H | H | H | H |
| 5-1294 | H | H | Me | 2 | —C≡C—(CH$_2$)$_2$—OCH$_2$-(3-PrO-Ph) | H | H | H | H |
| 5-1295 | H | H | Me | 2 | —C≡C—(CH$_2$)$_2$—OCH$_2$-(4-PrO-Ph) | H | H | H | H |
| 5-1296 | H | H | Me | 2 | —C≡C—(CH$_2$)$_2$—OCH$_2$-(3-iPrO-Ph) | H | H | H | H |
| 5-1297 | H | H | Me | 2 | —C≡C—(CH$_2$)$_2$—OCH$_2$-(4-iPrO-Ph) | H | H | H | H |
| 5-1298 | H | H | Me | 2 | —C≡C—(CH$_2$)$_2$—OCH$_2$-[3-(2-Et-PrO)Ph] | H | H | H | H |
| 5-1299 | H | H | Me | 2 | —C≡C—(CH$_2$)$_2$—OCH$_2$-[4-(2-Et-PrO)Ph] | H | H | H | H |
| 5-1300 | H | H | Me | 2 | —C≡C—(CH$_2$)$_2$—OCH$_2$-(3-iBuO-Ph) | H | H | H | H |
| 5-1301 | H | H | Me | 2 | —C≡C—(CH$_2$)$_2$—OCH$_2$-(4-iBuO-Ph) | H | H | H | H |
| 5-1302 | H | H | Me | 2 | —C≡C—(CH$_2$)$_2$—OCH$_2$-(3-MeS-Ph) | H | H | H | H |
| 5-1303 | H | H | Me | 2 | —C≡C—(CH$_2$)$_2$—OCH$_2$-(4-MeS-Ph) | H | H | H | H |
| 5-1304 | H | H | Me | 2 | —C≡C—(CH$_2$)$_2$—OCH$_2$-(3-EtS-Ph) | H | H | H | H |
| 5-1305 | H | H | Me | 2 | —C≡C—(CH$_2$)$_2$—OCH$_2$-(4-EtS-Ph) | H | H | H | H |
| 5-1306 | H | H | Me | 2 | —C≡C—(CH$_2$)$_2$—OCH$_2$-(3-PrS-Ph) | H | H | H | H |
| 5-1307 | H | H | Me | 2 | —C≡C—(CH$_2$)$_2$—OCH$_2$-(4-PrS-Ph) | H | H | H | H |
| 5-1308 | H | H | Me | 2 | —C≡C—(CH$_2$)$_2$—OCH$_2$-(3-iPrS-Ph) | H | H | H | H |
| 5-1309 | H | H | Me | 2 | —C≡C—(CH$_2$)$_2$—OCH$_2$-(4-iPrS-Ph) | H | H | H | H |
| 5-1310 | H | H | Me | 2 | —C≡C—(CH$_2$)$_2$—OCH$_2$-[3-(2-Et-PrS)Ph] | H | H | H | H |
| 5-1311 | H | H | Me | 2 | —C≡C—(CH$_2$)$_2$—OCH$_2$-[4-(2-Et-PrS)Ph] | H | H | H | H |
| 5-1312 | H | H | Me | 2 | —C≡C—(CH$_2$)$_2$—OCH$_2$-(3-iBuS-Ph) | H | H | H | H |
| 5-1313 | H | H | Me | 2 | —C≡C—(CH$_2$)$_2$—OCH$_2$-(4-iBuS-Ph) | H | H | H | H |
| 5-1314 | H | H | Me | 2 | —C≡C—(CH$_2$)$_2$—OCH$_2$-(3-cHx-Ph) | H | H | H | H |
| 5-1315 | H | H | Me | 2 | —C≡C—(CH$_2$)$_2$—OCH$_2$-(4-cHx-Ph) | H | H | H | H |

TABLE 5-continued

| | | | | | | | | | |
|---|---|---|---|---|---|---|---|---|---|
| 5-1316 | H | H | Me | 2 | —C≡C—(CH$_2$)$_2$—OCH$_2$-(3-Ph-Ph) | H | H | H | H |
| 5-1317 | H | H | Me | 2 | —C≡C—(CH$_2$)$_2$—OCH$_2$-(4-Ph-Ph) | H | H | H | H |
| 5-1318 | H | H | Me | 2 | —C≡C—(CH$_2$)$_2$—OCH$_2$-(2,4-diMe-Ph) | H | H | H | H |
| 5-1319 | H | H | Me | 2 | —C≡C—(CH$_2$)$_2$—OCH$_2$-(3,4-diMe-Ph) | H | H | H | H |
| 5-1320 | H | H | Me | 2 | —C≡C—(CH$_2$)$_2$—OCH$_2$-(3,5-diMe-Ph) | H | H | H | H |
| 5-1321 | H | H | Me | 2 | —C≡C—(CH$_2$)$_3$—OCH$_2$-cHx | H | H | H | H |
| 5-1322 | H | H | Me | 2 | —C≡C—(CH$_2$)$_3$—OCH$_2$-Ph | H | H | H | H |
| 5-1323 | H | H | Me | 2 | —C≡C—(CH$_2$)$_4$—OCH$_2$-cHx | H | H | H | H |
| 5-1324 | H | H | Me | 2 | —C≡C—(CH$_2$)$_4$—OCH$_2$-Ph | H | H | H | H |
| 5-1325 | H | H | Me | 2 | —CO—CH$_2$-(4-cHx-Ph) | H | H | H | H |
| 5-1326 | H | H | Me | 2 | —CO—CH$_2$-(4-Ph-Ph) | H | H | H | H |
| 5-1327 | H | H | Me | 2 | —CO—(CH$_2$)$_2$-cHx | H | H | H | H |
| 5-1328 | H | H | Me | 2 | —CO—(CH$_2$)$_2$-Ph | H | H | H | H |
| 5-1329 | H | H | Me | 2 | —CO—(CH$_2$)$_3$-cHx | H | H | H | H |
| 5-1330 | H | H | Me | 2 | —CO—(CH$_2$)$_3$-Ph | H | H | H | H |
| 5-1331 | H | H | Me | 2 | —CO—(CH$_2$)$_4$-cHx | H | H | H | H |
| 5-1332 | H | Me | Me | 2 | —CO—(CH$_2$)$_4$-cHx | H | H | H | H |
| 5-1333 | CO$_2$Me | H | Me | 2 | —CO—(CH$_2$)$_4$-cHx | H | H | H | H |
| 5-1334 | CO$_2$Et | H | Me | 2 | —CO—(CH$_2$)$_4$-cHx | H | H | H | H |
| 5-1335 | H | H | Me | 2 | —CO—(CH$_2$)$_4$-(4-F-cHx) | H | H | H | H |
| 5-1336 | H | H | Me | 2 | —CO—(CH$_2$)$_4$-(4-Me-cHx) | H | H | H | H |
| 5-1337 | H | H | Me | 2 | —CO—(CH$_2$)$_4$-(4-Et-cHx) | H | H | H | H |
| 5-1338 | H | H | Me | 2 | —CO—(CH$_2$)$_4$-(4-CF$_3$-cHx) | H | H | H | H |
| 5-1339 | H | H | Me | 2 | —CO—(CH$_2$)$_4$-(4-MeO-cHx) | H | H | H | H |
| 5-1340 | H | H | Me | 2 | —CO—(CH$_2$)$_4$-(4-EtO-cHx) | H | H | H | H |
| 5-1341 | H | H | Me | 2 | —CO—(CH$_2$)$_4$-(4-MeS-cHx) | H | H | H | H |
| 5-1342 | H | H | Me | 2 | —CO—(CH$_2$)$_4$-(4-cHx-cHx) | H | H | H | H |
| 5-1343 | H | H | Me | 2 | —CO—(CH$_2$)$_4$-(4-Ph-cHx) | H | H | H | H |
| 5-1344 | H | H | Me | 2 | —CO—(CH$_2$)$_4$-Ph | H | H | H | H |
| 5-1345 | H | Me | Me | 2 | —CO—(CH$_2$)$_4$-Ph | H | H | H | H |
| 5-1346 | CO$_2$Me | H | Me | 2 | —CO—(CH$_2$)$_4$-Ph | H | H | H | H |
| 5-1347 | CO$_2$Et | H | Me | 2 | —CO—(CH$_2$)$_4$-Ph | H | H | H | H |
| 5-1348 | H | H | Me | 2 | —CO—(CH$_2$)$_4$-(4-F-Ph) | H | H | H | H |
| 5-1349 | H | H | Me | 2 | —CO—(CH$_2$)$_4$-(4-Me-Ph) | H | H | H | H |
| 5-1350 | H | H | Me | 2 | —CO—(CH$_2$)$_4$-(4-Et-Ph) | H | H | H | H |
| 5-1351 | H | H | Me | 2 | —CO—(CH$_2$)$_4$-(4-CF$_3$-Ph) | H | H | H | H |
| 5-1352 | H | H | Me | 2 | —CO—(CH$_2$)$_4$-(4-MeO-Ph) | H | H | H | H |
| 5-1353 | H | H | Me | 2 | —CO—(CH$_2$)$_4$-(4-EtO-Ph) | H | H | H | H |
| 5-1354 | H | H | Me | 2 | —CO—(CH$_2$)$_4$-(4-MeS-Ph) | H | H | H | H |
| 5-1355 | H | H | Me | 2 | —CO—(CH$_2$)$_4$-(4-cHx-Ph) | H | H | H | H |
| 5-1356 | H | H | Me | 2 | —CO—(CH$_2$)$_4$-(4-Ph-Ph) | H | H | H | H |
| 5-1357 | H | H | Me | 2 | —CO—(CH$_2$)$_5$-cHx | H | H | H | H |
| 5-1358 | H | Me | Me | 2 | —CO—(CH$_2$)$_5$-cHx | H | H | H | H |
| 5-1359 | CO$_2$Me | H | Me | 2 | —CO—(CH$_2$)$_5$-cHx | H | H | H | H |
| 5-1360 | CO$_2$Et | H | Me | 2 | —CO—(CH$_2$)$_5$-cHx | H | H | H | H |
| 5-1361 | H | H | Me | 2 | —CO—(CH$_2$)$_5$-(4-F-cHx) | H | H | H | H |
| 5-1362 | H | H | Me | 2 | —CO—(CH$_2$)$_5$-(4-Me-cHx) | H | H | H | H |
| 5-1363 | H | H | Me | 2 | —CO—(CH$_2$)$_5$-(4-Et-cHx) | H | H | H | H |
| 5-1364 | H | H | Me | 2 | —CO—(CH$_2$)$_5$-(4-CF$_3$-cHx) | H | H | H | H |
| 5-1365 | H | H | Me | 2 | —CO—(CH$_2$)$_5$-(4-MeO-cHx) | H | H | H | H |
| 5-1366 | H | H | Me | 2 | —CO—(CH$_2$)$_5$-(4-EtO-cHx) | H | H | H | H |
| 5-1367 | H | H | Me | 2 | —CO—(CH$_2$)$_5$-(4-MeS-cHx) | H | H | H | H |
| 5-1368 | H | H | Me | 2 | —CO—(CH$_2$)$_5$-(4-cHx-cHx) | H | H | H | H |
| 5-1369 | H | H | Me | 2 | —CO—(CH$_2$)$_5$-(4-Ph-cHx) | H | H | H | H |
| 5-1370 | H | H | Me | 2 | —CO—(CH$_2$)$_5$-Ph | H | H | H | H |
| 5-1371 | H | Me | Me | 2 | —CO—(CH$_2$)$_5$-Ph | H | H | H | H |
| 5-1372 | CO$_2$Me | H | Me | 2 | —CO—(CH$_2$)$_5$-Ph | H | H | H | H |
| 5-1373 | CO$_2$Et | H | Me | 2 | —CO—(CH$_2$)$_5$-Ph | H | H | H | H |
| 5-1374 | H | H | Me | 2 | —CO—(CH$_2$)$_5$-(4-F-Ph) | H | H | H | H |
| 5-1375 | H | H | Me | 2 | —CO—(CH$_2$)$_5$-(4-Me-Ph) | H | H | H | H |
| 5-1376 | H | H | Me | 2 | —CO—(CH$_2$)$_5$-(4-Et-Ph) | H | H | H | H |
| 5-1377 | H | H | Me | 2 | —CO—(CH$_2$)$_5$-(4-CF$_3$-Ph) | H | H | H | H |
| 5-1378 | H | H | Me | 2 | —CO—(CH$_2$)$_5$-(4-MeO-Ph) | H | H | H | H |
| 5-1379 | H | H | Me | 2 | —CO—(CH$_2$)$_5$-(4-EtO-Ph) | H | H | H | H |
| 5-1380 | H | H | Me | 2 | —CO—(CH$_2$)$_5$-(4-MeS-Ph) | H | H | H | H |
| 5-1381 | H | H | Me | 2 | —CO—(CH$_2$)$_5$-(4-cHx-Ph) | H | H | H | H |
| 5-1382 | H | H | Me | 2 | —CO—(CH$_2$)$_5$-(4-Ph-Ph) | H | H | H | H |
| 5-1383 | H | H | Me | 2 | —CO—(CH$_2$)$_6$-cHx | H | H | H | H |
| 5-1384 | H | H | Me | 2 | —CO—(CH$_2$)$_6$-Ph | H | H | H | H |
| 5-1385 | H | H | Me | 2 | —CO—(CH$_2$)$_7$-cHx | H | H | H | H |
| 5-1386 | H | H | Me | 2 | —CO—(CH$_2$)$_7$-Ph | H | H | H | H |
| 5-1387 | H | H | Me | 2 | —CO—(CH$_2$)$_2$—O-cHx | H | H | H | H |
| 5-1388 | H | Me | Me | 2 | —CO—(CH$_2$)$_2$—O-cHx | H | H | H | H |
| 5-1389 | CO$_2$Me | H | Me | 2 | —CO—(CH$_2$)$_2$—O-cHx | H | H | H | H |
| 5-1390 | CO$_2$Et | H | Me | 2 | —CO—(CH$_2$)$_2$—O-cHx | H | H | H | H |
| 5-1391 | H | H | Me | 2 | —CO—(CH$_2$)$_2$—O-(4-F-cHx) | H | H | H | H |
| 5-1392 | H | H | Me | 2 | —CO—(CH$_2$)$_2$—O-(4-Me-cHx) | H | H | H | H |
| 5-1393 | H | H | Me | 2 | —CO—(CH$_2$)$_2$—O-(4-Et-cHx) | H | H | H | H |
| 5-1394 | H | H | Me | 2 | —CO—(CH$_2$)$_2$—O-(4-CF$_3$-cHx) | H | H | H | H |
| 5-1395 | H | H | Me | 2 | —CO—(CH$_2$)$_2$—O-(4-MeO-cHx) | H | H | H | H |

TABLE 5-continued

| | | | | | | | | |
|---|---|---|---|---|---|---|---|---|
| 5-1396 | H | H | Me | 2 | —CO—(CH$_2$)$_2$—O-(4-EtO-cHx) | H | H | H | H |
| 5-1397 | H | H | Me | 2 | —CO—(CH$_2$)$_2$—O-(4-MeS-cHx) | H | H | H | H |
| 5-1398 | H | H | Me | 2 | —CO—(CH$_2$)$_2$—O-(4-cHx-cHx) | H | H | H | H |
| 5-1399 | H | H | Me | 2 | —CO—(CH$_2$)$_2$—O-(4-Ph-cHx) | H | H | H | H |
| 5-1400 | H | H | Me | 2 | —CO—(CH$_2$)$_2$—O-Ph | H | H | H | H |
| 5-1401 | H | Me | Me | 2 | —CO—(CH$_2$)$_2$—O-Ph | H | H | H | H |
| 5-1402 | CO$_2$Me | H | Me | 2 | —CO—(CH$_2$)$_2$—O-Ph | H | H | H | H |
| 5-1403 | CO$_2$Et | H | Me | 2 | —CO—(CH$_2$)$_2$—O-Ph | H | H | H | H |
| 5-1404 | H | H | Me | 2 | —CO—(CH$_2$)$_2$—O-(4-F-Ph) | H | H | H | H |
| 5-1405 | H | H | Me | 2 | —CO—(CH$_2$)$_2$—O-(4-Me-Ph) | H | H | H | H |
| 5-1406 | H | H | Me | 2 | —CO—(CH$_2$)$_2$—O-(4-Et-Ph) | H | H | H | H |
| 5-1407 | H | H | Me | 2 | —CO—(CH$_2$)$_2$—O-(4-CF$_3$-Ph) | H | H | H | H |
| 5-1408 | H | H | Me | 2 | —CO—(CH$_2$)$_2$—O-(4-MeO-Ph) | H | H | H | H |
| 5-1409 | H | H | Me | 2 | —CO—(CH$_2$)$_2$—O-(4-EtO-Ph) | H | H | H | H |
| 5-1410 | H | H | Me | 2 | —CO—(CH$_2$)$_2$—O-(4-MeS-Ph) | H | H | H | H |
| 5-1411 | H | H | Me | 2 | —CO—(CH$_2$)$_2$—O-(4-cHx-Ph) | H | H | H | H |
| 5-1412 | H | H | Me | 2 | —CO—(CH$_2$)$_2$—O-(4-Ph-Ph) | H | H | H | H |
| 5-1413 | H | H | Me | 2 | —CO—(CH$_2$)$_3$—O-cPn | H | H | H | H |
| 5-1414 | H | H | Me | 2 | —CO—(CH$_2$)$_3$—O-cHx | H | H | H | H |
| 5-1415 | H | H | Me | 2 | —CO—(CH$_2$)$_3$—O-cHx | Me | H | H | H |
| 5-1416 | H | H | Me | 2 | —CO—(CH$_2$)$_3$—O-cHx | H | Me | H | H |
| 5-1417 | H | H | Me | 2 | —CO—(CH$_2$)$_3$—O-cHx | F | H | H | H |
| 5-1418 | H | H | Me | 2 | —CO—(CH$_2$)$_3$—O-cHx | H | F | H | H |
| 5-1419 | H | Me | Me | 2 | —CO—(CH$_2$)$_3$—O-cHx | H | H | H | H |
| 5-1420 | CO$_2$Me | H | Me | 2 | —CO—(CH$_2$)$_3$—O-cHx | H | H | H | H |
| 5-1421 | CO$_2$Et | H | Me | 2 | —CO—(CH$_2$)$_3$—O-cHx | H | H | H | H |
| 5-1422 | H | H | Me | 2 | —CO—(CH$_2$)$_3$—O-(3-F-cHx) | H | H | H | H |
| 5-1423 | H | H | Me | 2 | —CO—(CH$_2$)$_3$—O-(4-F-cHx) | H | H | H | H |
| 5-1424 | H | H | Me | 2 | —CO—(CH$_2$)$_3$—O-(4-Cl-cHx) | H | H | H | H |
| 5-1425 | H | H | Me | 2 | —CO—(CH$_2$)$_3$—O-(4-Br-cHx) | H | H | H | H |
| 5-1426 | H | H | Me | 2 | —CO—(CH$_2$)$_3$—O-(3-Me-cHx) | H | H | H | H |
| 5-1427 | H | H | Me | 2 | —CO—(CH$_2$)$_3$—O-(4-Me-cHx) | H | H | H | H |
| 5-1428 | H | H | Me | 2 | —CO—(CH$_2$)$_3$—O-(3-Et-cHx) | H | H | H | H |
| 5-1429 | H | H | Me | 2 | —CO—(CH$_2$)$_3$—O-(4-Et-cHx) | H | H | H | H |
| 5-1430 | H | H | Me | 2 | —CO—(CH$_2$)$_3$—O-(3-Pr-cHx) | H | H | H | H |
| 5-1431 | H | H | Me | 2 | —CO—(CH$_2$)$_3$—O-(4-Pr-cHx) | H | H | H | H |
| 5-1432 | H | H | Me | 2 | —CO—(CH$_2$)$_3$—O-(4-iPr-cHx) | H | H | H | H |
| 5-1433 | H | H | Me | 2 | —CO—(CH$_2$)$_3$—O-(3-Bu-cHx) | H | H | H | H |
| 5-1434 | H | H | Me | 2 | —CO—(CH$_2$)$_3$—O-(4-Bu-cHx) | H | H | H | H |
| 5-1435 | H | H | Me | 2 | —CO—(CH$_2$)$_3$—O-(3-CF$_3$-cHx) | H | H | H | H |
| 5-1436 | H | H | Me | 2 | —CO—(CH$_2$)$_3$—O-(4-CF$_3$-cHx) | H | H | H | H |
| 5-1437 | H | H | Me | 2 | —CO—(CH$_2$)$_3$—O-(3-MeO-cHx) | H | H | H | H |
| 5-1438 | H | H | Me | 2 | —CO—(CH$_2$)$_3$—O-(4-MeO-cHx) | H | H | H | H |
| 5-1439 | H | H | Me | 2 | —CO—(CH$_2$)$_3$—O-(3-EtO-cHx) | H | H | H | H |
| 5-1440 | H | H | Me | 2 | —CO—(CH$_2$)$_3$—O-(4-EtO-cHx) | H | H | H | H |
| 5-1441 | H | H | Me | 2 | —CO—(CH$_2$)$_3$—O-(3-PrO-cHx) | H | H | H | H |
| 5-1442 | H | H | Me | 2 | —CO—(CH$_2$)$_3$—O-(4-PrO-cHx) | H | H | H | H |
| 5-1443 | H | H | Me | 2 | —CO—(CH$_2$)$_3$—O-(3-iPrO-cHx) | H | H | H | H |
| 5-1444 | H | H | Me | 2 | —CO—(CH$_2$)$_3$—O-(4-iPrO-cHx) | H | H | H | H |
| 5-1445 | H | H | Me | 2 | —CO—(CH$_2$)$_3$—O-[3-(2-Et-PrO)cHx] | H | H | H | H |
| 5-1446 | H | H | Me | 2 | —CO—(CH$_2$)$_3$—O-[4-(2-Et-PrO)cHx] | H | H | H | H |
| 5-1447 | H | H | Me | 2 | —CO—(CH$_2$)$_3$—O-(3-iBuO-cHx) | H | H | H | H |
| 5-1448 | H | H | Me | 2 | —CO—(CH$_2$)$_3$—O-(4-iBuO-cHx) | H | H | H | H |
| 5-1449 | H | H | Me | 2 | —CO—(CH$_2$)$_3$—O-(3-MeS-cHx) | H | H | H | H |
| 5-1450 | H | H | Me | 2 | —CO—(CH$_2$)$_3$—O-(4-MeS-cHx) | H | H | H | H |
| 5-1451 | H | H | Me | 2 | —CO—(CH$_2$)$_3$—O-(3-EtS-cHx) | H | H | H | H |
| 5-1452 | H | H | Me | 2 | —CO—(CH$_2$)$_3$—O-(4-EtS-cHx) | H | H | H | H |
| 5-1453 | H | H | Me | 2 | —CO—(CH$_2$)$_3$—O-(3-PrS-cHx) | H | H | H | H |
| 5-1454 | H | H | Me | 2 | —CO—(CH$_2$)$_3$—O-(4-PrS-cHx) | H | H | H | H |
| 5-1455 | H | H | Me | 2 | —CO—(CH$_2$)$_3$—O-(3-iPrS-cHx) | H | H | H | H |
| 5-1456 | H | H | Me | 2 | —CO—(CH$_2$)$_3$—O-(4-iPrS-cHx) | H | H | H | H |
| 5-1457 | H | H | Me | 2 | —CO—(CH$_2$)$_3$—O-[3-(2-Et-PrS)cHx] | H | H | H | H |
| 5-1458 | H | H | Me | 2 | —CO—(CH$_2$)$_3$—O-[4-(2-Et-PrS)cHx] | H | H | H | H |
| 5-1459 | H | H | Me | 2 | —CO—(CH$_2$)$_3$—O-(3-iBuS-cHx) | H | H | H | H |
| 5-1460 | H | H | Me | 2 | —CO—(CH$_2$)$_3$—O-(4-iBuS-cHx) | H | H | H | H |
| 5-1461 | H | H | Me | 2 | —CO—(CH$_2$)$_3$—O-(3-cHx-cHx) | H | H | H | H |
| 5-1462 | H | H | Me | 2 | —CO—(CH$_2$)$_3$—O-(4-cHx-cHx) | H | H | H | H |
| 5-1463 | H | H | Me | 2 | —CO—(CH$_2$)$_3$—O-(3-Ph-cHx) | H | H | H | H |
| 5-1464 | H | H | Me | 2 | —CO—(CH$_2$)$_3$—O-(4-Ph-cHx) | H | H | H | H |
| 5-1465 | H | H | Me | 2 | —CO—(CH$_2$)$_3$—O-(2,4-diMe-cHx) | H | H | H | H |
| 5-1466 | H | H | Me | 2 | —CO—(CH$_2$)$_3$—O-(3,4-diMe-cHx) | H | H | H | H |
| 5-1467 | H | H | Me | 2 | —CO—(CH$_2$)$_3$—O-(3,5-diMe-cHx) | H | H | H | H |
| 5-1468 | H | H | Me | 2 | —CO—(CH$_2$)$_3$—O-Ph | H | H | H | H |
| 5-1469 | H | H | Me | 2 | —CO—(CH$_2$)$_3$—O-Ph | Me | H | H | H |
| 5-1470 | H | H | Me | 2 | —CO—(CH$_2$)$_3$—O-Ph | H | Me | H | H |
| 5-1471 | H | H | Me | 2 | —CO—(CH$_2$)$_3$—O-Ph | F | H | H | H |
| 5-1472 | H | H | Me | 2 | —CO—(CH$_2$)$_3$—O-Ph | H | F | H | H |
| 5-1473 | H | Me | Me | 2 | —CO—(CH$_2$)$_3$—O-Ph | H | H | H | H |
| 5-1474 | CO$_2$Me | H | Me | 2 | —CO—(CH$_2$)$_3$—O-Ph | H | H | H | H |
| 5-1475 | CO$_2$Et | H | Me | 2 | —CO—(CH$_2$)$_3$—O-Ph | H | H | H | H |

TABLE 5-continued

| | | | | | | | | | |
|---|---|---|---|---|---|---|---|---|---|
| 5-1476 | H | H | Me | 2 | —CO—(CH$_2$)$_3$—O-(3-F-Ph) | H | H | H | H |
| 5-1477 | H | H | Me | 2 | —CO—(CH$_2$)$_3$—O-(4-F-Ph) | H | H | H | H |
| 5-1478 | H | H | Me | 2 | —CO—(CH$_2$)$_3$—O-(4-Cl-Ph) | H | H | H | H |
| 5-1479 | H | H | Me | 2 | —CO—(CH$_2$)$_3$—O-(4-Br-Ph) | H | H | H | H |
| 5-1480 | H | H | Me | 2 | —CO—(CH$_2$)$_3$—O-(3-Me-Ph) | H | H | H | H |
| 5-1481 | H | H | Me | 2 | —CO—(CH$_2$)$_3$—O-(4-Me-Ph) | H | H | H | H |
| 5-1482 | H | H | Me | 2 | —CO—(CH$_2$)$_3$—O-(3-Et-Ph) | H | H | H | H |
| 5-1483 | H | H | Me | 2 | —CO—(CH$_2$)$_3$—O-(4-Et-Ph) | H | H | H | H |
| 5-1484 | H | H | Me | 2 | —CO—(CH$_2$)$_3$—O-(3-Pr-Ph) | H | H | H | H |
| 5-1485 | H | H | Me | 2 | —CO—(CH$_2$)$_3$—O-(4-Pr-Ph) | H | H | H | H |
| 5-1486 | H | H | Me | 2 | —CO—(CH$_2$)$_3$—O-(3-iPr-Ph) | H | H | H | H |
| 5-1487 | H | H | Me | 2 | —CO—(CH$_2$)$_3$—O-(4-iPr-Ph) | H | H | H | H |
| 5-1488 | H | H | Me | 2 | —CO—(CH$_2$)$_3$—O-(3-Bu-Ph) | H | H | H | H |
| 5-1489 | H | H | Me | 2 | —CO—(CH$_2$)$_3$—O-(4-Bu-Ph) | H | H | H | H |
| 5-1490 | H | H | Me | 2 | —CO—(CH$_2$)$_3$—O-(3-CF$_3$-Ph) | H | H | H | H |
| 5-1491 | H | H | Me | 2 | —CO—(CH$_2$)$_3$—O-(4-CF$_3$-Ph) | H | H | H | H |
| 5-1492 | H | H | Me | 2 | —CO—(CH$_2$)$_3$—O-(3-MeO-Ph) | H | H | H | H |
| 5-1493 | H | H | Me | 2 | —CO—(CH$_2$)$_3$—O-(4-MeO-Ph) | H | H | H | H |
| 5-1494 | H | H | Me | 2 | —CO—(CH$_2$)$_3$—O-(3-EtO-Ph) | H | H | H | H |
| 5-1495 | H | H | Me | 2 | —CO—(CH$_2$)$_3$—O-(4-EtO-Ph) | H | H | H | H |
| 5-1496 | H | H | Me | 2 | —CO—(CH$_2$)$_3$—O-(3-PrO-Ph) | H | H | H | H |
| 5-1497 | H | H | Me | 2 | —CO—(CH$_2$)$_3$—O-(4-PrO-Ph) | H | H | H | H |
| 5-1498 | H | H | Me | 2 | —CO—(CH$_2$)$_3$—O-(3-iPrO-Ph) | H | H | H | H |
| 5-1499 | H | H | Me | 2 | —CO—(CH$_2$)$_3$—O-(4-iPrO-Ph) | H | H | H | H |
| 5-1500 | H | H | Me | 2 | —CO—(CH$_2$)$_3$—O-[3-(2-Et-PrO)-Ph] | H | H | H | H |
| 5-1501 | H | H | Me | 2 | —CO—(CH$_2$)$_3$—O-[4-(2-Et-PrO)-Ph] | H | H | H | H |
| 5-1502 | H | H | Me | 2 | —CO—(CH$_2$)$_3$—O-(3-iBuO-Ph) | H | H | H | H |
| 5-1503 | H | H | Me | 2 | —CO—(CH$_2$)$_3$—O-(4-iBuO-Ph) | H | H | H | H |
| 5-1504 | H | H | Me | 2 | —CO—(CH$_2$)$_3$—O-(3-MeS-Ph) | H | H | H | H |
| 5-1505 | H | H | Me | 2 | —CO—(CH$_2$)$_3$—O-(4-MeS-Ph) | H | H | H | H |
| 5-1506 | H | H | Me | 2 | —CO—(CH$_2$)$_3$—O-(3-EtS-Ph) | H | H | H | H |
| 5-1507 | H | H | Me | 2 | —CO—(CH$_2$)$_3$—O-(4-EtS-Ph) | H | H | H | H |
| 5-1508 | H | H | Me | 2 | —CO—(CH$_2$)$_3$—O-(3-PrS-Ph) | H | H | H | H |
| 5-1509 | H | H | Me | 2 | —CO—(CH$_2$)$_3$—O-(4-PrS-Ph) | H | H | H | H |
| 5-1510 | H | H | Me | 2 | —CO—(CH$_2$)$_3$—O-(3-iPrS-Ph) | H | H | H | H |
| 5-1511 | H | H | Me | 2 | —CO—(CH$_2$)$_3$—O-(4-iPrS-Ph) | H | H | H | H |
| 5-1512 | H | H | Me | 2 | —CO—(CH$_2$)$_3$—O-[3-(2-Et-PrS)-Ph] | H | H | H | H |
| 5-1513 | H | H | Me | 2 | —CO—(CH$_2$)$_3$—O-[4-(2-Et-PrS)-Ph] | H | H | H | H |
| 5-1514 | H | H | Me | 2 | —CO—(CH$_2$)$_3$—O-(3-iBuS-Ph) | H | H | H | H |
| 5-1515 | H | H | Me | 2 | —CO—(CH$_2$)$_3$—O-(4-iBuS-Ph) | H | H | H | H |
| 5-1516 | H | H | Me | 2 | —CO—(CH$_2$)$_3$—O-(3-cHx-Ph) | H | H | H | H |
| 5-1517 | H | H | Me | 2 | —CO—(CH$_2$)$_3$—O-(4-cHx-Ph) | H | H | H | H |
| 5-1518 | H | H | Me | 2 | —CO—(CH$_2$)$_3$—O-(3-Ph-Ph) | H | H | H | H |
| 5-1519 | H | H | Me | 2 | —CO—(CH$_2$)$_3$—O-(4-Ph-Ph) | H | H | H | H |
| 5-1520 | H | H | Me | 2 | —CO—(CH$_2$)$_3$—O-(2,4-diMe-Ph) | H | H | H | H |
| 5-1521 | H | H | Me | 2 | —CO—(CH$_2$)$_3$—O-(3,4-diMe-Ph) | H | H | H | H |
| 5-1522 | H | H | Me | 2 | —CO—(CH$_2$)$_3$—O-(3,5-diMe-Ph) | H | H | H | H |
| 5-1523 | H | H | Me | 2 | —CO—(CH$_2$)$_4$—O-cHx | H | H | H | H |
| 5-1524 | H | H | Me | 2 | —CO—(CH$_2$)$_4$—O-Ph | H | H | H | H |
| 5-1525 | H | H | Me | 2 | —CO—(CH$_2$)$_5$—O-cHx | H | H | H | H |
| 5-1526 | H | H | Me | 2 | —CO—(CH$_2$)$_5$—O-Ph | H | H | H | H |
| 5-1527 | H | H | Me | 2 | —CO—(CH$_2$)$_2$—OCH$_2$-cHx | H | H | H | H |
| 5-1528 | H | Me | Me | 2 | —CO—(CH$_2$)$_2$—OCH$_2$-cHx | H | H | H | H |
| 5-1529 | CO$_2$Me | H | Me | 2 | —CO—(CH$_2$)$_2$—OCH$_2$-cHx | H | H | H | H |
| 5-1530 | CO$_2$Et | H | Me | 2 | —CO—(CH$_2$)$_2$—OCH$_2$-cHx | H | H | H | H |
| 5-1531 | H | H | Me | 2 | —CO—(CH$_2$)$_2$—OCH$_2$-(4-F-cHx) | H | H | H | H |
| 5-1532 | H | H | Me | 2 | —CO—(CH$_2$)$_2$—OCH$_2$-(4-Me-cHx) | H | H | H | H |
| 5-1533 | H | H | Me | 2 | —CO—(CH$_2$)$_2$—OCH$_2$-(4-Et-cHx) | H | H | H | H |
| 5-1534 | H | H | Me | 2 | —CO—(CH$_2$)$_2$—OCH$_2$-(4-CF$_3$-cHx) | H | H | H | H |
| 5-1535 | H | H | Me | 2 | —CO—(CH$_2$)$_2$—OCH$_2$-(4-MeO-cHx) | H | H | H | H |
| 5-1536 | H | H | Me | 2 | —CO—(CH$_2$)$_2$—OCH$_2$-(4-EtO-cHx) | H | H | H | H |
| 5-1537 | H | H | Me | 2 | —CO—(CH$_2$)$_2$—OCH$_2$-(4-MeS-cHx) | H | H | H | H |
| 5-1538 | H | H | Me | 2 | —CO—(CH$_2$)$_2$—OCH$_2$-(4-cHx-cHx) | H | H | H | H |
| 5-1539 | H | H | Me | 2 | —CO—(CH$_2$)$_2$—OCH$_2$-(4-Ph-cHx) | H | H | H | H |
| 5-1540 | H | H | Me | 2 | —CO—(CH$_2$)$_2$—OCH$_2$-Ph | H | H | H | H |
| 5-1541 | H | Me | Me | 2 | —CO—(CH$_2$)$_2$—OCH$_2$-Ph | H | H | H | H |
| 5-1542 | CO$_2$Me | H | Me | 2 | —CO—(CH$_2$)$_2$—OCH$_2$-Ph | H | H | H | H |
| 5-1543 | CO$_2$Et | H | Me | 2 | —CO—(CH$_2$)$_2$—OCH$_2$-Ph | H | H | H | H |
| 5-1544 | H | H | Me | 2 | —CO—(CH$_2$)$_2$—OCH$_2$-(4-F-Ph) | H | H | H | H |
| 5-1545 | H | H | Me | 2 | —CO—(CH$_2$)$_2$—OCH$_2$-(4-Me-Ph) | H | H | H | H |
| 5-1546 | H | H | Me | 2 | —CO—(CH$_2$)$_2$—OCH$_2$-(4-Et-Ph) | H | H | H | H |
| 5-1547 | H | H | Me | 2 | —CO—(CH$_2$)$_2$—OCH$_2$-(4-CF$_3$-Ph) | H | H | H | H |
| 5-1548 | H | H | Me | 2 | —CO—(CH$_2$)$_2$—OCH$_2$-(4-MeO-Ph) | H | H | H | H |
| 5-1549 | H | H | Me | 2 | —CO—(CH$_2$)$_2$—OCH$_2$-(4-EtO-Ph) | H | H | H | H |
| 5-1550 | H | H | Me | 2 | —CO—(CH$_2$)$_2$—OCH$_2$-(4-MeS-Ph) | H | H | H | H |
| 5-1551 | H | H | Me | 2 | —CO—(CH$_2$)$_2$—OCH$_2$-(4-cHx-Ph) | H | H | H | H |
| 5-1552 | H | H | Me | 2 | —CO—(CH$_2$)$_2$—OCH$_2$-(4-Ph-Ph) | H | H | H | H |
| 5-1553 | H | H | Me | 2 | —CO—(CH$_2$)$_3$—OCH$_2$—CH$_2$-cPn | H | H | H | H |
| 5-1554 | H | H | Me | 2 | —CO—(CH$_2$)$_3$—OCH$_2$-cHx | H | H | H | H |
| 5-1555 | H | H | Me | 2 | —CO—(CH$_2$)$_3$—OCH$_2$-cHx | Me | H | H | H |

TABLE 5-continued

| | | | | | | | | | |
|---|---|---|---|---|---|---|---|---|---|
| 5-1556 | H | H | Me | 2 | —CO—(CH$_2$)$_3$—OCH$_2$-cHx | H | Me | H | H |
| 5-1557 | H | H | Me | 2 | —CO—(CH$_2$)$_3$—OCH$_2$-cHx | F | H | H | H |
| 5-1558 | H | H | Me | 2 | —CO—(CH$_2$)$_3$—OCH$_2$-cHx | H | F | H | H |
| 5-1559 | H | Me | Me | 2 | —CO—(CH$_2$)$_3$—OCH$_2$-cHx | H | H | H | H |
| 5-1560 | COMe | H | Me | 2 | —CO—(CH$_2$)$_3$—OCH$_2$-cHx | H | H | H | H |
| 5-1561 | CO$_2$Et | H | Me | 2 | —CO—(CH$_2$)$_3$—OCH$_2$-cHx | H | H | H | H |
| 5-1562 | H | H | Me | 2 | —CO—(CH$_2$)$_3$—OCH$_2$-(3-F-cHx) | H | H | H | H |
| 5-1563 | H | H | Me | 2 | —CO—(CH$_2$)$_3$—OCH$_2$-(4-F-cHx) | H | H | H | H |
| 5-1564 | H | H | Me | 2 | —CO—(CH$_2$)$_3$—OCH$_2$-(4-Cl-cHx) | H | H | H | H |
| 5-1565 | H | H | Me | 2 | —CO—(CH$_2$)$_3$—OCH$_2$-(4-Br-cHx) | H | H | H | H |
| 5-1566 | H | H | Me | 2 | —CO—(CH$_2$)$_3$—OCH$_2$-(3-Me-cHx) | H | H | H | H |
| 5-1567 | H | H | Me | 2 | —CO—(CH$_2$)$_3$—OCH$_2$-(4-Me-cHx) | H | H | H | H |
| 5-1568 | H | H | Me | 2 | —CO—(CH$_2$)$_3$—OCH$_2$-(3-Et-cHx) | H | H | H | H |
| 5-1569 | H | H | Me | 2 | —CO—(CH$_2$)$_3$—OCH$_2$-(4-Et-cHx) | H | H | H | H |
| 5-1570 | H | H | Me | 2 | —CO—(CH$_2$)$_3$—OCH$_2$-(3-Pr-cHx) | H | H | H | H |
| 5-1571 | H | H | Me | 2 | —CO—(CH$_2$)$_3$—OCH$_2$-(4-Pr-cHx) | H | H | H | H |
| 5-1572 | H | H | Me | 2 | —CO—(CH$_2$)$_3$—OCH$_2$-(4-iPr-cHx) | H | H | H | H |
| 5-1573 | H | H | Me | 2 | —CO—(CH$_2$)$_3$—OCH$_2$-(3-Bu-cHx) | H | H | H | H |
| 5-1574 | H | H | Me | 2 | —CO—(CH$_2$)$_3$—OCH$_2$-(4-Bu-cHx) | H | H | H | H |
| 5-1575 | H | H | Me | 2 | —CO—(CH$_2$)$_3$—OCH$_2$-(3-CF$_3$-cHx) | H | H | H | H |
| 5-1576 | H | H | Me | 2 | —CO—(CH$_2$)$_3$—OCH$_2$-(4-CF$_3$-cHx) | H | H | H | H |
| 5-1577 | H | H | Me | 2 | —CO—(CH$_2$)$_3$—OCH$_2$-(3-MeO-cHx) | H | H | H | H |
| 5-1578 | H | H | Me | 2 | —CO—(CH$_2$)$_3$—OCH$_2$-(4-MeO-cHx) | H | H | H | H |
| 5-1579 | H | H | Me | 2 | —CO—(CH$_2$)$_3$—OCH$_2$-(3-EtO-cHx) | H | H | H | H |
| 5-1580 | H | H | Me | 2 | —CO—(CH$_2$)$_3$—OCH$_2$-(4-EtO-cHx) | H | H | H | H |
| 5-1581 | H | H | Me | 2 | —CO—(CH$_2$)$_3$—OCH$_2$-(3-PrO-cHx) | H | H | H | H |
| 5-1582 | H | H | Me | 2 | —CO—(CH$_2$)$_3$—OCH$_2$-(4-PrO-cHx) | H | H | H | H |
| 5-1583 | H | H | Me | 2 | —CO—(CH$_2$)$_3$—OCH$_2$-(3-iPrO-cHx) | H | H | H | H |
| 5-1584 | H | H | Me | 2 | —CO—(CH$_2$)$_3$—OCH$_2$-(4-iPrO-cHx) | H | H | H | H |
| 5-1585 | H | H | Me | 2 | —CO—(CH$_2$)$_3$—OCH$_2$-[3-(2-Et-PrO)cHx] | H | H | H | H |
| 5-1586 | H | H | Me | 2 | —CO—(CH$_2$)$_3$—OCH$_2$-[4-(2-Et-PrO)cHx] | H | H | H | H |
| 5-1587 | H | H | Me | 2 | —CO—(CH$_2$)$_3$—OCH$_2$-(3-iBuO-cHx) | H | H | H | H |
| 5-1588 | H | H | Me | 2 | —CO—(CH$_2$)$_3$—OCH$_2$-(4-iBuO-cHx) | H | H | H | H |
| 5-1589 | H | H | Me | 2 | —CO—(CH$_2$)$_3$—OCH$_2$-(3-MeS-cHx) | H | H | H | H |
| 5-1590 | H | H | Me | 2 | —CO—(CH$_2$)$_3$—OCH$_2$-(4-MeS-cHx) | H | H | H | H |
| 5-1591 | H | H | Me | 2 | —CO—(CH$_2$)$_3$—OCH$_2$-(3-EtS-cHx) | H | H | H | H |
| 5-1592 | H | H | Me | 2 | —CO—(CH$_2$)$_3$—OCH$_2$-(4-EtS-cHx) | H | H | H | H |
| 5-1593 | H | H | Me | 2 | —CO—(CH$_2$)$_3$—OCH$_2$-(3-PrS-cHx) | H | H | H | H |
| 5-1594 | H | H | Me | 2 | —CO—(CH$_2$)$_3$—OCH$_2$-(4-PrS-cHx) | H | H | H | H |
| 5-1595 | H | H | Me | 2 | —CO—(CH$_2$)$_3$—OCH$_2$-(3-iPrS-cHx) | H | H | H | H |
| 5-1596 | H | H | Me | 2 | —CO—(CH$_2$)$_3$—OCH$_2$-(4-iPrS-cHx) | H | H | H | H |
| 5-1597 | H | H | Me | 2 | —CO—(CH$_2$)$_3$—OCH$_2$-[3-(2-Et-PrS)cHx] | H | H | | |
| 5-1598 | H | H | Me | 2 | —CO—(CH$_2$)$_3$—OCH$_2$-[4-(2-Et-PrS)cHx] | H | H | | |
| 5-1599 | H | H | Me | 2 | —CO—(CH$_2$)$_3$—OCH$_2$-(3-iBuS-cHx) | H | H | H | H |
| 5-1600 | H | H | Me | 2 | —CO—(CH$_2$)$_3$—OCH$_2$-(4-iBuS-cHx) | H | H | H | H |
| 5-1601 | H | H | Me | 2 | —CO—(CH$_2$)$_3$—OCH$_2$-(3-cHx-cHx) | H | H | H | H |
| 5-1602 | H | H | Me | 2 | —CO—(CH$_2$)$_3$—OCH$_2$-(4-cHx-cHx) | H | H | H | H |
| 5-1603 | H | H | Me | 2 | —CO—(CH$_2$)$_3$—OCH$_2$-(3-Ph-cHx) | H | H | H | H |
| 5-1604 | H | H | Me | 2 | —CO—(CH$_2$)$_3$—OCH$_2$-(4-Ph-cHx) | H | H | H | H |
| 5-1605 | H | H | Me | 2 | —CO—(CH$_2$)$_3$—OCH$_2$-(2,4-diMe-cHx) | H | H | H | H |
| 5-1606 | H | H | Me | 2 | —CO—(CH$_2$)$_3$—OCH$_2$-(3,4-diMe-cHx) | H | H | H | H |
| 5-1607 | H | H | Me | 2 | —CO—(CH$_2$)$_3$—OCH$_2$-(3,5-diMe-cHx) | H | H | H | H |
| 5-1608 | H | H | Me | 2 | —CO—(CH$_2$)$_3$—OCH$_2$-Ph | H | H | H | H |
| 5-1609 | H | H | Me | 2 | —CO—(CH$_2$)$_3$—OCH$_2$-Ph | Me | H | H | H |
| 5-1610 | H | H | Me | 2 | —CO—(CH$_2$)$_3$—OCH$_2$-Ph | H | Me | H | H |
| 5-1611 | H | H | Me | 2 | —CO—(CH$_2$)$_3$—OCH$_2$-Ph | F | H | H | H |
| 5-1612 | H | H | Me | 2 | —CO—(CH$_2$)$_3$—OCH$_2$-Ph | H | F | H | H |
| 5-1613 | H | Me | Me | 2 | —CO—(CH$_2$)$_3$—OCH$_2$-Ph | H | H | H | H |
| 5-1614 | CO$_2$Me | H | Me | 2 | —CO—(CH$_2$)$_3$—OCH$_2$-Ph | H | H | H | H |
| 5-1615 | CO$_2$Me | H | Me | 2 | —CO—(CH$_2$)$_3$—OCH$_2$-Ph | H | H | H | H |
| 5-1616 | H | H | Me | 2 | —CO—(CH$_2$)$_3$—OCH$_2$-(3-F-Ph) | H | H | H | H |
| 5-1617 | H | H | Me | 2 | —CO—(CH$_2$)$_3$—OCH$_2$-(4-F-Ph) | H | H | H | H |
| 5-1618 | H | H | Me | 2 | —CO—(CH$_2$)$_3$—OCH$_2$-(4-Cl-Ph) | H | H | H | H |
| 5-1619 | H | H | Me | 2 | —CO—(CH$_2$)$_3$—OCH$_2$-(4-Br-Ph) | H | H | H | H |
| 5-1620 | H | H | Me | 2 | —CO—(CH$_2$)$_3$—OCH$_2$-(3-Me-Ph) | H | H | H | H |
| 5-1621 | H | H | Me | 2 | —CO—(CH$_2$)$_3$—OCH$_2$-(4-Me-Ph) | H | H | H | H |
| 5-1622 | H | H | Me | 2 | —CO—(CH$_2$)$_3$—OCH$_2$-(3-Et-Ph) | H | H | H | H |
| 5-1623 | H | H | Me | 2 | —CO—(CH$_2$)$_3$—OCH$_2$-(4-Et-Ph) | H | H | H | H |
| 5-1624 | H | H | Me | 2 | —CO—(CH$_2$)$_3$—OCH$_2$-(3-Pr-Ph) | H | H | H | H |
| 5-1625 | H | H | Me | 2 | —CO—(CH$_2$)$_3$—OCH$_2$-(4-Pr-Ph) | H | H | H | H |
| 5-1626 | H | H | Me | 2 | —CO—(CH$_2$)$_3$—OCH$_2$-(3-iPr-Ph) | H | H | H | H |
| 5-1627 | H | H | Me | 2 | —CO—(CH$_2$)$_3$—OCH$_2$-(4-iPr-Ph) | H | H | H | H |
| 5-1628 | H | H | Me | 2 | —CO—(CH$_2$)$_3$—OCH$_2$-(3-Bu-Ph) | H | H | H | H |
| 5-1629 | H | H | Me | 2 | —CO—(CH$_2$)$_3$—OCH$_2$-(4-Bu-Ph) | H | H | H | H |
| 5-1630 | H | H | Me | 2 | —CO—(CH$_2$)$_3$—OCH$_2$-(3-CF$_3$-Ph) | H | H | H | H |
| 5-1631 | H | H | Me | 2 | —CO—(CH$_2$)$_3$—OCH$_2$-(4-CF$_3$-Ph) | H | H | H | H |
| 5-1632 | H | H | Me | 2 | —CO—(CH$_2$)$_3$—OCH$_2$-(3-MeO-Ph) | H | H | H | H |
| 5-1633 | H | H | Me | 2 | —CO—(CH$_2$)$_3$—OCH$_2$-(4-MeO-Ph) | H | H | H | H |
| 5-1634 | H | H | Me | 2 | —CO—(CH$_2$)$_3$—OCH$_2$-(3-EtO-Ph) | H | H | H | H |
| 5-1635 | H | H | Me | 2 | —CO—(CH$_2$)$_3$—OCH$_2$-(4-EtO-Ph) | H | H | H | H |

TABLE 5-continued

| | | | | | | | | | |
|---|---|---|---|---|---|---|---|---|---|
| 5-1636 | H | H | Me | 2 | —CO—(CH$_2$)$_3$—OCH$_2$-(3-PrO-Ph) | H | H | H | H |
| 5-1637 | H | H | Me | 2 | —CO—(CH$_2$)$_3$—OCH$_2$-(4-PrO-Ph) | H | H | H | H |
| 5-1638 | H | H | Me | 2 | —CO—(CH$_2$)$_3$—OCH$_2$-(3-iPrO-Ph) | H | H | H | H |
| 5-1639 | H | H | Me | 2 | —CO—(CH$_2$)$_3$—OCH$_2$-(4-iPrO-Ph) | H | H | H | H |
| 5-1640 | H | H | Me | 2 | —CO—(CH$_2$)$_3$—OCH$_2$-[3-(2-Et-PrO)Ph] | H | H | H | H |
| 5-1641 | H | H | Me | 2 | —CO—(CH$_2$)$_3$—OCH$_2$-[4-(2-Et-PrO)Ph] | H | H | H | H |
| 5-1642 | H | H | Me | 2 | —CO—(CH$_2$)$_3$—OCH$_2$-(3-iBuO-Ph) | H | H | H | H |
| 5-1643 | H | H | Me | 2 | —CO—(CH$_2$)$_3$—OCH$_2$-(4-iBuO-Ph) | H | H | H | H |
| 5-1644 | H | H | Me | 2 | —CO—(CH$_2$)$_3$—OCH$_2$-(3-MeS-Ph) | H | H | H | H |
| 5-1645 | H | H | Me | 2 | —CO—(CH$_2$)$_3$—OCH$_2$-(4-MeS-Ph) | H | H | H | H |
| 5-1646 | H | H | Me | 2 | —CO—(CH$_2$)$_3$—OCH$_2$-(3-EtS-Ph) | H | H | H | H |
| 5-1647 | H | H | Me | 2 | —CO—(CH$_2$)$_3$—OCH$_2$-(4-EtS-Ph) | H | H | H | H |
| 5-1648 | H | H | Me | 2 | —CO—(CH$_2$)$_3$—OCH$_2$-(3-PrS-Ph) | H | H | H | H |
| 5-1649 | H | H | Me | 2 | —CO—(CH$_2$)$_3$—OCH$_2$-(4-PrS-Ph) | H | H | H | H |
| 5-1650 | H | H | Me | 2 | —CO—(CH$_2$)$_3$—OCH$_2$-(3-iPrS-Ph) | H | H | H | H |
| 5-1651 | H | H | Me | 2 | —CO—(CH$_2$)$_3$—OCH$_2$-(4-iPrS-Ph) | H | H | H | H |
| 5-1652 | H | H | Me | 2 | —CO—(CH$_2$)$_3$—OCH$_2$-[3-(2-Et-PrS)Ph] | H | H | H | H |
| 5-1653 | H | H | Me | 2 | —CO—(CH$_2$)$_3$—OCH$_2$-[4-(2-Et-PrS)Ph] | H | H | H | H |
| 5-1654 | H | H | Me | 2 | —CO—(CH$_2$)$_3$—OCH$_2$-(3-iBuS-Ph) | H | H | H | H |
| 5-1655 | H | H | Me | 2 | —CO—(CH$_2$)$_3$—OCH$_2$-(4-iBuS-Ph) | H | H | H | H |
| 5-1656 | H | H | Me | 2 | —CO—(CH$_2$)$_3$—OCH$_2$-(3-cHx-Ph) | H | H | H | H |
| 5-1657 | H | H | Me | 2 | —CO—(CH$_2$)$_3$—OCH$_2$-(4-cHx-Ph) | H | H | H | H |
| 5-1658 | H | H | Me | 2 | —CO—(CH$_2$)$_3$—OCH$_2$-(3-Ph-Ph) | H | H | H | H |
| 5-1659 | H | H | Me | 2 | —CO—(CH$_2$)$_3$—OCH$_2$-(4-Ph-Ph) | H | H | H | H |
| 5-1660 | H | H | Me | 2 | —CO—(CH$_2$)$_3$—OCH$_2$-(2,4-diMe-Ph) | H | H | H | H |
| 5-1661 | H | H | Me | 2 | —CO—(CH$_2$)$_3$—OCH$_2$-(3,4-diMe-Ph) | H | H | H | H |
| 5-1662 | H | H | Me | 2 | —CO—(CH$_2$)$_3$—OCH$_2$-(3,5-diMe-Ph) | H | H | H | H |
| 5-1663 | H | H | Me | 2 | —CO—(CH$_2$)$_4$—OCH$_2$-cHx | H | H | H | H |
| 5-1664 | H | H | Me | 2 | —CO—(CH$_2$)$_4$—OCH$_2$-Ph | H | H | H | H |
| 5-1665 | H | H | Me | 2 | —CO—(CH$_2$)$_5$—OCH$_2$-cHx | H | H | H | H |
| 5-1666 | H | H | Me | 2 | —CO—(CH$_2$)$_5$—OCH$_2$-Ph | H | H | H | H |
| 5-1667 | H | H | Me | 2 | —CH(OH)—CH$_2$-cHx | H | H | H | H |
| 5-1668 | H | H | Me | 2 | —CH(OH)—CH$_2$-Ph | H | H | H | H |
| 5-1669 | H | H | Me | 2 | —CH(OH)—(CH$_2$)$_2$-cHx | H | H | H | H |
| 5-1670 | H | H | Me | 2 | —CH(OH)—(CH$_2$)$_2$-Ph | H | H | H | H |
| 5-1671 | H | H | Me | 2 | —CH(OH)—(CH$_2$)$_3$-cHx | H | H | H | H |
| 5-1672 | H | H | Me | 2 | —CH(OH)—(CH$_2$)$_3$-Ph | H | H | H | H |
| 5-1673 | H | H | Me | 2 | —CH(OH)—(CH$_2$)$_4$-cHx | H | H | H | H |
| 5-1674 | H | Me | Me | 2 | —CH(OH)—(CH$_2$)$_4$-cHx | H | H | H | H |
| 5-1675 | CO$_2$Me | H | Me | 2 | —CH(OH)—(CH$_2$)$_4$-cHx | H | H | H | H |
| 5-1676 | CO$_2$Et | H | Me | 2 | —CH(OH)—(CH$_2$)$_4$-cHx | H | H | H | H |
| 5-1677 | H | H | Me | 2 | —CH(OH)—(CH$_2$)$_4$-(4-F-cHx) | H | H | H | H |
| 5-1678 | H | H | Me | 2 | —CH(OH)—(CH$_2$)$_4$-(4-Me-cHx) | H | H | H | H |
| 5-1679 | H | H | Me | 2 | —CH(OH)—(CH$_2$)$_4$-(4-Et-cHx) | H | H | H | H |
| 5-1680 | H | H | Me | 2 | —CH(OH)—(CH$_2$)$_4$-(4-CF$_3$-cHx) | H | H | H | H |
| 5-1681 | H | H | Me | 2 | —CH(OH)—(CH$_2$)$_4$-(4-MeO-cHx) | H | H | H | H |
| 5-1682 | H | H | Me | 2 | —CH(OH)—(CH$_2$)$_4$-(4-EtO-cHx) | H | H | H | H |
| 5-1683 | H | H | Me | 2 | —CH(OH)—(CH$_2$)$_4$-(4-MeS-cHx) | H | H | H | H |
| 5-1684 | H | H | Me | 2 | —CH(OH)—(CH$_2$)$_4$-(4-cHx-cHx) | H | H | H | H |
| 5-1685 | H | H | Me | 2 | —CH(OH)—(CH$_2$)$_4$-(4-Ph-cHx) | H | H | H | H |
| 5-1686 | H | H | Me | 2 | —CH(OH)—(CH$_2$)$_4$-Ph | H | H | H | H |
| 5-1687 | H | Me | Me | 2 | —CH(OH)—(CH$_2$)$_4$-Ph | H | H | H | H |
| 5-1688 | CO$_2$Me | H | Me | 2 | —CH(OH)—(CH$_2$)$_4$-Ph | H | H | H | H |
| 5-1689 | CO$_2$Et | H | Me | 2 | —CH(OH)—(CH$_2$)$_4$-Ph | H | H | H | H |
| 5-1690 | H | H | Me | 2 | —CH(OH)—(CH$_2$)$_4$-(4-F-Ph) | H | H | H | H |
| 5-1691 | H | H | Me | 2 | —CH(OH)—(CH$_2$)$_4$-(4-Me-Ph) | H | H | H | H |
| 5-1692 | H | H | Me | 2 | —CH(OH)—(CH$_2$)$_4$-(4-Et-Ph) | H | H | H | H |
| 5-1693 | H | H | Me | 2 | —CH(OH)—(CH$_2$)$_4$-(4-CF$_3$-Ph) | H | H | H | H |
| 5-1694 | H | H | Me | 2 | —CH(OH)—(CH$_2$)$_4$-(4-MeO-Ph) | H | H | H | H |
| 5-1695 | H | H | Me | 2 | —CH(OH)—(CH$_2$)$_4$-(4-EtO-Ph) | H | H | H | H |
| 5-1696 | H | H | Me | 2 | —CH(OH)—(CH$_2$)$_4$-(4-MeS-Ph) | H | H | H | H |
| 5-1697 | H | H | Me | 2 | —CH(OH)—(CH$_2$)$_4$-(4-cHx-Ph) | H | H | H | H |
| 5-1698 | H | H | Me | 2 | —CH(OH)—(CH$_2$)$_4$-(4-Ph-Ph) | H | H | H | H |
| 5-1699 | H | H | Me | 2 | —CH(OH)—(CH$_2$)$_5$-cHx | H | H | H | H |
| 5-1700 | H | Me | Me | 2 | —CH(OH)—(CH$_2$)$_5$-cHx | H | H | H | H |
| 5-1701 | CO$_2$Me | H | Me | 2 | —CH(OH)—(CH$_2$)$_5$-cHx | H | H | H | H |
| 5-1702 | CO$_2$Et | H | Me | 2 | —CH(OH)—(CH$_2$)$_5$-cHx | H | H | H | H |
| 5-1703 | H | H | Me | 2 | —CH(OH)—(CH$_2$)$_5$-(4-F-cHx) | H | H | H | H |
| 5-1704 | H | H | Me | 2 | —CH(OH)—(CH$_2$)$_5$-(4-Me-cHx) | H | H | H | H |
| 5-1705 | H | H | Me | 2 | —CH(OH)—(CH$_2$)$_5$-(4-Et-cHx) | H | H | H | H |
| 5-1706 | H | H | Me | 2 | —CH(OH)—(CH$_2$)$_5$-(4-CF$_3$-cHx) | H | H | H | H |
| 5-1707 | H | H | Me | 2 | —CH(OH)—(CH$_2$)$_5$-(4-MeO-cHx) | H | H | H | H |
| 5-1708 | H | H | Me | 2 | —CH(OH)—(CH$_2$)$_5$-(4-EtO-cHx) | H | H | H | H |
| 5-1709 | H | H | Me | 2 | —CH(OH)—(CH$_2$)$_5$-(4-MeS-cHx) | H | H | H | H |
| 5-1710 | H | H | Me | 2 | —CH(OH)—(CH$_2$)$_5$-(4-cHx-cHx) | H | H | H | H |
| 5-1711 | H | H | Me | 2 | —CH(OH)—(CH$_2$)$_5$-(4-Ph-cHx) | H | H | H | H |
| 5-1712 | H | H | Me | 2 | —CH(OH)—(CH$_2$)$_5$-Ph | H | H | H | H |
| 5-1713 | H | Me | Me | 2 | —CH(OH)—(CH$_2$)$_5$-Ph | H | H | H | H |
| 5-1714 | CO$_2$Me | H | Me | 2 | —CH(OH)—(CH$_2$)$_5$-Ph | H | H | H | H |
| 5-1715 | CO$_2$Et | H | Me | 2 | —CH(OH)—(CH$_2$)$_5$-Ph | H | H | H | H |

TABLE 5-continued

| | | | | | | | | | |
|---|---|---|---|---|---|---|---|---|---|
| 5-1716 | H | H | Me | 2 | —CH(OH)—(CH$_2$)$_5$-(4-F-Ph) | H | H | H | H |
| 5-1717 | H | H | Me | 2 | —CH(OH)—(CH$_2$)$_5$-(4-Me-Ph) | H | H | H | H |
| 5-1718 | H | H | Me | 2 | —CH(OH)—(CH$_2$)$_5$-(4-Et-Ph) | H | H | H | H |
| 5-1719 | H | H | Me | 2 | —CH(OH)—(CH$_2$)$_5$-(4-CF$_3$-Ph) | H | H | H | H |
| 5-1720 | H | H | Me | 2 | —CH(OH)—(CH$_2$)$_5$-(4-MeO-Ph) | H | H | H | H |
| 5-1721 | H | H | Me | 2 | —CH(OH)—(CH$_2$)$_5$-(4-EtO-Ph) | H | H | H | H |
| 5-1722 | H | H | Me | 2 | —CH(OH)—(CH$_2$)$_5$-(4-MeS-Ph) | H | H | H | H |
| 5-1723 | H | H | Me | 2 | —CH(OH)—(CH$_2$)$_5$-(4-cHx-Ph) | H | H | H | H |
| 5-1724 | H | H | Me | 2 | —CH(OH)—(CH$_2$)$_5$-(4-Ph-Ph) | H | H | H | H |
| 5-1725 | H | H | Me | 2 | —CH(OH)—(CH$_2$)$_6$-cHx | H | H | H | H |
| 5-1726 | H | H | Me | 2 | —CH(OH)—(CH$_2$)$_6$-Ph | H | H | H | H |
| 5-1727 | H | H | Me | 2 | —CH(OH)—(CH$_2$)$_7$-cHx | H | H | H | H |
| 5-1728 | H | H | Me | 2 | —CH(OH)—(CH$_2$)$_7$-Ph | H | H | H | H |
| 5-1729 | H | H | Me | 2 | 4-(cHx-CH$_2$O)Ph | H | H | H | H |
| 5-1730 | H | Me | Me | 2 | 4-(cHx-CH$_2$O)Ph | H | H | H | H |
| 5-1731 | CO$_2$Me | H | Me | 2 | 4-(cHx-CH$_2$O)Ph | H | H | H | H |
| 5-1732 | CO$_2$Et | H | Me | 2 | 4-(cHx-CH$_2$O)Ph | H | H | H | H |
| 5-1733 | H | H | Me | 2 | 4-(cHx-CH$_2$O)-2-F-Ph | H | H | H | H |
| 5-1734 | H | H | Me | 2 | 4-(cHx-CH$_2$O)-3-F-Ph | H | H | H | H |
| 5-1735 | H | H | Me | 2 | 4-(cHx-CH$_2$O)-2,3-diF-Ph | H | H | H | H |
| 5-1736 | H | H | Me | 2 | 4-(cHx-CH$_2$O)-2-Cl-Ph | H | H | H | H |
| 5-1737 | H | H | Me | 2 | 4-(cHx-CH$_2$O)-3-Cl-Ph | H | H | H | H |
| 5-1738 | H | H | Me | 2 | 4-(cHx-CH$_2$O)-2,3-diCl-Ph | H | H | H | H |
| 5-1739 | H | H | Me | 2 | 4-(cHx-CH$_2$O)-2-Me-Ph | H | H | H | H |
| 5-1740 | H | H | Me | 2 | 4-(cHx-CH$_2$O)-3-Me-Ph | H | H | H | H |
| 5-1741 | H | H | Me | 2 | 4-(cHx-CH$_2$O)-2,3-diMe-Ph | H | H | H | H |
| 5-1742 | H | H | Me | 2 | 4-[cHx-(CH$_2$)$_2$O]Ph | H | H | H | H |
| 5-1743 | H | H | Me | 2 | 4-[cHx-(CH$_2$)$_3$O]Ph | H | H | H | H |
| 5-1744 | H | H | Me | 2 | -(4-BzO-Ph) | H | H | H | H |
| 5-1745 | H | Me | Me | 2 | -(4-BzO-Ph) | H | H | H | H |
| 5-1746 | CO$_2$Me | H | Me | 2 | -(4-BzO-Ph) | H | H | H | H |
| 5-1747 | CO$_2$Et | H | Me | 2 | -(4-BzO-Ph) | H | H | H | H |
| 5-1748 | H | H | Me | 2 | -(4-BzO-2-F-Ph) | H | H | H | H |
| 5-1749 | H | H | Me | 2 | -(4-BzO-3-F-Ph) | H | H | H | H |
| 5-1750 | H | H | Me | 2 | -(4-BzO-2,3-diF-Ph) | H | H | H | H |
| 5-1751 | H | H | Me | 2 | -(4-BzO-2-Cl-Ph) | H | H | H | H |
| 5-1752 | H | H | Me | 2 | -(4-BzO-3-Cl-Ph) | H | H | H | H |
| 5-1753 | H | H | Me | 2 | -(4-BzO-2,3-diCl-Ph) | H | H | H | H |
| 5-1754 | H | H | Me | 2 | -(4-BzO-2-Me-Ph) | H | H | H | H |
| 5-1755 | H | H | Me | 2 | -(4-BzO-3-Me-Ph) | H | H | H | H |
| 5-1756 | H | H | Me | 2 | -(4-BzO-2,3-diMe-Ph) | H | H | H | H |
| 5-1757 | H | H | Me | 2 | 4-[Ph-(CH$_2$)$_2$O]-Ph | H | H | H | H |
| 5-1758 | H | H | Me | 2 | 4-[Ph-(CH$_2$)$_3$O]-Ph | H | H | H | H |
| 5-1759 | H | H | Et | 2 | —(CH$_2$)$_3$-cHx | H | H | H | H |
| 5-1760 | H | H | Et | 2 | —(CH$_2$)$_3$-Ph | H | H | H | H |
| 5-1761 | H | H | Et | 2 | —(CH$_2$)$_4$-cHx | H | H | H | H |
| 5-1762 | H | H | Et | 2 | —(CH$_2$)$_4$-Ph | H | H | H | H |
| 5-1763 | H | H | Et | 2 | —(CH$_2$)$_5$-cPn | H | H | H | H |
| 5-1764 | H | H | Et | 2 | —(CH$_2$)$_5$-cHx | H | H | H | H |
| 5-1765 | H | H | Et | 2 | —(CH$_2$)$_5$-cHx | Me | H | H | H |
| 5-1766 | H | H | Et | 2 | —(CH$_2$)$_5$-cHx | H | Me | H | H |
| 5-1767 | H | H | Et | 2 | —(CH$_2$)$_5$-cHx | F | H | H | H |
| 5-1768 | H | H | Et | 2 | —(CH$_2$)$_5$-cHx | H | F | H | H |
| 5-1769 | H | Me | Et | 2 | —(CH$_2$)$_5$-cHx | H | H | H | H |
| 5-1770 | CO$_2$Me | H | Et | 2 | —(CH$_2$)$_5$-cHx | H | H | H | H |
| 5-1771 | CO$_2$Et | H | Et | 2 | —(CH$_2$)$_5$-cHx | H | H | H | H |
| 5-1772 | H | H | Et | 2 | —(CH$_2$)$_5$-(4-F-cHx) | H | H | H | H |
| 5-1773 | H | H | Et | 2 | —(CH$_2$)$_5$-(4-Cl-cHx) | H | H | H | H |
| 5-1774 | H | H | Et | 2 | —(CH$_2$)$_5$-(4-Br-cHx) | H | H | H | H |
| 5-1775 | H | H | Et | 2 | —(CH$_2$)$_5$-(4-Me-cHx) | H | H | H | H |
| 5-1776 | H | H | Et | 2 | —(CH$_2$)$_5$-(4-Et-cHx) | H | H | H | H |
| 5-1777 | H | H | Et | 2 | —(CH$_2$)$_5$-(4-Pr-cHx) | H | H | H | H |
| 5-1778 | H | H | Et | 2 | —(CH$_2$)$_5$-(4-iPr-cHx) | H | H | H | H |
| 5-1779 | H | H | Et | 2 | —(CH$_2$)$_5$-(4-CF$_3$-cHx) | H | H | H | H |
| 5-1780 | H | H | Et | 2 | —(CH$_2$)$_5$-(4-MeO-cHx) | H | H | H | H |
| 5-1781 | H | H | Et | 2 | —(CH$_2$)$_5$-(4-EtO-cHx) | H | H | H | H |
| 5-1782 | H | H | Et | 2 | —(CH$_2$)$_5$-(4-PrO-cHx) | H | H | H | H |
| 5-1783 | H | H | Et | 2 | —(CH$_2$)$_5$-(4-iPrO-cHx) | H | H | H | H |
| 5-1784 | H | H | Et | 2 | —(CH$_2$)$_5$-(3-MeS-cHx) | H | H | H | H |
| 5-1785 | H | H | Et | 2 | —(CH$_2$)$_5$-(4-MeS-cHx) | H | H | H | H |
| 5-1786 | H | H | Et | 2 | —(CH$_2$)$_5$-(2,4-diMe-cHx) | H | H | H | H |
| 5-1787 | H | H | Et | 2 | —(CH$_2$)$_5$-(3,4-diMe-cHx) | H | H | H | H |
| 5-1788 | H | H | Et | 2 | —(CH$_2$)$_5$-(3,5-diMe-cHx) | H | H | H | H |
| 5-1789 | H | H | Et | 2 | —(CH$_2$)$_5$-Ph | H | H | H | H |
| 5-1790 | H | H | Et | 2 | —(CH$_2$)$_5$-Ph | Me | H | H | H |
| 5-1791 | H | H | Et | 2 | —(CH$_2$)$_5$-Ph | H | Me | H | H |
| 5-1792 | H | H | Et | 2 | —(CH$_2$)$_5$-Ph | F | H | H | H |
| 5-1793 | H | H | Et | 2 | —(CH$_2$)$_5$-Ph | H | F | H | H |
| 5-1794 | H | Me | Et | 2 | —(CH$_2$)$_5$-Ph | H | H | H | H |
| 5-1795 | CO$_2$Me | H | Et | 2 | —(CH$_2$)$_5$-Ph | H | H | H | H |

TABLE 5-continued

| | | | | | | | | | |
|---|---|---|---|---|---|---|---|---|---|
| 5-1796 | CO₂Et | H | Et | 2 | —(CH₂)₅-Ph | H | H | H | H |
| 5-1797 | H | H | Et | 2 | —(CH₂)₅-(4-F-Ph) | H | H | H | H |
| 5-1798 | H | H | Et | 2 | —(CH₂)₅-(4-Cl-Ph) | H | H | H | H |
| 5-1799 | H | H | Et | 2 | —(CH₂)₅-(4-Br-Ph) | H | H | H | H |
| 5-1800 | H | H | Et | 2 | —(CH₂)₅-(4-Me-Ph) | H | H | H | H |
| 5-1801 | H | H | Et | 2 | —(CH₂)₅-(4-Et-Ph) | H | H | H | H |
| 5-1802 | H | H | Et | 2 | —(CH₂)₅-(4-Pr-Ph) | H | H | H | H |
| 5-1803 | H | H | Et | 2 | —(CH₂)₅-(4-iPr-Ph) | H | H | H | H |
| 5-1804 | H | H | Et | 2 | —(CH₂)₅-(4-Bu-Ph) | H | H | H | H |
| 5-1805 | H | H | Et | 2 | —(CH₂)₅-(4-CF₃-Ph) | H | H | H | H |
| 5-1806 | H | H | Et | 2 | —(CH₂)₅-(4-MeO-Ph) | H | H | H | H |
| 5-1807 | H | H | Et | 2 | —(CH₂)₅-(4-EtO-Ph) | H | H | H | H |
| 5-1808 | H | H | Et | 2 | —(CH₂)₅-(4-PrO-Ph) | H | H | H | H |
| 5-1809 | H | H | Et | 2 | —(CH₂)₅-(4-iPrO-Ph) | H | H | H | H |
| 5-1810 | H | H | Et | 2 | —(CH₂)₅-(3-MeS-Ph) | H | H | H | H |
| 5-1811 | H | H | Et | 2 | —(CH₂)₅-(4-MeS-Ph) | H | H | H | H |
| 5-1812 | H | H | Et | 2 | —(CH₂)₅-(2,4-diMe-Ph) | H | H | H | H |
| 5-1813 | H | H | Et | 2 | —(CH₂)₅-(3,4-diMe-Ph) | H | H | H | H |
| 5-1814 | H | H | Et | 2 | —(CH₂)₅-(3,5-diMe-Ph) | H | H | H | H |
| 5-1815 | H | H | Et | 2 | —(CH₂)₆-cPn | H | H | H | H |
| 5-1816 | H | H | Et | 2 | —(CH₂)₆-cHx | H | H | H | H |
| 5-1817 | H | H | Et | 2 | —(CH₂)₆-cHx | Me | H | H | H |
| 5-1818 | H | H | Et | 2 | —(CH₂)₆-cHx | H | Me | H | H |
| 5-1819 | H | H | Et | 2 | —(CH₂)₆-cHx | F | H | H | H |
| 5-1820 | H | H | Et | 2 | —(CH₂)₆-cHx | H | F | H | H |
| 5-1821 | H | Me | Et | 2 | —(CH₂)₆-cHx | H | H | H | H |
| 5-1822 | CO₂Me | H | Et | 2 | —(CH₂)₆-cHx | H | H | H | H |
| 5-1823 | CO₂Et | H | Et | 2 | —(CH₂)₆-cHx | H | H | H | H |
| 5-1824 | H | H | Et | 2 | —(CH₂)₆-(4-F-cHx) | H | H | H | H |
| 5-1825 | H | H | Et | 2 | —(CH₂)₆-(4-Cl-cHx) | H | H | H | H |
| 5-1826 | H | H | Et | 2 | —(CH₂)₆-(4-Br-cHx) | H | H | H | H |
| 5-1827 | H | H | Et | 2 | —(CH₂)₆-(4-Me-cHx) | H | H | H | H |
| 5-1828 | H | H | Et | 2 | —(CH₂)₆-(4-Et-cHx) | H | H | H | H |
| 5-1829 | H | H | Et | 2 | —(CH₂)₆-(4-Pr-cHx) | H | H | H | H |
| 5-1830 | H | H | Et | 2 | —(CH₂)₆-(4-iPr-cHx) | H | H | H | H |
| 5-1831 | H | H | Et | 2 | —(CH₂)₆-(4-Bu-cHx) | H | H | H | H |
| 5-1832 | H | H | Et | 2 | —(CH₂)₆-(4-CF₃-cHx) | H | H | H | H |
| 5-1833 | H | H | Et | 2 | —(CH₂)₆-(4-MeO-cHx) | H | H | H | H |
| 5-1834 | H | H | Et | 2 | —(CH₂)₆-(4-EtO-cHx) | H | H | H | H |
| 5-1835 | H | H | Et | 2 | —(CH₂)₆-(4-PrO-cHx) | H | H | H | H |
| 5-1836 | H | H | Et | 2 | —(CH₂)₆-(4-iPrO-cHx) | H | H | H | H |
| 5-1837 | H | H | Et | 2 | —(CH₂)₆-(3-MeS-cHx) | H | H | H | H |
| 5-1838 | H | H | Et | 2 | —(CH₂)₆-(4-MeS-cHx) | H | H | H | H |
| 5-1839 | H | H | Et | 2 | —(CH₂)₆-(2,4-diMe-cHx) | H | H | H | H |
| 5-1840 | H | H | Et | 2 | —(CH₂)₆-(3,4-diMe-cHx) | H | H | H | H |
| 5-1841 | H | H | Et | 2 | —(CH₂)₆-(3,5-diMe-cHx) | H | H | H | H |
| 5-1842 | H | H | Et | 2 | —(CH₂)₆-Ph | H | H | H | H |
| 5-1843 | H | H | Et | 2 | —(CH₂)₆-Ph | Me | H | H | H |
| 5-1844 | H | H | Et | 2 | —(CH₂)₆-Ph | H | Me | H | H |
| 5-1845 | H | H | Et | 2 | —(CH₂)₆-Ph | F | H | H | H |
| 5-1846 | H | H | Et | 2 | —(CH₂)₆-Ph | H | F | H | H |
| 5-1847 | H | Me | Et | 2 | —(CH₂)₆-Ph | H | H | H | H |
| 5-1848 | CO₂Me | H | Et | 2 | —(CH₂)₆-Ph | H | H | H | H |
| 5-1849 | CO₂Et | H | Et | 2 | —(CH₂)₆-Ph | H | H | H | H |
| 5-1850 | H | H | Et | 2 | —(CH₂)₆-(4-F-Ph) | H | H | H | H |
| 5-1851 | H | H | Et | 2 | —(CH₂)₆-(4-Cl-Ph) | H | H | H | H |
| 5-1852 | H | H | Et | 2 | —(CH₂)₆-(4-Br-Ph) | H | H | H | H |
| 5-1853 | H | H | Et | 2 | —(CH₂)₆-(4-Me-Ph) | H | H | H | H |
| 5-1854 | H | H | Et | 2 | —(CH₂)₆-(4-Et-Ph) | H | H | H | H |
| 5-1855 | H | H | Et | 2 | —(CH₂)₆-(4-Pr-Ph) | H | H | H | H |
| 5-1856 | H | H | Et | 2 | —(CH₂)₆-(4-iPr-Ph) | H | H | H | H |
| 5-1857 | H | H | Et | 2 | —(CH₂)₆-(4-Bu-Ph) | H | H | H | H |
| 5-1858 | H | H | Et | 2 | —(CH₂)₆-(4-CF₃-Ph) | H | H | H | H |
| 5-1859 | H | H | Et | 2 | —(CH₂)₆-(4-MeO-Ph) | H | H | H | H |
| 5-1860 | H | H | Et | 2 | —(CH₂)₆-(4-EtO-Ph) | H | H | H | H |
| 5-1861 | H | H | Et | 2 | —(CH₂)₆-(4-PrO-Ph) | H | H | H | H |
| 5-1862 | H | H | Et | 2 | —(CH₂)₆-(4-iPrO-Ph) | H | H | H | H |
| 5-1863 | H | H | Et | 2 | —(CH₂)₆-(3-MeS-Ph) | H | H | H | H |
| 5-1864 | H | H | Et | 2 | —(CH₂)₆-(4-MeS-Ph) | H | H | H | H |
| 5-1865 | H | H | Et | 2 | —(CH₂)₆-(2,4-diMe-Ph) | H | H | H | H |
| 5-1866 | H | H | Et | 2 | —(CH₂)₆-(3,4-diMe-Ph) | H | H | H | H |
| 5-1867 | H | H | Et | 2 | —(CH₂)₆-(3,5-diMe-Ph) | H | H | H | H |
| 5-1868 | H | H | Et | 2 | —(CH₂)₇-cHx | H | H | H | H |
| 5-1869 | H | H | Et | 2 | —(CH₂)₇-Ph | H | H | H | H |
| 5-1870 | H | H | Et | 2 | —CH=CH-cHx | H | H | H | H |
| 5-1871 | H | H | Et | 2 | —CH=CH-Ph | H | H | H | H |
| 5-1872 | H | H | Et | 2 | —CH=CH—(CH₂)₃-cHx | H | H | H | H |
| 5-1873 | H | Me | Et | 2 | —CH=CH—(CH₂)₃-cHx | H | H | H | H |
| 5-1874 | CO₂Me | H | Et | 2 | —CH=CH—(CH₂)₃-cHx | H | H | H | H |
| 5-1875 | CO₂Et | H | Et | 2 | —CH=CH—(CH₂)₃-cHx | H | H | H | H |

TABLE 5-continued

| | | | | | | | | | |
|---|---|---|---|---|---|---|---|---|---|
| 5-1876 | H | H | Et | 2 | —CH=CH—(CH$_2$)$_3$-Ph | H | H | H | H |
| 5-1877 | H | Me | Et | 2 | —CH=CH—(CH$_2$)$_3$-Ph | H | H | H | H |
| 5-1878 | CO$_2$Me | H | Et | 2 | —CH=CH—(CH$_2$)$_3$-Ph | H | H | H | H |
| 5-1879 | CO$_2$Et | H | Et | 2 | —CH=CH—(CH$_2$)$_3$-Ph | H | H | H | H |
| 5-1880 | H | H | Et | 2 | —CH=CH—(CH$_2$)$_4$-cHx | H | H | H | H |
| 5-1881 | H | Me | Et | 2 | —CH=CH—(CH$_2$)$_4$-cHx | H | H | H | H |
| 5-1882 | CO$_2$Me | H | Et | 2 | —CH=CH—(CH$_2$)$_4$-cHx | H | H | H | H |
| 5-1883 | CO$_2$Et | H | Et | 2 | —CH=CH—(CH$_2$)$_4$-cHx | H | H | H | H |
| 5-1884 | H | H | Et | 2 | —CH=CH—(CH$_2$)$_4$-Ph | H | H | H | H |
| 5-1885 | H | Me | Et | 2 | —CH=CH—(CH$_2$)$_4$-Ph | H | H | H | H |
| 5-1886 | CO$_2$Me | H | Et | 2 | —CH=CH—(CH$_2$)$_4$-Ph | H | H | H | H |
| 5-1887 | CO$_2$Et | H | Et | 2 | —CH=CH—(CH$_2$)$_4$-Ph | H | H | H | H |
| 5-1888 | H | H | Et | 2 | —CH=CH—CH$_2$O-cHx | H | H | H | H |
| 5-1889 | H | H | Et | 2 | —CH=CH—CH$_2$O-Ph | H | H | H | H |
| 5-1890 | H | H | Et | 2 | —CH=CH—(CH$_2$)$_2$O-cHx | H | H | H | H |
| 5-1891 | H | H | Et | 2 | —CH=CH—(CH$_2$)$_2$O-Ph | H | H | H | H |
| 5-1892 | H | H | Et | 2 | —C≡C—CH$_2$-cHx | H | H | H | H |
| 5-1893 | H | Me | Et | 2 | —C≡C—CH$_2$-cHx | H | H | H | H |
| 5-1894 | CO$_2$Me | H | Et | 2 | —C≡C—CH$_2$-cHx | H | H | H | H |
| 5-1895 | CO$_2$Et | H | Et | 2 | —C≡C—CH$_2$-cHx | H | H | H | H |
| 5-1896 | H | H | Et | 2 | —C≡C—CH$_2$-Ph | H | H | H | H |
| 5-1897 | H | Me | Et | 2 | —C≡C—CH$_2$-Ph | H | H | H | H |
| 5-1898 | CO$_2$Me | H | Et | 2 | —C≡C—CH$_2$-Ph | H | H | H | H |
| 5-1899 | CO$_2$Et | H | Et | 2 | —C≡C—CH$_2$-Ph | H | H | H | H |
| 5-1900 | H | H | Et | 2 | —C≡C—(CH$_2$)$_2$-cHx | H | H | H | H |
| 5-1901 | H | Me | Et | 2 | —C≡C—(CH$_2$)$_2$-cHx | H | H | H | H |
| 5-1902 | CO$_2$Me | H | Et | 2 | —C≡C—(CH$_2$)$_2$-cHx | H | H | H | H |
| 5-1903 | CO$_2$Et | H | Et | 2 | —C≡C—(CH$_2$)$_2$-cHx | H | H | H | H |
| 5-1904 | H | H | Et | 2 | —C≡C—(CH$_2$)$_2$-Ph | H | H | H | H |
| 5-1905 | H | Me | Et | 2 | —C≡C—(CH$_2$)$_2$-Ph | H | H | H | H |
| 5-1906 | CO$_2$Me | H | Et | 2 | —C≡C—(CH$_2$)$_2$-Ph | H | H | H | H |
| 5-1907 | CO$_2$Et | H | Et | 2 | —C≡C—(CH$_2$)$_2$-Ph | H | H | H | H |
| 5-1908 | H | H | Et | 2 | —C≡C—(CH$_2$)$_3$-cPn | H | H | H | H |
| 5-1909 | H | H | Et | 2 | —C≡C—(CH$_2$)$_3$-cHx | H | H | H | H |
| 5-1910 | H | H | Et | 2 | —C≡C—(CH$_2$)$_3$-cHx | Me | H | H | H |
| 5-1911 | H | H | Et | 2 | —C≡C—(CH$_2$)$_3$-cHx | H | Me | H | H |
| 5-1912 | H | H | Et | 2 | —C≡C—(CH$_2$)$_3$-cHx | F | H | H | H |
| 5-1913 | H | H | Et | 2 | —C≡C—(CH$_2$)$_3$-cHx | H | F | H | H |
| 5-1914 | H | Me | Et | 2 | —C≡C—(CH$_2$)$_3$-cHx | H | H | H | H |
| 5-1915 | CO$_2$Me | H | Et | 2 | —C≡C—(CH$_2$)$_3$-cHx | H | H | H | H |
| 5-1916 | CO$_2$Et | H | Et | 2 | —C≡C—(CH$_2$)$_3$-cHx | H | H | H | H |
| 5-1917 | H | H | Et | 2 | —C≡C—(CH$_2$)$_3$-(4-F-cHx) | H | H | H | H |
| 5-1918 | H | H | Et | 2 | —C≡C—(CH$_2$)$_3$-(4-Cl-cHx) | H | H | H | H |
| 5-1919 | H | H | Et | 2 | —C≡C—(CH$_2$)$_3$-(4-Br-cHx) | H | H | H | H |
| 5-1920 | H | H | Et | 2 | —C≡C—(CH$_2$)$_3$-(4-Me-cHx) | H | H | H | H |
| 5-1921 | H | H | Et | 2 | —C≡C—(CH$_2$)$_3$-(4-Et-cHx) | H | H | H | H |
| 5-1922 | H | H | Et | 2 | —C≡C—(CH$_2$)$_3$-(4-Pr-cHx) | H | H | H | H |
| 5-1923 | H | H | Et | 2 | —C≡C—(CH$_2$)$_3$-(4-iPr-cHx) | H | H | H | H |
| 5-1924 | H | H | Et | 2 | —C≡C—(CH$_2$)$_3$-(4-Bu-cHx) | H | H | H | H |
| 5-1925 | H | H | Et | 2 | —C≡C—(CH$_2$)$_3$-(4-CF$_3$-cHx) | H | H | H | H |
| 5-1926 | H | H | Et | 2 | —C≡C—(CH$_2$)$_3$-(4-MeO-cHx) | H | H | H | H |
| 5-1927 | H | H | Et | 2 | —C≡C—(CH$_2$)$_3$-(4-EtO-cHx) | H | H | H | H |
| 5-1928 | H | H | Et | 2 | —C≡C—(CH$_2$)$_3$-(4-PrO-cHx) | H | H | H | H |
| 5-1929 | H | H | Et | 2 | —C≡C—(CH$_2$)$_3$-(4-iPrO-cHx) | H | H | H | H |
| 5-1930 | H | H | Et | 2 | —C≡C—(CH$_2$)$_3$-(3-MeS-cHx) | H | H | H | H |
| 5-1931 | H | H | Et | 2 | —C≡C—(CH$_2$)$_3$-(4-MeS-cHx) | H | H | H | H |
| 5-1932 | H | H | Et | 2 | —C≡C—(CH$_2$)$_3$-(2,4-diMe-cHx) | H | H | H | H |
| 5-1933 | H | H | Et | 2 | —C≡C—(CH$_2$)$_3$-(3,4-diMe-cHx) | H | H | H | H |
| 5-1934 | H | H | Et | 2 | —C≡C—(CH$_2$)$_3$-(3,5-diMe-cHx) | H | H | H | H |
| 5-1935 | H | H | Et | 2 | —C≡C—(CH$_2$)$_3$-Ph | H | H | H | H |
| 5-1936 | H | H | Et | 2 | —C≡C—(CH$_2$)$_3$-Ph | Me | H | H | H |
| 5-1937 | H | H | Et | 2 | —C≡C—(CH$_2$)$_3$-Ph | H | Me | H | H |
| 5-1938 | H | H | Et | 2 | —C≡C—(CH$_2$)$_3$-Ph | F | H | H | H |
| 5-1939 | H | H | Et | 2 | —C≡C—(CH$_2$)$_3$-Ph | H | F | H | H |
| 5-1940 | H | Me | Et | 2 | —C≡C—(CH$_2$)$_3$-Ph | H | H | H | H |
| 5-1941 | CO$_2$Me | H | Et | 2 | —C≡C—(CH$_2$)$_3$-Ph | H | H | H | H |
| 5-1942 | CO$_2$Et | H | Et | 2 | —C≡C—(CH$_2$)$_3$-Ph | H | H | H | H |
| 5-1943 | H | H | Et | 2 | —C≡C—(CH$_2$)$_3$-(4-F-Ph) | H | H | H | H |
| 5-1944 | H | H | Et | 2 | —C≡C—(CH$_2$)$_3$-(4-Cl-Ph) | H | H | H | H |
| 5-1945 | H | H | Et | 2 | —C≡C—(CH$_2$)$_3$-(4-Br-Ph) | H | H | H | H |
| 5-1946 | H | H | Et | 2 | —C≡C—(CH$_2$)$_3$-(4-Me-Ph) | H | H | H | H |
| 5-1947 | H | H | Et | 2 | —C≡C—(CH$_2$)$_3$-(4-Et-Ph) | H | H | H | H |
| 5-1948 | H | H | Et | 2 | —C≡C—(CH$_2$)$_3$-(4-Pr-Ph) | H | H | H | H |
| 5-1949 | H | H | Et | 2 | —C≡C—(CH$_2$)$_3$-(4-iPr-Ph) | H | H | H | H |
| 5-1950 | H | H | Et | 2 | —C≡C—(CH$_2$)$_3$-(4-Bu-Ph) | H | H | H | H |
| 5-1951 | H | H | Et | 2 | —C≡C—(CH$_2$)$_3$-(4-CF$_3$-Ph) | H | H | H | H |
| 5-1952 | H | H | Et | 2 | —C≡C—(CH$_2$)$_3$-(4-MeO-Ph) | H | H | H | H |
| 5-1953 | H | H | Et | 2 | —C≡C—(CH$_2$)$_3$-(4-EtO-Ph) | H | H | H | H |
| 5-1954 | H | H | Et | 2 | —C≡C—(CH$_2$)$_3$-(4-PrO-Ph) | H | H | H | H |
| 5-1955 | H | H | Et | 2 | —C≡C—(CH$_2$)$_3$-(4-iPrO-Ph) | H | H | H | H |

TABLE 5-continued

| | | | | | | | | | | |
|---|---|---|---|---|---|---|---|---|---|---|
| 5-1956 | H | H | Et | 2 | —C≡C—(CH$_2$)$_3$-(3-MeS-Ph) | H | H | H | H |
| 5-1957 | H | H | Et | 2 | —C≡C—(CH$_2$)$_3$-(4-MeS-Ph) | H | H | H | H |
| 5-1958 | H | H | Et | 2 | —C≡C—(CH$_2$)$_3$-(2,4-diMe-Ph) | H | H | H | H |
| 5-1959 | H | H | Et | 2 | —C≡C—(CH$_2$)$_3$-(3,4-diMe-Ph) | H | H | H | H |
| 5-1960 | H | H | Et | 2 | —C≡C—(CH$_2$)$_3$-(3,5-diMe-Ph) | H | H | H | H |
| 5-1961 | H | H | Et | 2 | —C≡C—(CH$_2$)$_4$-cPn | H | H | H | H |
| 5-1962 | H | H | Et | 2 | —C≡C—(CH$_2$)$_4$-cHx | H | H | H | H |
| 5-1963 | H | H | Et | 2 | —C≡C—(CH$_2$)$_4$-cHx | Me | H | H | H |
| 5-1964 | H | H | Et | 2 | —C≡C—(CH$_2$)$_4$-cHx | H | Me | H | H |
| 5-1965 | H | H | Et | 2 | —C≡C—(CH$_2$)$_4$-cHx | F | H | H | H |
| 5-1966 | H | H | Et | 2 | —C≡C—(CH$_2$)$_4$-cHx | H | F | H | H |
| 5-1967 | H | Me | Et | 2 | —C≡C—(CH$_2$)$_4$-cHx | H | H | H | H |
| 5-1968 | CO$_2$Me | H | Et | 2 | —C≡C—(CH$_2$)$_4$-cHx | H | H | H | H |
| 5-1969 | CO$_2$Et | H | Et | 2 | —C≡C—(CH$_2$)$_4$-cHx | H | H | H | H |
| 5-1970 | H | H | Et | 2 | —C≡C—(CH$_2$)$_4$-(4-F-cHx) | H | H | H | H |
| 5-1971 | H | H | Et | 2 | —C≡C—(CH$_2$)$_4$-(4-Cl-cHx) | H | H | H | H |
| 5-1972 | H | H | Et | 2 | —C≡C—(CH$_2$)$_4$-(4-Br-cHx) | H | H | H | H |
| 5-1973 | H | H | Et | 2 | —C≡C—(CH$_2$)$_4$-(4-Me-cHx) | H | H | H | H |
| 5-1974 | H | H | Et | 2 | —C≡C—(CH$_2$)$_4$-(4-Et-cHx) | H | H | H | H |
| 5-1975 | H | H | Et | 2 | —C≡C—(CH$_2$)$_4$-(4-Pr-cHx) | H | H | H | H |
| 5-1976 | H | H | Et | 2 | —C≡C—(CH$_2$)$_4$-(4-iPr-cHx) | H | H | H | H |
| 5-1977 | H | H | Et | 2 | —C≡C—(CH$_2$)$_4$-(4-Bu-cHx) | H | H | H | H |
| 5-1978 | H | H | Et | 2 | —C≡C—(CH$_2$)$_4$-(4-CF$_3$-cHx) | H | H | H | H |
| 5-1979 | H | H | Et | 2 | —C≡C—(CH$_2$)$_4$-(4-MeO-cHx) | H | H | H | H |
| 5-1980 | H | H | Et | 2 | —C≡C—(CH$_2$)$_4$-(4-EtO-cHx) | H | H | H | H |
| 5-1981 | H | H | Et | 2 | —C≡C—(CH$_2$)$_4$-(4-PrO-cHx) | H | H | H | H |
| 5-1982 | H | H | Et | 2 | —C≡C—(CH$_2$)$_4$-(4-iPrO-cHx) | H | H | H | H |
| 5-1983 | H | H | Et | 2 | —C≡C—(CH$_2$)$_4$-(4-MeS-cHx) | H | H | H | H |
| 5-1984 | H | H | Et | 2 | —C≡C—(CH$_2$)$_4$-(2,4-diMe-cHx) | H | H | H | H |
| 5-1985 | H | H | Et | 2 | —C≡C—(CH$_2$)$_4$-(3,4-diMe-cHx) | H | H | H | H |
| 5-1986 | H | H | Et | 2 | —C≡C—(CH$_2$)$_4$-(3,5-diMe-cHx) | H | H | H | H |
| 5-1987 | H | H | Et | 2 | —C≡C—(CH$_2$)$_4$-Ph | H | H | H | H |
| 5-1988 | H | H | Et | 2 | —C≡C—(CH$_2$)$_4$-Ph | Me | H | H | H |
| 5-1989 | H | H | Et | 2 | —C≡C—(CH$_2$)$_4$-Ph | H | Me | H | H |
| 5-1990 | H | H | Et | 2 | —C≡C—(CH$_2$)$_4$-Ph | F | H | H | H |
| 5-1991 | H | H | Et | 2 | —C≡C—(CH$_2$)$_4$-Ph | H | F | H | H |
| 5-1992 | H | Me | Et | 2 | —C≡C—(CH$_2$)$_4$-Ph | H | H | H | H |
| 5-1993 | CO$_2$Me | H | Et | 2 | —C≡C—(CH$_2$)$_4$-Ph | H | H | H | H |
| 5-1994 | CO$_2$Et | H | Et | 2 | —C≡C—(CH$_2$)$_4$-Ph | H | H | H | H |
| 5-1995 | H | H | Et | 2 | —C≡C—(CH$_2$)$_4$-(4-F-Ph) | H | H | H | H |
| 5-1996 | H | H | Et | 2 | —C≡C—(CH$_2$)$_4$-(4-Cl-Ph) | H | H | H | H |
| 5-1997 | H | H | Et | 2 | —C≡C—(CH$_2$)$_4$-(4-Br-Ph) | H | H | H | H |
| 5-1998 | H | H | Et | 2 | —C≡C—(CH$_2$)$_4$-(4-Me-Ph) | H | H | H | H |
| 5-1999 | H | H | Et | 2 | —C≡C—(CH$_2$)$_4$-(4-Et-Ph) | H | H | H | H |
| 5-2000 | H | H | Et | 2 | —C≡C—(CH$_2$)$_4$-(4-Pr-Ph) | H | H | H | H |
| 5-2001 | H | H | Et | 2 | —C≡C—(CH$_2$)$_4$-(4-iPr-Ph) | H | H | H | H |
| 5-2002 | H | H | Et | 2 | —C≡C—(CH$_2$)$_4$-(4-Bu-Ph) | H | H | H | H |
| 5-2003 | H | H | Et | 2 | —C≡C—(CH$_2$)$_4$-(4-CF$_3$-Ph) | H | H | H | H |
| 5-2004 | H | H | Et | 2 | —C≡C—(CH$_2$)$_4$-(4-MeO-Ph) | H | H | H | H |
| 5-2005 | H | H | Et | 2 | —C≡C—(CH$_2$)$_4$-(4-EtO-Ph) | H | H | H | H |
| 5-2006 | H | H | Et | 2 | —C≡C—(CH$_2$)$_4$-(4-PrO-Ph) | H | H | H | H |
| 5-2007 | H | H | Et | 2 | —C≡C—(CH$_2$)$_4$-(4-iPrO-Ph) | H | H | H | H |
| 5-2008 | H | H | Et | 2 | —C≡C—(CH$_2$)$_4$-(3-MeS-Ph) | H | H | H | H |
| 5-2009 | H | H | Et | 2 | —C≡C—(CH$_2$)$_4$-(4-MeS-Ph) | H | H | H | H |
| 5-2010 | H | H | Et | 2 | —C≡C—(CH$_2$)$_4$-(2,4-diMe-Ph) | H | H | H | H |
| 5-2011 | H | H | Et | 2 | —C≡C—(CH$_2$)$_4$-(3,4-diMe-Ph) | H | H | H | H |
| 5-2012 | H | H | Et | 2 | —C≡C—(CH$_2$)$_4$-(3,5-diMe-Ph) | H | H | H | H |
| 5-2013 | H | H | Et | 2 | —C≡C—(CH$_2$)$_5$-cHx | H | H | H | H |
| 5-2014 | H | Me | Et | 2 | —C≡C—(CH$_2$)$_5$-cHx | H | H | H | H |
| 5-2015 | CO$_2$Me | H | Et | 2 | —C≡C—(CH$_2$)$_5$-cHx | H | H | H | H |
| 5-2016 | CO$_2$Et | H | Et | 2 | —C≡C—(CH$_2$)$_5$-cHx | H | H | H | H |
| 5-2017 | H | H | Et | 2 | —C≡C—(CH$_2$)$_5$-Ph | H | H | H | H |
| 5-2018 | H | Me | Et | 2 | —C≡C—(CH$_2$)$_5$-Ph | H | H | H | H |
| 5-2019 | CO$_2$Me | H | Et | 2 | —C≡C—(CH$_2$)$_5$-Ph | H | H | H | H |
| 5-2020 | CO$_2$Et | H | Et | 2 | —C≡C—(CH$_2$)$_5$-Ph | H | H | H | H |
| 5-2021 | H | H | Et | 2 | —C≡C—(CH$_2$)$_6$-cHx | H | H | H | H |
| 5-2022 | H | Me | Et | 2 | —C≡C—(CH$_2$)$_6$-cHx | H | H | H | H |
| 5-2023 | CO$_2$Me | H | Et | 2 | —C≡C—(CH$_2$)$_6$-cHx | H | H | H | H |
| 5-2024 | CO$_2$Et | H | Et | 2 | —C≡C—(CH$_2$)$_6$-cHx | H | H | H | H |
| 5-2025 | H | H | Et | 2 | —C≡C—(CH$_2$)$_6$-Ph | H | H | H | H |
| 5-2026 | H | Me | Et | 2 | —C≡C—(CH$_2$)$_6$-Ph | H | H | H | H |
| 5-2027 | CO$_2$Me | H | Et | 2 | —C≡C—(CH$_2$)$_6$-Ph | H | H | H | H |
| 5-2028 | CO$_2$Et | H | Et | 2 | —C≡C—(CH$_2$)$_6$-Ph | H | H | H | H |
| 5-2029 | H | H | Et | 2 | —C≡C—CH$_2$O-cHx | H | H | H | H |
| 5-2030 | H | Me | Et | 2 | —C≡C—CH$_2$O-cHx | H | H | H | H |
| 5-2031 | CO$_2$Me | H | Et | 2 | —C≡C—CH$_2$O-cHx | H | H | H | H |
| 5-2032 | CO$_2$Et | H | Et | 2 | —C≡C—CH$_2$O-cHx | H | H | H | H |
| 5-2033 | H | H | Et | 2 | —C≡C—CH$_2$O-Ph | H | H | H | H |
| 5-2034 | H | Me | Et | 2 | —C≡C—CH$_2$O-Ph | H | H | H | H |
| 5-2035 | CO$_2$Me | H | Et | 2 | —C≡C—CH$_2$O-Ph | H | H | H | H |

TABLE 5-continued

| | | | | | | | | | |
|---|---|---|---|---|---|---|---|---|---|
| 5-2036 | CO₂Et | H | Et | 2 | —C≡C—CH₂O-Ph | H | H | H | H |
| 5-2037 | H | H | Et | 2 | —C≡C—(CH₂)₂O-cPn | H | H | H | H |
| 5-2038 | H | H | Et | 2 | —C≡C—(CH₂)₂O-cHx | H | H | H | H |
| 5-2039 | H | H | Et | 2 | —C≡C—(CH₂)₂O-cHx | Me | H | H | H |
| 5-2040 | H | H | Et | 2 | —C≡C—(CH₂)₂O-cHx | H | Me | H | H |
| 5-2041 | H | H | Et | 2 | —C≡C—(CH₂)₂O-cHx | F | H | H | H |
| 5-2042 | H | H | Et | 2 | —C≡C—(CH₂)₂O-cHx | H | F | H | H |
| 5-2043 | H | Me | Et | 2 | —C≡C—(CH₂)₂O-cHx | H | H | H | H |
| 5-2044 | CO₂Me | H | Et | 2 | —C≡C—(CH₂)₂O-cHx | H | H | H | H |
| 5-2045 | CO₂Et | H | Et | 2 | —C≡C—(CH₂)₂O-cHx | H | H | H | H |
| 5-2046 | H | H | Et | 2 | —C≡C—(CH₂)₂O-(4-F-cHx) | H | H | H | H |
| 5-2047 | H | H | Et | 2 | —C≡C—(CH₂)₂O-(4-Cl-cHx) | H | H | H | H |
| 5-2048 | H | H | Et | 2 | —C≡C—(CH₂)₂O-(4-Br-cHx) | H | H | H | H |
| 5-2049 | H | H | Et | 2 | —C≡C—(CH₂)₂O-(4-Me-cHx) | H | H | H | H |
| 5-2050 | H | H | Et | 2 | —C≡C—(CH₂)₂O-(4-Et-cHx) | H | H | H | H |
| 5-2051 | H | H | Et | 2 | —C≡C—(CH₂)₂O-(4-Pr-cHx) | H | H | H | H |
| 5-2052 | H | H | Et | 2 | —C≡C—(CH₂)₂O-(4-iPr-cHx) | H | H | H | H |
| 5-2053 | H | H | Et | 2 | —C≡C—(CH₂)₂O-(4-Bu-cHx) | H | H | H | H |
| 5-2054 | H | H | Et | 2 | —C≡C—(CH₂)₂O-(4-CF₃-cHx) | H | H | H | H |
| 5-2055 | H | H | Et | 2 | —C≡C—(CH₂)₂O-(4-MeO-cHx) | H | H | H | H |
| 5-2056 | H | H | Et | 2 | —C≡C—(CH₂)₂O-(4-EtO-cHx) | H | H | H | H |
| 5-2057 | H | H | Et | 2 | —C≡C—(CH₂)₂O-(4-PrO-cHx) | H | H | H | H |
| 5-2058 | H | H | Et | 2 | —C≡C—(CH₂)₂O-(4-iPrO-cHx) | H | H | H | H |
| 5-2059 | H | H | Et | 2 | —C≡C—(CH₂)₂O-(3-MeS-cHx) | H | H | H | H |
| 5-2060 | H | H | Et | 2 | —C≡C—(CH₂)₂O-(4-MeS-cHx) | H | H | H | H |
| 5-2061 | H | H | Et | 2 | —C≡C—(CH₂)₂O-(2,4-diMe-cHx) | H | H | H | H |
| 5-2062 | H | H | Et | 2 | —C≡C—(CH₂)₂O-(3,4-diMe-cHx) | H | H | H | H |
| 5-2063 | H | H | Et | 2 | —C≡C—(CH₂)₂O-(3,5-diMe-cHx) | H | H | H | H |
| 5-2064 | H | H | Et | 2 | —C≡C—(CH₂)₂O-Ph | H | H | H | H |
| 5-2065 | H | H | Et | 2 | —C≡C—(CH₂)₂O-Ph | Me | H | H | H |
| 5-2066 | H | H | Et | 2 | —C≡C—(CH₂)₂O-Ph | H | Me | H | H |
| 5-2067 | H | H | Et | 2 | —C≡C—(CH₂)₂O-Ph | F | H | H | H |
| 5-2068 | H | H | Et | 2 | —C≡C—(CH₂)₂O-Ph | H | F | H | H |
| 5-2069 | H | Me | Et | 2 | —C≡C—(CH₂)₂—OCH₂-Ph | H | H | H | H |
| 5-2070 | CO₂Me | H | Et | 2 | —C≡C—(CH₂)₂O-Ph | H | H | H | H |
| 5-2071 | CO₂Et | H | Et | 2 | —C≡C—(CH₂)₂O-Ph | H | H | H | H |
| 5-2072 | H | H | Et | 2 | —C≡C—(CH₂)₂O-(4-F-Ph) | H | H | H | H |
| 5-2073 | H | H | Et | 2 | —C≡C—(CH₂)₂O-(4-Cl-Ph) | H | H | H | H |
| 5-2074 | H | H | Et | 2 | —C≡C—(CH₂)₂O-(4-Br-Ph) | H | H | H | H |
| 5-2075 | H | H | Et | 2 | —C≡C—(CH₂)₂O-(4-Me-Ph) | H | H | H | H |
| 5-2076 | H | H | Et | 2 | —C≡C—(CH₂)₂O-(4-Et-Ph) | H | H | H | H |
| 5-2077 | H | H | Et | 2 | —C≡C—(CH₂)₂O-(4-Pr-Ph) | H | H | H | H |
| 5-2078 | H | H | Et | 2 | —C≡C—(CH₂)₂O-(4-iPr-Ph) | H | H | H | H |
| 5-2079 | H | H | Et | 2 | —C≡C—(CH₂)₂O-(4-Bu-Ph) | H | H | H | H |
| 5-2080 | H | H | Et | 2 | —C≡C—(CH₂)₂O-(4-CF₃-Ph) | H | H | H | H |
| 5-2081 | H | H | Et | 2 | —C≡C—(CH₂)₂O-(4-MeO-Ph) | H | H | H | H |
| 5-2082 | H | H | Et | 2 | —C≡C—(CH₂)₂O-(4-EtO-Ph) | H | H | H | H |
| 5-2083 | H | H | Et | 2 | —C≡C—(CH₂)₂O-(4-PrO-Ph) | H | H | H | H |
| 5-2084 | H | H | Et | 2 | —C≡C—(CH₂)₂O-(4-iPrO-Ph) | H | H | H | H |
| 5-2085 | H | H | Et | 2 | —C≡C—(CH₂)₂O-(4-MeS-Ph) | H | H | H | H |
| 5-2086 | H | H | Et | 2 | —C≡C—(CH₂)₂O-(2,4-diMe-Ph) | H | H | H | H |
| 5-2087 | H | H | Et | 2 | —C≡C—(CH₂)₂O-(3,4-diMe-Ph) | H | H | H | H |
| 5-2088 | H | H | Et | 2 | —C≡C—(CH₂)₂O-(3,5-diMe-Ph) | H | H | H | H |
| 5-2089 | H | H | Et | 2 | —CO—(CH₂)₃-cHx | H | H | H | H |
| 5-2090 | H | Me | Et | 2 | —CO—(CH₂)₃-cHx | H | H | H | H |
| 5-2091 | CO₂Me | H | Et | 2 | —CO—(CH₂)₃-cHx | H | H | H | H |
| 5-2092 | CO₂Et | H | Et | 2 | —CO—(CH₂)₃-cHx | H | H | H | H |
| 5-2093 | H | H | Et | 2 | —CO—(CH₂)₃-Ph | H | H | H | H |
| 5-2094 | H | Me | Et | 2 | —CO—(CH₂)₃-Ph | H | H | H | H |
| 5-2095 | CO₂Me | H | Et | 2 | —CO—(CH₂)₃-Ph | H | H | H | H |
| 5-2096 | CO₂Et | H | Et | 2 | —CO—(CH₂)₃-Ph | H | H | H | H |
| 5-2097 | H | H | Et | 2 | —CO—(CH₂)₄-cHx | H | H | H | H |
| 5-2098 | H | Me | Et | 2 | —CO—(CH₂)₄-cHx | H | H | H | H |
| 5-2099 | CO₂Me | H | Et | 2 | —CO—(CH₂)₄-cHx | H | H | H | H |
| 5-2100 | CO₂Et | H | Et | 2 | —CO—(CH₂)₄-cHx | H | H | H | H |
| 5-2101 | H | H | Et | 2 | —CO—(CH₂)₄-Ph | H | H | H | H |
| 5-2102 | H | Me | Et | 2 | —CO—(CH₂)₄-Ph | H | H | H | H |
| 5-2103 | CO₂Me | H | Et | 2 | —CO—(CH₂)₄-Ph | H | H | H | H |
| 5-2104 | CO₂Et | H | Et | 2 | —CO—(CH₂)₄-Ph | H | H | H | H |
| 5-2105 | H | H | Et | 2 | —CO—(CH₂)₅-cHx | H | H | H | H |
| 5-2106 | H | Me | Et | 2 | —CO—(CH₂)₅-cHx | H | H | H | H |
| 5-2107 | CO₂Me | H | Et | 2 | —CO—(CH₂)₅-cHx | H | H | H | H |
| 5-2108 | CO₂Et | H | Et | 2 | —CO—(CH₂)₅-cHx | H | H | H | H |
| 5-2109 | H | H | Et | 2 | —CO—(CH₂)₅-Ph | H | H | H | H |
| 5-2110 | H | Me | Et | 2 | —CO—(CH₂)₅-Ph | H | H | H | H |
| 5-2111 | CO₂Me | H | Et | 2 | —CO—(CH₂)₅-Ph | H | H | H | H |
| 5-2112 | CO₂Et | H | Et | 2 | —CO—(CH₂)₅-Ph | H | H | H | H |
| 5-2113 | H | H | Et | 2 | —CH(OH)—(CH₂)₄-cHx | H | H | H | H |
| 5-2114 | H | Me | Et | 2 | —CH(OH)—(CH₂)₄-cHx | H | H | H | H |
| 5-2115 | CO₂Me | H | Et | 2 | —CH(OH)—(CH₂)₄-cHx | H | H | H | H |

TABLE 5-continued

| | | | | | | | | | |
|---|---|---|---|---|---|---|---|---|---|
| 5-2116 | CO$_2$Et | H | Et | 2 | —CH(OH)—(CH$_2$)$_4$-cHx | H | H | H | H |
| 5-2117 | H | H | Et | 2 | —CH(OH)—(CH$_2$)$_4$-Ph | H | H | H | H |
| 5-2118 | H | Me | Et | 2 | —CH(OH)—(CH$_2$)$_4$-Ph | H | H | H | H |
| 5-2119 | CO$_2$Me | H | Et | 2 | —CH(OH)—(CH$_2$)$_4$-Ph | H | H | H | H |
| 5-2120 | CO$_2$Et | H | Et | 2 | —CH(OH)—(CH$_2$)$_4$-Ph | H | H | H | H |
| 5-2121 | H | H | Et | 2 | —CH(OH)—(CH$_2$)$_5$-cHx | H | H | H | H |
| 5-2122 | H | Me | Et | 2 | —CH(OH)—(CH$_2$)$_5$-cHx | H | H | H | H |
| 5-2123 | CO$_2$Me | H | Et | 2 | —CH(OH)—(CH$_2$)$_5$-cHx | H | H | H | H |
| 5-2124 | CO$_2$Et | H | Et | 2 | —CH(OH)—(CH$_2$)$_5$-cHx | H | H | H | H |
| 5-2125 | H | H | Et | 2 | —CH(OH)—(CH$_2$)$_5$-Ph | H | H | H | H |
| 5-2126 | H | Me | Et | 2 | —CH(OH)—(CH$_2$)$_5$-Ph | H | H | H | H |
| 5-2127 | CO$_2$Me | H | Et | 2 | —CH(OH)—(CH$_2$)$_5$-Ph | H | H | H | H |
| 5-2128 | CO$_2$Et | H | Et | 2 | —CH(OH)—(CH$_2$)$_5$-Ph | H | H | H | H |
| 5-2129 | H | H | Et | 2 | -4-(cHx-CH$_2$O)Ph | H | H | H | H |
| 5-2130 | H | Me | Et | 2 | -4-(cHx-CH$_2$O)Ph | H | H | H | H |
| 5-2131 | CO$_2$Me | H | Et | 2 | -4-(cHx-CH$_2$O)Ph | H | H | H | H |
| 5-2132 | CO$_2$Et | H | Et | 2 | -4-(cHx-CH$_2$O)Ph | H | H | H | H |
| 5-2133 | H | H | Et | 2 | -4-[cHx-(CH$_2$)$_2$O]Ph | H | H | H | H |
| 5-2134 | H | H | Et | 2 | -4-[cHx-(CH$_2$)$_3$O]Ph | H | H | H | H |
| 5-2135 | H | H | Et | 2 | -(4-BzO-Ph) | H | H | H | H |
| 5-2136 | H | Me | Et | 2 | -(4-BzO-Ph) | H | H | H | H |
| 5-2137 | CO$_2$Me | H | Et | 2 | -(4-BzO-Ph) | H | H | H | H |
| 5-2138 | CO$_2$Et | H | Et | 2 | -(4-BzO-Ph) | H | H | H | H |
| 5-2139 | H | H | Et | 2 | -(4-BzO-2-F-Ph) | H | H | H | H |
| 5-2140 | H | H | Et | 2 | -(4-BzO-3-F-Ph) | H | H | H | H |
| 5-2141 | H | H | Et | 2 | -(4-BzO-2,3-diF-Ph) | H | H | H | H |
| 5-2142 | H | H | Et | 2 | -(4-BzO-2-Cl-Ph) | H | H | H | H |
| 5-2143 | H | H | Et | 2 | -(4-BzO-3-Cl-Ph) | H | H | H | H |
| 5-2144 | H | H | Et | 2 | -(4-BzO-2,3-diCl-Ph) | H | H | H | H |
| 5-2145 | H | H | Et | 2 | -(4-BzO-2-Me-Ph) | H | H | H | H |
| 5-2146 | H | H | Et | 2 | -(4-BzO-3-Me-Ph) | H | H | H | H |
| 5-2147 | H | H | Et | 2 | -(4-BzO-2,3-diMe-Ph) | H | H | H | H |
| 5-2148 | H | H | Et | 2 | 4-[Ph-(CH$_2$)$_2$O]-Ph | H | H | H | H |
| 5-2149 | H | H | Et | 2 | 4-[Ph-(CH$_2$)$_3$O]-Ph | H | H | H | H |
| 5-2150 | H | H | Pr | 2 | —(CH$_2$)$_5$-cHx | H | H | H | H |
| 5-2151 | H | H | Pr | 2 | —(CH$_2$)$_5$-Ph | H | H | H | H |
| 5-2152 | H | H | Pr | 2 | —(CH$_2$)$_6$-cHx | H | H | H | H |
| 5-2153 | H | H | Pr | 2 | —(CH$_2$)$_6$-Ph | H | H | H | H |
| 5-2154 | H | H | Pr | 2 | —C≡C—CH$_2$-cHx | H | H | H | H |
| 5-2155 | H | H | Pr | 2 | —C≡C—(CH$_2$)$_3$-cHx | H | H | H | H |
| 5-2156 | H | H | Pr | 2 | —C≡C—(CH$_2$)$_3$-Ph | H | H | H | H |
| 5-2157 | H | H | Pr | 2 | —C≡C—(CH$_2$)$_4$-cHx | H | H | H | H |
| 5-2158 | H | H | Pr | 2 | —C≡C—(CH$_2$)$_4$-Ph | H | H | H | H |
| 5-2159 | CO$_2$Me | H | Pr | 2 | —C≡C—CH$_2$O-Ph | H | H | H | H |
| 5-2160 | CO$_2$Et | H | Pr | 2 | —C≡C—CH$_2$O-Ph | H | H | H | H |
| 5-2161 | H | H | Pr | 2 | —C≡C—(CH$_2$)$_2$O-cHx | H | H | H | H |
| 5-2162 | H | H | Pr | 2 | —C≡C—(CH$_2$)$_2$O-Ph | H | H | H | H |
| 5-2163 | H | H | Pr | 2 | -4-(cHx-CH$_2$O)Ph | H | H | H | H |
| 5-2164 | H | H | Pr | 2 | -(4-BzO-Ph) | H | H | H | H |
| 5-2165 | H | H | Me | 3 | —(CH$_2$)$_5$-cHx | H | H | H | H |
| 5-2166 | H | H | Me | 3 | —(CH$_2$)$_6$-cHx | H | H | H | H |
| 5-2167 | H | H | Me | 3 | —CH=CH—(CH$_2$)$_3$-cHx | H | H | H | H |
| 5-2168 | H | H | Me | 3 | —CH=CH—(CH$_2$)$_4$-cHx | H | H | H | H |
| 5-2169 | H | H | Me | 3 | —C≡C—(CH$_2$)$_3$-cHx | H | H | H | H |
| 5-2170 | H | H | Me | 3 | —C≡C—(CH$_2$)$_4$-cHx | H | H | H | H |
| 5-2171 | H | H | Me | 3 | —CO—(CH$_2$)$_4$-cHx | H | H | H | H |
| 5-2172 | H | H | Me | 3 | —CO—(CH$_2$)$_5$-cHx | H | H | H | H |
| 5-2173 | H | H | Me | 3 | —CO—(CH$_2$)$_4$-Ph | H | H | H | H |
| 5-2174 | H | H | Me | 3 | —CO—(CH$_2$)$_5$-Ph | H | H | H | H |
| 5-2175 | H | H | Me | 3 | —CH(OH)—(CH$_2$)$_4$-cHx | H | H | H | H |
| 5-2176 | H | H | Me | 3 | —CH(OH)—(CH$_2$)$_5$-cHx | H | H | H | H |
| 5-2177 | H | H | Me | 3 | -4-(cHx-CH$_2$O)Ph | H | H | H | H |
| 5-2178 | H | H | Me | 3 | -(4-BzO-Ph) | H | H | H | H |
| 5-2179 | H | H | Me | 3 | —C≡C—CH$_2$O-cPn | H | H | H | H |
| 5-2180 | H | H | Me | 3 | —C≡C—(CH$_2$)$_2$O-cPn | H | H | H | H |
| 5-2181 | H | H | Me | 3 | —C≡C—CH$_2$O-cHx | H | H | H | H |
| 5-2182 | H | H | Me | 3 | —C≡C—(CH$_2$)$_2$O-cHx | H | H | H | H |
| 5-2183 | H | H | Me | 3 | —C≡C—CH$_2$O-Ph | H | H | H | H |
| 5-2184 | H | H | Me | 3 | —C≡C—(CH$_2$)$_2$O-Ph | H | H | H | H |
| 5-2185 | H | H | Me | 2 | —(CH$_2$)$_4$-(3-F-Ph) | H | H | H | H |
| 5-2186 | H | H | Me | 2 | —(CH$_2$)$_4$-(3,4-diF-Ph) | H | H | H | H |
| 5-2187 | H | H | Me | 2 | —(CH$_2$)$_4$-(3,5-diF-Ph) | H | H | H | H |
| 5-2188 | H | H | Me | 2 | —(CH$_2$)$_4$-(3-Cl-Ph) | H | H | H | H |
| 5-2189 | H | H | Me | 2 | —(CH$_2$)$_4$-(4-Cl-Ph) | H | H | H | H |
| 5-2190 | H | H | Me | 2 | —(CH$_2$)$_4$-(3,4-diCl-Ph) | H | H | H | H |
| 5-2191 | H | H | Me | 2 | —(CH$_2$)$_4$-(3,5-diCl-Ph) | H | H | H | H |
| 5-2192 | H | H | Me | 2 | —(CH$_2$)$_4$-(3-Me-Ph) | H | H | H | H |
| 5-2193 | H | H | Me | 2 | —(CH$_2$)$_4$-(3,4-diMe-Ph) | H | H | H | H |
| 5-2194 | H | H | Me | 2 | —(CH$_2$)$_4$-(3,5-diMe-PH) | H | H | H | H |
| 5-2195 | H | H | Me | 2 | —(CH$_2$)$_4$-(3-CF$_3$-Ph) | H | H | H | H |

TABLE 5-continued

| | | | | | | | | | |
|---|---|---|---|---|---|---|---|---|---|
| 5-2196 | H | H | Me | 2 | —(CH$_2$)$_4$-(3,4-diCF$_3$-Ph) | H | H | H | H |
| 5-2197 | H | H | Me | 2 | —(CH$_2$)$_4$-(3,5-diCF$_3$-Ph) | H | H | H | H |
| 5-2198 | H | H | Me | 2 | —(CH$_2$)$_4$-(3-MeO-Ph) | H | H | H | H |
| 5-2199 | H | H | Me | 2 | —(CH$_2$)$_4$-(3,4-diMeO-Ph) | H | H | H | H |
| 5-2200 | H | H | Me | 2 | —(CH$_2$)$_4$-(3,5-diMeO-Ph) | H | H | H | H |
| 5-2201 | H | H | Me | 2 | —(CH$_2$)$_4$-(3,4,5-triMeO-Ph) | H | H | H | H |
| 5-2202 | H | H | Me | 2 | —(CH$_2$)$_4$-(3-Ac-Ph) | H | H | H | H |
| 5-2203 | H | H | Me | 2 | —(CH$_2$)$_4$-(4-Ac-Ph) | H | H | H | H |
| 5-2204 | H | H | Me | 2 | —(CH$_2$)$_5$-(3,4-diF-Ph) | H | H | H | H |
| 5-2205 | H | H | Me | 2 | —(CH$_2$)$_5$-(3,5-diF-Ph) | H | H | H | H |
| 5-2206 | H | H | Me | 2 | —(CH$_2$)$_5$-(3-Cl-Ph) | H | H | H | H |
| 5-2207 | H | H | Me | 2 | —(CH$_2$)$_5$-(3,4-diCl-Ph) | H | H | H | H |
| 5-2208 | H | H | Me | 2 | —(CH$_2$)$_5$-(3,5-diCl-Ph) | H | H | H | H |
| 5-2209 | H | H | Me | 2 | —(CH$_2$)$_5$-(3,4-diCF$_3$-Ph) | H | H | H | H |
| 5-2210 | H | H | Me | 2 | —(CH$_2$)$_5$-(3,5-diCF$_3$-Ph) | H | H | H | H |
| 5-2211 | H | H | Me | 2 | —(CH$_2$)$_5$-(3,4-diMeO-Ph) | H | H | H | H |
| 5-2212 | H | H | Me | 2 | —(CH$_2$)$_5$-(3,5-diMeO-Ph) | H | H | H | H |
| 5-2213 | H | H | Me | 2 | —(CH$_2$)$_5$-(3,4,5-triMeO-Ph) | H | H | H | H |
| 5-2214 | H | H | Me | 2 | —(CH$_2$)$_5$-(3-Ac-Ph) | H | H | H | H |
| 5-2215 | H | H | Me | 2 | —(CH$_2$)$_5$-(4-Ac-Ph) | H | H | H | H |
| 5-2216 | H | H | Me | 2 | —(CH$_2$)$_3$—O-(3-F-Ph) | H | H | H | H |
| 5-2217 | H | H | Me | 2 | —(CH$_2$)$_3$—O-(3,4-diF-Ph) | H | H | H | H |
| 5-2218 | H | H | Me | 2 | —(CH$_2$)$_3$—O-(3,5-diF-Ph) | H | H | H | H |
| 5-2219 | H | H | Me | 2 | —(CH$_2$)$_3$—O-(3-Me-Ph) | H | H | H | H |
| 5-2220 | H | H | Me | 2 | —(CH$_2$)$_3$—O-(3,4-diMe-Ph) | H | H | H | H |
| 5-2221 | H | H | Me | 2 | —(CH$_2$)$_3$—O-(3,5-diMe-Ph) | H | H | H | H |
| 5-2222 | H | H | Me | 2 | —(CH$_2$)$_3$—O-(3-CF$_3$-Ph) | H | H | H | H |
| 5-2223 | H | H | Me | 2 | —(CH$_2$)$_3$—O-(3,4-diCF$_3$-Ph) | H | H | H | H |
| 5-2224 | H | H | Me | 2 | —(CH$_2$)$_3$—O-(3,5-diCF$_3$-Ph) | H | H | H | H |
| 5-2225 | H | H | Me | 2 | —(CH$_2$)$_3$—O-(3-MeO-Ph) | H | H | H | H |
| 5-2226 | H | H | Me | 2 | —(CH$_2$)$_3$—O-(3,4-diMeO-Ph) | H | H | H | H |
| 5-2227 | H | H | Me | 2 | —(CH$_2$)$_3$—O-(3,5-diMeO-Ph) | H | H | H | H |
| 5-2228 | H | H | Me | 2 | —(CH$_2$)$_3$—O-(3,4,5-triMeO-Ph) | H | H | H | H |
| 5-2229 | H | H | Me | 2 | —(CH$_2$)$_3$—O-(3-Ac-Ph) | H | H | H | H |
| 5-2230 | H | H | Me | 2 | —(CH$_2$)$_3$—O-(4-Ac-Ph) | H | H | H | H |
| 5-2231 | H | H | Me | 2 | —(CH$_2$)$_4$—O-(3,4-diF-Ph) | H | H | H | H |
| 5-2232 | H | H | Me | 2 | —(CH$_2$)$_4$—O-(3,5-diF-Ph) | H | H | H | H |
| 5-2233 | H | H | Me | 2 | —(CH$_2$)$_4$—O-(3,4-diMeO-Ph) | H | H | H | H |
| 5-2234 | H | H | Me | 2 | —(CH$_2$)$_4$—O-(3,5-diMeO-Ph) | H | H | H | H |
| 5-2235 | H | H | Me | 2 | —(CH$_2$)$_4$—O-(3,4,5-triMeO-Ph) | H | H | H | H |
| 5-2236 | H | H | Me | 2 | —(CH$_2$)$_4$—O-(3-Ac-Ph) | H | H | H | H |
| 5-2237 | H | H | Me | 2 | —(CH$_2$)$_4$—O-(4-Ac-Ph) | H | H | H | H |
| 5-2238 | H | H | Me | 2 | —C≡C—(CH$_2$)$_2$-(3-F-Ph) | H | H | H | H |
| 5-2239 | H | H | Me | 2 | —C≡C—(CH$_2$)$_2$-(3,4-diF-Ph) | H | H | H | H |
| 5-2240 | H | H | Me | 2 | —C≡C—(CH$_2$)$_2$-(3,5-diF-Ph) | H | H | H | H |
| 5-2241 | H | H | Me | 2 | —C≡C—(CH$_2$)$_2$-(3-Cl-Ph) | H | H | H | H |
| 5-2242 | H | H | Me | 2 | —C≡C—(CH$_2$)$_2$-(4-Cl-Ph) | H | H | H | H |
| 5-2243 | H | H | Me | 2 | —C≡C—(CH$_2$)$_2$-(3,4-diCl-Ph) | H | H | H | H |
| 5-2244 | H | H | Me | 2 | —C≡C—(CH$_2$)$_2$-(3,5-diCl-Ph) | H | H | H | H |
| 5-2245 | H | H | Me | 2 | —C≡C—(CH$_2$)$_2$-(3-Me-Ph) | H | H | H | H |
| 5-2246 | H | H | Me | 2 | —C≡C—(CH$_2$)$_2$-(3,4-diMe-Ph) | H | H | H | H |
| 5-2247 | H | H | Me | 2 | —C≡C—(CH$_2$)$_2$-(3,5-diMe-Ph) | H | H | H | H |
| 5-2248 | H | H | Me | 2 | —C≡C—(CH$_2$)$_2$-(3-CF$_3$-Ph) | H | H | H | H |
| 5-2249 | H | H | Me | 2 | —C≡C—(CH$_2$)$_2$-(3,4-diCF$_3$-Ph) | H | H | H | H |
| 5-2250 | H | H | Me | 2 | —C≡C—(CH$_2$)$_2$-(3,5-diCF$_3$-Ph) | H | H | H | H |
| 5-2251 | H | H | Me | 2 | —C≡C—(CH$_2$)$_2$-(3-MeO-Ph) | H | H | H | H |
| 5-2252 | H | H | Me | 2 | —C≡C—(CH$_2$)$_2$-(3,4-diMeO-Ph) | H | H | H | H |
| 5-2253 | H | H | Me | 2 | —C≡C—(CH$_2$)$_2$-(3,5-diMeO-Ph) | H | H | H | H |
| 5-2254 | H | H | Me | 2 | —C≡C—(CH$_2$)$_2$-(3,4,5-triMeO-Ph) | H | H | H | H |
| 5-2255 | H | H | Me | 2 | —C≡C—(CH$_2$)$_2$-(3-Ac-Ph) | H | H | H | H |
| 5-2256 | H | H | Me | 2 | —C≡C—(CH$_2$)$_2$-(4-Ac-Ph) | H | H | H | H |
| 5-2257 | H | H | Me | 2 | —C≡C—(CH$_2$)$_3$-(3,4-diF-Ph) | H | H | H | H |
| 5-2258 | H | H | Me | 2 | —C≡C—(CH$_2$)$_3$-(3,5-diF-Ph) | H | H | H | H |
| 5-2259 | H | H | Me | 2 | —C≡C—(CH$_2$)$_3$-(3-Cl-Ph) | H | H | H | H |
| 5-2260 | H | H | Me | 2 | —C≡C—(CH$_2$)$_3$-(3,4-diCl-Ph) | H | H | H | H |
| 5-2261 | H | H | Me | 2 | —C≡C—(CH$_2$)$_3$-(3,5-diCl-Ph) | H | H | H | H |
| 5-2262 | H | H | Me | 2 | —C≡C—(CH$_2$)$_3$-(3,4-diCF$_3$-Ph) | H | H | H | H |
| 5-2263 | H | H | Me | 2 | —C≡C—(CH$_2$)$_3$-(3,5-diCF$_3$-Ph) | H | H | H | H |
| 5-2264 | H | H | Me | 2 | —C≡C—(CH$_2$)$_3$-(3,4-diMeO-Ph) | H | H | H | H |
| 5-2265 | H | H | Me | 2 | —C≡C—(CH$_2$)$_3$-(3,5-diMeO-Ph) | H | H | H | H |
| 5-2266 | H | H | Me | 2 | —C≡C—(CH$_2$)$_3$-(3,4,5-triMeO-Ph) | H | H | H | H |
| 5-2267 | H | H | Me | 2 | —C≡C—(CH$_2$)$_3$-(3-Ac-Ph) | H | H | H | H |
| 5-2268 | H | H | Me | 2 | —C≡C—(CH$_2$)$_3$-(4-Ac-Ph) | H | H | H | H |
| 5-2269 | H | H | Me | 2 | —C≡C—CH$_2$—O-(3-F-Ph) | H | H | H | H |
| 5-2270 | H | H | Me | 2 | —C≡C—CH$_2$—O-(3,4-diF-Ph) | H | H | H | H |
| 5-2271 | H | H | Me | 2 | —C≡C—CH$_2$—O-(3,5-diF-Ph) | H | H | H | H |
| 5-2272 | H | H | Me | 2 | —C≡C—CH$_2$—O-(3-Cl-Ph) | H | H | H | H |
| 5-2273 | H | H | Me | 2 | —C≡C—CH$_2$—O-(4-Cl-Ph) | H | H | H | H |
| 5-2274 | H | H | Me | 2 | —C≡C—CH$_2$—O-(3,4-diCl-Ph) | H | H | H | H |
| 5-2275 | H | H | Me | 2 | —C≡C—CH$_2$—O-(3,5-diCl-Ph) | H | H | H | H |

TABLE 5-continued

| | | | | | | | | | |
|---|---|---|---|---|---|---|---|---|---|
| 5-2276 | H | H | Me | 2 | —C≡C—CH$_2$—O-(3-Me-Ph) | H | H | H | H |
| 5-2277 | H | H | Me | 2 | —C≡C—CH$_2$—O-(2,4-diMe-Ph) | H | H | H | H |
| 5-2278 | H | H | Me | 2 | —C≡C—CH$_2$—O-(3,4-diMe-Ph) | H | H | H | H |
| 5-2279 | H | H | Me | 2 | —C≡C—CH$_2$—O-(3,5-diMe-Ph) | H | H | H | H |
| 5-2280 | H | H | Me | 2 | —C≡C—CH$_2$—O-(3-CF$_3$-Ph) | H | H | H | H |
| 5-2281 | H | H | Me | 2 | —C≡C—CH$_2$—O-(3,4-diCF$_3$-Ph) | H | H | H | H |
| 5-2282 | H | H | Me | 2 | —C≡C—CH$_2$—O-(3,5-diCF$_3$-Ph) | H | H | H | H |
| 5-2283 | H | H | Me | 2 | —C≡C—CH$_2$—O-(3-MeO-Ph) | H | H | H | H |
| 5-2284 | H | H | Me | 2 | —C≡C—CH$_2$—O-(3,4-diMeO-Ph) | H | H | H | H |
| 5-2285 | H | H | Me | 2 | —C≡C—CH$_2$—O-(3,5-diMeO-Ph) | H | H | H | H |
| 5-2286 | H | H | Me | 2 | —C≡C—CH$_2$—O-(3,4,5-triMeO-Ph) | H | H | H | H |
| 5-2287 | H | H | Me | 2 | —C≡C—CH$_2$—O-(3-Ac-Ph) | H | H | H | H |
| 5-2288 | H | H | Me | 2 | —C≡C—CH$_2$—O-(4-Ac-Ph) | H | H | H | H |
| 5-2289 | H | H | Me | 2 | —C≡C—CH$_2$—O-(4-CO$_2$H-Ph) | H | H | H | H |
| 5-2290 | H | H | Me | 2 | —C≡C—(CH$_2$)$_2$—O-(3,4-diF-Ph) | H | H | H | H |
| 5-2291 | H | H | Me | 2 | —C≡C—(CH$_2$)$_2$—O-(3,5-diF-Ph) | H | H | H | H |
| 5-2292 | H | H | Me | 2 | —C≡C—(CH$_2$)$_2$—O-(3-Cl-Ph) | H | H | H | H |
| 5-2293 | H | H | Me | 2 | —C≡C—(CH$_2$)$_2$—O-(3,4-diCl-Ph) | H | H | H | H |
| 5-2294 | H | H | Me | 2 | —C≡C—(CH$_2$)$_2$—O-(3,5-diCl-Ph) | H | H | H | H |
| 5-2295 | H | H | Me | 2 | —C≡C—(CH$_2$)$_2$—O-(3,4-diCF$_3$-Ph) | H | H | H | H |
| 5-2296 | H | H | Me | 2 | —C≡C—(CH$_2$)$_2$—O-(3,5-diCF$_3$-Ph) | H | H | H | H |
| 5-2297 | H | H | Me | 2 | —C≡C—(CH$_2$)$_2$—O-(3,4-diMeO-Ph) | H | H | H | H |
| 5-2298 | H | H | Me | 2 | —C≡C—(CH$_2$)$_2$—O-(3,5-diMeO-Ph) | H | H | H | H |
| 5-2299 | H | H | Me | 2 | —C≡C—(CH$_2$)$_2$—O-(3,4,5-triMeO-Ph) | H | H | H | H |
| 5-2300 | H | H | Me | 2 | —C≡C—(CH$_2$)$_2$—O-(3-Ac-Ph) | H | H | H | H |
| 5-2301 | H | H | Me | 2 | —C≡C—(CH$_2$)$_2$—O-(4-Ac-Ph) | H | H | H | H |
| 5-2302 | H | H | Me | 2 | —CO—(CH$_2$)$_3$-(3-F-Ph) | H | H | H | H |
| 5-2303 | H | H | Me | 2 | —CO—(CH$_2$)$_3$-(4-F-Ph) | H | H | H | H |
| 5-2304 | H | H | Me | 2 | —CO—(CH$_2$)$_3$-(3,4-diF-Ph) | H | H | H | H |
| 5-2305 | H | H | Me | 2 | —CO—(CH$_2$)$_3$-(3,5-diF-Ph) | H | H | H | H |
| 5-2306 | H | H | Me | 2 | —CO—(CH$_2$)$_3$-(3-Cl-Ph) | H | H | H | H |
| 5-2307 | H | H | Me | 2 | —CO—(CH$_2$)$_3$-(4-Cl-Ph) | H | H | H | H |
| 5-2308 | H | H | Me | 2 | —CO—(CH$_2$)$_3$-(3,4-diCl-Ph) | H | H | H | H |
| 5-2309 | H | H | Me | 2 | —CO—(CH$_2$)$_3$-(3,5-diCl-Ph) | H | H | H | H |
| 5-2310 | H | H | Me | 2 | —CO—(CH$_2$)$_3$-(3-Me-Ph) | H | H | H | H |
| 5-2311 | H | H | Me | 2 | —CO—(CH$_2$)$_3$-(4-Me-Ph) | H | H | H | H |
| 5-2312 | H | H | Me | 2 | —CO—(CH$_2$)$_3$-(3,4-diMe-Ph) | H | H | H | H |
| 5-2313 | H | H | Me | 2 | —CO—(CH$_2$)$_3$-(3,5-diMe-Ph) | H | H | H | H |
| 5-2314 | H | H | Me | 2 | —CO—(CH$_2$)$_3$-(3-Et-Ph) | H | H | H | H |
| 5-2315 | H | H | Me | 2 | —CO—(CH$_2$)$_3$-(4-Et-Ph) | H | H | H | H |
| 5-2316 | H | H | Me | 2 | —CO—(CH$_2$)$_3$-(3-CF$_3$-Ph) | H | H | H | H |
| 5-2317 | H | H | Me | 2 | —CO—(CH$_2$)$_3$-(4-CF$_3$-Ph) | H | H | H | H |
| 5-2318 | H | H | Me | 2 | —CO—(CH$_2$)$_3$-(3,4-diCF$_3$-Ph) | H | H | H | H |
| 5-2319 | H | H | Me | 2 | —CO—(CH$_2$)$_3$-(3,5-diCF$_3$-Ph) | H | H | H | H |
| 5-2320 | H | H | Me | 2 | —CO—(CH$_2$)$_3$-(3-MeO-Ph) | H | H | H | H |
| 5-2321 | H | H | Me | 2 | —CO—(CH$_2$)$_3$-(4-MeO-Ph) | H | H | H | H |
| 5-2322 | H | H | Me | 2 | —CO—(CH$_2$)$_3$-(3,4-diMeO-Ph) | H | H | H | H |
| 5-2323 | H | H | Me | 2 | —CO—(CH$_2$)$_3$-(3,5-diMeO-Ph) | H | H | H | H |
| 5-2324 | H | H | Me | 2 | —CO—(CH$_2$)$_3$-(3,4,5-triMeO-Ph) | H | H | H | H |
| 5-2325 | H | H | Me | 2 | —CO—(CH$_2$)$_3$-(4-MeS-Ph) | H | H | H | H |
| 5-2326 | H | H | Me | 2 | —CO—(CH$_2$)$_3$-(3-Ac-Ph) | H | H | H | H |
| 5-2327 | H | H | Me | 2 | —CO—(CH$_2$)$_3$-(4-Ac-Ph) | H | H | H | H |
| 5-2328 | H | H | Me | 2 | —CO—(CH$_2$)$_4$-(3-F-Ph) | H | H | H | H |
| 5-2329 | H | H | Me | 2 | —CO—(CH$_2$)$_4$-(3,4-diF-Ph) | H | H | H | H |
| 5-2330 | H | H | Me | 2 | —CO—(CH$_2$)$_4$-(3,5-diF-Ph) | H | H | H | H |
| 5-2331 | H | H | Me | 2 | —CO—(CH$_2$)$_4$-(3-Cl-Ph) | H | H | H | H |
| 5-2332 | H | H | Me | 2 | —CO—(CH$_2$)$_4$-(4-Cl-Ph) | H | H | H | H |
| 5-2333 | H | H | Me | 2 | —CO—(CH$_2$)$_4$-(3,4-diCl-Ph) | H | H | H | H |
| 5-2334 | H | H | Me | 2 | —CO—(CH$_2$)$_4$-(3,5-diCl-Ph) | H | H | H | H |
| 5-2335 | H | H | Me | 2 | —CO—(CH$_2$)$_4$-(3-Me-Ph) | H | H | H | H |
| 5-2336 | H | H | Me | 2 | —CO—(CH$_2$)$_4$-(3,4-diMe-Ph) | H | H | H | H |
| 5-2337 | H | H | Me | 2 | —CO—(CH$_2$)$_4$-(3,5-diMe-Ph) | H | H | H | H |
| 5-2338 | H | H | Me | 2 | —CO—(CH$_2$)$_4$-(3-CF$_3$-Ph) | H | H | H | H |
| 5-2339 | H | H | Me | 2 | —CO—(CH$_2$)$_4$-(3,4-diCF$_3$-Ph) | H | H | H | H |
| 5-2340 | H | H | Me | 2 | —CO—(CH$_2$)$_4$-(3,5-diCF$_3$-Ph) | H | H | H | H |
| 5-2341 | H | H | Me | 2 | —CO—(CH$_2$)$_4$-(3-MeO-Ph) | H | H | H | H |
| 5-2342 | H | H | Me | 2 | —CO—(CH$_2$)$_4$-(3,4-diMeO-Ph) | H | H | H | H |
| 5-2343 | H | H | Me | 2 | —CO—(CH$_2$)$_4$-(3,5-diMeO-Ph) | H | H | H | H |
| 5-2344 | H | H | Me | 2 | —CO—(CH$_2$)$_4$-(3,4,5-triMeO-Ph) | H | H | H | H |
| 5-2345 | H | H | Me | 2 | —CO—(CH$_2$)$_4$-(3-Ac-Ph) | H | H | H | H |
| 5-2346 | H | H | Me | 2 | —CO—(CH$_2$)$_4$-(4-Ac-Ph) | H | H | H | H |
| 5-2347 | H | H | Me | 2 | —CH(OH)—(CH$_2$)$_3$-(3-F-Ph) | H | H | H | H |
| 5-2348 | H | H | Me | 2 | —CH(OH)—(CH$_2$)$_3$-(4-F-Ph) | H | H | H | H |
| 5-2349 | H | H | Me | 2 | —CH(OH)—(CH$_2$)$_3$-(3,4-diF-Ph) | H | H | H | H |
| 5-2350 | H | H | Me | 2 | —CH(OH)—(CH$_2$)$_3$-(3,5-diF-Ph) | H | H | H | H |
| 5-2351 | H | H | Me | 2 | —CH(OH)—(CH$_2$)$_3$-(3-Cl-Ph) | H | H | H | H |
| 5-2352 | H | H | Me | 2 | —CH(OH)—(CH$_2$)$_3$-(4-Cl-Ph) | H | H | H | H |
| 5-2353 | H | H | Me | 2 | —CH(OH)—(CH$_2$)$_3$-(3,4-diCl-Ph) | H | H | H | H |
| 5-2354 | H | H | Me | 2 | —CH(OH)—(CH$_2$)$_3$-(3,5-diCl-Ph) | H | H | H | H |
| 5-2355 | H | H | Me | 2 | —CH(OH)—(CH$_2$)$_3$-(3-Me-Ph) | H | H | H | H |

TABLE 5-continued

| | | | | | | | | | |
|---|---|---|---|---|---|---|---|---|---|
| 5-2356 | H | H | Me | 2 | —CH(OH)—(CH$_2$)$_3$-(4-Me-Ph) | H | H | H | H |
| 5-2357 | H | H | Me | 2 | —CH(OH)—(CH$_2$)$_3$-(3,4-diMe-Ph) | H | H | H | H |
| 5-2358 | H | H | Me | 2 | —CH(OH)—(CH$_2$)$_3$-(3,5-diMe-Ph) | H | H | H | H |
| 5-2359 | H | H | Me | 2 | —CH(OH)—(CH$_2$)$_3$-(3-Et-Ph) | H | H | H | H |
| 5-2360 | H | H | Me | 2 | —CH(OH)—(CH$_2$)$_3$-(4-Et-Ph) | H | H | H | H |
| 5-2361 | H | H | Me | 2 | —CH(OH)—(CH$_2$)$_3$-(3-CF$_3$-Ph) | H | H | H | H |
| 5-2362 | H | H | Me | 2 | —CH(OH)—(CH$_2$)$_3$-(4-CF$_3$-Ph) | H | H | H | H |
| 5-2363 | H | H | Me | 2 | —CH(OH)—(CH$_2$)$_3$-(3,4-diCF$_3$-Ph) | H | H | H | H |
| 5-2364 | H | H | Me | 2 | —CH(OH)—(CH$_2$)$_3$-(3,5-diCF$_3$-Ph) | H | H | H | H |
| 5-2365 | H | H | Me | 2 | —CH(OH)—(CH$_2$)$_3$-(3-MeO-Ph) | H | H | H | H |
| 5-2366 | H | H | Me | 2 | —CH(OH)—(CH$_2$)$_3$-(4-MeO-Ph) | H | H | H | H |
| 5-2367 | H | H | Me | 2 | —CH(OH)—(CH$_2$)$_3$-(3,4-diMeO-Ph) | H | H | H | H |
| 5-2368 | H | H | Me | 2 | —CH(OH)—(CH$_2$)$_3$-(3,5-diMeO-Ph) | H | H | H | H |
| 5-2369 | H | H | Me | 2 | —CH(OH)—(CH$_2$)$_3$-(3,4,5-triMeO-Ph) | H | H | H | H |
| 5-2370 | H | H | Me | 2 | —CH(OH)—(CH$_2$)$_3$-(4-MeS-Ph) | H | H | H | H |
| 5-2371 | H | H | Me | 2 | —CH(OH)—(CH$_2$)$_3$-(3-Ac-Ph) | H | H | H | H |
| 5-2372 | H | H | Me | 2 | —CH(OH)—(CH$_2$)$_3$-(4-Ac-Ph) | H | H | H | H |
| 5-2373 | H | H | Me | 2 | —CH(OH)—(CH$_2$)$_4$-(3-F-Ph) | H | H | H | H |
| 5-2374 | H | H | Me | 2 | —CH(OH)—(CH$_2$)$_4$-(3,4-diF-Ph) | H | H | H | H |
| 5-2375 | H | H | Me | 2 | —CH(OH)—(CH$_2$)$_4$-(3,5-diF-Ph) | H | H | H | H |
| 5-2376 | H | H | Me | 2 | —CH(OH)—(CH$_2$)$_4$-(3-Cl-Ph) | H | H | H | H |
| 5-2377 | H | H | Me | 2 | —CH(OH)—(CH$_2$)$_4$-(4-Cl-Ph) | H | H | H | H |
| 5-2378 | H | H | Me | 2 | —CH(OH)—(CH$_2$)$_4$-(3,4-diCl-Ph) | H | H | H | H |
| 5-2379 | H | H | Me | 2 | —CH(OH)—(CH$_2$)$_4$-(3,5-diCl-Ph) | H | H | H | H |
| 5-2380 | H | H | Me | 2 | —CH(OH)—(CH$_2$)$_4$-(3-Me-Ph) | H | H | H | H |
| 5-2381 | H | H | Me | 2 | —CH(OH)—(CH$_2$)$_4$-(3,4-diMe-Ph) | H | H | H | H |
| 5-2382 | H | H | Me | 2 | —CH(OH)—(CH$_2$)$_4$-(3,5-diMe-Ph) | H | H | H | H |
| 5-2383 | H | H | Me | 2 | —CH(OH)—(CH$_2$)$_4$-(3-CF$_3$-Ph) | H | H | H | H |
| 5-2384 | H | H | Me | 2 | —CH(OH)—(CH$_2$)$_4$-(3,4-diCF$_3$-Ph) | H | H | H | H |
| 5-2385 | H | H | Me | 2 | —CH(OH)—(CH$_2$)$_4$-(3,5-diCF$_3$-Ph) | H | H | H | H |
| 5-2386 | H | H | Me | 2 | —CH(OH)—(CH$_2$)$_4$-(3-MeO-Ph) | H | H | H | H |
| 5-2387 | H | H | Me | 2 | —CH(OH)—(CH$_2$)$_4$-(3,4-diMeO-Ph) | H | H | H | H |
| 5-2388 | H | H | Me | 2 | —CH(OH)—(CH$_2$)$_4$-(3,5-diMeO-Ph) | H | H | H | H |
| 5-2389 | H | H | Me | 2 | —CH(OH)—(CH$_2$)$_4$-(3,4,5-triMeO-Ph) | H | H | H | H |
| 5-2390 | H | H | Me | 2 | —CH(OH)—(CH$_2$)$_4$-(3-Ac-Ph) | H | H | H | H |
| 5-2391 | H | H | Me | 2 | —CH(OH)—(CH$_2$)$_4$-(4-Ac-Ph) | H | H | H | H |
| 5-2392 | H | H | Me | 2 | —O—(CH$_2$)$_3$-cHx | H | H | H | H |
| 5-2393 | H | H | Me | 2 | —O—(CH$_2$)$_4$-cHx | H | H | H | H |
| 5-2394 | H | H | Me | 2 | —O—(CH$_2$)$_5$-cHx | H | H | H | H |
| 5-2395 | H | H | Me | 2 | —O—(CH$_2$)$_3$-Ph | H | H | H | H |
| 5-2396 | H | H | Me | 2 | —O—(CH$_2$)$_4$-Ph | H | H | H | H |
| 5-2397 | H | H | Me | 2 | —O—(CH$_2$)$_5$-Ph | H | H | H | H |
| 5-2398 | COCH$_3$ | H | Me | 2 | —(CH$_2$)$_4$-cHx | H | H | H | H |
| 5-2399 | COC$_2$H$_5$ | H | Me | 2 | —(CH$_2$)$_4$-cHx | H | H | H | H |
| 5-2400 | COC$_3$H$_7$ | H | Me | 2 | —(CH$_2$)$_4$-cHx | H | H | H | H |
| 5-2401 | COC$_4$H$_9$ | H | Me | 2 | —(CH$_2$)$_4$-cHx | H | H | H | H |
| 5-2402 | COC$_5$H$_{11}$ | H | Me | 2 | —(CH$_2$)$_4$-cHx | H | H | H | H |
| 5-2403 | COC$_6$H$_{13}$ | H | Me | 2 | —(CH$_2$)$_4$-cHx | H | H | H | H |
| 5-2404 | COC$_7$H$_{15}$ | H | Me | 2 | —(CH$_2$)$_4$-cHx | H | H | H | H |
| 5-2405 | COC$_8$H$_{17}$ | H | Me | 2 | —(CH$_2$)$_4$-cHx | H | H | H | H |
| 5-2406 | COCH$_3$ | H | Me | 2 | —(CH$_2$)$_4$-Ph | H | H | H | H |
| 5-2407 | COC$_2$H$_5$ | H | Me | 2 | —(CH$_2$)$_4$-Ph | H | H | H | H |
| 5-2408 | COC$_3$H$_7$ | H | Me | 2 | —(CH$_2$)$_4$-Ph | H | H | H | H |
| 5-2409 | COC$_4$H$_9$ | H | Me | 2 | —(CH$_2$)$_4$-Ph | H | H | H | H |
| 5-2410 | COC$_5$H$_{11}$ | H | Me | 2 | —(CH$_2$)$_4$-Ph | H | H | H | H |
| 5-2411 | COC$_6$H$_{13}$ | H | Me | 2 | —(CH$_2$)$_4$-Ph | H | H | H | H |
| 5-2412 | COC$_7$H$_{15}$ | H | Me | 2 | —(CH$_2$)$_4$-Ph | H | H | H | H |
| 5-2413 | COC$_8$H$_{17}$ | H | Me | 2 | —(CH$_2$)$_4$-Ph | H | H | H | H |
| 5-2414 | COCH$_3$ | H | Me | 2 | —(CH$_2$)$_5$-cHx | H | H | H | H |
| 5-2415 | COC$_2$H$_5$ | H | Me | 2 | —(CH$_2$)$_5$-cHx | H | H | H | H |
| 5-2416 | COC$_3$H$_7$ | H | Me | 2 | —(CH$_2$)$_5$-cHx | H | H | H | H |
| 5-2417 | COC$_4$H$_9$ | H | Me | 2 | —(CH$_2$)$_5$-cHx | H | H | H | H |
| 5-2418 | COC$_5$H$_{11}$ | H | Me | 2 | —(CH$_2$)$_5$-cHx | H | H | H | H |
| 5-2419 | COC$_6$H$_{13}$ | H | Me | 2 | —(CH$_2$)$_5$-cHx | H | H | H | H |
| 5-2420 | COC$_7$H$_{15}$ | H | Me | 2 | —(CH$_2$)$_5$-cHx | H | H | H | H |
| 5-2421 | COC$_8$H$_{17}$ | H | Me | 2 | —(CH$_2$)$_5$-cHx | H | H | H | H |
| 5-2422 | COCH$_3$ | H | Me | 2 | —(CH$_2$)$_5$-Ph | H | H | H | H |
| 5-2423 | COC$_2$H$_5$ | H | Me | 2 | —(CH$_2$)$_5$-Ph | H | H | H | H |
| 5-2424 | COC$_3$H$_7$ | H | Me | 2 | —(CH$_2$)$_5$-Ph | H | H | H | H |
| 5-2425 | COC$_4$H$_9$ | H | Me | 2 | —(CH$_2$)$_5$-Ph | H | H | H | H |
| 5-2426 | COC$_5$H$_{11}$ | H | Me | 2 | —(CH$_2$)$_5$-Ph | H | H | H | H |
| 5-2427 | COC$_6$H$_{13}$ | H | Me | 2 | —(CH$_2$)$_5$-Ph | H | H | H | H |
| 5-2428 | COC$_7$H$_{15}$ | H | Me | 2 | —(CH$_2$)$_5$-Ph | H | H | H | H |
| 5-2429 | COC$_8$H$_{17}$ | H | Me | 2 | —(CH$_2$)$_5$-Ph | H | H | H | H |
| 5-2430 | COCH$_3$ | H | Me | 2 | —C≡C—(CH$_2$)$_2$-cHx | H | H | H | H |
| 5-2431 | COC$_2$H$_5$ | H | Me | 2 | —C≡C—(CH$_2$)$_2$-cHx | H | H | H | H |
| 5-2432 | COC$_3$H$_7$ | H | Me | 2 | —C≡C—(CH$_2$)$_2$-cHx | H | H | H | H |
| 5-2433 | COC$_4$H$_9$ | H | Me | 2 | —C≡C—(CH$_2$)$_2$-cHx | H | H | H | H |
| 5-2434 | COC$_5$H$_{11}$ | H | Me | 2 | —C≡C—(CH$_2$)$_2$-cHx | H | H | H | H |
| 5-2435 | COC$_6$H$_{13}$ | H | Me | 2 | —C≡C—(CH$_2$)$_2$-cHx | H | H | H | H |

TABLE 5-continued

| | | | | | | | | | |
|---|---|---|---|---|---|---|---|---|---|
| 5-2436 | COC$_7$H$_{15}$ | H | Me | 2 | —C≡C—(CH$_2$)$_2$-cHx | H | H | H | H |
| 5-2437 | COC$_8$H$_{17}$ | H | Me | 2 | —C≡C—(CH$_2$)$_2$-cHx | H | H | H | H |
| 5-2438 | COCH$_3$ | H | Me | 2 | —C≡C—(CH$_2$)$_2$-Ph | H | H | H | H |
| 5-2439 | COC$_2$H$_5$ | H | Me | 2 | —C≡C—(CH$_2$)$_2$-Ph | H | H | H | H |
| 5-2440 | COC$_3$H$_7$ | H | Me | 2 | —C≡C—(CH$_2$)$_2$-Ph | H | H | H | H |
| 5-2441 | COC$_4$H$_9$ | H | Me | 2 | —C≡C—(CH$_2$)$_2$-Ph | H | H | H | H |
| 5-2442 | COC$_5$H$_{11}$ | H | Me | 2 | —C≡C—(CH$_2$)$_2$-Ph | H | H | H | H |
| 5-2443 | COC$_6$H$_{13}$ | H | Me | 2 | —C≡C—(CH$_2$)$_2$-Ph | H | H | H | H |
| 5-2444 | COC$_7$H$_{15}$ | H | Me | 2 | —C≡C—(CH$_2$)$_2$-Ph | H | H | H | H |
| 5-2445 | COC$_8$H$_{17}$ | H | Me | 2 | —C≡C—(CH$_2$)$_2$-Ph | H | H | H | H |
| 5-2446 | COCH$_3$ | H | Me | 2 | —C≡C—(CH$_2$)$_3$-cHx | H | H | H | H |
| 5-2447 | COC$_2$H$_5$ | H | Me | 2 | —C≡C—(CH$_2$)$_3$-cHx | H | H | H | H |
| 5-2448 | COC$_3$H$_7$ | H | Me | 2 | —C≡C—(CH$_2$)$_3$-cHx | H | H | H | H |
| 5-2449 | COC$_4$H$_9$ | H | Me | 2 | —C≡C—(CH$_2$)$_3$-cHx | H | H | H | H |
| 5-2450 | COC$_5$H$_{11}$ | H | Me | 2 | —C≡C—(CH$_2$)$_3$-cHx | H | H | H | H |
| 5-2451 | COC$_6$H$_{13}$ | H | Me | 2 | —C≡C—(CH$_2$)$_3$-cHx | H | H | H | H |
| 5-2452 | COC$_7$H$_{15}$ | H | Me | 2 | —C≡C—(CH$_2$)$_3$-cHx | H | H | H | H |
| 5-2453 | COC$_8$H$_{17}$ | H | Me | 2 | —C≡C—(CH$_2$)$_3$-cHx | H | H | H | H |
| 5-2454 | COCH$_3$ | H | Me | 2 | —C≡C—(CH$_2$)$_3$-Ph | H | H | H | H |
| 5-2455 | COC$_2$H$_5$ | H | Me | 2 | —C≡C—(CH$_2$)$_3$-Ph | H | H | H | H |
| 5-2456 | COC$_3$H$_7$ | H | Me | 2 | —C≡C—(CH$_2$)$_3$-Ph | H | H | H | H |
| 5-2457 | COC$_4$H$_9$ | H | Me | 2 | —C≡C—(CH$_2$)$_3$-Ph | H | H | H | H |
| 5-2458 | COC$_5$H$_{11}$ | H | Me | 2 | —C≡C—(CH$_2$)$_3$-Ph | H | H | H | H |
| 5-2459 | COC$_6$H$_{13}$ | H | Me | 2 | —C≡C—(CH$_2$)$_3$-Ph | H | H | H | H |
| 5-2460 | COC$_7$H$_{15}$ | H | Me | 2 | —C≡C—(CH$_2$)$_3$-Ph | H | H | H | H |
| 5-2461 | COC$_8$H$_{17}$ | H | Me | 2 | —C≡C—(CH$_2$)$_3$-Ph | H | H | H | H |
| 5-2462 | COCH$_3$ | H | Me | 2 | —C≡C—(CH$_2$)$_4$-cHx | H | H | H | H |
| 5-2463 | COC$_2$H$_5$ | H | Me | 2 | —C≡C—(CH$_2$)$_4$-cHx | H | H | H | H |
| 5-2464 | COC$_3$H$_7$ | H | Me | 2 | —C≡C—(CH$_2$)$_4$-cHx | H | H | H | H |
| 5-2465 | COC$_4$H$_9$ | H | Me | 2 | —C≡C—(CH$_2$)$_4$-cHx | H | H | H | H |
| 5-2466 | COC$_5$H$_{11}$ | H | Me | 2 | —C≡C—(CH$_2$)$_4$-cHx | H | H | H | H |
| 5-2467 | COC$_6$H$_{13}$ | H | Me | 2 | —C≡C—(CH$_2$)$_4$-cHx | H | H | H | H |
| 5-2468 | COC$_7$H$_{15}$ | H | Me | 2 | —C≡C—(CH$_2$)$_4$-cHx | H | H | H | H |
| 5-2469 | COC$_8$H$_{17}$ | H | Me | 2 | —C≡C—(CH$_2$)$_4$-cHx | H | H | H | H |
| 5-2470 | COCH$_3$ | H | Me | 2 | —C≡C—(CH$_2$)$_4$-Ph | H | H | H | H |
| 5-2471 | COC$_2$H$_5$ | H | Me | 2 | —C≡C—(CH$_2$)$_4$-Ph | H | H | H | H |
| 5-2472 | COC$_3$H$_7$ | H | Me | 2 | —C≡C—(CH$_2$)$_4$-Ph | H | H | H | H |
| 5-2473 | COC$_4$H$_9$ | H | Me | 2 | —C≡C—(CH$_2$)$_4$-Ph | H | H | H | H |
| 5-2474 | COC$_5$H$_{11}$ | H | Me | 2 | —C≡C—(CH$_2$)$_4$-Ph | H | H | H | H |
| 5-2475 | COC$_6$H$_{13}$ | H | Me | 2 | —C≡C—(CH$_2$)$_4$-Ph | H | H | H | H |
| 5-2476 | COC$_7$H$_{15}$ | H | Me | 2 | —C≡C—(CH$_2$)$_4$-Ph | H | H | H | H |
| 5-2477 | COC$_8$H$_{17}$ | H | Me | 2 | —C≡C—(CH$_2$)$_4$-Ph | H | H | H | H |
| 5-2478 | COCH$_3$ | H | Me | 2 | —C≡C—(CH$_2$)$_2$O-cHx | H | H | H | H |
| 5-2479 | COC$_2$H$_5$ | H | Me | 2 | —C≡C—(CH$_2$)$_2$O-cHx | H | H | H | H |
| 5-2480 | COC$_3$H$_7$ | H | Me | 2 | —C≡C—(CH$_2$)$_2$O-cHx | H | H | H | H |
| 5-2481 | COC$_4$H$_9$ | H | Me | 2 | —C≡C—(CH$_2$)$_2$O-cHx | H | H | H | H |
| 5-2482 | COC$_5$H$_{11}$ | H | Me | 2 | —C≡C—(CH$_2$)$_2$O-cHx | H | H | H | H |
| 5-2483 | COC$_6$H$_{13}$ | H | Me | 2 | —C≡C—(CH$_2$)$_2$O-cHx | H | H | H | H |
| 5-2484 | COC$_7$H$_{15}$ | H | Me | 2 | —C≡C—(CH$_2$)$_2$O-cHx | H | H | H | H |
| 5-2485 | COC$_8$H$_{17}$ | H | Me | 2 | —C≡C—(CH$_2$)$_2$O-cHx | H | H | H | H |
| 5-2486 | COCH$_3$ | H | Me | 2 | —C≡C—(CH$_2$)$_2$O-Ph | H | H | H | H |
| 5-2487 | COC$_2$H$_5$ | H | Me | 2 | —C≡C—(CH$_2$)$_2$O-Ph | H | H | H | H |
| 5-2488 | COC$_3$H$_7$ | H | Me | 2 | —C≡C—(CH$_2$)$_2$O-Ph | H | H | H | H |
| 5-2489 | COC$_4$H$_9$ | H | Me | 2 | —C≡C—(CH$_2$)$_2$O-Ph | H | H | H | H |
| 5-2490 | COC$_5$H$_{11}$ | H | Me | 2 | —C≡C—(CH$_2$)$_2$O-Ph | H | H | H | H |
| 5-2491 | COC$_6$H$_{13}$ | H | Me | 2 | —C≡C—(CH$_2$)$_2$O-Ph | H | H | H | H |
| 5-2492 | COC$_7$H$_{15}$ | H | Me | 2 | —C≡C—(CH$_2$)$_2$O-Ph | H | H | H | H |
| 5-2493 | COC$_8$H$_{17}$ | H | Me | 2 | —C≡C—(CH$_2$)$_2$O-Ph | H | H | H | H |
| 5-2494 | COCH$_3$ | H | Me | 2 | —CO—(CH$_2$)$_3$-cHx | H | H | H | H |
| 5-2495 | COC$_2$H$_5$ | H | Me | 2 | —CO—(CH$_2$)$_3$-cHx | H | H | H | H |
| 5-2496 | COC$_3$H$_7$ | H | Me | 2 | —CO—(CH$_2$)$_3$-cHx | H | H | H | H |
| 5-2497 | COC$_4$H$_9$ | H | Me | 2 | —CO—(CH$_2$)$_3$-cHx | H | H | H | H |
| 5-2498 | COC$_5$H$_{11}$ | H | Me | 2 | —CO—(CH$_2$)$_3$-cHx | H | H | H | H |
| 5-2499 | COC$_6$H$_{13}$ | H | Me | 2 | —CO—(CH$_2$)$_3$-cHx | H | H | H | H |
| 5-2500 | COC$_7$H$_{15}$ | H | Me | 2 | —CO—(CH$_2$)$_3$-cHx | H | H | H | H |
| 5-2501 | COC$_8$H$_{17}$ | H | Me | 2 | —CO—(CH$_2$)$_3$-cHx | H | H | H | H |
| 5-2502 | COCH$_3$ | H | Me | 2 | —CO—(CH$_2$)$_3$-Ph | H | H | H | H |
| 5-2503 | COC$_2$H$_5$ | H | Me | 2 | —CO—(CH$_2$)$_3$-Ph | H | H | H | H |
| 5-2504 | COC$_3$H$_7$ | H | Me | 2 | —CO—(CH$_2$)$_3$-Ph | H | H | H | H |
| 5-2505 | COC$_4$H$_9$ | H | Me | 2 | —CO—(CH$_2$)$_3$-Ph | H | H | H | H |
| 5-2506 | COC$_5$H$_{11}$ | H | Me | 2 | —CO—(CH$_2$)$_3$-Ph | H | H | H | H |
| 5-2507 | COC$_6$H$_{13}$ | H | Me | 2 | —CO—(CH$_2$)$_3$-Ph | H | H | H | H |
| 5-2508 | COC$_7$H$_{15}$ | H | Me | 2 | —CO—(CH$_2$)$_3$-Ph | H | H | H | H |
| 5-2509 | COC$_8$H$_{17}$ | H | Me | 2 | —CO—(CH$_2$)$_3$-Ph | H | H | H | H |
| 5-2510 | COCH$_3$ | H | Me | 2 | —CO—(CH$_2$)$_4$-cHx | H | H | H | H |
| 5-2511 | COC$_2$H$_5$ | H | Me | 2 | —CO—(CH$_2$)$_4$-cHx | H | H | H | H |
| 5-2512 | COC$_3$H$_7$ | H | Me | 2 | —CO—(CH$_2$)$_4$-cHx | H | H | H | H |
| 5-2513 | COC$_4$H$_9$ | H | Me | 2 | —CO—(CH$_2$)$_4$-cHx | H | H | H | H |
| 5-2514 | COC$_5$H$_{11}$ | H | Me | 2 | —CO—(CH$_2$)$_4$-cHx | H | H | H | H |
| 5-2515 | COC$_6$H$_{13}$ | H | Me | 2 | —CO—(CH$_2$)$_4$-cHx | H | H | H | H |

TABLE 5-continued

| | | | | | | | | | |
|---|---|---|---|---|---|---|---|---|---|
| 5-2516 | COC$_7$H$_{15}$ | H | Me | 2 | —CO—(CH$_2$)$_4$-cHx | H | H | H | H |
| 5-2517 | COC$_8$H$_{17}$ | H | Me | 2 | —CO—(CH$_2$)$_4$-cHx | H | H | H | H |
| 5-2518 | COCH$_3$ | H | Me | 2 | —CO—(CH$_2$)$_4$-Ph | H | H | H | H |
| 5-2519 | COC$_2$H$_5$ | H | Me | 2 | —CO—(CH$_2$)$_4$-Ph | H | H | H | H |
| 5-2520 | COC$_3$H$_7$ | H | Me | 2 | —CO—(CH$_2$)$_4$-Ph | H | H | H | H |
| 5-2521 | COC$_4$H$_9$ | H | Me | 2 | —CO—(CH$_2$)$_4$-Ph | H | H | H | H |
| 5-2522 | COC$_5$H$_{11}$ | H | Me | 2 | —CO—(CH$_2$)$_4$-Ph | H | H | H | H |
| 5-2523 | COC$_6$H$_{13}$ | H | Me | 2 | —CO—(CH$_2$)$_4$-Ph | H | H | H | H |
| 5-2524 | COC$_7$H$_{15}$ | H | Me | 2 | —CO—(CH$_2$)$_4$-Ph | H | H | H | H |
| 5-2525 | COC$_8$H$_{17}$ | H | Me | 2 | —CO—(CH$_2$)$_4$-Ph | H | H | H | H |
| 5-2526 | COCH$_3$ | H | Me | 2 | —CO—(CH$_2$)$_5$-cHx | H | H | H | H |
| 5-2527 | COC$_2$H$_5$ | H | Me | 2 | —CO—(CH$_2$)$_5$-cHx | H | H | H | H |
| 5-2528 | COC$_3$H$_7$ | H | Me | 2 | —CO—(CH$_2$)$_5$-cHx | H | H | H | H |
| 5-2529 | COC$_4$H$_9$ | H | Me | 2 | —CO—(CH$_2$)$_5$-cHx | H | H | H | H |
| 5-2530 | COC$_5$H$_{11}$ | H | Me | 2 | —CO—(CH$_2$)$_5$-cHx | H | H | H | H |
| 5-2531 | COC$_6$H$_{13}$ | H | Me | 2 | —CO—(CH$_2$)$_5$-cHx | H | H | H | H |
| 5-2532 | COC$_7$H$_{15}$ | H | Me | 2 | —CO—(CH$_2$)$_5$-cHx | H | H | H | H |
| 5-2533 | COC$_8$H$_{17}$ | H | Me | 2 | —CO—(CH$_2$)$_5$-cHx | H | H | H | H |
| 5-2534 | COCH$_3$ | H | Me | 2 | —CO—(CH$_2$)$_5$-Ph | H | H | H | H |
| 5-2535 | COC$_2$H$_5$ | H | Me | 2 | —CO—(CH$_2$)$_5$-Ph | H | H | H | H |
| 5-2536 | COC$_3$H$_7$ | H | Me | 2 | —CO—(CH$_2$)$_5$-Ph | H | H | H | H |
| 5-2537 | COC$_4$H$_9$ | H | Me | 2 | —CO—(CH$_2$)$_5$-Ph | H | H | H | H |
| 5-2538 | COC$_5$H$_{11}$ | H | Me | 2 | —CO—(CH$_2$)$_5$-Ph | H | H | H | H |
| 5-2539 | COC$_6$H$_{13}$ | H | Me | 2 | —CO—(CH$_2$)$_5$-Ph | H | H | H | H |
| 5-2540 | COC$_7$H$_{15}$ | H | Me | 2 | —CO—(CH$_2$)$_5$-Ph | H | H | H | H |
| 5-2541 | COC$_8$H$_{17}$ | H | Me | 2 | —CO—(CH$_2$)$_5$-Ph | H | H | H | H |
| 5-2542 | COCH$_3$ | H | Me | 2 | —CH(OH)—(CH$_2$)$_4$-cHx | H | H | H | H |
| 5-2543 | COC$_2$H$_5$ | H | Me | 2 | —CH(OH)—(CH$_2$)$_4$-cHx | H | H | H | H |
| 5-2544 | COC$_3$H$_7$ | H | Me | 2 | —CH(OH)—(CH$_2$)$_4$-cHx | H | H | H | H |
| 5-2545 | COC$_4$H$_9$ | H | Me | 2 | —CH(OH)—(CH$_2$)$_4$-cHx | H | H | H | H |
| 5-2546 | COC$_5$H$_{11}$ | H | Me | 2 | —CH(OH)—(CH$_2$)$_4$-cHx | H | H | H | H |
| 5-2547 | COC$_6$H$_{13}$ | H | Me | 2 | —CH(OH)—(CH$_2$)$_4$-cHx | H | H | H | H |
| 5-2548 | COC$_7$H$_{15}$ | H | Me | 2 | —CH(OH)—(CH$_2$)$_4$-cHx | H | H | H | H |
| 5-2549 | COC$_8$H$_{17}$ | H | Me | 2 | —CH(OH)—(CH$_2$)$_4$-cHx | H | H | H | H |
| 5-2550 | COCH$_3$ | H | Me | 2 | —CH(OH)—(CH$_2$)$_4$-Ph | H | H | H | H |
| 5-2551 | COC$_2$H$_5$ | H | Me | 2 | —CH(OH)—(CH$_2$)$_4$-Ph | H | H | H | H |
| 5-2552 | COC$_3$H$_7$ | H | Me | 2 | —CH(OH)—(CH$_2$)$_4$-Ph | H | H | H | H |
| 5-2553 | COC$_4$H$_9$ | H | Me | 2 | —CH(OH)—(CH$_2$)$_4$-Ph | H | H | H | H |
| 5-2554 | COC$_5$H$_{11}$ | H | Me | 2 | —CH(OH)—(CH$_2$)$_4$-Ph | H | H | H | H |
| 5-2555 | COC$_6$H$_{13}$ | H | Me | 2 | —CH(OH)—(CH$_2$)$_4$-Ph | H | H | H | H |
| 5-2556 | COC$_7$H$_{15}$ | H | Me | 2 | —CH(OH)—(CH$_2$)$_4$-Ph | H | H | H | H |
| 5-2557 | COC$_8$H$_{17}$ | H | Me | 2 | —CH(OH)—(CH$_2$)$_4$-Ph | H | H | H | H |

TABLE 6

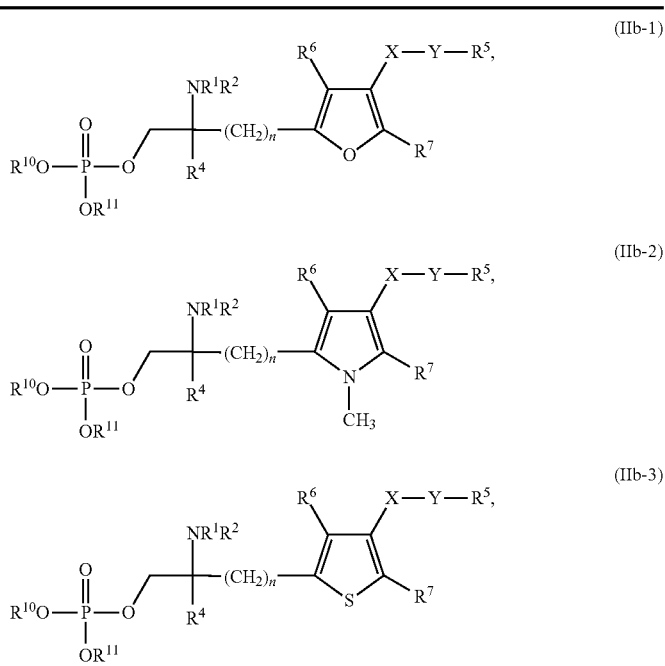

TABLE 6-continued (IIIb-1) (IIIb-2) (IIIb-3) structures shown.

| Compd. | R¹ | R² | R⁴ | n | —Y—Z—R⁵ | R⁶ | R⁷ | R¹⁰ | R¹¹ |
|---|---|---|---|---|---|---|---|---|---|
| 6-1 | H | H | Me | 1 | —(CH₂)₅-cHx | H | H | H | H |
| 6-2 | H | H | Me | 1 | —(CH₂)₆-cHx | H | H | H | H |
| 6-3 | H | H | Me | 1 | —C≡C—(CH₂)₃-cHx | H | H | H | H |
| 6-4 | H | H | Me | 1 | —C≡C—(CH₂)₄-cHx | H | H | H | H |
| 6-5 | H | H | Me | 1 | -4-(cHx-CH₂O)Ph | H | H | H | H |
| 6-6 | H | H | Me | 1 | -(4-BzO-Ph) | H | H | H | H |
| 6-7 | H | H | Me | 1 | —C≡C—(CH₂)₂O-cHx | H | H | H | H |
| 6-8 | H | H | Me | 1 | —C≡C—(CH₂)₂O-Ph | H | H | H | H |
| 6-9 | H | H | Me | 2 | —(CH₂)₃-cHx | H | H | H | H |
| 6-10 | H | H | Me | 2 | —(CH₂)₃-Ph | H | H | H | H |
| 6-11 | H | H | Me | 2 | —(CH₂)₄-cHx | H | H | H | H |
| 6-12 | H | H | Me | 2 | —(CH₂)₄-Ph | H | H | H | H |
| 6-13 | H | H | Me | 2 | —(CH₂)₅-cPn | H | H | H | H |
| 6-14 | H | H | Me | 2 | —(CH₂)₅-cHx | H | H | H | H |
| 6-15 | H | H | Me | 2 | —(CH₂)₅-cHx | Me | H | H | H |
| 6-16 | H | H | Me | 2 | —(CH₂)₅-cHx | H | Me | H | H |
| 6-17 | H | H | Me | 2 | —(CH₂)₅-cHx | F | H | H | H |
| 6-18 | H | H | Me | 2 | —(CH₂)₅-cHx | H | F | H | H |
| 6-19 | H | Me | Me | 2 | —(CH₂)₅-cHx | H | H | H | H |
| 6-20 | CO₂Me | H | Me | 2 | —(CH₂)₅-cHx | H | H | H | H |
| 6-21 | CO₂Et | H | Me | 2 | —(CH₂)₅-cHx | H | H | H | H |
| 6-22 | H | H | Me | 2 | —(CH₂)₅-(4-F-cHx) | H | H | H | H |
| 6-23 | H | H | Me | 2 | —(CH₂)₅-(4-Cl-cHx) | H | H | H | H |
| 6-24 | H | H | Me | 2 | —(CH₂)₅-(4-Br-cHx) | H | H | H | H |
| 6-25 | H | H | Me | 2 | —(CH₂)₅-(4-Me-cHx) | H | H | H | H |
| 6-26 | H | H | Me | 2 | —(CH₂)₅-(4-Et-cHx) | H | H | H | H |
| 6-27 | H | H | Me | 2 | —(CH₂)₅-(4-Pr-cHx) | H | H | H | H |
| 6-28 | H | H | Me | 2 | —(CH₂)₅-(4-iPr-cHx) | H | H | H | H |
| 6-29 | H | H | Me | 2 | —(CH₂)₅-(4-CF₃-cHx) | H | H | H | H |
| 6-30 | H | H | Me | 2 | —(CH₂)₅-(4-MeO-cHx) | H | H | H | H |
| 6-31 | H | H | Me | 2 | —(CH₂)₅-(4-EtO-cHx) | H | H | H | H |
| 6-32 | H | H | Me | 2 | —(CH₂)₅-(4-PrO-cHx) | H | H | H | H |
| 6-33 | H | H | Me | 2 | —(CH₂)₅-(4-iPrO-cHx) | H | H | H | H |
| 6-34 | H | H | Me | 2 | —(CH₂)₅-(3-MeS-cHx) | H | H | H | H |
| 6-35 | H | H | Me | 2 | —(CH₂)₅-(4-MeS-cHx) | H | H | H | H |
| 6-36 | H | H | Me | 2 | —(CH₂)₅-(6-4-diMe-cHx) | H | H | H | H |
| 6-37 | H | H | Me | 2 | —(CH₂)₅-(3,4-diMe-cHx) | H | H | H | H |
| 6-38 | H | H | Me | 2 | —(CH₂)₅-(3,5-diMe-cHx) | H | H | H | H |
| 6-39 | H | N | Me | 2 | —(CH₂)₅-Ph | H | H | H | H |
| 6-40 | H | H | Me | 2 | —(CH₂)₅-Ph | Me | H | H | H |
| 6-41 | H | N | Me | 2 | —(CH₂)₅-Ph | H | Me | H | H |
| 6-42 | H | H | Me | 2 | —(CH₂)₅-Ph | F | H | H | H |
| 6-43 | W | H | Me | 2 | —(CH₂)₅-Ph | H | F | H | H |
| 6-44 | H | Me | Me | 2 | —(CH₂)₅-Ph | H | H | H | H |
| 6-45 | CO₂Me | H | Me | 2 | —(CH₂)₅-Ph | H | H | H | H |
| 6-46 | CO₂Et | H | Me | 2 | —(CH₂)₅-Ph | H | H | H | H |

TABLE 6-continued

| | | | | | | | | | |
|---|---|---|---|---|---|---|---|---|---|
| 6-47 | H | H | Me | 2 | —(CH$_2$)$_5$-(4-F-Ph) | H | H | H | H |
| 6-48 | H | H | Me | 2 | —(CH$_2$)$_5$-(4-Cl-Ph) | H | H | H | H |
| 6-49 | H | H | Me | 2 | —(CH$_2$)$_5$-(4-Br-Ph) | H | H | H | H |
| 6-50 | H | H | Me | 2 | —(CH$_2$)$_5$-(4-Me-Ph) | H | H | H | H |
| 6-51 | H | H | Me | 2 | —(CH$_2$)$_5$-(4-Et-Ph) | H | H | H | H |
| 6-52 | H | H | Me | 2 | —(CH$_2$)$_5$-(4-Pr-Ph) | H | H | H | H |
| 6-53 | H | H | Me | 2 | —(CH$_2$)$_5$-(4-iPr-Ph) | H | H | H | H |
| 6-54 | H | H | Me | 2 | —(CH$_2$)$_5$-(4-Bu-Ph) | H | H | H | H |
| 6-55 | H | H | Me | 2 | —(CH$_2$)$_5$-(4-CF$_3$-Ph) | H | H | H | H |
| 6-56 | H | H | Me | 2 | —(CH$_2$)$_5$-(4-MeO-Ph) | H | H | H | H |
| 6-57 | H | H | Me | 2 | —(CH$_2$)$_5$-(4-EtO-Ph) | H | H | H | H |
| 6-58 | H | H | Me | 2 | —(CH$_2$)$_5$-(4-PrO-Ph) | H | H | H | H |
| 6-59 | H | H | Me | 2 | —(CH$_2$)$_5$-(4-iPrO-Ph) | H | H | H | H |
| 6-60 | H | H | Me | 2 | —(CH$_2$)$_5$-(3-MeS-Ph) | H | H | H | H |
| 6-61 | H | H | Me | 2 | —(CH$_2$)$_5$-(4-MeS-Ph) | H | H | H | H |
| 6-62 | H | H | Me | 2 | —(CH$_2$)$_5$-(6-4-diMe-Ph) | H | H | H | H |
| 6-63 | H | H | Me | 2 | —(CH$_2$)$_5$-(3,4-diMe-Ph) | H | H | H | H |
| 6-64 | H | H | Me | 2 | —(CH$_2$)$_5$-(3,5-diMe-Ph) | H | H | H | H |
| 6-65 | H | H | Me | 2 | —(CH$_2$)$_6$-cPn | H | H | H | H |
| 6-66 | H | H | Me | 2 | —(CH$_2$)$_6$-cHx | H | H | H | H |
| 6-67 | H | H | Me | 2 | —(CH$_2$)$_6$-cHx | Me | H | H | H |
| 6-68 | H | H | Me | 2 | —(CH$_2$)$_6$-cHx | H | Me | H | H |
| 6-69 | H | H | Me | 2 | —(CH$_2$)$_6$-cHx | F | H | H | H |
| 6-70 | H | H | Me | 2 | —(CH$_2$)$_6$-cHx | H | F | H | H |
| 6-72 | H | Me | Me | 2 | —(CH$_2$)$_6$-cHx | H | H | H | H |
| 6-72 | CO$_2$Me | H | Me | 2 | —(CH$_2$)$_6$-cHx | H | H | H | H |
| 6-73 | CO$_2$Et | H | Me | 2 | —(CH$_2$)$_6$-cHx | H | H | H | H |
| 6-74 | H | H | Me | 2 | —(CH$_2$)$_6$-(4-F-cHx) | H | H | H | H |
| 6-75 | H | H | Me | 2 | —(CH$_2$)$_6$-(4-Cl-cHx) | H | H | H | H |
| 6-76 | H | H | Me | 2 | —(CH$_2$)$_6$-(4-Br-cHx) | H | H | H | H |
| 6-77 | H | H | Me | 2 | —(CH$_2$)$_6$-(4-Me-cHx) | H | H | H | H |
| 6-78 | H | H | Me | 2 | —(CH$_2$)$_6$-(4-Et-cHx) | H | H | H | H |
| 6-79 | H | H | Me | 2 | —(CH$_2$)$_6$-(4-Pr-cHx) | H | H | H | H |
| 6-80 | H | H | Me | 2 | —(CH$_2$)$_6$-(4-iPr-cHx) | H | H | H | H |
| 6-81 | H | H | Me | 2 | —(CH$_2$)$_6$-(4-Bu-cHx) | H | H | H | H |
| 6-82 | H | H | Me | 2 | —(CH$_2$)$_6$-(4-CF$_3$-cHx) | H | H | H | H |
| 6-83 | H | H | Me | 2 | —(CH$_2$)$_6$-(4-MeO-cHx) | H | H | H | H |
| 6-84 | H | H | Me | 2 | —(CH$_2$)$_6$-(4-EtO-cHx) | H | H | H | H |
| 6-85 | H | H | Me | 2 | —(CH$_2$)$_6$-(4-PrO-cHx) | H | H | H | H |
| 6-86 | H | H | Me | 2 | —(CH$_2$)$_6$-(4-iPrO-cHx) | H | H | H | H |
| 6-87 | H | H | Me | 2 | —(CH$_2$)$_6$-(3-MeS-cHx) | H | H | H | H |
| 6-88 | H | H | Me | 2 | —(CH$_2$)$_6$-(4-MeS-cHx) | H | H | H | H |
| 6-89 | H | H | Me | 2 | —(CH$_2$)$_6$-(6-4-diMe-cHx) | H | H | H | H |
| 6-90 | H | H | Me | 2 | —(CH$_2$)$_6$-(3,4-diMe-cHx) | H | H | H | H |
| 6-91 | H | H | Me | 2 | —(CH$_2$)$_6$-(3,5-diMe-cHx) | H | H | H | H |
| 6-92 | H | H | Me | 2 | —(CH$_2$)$_6$-Ph | H | H | H | H |
| 6-93 | H | H | Me | 2 | —(CH$_2$)$_6$-Ph | Me | H | H | H |
| 6-94 | H | H | Me | 2 | —(CH$_2$)$_6$-Ph | H | Me | H | H |
| 6-95 | H | H | Me | 2 | —(CH$_2$)$_6$-Ph | F | H | H | H |
| 6-96 | H | H | Me | 2 | —(CH$_2$)$_6$-Ph | H | F | H | H |
| 6-97 | H | Me | Me | 2 | —(CH$_2$)$_6$-Ph | H | H | H | H |
| 6-98 | CO$_2$Me | H | Me | 2 | —(CH$_2$)$_6$-Ph | H | H | H | H |
| 6-99 | CO$_2$Et | H | Me | 2 | —(CH$_2$)$_6$-Ph | H | H | H | H |
| 6-100 | H | H | Me | 2 | —(CH$_2$)$_6$-(4-F-Ph) | H | H | H | H |
| 6-101 | H | H | Me | 2 | —(CH$_2$)$_6$-(4-Cl-Ph) | H | H | H | H |
| 6-102 | H | H | Me | 2 | —(CH$_2$)$_6$-(4-Br-Ph) | H | H | H | H |
| 6-103 | H | H | Me | 2 | —(CH$_2$)$_6$-(4-Me-Ph) | H | H | H | H |
| 6-104 | H | H | Me | 2 | —(CH$_2$)$_6$-(4-Et-Ph) | H | H | H | H |
| 6-105 | H | H | Me | 2 | —(CH$_2$)$_6$-(4-Pr-Ph) | H | H | H | H |
| 6-106 | H | H | Me | 2 | —(CH$_2$)$_6$-(4-iPr-Ph) | H | H | H | H |
| 6-107 | H | H | Me | 2 | —(CH$_2$)$_6$-(4-Bu-Ph) | H | H | H | H |
| 6-108 | H | H | Me | 2 | —(CH$_2$)$_6$-(4-CF$_3$-Ph) | H | H | H | H |
| 6-109 | H | H | Me | 2 | —(CH$_2$)$_6$-(4-MeO-Ph) | H | H | H | H |
| 6-110 | H | H | Me | 2 | —(CH$_2$)$_6$-(4-EtO-Ph) | H | H | H | H |
| 6-111 | H | H | Me | 2 | —(CH$_2$)$_6$-(4-PrO-Ph) | H | H | H | H |
| 6-112 | H | H | Me | 2 | —(CH$_2$)$_6$-(4-iPrO-Ph) | H | H | H | H |
| 6-113 | H | H | Me | 2 | —(CH$_2$)$_6$-(3-MeS-Ph) | H | H | H | H |
| 6-114 | H | H | Me | 2 | —(CH$_2$)$_6$-(4-MeS-Ph) | H | H | H | H |
| 6-115 | H | H | Me | 2 | —(CH$_2$)$_6$-(6-4-diMe-Ph) | H | H | H | H |
| 6-116 | H | H | Me | 2 | —(CH$_2$)$_6$-(3,4-diMe-Ph) | H | H | H | H |
| 6-117 | H | H | Me | 2 | —(CH$_2$)$_6$-(3,5-diMe-Ph) | H | H | H | H |
| 6-118 | H | H | Me | 2 | —(CH$_2$)$_7$-cHx | H | H | H | H |
| 6-119 | H | H | Me | 2 | —(CH$_2$)$_7$-Ph | H | H | H | H |
| 6-120 | H | H | Me | 2 | —(CH$_2$)$_8$-cHx | H | H | H | H |
| 6-121 | H | H | Me | 2 | —(CH$_2$)$_8$-Ph | H | H | H | H |
| 6-122 | H | H | Me | 2 | —CH=CH—(CH$_2$)$_3$-cHx | H | H | H | H |
| 6-123 | H | Me | Me | 2 | —CH=CH—(CH$_2$)$_3$-cHx | H | H | H | H |
| 6-124 | CO$_2$Me | H | Me | 2 | —CH=CH—(CH$_2$)$_3$-cHx | H | H | H | H |
| 6-125 | CO$_2$Et | H | Me | 2 | —CH=CH—(CH$_2$)$_3$-cHx | H | H | H | H |
| 6-126 | H | H | Me | 2 | —CH=CH—(CH$_2$)$_3$-Ph | H | H | H | H |

TABLE 6-continued

| | | | | | | | | | |
|---|---|---|---|---|---|---|---|---|---|
| 6-127 | H | Me | Me | 2 | —CH=CH—(CH$_2$)$_3$-Ph | H | H | H | H |
| 6-128 | CO$_2$Me | H | Me | 2 | —CH=CH—(CH$_2$)$_3$-Ph | H | H | H | H |
| 6-129 | CO$_2$Et | H | Me | 2 | —CH=CH—(CH$_2$)$_3$-Ph | H | H | H | H |
| 6-130 | H | H | Me | 2 | —CH=CH—(CH$_2$)$_4$-cHx | H | H | H | H |
| 6-131 | H | Me | Me | 2 | —CH=CH—(CH$_2$)$_4$-cHx | H | H | H | H |
| 6-132 | CO$_2$Me | H | Me | 2 | —CH=CH—(CH$_2$)$_4$-cHx | H | H | H | H |
| 6-133 | CO$_2$Et | H | Me | 2 | —CH=CH—(CH$_2$)$_4$-cHx | H | H | H | H |
| 6-134 | H | H | Me | 2 | —CH=CH—(CH$_2$)$_4$-Ph | H | H | H | H |
| 6-135 | H | Me | Me | 2 | —CH=CH—(CH$_2$)$_4$-Ph | H | H | H | H |
| 6-136 | CO$_2$Me | H | Me | 2 | —CH=CH—(CH$_2$)$_4$-Ph | H | H | H | H |
| 6-137 | CO$_2$Et | H | Me | 2 | —CH=CH—(CH$_2$)$_4$-Ph | H | H | H | H |
| 6-138 | H | H | Me | 2 | —C≡C—CH$_2$O-cHx | H | H | H | H |
| 6-139 | H | H | Me | 2 | —C≡C—CH$_2$O-Ph | H | H | H | H |
| 6-140 | H | H | Me | 2 | —C≡C—(CH$_2$)$_2$O-cHx | H | H | H | H |
| 6-141 | H | H | Me | 2 | —C≡C—(CH$_2$)$_2$O-Ph | H | H | H | H |
| 6-142 | H | H | Me | 2 | —C≡C—CH$_2$-Hx | H | H | H | H |
| 6-143 | H | Me | Me | 2 | —C≡C—CH$_2$-cHx | H | H | H | H |
| 6-144 | CO$_2$Me | H | Me | 2 | —C≡C—CH$_2$-cHx | H | H | H | H |
| 6-145 | CO$_2$Et | H | Me | 2 | —C≡C—CH$_2$-cHx | H | H | H | H |
| 6-146 | H | H | Me | 2 | —C≡C—CH$_2$-Ph | H | H | H | H |
| 6-147 | H | Me | Me | 2 | —C≡C—CH$_2$-Ph | H | H | H | H |
| 6-148 | CO$_2$Me | H | Me | 2 | —C≡C—CH$_2$-Ph | H | H | H | H |
| 6-149 | CO$_2$Et | H | Me | 2 | —C≡C—CH$_2$-Ph | H | H | H | H |
| 6-150 | H | H | Me | 2 | —C≡C—(CH$_2$)$_2$-cHx | H | H | H | H |
| 6-151 | H | Me | Me | 2 | —C≡C—(CH$_2$)$_2$-cHx | H | H | H | H |
| 6-152 | CO$_2$Me | H | Me | 2 | —C≡C—(CH$_2$)$_2$-cHx | H | H | H | H |
| 6-153 | CO$_2$Et | H | Me | 2 | —C≡C—(CH$_2$)$_2$-cHx | H | H | H | H |
| 6-154 | H | H | Me | 2 | —C≡C—(CH$_2$)$_2$-Ph | H | H | H | H |
| 6-155 | H | Me | Me | 2 | —C≡C—(CH$_2$)$_2$-Ph | H | H | H | H |
| 6-156 | CO$_2$Me | H | Me | 2 | —C≡C—(CH$_2$)$_2$-Ph | H | H | H | H |
| 6-157 | CO$_2$Et | H | Me | 2 | —C≡C—(CH$_2$)$_2$-Ph | H | H | H | H |
| 6-158 | H | H | Me | 2 | —C≡C—(CH$_2$)$_3$-cPn | H | H | H | H |
| 6-159 | H | H | Me | 2 | —C≡C—(CH$_2$)$_3$-cHx | H | H | H | H |
| 6-160 | H | H | Me | 2 | —C≡C—(CH$_2$)$_3$-cHx | Me | H | H | H |
| 6-161 | H | H | Me | 2 | —C≡C—(CH$_2$)$_3$-cHx | H | Me | H | H |
| 6-162 | H | H | Me | 2 | —C≡C—(CH$_2$)$_3$-cHx | F | H | H | H |
| 6-163 | H | H | Me | 2 | —C≡C—(CH$_2$)$_3$-cHx | H | F | H | H |
| 6-164 | H | Me | Me | 2 | —C≡C—(CH$_2$)$_3$-cHx | H | H | H | H |
| 6-165 | CO$_2$Me | H | Me | 2 | —C≡C—(CH$_2$)$_3$-cHx | H | H | H | H |
| 6-166 | CO$_2$Et | H | Me | 2 | —C≡C—(CH$_2$)$_3$-cHx | H | H | H | H |
| 6-167 | H | H | Me | 2 | —C≡C—(CH$_2$)$_3$-(4-F-cHx) | H | H | H | H |
| 6-168 | H | H | Me | 2 | —C≡C—(CH$_2$)$_3$-(4-Cl-cHx) | H | H | H | H |
| 6-169 | H | H | Me | 2 | —C≡C—(CH$_2$)$_3$-(4-Br-cHx) | H | H | H | H |
| 6-170 | H | H | Me | 2 | —C≡C—(CH$_2$)$_3$-(4-Me-cHx) | H | H | H | H |
| 6-171 | H | H | Me | 2 | —C≡C—(CH$_2$)$_3$-(4-Et-cHx) | H | H | H | H |
| 6-172 | H | H | Me | 2 | —C≡C—(CH$_2$)$_3$-(4-Pr-cHx) | H | H | H | H |
| 6-173 | H | H | Me | 2 | —C≡C—(CH$_2$)$_3$-(4-iPr-cHx) | H | H | H | H |
| 6-174 | H | H | Me | 2 | —C≡C—(CH$_2$)$_3$-(4-Bu-cHx) | H | H | H | H |
| 6-175 | H | H | Me | 2 | —C≡C—(CH$_2$)$_3$-(4-CF$_3$-cHx) | H | H | H | H |
| 6-176 | H | H | Me | 2 | —C≡C—(CH$_2$)$_3$-(4-MeO-cHx) | H | H | H | H |
| 6-177 | H | H | Me | 2 | —C≡C—(CH$_2$)$_3$-(4-EtO-cHx) | H | H | H | H |
| 6-178 | H | H | Me | 2 | —C≡C—(CH$_2$)$_3$-(4-PrO-cHx) | H | H | H | H |
| 6-179 | H | H | Me | 2 | —C≡C—(CH$_2$)$_3$-(4-iPrO-cHx) | H | H | H | H |
| 6-180 | H | H | Me | 2 | —C≡C—(CH$_2$)$_3$-(3-MeS-cHx) | H | H | H | H |
| 6-181 | H | H | Me | 2 | —C≡C—(CH$_2$)$_3$-(4-MeS-cHx) | H | H | H | H |
| 6-182 | H | H | Me | 2 | —C≡C—(CH$_2$)$_3$-(6-4-diMe-cHx) | H | H | H | H |
| 6-183 | H | H | Me | 2 | —C≡C—(CH$_2$)$_3$-(3,4-diMe-cHx) | H | H | H | H |
| 6-184 | H | H | Me | 2 | —C≡C—(CH$_2$)$_3$-(3,5-diMe-cHx) | H | H | H | H |
| 6-185 | H | H | Me | 2 | —C≡C—(CH$_2$)$_3$-Ph | H | H | H | H |
| 6-186 | H | H | Me | 2 | —C≡C—(CH$_2$)$_3$-Ph | Me | H | H | H |
| 6-187 | H | H | Me | 2 | —C≡C—(CH$_2$)$_3$-Ph | H | Me | H | H |
| 6-188 | H | H | Me | 2 | —C≡C—(CH$_2$)$_3$-Ph | F | H | H | H |
| 6-189 | H | H | Me | 2 | —C≡C—(CH$_2$)$_3$-Ph | H | F | H | H |
| 6-190 | H | Me | Me | 2 | —C≡C—(CH$_2$)$_3$-Ph | H | H | H | H |
| 6-191 | CO$_2$Me | H | Me | 2 | —C≡C—(CH$_2$)$_3$-Ph | H | H | H | H |
| 6-192 | CO$_2$Et | H | Me | 2 | —C≡C—(CH$_2$)$_3$-Ph | H | H | H | H |
| 6-193 | H | H | Me | 2 | —C≡C—(CH$_2$)$_3$-(4-F-Ph) | H | H | H | H |
| 6-194 | H | H | Me | 2 | —C≡C—(CH$_2$)$_3$-(4-Cl-Ph) | H | H | H | H |
| 6-195 | H | H | Me | 2 | —C≡C—(CH$_2$)$_3$-(4-Br-Ph) | H | H | H | H |
| 6-196 | H | H | Me | 2 | —C≡C—(CH$_2$)$_3$-(4-Me-Ph) | H | H | H | H |
| 6-197 | H | H | Me | 2 | —C≡C—(CH$_2$)$_3$-(4-Et-Ph) | H | H | H | H |
| 6-198 | H | H | Me | 2 | —C≡C—(CH$_2$)$_3$-(4-Pr-Ph) | H | H | H | H |
| 6-199 | H | H | Me | 2 | —C≡C—(CH$_2$)$_3$-(4-iPr-Ph) | H | H | H | H |
| 6-200 | H | H | Me | 2 | —C≡C—(CH$_2$)$_3$-(4-Bu-Ph) | H | H | H | H |
| 6-201 | H | H | Me | 2 | —C≡C—(CH$_2$)$_3$-(4-CF$_3$-Ph) | H | H | H | H |
| 6-202 | H | H | Me | 2 | —C≡C—(CH$_2$)$_3$-(4-MeO-Ph) | H | H | H | H |
| 6-203 | H | H | Me | 2 | —C≡C—(CH$_2$)$_3$-(4-EtO-Ph) | H | H | H | H |

TABLE 6-continued

| | | | | | | | | | |
|---|---|---|---|---|---|---|---|---|---|
| 6-204 | H | H | Me | 2 | —C≡C—(CH$_2$)$_3$-(4-PrO-Ph) | H | H | H | H |
| 6-205 | H | H | Me | 2 | —C≡C—(CH$_2$)$_3$-(4-iPrO-Ph) | H | H | H | H |
| 6-206 | H | H | Me | 2 | —C≡C—(CH$_2$)$_3$-(3-MeS-Ph) | H | H | H | H |
| 6-207 | H | H | Me | 2 | —C≡C—(CH$_2$)$_3$-(4-MeS-Ph) | H | H | H | H |
| 6-208 | H | H | Me | 2 | —C≡C—(CH$_2$)$_3$-(6-4-diMe-Ph) | H | H | H | H |
| 6-209 | H | H | Me | 2 | —C≡C—(CH$_2$)$_3$-(3,4-diMe-Ph) | H | H | H | H |
| 6-210 | H | H | Me | 2 | —C≡C—(CH$_2$)$_3$-(3,5-diMe-Ph) | H | H | H | H |
| 6-211 | H | H | Me | 2 | —C≡C—(CH$_2$)$_4$-cPn | H | H | H | H |
| 6-212 | H | H | Me | 2 | —C≡C—(CH$_2$)$_4$-cHx | H | H | H | H |
| 6-213 | H | H | Me | 2 | —C≡C—(CH$_2$)$_4$-cHx | Me | H | H | H |
| 6-214 | H | H | Me | 2 | —C≡C—(CH$_2$)$_4$-cHx | H | Me | H | H |
| 6-215 | H | H | Me | 2 | —C≡C—(CH$_2$)$_4$-cHx | F | H | H | H |
| 6-216 | H | H | Me | 2 | —C≡C—(CH$_2$)$_4$-cHx | H | F | H | H |
| 6-217 | H | Me | Me | 2 | —C≡C—(CH$_2$)$_4$-cHx | H | H | H | H |
| 6-218 | CO$_2$Me | H | Me | 2 | —C≡C—(CH$_2$)$_4$-cHx | H | H | H | H |
| 6-219 | CO$_2$Et | H | Me | 2 | —C≡C—(CH$_2$)$_4$-cHx | H | H | H | H |
| 6-220 | H | H | Me | 2 | —C≡C—(CH$_2$)$_4$-(4-F-cHx) | H | H | H | H |
| 6-221 | H | H | Me | 2 | —C≡C—(CH$_2$)$_4$-(4-Cl-cHx) | H | H | H | H |
| 6-222 | H | H | Me | 2 | —C≡C—(CH$_2$)$_4$-(4-Br-cHx) | H | H | H | H |
| 6-223 | H | H | Me | 2 | —C≡C—(CH$_2$)$_4$-(4-Me-cHx) | H | H | H | H |
| 6-224 | H | H | Me | 2 | —C≡C—(CH$_2$)$_4$-(4-Et-cHx) | H | H | H | H |
| 6-225 | H | H | Me | 2 | —C≡C—(CH$_2$)$_4$-(4-Pr-cHx) | H | H | H | H |
| 6-226 | H | H | Me | 2 | —C≡C—(CH$_2$)$_4$-(4-iPr-cHx) | H | H | H | H |
| 6-227 | H | H | Me | 2 | —C≡C—(CH$_2$)$_4$-(4-Bu-cHx) | H | H | H | H |
| 6-228 | H | H | Me | 2 | —C≡C—(CH$_2$)$_4$-(4-CF$_3$-cHx) | H | H | H | H |
| 6-229 | H | H | Me | 2 | —C≡C—(CH$_2$)$_4$-(4-MeO-cHx) | H | H | H | H |
| 6-230 | H | H | Me | 2 | —C≡C—(CH$_2$)$_4$-(4-EtO-cHx) | H | H | H | H |
| 6-231 | H | H | Me | 2 | —C≡C—(CH$_2$)$_4$-(4-PrO-cHx) | H | H | H | H |
| 6-232 | H | H | Me | 2 | —C≡C—(CH$_2$)$_4$-(4-iPrO-cHx) | H | H | H | H |
| 6-233 | H | H | Me | 2 | —C≡C—(CH$_2$)$_4$-(4-MeS-cHx) | H | H | H | H |
| 6-234 | H | H | Me | 2 | —C≡C—(CH$_2$)$_4$-(6-4-diMe-cHx) | H | H | H | H |
| 6-235 | H | H | Me | 2 | —C≡C—(CH$_2$)$_4$-(3,4-diMe-cHx) | H | H | H | H |
| 6-236 | H | H | Me | 2 | —C≡C—(CH$_2$)$_4$-(3,5-diMe-cHx) | H | H | H | H |
| 6-237 | H | H | Me | 2 | —C≡C—(CH$_2$)$_4$-Ph | H | H | H | H |
| 6-238 | H | H | Me | 2 | —C≡C—(CH$_2$)$_4$-Ph | Me | H | H | H |
| 6-239 | H | H | Me | 2 | —C≡C—(CH$_2$)$_4$-Ph | H | Me | H | H |
| 6-240 | H | H | Me | 2 | —C≡C—(CH$_2$)$_4$-Ph | F | H | H | H |
| 6-241 | H | H | Me | 2 | —C≡C—(CH$_2$)$_4$-Ph | H | F | H | H |
| 6-242 | H | Me | Me | 2 | —C≡C—(CH$_2$)$_4$-Ph | H | H | H | H |
| 6-243 | CO$_2$Me | H | Me | 2 | —C≡C-(CH$_2$)$_4$-Ph | H | H | H | H |
| 6-244 | CO$_2$Et | H | Me | 2 | —C≡C-(CH$_2$)$_4$-Ph | H | H | H | H |
| 6-245 | H | H | Me | 2 | —C≡C—(CH$_2$)$_4$-(4-F-Ph) | H | H | H | H |
| 6-246 | H | H | Me | 2 | —C≡C—(CH$_2$)$_4$-(4-Cl-Ph) | H | H | H | H |
| 6-247 | H | H | Me | 2 | —C≡C—(CH$_2$)$_4$-(4-Br-Ph) | H | H | H | H |
| 6-248 | H | H | Me | 2 | —C≡C—(CH$_2$)$_4$-(4-Me-Ph) | H | H | H | H |
| 6-249 | H | H | Me | 2 | —C≡C—(CH$_2$)$_4$-(4-Et-Ph) | H | H | H | H |
| 6-250 | H | H | Me | 2 | —C≡C—(CH$_2$)$_4$-(4-Pr-Ph) | H | H | H | H |
| 6-251 | H | H | Me | 2 | —C≡C—(CH$_2$)$_4$-(4-iPr-Ph) | H | H | H | H |
| 6-252 | H | H | Me | 2 | —C≡C—(CH$_2$)$_4$-(4-Bu-Ph) | H | H | H | H |
| 6-253 | H | H | Me | 2 | —C≡C—(CH$_2$)$_4$-(4-CF$_3$-Ph) | H | H | H | H |
| 6-254 | H | H | Me | 2 | —C≡C—(CH$_2$)$_4$-(4-MeO-Ph) | H | H | H | H |
| 6-255 | H | H | Me | 2 | —C≡C—(CH$_2$)$_4$-(4-EtO-Ph) | H | H | H | H |
| 6-256 | H | H | Me | 2 | —C≡C—(CH$_2$)$_4$-(4-PrO-Ph) | H | H | H | H |
| 6-257 | H | H | Me | 2 | —C≡C—(CH$_2$)$_4$-(4-iPrO-Ph) | H | H | H | H |
| 6-258 | H | H | Me | 2 | —C≡C—(CH$_2$)$_4$-(3-MeS-Ph) | H | H | H | H |
| 6-259 | H | H | Me | 2 | —C≡C—(CH$_2$)$_4$-(4-MeS-Ph) | H | H | H | H |
| 6-260 | H | H | Me | 2 | —C≡C—(CH$_2$)$_4$-(6-4-diMe-Ph) | H | H | H | H |
| 6-261 | H | H | Me | 2 | —C≡C—(CH$_2$)$_4$-(3,4-diMe-Ph) | H | H | H | H |
| 6-262 | H | H | Me | 2 | —C≡C—(CH$_2$)$_4$-(3,5-diMe-Ph) | H | H | H | H |
| 6-263 | H | H | Me | 2 | —C≡C—(CH$_2$)$_5$-cHx | H | H | H | H |
| 6-264 | H | Me | Me | 2 | —C≡C—(CH$_2$)$_5$-cHx | H | H | H | H |
| 6-265 | CO$_2$Me | H | Me | 2 | —C≡C—(CH$_2$)$_5$-cHx | H | H | H | H |
| 6-266 | CO$_2$Et | H | Me | 2 | —C≡C—(CH$_2$)$_5$-cHx | H | H | H | H |
| 6-267 | H | H | Me | 2 | —C≡C—(CH$_2$)$_5$-Ph | H | H | H | H |
| 6-268 | H | Me | Me | 2 | —C≡C—(CH$_2$)$_5$-Ph | H | H | H | H |
| 6-269 | CO$_2$Me | H | Me | 2 | —C≡C—(CH$_2$)$_5$-Ph | H | H | H | H |
| 6-270 | CO$_2$Et | H | Me | 2 | —C≡C—(CH$_2$)$_5$-Ph | H | H | H | H |
| 6-271 | H | H | Me | 2 | —C≡C—(CH$_2$)$_6$-cHx | H | H | H | H |
| 6-272 | H | Me | Me | 2 | —C≡C—(CH$_2$)$_6$-cHx | H | H | H | H |
| 6-273 | CO$_2$Me | H | Me | 2 | —C≡C—(CH$_2$)$_6$-cHx | H | H | H | H |
| 6-274 | CO$_2$Et | H | Me | 2 | —C≡C—(CH$_2$)$_6$-cHx | H | H | H | H |

TABLE 6-continued

| | | | | | | | | | |
|---|---|---|---|---|---|---|---|---|---|
| 6-275 | H | H | Me | 2 | —C≡C—(CH$_2$)$_6$-Ph | H | H | H | H |
| 6-276 | H | Me | Me | 2 | —C≡C—(CH$_2$)$_6$-Ph | H | H | H | H |
| 6-277 | CO$_2$Me | H | Me | 2 | —C≡C—(CH$_2$)$_6$-Ph | H | H | H | H |
| 6-278 | CO$_2$Et | H | Me | 2 | —C≡C—(CH$_2$)$_6$-Ph | H | H | H | H |
| 6-279 | H | H | Me | 2 | —C≡C—CH$_2$O-cHx | H | H | H | H |
| 6-280 | H | Me | Me | 2 | —C≡C—CH$_2$O-cHx | H | H | H | H |
| 6-281 | CO$_2$Me | H | Me | 2 | —C≡C—CH$_2$O-cHx | H | H | H | H |
| 6-282 | CO$_2$Et | H | Me | 2 | —C≡C—CH$_2$O-cHx | H | H | H | H |
| 6-283 | H | H | Me | 2 | —C≡C—CH$_2$O-Ph | H | H | H | H |
| 6-284 | H | Me | Me | 2 | —C≡C—CH$_2$O-Ph | H | H | H | H |
| 6-285 | CO$_2$Me | H | Me | 2 | —C≡C—CH$_2$O-Ph | H | H | H | H |
| 6-286 | CO$_2$Et | H | Me | 2 | —C≡C—CH$_2$O-Ph | H | H | H | H |
| 6-287 | H | H | Me | 2 | —C≡C—(CH$_2$)$_2$O-cPn | H | H | H | H |
| 6-288 | H | H | Me | 2 | —C≡C—(CH$_2$)$_2$O-cHx | H | H | H | H |
| 6-289 | H | H | Me | 2 | —C≡C—(CH$_2$)$_2$O-cHx | Me | H | H | H |
| 6-290 | H | H | Me | 2 | —C≡C—(CH$_2$)$_2$O-cHx | H | Me | H | H |
| 6-291 | H | H | Me | 2 | —C≡C—(CH$_2$)$_2$O-cHx | F | H | H | H |
| 6-292 | H | H | Me | 2 | —C≡C—(CH$_2$)$_2$O-cHx | H | F | H | H |
| 6-293 | H | Me | Me | 2 | —C≡C—(CH$_2$)$_2$—OCH$_2$-cHx | H | H | H | H |
| 6-294 | CO$_2$Me | H | Me | 2 | —C≡C—(CH$_2$)$_2$O-cHx | H | H | H | H |
| 6-295 | CO$_2$Et | H | Me | 2 | —C≡C—(CH$_2$)$_2$O-cHx | H | H | H | H |
| 6-296 | H | H | Me | 2 | —C≡C—(CH$_2$)$_2$O-(4-F-cHx) | H | H | H | H |
| 6-297 | H | H | Me | 2 | —C≡C—(CH$_2$)$_2$O-(4-Cl-cHx) | H | H | H | H |
| 6-298 | H | H | Me | 2 | —C≡C—(CH$_2$)$_2$O-(4-Br-cHx) | H | H | H | H |
| 6-299 | H | H | Me | 2 | —C≡C—(CH$_2$)$_2$O-(4-Me-cHx) | H | H | H | H |
| 6-300 | H | H | Me | 2 | —C≡C—(CH$_2$)$_2$O-(4-Et-cHx) | H | H | H | H |
| 6-301 | H | H | Me | 2 | —C≡C—(CH$_2$)$_2$O-(4-Pr-cHx) | H | H | H | H |
| 6-302 | H | H | Me | 2 | —C≡C—(CH$_2$)$_2$O-(4-iPr-cHx) | H | H | H | H |
| 6-303 | H | H | Me | 2 | —C≡C—(CH$_2$)$_2$O-(4-Bu-cHx) | H | H | H | H |
| 6-304 | H | H | Me | 2 | —C≡C—(CH$_2$)$_2$O-(4-CF$_3$-cHx) | H | H | H | H |
| 6-305 | H | H | Me | 2 | —C≡C—(CH$_2$)$_2$O-(4-MeO-cHx) | H | H | H | H |
| 6-306 | H | H | Me | 2 | —C≡C—(CH$_2$)$_2$O-(4-EtO-cHx) | H | H | H | H |
| 6-307 | H | H | Me | 2 | —C≡C—(CH$_2$)$_2$O-(4-PrO-cHx) | H | H | H | H |
| 6-308 | H | H | Me | 2 | —C≡C—(CH$_2$)$_2$O-(4-iPrO-cHx) | H | H | H | H |
| 6-309 | H | H | Me | 2 | —C≡C—(CH$_2$)$_2$O-(3-MeS-cHx) | H | H | H | H |
| 6-310 | H | H | Me | 2 | —C≡C—(CH$_2$)$_2$O-(4-MeS-cHx) | H | H | H | H |
| 6-311 | H | H | Me | 2 | —C≡C—(CH$_2$)$_2$O-(6-4-diMe-cHx) | H | H | H | H |
| 6-312 | H | H | Me | 2 | —C≡C—(CH$_2$)$_2$O-(3,4-diMe-cHx) | H | H | H | H |
| 6-313 | H | H | Me | 2 | —C≡C—(CH$_2$)$_2$O-(3,5-diMe-cHx) | H | H | H | H |
| 6-314 | H | H | Me | 2 | —C≡C—(CH$_2$)$_2$O-Ph | H | H | H | H |
| 6-315 | H | H | Me | 2 | —C≡C—(CH$_2$)$_2$O-Ph | Me | H | H | H |
| 6-316 | H | H | Me | 2 | —C≡C—(CH$_2$)$_2$O-Ph | H | Me | H | H |
| 6-317 | H | H | Me | 2 | —C≡C—(CH$_2$)$_2$O-Ph | F | H | H | H |
| 6-318 | H | H | Me | 2 | —C≡C—(CH$_2$)$_2$O-Ph | H | F | H | H |
| 6-319 | H | Me | Me | 2 | —C≡C—(CH$_2$)$_2$—OCH$_2$-Ph | H | H | H | H |
| 6-320 | CO$_2$Me | H | Me | 2 | —C≡C—(CH$_2$)$_2$O-Ph | H | H | H | H |
| 6-321 | CO$_2$Et | H | Me | 2 | —C≡C—(CH$_2$)$_2$O-Ph | H | H | H | H |
| 6-322 | H | H | Me | 2 | —C≡C—(CH$_2$)$_2$O-(4-F-Ph) | H | H | H | H |
| 6-323 | H | H | Me | 2 | —C≡C—(CH$_2$)$_2$O-(4-Cl-Ph) | H | H | H | H |
| 6-324 | H | H | Me | 2 | —C≡C—(CH$_2$)$_2$O-(4-Br-Ph) | H | H | H | H |
| 6-325 | H | H | Me | 2 | —C≡C—(CH$_2$)$_2$O-(4-Me-Ph) | H | H | H | H |
| 6-326 | H | H | Me | 2 | —C≡C—(CH$_2$)$_2$O-(4-Et-Ph) | H | H | H | H |
| 6-327 | H | H | Me | 2 | —C≡C—(CH$_2$)$_2$O-(4-Pr-Ph) | H | H | H | H |
| 6-328 | H | H | Me | 2 | —C≡C—(CH$_2$)$_2$O-(4-iPr-Ph) | H | H | H | H |
| 6-329 | H | H | Me | 2 | —C≡C—(CH$_2$)$_2$O-(4-Bu-Ph) | H | H | H | H |
| 6-330 | H | H | Me | 2 | —C≡C—(CH$_2$)$_2$O-(4-CF$_3$-Ph) | H | H | H | H |
| 6-331 | H | H | Me | 2 | —C≡C—(CH$_2$)$_2$O-(4-MeO-Ph) | H | H | H | H |
| 6-332 | H | H | Me | 2 | —C≡C—(CH$_2$)$_2$O-(4-EtO-Ph) | H | H | H | H |
| 6-333 | H | H | Me | 2 | —C≡C—(CH$_2$)$_2$O-(4-PrO-Ph) | H | H | H | H |
| 6-334 | H | H | Me | 2 | —C≡C—(CH$_2$)$_2$O-(4-iPrO-Ph) | H | H | H | H |
| 6-335 | H | H | Me | 2 | —C≡C—(CH$_2$)$_2$O-(4-MeS-Ph) | H | H | H | H |
| 6-336 | H | H | Me | 2 | —C≡C—(CH$_2$)$_2$O-(6-4-diMe-Ph) | H | H | H | H |
| 6-337 | H | H | Me | 2 | —C≡C—(CH$_2$)$_2$O-(3,4-diMe-Ph) | H | H | H | H |
| 6-338 | H | H | Me | 2 | —C≡C—(CH$_2$)$_2$O-(3,5-diMe-Ph) | H | H | H | H |
| 6-339 | H | H | Me | 2 | —CO—(CH$_2$)$_4$-cHx | H | H | H | H |
| 6-340 | H | Me | Me | 2 | —CO—(CH$_2$)$_4$-cHx | H | H | H | H |
| 6-341 | CO$_2$Me | H | Me | 2 | —CO—(CH$_2$)$_4$-cHx | H | H | H | H |
| 6-342 | CO$_2$Et | H | Me | 2 | —CO—(CH$_2$)$_4$-cHx | H | H | H | H |
| 6-343 | H | H | Me | 2 | —CO—(CH$_2$)$_4$-Ph | H | H | H | H |
| 6-344 | H | Me | Me | 2 | —CO—(CH$_2$)$_4$-Ph | H | H | H | H |
| 6-345 | CO$_2$Me | H | Me | 2 | —CO—(CH$_2$)$_4$-Ph | H | H | H | H |
| 6-346 | CO$_2$Et | H | Me | 2 | —CO—(CH$_2$)$_4$-Ph | H | H | H | H |
| 6-347 | H | H | Me | 2 | —CO—(CH$_2$)$_5$-cHx | H | H | H | H |

TABLE 6-continued

| | | | | | | | | | |
|---|---|---|---|---|---|---|---|---|---|
| 6-348 | H | Me | Me | 2 | —CO—(CH$_2$)$_5$-cHx | H | H | H | H |
| 6-349 | CO$_2$Me | H | Me | 2 | —CO—(CH$_2$)$_5$-cHx | H | H | H | H |
| 6-350 | CO$_2$Et | H | Me | 2 | —CO—(CH$_2$)$_5$-cHx | H | H | H | H |
| 6-351 | H | H | Me | 2 | —CO—(CH$_2$)$_5$-Ph | H | H | H | H |
| 6-352 | H | Me | Me | 2 | —CO—(CH$_2$)$_5$-Ph | H | H | H | H |
| 6-353 | CO$_2$Me | H | Me | 2 | —CO—(CH$_2$)$_5$-Ph | H | H | H | H |
| 6-354 | CO$_2$Et | H | Me | 2 | —CO—(CH$_2$)$_5$-Ph | H | H | H | H |
| 6-355 | H | H | Me | 2 | —CH(OH)—(CH$_2$)$_4$-cHx | H | H | H | H |
| 6-356 | H | Me | Me | 2 | —CH(OH)—(CH$_2$)$_4$-cHx | H | H | H | H |
| 6-357 | CO$_2$Me | H | Me | 2 | —CH(OH)—(CH$_2$)$_4$-cHx | H | H | H | H |
| 6-358 | CO$_2$Et | H | Me | 2 | —CH(OH)—(CH$_2$)$_4$-cHx | H | H | H | H |
| 6-359 | H | H | Me | 2 | —CH(OH)—(CH$_2$)$_4$-Ph | H | H | H | H |
| 6-360 | H | Me | Me | 2 | —CH(OH)—(CH$_2$)$_4$-Ph | H | H | H | H |
| 6-361 | CO$_2$Me | H | Me | 2 | —CH(OH)—(CH$_2$)$_4$-Ph | H | H | H | H |
| 6-362 | CO$_2$Et | H | Me | 2 | —CH(OH)—(CH$_2$)$_4$-Ph | H | H | H | H |
| 6-363 | H | H | Me | 2 | —CH(OH)—(CH$_2$)$_5$-cHx | H | H | H | H |
| 6-364 | H | Me | Me | 2 | —CH(OH)—(CH$_2$)$_5$-cHx | H | H | H | H |
| 6-365 | CO$_2$Me | H | Me | 2 | —CH(OH)—(CH$_2$)$_5$-cHx | H | H | H | H |
| 6-366 | CO$_2$Et | H | Me | 2 | —CH(OH)—(CH$_2$)$_5$-cHx | H | H | H | H |
| 6-367 | H | H | Me | 2 | —CH(OH)—(CH$_2$)$_5$-Ph | H | H | H | H |
| 6-368 | H | Me | Me | 2 | —CH(OH)—(CH$_2$)$_5$-Ph | H | H | H | H |
| 6-369 | CO$_2$Me | H | Me | 2 | —CH(OH)—(CH$_2$)$_5$-Ph | H | H | H | H |
| 6-370 | CO$_2$Et | H | Me | 2 | —CH(OH)—(CH$_2$)$_5$-Ph | H | H | H | H |
| 6-371 | H | H | Me | 2 | 4-(cHx-CH$_2$O)Ph | H | H | H | H |
| 6-372 | H | Me | Me | 2 | 4-(cHx-CH$_2$O)Ph | H | H | H | H |
| 6-373 | CO$_2$Me | H | Me | 2 | 4-(cHx-CH$_2$O)Ph | H | H | H | H |
| 6-374 | CO$_2$Et | H | Me | 2 | 4-(cHx-CH$_2$O)Ph | H | H | H | H |
| 6-375 | H | H | Me | 2 | 4-[cHx-(CH$_2$)$_2$O]Ph | H | H | H | H |
| 6-376 | H | H | Me | 2 | 4-[cHx-(CH$_2$)$_3$O]Ph | H | H | H | H |
| 6-377 | H | H | Me | 2 | -(4-BzO-Ph) | H | H | H | H |
| 6-378 | H | Me | Me | 2 | -(4-BzO-Ph) | H | H | H | H |
| 6-379 | CO$_2$Me | H | Me | 2 | -(4-BzO-Ph) | H | H | H | H |
| 6-380 | CO$_2$Et | H | Me | 2 | -(4-BzO-Ph) | H | H | H | H |
| 6-381 | H | H | Me | 2 | -(4-BzO-2-F-Ph) | H | H | H | H |
| 6-382 | H | H | Me | 2 | -(4-BzO-3-F-Ph) | H | H | H | H |
| 6-383 | H | H | Me | 2 | -(4-BzO-6-3-diF-Ph) | H | H | H | H |
| 6-384 | H | H | Me | 2 | -(4-BzO-2-Cl-Ph) | H | H | H | H |
| 6-385 | H | H | Me | 2 | -(4-BzO-3-Cl-Ph) | H | H | H | H |
| 6-386 | H | H | Me | 2 | -(4-BzO-6-3-diCl-Ph) | H | H | H | H |
| 6-387 | H | H | Me | 2 | -(4-BzO-2-Me-Ph) | H | H | H | H |
| 6-388 | H | H | Me | 2 | -(4-BzO-3-Me-Ph) | H | H | H | H |
| 6-389 | H | H | Me | 2 | -(4-BzO-6-3-diMe-Ph) | H | H | H | H |
| 6-390 | H | H | Me | 2 | 4-[Ph-(CH$_2$)$_2$O]-Ph | H | H | H | H |
| 6-391 | H | H | Me | 2 | 4-[Ph-(CH$_2$)$_3$O]-Ph | H | H | H | H |
| 6-392 | H | H | Et | 2 | —(CH$_2$)$_5$-cHx | H | H | H | H |
| 6-393 | H | H | Et | 2 | —(CH$_2$)$_6$-cHx | H | H | H | H |
| 6-394 | H | H | Et | 2 | —C≡C—(CH$_2$)$_3$-cHx | H | H | H | H |
| 6-395 | H | H | Et | 2 | —C≡C—(CH$_2$)$_4$-cHx | H | H | H | H |
| 6-396 | H | H | Et | 2 | 4-(cHx-CH$_2$O)Ph | H | H | H | H |
| 6-397 | H | H | Et | 2 | -(4-BzO-Ph) | H | H | H | H |
| 6-398 | H | H | Et | 2 | —C≡C—(CH$_2$)$_2$O-cHx | H | H | H | H |
| 6-399 | H | H | Et | 2 | —C≡C—(CH$_2$)$_2$O-Ph | H | H | H | H |
| 6-400 | H | H | Pr | 2 | —(CH$_2$)$_5$-cHx | H | H | H | H |
| 6-401 | H | H | Pr | 2 | —(CH$_2$)$_6$-cHx | H | H | H | H |
| 6-402 | H | H | Pr | 2 | —C≡C—(CH$_2$)$_3$-cHx | H | H | H | H |
| 6-403 | H | H | Pr | 2 | —C≡C—(CH$_2$)$_4$-cHx | H | H | H | H |
| 6-404 | H | H | Pr | 2 | 4-(cHx-CH$_2$O)Ph | H | H | H | H |
| 6-405 | H | H | Pr | 2 | -(4-BzO-Ph) | H | H | H | H |
| 6-406 | H | H | Pr | 2 | —C≡C—(CH$_2$)$_2$O-cHx | H | H | H | H |
| 6-407 | H | H | Pr | 2 | —C≡C—(CH$_2$)$_2$O-Ph | H | H | H | H |
| 6-408 | H | H | Me | 3 | —(CH$_2$)$_5$-cHx | H | H | H | H |
| 6-409 | H | H | Me | 3 | —(CH$_2$)$_6$-cHx | H | H | H | H |
| 6-410 | H | H | Me | 3 | —C≡C—(CH$_2$)$_3$-cHx | H | H | H | H |
| 6-411 | H | H | Me | 3 | —C≡C—(CH$_2$)$_4$-cHx | H | H | H | H |
| 6-412 | H | H | Me | 3 | 4-(cHx-CH$_2$O)Ph | H | H | H | H |
| 6-413 | H | H | Me | 3 | -(4-BzO-Ph) | H | H | H | H |
| 6-414 | H | H | Me | 3 | —C≡C—(CH$_2$)$_2$O-cHx | H | H | H | H |
| 6-415 | H | H | Me | 3 | —C≡C—(CH$_2$)$_2$O-Ph | H | H | H | H |
| 6-416 | COCH$_3$ | H | Me | 2 | —(CH$_2$)$_4$-cHx | H | H | H | H |
| 6-417 | COC$_2$H$_5$ | H | Me | 2 | —(CH$_2$)$_4$-cHx | H | H | H | H |
| 6-418 | COC$_3$H$_7$ | H | Me | 2 | —(CH$_2$)$_4$-cHx | H | H | H | H |
| 6-419 | COC$_4$H$_9$ | H | Me | 2 | —(CH$_2$)$_4$-cHx | H | H | H | H |
| 6-420 | COC$_5$H$_{11}$ | H | Me | 2 | —(CH$_2$)$_4$-cHx | H | H | H | H |
| 6-421 | COC$_6$H$_{13}$ | H | Me | 2 | —(CH$_2$)$_4$-cHx | H | H | H | H |
| 6-422 | COC$_7$H$_{15}$ | H | Me | 2 | —(CH$_2$)$_4$-cHx | H | H | H | H |
| 6-423 | COC$_8$H$_{17}$ | H | Me | 2 | —(CH$_2$)$_4$-cHx | H | H | H | H |
| 6-424 | COCH$_3$ | H | Me | 2 | —(CH$_2$)$_4$-Ph | H | H | H | H |
| 6-425 | COC$_2$H$_5$ | H | Me | 2 | —(CH$_2$)$_4$-Ph | H | H | H | H |
| 6-426 | COC$_3$H$_7$ | H | Me | 2 | —(CH$_2$)$_4$-Ph | H | H | H | H |
| 6-427 | COC$_4$H$_9$ | H | Me | 2 | —(CH$_2$)$_4$-Ph | H | H | H | H |

TABLE 6-continued

| | | | | | | | | | |
|---|---|---|---|---|---|---|---|---|---|
| 6-428 | COC$_5$H$_{11}$ | H | Me | 2 | —(CH$_2$)$_4$-Ph | H | H | H | H |
| 6-429 | COC$_6$H$_{13}$ | H | Me | 2 | —(CH$_2$)$_4$-Ph | H | H | H | H |
| 6-430 | COC$_7$H$_{15}$ | H | Me | 2 | —(CH$_2$)$_4$-Ph | H | H | H | H |
| 6-431 | COC$_8$H$_{17}$ | H | Me | 2 | —(CH$_2$)$_4$-Ph | H | H | H | H |
| 6-432 | COCH$_3$ | H | Me | 2 | —(CH$_2$)$_5$-cHx | H | H | H | H |
| 6-433 | COC$_2$H$_5$ | H | Me | 2 | —(CH$_2$)$_5$-cHx | H | H | H | H |
| 6-434 | COC$_3$H$_7$ | H | Me | 2 | —(CH$_2$)$_5$-cHx | H | H | H | H |
| 6-435 | COC$_4$H$_9$ | H | Me | 2 | —(CH$_2$)$_5$-cHx | H | H | H | H |
| 6-436 | COC$_5$H$_{11}$ | H | Me | 2 | —(CH$_2$)$_5$-cHx | H | H | H | H |
| 6-437 | COC$_6$H$_{13}$ | H | Me | 2 | —(CH$_2$)$_5$-cHx | H | H | H | H |
| 6-438 | COC$_7$H$_{15}$ | H | Me | 2 | —(CH$_2$)$_5$-cHx | H | H | H | H |
| 6-439 | COC$_8$H$_{17}$ | H | Me | 2 | —(CH$_2$)$_5$-cHx | H | H | H | H |
| 6-440 | COCH$_3$ | H | Me | 2 | —(CH$_2$)$_5$-Ph | H | H | H | H |
| 6-441 | COC$_2$H$_5$ | H | Me | 2 | —(CH$_2$)$_5$-Ph | H | H | H | H |
| 6-442 | COC$_3$H$_7$ | H | Me | 2 | —(CH$_2$)$_5$-Ph | H | H | H | H |
| 6-443 | COC$_4$H$_9$ | H | Me | 2 | —(CH$_2$)$_5$-Ph | H | H | H | H |
| 6-444 | COC$_5$H$_{11}$ | H | Me | 2 | —(CH$_2$)$_5$-Ph | H | H | H | H |
| 6-445 | COC$_6$H$_{13}$ | H | Me | 2 | —(CH$_2$)$_5$-Ph | H | H | H | H |
| 6-446 | COC$_7$H$_{15}$ | H | Me | 2 | —(CH$_2$)$_5$-Ph | H | H | H | H |
| 6-447 | COC$_8$H$_{17}$ | H | Me | 2 | —(CH$_2$)$_5$-Ph | H | H | H | H |
| 6-448 | COCH$_3$ | H | Me | 2 | —C≡C—(CH$_2$)$_3$-cHx | H | H | H | H |
| 6-449 | COC$_2$H$_5$ | H | Me | 2 | —C≡C—(CH$_2$)$_3$-cHx | H | H | H | H |
| 6-450 | COC$_3$H$_7$ | H | Me | 2 | —C≡C—(CH$_2$)$_3$-cHx | H | H | H | H |
| 6-451 | COC$_4$H$_9$ | H | Me | 2 | —C≡C—(CH$_2$)$_3$-cHx | H | H | H | H |
| 6-452 | COC$_5$H$_{11}$ | H | Me | 2 | —C≡C—(CH$_2$)$_3$-cHx | H | H | H | H |
| 6-453 | COC$_6$H$_{13}$ | H | Me | 2 | —C≡C—(CH$_2$)$_3$-cHx | H | H | H | H |
| 6-454 | COC$_7$H$_{15}$ | H | Me | 2 | —C≡C—(CH$_2$)$_3$-cHx | H | H | H | H |
| 6-455 | COC$_8$H$_{17}$ | H | Me | 2 | —C≡C—(CH$_2$)$_3$-cHx | H | H | H | H |
| 6-456 | COCH$_3$ | H | Me | 2 | —C≡C—(CH$_2$)$_3$-Ph | H | H | H | H |
| 6-457 | COC$_2$H$_5$ | H | Me | 2 | —C≡C—(CH$_2$)$_3$-Ph | H | H | H | H |
| 6-458 | COC$_3$H$_7$ | H | Me | 2 | —C≡C—(CH$_2$)$_3$-Ph | H | H | H | H |
| 6-459 | COC$_4$H$_9$ | H | Me | 2 | —C≡C—(CH$_2$)$_3$-Ph | H | H | H | H |
| 6-460 | COC$_5$H$_{11}$ | H | Me | 2 | —C≡C—(CH$_2$)$_3$-Ph | H | H | H | H |
| 6-461 | COC$_6$H$_{13}$ | H | Me | 2 | —C≡C—(CH$_2$)$_3$-Ph | H | H | H | H |
| 6-462 | COC$_7$H$_{15}$ | H | Me | 2 | —C≡C—(CH$_2$)$_3$-Ph | H | H | H | H |
| 6-463 | COC$_8$H$_{17}$ | H | Me | 2 | —C≡C—(CH$_2$)$_3$-Ph | H | H | H | H |
| 6-464 | COCH$_3$ | H | Me | 2 | —C≡C—(CH$_2$)$_4$-cHx | H | H | H | H |
| 6-465 | COC$_2$H$_5$ | H | Me | 2 | —C≡C—(CH$_2$)$_4$-cHx | H | H | H | H |
| 6-466 | COC$_3$H$_7$ | H | Me | 2 | —C≡C—(CH$_2$)$_4$-cHx | H | H | H | H |
| 6-467 | COC$_4$H$_9$ | H | Me | 2 | —C≡C—(CH$_2$)$_4$-cHx | H | H | H | H |
| 6-468 | COC$_5$H$_{11}$ | H | Me | 2 | —C≡C—(CH$_2$)$_4$-cHx | H | H | H | H |
| 6-469 | COC$_6$H$_{13}$ | H | Me | 2 | —C≡C—(CH$_2$)$_4$-cHx | H | H | H | H |
| 6-470 | COC$_7$H$_{15}$ | H | Me | 2 | —C≡C—(CH$_2$)$_4$-cHx | H | H | H | H |
| 6-471 | COC$_8$H$_{17}$ | H | Me | 2 | —C≡C—(CH$_2$)$_4$-cHx | H | H | H | H |
| 6-472 | COCH$_3$ | H | Me | 2 | —C≡C—(CH$_2$)$_4$-Ph | H | H | H | H |
| 6-473 | COC$_2$H$_5$ | H | Me | 2 | —C≡C—(CH$_2$)$_4$-Ph | H | H | H | H |
| 6-474 | COC$_3$H$_7$ | H | Me | 2 | —C≡C—(CH$_2$)$_4$-Ph | H | H | H | H |
| 6-475 | COC$_4$H$_9$ | H | Me | 2 | —C≡C—(CH$_2$)$_4$-Ph | H | H | H | H |
| 6-476 | COC$_5$H$_{11}$ | H | Me | 2 | —C≡C—(CH$_2$)$_4$-Ph | H | H | H | H |
| 6-477 | COC$_6$H$_{13}$ | H | Me | 2 | —C≡C—(CH$_2$)$_4$-Ph | H | H | H | H |
| 6-478 | COC$_7$H$_{15}$ | H | Me | 2 | —C≡C—(CH$_2$)$_4$-Ph | H | H | H | H |
| 6-479 | COC$_8$H$_{17}$ | H | Me | 2 | —C≡C—(CH$_2$)$_4$-Ph | H | H | H | H |
| 6-480 | COCH$_3$ | H | Me | 2 | —C≡C—(CH$_2$)$_2$O-cHx | H | H | H | H |
| 6-481 | COC$_2$H$_5$ | H | Me | 2 | —C≡C—(CH$_2$)$_2$O-cHx | H | H | H | H |
| 6-482 | COC$_3$H$_7$ | H | Me | 2 | —C≡C—(CH$_2$)$_2$O-cHx | H | H | H | H |
| 6-483 | COC$_4$H$_9$ | H | Me | 2 | —C≡C—(CH$_2$)$_2$O-cHx | H | H | H | H |
| 6-484 | COC$_5$H$_{11}$ | H | Me | 2 | —C≡C—(CH$_2$)$_2$O-cHx | H | H | H | H |
| 6-485 | COC$_6$H$_{13}$ | H | Me | 2 | —C≡C—(CH$_2$)$_2$O-cHx | H | H | H | H |
| 6-486 | COC$_7$H$_{15}$ | H | Me | 2 | —C≡C—(CH$_2$)$_2$O-cHx | H | H | H | H |
| 6-487 | COC$_8$H$_{17}$ | H | Me | 2 | —C≡C—(CH$_2$)$_2$O-cHx | H | H | H | H |
| 6-488 | COCH$_3$ | H | Me | 2 | —C≡C—(CH$_2$)$_2$O-Ph | H | H | H | H |
| 6-489 | COC$_2$H$_5$ | H | Me | 2 | —C≡C—(CH$_2$)$_2$O-Ph | H | H | H | H |
| 6-490 | COC$_3$H$_7$ | H | Me | 2 | —C≡C—(CH$_2$)$_2$O-Ph | H | H | H | H |
| 6-491 | COC$_4$H$_9$ | H | Me | 2 | —C≡C—(CH$_2$)$_2$O-Ph | H | H | H | H |
| 6-492 | COC$_5$H$_{11}$ | H | Me | 2 | —C≡C—(CH$_2$)$_2$O-Ph | H | H | H | H |
| 6-493 | COC$_6$H$_{13}$ | H | Me | 2 | —C≡C—(CH$_2$)$_2$O-Ph | H | H | H | H |
| 6-494 | COC$_7$H$_{15}$ | H | Me | 2 | —C≡C—(CH$_2$)$_2$O-Ph | H | H | H | H |
| 6-495 | COC$_8$H$_{17}$ | H | Me | 2 | —C≡C—(CH$_2$)$_2$O-Ph | H | H | H | H |
| 6-496 | COCH$_3$ | H | Me | 2 | —CO—(CH$_2$)$_4$-cHx | H | H | H | H |
| 6-497 | COC$_2$H$_5$ | H | Me | 2 | —CO—(CH$_2$)$_4$-cHx | H | H | H | H |
| 6-498 | COC$_3$H$_7$ | H | Me | 2 | —CO—(CH$_2$)$_4$-cHx | H | H | H | H |
| 6-499 | COC$_4$H$_9$ | H | Me | 2 | —CO—(CH$_2$)$_4$-cHx | H | H | H | H |
| 6-500 | COC$_5$H$_{11}$ | H | Me | 2 | —CO—(CH$_2$)$_4$-cHx | H | H | H | H |
| 6-501 | COC$_6$H$_{13}$ | H | Me | 2 | —CO—(CH$_2$)$_4$-cHx | H | H | H | H |
| 6-502 | COC$_7$H$_{15}$ | H | Me | 2 | —CO—(CH$_2$)$_4$-cHx | H | H | H | H |
| 6-503 | COC$_8$H$_{17}$ | H | Me | 2 | —CO—(CH$_2$)$_4$-cHx | H | H | H | H |
| 6-504 | COCH$_3$ | H | Me | 2 | —CO—(CH$_2$)$_4$-Ph | H | H | H | H |
| 6-505 | COC$_2$H$_5$ | H | Me | 2 | —CO—(CH$_2$)$_4$-Ph | H | H | H | H |
| 6-506 | COC$_3$H$_7$ | H | Me | 2 | —CO—(CH$_2$)$_4$-Ph | H | H | H | H |
| 6-507 | COC$_4$H$_9$ | H | Me | 2 | —CO—(CH$_2$)$_4$-Ph | H | H | H | H |

TABLE 6-continued

| | | | | | | | | | |
|---|---|---|---|---|---|---|---|---|---|
| 6-508 | COC$_5$H$_{11}$ | H | Me | 2 | —CO—(CH$_2$)$_4$-Ph | H | H | H | H |
| 6-509 | COC$_6$H$_{13}$ | H | Me | 2 | —CO—(CH$_2$)$_4$-Ph | H | H | H | H |
| 6-510 | COC$_7$H$_{15}$ | H | Me | 2 | —CO—(CH$_2$)$_4$-Ph | H | H | H | H |
| 6-511 | COC$_8$H$_{17}$ | H | Me | 2 | —CO—(CH$_2$)$_4$-Ph | H | H | H | H |

TABLE 7

(IIa-4)

| Compd. | R$^1$ | R$^2$ | R$^4$ | n | —Y—Z—R$^5$ | R$^6$ | R$^7$ | R$^{10}$ | R$^{11}$ |
|---|---|---|---|---|---|---|---|---|---|
| 7-1 | H | H | Me | 2 | —(CH$_2$)$_4$-cHx | H | H | H | H |
| 7-2 | H | H | Me | 2 | —(CH$_2$)$_4$-Ph | H | H | H | H |
| 7-3 | H | H | Me | 2 | —(CH$_2$)$_5$-cHx | H | H | H | H |
| 7-4 | H | H | Me | 2 | —(CH$_2$)$_5$-Ph | H | H | H | H |
| 7-5 | H | H | Me | 2 | —C≡C—(CH$_2$)$_2$-cHx | H | H | H | H |
| 7-6 | H | H | Me | 2 | —C≡C—(CH$_2$)$_2$-Ph | H | H | H | H |
| 7-7 | H | H | Me | 2 | —C≡C—(CH$_2$)$_3$-cHx | H | H | H | H |
| 7-8 | H | H | Me | 2 | —C≡C—(CH$_2$)$_3$-Ph | H | H | H | H |
| 7-9 | H | H | Me | 2 | —CO—(CH$_2$)$_3$-cHx | H | H | H | H |
| 7-10 | H | H | Me | 2 | —CO—(CH$_2$)$_3$-Ph | H | H | H | H |
| 7-11 | H | H | Me | 2 | —CO—(CH$_2$)$_4$-cHx | H | H | H | H |
| 7-12 | H | H | Me | 2 | —CO—(CH$_2$)$_4$-Ph | H | H | H | H |

TABLE 8

(IIIa-4)

| Compd. | R$^1$ | R$^2$ | R$^4$ | n | —Y—Z—R$^5$ | R$^6$ | R$^7$ | R$^{10}$ | R$^{11}$ |
|---|---|---|---|---|---|---|---|---|---|
| 8-1 | H | H | Me | 2 | —(CH$_2$)$_4$-cHx | H | H | H | H |
| 8-2 | H | H | Me | 2 | —(CH$_2$)$_4$-Ph | H | H | H | H |
| 8-3 | H | H | Me | 2 | —(CH$_2$)$_5$-cHx | H | H | H | H |
| 8-4 | H | H | Me | 2 | —(CH$_2$)$_5$-Ph | H | H | H | H |
| 8-5 | H | H | Me | 2 | —C≡C—(CH$_2$)$_2$-cHx | H | H | H | H |
| 8-6 | H | H | Me | 2 | —C≡C—(CH$_2$)$_2$-Ph | H | H | H | H |
| 8-7 | H | H | Me | 2 | —C≡C—(CH$_2$)$_3$-cHx | H | H | H | H |
| 8-8 | H | H | Me | 2 | —C≡C—(CH$_2$)$_3$-Ph | H | H | H | H |
| 8-9 | H | H | Me | 2 | —CO—(CH$_2$)$_3$-cHx | H | H | H | H |
| 8-10 | H | H | Me | 2 | —CO—(CH$_2$)$_3$-Ph | H | H | H | H |
| 8-11 | H | H | Me | 2 | —CO—(CH$_2$)$_4$-cHx | H | H | H | H |
| 8-12 | H | H | Me | 2 | —CO—(CH$_2$)$_4$-Ph | H | H | H | H |

The exemplification compound numbers of preferred compounds having formula (I) in the table 1 (formula (Ia-1), (Ia-2) and (1a-3)), the table 2 (formula (Ib-1), (Ib-2) and (1b-3), the table 3 (formula (1a-4) and the table 4 (formula (1a-5)) include:

1-21, from 1-30 to 1-46, from 1-93 to 1-152, from 1-199 to 1-253, from 1-263 to 1-272, from 1-283 to 1-298, from 1-345 to 1-401, from 1-411 to 1-426, from 1-473 to 1-528, from 1-548 to 1-549, from 1-559 to 1-574, from 1-621 to 1-680, from 1-727 to 1-781, from 1-791 to 1-801, from 1-831 to 1-836, from 1-896 to 1-949, from 1-959 to 1-974, from 1-1021 to 1-1078, from 1-1081 to 1-1083, from 1-1093 to 1-1103, from 1-1113 to 1-1127, from 1-1137 to 1-1152, from 1-1199 to 1-1255, from 1-1265 to 1-1280, from 1-1327 to 1-1389, from 1-1399 to 1-1049, from 1-1419 to 1-1430, 1-1433, from 1-1443 to 1-1445, from 1-1457 to 1-1466, from 1-1484 to 1-1512, from 1-1531 to 1-1555, from 1-1558 to 1-1565, from 1-1584 to 1-1612, from 1-1630 to 1-1654, from 1-1657 to 1-1664, from 1-1683 to 1-1729, from 1-1743 to 1-1949, from 2-1 to 2-10, from 2-28 to 2-56, from 2-75 to 2-99, from 2-104 to 2-111, from 2-130 to 2-158, from 2-176 to 2-200, from 2-203 to 2-210, from 2-229 to 2-281, and from 4-9 to 4-12.

The exemplification compound numbers of the more preferred compounds include 1-21, from 1-31 to 1-38, from 1-41 to 1-46, from 1-93 to 1-105, from 1-112 to 1-117, from 1-142 to 1-144, from 1-147 to 1-152, from 1-199 to 1-211, from 1-248 to 1-250, 1-253, from 1-263 to 1-269, from 1-284 to 1-289, from 1-293 to 1-298, from 1-345 to 1-357, from 1-364 to 1-369, from 1-394 to 1-401, from 1-411 to 1-417, from 1-421 to 1-426, from 1-474 to 1-485, from 1-492 to 1-497, from 1-522 to 1-528, 1-549, from 1-559 to 1-565 from 1-568 to 1-574, from 1-621 to 1-633, 1-640, 1-643, from 1-670 to 1-672, from 1-676 to 1-680, from 1-727 to 1-739, from 1-776 to 1-778, 1-781, from 1-831 to 1-838, from 1-842 to 1-846, from 1-893 to 1-905, from 1-912 to 1-917, from 1-942 to 1-946, 1-949, from 1-959 to 1-965, from 1-970 to 1-974, from 1-1021 to 1-1033, from 1-1040 to 1-1045, from 1-1070 to 1-1073, from 1-1081 to 1-1083, from 1-1093 to 1-1099, 1-1103, from 1-1113 to 1-1119, from 1-1148 to 1-1152, from 1-1199 to 1-1211, from 1-1248 to 1-1252, from 1-1265 to 1-1271, from 1-1276 to 1-1280, from 1-1327 to 1-1339, from 1-1376 to 1-1380, 1-1433, from 1-1443 to 1-1445; from 1-1459 to 1-1466, from 1-1484 to 1-1499, from 1-1504 to 1-1512, from 1-1558 to 1-1565, from 1-1584 to 1-1599, from 1-1604 to 1-1612, from 1-1630 to 1-1639, from 1-1657 to 1-1658, from 1-1660 to 1-1664, from 1-1683 to 1-1692, from 1-1702 to 1-1710, from 1-1743 to 1-1773, from 1-1796 to 1-1846, from 1-1848 to 1-1876, from 1-1886 to 1-1904, from 2-3 to 2-10, from 2-28 to 2-37, from 2-52 to 2-56, from 2-75 to 2-84, from 2-88 to 2-90, from 2-95 to 2-99, from 2-104 to 2-111, from 2-130 to 2-139, from 2-143 to 2-146, from 2-150 to 2-158, from 2-176 to 2-185, from 2-189 to 2-191, from 2-196 to 2-200, from 2-203 to 2-210, from 2-229 to 2-238, from 2-242 to 2-244, from 2-248 to 2-252, and from 4-9 to 4-12.

The exemplification compound numbers of the more preferred compounds include 1-21, 1-42, from 1-93 to 1-105, from 1-112 to 1-117, from 1-142 to 1-144, from 1-147 to 1-152, from 1-199 to 1-211, from 1-248 to 1-250, from 1-294 to 1-298, 1-351, 1-367, 1-411, 1-549, from 1-559 to 1-565, from 1-569 to 1-574, from 621 to 1-633, 1-643, from 1-670 to 1-672, from 1-676 to 1-680, from 1-831 to 1-838, from 1-842 to 1-846, from 1-893 to 1-905, from 1-912 to 1-917, from 1-942 to 1-944, 1-949, 1-1021, from 1081 to 1-1083, from 1-1093 to 1-1099, 1-1462, from 1-1558 to 1-1565, from 1-1584 to 1-1599, from 1-1604 to 1-1612, from 1-1660 to 1664, from 1-1707 to 1-1710, from 1762 to 1-1773, from 1816 to 1846, from 1-1848 to 1-1859, from 1-1886 to 1-1904, and
from 4-9 to 4-12.

The exemplification compound numbers of the still more preferred compounds include Exemplification compound number 1-93 having formula (Ia-1): 2-amino-2-methyl-4-[5-(5-phenylpentyl)furan-2-yl]butan-1-ol, Exemplification compound number 1-570 having formula (Ia-1): 2-amino-2-methyl-4-[5-(5-cyclohexylpent-1-ynyl)furan-2-yl]butan-1-ol, Exemplification compound number 1-621 having formula (Ia-1): 2-amino-2-methyl-4-[5-(5-phenylpent-1-ynyl)furan-2-yl]butan-1-ol, Exemplification compound number 1-833 having formula (Ia-1): 2-amino-2-methyl-4-{5-[3-(4-methylphenoxy)prop-1-ynyl]furan-2-yl}butan-1-ol, Exemplification compound number 1-842 having formula (Ia-1): 2-amino-2-methyl-4-[5-(4-cyclohexyloxybut-1-ynyl) furan-2-yl]butan-1-ol, Exemplification compound number 1-1083 having formula (Ia-1): 2-amino-2-methyl-4-[5-(5-cyclohexylpentanoyl)furan-2-yl]butan-1-ol, Exemplification compound number 1-1836 having formula (Ia-1): 2-amino-2-methyl-4-{5-[3-(3,4-dimethylphenoxy)prop-1-ynyl]furan-2-yl}butan-1-ol, Exemplification compound number 1-628 having formula (Ia-1): 2-amino-2-methyl-4-{5-[5-(4-chlorophenyl)pent-1-ynyl]furan-2-yl}butan-1-ol, Exemplification compound number 1-640 having formula (Ia-1): 2-amino-2-methyl-4-{5-[5-(3-trifluoromethylphenyl)pent-1-ynyl]furan-2-yl}butan-1-ol, Exemplification compound number 1-835 having formula (Ia-1): 2-amino-2-methyl-4-{5-[3-(4-trifluoromethylphenoxy)prop-1-ynyl]furan-2-yl}butan-1-ol, Exemplification compound number 1-1831 having formula (Ia-1): 2-amino-2-methyl-4-{5-[3-(4-chlorophenoxy)prop-1-ynyl]furan-2-yl}butan-1-ol, Exemplification compound number 1-1838 having formula (Ia-1): 2-amino-2-methyl-4-{5-[3-(3-trifluoromethylphenoxy)prop-1-ynyl]furan-2-yl}butan-1-ol, Exemplification compound number 1-1842 having formula (Ia-1): 2-amino-2-methyl-4-{5-[3-(3,4-dimethoxyphenoxy)prop-1-ynyl]furan-2-yl}butan-1-ol, Exemplification compound number 1-621 having formula (Ia-2): 2-amino-2-methyl-4-[1-methyl-5-(5-phenylpent-1-ynyl)pyrrol-2-yl]butan-1-ol, Exemplification compound number 1-833 having formula (Ia-2): 2-amino-2-methyl-4-{1-methyl-5-[3-(4-methyl)phenoxyprop-1-ynyl]pyrrol-2-yl}butan-1-ol, Exemplification compound number 1-842 having formula (Ia-2): 2-amino-2-methyl-4-[1-methyl-5-(4-cyclohexylbut-1-ynyl)pyrrol-2-yl]butan-1-ol, Exemplification compound number 1-1836 having formula (Ia-2): 2-amino-2-methyl-4-{1-methyl-5-[3-(3,4-dimethylphenoxy)prop-1-ynyl]pyrrol-2-yl}butan-1-ol, Exemplification compound number 1-93 having formula (Ia-2): 2-amino-2-methyl-4-[1-methyl-5-(5-phenylpentyl)pyrrol-2-yl]butan-1-ol, Exemplification compound number 1-1093 having formula (Ia-2): 2-amino-2-methyl-4-[1-methyl-5-(5-phenylpentanoyl)pyrrol-2-yl]butan-1-ol, Exemplification compound number 1-1890 having formula (Ia-2): 2-amino-2-methyl-4-{1-methyl-5-[5-(4-chlorophenyl)pentanoyl]pyrrol-2-yl}butan-1-ol, Exemplification compound number 1-1896 having formula (Ia-2): 2-amino-2-methyl-4-{1-methyl-5-[5-(3-trifluoromethylphenyl)pentanoyl]pyrrol-2-yl}butan-1-ol, Exemplification compound number 1-1083 having formula (Ia-2): 2-amino-2-methyl-4-[1-methyl-5-(5-cyclohexylpentanoyl)pyrrol-2-yl]butan-1-ol, Exemplification compound number 1-1082 having formula (Ia-2): 2-amino-2-methyl-4-[1-methyl-5-(4-phenylbutanoyl)pyrrol-2-yl]butan-1-ol, Exemplification compound number 1-1081 having formula (Ia-2): 2-amino-2-methyl-4-[1-methyl-5-(4-cyclohexylbutanoyl)pyrrol-2-yl]butan-1-ol, Exemplification compound number 4-12 having formula (Ia-5): 2-amino-2-methyl-4-[1-ethyl-5-(5-phenylpentanoyl)pyrrol-2-yl]butan-1-ol, Exemplification compound number 4-11 having formula (Ia-5): 2-amino-2-methyl-4-[1-ethyl-5-(5-cyclohexylpentanoyl)pyrrol-2-yl]butan-1-ol, Exemplification compound number 4-10 having formula (Ia-5): 2-amino-2-methyl-4-[1-ethyl-5-(4-phenylbutanoyl)pyrrol-2-yl]butan-1-ol, Exemplification compound number 4-9 having formula (Ia-5): 2-amino-2-methyl-4-[1-ethyl-5-(4-cyclohexylbutanoyl)pyrrol-2-yl]butan-1-ol, Exemplification compound number 1-21 having formula (Ia-3): 2-amino-2-methyl-4-[5-(4-cyclohexylbutyl)thiophen-2-yl]butan-1-ol, Exemplification compound number 1-42 having formula (Ia-3): 2-amino-2-methyl-4-[5-(5-cyclohexylpentyl)thiophen-2-yl]butan-1-ol, Exemplification compound number 1-93 having formula (Ia-3): 2-amino-2-methyl-4-[5-(5-phenylpentyl)thiophen-2-yl]butan-1-ol, Exemplification compound number 1-294 having formula (Ia-3): 2-amino-2-methyl-4-[5-(4-cyclohexyloxybutyl)thiophen-2-yl]butan-1-ol, Exemplification compound number 1-351 having formula (Ia-3): 2-amino-2-methyl-4-{5-[4-(4-fluorophenoxy)butyl]thiophen-2-yl}butan-1-ol, Exemplification compound number 1-367 having formula (Ia-3): 2-amino-2-methyl-4-{5-[4-(4-methoxyphenoxy)butyl]thiophen-2-yl}butan-1-ol, Exemplification compound number 1-473 having formula (Ia-3): 2-amino-2-methyl-4-[5-(4-benzyloxybutyl)thiophen-2-yl]butan-1-ol, Exemplification compound number 1-549 having formula (Ia-3): 2-amino-2-methyl-4-[5-(4-cyclohexylbut-1-ynyl)thiophen-2-yl]butan-1-ol, Exemplification compound number 1-559 having formula (Ia-3): 2-amino-2-methyl-4-[5-(4-phenylbut-1-ynyl)thiophen-2-yl]butan-1-ol, Exemplification compound number 1-570 having formula (Ia-3): 2-amino-2-methyl-4-[5-(4-cyclohexylpent-1-ynyl)thiophen-2-yl]butan-1-ol, Exemplification compound number 1-621 having formula (Ia-3): 2-amino-2-methyl-4-[5-(5-phenylpent-1-ynyl)thiophen-2-yl]butan-1-ol, Exemplification compound number 1-627 having formula (Ia-3): 2-amino-2-methyl-4-{5-[5-(4-fluorophenyl)pent-1-ynyl]thiophen-2-yl}butan-1-ol, Exemplification compound number 1-643 having formula (Ia-3): 2-amino-2-methyl-4-{5-[5-(4-methoxyphenyl)pent-1-ynyl]thiophen-2-yl}butan-1-ol, Exemplification compound number 1-833 having formula (Ia-3): 2-amino-2-methyl-4-{5-[3-(4-methylphenoxy)prop-1-ynyl]thiophen-2-yl}butan-1-ol, Exemplification compound number 1-834 having formula (Ia-3): 2-amino-2-methyl-4-{5-[3-(4-ethylphenoxy)prop-1-ynyl]thiophen-2-yl}butan-1-ol, Exemplification compound number 1-838 having formula (Ia-3): 2-amino-2-methyl-4-{5-[3-(4-methylthiophenoxy)prop-1-ynyl]thiophen-2-yl}butan-1-ol, Exemplification compound number 1-842 having formula (Ia-3): 2-amino-2-methyl-4-[5-(4-cyclohexyloxybut-1-ynyl)thiophen-2-yl]butan-1-ol, Exemplification compound number 1-899 having formula (Ia-3): 2-amino-2-methyl-4-{5-[4-(4-fluorophenoxy)but-1-ynyl]thiophen-2-yl}butan-1-ol, Exemplification compound number 1-903 having formula (Ia-3): 2-amino-2-methyl-4-{5-[4-(4-methylphenoxy)but-1-ynyl]thiophen-2-yl}butan-1-ol, Exemplification compound number 1-949 having formula (Ia-3): 2-amino-2-methyl-4-[5-(3-cyclohexylmethoxyprop-1-ynyl)thiophen-2-yl]butan-1-ol, Exemplification compound number 1-1021 having formula (Ia-3): 2-amino-2-methyl-4-[5-(4-benzyloxybut-1-ynyl)thiophen-2-yl]butan-1-ol, Exemplification compound number 1-1081 having formula (Ia-3): 2-amino-2-methyl-4-[5-(4-cyclohexylbutanoyl)thiophen-2-yl]butan-1-ol, Exemplification compound number 1-1082 having formula (Ia-3): 2-amino-2-methyl-4-[5-(4-phenylbutanoyl)thiophen-2-yl]butan-1-ol, Exemplification compound number 1-1083 having formula (Ia-3): 2-amino-2-methyl-4-[5-(5-cyclohexylpentanoyl)thiophen-2-yl]butan-1-ol, Exemplification compound number 1-1093 having formula (Ia-3): 2-amino-2-methyl-4-[5-(5-phenylpentanoyl)thiophen-2-yl]butan-1-ol, Exemplification compound number 1-1094 having formula (Ia-3): 2-amino-2-methyl-4-{5-[5-(4-fluorophenyl)pentanoyl]thiophen-2-yl}butan-1-ol, Exemplification compound number 1-1462 having formula (Ia-3): 2-amino-2-ethyl-4-[5-(5-cyclohexylpentyl)thiophen-2-yl]butan-1-ol, Exemplification compound number 1-1561 having formula (Ia-3): 2-amino-2-ethyl-4-[5-(5-cyclohexylpent-1-ynyl)thiophen-2-yl]butan-1-ol, Exemplification compound number 1-1707 having formula (Ia-3): 2-amino-2-ethyl-4-[5-(5-cyclohexylpentanoyl)thiophen-2-yl]butan-1-ol, Exemplification compound number 1-1831 having formula (Ia-3): 2-amino-2-methyl-4-{5-[3-(4-chlorophenoxy)prop-1-ynyl]thiophen-2-yl}butan-1-ol, Exemplification compound number 1-1834 having formula (Ia-3): 2-amino-2-methyl-4-{5-[3-(3-methylphenoxy)prop-1-ynyl]thiophen-2-yl}butan-1-ol, Exemplification compound number 1-1836 having formula (Ia-3): 2-amino-2-methyl-4-{5-[3-(3,4-dimethylphenoxy)prop-1-ynyl-]thiophen-2-yl}butan-1-ol, Exemplification compound number 1-1841 having formula (Ia-3): 2-amino-2-methyl-4-{5-[3-(3-methoxyphenoxy)prop-1-ynyl]thiophen-2-yl}butan-1-ol, Exemplification compound number 1-1842 having formula (Ia-3): 2-amino-2-methyl-4-{5-[3-(3,4-dimethoxyphenoxy)prop-1-ynyl]thiophen-2-yl}butan-1-ol, Exemplification compound number 1-1843 having formula (Ia-3): 2-amino-2-methyl-4-{5-[3-(3,5-dimethoxyphenoxy)prop-1-ynyl]thiophen-2-yl}butan-1-ol, Exemplification compound number 1-1845 having formula (Ia-3): 2-amino-2-methyl-4-{5-[3-(3-acetylphenoxy)prop-1-ynyl]thiophen-2-yl}butan-1-ol, and Exemplification compound number 1-1846 having formula (Ia-3): 2-amino-2-methyl-4-{5-[3-(4-acetylphenoxy)prop-1-ynyl]thiophen-2-yl}butan-1-ol.

The exemplification compound numbers of particularly preferred compounds include Exemplification compound number 1-93 having formula (Ia-1): 2-amino-2-methyl-4-[5-(5-phenylpentyl)furan-2-yl]butan-1-ol, Exemplification compound number 1-570 having formula (Ia-1): 2-amino-2-methyl-4-[5-(5-cyclohexylpent-1-ynyl)furan-2-yl]butan-1-ol, Exemplification compound number 1-621 having formula (Ia-1): 2-amino-2-methyl-4-[5-(5-phenylpent-1-ynyl)furan-2-yl]butan-1-ol, Exemplification compound number 1-842 having formula (Ia-1): 2-amino-2-methyl-4-[5-(4-cyclohexyloxybut-1-ynyl)furan-2-yl]butan-1-ol, Exemplification compound number 1-1083 having formula (Ia-1): 2-amino-2-methyl-4-[5-(5-cyclohexylpentanoyl)furan-2-yl]butan-1-ol, Exemplification compound number 1-1836 having formula (Ia-1): 2-amino-2-methyl-4-{5-[3-(3,4-dimethylphenoxy)prop-1-ynyl]furan-2-yl}butan-1-ol Exemplification compound number 1-621 having formula (Ia-2): 2-amino-2-methyl-4-[1-methyl-5-(5-phenylpent-1-ynyl)pyrrol-2-yl]butan-1-ol, Exemplification compound number 1-833 having formula (Ia-2): 2-amino-2-methyl-4-{1-methyl-5-[3-(4-methyl)phenoxyprop-1-ynyl]pyrrol-2-yl}butan-1-ol, Exemplification compound number 1-842 having formula (Ia-2): 2-amino-2-methyl-4-[1-methyl-5-(4-cyclohexyloxybut-1-ynyl)pyrrol-2-yl]butan-1-ol, Exemplification compound number 1-1093 having formula (Ia-2): 2-amino-2-methyl-4-[1-methyl-5-(5-phenylpentanoyl)pyrrol-2-yl]butan-1-ol, Exemplification compound number 1-1836 having formula (Ia-2): 2-amino-2-methyl-4-{1-methyl-5-[3-(3,4-dimethyl)phenoxyprop-1-ynyl]pyrrol-2-yl}butan-1-ol, Exemplification compound number 1-1083 having formula (Ia-2): 2-amino-2-methyl-4-[1-methyl-5-(5-cyclhexylpentanoyl)pyrrol-2-yl]butan-1-ol, Exemplification compound number 1-1082 having formula (Ia-2): 2-amino-2-methyl-4-[1-methyl-5-(4-phenylbutanoyl)pyrrol-2-yl]butan-1-ol, Exemplification compound number 1-1081 having formula (Ia-2): 2-amino-2-methyl-4-[1-methyl-5-(4-cyclohexylbutanoyl)pyrrol-2-yl]butan-1-ol, Exemplification compound number 4-12 having formula (Ia-5): 2-amino-2-methyl-4-[1-ethyl-5-(5-phenylpentanoyl)pyrrol-2-yl]butan-1-ol, Exemplification compound number 4-11 having formula (Ia-5): 2-amino-2-methyl-4-[1-ethyl-5-(5-cyclohexylpentanoyl)pyrrol-2-yl]butan-1-ol, Exemplification compound number 4-10 having formula (Ia-5): 2-amino-2-methyl-4-[1-ethyl-5-(4-phenylbutanoyl)pyrrol-2-yl]butan-1-ol, Exemplification compound number 4-9 having formula (Ia-5): 2-amino-2-methyl-4-[1-ethyl-5-(4-cyclohexylbutanoyl)pyrrol-2-yl]butan-1-ol, Exemplification compound number 1-21 having formula (Ia-3): 2-amino-2-methyl-4-[5-(4-cyclohexylbutyl)thiophen-2-yl]butan-1-ol, Exemplification compound number 1-42 having formula (Ia-3): 2-amino-2-methyl-4-[5-(5-cyclohexylpentyl)thiophen-2-yl]butan-1-ol, Exemplification compound number 1-93 having formula (Ia-3): 2-amino-2-methyl-4-[5-(5-phenylpentyl)thiophen-2-yl]butan-1-ol, Exemplification compound number-1-294 having formula (Ia-3): 2-amino-2-methyl-4-[5-(4-cyclohexyloxybutyl)thiophen-2-yl]butan-1-ol, Exemplification compound number 1-351 having formula (Ia-3): 2-amino-2-methyl-4-{5-[4-(4-fluorophenoxy)butyl]thiophen-2-yl}butan-1-ol, Exemplification compound number 1-367 having formula (Ia-3): 2-amino-2-methyl-4-{5-[4-(4-methoxyphenoxy)butyl]thiophen-2-yl}butan-1-ol, Exemplification compound number 1-473 having formula (Ia-3): 2-amino-2-methyl-4-[5-(4-benzyloxybutyl)thiophen-2-yl]butan-1-ol, Exemplification compound number 1-549 having formula (Ia-3): 2-amino-2-methyl-4-[5-(4-cyclohexylbut-1-ynyl)thiophen-2-yl]butan-1-ol, Exemplification compound number 1-559 having formula (Ia-3): 2-amino-2-methyl-4-[5-(4-phenylbut-1-ynyl)thiophen-2-yl]butan-1-ol, Exemplification compound number 1-570 having formula (Ia-3): 2-amino-2-methyl-4-[5-(5-cyclohexylpent-1-ynyl)thiophen-2-yl]butan-1-ol, Exemplification compound number 1-621 having formula (Ia-3): 2-amino-2-methyl-4-[5-(5-phenylpent-1-ynyl)thiophen-2-yl]butan-1-ol, Exemplification compound number 1-627 having formula (Ia-3): 2-amino-2-methyl-4-{5-[5-(4-fluorophenyl)pent-1-ynyl]thiophen-2-yl}butan-1-ol, Exemplification compound number 1-643 having formula (Ia-3): 2-amino-2-methyl-4-{5-[5-(4-methoxyphenyl)pent-1-ynyl]thiophen-2-yl}butan-1-ol, Exemplification compound number 1-833 having formula (Ia-3): 2-amino-2-methyl-4-{5-[3-(4-methylphenoxy)prop-1-ynyl]thiophen-2-yl}butan-1-ol, Exemplification compound number 1-834 having formula (Ia-3): 2-amino-2-methyl-4-{5-[3-(4-ethylphenoxy)prop-1-ynyl]thiophen-2-yl}butan-1-ol, Exemplification compound number 1-838 having formula (Ia-3): 2-amino-2-methyl-4-{5-[3-(4-methylthiophenoxy)prop-1-ynyl]thiophen-2-yl}butan-1-ol, Exemplification compound number 1-842 having formula (Ia-3): 2-amino-2-methyl-4-[5-(4-cyclohexyloxybut-1-ynyl)thiophen-2-yl]butan-1-ol, Exemplification compound number 1-899 having formula (Ia-3): 2-amino-2-methyl-4-{5-[4-(4-fluorophenoxy)but-1-ynyl]thiophen-2-yl}butan-1-ol, Exemplification compound number 1-903 having formula (Ia-3): 2-amino-2-methyl-4-{5-[4-(4-methylphenoxy)but-1-ynyl]thiophen-2-yl}butan-1-ol, Exemplification compound number 1-949 having formula (Ia-3): 2-amino-2-methyl-4-[5-(3-cyclohexylmethoxyprop-1-ynyl)thiophen-2-yl]butan-1-ol, Exemplification compound number 1-1021 having formula (Ia-3): 2-amino-2-methyl-4-[5-(4-benzyloxybut-1-ynyl)thiophen-2-yl]butan-1-ol, Exemplification compound number 1-1081 having formula (Ia-3): 2-amino-2-methyl-4-[5-(4-cyclohexylbutanoyl)thiophen-2-yl]butan-1-ol, Exemplification compound number 1-1082 having formula (Ia-3): 2-amino-2-methyl-4-[5-(4-phenylbutanoyl)thiophen-2-yl]butan-1-ol, Exemplification compound number 1-1083 having formula (Ia-3): 2-amino-2-methyl-4-[5-(5-cyclohexylpentanoyl)thiophen-2-yl]butan-1-ol, Exemplification compound number 1-1093 having formula (Ia-3): 2-amino-2-methyl-4-[5-(5-phenylpentanoyl)thiophen-2-yl]butan-1-ol, Exemplification compound number 1-1094 having formula (Ia-3): 2-amino-2-methyl-4-{5-[5-(4-fluorophenyl)pentanoyl]thiophen-2-yl}butan-1-ol, Exemplification compound number 1-1462 having formula (Ia-3): 2-amino-2-ethyl-4-[5-(5-cyclohexylpentyl)thiophen-2-yl]butan-1-ol, Exemplification compound number 1-1561 having formula (Ia-3): 2-amino-2-ethyl-4-[5-(5-cyclohexylpent-1-ynyl)thiophen-2-yl]butan-1-ol, Exemplification compound number 1-1707 having formula (Ia-3): 2-amino-2-ethyl-4-[5-(5-cyclohexylpentanoyl)thiophen-2-yl]butan-1-ol, Exemplification compound number 1-1831 having formula (Ia-3): 2-amino-2-methyl-4-{5-[3-(4-chlorophenoxy)prop-1-ynyl]thiophen-2-yl}butan-1-ol, Exemplification compound number 1-1834 having formula (Ia-3): 2-amino-2-methyl-4-{5-[3-(3-methylphenoxy)prop-1-ynyl]thiophen-2-yl}butan-1-ol, Exemplification compound number 1-1836 having formula (Ia-3): 2-amino-2-methyl-4-{5-[3-(3,4-dimethylphenoxy)prop-1-ynyl]thiophen-2-yl}butan-1-ol, Exemplification compound number 1-1841 having formula (Ia-3): 2-amino-2-methyl-4-{5-[3-(3-methoxyphenoxy)prop-1-ynyl]thiophen-2-yl}butan-1-ol, Exemplification compound number 1-1842 having formula (Ia-3): 2-amino-2-methyl-4-{5-[3-(3,4-dimethoxyphenoxy)prop-1-ynyl]thiophen-2-yl}butan-1-ol, Exemplification compound number 1-1843 having formula (Ia-3): 2-amino-2-methyl-4-{5-[3-(3,5-dimethoxyphenoxy)prop-1-ynyl]thiophen-2-yl}butan-1-ol, Exemplification compound number 1-1845 having formula (Ia-3): 2-amino-2-methyl-4-{5-[3-(3-acetylphenoxy)prop-1-ynyl]thiophen-2-yl}butan-1-ol, and Exemplification compound number 1-1846 having formula (Ia-3): 2-amino-2-methyl-4-{5-[3-(4-acetylphenoxy)prop-1-ynyl]thiophen-2-yl}butan-1-ol.

The exemplification compound numbers of preferred compounds having formula (II) in the table 5 (formula (IIa-1), (IIa-2) and (IIa-3)), the table 6 (formula (IIb-1), (IIb-2) and (IIb-3)), and the table 7 (formula (IIa-4)) include: 5-19, from 5-23 to 5-32, from 5-36 to 5-45, from 5-49 to 5-58, from 5-62 to 5-71, from 5-75 to 5-84, from 5-88 to 5-102, from 5-106 to 5-156, from 5-160 to 5-214, from 5-218 to 5-268, from 5-272 to 5-321, from 5-325 to 5-334, from 5-338 to 5-347, from 5-351 to 5-360, from 5-364 to 5-373, from 5-377 to 5-386, from 5-390 to 5-404, from 5-408 to 5-458, from 5-462 to 5-513, from 5-517 to 5-526, from 5-530 to 5-544, from 5-548 to 5-598, from 5-602 to 5-657, 5-670, from 5-674 to 5-683, 5-696, from 5-700 to 5-717, from 5-721 to 5-730, from 5-734 to 5-743, from 5-747 to 5-756, from 5-760 to 5-774, from 5-778 to 5-828, from 5-832 to 5-886, from 5-890 to 5-940, from 5-944 to 5-993, from 5-997 to 5-1006, from 5-1010 to 5-1019, 5-1045, from 5-1049 to 5-1058, from 5-1062 to 5-1076, from 5-1080 to 5-1130, from 5-1134 to 5-1185, from 5-1189 to 5-1198, from 5-1202 to 5-1208, from 5-1212 to 5-1216, from 5-1220 to 5-1270, from 5-1274 to 5-1331, from 5-1335 to 5-1344, from 5-1348 to 5-1357, from 5-1361 to 5-1370, from 5-1374 to 5-1387, from 5-1391 to 5-1400, from 5-1404 to 5-1418, from 5-1422 to 5-1472, from 5-1476 to 5-1527, from 5-1531 to 5-1540, from 5-1544 to 5-1558, from 5-1562 to 5-1612, from 5-1616 to 5-1673, from 5-1677 to 5-1686, from 5-1690 to 1-1699, from 5-1703 to 5-1712, from 5-1716 to 5-1729, from 5-1733 to 5-1744, from 5-1748 to 5-1768, from 5-1772 to 5-1793, from 5-1797 to 5-1820, from 5-1824 to 5-1846, from 5-1850 to 5-1869, 5-1872, 5-1876, 5-1880, 5-1884, from 5-1888 to 5-1892, 5-1896, 5-1900, from 5-1908 to 5-1913, from 5-1917 to 5-1939, from 5-1943 to 5-1966, from 5-1970 to 5-1991, from 5-1995 to 5-2013, 5-2017, 5-2021, 5-2025, 5-2029, 5-2033, from 5-2037 to 5-2042, from 5-2046 to 5-2068, from 5-2072 to 5-2089, 5-2093, 5-2097, 5-2101, 5-2105, 5-2109, 5-2113, 5-2117, 5-2121, 5-2125, 5-2129, 5-2133, 5-2135, from 5-2139 to 5-2158, from 5-2161 to 5-2164, from 5-2185 to 5-2346, from 5-2398 to 5-2557, from 6-9 to 6-18, from 6-22 to 6-43, from 6-47 to 6-70, from 6-74 to 6-96, from 6-100 to 6-119, 6-142, 6-146, 6-150, 6-154, from 6-158 to 6-163, from 6-167 to 6-183, from 6-185 to 6-189, from 6-193 to 6-216, from 6-220 to 6-241, from 6-245 to 6-263, 6-267, 6-271, 6-275, 6-279, 6-283, from 6-287 to 6-292, from 6-296 to 6-318, from 6-322 to 6-338, 6-343, 6-347, 6-351, 6-371, from 6-375 to 6-377, from 6-381 to 6-407, from 6-416 to 6-511, and from 7-9 to 7-12.

The exemplification compound numbers of the more preferred compounds include:

5-19, 5-32, from 5-36 to 5-45, 5-57, from 5-62 to 5-71, 5-84, 5-88, from 5-97 to 5-100, from 5-152 to 5-154, from 5-160 to 5-214, from 5-218 to 5-227, from 5-264 to 5-268, from 5-272 to 5-321, 5-334, 5-347, 5-360, 5-373, 5-386, from 5-390 to 5-402, from 5-454 to 5-458, from 5-462 to 5-513, 5-526, from 5-530 to 5-542, from 5-594 to 5-598, from 5-602 to 5-653, 5-743, 5-756, from 5-760 to 5-768, from 5-770 to 5-774, from 5-778 to 5-828, from 5-832 to 5-886, from 5-890 to 5-940, from 5-944 to 5-993, 5-1045, 5-1058, from 5-1062 to 5-1074, from 5-1126 to 5-1130, from 5-1134 to 5-1185, 5-1198, from 5-1202 to 5-1208, from 5-1212 to 5-1214, from 5-1266 to 5-1270, from 5-1274 to 5-1331, 5-1344, from 5-1348 to 5-1357, 5-1370, from 5-1374 to 5-1387, 5-1400, from 5-1404 to 5-1416, from 5-1468 to 5-1472, from 5-1476 to 5-1527, 5-1540, from 5-1544 to 5-1556, from 5-1608 to 5-1612, from 5-1616 to 5-1666, 5-1729, 5-1742, 5-1744, from 5-1759 to 5-1767, from 5-1789 to 5-1793, from 5-1797 to 5-1818, from 5-1842 to 5-1846, 5-1900, from 5-1908 to 5-1913, from 5-1935 to 5-1939, from 5-1943 to 5-1966, from 5-1987 to 5-1991, 5-2013, 5-2017, 5-2029, 5-2033, from 5-2037 to 5-2042, from 5-2064 to 5-2068, from 5-2072 to 5-2089, 5-2093, 5-2097, 5-2101, 5-2105, 5-2109, 5-2129, 5-2133, 5-2135, from 5-2185 to 5-2346, from 5-2398 to 5-2557, from 6-11 to 6-18, from 6-39 to 6-43, from 6-47 to 6-70, 6-185 to 6-189, from 6-193 to 6-216, from 6-287 to 6-292, 6-338, 6-343, 6-347, 6-351, from 6-416 to 6-511, and from 7-9 to 7-12.

The exemplification compound numbers of the more preferred compounds include:

5-45, 5-71, 5-84, 5-88, from 5-97 to 5-100, from 5-152 to 5-154, from 5-160 to 5-206, from 5-209 to 5-212, from 5-264 to 5-266, 5-334, 5-373, 5-386, from 5-390 to 5-402, from 5-454 to 5-458, from 5-462 to 5-485, 5-509, 5-510, 5-513, 5-526, from 5-530 to 5-542, from 5-594 to 5-598, from 5-602 to 5-613, 5-649, 5-650, 5-743, 5-756, from 5-760 to 5-768, from 5-770 to 5-772, from 5-824 to 5-828, from 5-832 to 5-884, 5-936, 5-1045, 5-1058, from 5-1062 to 5-1074, from 5-1126 to 5-1130, from 5-1134 to 5-1145, from 5-1148 to 5-1151, 5-1162, 5-1163, from 5-1179 to 5-1182, 5-1185, 5-1198, from 5-1202 to 5-1208, 5-1212, 5-1213, 5-1214, from 5-1266 to 5-1270, from 5-1274 to 5-1285, from 5-1288 to 5-1291, from 5-1319 to 5-1322, from 5-1329 to 5-1331, 5-1344, from 5-1348 to 5-1357, 5-1370, 5-1387, 5-1400, from 5-1404 to 5-1416, from 5-1468 to 5-1472, from 5-1476 to 5-1487, from 5-1490 to 5-1493, 5-1504, 5-1505, from 5-1521 to 5-1524, 5-1527, 5-1540, from 5-1544 to 5-1556, from 5-1608 to 5-1612, from 5-1616 to 5-1627, 5-1663, 5-1664, 5-1729, 5-1742, 5-1744, from 5-1761 to 5-1766, from 5-1789 to 5-1791, from 5-1815 to 5-1818, 5-1900, 5-1909, 5-1962, from 5-2064 to 5-2066, 5-2089, 5-2093, 5-2097, 5-2101, 5-2105, 5-2133, from 5-2216 to 5-2288, from 5-2290 to 5-2346, from 5-2398 to 5-2557, and from 7-9 to 7-12.

The exemplification compound numbers of the still more preferred compounds include:

Exemplification compound number 5-84 having formula (IIa-1): mono 2-amino-2-methyl-4-[5-(5-phenylpentyl)furan-2-yl]-1-butyl phosphate, Exemplification compound number 5-770 having formula (IIa-1): mono 2-amino-2-methyl-4-[5-(5-cyclohexylpent-1-ynyl)furan-2-yl]-1-butyl phosphate, Exemplification compound number 5-824 having formula (IIa-1): mono 2-amino-2-methyl-4-[5-(5-phenylpent-1-ynyl)furan-2-yl]-1-butyl phosphate, Exemplification compound number 5-1063 having formula (IIa-1): mono 2-amino-2-methyl-4-{5-[3-(4-methylphenoxyl)prop-1-ynyl]furan-2-yl}-1-butyl phosphate, Exemplification compound number 5-1072 having formula (IIa-1): mono 2-amino-2-methyl-4-[5-(4-cyclohexyloxybut-1-ynyl)furan-2-yl]-1-butyl phosphate, Exemplification compound number 5-1331 having formula (IIa-1): mono 2-amino-2-methyl-4-[5-(5-cyclohexylpentanoyl)furan-2-yl]-1-butyl phosphate, Exemplification compound number 5-2278 having formula (IIa-1): mono 2-amino-2-methyl-4-{5-[3-(3,4-dimethylphenoxy)prop-1-ynyl]furan-2-yl}-1-butyl phosphate, Exemplification compound number 5-834 having formula (IIa-1): mono 2-amino-2-methyl-4-{5-[5-(4-chlorophenyl)pent-1-ynyl]furan-2-yl}-1-butyl phosphate, Exemplification compound number 5-846 having formula (IIa-1): mono 2-amino-2-methyl-4-{5-[5-(3-trifluoromethylphenyl)pent-1-ynyl]furan-2-yl}-1-butyl phosphate, Exemplification compound number 5-1065 having formula (IIa-1): mono 2-amino-2-methyl-4-{5-[3-(4-trifluoromethylphenoxyl)prop-1-ynyl]furan-2-yl}-1-butyl phosphate, Exemplification compound number 5-2273 having formula (IIa-1): mono 2-amino-2-methyl-4-{5-[3-(4-chlorophenoxyl)prop-1-ynyl]furan-2-yl}-1-butyl phosphate, Exemplification compound number 5-2280 having formula (IIa-1): mono 2-amino-2-methyl-4-{5-[3-(3-trifluoromethylphenoxyl)prop-1-ynyl]furan-2-yl}-1-butyl phosphate, Exemplification compound number 5-2284 having formula (IIa-1): mono 2-amino-2-methyl-4-{5-[3-(3,4-dimethoxyphenoxy)prop-1-ynyl]furan-2-yl}-1-butyl phosphate, Exemplification compound number 5-824 having formula (IIa-2): mono 2-amino-2-methyl-4-[1-methyl-5-(5-phenylpent-1-ynyl)pyrrol-2-yl]-1-butyl phosphate, Exemplification compound number 5-1063 having formula (IIa-2): mono 2-amino-2-methyl-4-{1-methyl-5-[3-(4-methyl)phenoxyprop-1-ynyl]pyrrol-2-yl}-1-butyl phosphate, Exemplification compound number 5-1072 having formula (IIa-2): mono 2-amino-2-methyl-4-[1-methyl-5-(4-cyclohexyloxybut-1-ynyl)pyrrol-2-yl]-1-butyl phosphate, Exemplification compound number 5-2278 having formula (IIa-2): mono 2-amino-2-methyl-4-{1-methyl-5-[3-(3,4-dimethylphenoxy)prop-1-ynyl]pyrrol-2-yl}-1-butyl phosphate, Exemplification compound number 5-84 having formula (IIa-2): mono 2-amino-2-methyl-4-[1-methyl-5-(5-phenylpentyl)pyrrol-2-yl]-1-butyl phosphate, Exemplification compound number 5-1344 having formula (IIa-2): mono 2-amino-2-methyl-4-[1-methyl-5-(5-phenylpentanoyl)pyrrol-2-yl]-1-butyl phosphate, Exemplification compound number 5-2332 having formula (IIa-2): mono 2-amino-2-methyl-4-{1-methyl-5-[5-(4-chlorophenyl)pentanoyl]pyrrol-2-yl}-1-butyl phosphate, Exemplification compound number 5-2338 having formula (IIa-2): mono 2-amino-2-methyl-4-{1-methyl-5-[5-(3-trifluoromethylphenyl)pentanoyl]pyrrol-2-yl}-1-butyl phosphate, Exemplification compound number 5-1331 having formula (IIa-2): mono 2-amino-2-methyl-4-[1-methyl-5-(5-cyclohexylpentanoyl)pyrrol-2-yl]-1-butyl phosphate, Exemplification compound number 5-1330 having formula (IIa-2): mono 2-amino-2-methyl-4-[1-methyl-5-(4-phenylbutanoyl)pyrrol-2-yl]-1-butyl phosphate, Exemplification compound number 5-1329 having formula (IIa-2): mono 2-amino-2-methyl-4-[1-methyl-5-(4-cyclohexylbutanoyl)pyrrol-2-yl]-1-butyl phosphate, Exemplification compound number 7-12 having formula (IIa-4): mono 2-amino-2-methyl-4-[1-ethyl-5-(5-phenylpentanoyl)pyrrol-2-yl]-1-butyl phosphate, Exemplification compound number 7-11 having formula (IIa-4): mono 2-amino-2-methyl-4-[1-ethyl-5-(5-cyclohexylpentanoyl)pyrrol-2-yl]-1-butyl phosphate, Exemplification compound number 7-10 having formula (IIa-4): mono 2-amino-2-methyl-4-[1-ethyl-5-(4-phenylbutanoyl)pyrrol-2-yl]-1-butyl phosphate, Exemplification compound number 7-9 having formula (IIa-4): mono 2-amino-2-methyl-4-[1-ethyl-5-(4-cyclohexylbutanoyl)pyrrol-2-yl]-1-butyl phosphate, Exemplification compound number 5-71 having formula (IIa-3): mono 2-amino-2-methyl-4-[5-(4-cyclohexylbutyl)thiophen-2-yl]-1-butyl phosphate, Exemplification compound number 5-84 having formula (IIa-3): mono 2'-amino-2-methyl-4-[5-(4-phenylbutyl)thiophen-2-yl]-1-butyl phosphate, Exemplification compound number 5-98 having formula (IIa-3): mono 2-amino-2-methyl-4-[5-(5-cyclohexylpentyl)thiophen-2-yl]-1-butyl phosphate, Exemplification compound number 5-152 having formula (IIa-3): mono 2-amino-2-methyl-4-[5-(5-phenylpentyl)thiophen-2-yl]-1-butyl phosphate, Exemplification compound number-5-210 having formula (IIa-3): mono 2-amino-2-methyl-4-[5-(6-cyclohexylhexyl)thiophen-2-yl]-1-butyl phosphate, Exemplification compound number 5-264 having formula (IIa-3): mono 2-amino-2-methyl-4-[5-(6-phenylhexyl)thiophen-2-yl]-1-butyl phosphate, Exemplification compound number 5-373 having formula (IIa-3): mono 2-amino-2-methyl-4-[5-(3-cyclohexyloxypropyl)thiophen-2-yl]-1-butyl phosphate, Exemplification compound number 5-386 having formula (IIa-3): mono 2-amino-2-methyl-4-[5-(3-phenoxypropyl)thiophen-2-yl]-1-butyl phosphate, Exemplification compound number 5-400 having formula (IIa-3): mono 2-amino-2-methyl-4-[5-(4-cyclohexyloxybutyl)thiophen-2-yl]-1-butyl phosphate, Exemplification compound number 5-454 having formula (IIa-3): mono 2-amino-2-methyl-4-[5-(4-phenoxylbutyl)thiophen-2-yl]-1-butyl phosphate, Exemplification compound number 5-509 having formula (IIa-3): mono 2-amino-2-methyl-4-[5-(5-cyclohexyloxypentyl)thiophen-2-yl]-1-butyl phosphate, Exemplification compound number 5-510 having formula (IIa-3): mono 2-amino-2-methyl-4-[5-(5-phenoxypentyl)thiophen-2-yl]-1-butyl phosphate, Exemplification compound number 5-513 having formula (IIa-3): mono 2-amino-2-methyl-4-[5-(3-cyclohexylmethoxypropyl)thiophen-2-yl]-1-butyl phosphate, Exemplification compound number 5-743 having formula (IIa-3): mono 2-amino-2-methyl-4-[5-(4-cyclohexylbut-1-ynyl)thiophen-2-yl]-1-butyl phosphate, Exemplification compound number 5-756 having formula (IIa-3): mono 2-amino-2-methyl-4-[5-(4-phenylbut-1-ynyl)thiophen-2-yl]-1-butyl phosphate, Exemplification compound number 5-770 having formula (IIa-3): mono 2-amino-2-methyl-4-[5-(5-cyclohexylpent-1-ynyl)thiophen-2-yl]-1-butyl phosphate, Exemplification compound number 5-824 having formula (IIa-3): mono 2-amino-2-methyl-4-[5-(5-phenylpent-1-ynyl)thiophen-2-yl]-1-butyl phosphate, Exemplification compound number 5-882 having formula (IIa-3): mono 2-amino-2-methyl-4-[5-(6-cyclohexylhex-1-ynyl)thiophen-2-yl]-1-butyl phosphate, Exemplification compound number 5-936 having formula (IIa-3): mono 2-amino-2-methyl-4-[5-(6-phenylhex-1-ynyl)thiophen-2-yl]-1-butyl phosphate, Exemplification compound number 5-1045 having formula (IIa-3): mono 2-amino-2-methyl-4-[5-(3-cyclohexyloxyprop-1-ynyl)thiophen-2-yl]-1-butyl phosphate, Exemplification compound number 5-1058 having formula (IIa-3): mono 2-amino-2-methyl-4-[5-(3-phenoxyprop-1-ynyl)thiophen-2-yl]-1-butyl phosphate, Exemplification compound number 5-1072 having formula (IIa-3): mono 2-amino-2-methyl-4-[5-(4-cyclohexyloxybut-1-ynyl)thiophen-2-yl]-1-butyl phosphate, Exemplification compound number 5-1126 having formula (IIa-3): mono 2-amino-2-methyl-4-[5-(4-phenoxybut-1-ynyl)thiophen-2-yl]-1-butyl phosphate, Exemplification compound number 5-1181 having formula (IIa-3): mono 2-amino-2-methyl-4-[5-(5-cyclohexyloxypent-1-ynyl)thiophen-2-yl]-1-butyl phosphate, Exemplification compound number 5-1182 having formula (IIa-3): mono 2-amino-2-methyl-4-[5-(5-phenoxypent-1-ynyl)thiophen-2-yl]-1-butyl phosphate, Exemplification compound number 5-1185 having formula (IIa-3): mono 2-amino-2-methyl-4-[5-(3-cyclohexylmethoxyprop-1-ynyl)thiophen-2-yl]-1-butyl phosphate, Exemplification compound number 5-1329 having formula (IIa-3): mono 2-amino-2-methyl-4-[5-(4-cyclohexylbutanoyl)thiophen-2-yl]-1-butyl phosphate, Exemplification compound number 5-1330 having formula (IIa-3) mono 2-amino-2-methyl-4-[5-(4-phenylbutanoyl)thiophen-2-yl]-1-butyl phosphate, Exemplification compound number 5-1331 having formula (IIa-3): mono 2-amino-2-methyl-4-[5-(5-cyclohexylpentanoyl)thiophen-2-yl]-1-butyl phosphate, Exemplification compound number 5-1344 having formula (IIa-3): mono-2-amino-2-methyl-4-[5-(5-phenylpentanoyl)thiophen-2-yl]-1-butyl phosphate, Exemplification compound number 5-1357 having formula (IIa-3): mono 2-amino-2-methyl-4-[5-(6-cyclohexylhexanoyl)thiophen-2-yl]-1-butyl phosphate, Exemplification compound number 5-1370 having formula (IIa-3): mono 2-amino-2-methyl-4-[5-(6-phenylhexanoyl)thiophen-2-yl]-1-butyl phosphate, Exemplification compound number 5-1387 having formula (IIa-3): mono 2-amino-2-methyl-4-[5-(3-cyclohexyloxypropanoyl)thiophen-2-yl]-1-butyl phosphate, Exemplification compound number 5-1400 having formula (IIa-3): mono 2-amino-2-methyl-4-[5-(3-phenoxypropanoyl)thiophen-2-yl]-1-butyl phosphate, Exemplification compound number 5-1414 having formula (IIa-3): mono 2-amino-2-methyl-4-[5-(4-cyclohexyloxybutanoyl)thiophen-2-yl]-1-butyl phosphate, Exemplification compound number 5-1468 having formula (IIa-3): mono 2-amino-2-methyl-4-[5-(4-phenoxybutanoyl)thiophen-2-yl]-1-butyl phosphate, Exemplification compound number 5-1523 having formula (IIa-3): mono 2-amino-2-methyl-4-[5-(5-cyclohexyloxypentanoyl)thiophen-2-yl]-1-butyl phosphate, Exemplification compound number 5-1524 having formula (IIa-3): mono 2-amino-2-methyl-4-[5-(5-phenoxypentanoyl)thiophen-2-yl]-1-butyl phosphate, Exemplification compound number 5-1527 having formula (IIa-3): mono 2-amino-2-methyl-4-[5-(3-cyclohexylmethoxypropanoyl)thiophen-2-yl]-1-butyl phosphate, Exemplification compound number 5-1729 having formula (IIa-3): mono 2-amino-2-methyl-4-[5-(4-cyclohexylmethoxyphenyl)thiophen-2-yl]-1-butyl phosphate, Exemplification compound number 5-1742 having formula (IIa-3): mono 2-amino-2-methyl-4-[5-(4-cyclohexylethoxyphenyl)thiophen-2-yl]-1-butyl phosphate, Exemplification compound number 5-1744 having formula (IIa-3): mono 2-amino-2-methyl-4-[5-(4-benzyloxyphenyl)thiophen-2-yl]-1-butyl phosphate, Exemplification compound number 5-1761 having formula (IIa-3): mono 2-amino-2-ethyl-4-[5-(4-cyclohexylbutyl)thiophen-2-yl]-1-butyl phosphate, Exemplification compound number 5-1764 having formula (IIa-3): mono 2-amino-2-ethyl-4-[5-(5-cyclohexylpentyl)thiophen-2-yl]-1-butyl phosphate, Exemplification compound number 5-1816 having formula (IIa-3): mono 2-amino-2-ethyl-4-[5-(6-cyclohexylhexyl)thiophen-2-yl]-1-butyl phosphate, Exemplification compound number 5-1900 having formula (IIa-3): mono 2-amino-2-ethyl-4-[5-(4-cyclohexylbut-1-ynyl)thiophen-2-yl]-1-butyl phosphate, Exemplification compound number 5-1909 having formula (IIa-3): mono 2-amino-2-ethyl-4-[5-(5-cyclohexylpent-1-ynyl)thiophen-2-yl]-1-butyl phosphate, Exemplification compound number 5-1962 having formula (IIa-3): mono 2-amino-2-ethyl-4-[5-(6-cyclohexylhex-1-ynyl)thiophen-2-yl]-1-butyl phosphate, Exemplification compound number 5-2089 having formula (IIa-3): mono 2-amino-2-ethyl-4-[5-(4-cyclohexylbutanoyl)thiophen-2-yl]-1-butyl phosphate, Exemplification compound number 5-2097 having formula (IIa-3): mono 2-amino-2-ethyl-4-[5-(5-cyclohexylpentanoyl)thiophen-2-yl]-1-butyl phosphate, and Exemplification compound number 5-2105 having formula (IIa-3): mono 2-amino-2-ethyl-4-[5-(6-cyclohexylhexanoyl)thiophen-2-yl]-1-butyl phosphate, and Exemplification compound number 5-463 having formula (IIa-3): mono 2-amino-2-methyl-4-{5-[4-(4-fluorophenoxy)butyl]thiophen-2-yl}-1-butyl phosphate, Exemplification compound number 5-479 having formula (IIa-3): mono 2-amino-2-methyl-4-{5-[4-(4-methoxyphenoxy)butyl]thiophen-2-yl}-1-butyl phosphate, Exemplification compound number 5-594 having formula (IIa-3): mono 2-amino-2-methyl-4-[5-(4-benzyloxybutyl)thiophen-2-yl]-1-butyl phosphate, Exemplification compound number 5-760 having formula (IIa-3): mono 2-amino-2-methyl-4-{5-[4-(4-fluorophenyl)but-1-ynyl]thiophen-2-yl}-1-butyl phosphate, Exemplification compound number 5-761 having formula (IIa-3): mono 2-amino-2-methyl-4-{5-[4-(4-methylphenyl)but-1-ynyl]thiophen-2-yl}-1-butyl phosphate, Exemplification compound number 5-762 having formula (IIa-3): mono 2-amino-2-methyl-4-{5-[4-(4-ethylphenyl)but-1-ynyl]thiophen-2-yl}-1-butyl phosphate, Exemplification compound number 5-763 having formula (IIa-3): mono 2-amino-2-methyl-4-{5-[4-(4-trifluoromethylphenyl)but-1-ynyl]thiophen-2-yl}-1-butyl phosphate, Exemplification compound number 5-764 having formula (IIa-3): mono 2-amino-2-methyl-4-{5-[4-(4-methoxyphenyl)but-1-ynyl]thiophen-2-yl}-1-butyl phosphate, Exemplification compound number 5-765 having formula (IIa-3): mono 2-amino-2-methyl-4-{5-[4-(4-ethoxyphenyl)but-1-ynyl]thiophen-2-yl}-1-butyl phosphate, Exemplification compound number 5-766 having formula (IIa-3): mono 2-amino-2-methyl-4-{5-[4-(4-methylthiophenyl)but-1-ynyl]thiophen-2-yl}-1-butyl phosphate, Exemplification compound number 5-832 having formula (IIa-3): mono 2-amino-2-methyl-4-{5-[5-(3-fluorophenyl)pent-1-ynyl]thiophen-2-yl}-1-butyl phosphate, Exemplification compound number 5-833 having formula (IIa-3): mono 2-amino-2-methyl-4-{5-[5-(4-fluorophenyl)pent-1-ynyl]thiophen-2-yl}-1-butyl phosphate, Exemplification compound number 5-834 having formula (IIa-3): mono 2-amino-2-methyl-4-{5-[5-(4-chlorophenyl)pent-1-ynyl]thiophen-2-yl}-1-butyl phosphate, Exemplification compound number 5-836 having formula (IIa-3): mono 2-amino-2-methyl-4-{5-[5-(3-methylphenyl)pent-1-ynyl]thiophen-2-yl}-1-butyl phosphate, Exemplification compound number 5-837 having formula (IIa-3): mono 2-amino-2-methyl-4-{5-[5-(4-methlyphenyl)pent-1-ynyl]thiophen-2-yl}-1-butyl phosphate, Exemplification compound number 5-846 having formula (IIa-3): mono 2-amino-2-methyl-4-{5-[5-(3-trifluoromethylphenyl)pent-1-ynyl]thiophen-2-yl}-1-butyl phosphate, Exemplification compound number 5-847 having formula (IIa-3): mono 2-amino-2-methyl-4-{5-[5-(4-trifluorophenyl)pent-1-ynyl]thiophen-2-yl}-1-butyl phosphate, Exemplification compound number 5-848 having formula (IIa-3): mono 2-amino-2-methyl-4-{5-[5-(3-methoxyphenyl)pent-1-ynyl]thiophen-2-yl}-1-butyl phosphate, Exemplification compound number 5-849 having formula (IIa-3): mono 2-amino-2-methyl-4-{5-[5-(4-methoxyphenyl)pent-1-ynyl]thiophen-2-yl}-1-butyl phosphate, Exemplification compound number 5-860 having formula (IIa-3): mono 2-amino-2-methyl-4-{5-[5-(3-methylthiophenyl)pent-1-ynyl]thiophen-2-yl}-1-butyl phosphate, Exemplification compound number 5-861 having formula (IIa-3): mono 2-amino-2-methyl-4-{5-[5-(4-methylthiophenyl)pent-1-ynyl]thiophen-2-yl}-1-butyl phosphate, Exemplification compound number 5-877 having formula (IIa-3): mono 2-amino-2-methyl-4-{5-[5-(3,4-dimethylphenyl)pent-1-ynyl]thiophen-2-yl}-1-butyl phosphate, Exemplification compound number 5-878 having formula (IIa-3): mono 2-amino-2-methyl-4-{5-[5-(3,5-dimethylphenyl)pent-1-ynyl]thiophen-2-yl}-1-butyl phosphate, Exemplification compound number 5-10-50 having formula (IIa-3): mono 2-amino-2-methyl-4-{5-[3-(4-methylcyclohexyloxy)prop-1-ynyl]thiophen-2-yl}-1-butyl phosphate, Exemplification compound number 5-1062 having formula (IIa-3): mono 2-amino-2-methyl-4-{5-[3-(4-fluorophenoxy)prop-1-ynyl]thiophen-2-yl}-1-butyl phosphate, Exemplification compound number 5-1063 having formula (IIa-3): mono 2-amino-2-methyl-4-{5-[3-(4-methylphenoxy)prop-1-ynyl]thiophen-2-yl}-1-butyl phosphate, Exemplification compound number 5-1064 having formula (IIa-3): mono 2-amino-2-methyl-4-{5-[3-(4-ethylphenoxy)prop-1-ynyl]thiophen-2-yl}-1-butyl phosphate, Exemplification compound number 5-1065 having formula (IIa-3): mono 2-amino-2-methyl-4-{5-[3-(4-trifluoromethylphenoxyl)prop-1-ynyl]thiophen-2-yl}-1-butyl phosphate, Exemplification compound number 5-1066 having formula (IIa-3): mono 2-amino-2-methyl-4-{5-[3-(4-methoxyphenoxy)prop-1-ynyl]thiophen-2-yl}-1-butyl phosphate, Exemplification compound number 5-1067 having formula (IIa-3): mono 2-amino-2-methyl-4-{5-[3-(4-ethoxyphenoxy)prop-1-ynyl]thiophen-2-yl}-1-butyl phosphate, Exemplification compound number 5-1068 having formula (IIa-3): mono 2-amino-2-methyl-4-{5-[3-(4-methylthiophenoxy)prop-1-ynyl]thiophen-2-yl}-1-butyl phosphate, Exemplification compound number 5-1134 having formula (IIa-3): mono 2-amino-2-methyl-4-{5-[4-(3-fluorophenoxy)but-1-ynyl]thiophen-2-yl}-1-butyl phosphate, Exemplification compound number 5-1135 having formula (IIa-3): mono 2-amino-2-methyl-4-{5-[4-(4-fluorophenoxy)but-1-ynyl]thiophen-2-yl}-1-butyl phosphate, Exemplification compound number 5-1136 having formula (IIa-3): mono 2-amino-2-methyl-4-{5-[4-(4-chlorophenoxy)but-1-ynyl]thiophen-2-yl}-1-butyl phosphate, Exemplification compound number 5-1138 having formula (IIa-3): mono 2-amino-2-methyl-4-{5-[4-(3-methylphenoxy)but-1-ynyl]thiophen-2-yl}-1-butyl phosphate, Exemplification compound number 5-1139 having formula (IIa-3): mono 2-amino-2-methyl-4-{5-[4-(4-methylphenoxy)but-1-ynyl]thiophen-2-yl}-1-butyl phosphate, Exemplification compound number 5-1148 having formula (IIa-3): mono 2-amino-2-methyl-4-{5-[4-(3-trifluoromethylphenoxy)but-1-ynyl]thiophen-2-yl}-1-butyl phosphate, Exemplification compound number 5-1149 having formula (IIa-3): mono 2-amino-2-methyl-4-{5-[4-(4-trifluoromethylphenoxy)but-1-ynyl]thiophen-2-yl}-1-butyl phosphate, Exemplification compound number 5-1150 having formula (IIa-3): mono 2-amino-2-methyl-4-{5-[4-(3-methoxyphenoxy)but-1-ynyl]thiophen-2-yl}-1-butyl phosphate, Exemplification compound number 5-1151 having formula (IIa-3): mono 2-amino-2-methyl-4-{5-[4-(4-methoxyphenoxy)but-1-ynyl]thiophen-2-yl}-1-butyl phosphate, Exemplification compound number 5-1162 having formula (IIa-3): mono 2-amino-2-methyl-4-{5-[4-(3-methylthiophenoxy)but-1-ynyl]thiophen-2-yl}-1-butyl phosphate, Exemplification compound number 5-1163 having formula (IIa-3): mono 2-amino-2-methyl-4-{5-[4-(4-methylthiophenoxy)but-1-ynyl]thiophen-2-yl}-1-butyl phosphate, Exemplification compound number 5-1179 having formula (IIa-3): mono 2-amino-2-methyl-4-{5-[4-(3,4-dimethylphenoxy)but-1-ynyl]thiophen-2-yl}-1-butyl phosphate, Exemplification compound number 5-1180 having formula (IIa-3): mono 2-amino-2-methyl-4-{5-[4-(3,5-dimethylphenoxy)but-1-ynyl]thiophen-2-yl}-1-butyl phosphate, Exemplification compound number 5-1198 having formula (IIa-3): mono 2-amino-2-methyl-4-[5-(3-benzyloxyprop-1-ynyl)thiophen-2-yl]-1-butyl phosphate, Exemplification compound number 5-1202 having formula (IIa-3): mono 2-amino-2-methyl-4-{5-[3-(4-fluorophenyl)methoxyprop-1-ynyl]thiophen-2-yl}-1-butyl phosphate, Exemplification compound number 5-1203 having formula (IIa-3): mono 2-amino-2-methyl-4-{5-[3-(4-methylphenyl)methoxyprop-1-ynyl]thiophen-2-yl}-1-butyl phosphate, Exemplification compound number-5-1204 having formula (IIa-3): mono 2-amino-2-methyl-4-{5-[3-(4-ethylphenyl)methoxyprop-1-ynyl]thiophen-2-yl}-1-butyl phosphate, Exemplification compound number 5-1205 having formula (IIa-3): mono 2-amino-2-methyl-4-{5-[3-(4-trifluoromethylphenyl)methoxyprop-1-ynyl]thiophen-2-yl}-1-butyl phosphate, Exemplification compound number 5-1206 having formula (IIa-3): mono 2-amino-2-methyl-4-{5-[3-(4-methoxyphenyl)methoxyprop-1-ynyl]thiophen-2-yl}-1-butyl phosphate, Exemplification compound number 5-1207 having formula (IIa-3): mono 2-amino-2-methyl-4-{5-[3-(4-ethoxyphenyl)methoxyprop-1-ynyl]thiophen-2-yl}-1-butyl phosphate, Exemplification compound number 5-1208 having formula (IIa-3): mono 2-amino-2-methyl-4-{5-[3-(4-methylthiophenyl)methoxyprop-1-ynyl]thiophen-2-yl}-1-butyl phosphate, Exemplification compound number 5-1212 having formula (IIa-3): mono 2-amino-2-methyl-4-[5-(4-cyclohexylmethoxybut-1-ynyl)thiophen-2-yl]-1-butyl phosphate, Exemplification compound number 5-1266 having formula (IIa-3): mono 2-amino-2-methyl-4-[5-(4-benzyloxybut-1-ynyl)thiophen-2-yl]-1-butyl phosphate, Exemplification compound number 5-1274 having formula (IIa-3): mono 2-amino-2-methyl-4-{5-[4-(3-fluorophenyl)methoxybut-1-ynyl]thiophen-2-yl}-1-butyl phosphate, Exemplification compound number 5-1275 having formula (IIa-3): mono 2-amino-2-methyl-4-{5-[4-(4-fluorophenyl)methoxybut-1-ynyl]thiophen-2-yl}-1-butyl phosphate, Exemplification compound number 5-1276 having formula (IIa-3): mono 2-amino-2-methyl-4-{5-[4-(4-chlorophenyl)methoxybut-1-ynyl]thiophen-2-yl}-1-butyl phosphate, Exemplification compound number 5-1278 having formula (IIa-3): mono 2-amino-2-methyl-4-{5-[4-(3-methylphenyl)methoxybut-1-ynyl]thiophen-2-yl}-1-butyl phosphate, Exemplification compound number 5-1279 having formula (IIa-3): mono 2-amino-2-methyl-4-{5-[4-(4-methylphenyl)methoxybut-1-ynyl]thiophen-2-yl}-1-butyl phosphate, Exemplification compound number 5-1288 having formula (IIa-3): mono 2-amino-2-methyl-4-{5-[4-(3-trifluoromethylphenyl)methoxybut-1-ynyl]thiophen-2-yl}-1-butyl phosphate, Exemplification compound number 5-1289 having formula (IIa-3): mono 2-amino-2-methyl-4-{5-[4-(4-trifluoromethylphenyl)methoxybut-1-ynyl]thiophen-2-yl}-1-butyl phosphate, Exemplification compound number 5-1290 having formula (IIa-3): mono 2-amino-2-methyl-4-{5-[4-(3-methoxyphenyl)methoxybut-1-ynyl]thiophen-2-yl}-1-butyl phosphate, Exemplification compound number 5-1291 having formula (IIa-3): mono 2-amino-2-methyl-4-{5-[4-(4-methoxyphenyl)methoxybut-1-ynyl]thiophen-2-yl}-1-butyl phosphate, Exemplification compound number 5-1319 having formula (IIa-3): mono 2-amino-2-methyl-4-{5-[4-(3,4-dimethylphenyl)methoxybut-1-ynyl]thiophen-2-yl}-1-butyl phosphate, Exemplification compound number 5-1320 having formula (IIa-3): mono 2-amino-2-methyl-4-{5-[4-(3,5-dimethylphenyl)methoxybut-1-ynyl]thiophen-2-yl}-1-butyl phosphate, Exemplification compound number 5-1348 having formula (IIa-3): mono 2-amino-2-methyl-4-{5-[5-(4-fluorophenyl)pentanoyl]thiophen-2-yl}-1-butyl phosphate, Exemplification compound number 5-1349 having formula (IIa-3): mono 2-amino-2-methyl-4-{5-[5-(4-methylphenyl)pentanoyl]thiophen-2-yl}-1-butyl phosphate, Exemplification compound number 5-1350 having formula (IIa-3): mono 2-amino-2-methyl-4-{5-[5-(4-ethylphenyl)pentanoyl]thiophen-2-yl}-1-butyl phosphate, Exemplification compound number 5-1351 having formula (IIa-3): mono 2-amino-2-methyl-4-{5-[5-(4-trifluoromethylphenyl)pentanoyl]thiophen-2-yl}-1-butyl phosphate, Exemplification compound number 5-1352 having formula (IIa-3): mono 2-amino-2-methyl-4-{5-[5-(4-methoxyphenyl)pentanoyl]thiophen-2-yl}-1-butyl phosphate, Exemplification compound number 5-1353 having formula (IIa-3): mono 2-amino-2-methyl-4-{5-[5-(4-ethoxyphenyl)pentanoyl]thiophen-2-yl}-1-butyl phosphate, Exemplification compound number 5-1354 having formula (IIa-3): mono 2-amino-2-methyl-4-{5-[5-(4-methylthiophenyl)pentanoyl]thiophen-2-yl}-1-butyl phosphate, Exemplification compound number 5-1476 having formula (IIa-3): mono 2-amino-2-methyl-4-{5-[4-(3-fluorophenoxy)butanoyl]thiophen-2-yl}-1-butyl phosphate, Exemplification compound number 5-1477 having formula (IIa-3): mono 2-amino-2-methyl-4-{5-[4-(4-fluorophenoxy)butanoyl]thiophen-2-yl}-1-butyl phosphate, Exemplification compound number 5-1478 having formula (IIa-3): mono 2-amino-2-methyl-4-{5-[4-(4-chlorophenoxy)butanoyl]thiophen-2-yl}-1-butyl phosphate, Exemplification compound number 5-1480 having formula (IIa-3): mono 2-amino-2-methyl-4-{5-[4-(3-methylphenoxy)butanoyl]thiophen-2-yl}-1-butyl phosphate, Exemplification compound number 5-1481 having formula (IIa-3): mono 2-amino-2-methyl-4-{5-[4-(4-methylphenoxy)butanoyl]thiophen-2-yl}-1-butyl phosphate, Exemplification compound number 5-1490 having formula (IIa-3): mono 2-amino-2-methyl-4-{5-[4-(3-trifluoromethylphenoxy)butanoyl]thiophen-2-yl}-1-butyl phosphate, Exemplification compound number 5-1491 having formula (IIa-3): mono 2-amino-2-methyl-4-{5-[4-(4-trifluoromethylphenoxy)butanoyl]thiophen-2-yl}-1-butyl phosphate, Exemplification compound number 5-1492 having formula (IIa-3): mono 2-amino-2-methyl-4-{5-[4-(3-methoxyphenoxy)butanoyl]thiophen-2-yl}-1-butyl phosphate, Exemplification compound number 5-1493 having formula (IIa-3): mono 2-amino-2-methyl-4-{5-[4-(4-methoxyphenoxy)butanoyl]thiophen-2-yl}-1-butyl phosphate, Exemplification compound number 5-1504 having formula (IIa-3): mono 2-amino-2-methyl-4-{5-[4-(3-methylthiophenoxy)butanoyl]thiophen-2-yl}-1-butyl phosphate, Exemplification compound number 5-1505 having formula (IIa-3): mono 2-amino-2-methyl-4-{5-[4-(4-methylthiophenoxy)butanoyl]thiophen-2-yl}-1-butyl phosphate, Exemplification compound number 5-1521 having formula (IIa-3): mono 2-amino-2-methyl-4-{5-[4-(3,4-dimethylphenoxy)butanoyl]thiophen-2-yl}-1-butyl phosphate, Exemplification compound number 5-1522 having formula (IIa-3): mono 2-amino-2-methyl-4-{5-[4-(3,5-dimethylphenoxy)butanoyl]thiophen-2-yl}-1-butyl phosphate, Exemplification compound number 5-2093 having formula (IIa-3): mono 2-amino-2-ethyl-4-[5-(4-phenylbutanoyl)thiophen-2-yl]-1-butyl phosphate, Exemplification compound number 5-2101 having formula (IIa-3): mono 2-amino-2-ethyl-4-[5-(5-phenylpentanoyl)thiophen-2-yl]-1-butyl phosphate, Exemplification compound number 5-2109 having formula (IIa-3): mono 2-amino-2-ethyl-4-[5-(6-phenylhexanoyl)thiophen-2-yl]-1-butyl phosphate, Exemplification compound number 5-2257 having formula (IIa-3): mono 2-amino-2-methyl-4-{5-[5-(3,4-difluorophenyl)pent-1-ynyl]thiophen-2-yl}-1-butyl phosphate, Exemplification compound number 5-2258 having formula (IIa-3): mono 2-amino-2-methyl-4-{5-[5-(3,5-difluorophenyl)pent-1-ynyl]thiophen-2-yl}-1-butyl phosphate, Exemplification compound number 5-2259 having formula (IIa-3): mono 2-amino-2-methyl-4-{5-[5-(3-chlorophenyl)pent-1-ynyl]thiophen-2-yl}-1-butyl phosphate, Exemplification compound number 5-2260 having formula (IIa-3): mono 2-amino-2-methyl-4-{5-[5-(3,4-dichlorophenyl)pent-1-ynyl]thiophen-2-yl}-1-butyl phosphate, Exemplification compound number 5-2261 having formula (IIa-3): mono 2-amino-2-methyl-4-{5-[5-(3,5-dichlorophenyl)pent-1-ynyl]thiophen-2-yl}-1-butyl phosphate, Exemplification compound number 5-2262 having formula (IIa-3): mono 2-amino-2-methyl-4-{5-[5-(3,4-ditrifluoromethylphenyl)pent-1-ynyl]thiophen-2-yl}-1-butyl phosphate, Exemplification compound number 5-2263 having formula (IIa-3): mono 2-amino-2-methyl-4-{5-[5-(3,5-ditrifluoromethylphenyl)pent-1-ynyl]thiophen-2-yl}-1-butyl phosphate, Exemplification compound number 5-2264 having formula (IIa-3): mono 2-amino-2-methyl-4-{5-[5-(3,4-dimethoxyphenyl)pent-1-ynyl]thiophen-2-yl}-1-butyl phosphate, Exemplification compound number 5-2265 having formula (IIa-3): mono 2-amino-2-methyl-4-{5-[5-(3,5-dimethoxyphenyl)pent-1-ynyl]thiophen-2-yl}-1-butyl phosphate, Exemplification compound number 5-2266 having formula (IIa-3): mono 2-amino-2-methyl-4-{5-[5-(3,4,5-trimethoxyphenyl)pent-1-ynyl]thiophen-2-yl}-1-butyl phosphate, Exemplification compound number 5-2267 having formula (IIa-3): mono 2-amino-2-methyl-4-{5-[5-(3-acetylphenyl)pent-1-ynyl]thiophen-2-yl}-1-butyl phosphate, Exemplification compound number 5-2268 having formula (IIa-3): mono 2-amino-2-methyl-4-{5-[5-(4-acetylphenyl)pent-1-ynyl]thiophen-2-yl}-1-butyl phosphate, Exemplification compound number 5-2269 having formula (IIa-3): mono 2-amino-2-methyl-4-{5-[3-(3-fluorophenoxy)prop-1-ynyl]thiophen-2-yl}-1-butyl phosphate, Exemplification compound number 5-2270 having formula (IIa-3): mono 2-amino-2-methyl-4-{5-[3-(3,4-difluorophenoxy)prop-1-ynyl]thiophen-2-yl}-1-butyl phosphate, Exemplification compound number 5-2271 having formula (IIa-3): mono 2-amino-2-methyl-4-{5-[3-(3,5-difluorophenoxy)prop-1-ynyl]thiophen-2-yl}-1-butyl phosphate, Exemplification compound number 5-2272 having formula (IIa-3): mono 2-amino-2-methyl-4-{5-[3-(3-chlorophenoxy)prop-1-ynyl]thiophen-2-yl}-1-butyl phosphate, Exemplification compound number 5-2273 having formula (IIa-3): mono 2-amino-2-methyl-4-{5-[3-(4-chlorophenoxy)prop-1-ynyl]thiophen-2-yl}-1-butyl phosphate, Exemplification compound number 5-2274 having formula (IIa-3): mono 2-amino-2-methyl-4-{5-[3-(3,4-dichlorophenoxy)prop-1-ynyl]thiophen-2-yl}-1-butyl phosphate, Exemplification compound number 5-2275 having formula (IIa-3): mono 2-amino-2-methyl-4-{5-[3-(3,5-dichlorophenoxy)prop-1-ynyl]thiophen-2-yl}-1-butyl phosphate, Exemplification compound number 5-2276 having formula (IIa-3): mono 2-amino-2-methyl-4-{5-[3-(3-methylphenoxy)prop-1-ynyl]thiophen-2-yl}-1-butyl phosphate, Exemplification compound number 5-2278 having formula (IIa-3): mono 2-amino-2-methyl-4-{5-[3-(3,4-dimethylphenoxy)prop-1-ynyl]thiophen-2-yl}-1-butyl phosphate, Exemplification compound number 5-2279 having formula (IIa-3): mono 2-amino-2-methyl-4-{5-[3-(3,5-dimethylphenoxy)prop-1-ynyl]thiophen-2-yl}-1-butyl phosphate, Exemplification compound number 5-2280 having formula (IIa-3): mono 2-amino-2-methyl-4-{5-[3-(3-trifluoromethylphenoxy)prop-1-ynyl]thiophen-2-yl}-1-butyl phosphate, Exemplification compound number 5-2281 having formula (IIa-3): mono 2-amino-2-methyl-4-{5-[3-(3,4-ditrifluoromethylphenoxy)prop-1-ynyl]thiophen-2-yl}-1-butyl phosphate, Exemplification compound number 5-2282 having formula (IIa-3): mono 2-amino-2-methyl-4-{5-[3-(3,5-ditrifluoromethylphenoxy)prop-1-ynyl]thiophen-2-yl}-1-butyl phosphate, Exemplification compound number 5-2283 having formula (IIa-3): mono 2-amino-2-methyl-4-{5-[3-(3-methoxyphenoxy)prop-1-ynyl]thiophen-2-yl}-1-butyl phosphate, Exemplification compound number 5-2284 having formula (IIa-3): mono 2-amino-2-methyl-4-{5-[3-(3,4-dimethoxyphenoxy)prop-1-ynyl]thiophen-2-yl}-1-butyl phosphate, Exemplification compound number 5-2285 having formula (IIa-3): mono 2-amino-2-methyl-4-{5-[3-(3,5-dimethoxyphenoxy)prop-1-ynyl]thiophen-2-yl}-1-butyl phosphate, Exemplification compound number 5-2286 having formula (IIa-3): mono 2-amino-2-methyl-4-{5-[3-(3,4,5-trimethoxyphenoxy)prop-1-ynyl]thiophen-2-yl}-1-butyl phosphate, Exemplification compound number 5-2287 having formula (IIa-3): mono 2-amino-2-methyl-4-{5-[3-(3-acetylphenoxy)prop-1-ynyl]thiophen-2-yl}-1-butyl phosphate, Exemplification compound number 5-2288 having formula (IIa-3): mono 2-amino-2-methyl-4-{5-[3-(4-acetylphenoxy)prop-1-ynyl]thiophen-2-yl}-1-butyl phosphate, Exemplification compound number 5-2290 having formula (IIa-3): mono 2-amino-2-methyl-4-{5-[4-(3,4-difluorophenoxy)but-1-ynyl]thiophen-2-yl}-1-butyl phosphate, Exemplification compound number 5-2291 having formula (IIa-3): mono 2-amino-2-methyl-4-{5-[4-(3,5-difluorophenoxy)but-1-ynyl]thiophen-2-yl}-1-butyl phosphate, Exemplification compound number 5-2292 having formula (IIa-3): mono 2-amino-2-methyl-4-{5-[4-(3-chlorophenoxy)but-1-ynyl]thiophen-2-yl}-1-butyl phosphate, Exemplification compound number 5-2293 having formula (IIa-3): mono 2-amino-2-methyl-4-{5-[4-(3,4-dichlorophenoxy)but-1-ynyl]thiophen-2-yl}-1-butyl phosphate, Exemplification compound number 5-2294 having formula (IIa-3): mono 2-amino-2-methyl-4-{5-[4-(3,5-dichlorophenoxy)but-1-ynyl]thiophen-2-yl}-1-butyl phosphate, Exemplification compound number 5-2295 having formula (IIa-3): mono 2-amino-2-methyl-4-{5-[4-(3,4-di(trifluoromethyl)phenoxy)but-1-ynyl]thiophen-2-yl}-1-butyl phosphate, Exemplification compound number 5-2296 having formula (IIa-3): mono 2-amino-2-methyl-4-{5-[4-(3,5-di(trifluoromethyl)phenoxy)but-1-ynyl]thiophen-2-yl}-1-butyl phosphate, Exemplification compound number 5-2297 having formula (IIa-3): mono 2-amino-2-methyl-4-{5-[4-(3,4-dimethoxyphenoxy)but-1-ynyl]thiophen-2-yl}-1-butyl phosphate, Exemplification compound number 5-2298 having formula (IIa-3): mono 2-amino-2-methyl-4-{5-[4-(3,5-dimethoxyphenoxy)but-1-ynyl]thiophen-2-yl}-1-butyl phosphate, Exemplification compound number 5-2299 having formula (IIa-3): mono 2-amino-2-methyl-4-{5-[4-(3,4,5-trimethoxyphenoxy)but-1-ynyl]thiophen-2-yl}-1-butyl phosphate, Exemplification compound number 5-2300 having formula (IIa-3): mono 2-amino-2-methyl-4-{5-[4-(3-acetylphenoxy)but-1-ynyl]thiophen-2-yl}-1-butyl phosphate, Exemplification compound number 5-2301 having formula (IIa-3): mono 2-amino-2-methyl-4-{5-[4-(4-acetylphenoxy)but-1-ynyl]thiophen-2-yl}-1-butyl phosphate, Exemplification compound number 5-2328 having formula (IIa-3): mono 2-amino-2-methyl-4-{5-(5-(3-fluorophenyl)pentanoyl}thiophen-2-yl)-1-butyl phosphate, Exemplification compound number 5-2329 having formula (IIa-3): mono 2-amino-2-methyl-4-{5-[5-(3,4-difluorophenyl)pentanoyl]thiophen-2-yl}-1-butyl phosphate, Exemplification compound number 5-2330 having formula (IIa-3): mono 2-amino-2-methyl-4-{5-[5-(3,5-difluorophenyl)pentanoyl]thiophen-2-yl}-1-butyl phosphate, Exemplification compound number 5-2331 having formula (IIa-3): mono 2-amino-2-methyl-4-{(5-[5-(3-chlorophenyl)pentanoyl]thiophen-2-yl}-1-butyl phosphate, Exemplification compound number 5-2332 having formula (IIa-3): mono 2-amino-2-methyl-4-{5-[5-(4-chlorophenyl)pentanoyl]thiophen-2-yl}-1-butyl phosphate, Exemplification compound number 5-2333 having formula (IIa-3): mono 2-amino-2-methyl-4-{5-[5-(3,4-dichlorophenyl)pentanoyl]thiophen-2-yl}-1-butyl phosphate, Exemplification compound number 5-2334 having formula (IIa-3): mono 2-amino-2-methyl-4-{5-[5-(3,5-dichlorophenyl)pentanoyl]thiophen-2-yl}-1-butyl phosphate, Exemplification compound number 5-2335 having formula (IIa-3): mono 2-amino-2-methyl-4-{5-[5-(3-methylphenyl)pentanoyl]thiophen-2-yl}-1-butyl phosphate, Exemplification compound number 5-2336 having formula (IIa-3): mono 2-amino-2-methyl-4-{5-[5-(3,4-dimethylphenyl)pentanoyl]thiophen-2-yl}-1-butyl phosphate, Exemplification compound number 5-2337 having formula (IIa-3): mono 2-amino-2-methyl-4-{5-[5-(3,5-dimethylphenyl)pentanoyl]thiophen-2-yl}-1-butyl phosphate, Exemplification compound number 5-2338 having formula (IIa-3): mono 2-amino-2-methyl-4-{5-[5-(3-trifluoromethylphenyl)pentanoyl]thiophen-2-yl}-1-butyl phosphate, Exemplification compound number 5-2339 having formula (IIa-3): mono 2-amino-2-methyl-4-{5-[5-(3,4-ditrifluoromethylphenyl)pentanoyl]thiophen-2-yl}-1-butyl phosphate, Exemplification compound number 5-2340 having formula (IIa-3): mono 2-amino-2-methyl-4-{5-[5-(3,5-ditrifluoromethylphenyl)pentanoyl]thiophen-2-yl}-1-butyl phosphate, Exemplification compound number 5-2341 having formula (IIa-3): mono 2-amino-2-methyl-4-{5-[5-(3-methoxyphenyl)pentanoyl]thiophen-2-yl}-1-butyl phosphate, Exemplification compound number 5-2342 having formula (IIa-3): mono 2-amino-2-methyl-4-{5-[5-(3,4-dimethoxyphenyl)pentanoyl]thiophen-2-yl}-1-butyl phosphate, Exemplification compound number 5-2343 having formula (IIa-3): mono 2-amino-2-methyl-4-{5-[5-(3,5-dimethoxyphenyl)pentanoyl]thiophen-2-yl}-1-butyl phosphate, Exemplification compound number 5-2344 having formula (IIa-3): mono 2-amino-2-methyl-4-{5-[5-(3,4,5-trimethoxyphenyl)pentanoyl]thiophen-2-yl}-1-butyl phosphate, Exemplification compound number 5-2345 having formula (IIa-3): mono 2-amino-2-methyl-4-{5-[5-(3-acetylphenyl)pentanoyl]thiophen-2-yl}-1-butyl phosphate, and Exemplification compound number 5-2346 having formula (IIa-3): mono 2-amino-2-methyl-4-{5-[5-(4-acetylphenyl)pentanoyl]thiophen-2-yl}-1-butyl phosphate.

The exemplification compound numbers of the most preferred compounds include:

Exemplification compound number 5-84 having formula (IIa-1): mono 2-amino-2-methyl-4-[5-(5-phenylpentyl)furan-2-yl]-1-butyl phosphate, Exemplification compound number 5-770 having formula (IIa-1): mono 2-amino-2-methyl-4-[5-(5-cyclohexylpent-1-ynyl)furan-2-yl]-1-butyl phosphate, Exemplification compound number 5-824 having formula (IIa-1): mono 2-amino-2-methyl-4-[5-(5-phenylpent-1-ynyl)furan-2-yl]-1-butyl phosphate, Exemplification compound number 5-1072 having formula (IIa-1): mono 2-amino-2-methyl-4-[5-(4-cyclohexyloxybut-1-ynyl)furan-2-yl]-1-butyl phosphate, Exemplification compound number 5-1331 having formula (IIa-1): mono 2-amino-2-methyl-4-[5-(5-cyclohexylpentanoyl)furan-2-yl]-1-butyl phosphate, Exemplification compound number 5-2278 having formula (IIa-1): mono 2-amino-2-methyl-4-{5-[3-(3,4-dimethylphenoxy)prop-1-ynyl]furan-2-yl}-1-butyl phosphate, Exemplification compound number 5-824 having formula (IIa-2): mono 2-amino-2-methyl-4-[1-methyl-5-(5-phenylpent-1-ynyl)pyrrol-2-yl]-1-butyl phosphate, Exemplification compound number 5-1063 having formula (IIa-2): mono 2-amino-2-methyl-4-{1-methyl-5-[3-(4-methyl)phenoxyprop-1-ynyl]pyrrol-2-yl}-1-butyl phosphate, Exemplification compound number 5-1072 having formula (IIa-2): mono 2-amino-2-methyl-4-[1-methyl-5-(4-cyclohexyloxybut-1-ynyl)pyrrol-2-yl]-1-butyl phosphate, Exemplification compound number 5-2278 having formula (IIa-2): mono 2-amino-2-methyl-4-{1-methyl-5-[3-(3,4-dimethylphenoxy)prop-1-ynyl]pyrrol-2-yl}-1-butyl phosphate, Exemplification compound number 5-1344 having formula (IIa-2): mono 2-amino-2-methyl-4-[1-methyl-5-(5-phenylpentanoyl)pyrrol-2-yl]-1-butyl phosphate, Exemplification compound number 5-1331 having formula (IIa-2): mono 2-amino-2-methyl-4-[1-methyl-5-(5-cyclohexylpentanoyl)pyrrol-2-yl]-1-butyl phosphate, Exemplification compound number 5-1330 having formula (IIa-2): mono 2-amino-2-methyl-4-[1-methyl-5-(4-phenylbutanoyl)pyrrol-2-yl]-1-butyl phosphate, Exemplification compound number 5-1329 having formula (IIa-2): mono 2-amino-2-methyl-4-[1-methyl-5-(4-cyclohexylbutanoyl)pyrrol-2-yl]-1-butyl phosphate, Exemplification compound number 7-12 having formula (IIa-4): mono 2-amino-2-methyl-4-[1-ethyl-5-(5-phenylpentanoyl)pyrrol-2-yl]-1-butyl phosphate, Exemplification compound number 7-11 having formula (IIa-4): mono 2-amino-2-methyl-4-[1-ethyl-5-(5-cyclohexylpentanoyl)pyrrol-2-yl]-1-butyl phosphate, Exemplification compound number 7-10 having formula (IIa-4): mono 2-amino-2-methyl-4-[1-ethyl-5-(4-phenylbutanoyl)pyrrol-2-yl]-1-butyl phosphate, Exemplification compound number 7-9 having formula (IIa-4): mono 2-amino-2-methyl-4-[1-ethyl-5-(4-cyclohexylbutanoyl)pyrrol-2-yl]-1-butyl phosphate, Exemplification compound number 5-71 having formula (IIa-3): mono 2-amino-2-methyl-4-[5-(4-cyclohexylbutyl)thiophen-2-yl]-1-butyl phosphate, Exemplification compound number 5-98 having formula (IIa-3): mono 2-amino-2-methyl-4-[5-(5-cyclohexylpentyl)thiophen-2-yl]-1-butyl phosphate, Exemplification compound number 5-152 having formula (IIa-3): mono 2-amino-2-methyl-4-[5-(5-phenylpentyl)thiophen-2-yl]-1-butyl phosphate, Exemplification compound number 5-400 having formula (IIa-3): mono 2-amino-2-methyl-4-[5-(4-cyclohexyloxybutyl)thiophen-2-yl]-1-butyl phosphate, Exemplification compound number 5-463 having formula (IIa-3): mono 2-amino-2-methyl-4-{5-[4-(4-fluorophenoxy)butyl]thiophene-2-yl}-1-butyl phosphate, Exemplification compound number 5-479 having formula (IIa-3): mono 2-amino-2-methyl-4-{5-[4-(4-methoxyphenoxy)butyl]thiophne-2-yl}-1-butyl phosphate, Exemplification compound number 5-594 having formula (IIa-3): mono 2-amino-2-methyl-4-[5-(4-benzyloxybutyl)thiophne-2-yl]-1-butyl phosphate, Exemplification compound number 5-743 having formula (IIa-3): mono 2-amino-2-methyl-4-[5-(4-cyclohexylbut-1-ynyl)thiophen-2-yl]-1-butyl phosphate, Exemplification compound number 5-756 having formula (IIa-3): mono 2-amino-2-methyl-4-[5-(4-phenylbut-1-ynyl)thiophen-2-yl]-1-butyl phosphate, Exemplification compound number 5-770 having formula (IIa-3): mono 2-amino-2-methyl-4-[5-(5-cyclohexylpent-1-ynyl)thiophen-2-yl]-1-butyl phosphate, Exemplification compound number 5-824 having formula (IIa-3): mono 2-amino-2-methyl-4-[5-(5-phenylpent-1-ynyl)thiophen-2-yl]-1-butyl phosphate, Exemplification compound number 5-833 having formula (IIa-3): mono 2-amino-2-methyl-4-{5-[5-(4-fluorophenyl)pent-1-ynyl]thiophen-2-yl}-1-butyl phosphate, Exemplification compound number 5-849 having formula (IIa-3): mono 2-amino-2-methyl-4-{5-[5-(4-methoxyphenyl)pent-1-ynyl]thiophen-2-yl}-1-butyl phosphate, Exemplification compound number 5-1050 having formula (IIa-3): mono 2-amino-2-methyl-4-{5-[3-(4-methylcyclohexyloxy)prop-1-ynyl]thiophen-2-yl}-1-butyl phosphate, Exemplification compound number 5-1063 having formula (IIa-3): mono 2-amino-2-methyl-4-{5-[3-(4-methylphenoxy)-prop-1-ynyl]thiophen-2-yl}-1-butyl phosphate, Exemplification compound number 5-1064 having formula (IIa-3): mono 2-amino-2-methyl-4-{5-[3-(4-ethylphenoxy)prop-1-ynyl]thiophen-2-yl}-1-butyl phosphate, Exemplification compound number 5-1068 having formula (IIa-3): mono 2-amino-2-methyl-4-{5-[3-(4-methylthiophenoxy)prop-1-ynyl]thiophen-2-yl}-1-butyl phosphate,
Exemplification compound number 5-1072 having formula (IIa-3): mono 2-amino-2-methyl-4-[5-(4-cyclohexyloxybut-1-ynyl)thiophen-2-yl]-1-butyl phosphate,
Exemplification compound number 5-1135 having formula (IIa-3): mono 2-amino-2-methyl-4-{5-[4-(4-fluorophenoxy)but-1-ynyl]thiophen-2-yl}-1-butyl phosphate,
Exemplification compound number 5-1139 having formula (IIa-3): mono 2-amino-2-methyl-4-[5-[4-(4-methylphenoxy)but-1-ynyl]thiophen-2-yl]-1-butyl phosphate,
Exemplification compound number 5-1185 having formula (IIa-3): mono 2-amino-2-methyl-4-[5-(3-cyclohexylmethoxyprop-1-ynyl)thiophen-2-yl]-1-butyl phosphate,
Exemplification compound number 5-1266 having formula (IIa-3): mono 2-amino-2-methyl-4-[5-(4-benzyloxybut-1-ynyl)thiophen-2-yl]-1-butyl phosphate,
Exemplification compound number 5-1329 having formula (IIa-3): mono 2-amino-2-methyl-4-[5-(4-cyclohexylbutanoyl)thiophen-2-yl]-1-butyl phosphate,
Exemplification compound number 5-1330 having formula (IIa-3): mono 2-amino-2-methyl-4-[5-(4-phenylbutanoyl)thiophen-2-yl]-1-butyl phosphate,
Exemplification compound number 5-1331 having formula (IIa-3): mono 2-amino-2-methyl-4-[5-(5-cyclohexylpentanoyl)thiophen-2-yl]-1-butyl phosphate,
Exemplification compound number 5-1344 having formula (IIa-3): mono 2-amino-2-methyl-4-[5-(5-phenylpentanoyl)thiophen-2-yl]-1-butyl phosphate,
Exemplification compound number 5-1348 having formula (IIa-3): mono 2-amino-2-methyl-4-{5-[5-(4-fluorophenyl)pentanoyl]thiophen-2-yl}-1-butyl phosphate,
Exemplification compound number 5-1764 having formula (IIa-3): mono 2-amino-2-ethyl-4-[5-(5-cyclohexylpentyl)thiophen-2-yl]-1-butyl phosphate,
Exemplification compound number 5-1909 having formula (IIa-3): mono 2-amino-2-ethyl-4-[5-(5-cyclohexylpent-1-ynyl)thiophen-2-yl]-1-butyl phosphate,
Exemplification compound number 5-2097 having formula (IIa-3): mono 2-amino-2-ethyl-4-[5-(5-cyclohexylpentanoyl)thiophen-2-yl]-1-butyl phosphate,
Exemplification compound number 5-2273 having formula (IIa-3): mono 2-amino-2-methyl-4-{5-[3-(4-chlorophenoxy)prop-1-ynyl]thiophen-2-yl}-1-butyl phosphate,
Exemplification compound number 5-2276 having formula (IIa-3): mono 2-amino-2-methyl-4-{5-[3-(3-methylphenoxy)prop-1-ynyl]thiophen-2-yl}-1-butyl phosphate,
Exemplification compound number 5-2278 having formula (IIa-3): mono 2-amino-2-methyl-4-{5-[3-(3,4-dimethylphenoxy)prop-1-ynyl]thiophen-2-yl}-1-butyl phosphate,
Exemplification compound number 5-2283 having formula (IIa-3): mono 2-amino-2-methyl-4-{5-[3-(3-methoxyphenoxyl)prop-1-ynyl]thiophen-2-yl}-1-butyl phosphate,
Exemplification compound number 5-2284 having formula (IIa-3): mono 2-amino-2-methyl-4-{5-[3-(3,4-dimethoxyphenoxy)prop-1-ynyl]thiophen-2-yl}-1-butyl phosphate,
Exemplification compound number 5-2285 having formula (IIa-3): mono 2-amino-2-methyl-4-{5-[3-(3,5-dimethoxyphenoxyl)prop-1-ynyl]thiophen-2-yl}-1-butyl phosphate,
Exemplification compound number 5-2287 having formula (IIa-3): mono 2-amino-2-methyl-4-{5-[3-(3-acetylphenoxy)prop-1-ynyl]thiophen-2-yl}-1-butyl phosphate, and
Exemplification compound number 5-2288 having formula (IIa-3): mono 2-amino-2-methyl-4-{5-[3-(4-acetylphenoxy)prop-1-ynyl]thiophen-2-yl}-1-butyl phosphate.

The exemplification compound numbers of preferred compounds having formula (III) in the table 5 (formula (IIIa-1), (IIIa-2) and (IIIa-3)), the table 6 (formula (IIIb-1), (IIIb-2) and (IIIb-3), and the table 8 (formula (IIIa-4)) include:
5-19, from 5-23 to 5-32, from 5-36 to 5-45, from 5-49 to 5-58, from 5-62 to 5-71, from 5-75 to 5-84, from 5-88 to 5-102, from to 5-156, from 5-160 to 5-214, from 5-218 to 5-268, from to 5-321, from 5-325 to 5-334, from 5-338 to 5-347, from to 5-360, from 5-364 to 5-373, from 5-377 to 5-386, from to 5-404, from 5-408 to 5-458, from 5-462 to 5-513, from to 5-526, from 5-530 to 5-544, from 5-548 to 5-598, from to 5-657, 5-670, from 5-674 to 5-683, 5-696, from 5-700 to 5-717, from 5-721 to 5-730, from 5-734 to 5-743, from 5-747 to 5-756, from 5-760 to 5-774, from 5-778 to 5-828, from 5-832 to 5-886, from 5-890 to 5-940, from 5-944 to 5-993, from 5-997 to 5-1006, from 5-1010 to 5-1019, 5-1045, from 5-1049 to 5-1058, from 5-1062 to 5-1076, from 5-1080 to 5-1130, from 5-1134 to 5-1185, from 5-1189 to 5-1198, from 5-1202 to 5-1208, from 5-1212 to 5-1216, from 5-1220 to 5-1270, from 5-1274 to 5-1331, from 5-1335 to 5-1344, from 5-1348 to 5-1357, from 5-1361 to 5-1370, from 5-1374 to 5-1387, from 5-1391 to 5-1400, from 5-1404 to 5-1418, from 5-1422 to 5-1472, from 5-1476 to 5-1527, from 5-1531 to 5-1540, from 5-1544 to 5-1558, from 5-1562 to 5-1612, from 5-1616 to 5-1673, from 5-1677 to 5-1686, from 5-1690 to 1-1699, from 5-1703 to 5-1712, from 5-1716 to 5-1729, from 5-1733 to 5-1744, from 5-1748 to 5-1768, from 5-1772 to 5-1793, from 5-1797 to 5-1820, from 5-1824 to 5-1846, from 5-1850 to 5-1869, 5-1872, 5-1876, 5-1880, 5-1884, from 5-1888 to 5-1892, 5-1896, 5-1900, from 5-1908 to 5-1913, from 5-1917 to 5-1939, from 5-1943 to 5-1966, from 5-1970 to 5-1991, from 5-1995 to 5-2013, 5-2017, 5-2021, 5-2025, 5-2029, 5-2033, from 5-2037 to 5-2042, from 5-2046 to 5-2068, from 5-2072 to 5-2089, 5-2093, 5-2097, 5-2101, 5-2105, 5-2109, 5-2113, 5-2117, 5-2121, 5-2125, 5-2129, 5-2133, 5-2135, from 5-2139 to 5-2158, from 5-2161 to 5-2164, from 5-2185 to 5-2346, from 5-2398 to 5-2557, from 6-9 to 6-18, from 6-22 to 6-43, from 6-47 to 6-70, from 6-74 to 6-96, from 6-100 to 6-119, 6-142, 6-146, 6-150, 6-154, from 6-158 to 6-163, from 6-167 to 6-183, from 6-185 to 6-189, from 6-193 to 6-216, from 6-220 to 6-241, from 6-245 to 6-263, 6-267, 6-271, 6-275, 6-279, 6-283, from 6-287 to 6-292, from 6-296 to 6-318, from 6-322 to 6-338, 6-343, 6-347, 6-351, 6-371, from 6-375 to 6-377, from 6-381 to 6-407, from 6-416 to 6-511, and from 8-9 to 8-12.

The exemplification compound numbers of the more preferred compounds include:
5-19, 5-32, from 5-36 to 5-45, 5-57, from 5-62 to 5-71, 5-84, 5-88, from 5-97 to 5-100, from 5-152 to 5-154, from 5-160 to 5-214, from 5-218 to 5-227, from 5-264 to 5-268, from 5-272 to 5-321, 5-334, 5-347, 5-360, 5-373, 5-386, from 5-390 to 5-402, from 5-454 to 5-458, from 5-462 to 5-513, 5-526, from 5-530 to 5-542, from 5-594 to 5-598, from 5-602 to 5-653, 5-743, 5-756, from 5-760 to 5-768, from 5-770 to 5-774, from 5-778 to 5-828, from 5-832 to 5-886, from 5-890 to 5-940, from 5-944 to 5-993, 5-1045, 5-1058, from 5-1062 to 5-1074, from 5-1126 to 5-1130, from 5-1134 to 5-1185, 5-1198, from 5-1202 to 5-1208, from 5-1212 to 5-1214, from 5-1266 to 5-1270, from 5-1274 to 5-1331, 5-1344, from 5-1348 to 5-1357, 5-1370, from 5-1374 to 5-1387, 5-1400, from 5-1404 to 5-1416, from 5-1468 to 5-1472, from 5-1476 to 5-1527, 5-1540, from 5-1544 to 5-1556, from 5-1608 to 5-1612, 5-1616 to 5-1666, 5-1729, 5-1742, 5-1744, from 5-1759 to 5-1767, from 5-1789 to 5-1793, from 5-1797 to 5-1818, from 5-1842 to 5-1846, 5-1900, from 5-1908 to 5-1913, from 5-1935 to 5-1939, from 5-1943 to 5-1966, from 5-1987 to 5-1991, 5-2013, 5-2017, 5-2029, 5-2033, from 5-2037 to 5-2042, from 5-2064 to 5-2068, from 5-2072 to 5-2089, 5-2093, 5-2097, 5-2101, 5-2105, 5-2109, 5-2129, 5-2133, 5-2135, from 5-2185 to 5-2346, from 5-2398 to 5-2557, from 6-11 to 6-18, from 6-39 to 6-43, from 6-47 to 6-70, from 6-185 to 6-189, from 6-193 to 6-216, from 6-287 to 6-292, 6-338, 6-343, 6-347, 6-351, from 6-416 to 6-511, and from 8-9 to 8-12.

The exemplification compound numbers of the more preferred compounds include:
5-45, 5-71, 5-84, 5-88, from 5-97 to 5-100, from 5-152 to 5-154, from 5-160 to 5-206, from 5-209 to 5-212, from 5-264 to 5-266, 5-334, 5-373, 5-386, from 5-390 to 5-402, from 5-454 to 5-458, from 5-462 to 5-485, 5-509, 5-510, 5-513, 5-526, from 5-530 to 5-542, from 5-594 to 5-598, from 5-602 to 5-613, 5-649, 5-650, 5-743, 5-756, from 5-760 to 5-768, from 5-770 to 5-772, from 5-824 to 5-828, from 5-832 to 5-884, 5-936, 5-1045, 5-1058, from 5-1062 to 5-1074, from 5-1126 to 5-1130, from 5-1134 to 5-1145, from 5-1148 to 5-1151, 5-1162, 5-1163, from 5-1179 to 5-1182, 5-1185, 5-1198, from 5-1202 to 5-1208, 5-1212, 5-1213, 5-1214, from 5-1266 to 5-1270, from 5-1274 to 5-1285, from 5-1288 to 5-1291, from 5-1319 to 5-1322, from 5-1329 to 5-1331, 5-1344, from 5-1348 to 5-1357, 5-1370, 5-1387, 5-1400, from 5-1404 to 5-1416, from 5-1468 to 5-1472, from 5-1476 to 5-1487, from 5-1490 to 5-1493, 5-1504, 5-1505, from 5-1521 to 5-1524, 5-1527, 5-1540, from 5-1544 to 5-1556, from 5-1608 to 5-1612, from 5-1616 to 5-1627, 5-1663, 5-1664, 5-1729, 5-1742, 5-1744, from 5-1761 to 5-1766, from 5-1789 to 5-1791, from 5-1815 to 5-1818, 5-1900, 5-1909, 5-1962, from 5-2064 to 5-2066, 5-2089, 5-2093, 5-2097, 5-2105, 5-2133, from 5-2216 to 5-2288, from 5-2290 to 5-2346, from 5-2398 to 5-2557, and from 8-9 to 8-12.

The exemplification compound numbers of the still more preferred compounds include:
Exemplification compound number 5-84 having formula (IIIa-1): 3-amino-3-methyl-5-[5-(5-phenylpentyl)furan-2-yl]pentylphosphonic acid,
Exemplification compound number 5-770 having formula (IIIa-1): 3-amino-3-methyl-5-[5-(5-cyclohexylpent-1-ynyl)furan-2-yl]pentylphosphonic acid,
Exemplification compound number 5-824 having formula (IIIa-1): 3-amino-3-methyl-5-[5-(5-phenylpent-1-ynyl)furan-2-yl]pentylphosphonic acid,
Exemplification compound number 5-1063 having formula (IIIa-1): 3-amino-3-methyl-5-[5-[3-(4-methylphenoxy)prop-1-ynyl]furan-2-yl]pentylphosphonic acid,
Exemplification compound number 5-1072 having formula (IIIa-1): 3-amino-3-methyl-5-[5-(4-cyclohexyloxybut-1-ynyl)furan-2-yl]pentylphosphonic acid,
Exemplification compound number 5-1331 having formula (IIIa-1): 3-amino-3-methyl-5-[5-(5-cyclohexylpentanoyl)furan-2-yl]pentylphosphonic acid,
Exemplification compound number 5-2278 having formula (IIIa-1): 3-amino-3-methyl-5-{5-[3-(3,4-dimethylphenoxy)prop-1-ynyl]furan-2-yl}pentylphosphonic acid,
Exemplification compound number 5-834 having formula (IIIa-1): 3-amino-3-methyl-5-{5-[5-(4-chlorophenyl)pent-1-ynyl]furan-2-yl}pentylphosphonic acid,
Exemplification compound number 5-846 having formula (IIIa-1): 3-amino-3-methyl-5-{5-[5-(3-trifluoromethylphenyl)pent-1-ynyl]furan-2-yl}pentylphosphonic acid,
Exemplification compound number 5-1065 having formula (IIIa-1): 3-amino-3-methyl-5-{5-[3-(4-trifluoromethylphenoxy)prop-1-ynyl]furan-2-yl}pentylphosphonic acid,
Exemplification compound number 5-2273 having formula (IIIa-1): 3-amino-3-methyl-5-{5-[3-(4-chlorophenoxy)prop-1-ynyl]furan-2-yl}pentylphosphonic acid,
Exemplification compound number 5-2280 having formula (IIIa-1): 3-amino-3-methyl-5-{5-[3-(3-trifluoromethylphenoxy)prop-1-ynyl]furan-2-yl}pentylphosphonic acid,
Exemplification compound number 5-2284 having formula (IIIa-1): 3-amino-3-methyl-5-{5-[3-(3,4-dimethoxyphenoxy)prop-1-ynyl]furan-2-yl}pentylphosphonic acid,
Exemplification compound number 5-824 having formula (IIIa-2): 3-amino-3-methyl-5-[1-methyl-5-(5-phenylpent-1-ynyl)pyrrol-2-yl]pentylphosphonic acid,
Exemplification compound number 5-1063 having formula (IIIa-2): 3-amino-3-methyl-5-{1-methyl-5-[3-(4-methyl)phenoxyprop-1-ynyl]pyrrol-2-yl}pentylphosphonic acid,
Exemplification compound number 5-1072 having formula (IIIa-2): 3-amino-3-methyl-5-[1-methyl-5-(4-cyclohexyloxybut-1-ynyl)pyrrol-2-yl]pentylphosphonic acid,
Exemplification compound number 5-2278 having formula (IIIa-2): 3-amino-3-methyl-5-{1-methyl-5-[3-(3,4-dimethylphenoxy)prop-1-ynyl]pyrrol-2-yl}pentylphosphonic acid,
Exemplification compound number 5-84 having formula (IIIa-2): 3-amino-3-methyl-5-[1-methyl-5-(5-phenylpentyl)pyrrol-2-yl]pentylphosphonic acid,
Exemplification compound number 5-1344 having formula (IIIa-2): 3-amino-3-methyl-5-[1-methyl-5-(5-phenylpentanoyl)pyrrol-2-yl]pentylphosphonic acid,
Exemplification compound number 5-2332 having formula (IIIa-2): 3-amino-3-methyl-5-{1-methyl-5-[5-(4-chlorophenyl)pentanoyl]pyrrol-2-yl}pentylphosphonic acid,
Exemplification compound number 5-2338 having formula (IIIa-2): 3-amino-3-methyl-5-{1-methyl-5-[5-(3-trifluoromethylphenyl)pentanoyl]pyrrol-2-yl}pentylphosphonic acid,
Exemplification compound number 5-1331 having formula (IIIa-2): 3-amino-3-methyl-5-[1-methyl-5-(5-cyclohexylpentanoyl)pyrrol-2-yl]pentylphosphonic acid,
Exemplification compound number 5-1330 having formula (IIIa-2): 3-amino-3-methyl-5-[1-methyl-5-(4-phenylbutanoyl)pyrrol-2-yl]pentylphosphonic acid,
Exemplification compound number 5-1329 having formula (IIIa-2): 3-amino-3-methyl-5-[1-methyl-5-(4-cyclohexylbutanoyl)pyrrol-2-yl]pentylphosphonic acid,
Exemplification compound number 8-12 having formula (IIIa-4): 3-amino-3-methyl-5-[1-ethyl-5-(5-phenylpentanoyl)pyrrol-2-yl]pentylphosphonic acid,
Exemplification compound number 8-11 having formula (IIIa-4): 3-amino-3-methyl-5-[1-ethyl-5-(5-cyclohexylpentanoyl)pyrrol-2-yl]pentylphosphonic acid,
Exemplification compound number 8-10 having formula (IIIa-4): 3-amino-3-methyl-5-[1-ethyl-5-(4-phenylbutanoyl)pyrrol-2-yl]pentylphosphonic acid,
Exemplification compound number 8-9 having formula (IIIa-4): 3-amino-3-methyl-5-[1-ethyl-5-(4-cyclohexylbutanoyl)pyrrol-2-yl]pentylphosphonic acid,
Exemplification compound number 5-71 having formula (IIIa-3): 3-amino-3-methyl-5-[5-(4-cyclohexylbutyl)thiophen-2-yl]pentylphosphonic acid,
Exemplification compound number 5-84 having formula (IIIa-3): 3-amino-3-methyl-5-[5-(4-phenylbutyl)thiophen-2-yl]pentylphosphonic acid, Exemplification compound number 5-98 having formula (IIIa-3): 3-amino-3-methyl-5-[5-(5-cyclohexylpentyl)thiophen-2-yl]pentylphosphonic acid, Exemplification compound number 5-152 having formula (IIIa-3): 3-amino-3-methyl-5-[5-(5-phenylpentyl)thiophen-2-yl]pentylphosphonic acid, Exemplification compound number 5-210 having formula (IIIa-3): 3-amino-3-methyl-5-[5-(6-cyclohexylhexyl)thiophen-2-yl]pentylphosphonic acid, Exemplification compound number 5-264 having formula (IIIa-3): 3-amino-3-methyl-5-[5-(6-phenylhexyl)thiophen-2-yl]pentylphosphonic acid, Exemplification compound number 5-373 having formula (IIIa-3): 3-amino-3-methyl-5-[5-(3-cyclohexyloxypropyl)thiophen-2-yl]pentylphosphonic acid, Exemplification compound number 5-386 having formula (IIIa-3): 3-amino-3-methyl-5-[5-(3-phenoxypropyl)thiophen-2-yl]pentylphosphonic acid, Exemplification compound number 5-400 having formula (IIIa-3): 3-amino-3-methyl-5-[5-(4-cyclohexyloxybutyl)thiophen-2-yl]pentylphosphonic acid, Exemplification compound number 5-454 having formula (IIIa-3): 3-amino-3-methyl-5-[5-(4-phenoxybutyl)thiophen-2-yl]pentylphosphonic acid, Exemplification compound number 5-509 having formula (IIIa-3): 3-amino-3-methyl-5-[5-(5-cyclohexyloxypentyl)thiophen-2-yl]pentylphosphonic acid, Exemplification compound number 5-510 having formula (IIIa-3): 3-amino-3-methyl-5-[5-(5-phenoxypentyl)thiophen-2-yl]pentylphosphonic acid, Exemplification compound number 5-513 having formula (IIIa-3): 3-amino-3-methyl-5-[5-(3-cyclohexylmethoxypropyl)thiophen-2-yl]pentylphosphonic acid, Exemplification compound number 5-1329 having formula (IIIa-3): 3-amino-3-methyl-5-[5-(4-cyclohexylbutanoyl)thiophen-2-yl]pentylphosphonic acid, Exemplification compound number 5-1330 having formula (IIIa-3): 3-amino-3-methyl-5-[5-(4-phenylbutanoyl)thiophen-2-yl]pentylphosphonic acid, Exemplification compound number 5-1331 having formula (IIIa-3): 3-amino-3-methyl-5-[5-(5-cyclohexylpentanoyl)thiophen-2-yl]pentylphosphonic acid, Exemplification compound number 5-1344 having formula (IIIa-3): 3-amino-3-methyl-5-[5-(5-phenylpentanoyl)thiophen-2-yl]pentylphosphonic acid, Exemplification compound number 5-1357 having formula (IIIa-3): 3-amino-3-methyl-5-[5-(6-cyclohexylhexanoyl)thiophen-2-yl]pentylphosphonic acid, Exemplification compound number 5-1370 having formula (IIIa-3): 3-amino-3-methyl-5-[5-(6-phenylhexanoyl)thiophen-2-yl]pentylphosphonic acid, Exemplification compound number 5-1387 having formula (IIIa-3): 3-amino-3-methyl-5-[5-(3-cyclohexyloxypropanoyl)thiophen-2-yl]pentylphosphonic acid, Exemplification compound number 5-1400 having formula (IIIa-3): 3-amino-3-methyl-5-[5-(3-phenoxypropanoyl)thiophen-2-yl]pentylphosphonic acid, Exemplification compound number 5-1414 having formula (IIIa-3): 3-amino-3-methyl-5-[5-(4-cyclohexyloxybutanoyl)thiophen-2-yl]pentylphosphonic acid, Exemplification compound number 5-1468 having formula (IIIa-3): 3-amino-3-methyl-5-[5-(4-phenoxybutanoyl)thiophen-2-yl]pentylphosphonic acid, Exemplification compound number 5-1523 having formula (IIIa-3): 3-amino-3-methyl-5-[5-(5-cyclohexyloxypentanoyl)thiophen-2-yl]pentylphosphonic acid, Exemplification compound number 5-1524 having formula (IIIa-3): 3-amino-3-methyl-5-[5-(5-phenoxypentanoyl)thiophen-2-yl]pentylphosphonic acid, Exemplification compound number 5-1527 having formula (IIIa-3): 3-amino-3-methyl-5-[5-(3-cyclohexylmethoxypropanoyl)thiophen-2-yl]pentylphosphonic acid, Exemplification compound number 5-1729 having formula (IIIa-3): 3-amino-3-methyl-5-[5-(4-cyclohexylmethoxyphenyl)thiophen-2-yl]pentylphosphonic acid, Exemplification compound number 5-1742 having formula (IIIa-3): 3-amino-3-methyl-5-[5-(4-cyclohexylethoxyphenyl)thiophen-2-yl]pentylphosphonic acid, Exemplification compound number 5-1744 having formula (IIIa-3): 3-amino-3-methyl-5-[5-(4-benzyloxyphenyl)thiophen-2-yl]pentylphosphonic acid, Exemplification compound number 5-1761 having formula (IIIa-3): 3-amino-3-ethyl-5-[5-(4-cyclohexylbutyl)thiophen-2-yl]pentylphosphonic acid, Exemplification compound number 5-1764 having formula (IIIa-3): 3-amino-3-ethyl-5-[5-(5-cyclohexylpentyl)thiophen-2-yl]pentylphosphonic acid, Exemplification compound number 5-1816 having formula (IIIa-3): 3-amino-3-ethyl-5-[5-(6-cyclohexylhexyl)thiophen-2-yl]pentylphosphonic acid, Exemplification compound number 5-2089 having formula (IIIa-3): 3-amino-3-ethyl-5-[5-(4-cyclohexylbutanoyl)thiophen-2-yl]pentylphosphonic acid, Exemplification compound number 5-2097 having formula (IIIa-3): 3-amino-3-ethyl-5-[5-(5-cyclohexylpentanoyl)thiophen-2-yl]pentylphosphonic acid, and Exemplification compound number 5-2105 having formula (IIIa-3): 3-amino-3-ethyl-5-[5-(6-cyclohexylhexanoyl)thiophen-2-yl]pentylphosphonic acid, and Exemplification compound number 5-463 having formula (IIIa-3): 3-amino-3-methyl-5-{5-[4-(4-fluorophenoxy)butyl]thiophen-2-yl}pentylphosphonic acid, Exemplification compound number 5-479 having formula (IIIa-3): 3-amino-3-methyl-5-{5-[4-(4-methoxyphenoxy)butyl]thiophen-2-yl}pentylphosphonic acid, Exemplification compound number 5-594 having formula (IIIa-3): 3-amino-3-methyl-5-[5-(4-benzyloxybutyl)thiophen-2-yl]pentylphosphonic acid, Exemplification compound number 5-1348 having formula (IIIa-3): 3-amino-3-methyl-5-{5-[5-(4-fluorophenyl)pentanoyl]thiophen-2-yl}pentylphosphonic acid, Exemplification compound number 5-1349 having formula (IIIa-3): 3-amino-3-methyl-5-{5-[5-(4-methylphenyl)pentanoyl]thiophen-2-yl}pentylphosphonic acid, Exemplification compound number 5-1350 having formula (IIIa-3): 3-amino-3-methyl-5-{5-[5-(4-ethylphenyl)pentanoyl]thiophen-2-yl}pentylphosphonic acid, Exemplification compound number 5-1351 having formula (IIIa-3): 3-amino-3-methyl-5-{5-[5-(4-trifluoromethylphenyl)pentanoyl]thiophen-2-yl}pentylphosphonic acid, Exemplification compound number 5-1352 having formula (IIIa-3): 3-amino-3-methyl-5-{5-[5-(4-methoxyphenyl)pentanoyl]thiophen-2-yl}pentylphosphonic acid, Exemplification compound number 5-1353 having formula (IIIa-3): 3-amino-3-methyl-5-{5-[5-(4-ethoxyphenyl)pentanoyl]thiophen-2-yl}pentylphosphonic acid, Exemplification compound number 5-1354 having formula (IIIa-3): 3-amino-3-methyl-5-{5-[5-(4-methylthiophenyl)pentanoyl]thiophen-2-yl}pentylphosphonic acid, Exemplification compound number 5-1476 having formula (IIIa-3): 3-amino-3-methyl-5-{5-[4-(3-fluorophenoxy)butanoyl]thiophen-2-yl}pentylphosphonic acid, Exemplification compound number 5-1477 having formula (IIIa-3): 3-amino-3-methyl-5-{5-[4-(4-fluorophenoxy)butanoyl]thiophen-2-yl}pentylphosphonic acid, Exemplification compound number 5-1478 having formula (IIIa-3): 3-amino-3-methyl-5-{5-[4-(4-chlorophenoxy)butanoyl]thiophen-2-yl}-pentylphosphonic acid, Exemplification compound number 5-1480 having formula (IIIa-3): 3-amino-3-methyl-5-{5-[4-(3-methylphenoxy)butanoyl]thiophen-2-yl}pentylphosphonic acid, Exemplification compound number 5-1481 having formula (IIIa-3): 3-amino-3-methyl-5-{5-[4-(4-methylphenoxy)butanoyl]thiophen-2-yl}pentylphosphonic acid, Exemplification compound number 5-1490 having formula (IIIa-3): 3-amino-3-methyl-5-{5-[4-(3-trifluoromethylphenoxy)butanoyl]thiophen-2-yl}pentylphosphonic acid, Exemplification compound number 5-1491 having formula (IIIa-3): 3-amino-3-methyl-5-{5-[4-(4-trifluoromethylphenoxy)butanoyl]thiophen-2-yl}pentylphosphonic acid, Exemplification compound number 5-1492 having formula (IIIa-3): 3-amino-3-methyl-5-{5-[4-(3-methoxyphenoxy)butanoyl]thiophen-2-yl)}pentylphosphonic acid, Exemplification compound number 5-1493 having formula (IIIa-3): 3-amino-3-methyl-5-{5-[4-(4-methoxyphenoxy)butanoyl]thiophen-2-yl}pentylphosphonic acid, Exemplification compound number 5-1504 having formula (IIIa-3): 3-amino-3-methyl-5-{5-[4-(3-methylthiophenoxy)butanoyl]thiophen-2-yl}pentylphosphonic acid, Exemplification compound number 5-1505 having formula (IIIa-3): 3-amino-3-methyl-5-{5-[4-(4-methylthiophenoxy)butanoyl]thiophen-2-yl}pentylphosphonic acid, Exemplification compound number 5-1521 having formula (IIIa-3): 3-amino-3-methyl-5-{5-[4-(3,4-dimethylphenoxy)butanoyl]thiophen-2-yl}pentylphosphonic acid, Exemplification compound number 5-1522 having formula (IIIa-3): 3-amino-3-methyl-5-{5-[4-(3,5-dimethylphenoxy)butanoyl]thiophen-2-yl}pentylphosphonic acid, Exemplification compound number 5-2093 having formula (IIIa-3): 3-amino-3-ethyl-5-[5-(4-phenylbutanoyl)thiophen-2-yl]pentylphosphonic acid, Exemplification compound number 5-2101 having formula (IIIa-3): 3-amino-3-ethyl-5-[5-(5-phenylpentanoyl)thiophen-2-yl]pentylphosphonic acid, Exemplification compound number 5-2109 having formula (IIIa-3): 3-amino-3-ethyl-5-[5-(6-phenylhexanoyl)thiophen-2-yl]pentylphosphonic acid, Exemplification compound number 5-2328 having formula (IIIa-3): 3-amino-3-methyl-5-{5-[5-(3-fluorophenyl)pentanoyl]thiophen-2-yl}pentylphosphonic acid, Exemplification compound number 5-2329 having formula (IIIa-3): 3-amino-3-methyl-5-{5-[5-(3,4-difluorophenyl)pentanoyl]thiophen-2-yl}pentylphosphonic acid, Exemplification compound number 5-2330 having formula (IIIa-3): 3-amino-3-methyl-5-{5-[5-(3,5-difluorophenyl)pentanoyl]thiophen-2-yl}pentylphosphonic acid, Exemplification compound number 5-2331 having formula (IIIa-3): 3-amino-3-methyl-5-{5-[5-(3-chlorophenyl)pentanoyl]thiophen-2-yl}pentylphosphonic-acid, Exemplification compound number 5-2332 having formula (IIIa-3): 3-amino-3-methyl-5-{5-[5-(4-chlorophenyl)pentanoyl]thiophen-2-yl}pentylphosphonic acid, Exemplification compound number 5-2333 having formula (IIIa-3): 3-amino-3-methyl-5-{5-[5-(3,4-dichlorophenyl)pentanoyl]thiophen-2-yl}pentylphosphonic acid, Exemplification compound number 5-2334 having formula (IIIa-3): 3-amino-3-methyl-5-{5-[5-(3,5-dichlorophenyl)pentanoyl]thiophen-2-yl}pentylphosphonic acid, Exemplification compound number 5-2335 having formula (IIIa-3): 3-amino-3-methyl-5-{5-[5-(3-methylphenyl)pentanoyl]thiophen-2-yl}pentylphosphonic acid, Exemplification compound number 5-2336 having formula (IIIa-3): 3-amino-3-methyl-5-{5-[5-(3,4-dimethylphenyl)pentanoyl]thiophen-2-yl}pentylphosphonic acid, Exemplification compound number 5-2337 having formula (IIIa-3): 3-amino-3-methyl-5-{5-[5-(3,5-dimethylphenyl)pentanoyl]thiophen-2-yl}pentylphosphonic acid, Exemplification compound number 5-2338 having formula (IIIa-3): 3-amino-3-methyl-5-{5-[5-(3-trifluoromethylphenyl)pentanoyl]thiophen-2-yl}pentylphosphonic acid, Exemplification compound number 5-2339 having formula (IIIa-3): 3-amino-3-methyl-5-{5-[5-(3,4-ditrifluoromethylphenyl)pentanoyl]thiophen-2-yl}pentylphosphonic acid, Exemplification compound number 5-2340 having formula (IIIa-3): 3-amino-3-methyl-5-{5-[5-(3,5-ditrifluoromethylphenyl)pentanoyl]thiophen-2-yl}pentylphosphonic acid, Exemplification compound number 5-2341 having formula (IIIa-3): 3-amino-3-methyl-5-{5-[5-(3-methoxyphenyl)pentanoyl]thiophen-2-yl}pentylphosphonic acid, Exemplification compound number 5-2342 having formula (IIIa-3): 3-amino-3-methyl-5-{5-[5-(3,4-dimethoxyphenyl)pentanoyl]thiophen-2-yl}pentylphosphonic acid, Exemplification compound number 5-2343 having formula (IIIa-3): 3-amino-3-methyl-5-{5-[5-(3,5-dimethoxyphenyl)pentanoyl]thiophen-2-yl}pentylphosphonic acid, Exemplification compound number 5-2344 having formula (IIIa-1-3): 3-amino-3-methyl-5-{5-[5-(3,4,5-trimethoxyphenyl)pentanoyl]thiophen-2-yl}pentylphosphonic acid, Exemplification compound number 5-2345 having formula (IIIa-3): 3-amino-3-methyl-5-{5-[5-(3-acetylphenyl)pentanoyl]thiophen-2-yl}pentylphosphonic acid, and Exemplification compound number 5-2346 having formula (IIIa-3): 3-amino-3-methyl-5-{5-[5-(4-acetylphenyl)pentanoyl]thiophen-2-yl}pentylphosphonic acid.

The exemplification compounds numbers of the most preferred compounds include:

Exemplification compound number 5-84 having formula (IIIa-1): 3-amino-3-methyl-5-[5-(5-phenylpentyl)furan-2-yl]pentylphosphonic acid, Exemplification compound number 5-770 having formula (IIIa-1): 3-amino-3-methyl-5-[5-(5-cyclohexylpent-1-ynyl)furan-2-yl]pentylphosphonic acid, Exemplification compound number 5-824 having formula (IIIa-1): 3-amino-3-methyl-5-[5-(5-phenylpent-1-ynyl)furan-2-yl]pentylphosphonic acid, Exemplification compound number 5-1072 having formula (IIIa-1): 3-amino-3-methyl-5-[5-(4-cyclohexyloxybut-1-ynyl)furan-2-yl]pentylphosphonic acid, Exemplification compound number 5-1331 having formula (IIIa-1): 3-amino-3-methyl-5-[5-(5-cyclohexylpentanoyl)furan-2-yl]pentylphosphonic acid, Exemplification compound number 5-2278 having formula (IIIa-1): 3-amino-3-methyl-5-{5-[3-(3,4-dimethylphenoxy)prop-1-ynyl]furan-2-yl}pentylphosphonic acid, Exemplification compound number 5-824 having formula (IIIa-2): 3-amino-3-methyl-5-[1-methyl-5-(5-phenylpent-1-ynyl)pyrrol-2-yl]pentylphosphonic acid, Exemplification compound number 5-1063 having formula (IIIa-2): 3-amino-3-methyl-5-{1-methyl-5-[3-(4-methyl)phenoxyprop-1-ynyl]pyrrol-2-yl}pentylphosphonic acid, Exemplification compound number 5-1072 having formula (IIIa-2): 3-amino-3-methyl-5-[1-methyl-5-(4-cyclohexyloxybut-1-ynyl)pyrrol-2-yl]pentylphosphonic acid, Exemplification compound number 5-2278 having formula (IIIa-2): 3-amino-3-methyl-5-{1-methyl-5-[3-(3,4-dimethylphenoxy)prop-1-ynyl]pyrrol-2-yl}pentylphosphonic acid, Exemplification compound number 5-1344 having formula (IIIa-2): 3-amino-3-methyl-5-[1-methyl-5-(5-phenylpentanoyl)pyrrol-2-yl]pentylphosphonic acid, Exemplification compound number 5-1331 having formula (IIIa-2): 3-amino-3-methyl-5-[1-methyl-5-(5-cyclohexylpentanoyl)pyrrol-2-yl]pentylphosphonic acid, Exemplification compound number 5-1330 having formula (IIIa-2): 3-amino-3-methyl-5-[1-methyl-5-(4-phenylbutanoyl)pyrrol-2-yl]pentylphosphonic acid, Exemplification compound number 5-1329 having formula (IIIa-2): 3-amino-3-methyl-5-[1-methyl-5-(4-cyclohexylbutanoyl)pyrrol-2-yl]pentylphosphonic acid, Exemplification compound number 8-12 having formula (IIIa-4): 3-amino-3-methyl-5-[1-ethyl-5-(5-phenylpentanoyl)pyrrol-2-yl]pentylphosphonic acid, Exemplification compound number 8-11 having formula (IIIa-4): 3-amino-3-methyl-5-[1-ethyl-5-(5-cyclohexylpentanoyl)pyrrol-2-yl]pentylphosphonic acid, Exemplification compound number 8-10 having formula (IIIa-4): 3-amino-3-methyl-5-[1-ethyl-5-(4-phenylbutanoyl)pyrrol-2-yl]pentylphosphonic acid, Exemplification compound number 8-9 having formula (IIIa-4): 3-amino-3-methyl-5-[1-ethyl-5-(4-cyclohexylbutanoyl)pyrrol-2-yl]pentylphosphonic acid, Exemplification compound number 5-71 having formula (IIIa-3): 3-amino-3-methyl-5-[5-(4-cyclohexylbutyl)thiophen-2-yl]pentylphosphonic acid, Exemplification compound number 5-98 having formula (IIIa-3): 3-amino-3-methyl-5-[5-(5-cyclohexylpentyl)thiophen-2-yl]pentylphosphonic acid, Exemplification compound number 5-152 having formula (IIIa-3): 3-amino-3-methyl-5-[5-(5-phenylpentyl)thiophen-2-yl]pentylphosphonic acid, Exemplification compound number 5-400 having formula (IIIa-3): 3-amino-3-methyl-5-[5-(4-cyclohexyloxybutyl)thiophen-2-yl]pentylphosphonic acid, Exemplification compound number 5-463 having formula (IIIa-3): 3-amino-3-methyl-5-{5-[4-(4-fluorophenoxy)butyl]thiophen-2-yl}pentylphosphonic acid, Exemplification compound number 5-479 having formula (IIIa-3): 3-amino-3-methyl-5-{5-[4-(4-methoxyphenoxy)butyl]thiophen-2-yl}pentylphosphonic acid, Exemplification compound number 5-594 having formula (IIIa-3): 3-amino-3-methyl-5-[5-(4-benzyloxybutyl)thiophen-2-yl]pentylphosphonic acid, Exemplification compound number 5-1329 having formula (IIIa-3): 3-amino-3-methyl-5-[5-(4-cyclohexylbutanoyl)thiophen-2-yl]pentylphosphonic acid, Exemplification compound number 5-1330 having formula (IIIa-3): 3-amino-3-methyl-5-[5-(4-phenylbutanoyl)thiophen-2-yl]pentylphosphonic acid, Exemplification compound number 5-1331 having formula (IIIa-3): 3-amino-3-methyl-5-[5-(5-cyclohexylpentanoyl)thiophen-2-yl]pentylphosphonic acid, Exemplification compound number 5-1344 having formula (IIIa-3): 3-amino-3-methyl-5-[5-(5-phenylpentanoyl)thiophen-2-yl]pentylphosphonic acid, Exemplification compound number 5-1348 having formula (IIIa-3): 3-amino-3-methyl-5-{5-[5-(4-fluorophenyl)pentanoyl]thiophen-2-yl}pentylphosphonic acid, Exemplification compound number 5-1764 having formula (IIIa-3): 3-amino-3-ethyl-5-[5-(5-cyclohexylpentyl)thiophen-2-yl]pentylphosphonic acid, and Exemplification compound number 5-2097 having formula (IIIa-3): 3-amino-3-ethyl-5-[5-(5-cyclohexylpentanoyl)thiophen-2-yl]pentylphosphonic acid.

The compounds of formulae (I), (II) and (III) of the present invention can be prepared according to the methods described hereinafter.

(Method A)

Method A is a process for the preparation of compounds of formula (I) which include compounds of formula (Ic) wherein Y is an ethynylene group, compounds of formula (Id) wherein Y is a vinylene group, compounds of formula (Ie) wherein Y is an ethylene group, compounds of formula (If) wherein Y is a group of formula —CO—CH$_2$—, compounds of formula (Ig) wherein Y is a group of formula —CH(OH)—CH$_2$— and compounds of formula (Ih) wherein Y is an aryl group or an aryl group substituted with from 1 to 3 substituents selected from Substituent group (a).

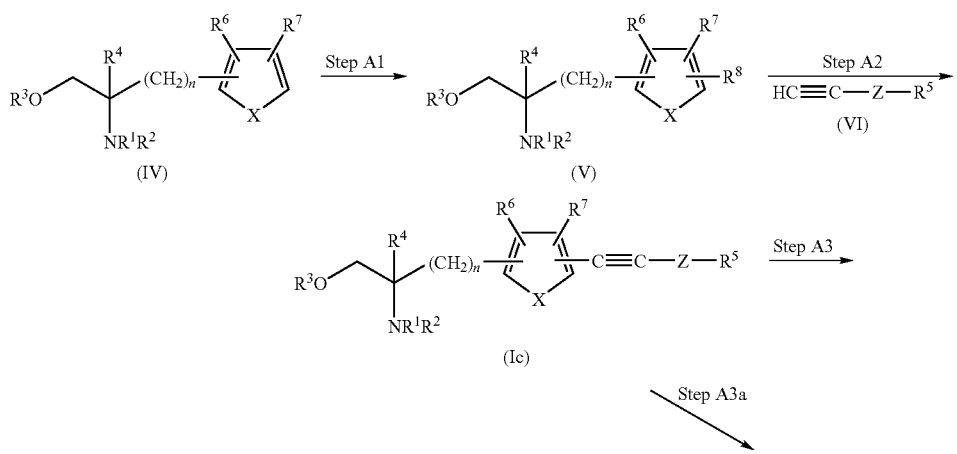

Method A

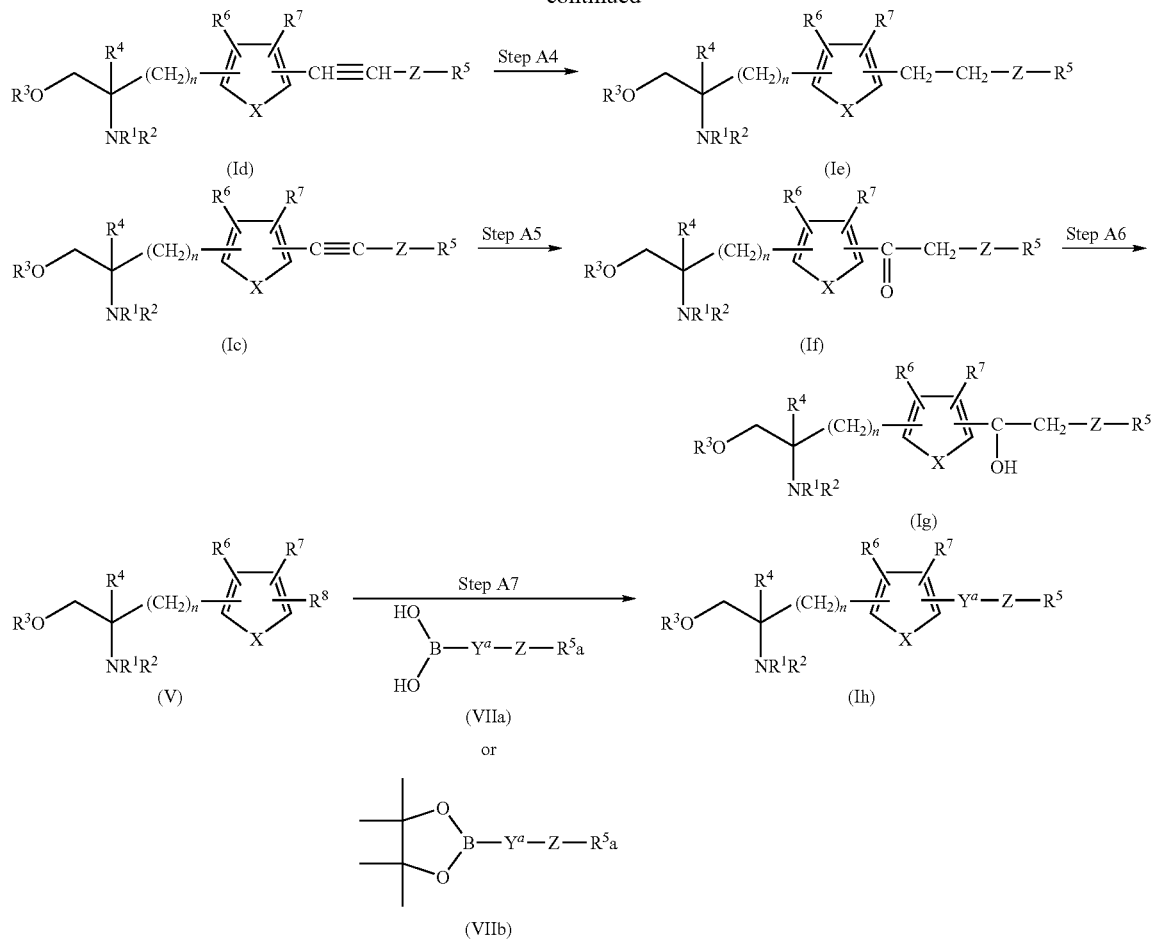

In the above reaction scheme $R^1$, $R^2$, $R^3$, $R^4$, $R^5$, $R^6$, $R^7$, X, Z, and n have the same meanings as those indicated hereinbefore. $R^8$ represents a bromine or iodine atom. $R^5_a$ represents the same meanings as those indicated for $R^5$ or is a group corresponding to $R^5$ wherein it may have one or more protected amino, hydroxyl, and/or carboxyl groups when the $R^5$ group has one or more amino, hydroxyl and/or carboxyl groups. Ring $Y^a$ represents an aryl group or an aryl group substituted with from 1 to 3 substituents selected from Substituent group (a).

The protecting group of the amino group in the definition of $R^5_a$ is not particularly restricted, provided that the protecting group of the amino group can generally be used in organic chemistry, and has the same meanings as those indicated hereinbefore. The protecting group of the amino group is preferably a lower alkoxycarbonyl group and most preferably a tert-butoxycarbonyl group.

The protecting group of the hydroxyl group in the definition of $R^5_a$ is not particularly restricted, provided that the protecting group of the hydroxyl group can generally be used in organic chemistry and, for example, has the same meanings as those indicated in the definition of the "general protecting group in chemical reactions related to the ester of a hydroxyl group". The protecting group of the hydroxyl group is preferably a lower aliphatic acyl group, aromatic acyl group, lower alkoxycarbonyl group or (lower alkoxy)methyl group; more preferably a lower aliphatic acyl group or (lower alkoxy)methyl group and most preferably an acetyl or methoxymethyl group.

The protecting group of the carboxyl group in the definition of $R^5_a$ is not particularly restricted, provided that the protecting group of the carboxyl group can generally be used in organic chemistry, and has, for example, the same meanings as those indicated in the definition of the "general protecting group in chemical reactions related to the ester of a carboxyl group". The protecting group of the carboxyl group is preferably a lower alkyl group and most preferably a methyl group.

Step A1

Step A1 is a process for the preparation of compounds of general formula (V). Step A1 is accomplished by the reaction of a compound of general formula (IV) with a brominating or iodinating agent in the presence or absence of a base in an inert solvent.

The inert solvent employed in the above reaction is not particularly restricted provided that it has no adverse effect on the reaction and, for example, can be a halogenated hydrocarbon such as dichloromethane, chloroform, carbon tetrachloride, dichloroethane, chlorobenzene, or dichlorobenzene; an ether such as diethyl ether, diisopropyl ether, tetrahydrofuran, dioxane, dimethoxyethane, or di(ethylene glycol) dimethyl ether; or an amide such as formamide, N,N-dimethylformamide, N,N-dimethylacetamide, or hexamethylphosphoric triamide. In the bromination reaction the inert solvent is preferably an amide (most preferably N,N-dimethylformamide). In the iodination reaction the inert solvent is preferably a halogenated hydrocarbon (most preferably dichloromethane or chloroform).

The brominating reagent employed in the above reaction is not particularly restricted and, for example, can be a brominating reagent described in "Comprehensive Organic Transformation" (Larlock, VCH, page from 316 to 317). The preferred brominating reagent is N-bromosuccinimide.

The iodinating reagent employed in the above reaction is not particularly restricted and, for example, can be an iodinating reagent described in "Comprehensive Organic Transformation" (Larlock, VCH, page from 317 to 318). The preferred iodinating reagent is iodine.

The base employed in the above reaction is not particularly restricted provided that it has no adverse effect on substituent(s) other than halogen atoms, and can be, for example, an alkali metal carbonate such as lithium carbonate, sodium carbonate, or potassium carbonate; an alkali metal hydrogencarbonate such as lithium hydrogencarbonate, sodium hydrogencarbonate, or potassium hydrogencarbonate; a metal alkoxide such as lithium methoxide, sodium methoxide, sodium ethoxide, or potassium tert-butoxide; an organic amine such as triethylamine, tributylamine, diisopropylethylamine, N-methylmorpholine, pyridine, 2,6-lutidine, 4-(N,N-dimethylamino)pyridine, N,N-dimethylaniline, N,N-diethylaniline, 1,5-diazabicyclo[4.3.0]non-5-ene, 1,4-diazabicyclo[2,2,2]octane (DABCO), or 1,8-diazabicyclo[5.4.0]undec-7-ene (DBU); or an organometallic base such as butyllithium, lithium diisopropylamide (LDA) or lithium bis(trimethylsilyl)amide; or a combination of the bases indicated hereinbefore. The base is preferably an organic amine (most preferably pyridine).

The reaction temperature depends on the starting material, the brominating or iodinating reagent, the solvent and the like employed in the above reaction and is generally between $-78°$ C. and $150°$ C., preferably between $-20°$ C. and $100°$ C. (most preferably between $0°$ C. and $60°$ C.).

The reaction time depends on the reaction temperature, the starting material, the reagent and the solvent employed in the above reaction and is generally from 5 minutes to 60 hours, preferably from 15 minutes to 24 hours (most preferably from 30 minutes to 4 hours).

After the reaction, the desired compound of Step A1 and those of Steps A2~A7 described hereinafter can be isolated from the reaction mixture by conventional treatments, for example, neutralization of the reaction mixture, if necessary, or filtration of the reaction mixture when insoluble material is present in the reaction mixture, addition of a solvent immiscible with water such as ethyl acetate to the neutralized solution or the filtrate, washing the resulting organic layer with water, separation of the organic layer containing the desired compound, drying of the organic layer over anhydrous magnesium sulfate, anhydrous sodium sulfate or the like, and then evaporation of the organic solvent to give the desired product. The product thus obtained, if necessary, is further purified by conventional treatments, for example by recrystallization or reprecipitation, or by conventional procedures in organic chemistry, for example, absorption column chromatography using carrier such as silica gel, alumina, or Florisil consisting of magnesium and silica gel; partition column chromatography using a synthetic absorbent such as Sephadex LH-20 (product of Pharmacia Co., Ltd.), Amberlite XAD-11 (product of Rohm & Hass Co., Ltd.), or Diaion HP-20 (product of Mitsubishi Chemicals Co., Ltd.); ion exchange chromatography; normal phase or reversed phase column chromatography using silica gel or alkylated silica gel (preferably high performance liquid column chromatography); or an appropriate combination of these chromatographic techniques; and elution using an appropriate solvent to isolate and purify the desired product.

Step A2

Step A2 is a process for the preparation of compounds of general formula (Ic). Step A2 is accomplished by the Sonogashira coupling reaction of a compound of general formula (V) with a compound of formula (VI) in the presence of a base and a palladium catalyst in an inert solvent under an atmosphere of nitrogen, followed by removal, if necessary, of one or more protecting groups of the hydroxyl, amino and/or carboxyl group.

The inert solvent employed in the above reaction is not particularly restricted provided that it has no adverse effect on the reaction and, for example, is an aliphatic hydrocarbon such as hexane, heptane, ligroin, or petroleum ether; an aromatic hydrocarbon such as benzene, toluene, or xylene; a halogenated hydrocarbon such as dichloromethane, chloroform, carbon tetrachloride, dichloroethane, chlorobenzene, or dichlorobenzene; an ester such as ethyl formate, ethyl acetate, propyl acetate, butyl acetate, or diethyl carbonate; an ether such as diethyl ether, diisopropyl ether, tetrahydrofuran, dioxane, dimethoxyethane, or di(ethylene glycol) dimethyl ether; a ketone such as acetone, methyl ethyl ketone, methyl isobutyl ketone, isophorone, or cyclohexanone; a nitrile such as acetonitrile or isobutyronitrile; an amide such as formamide, N,N-dimethylformamide, N,N-dimethylacetamide, or hexamethylphosphoric triamide; a sulfoxide such as dimethyl sulfoxide or a sulfone such as sulfolane. The inert solvent is preferably an ether, an amide or a sulfoxide (most preferably an ether or amide). In some cases the presence of a small amount of water in the solvent may enhance the rate of the reaction.

The base employed in the above reaction is not particularly restricted provided that it can generally be used for the Sonogashira coupling reaction and, for example, is an alkali metal carbonate such as lithium carbonate, sodium carbonate, or potassium carbonate; an alkali metal hydrogencarbonate such as lithium hydrogencarbonate, sodium hydrogencarbonate, or potassium hydrogencarbonate; an alkali metal hydride such as lithium hydride, sodium hydride, or potassium hydride; an alkali metal hydroxide such as lithium hydroxide, sodium hydroxide, or potassium hydroxide; an alkali metal alkoxide such as lithium methoxide, sodium methoxide, sodium ethoxide, or potassium tert-butoxide: or an organic amine such as triethylamine, tributylamine; diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2,2,2]octane (DABCO), or 1,8-diazabicyclo[5.4.0]undec-7-ene (DBU). The base is preferably an organic amine (most preferably triethylamine).

The palladium catalyst employed above reaction is not particularly restricted provided that it can generally be used in the Sonogashira coupling reaction and, for example, can be a palladium salt such as palladium acetate, palladium chloride, palladium carbonate; a palladium salt complex such as dichlorobis(triphenylphosphine)palladium complex which is complexed by a ligand; or palladium-charcoal. In addition, copper (I) iodide and/or benzyltriethylammonium chloride as an additive reagent can increase the yield of the desired product.

The reaction temperature depends on the starting material, base, solvent and the like employed in the above reaction and is generally between $-20°$ C. and $200°$ C., (preferably between $0°$ C. and $120°$ C.).

The reaction time depends on the starting material, base, solvent, reaction temperature, and the like employed in the above reaction and is generally from 5 minutes to 48 hours (preferably from 15 minutes to 24 hours).

The removal of the protecting groups of the hydroxyl, amino and/or carboxyl group in $R^1$, $R^2$, and $R^3$, is carried out by the same procedure as that indicated hereinafter in the removal of the protecting group in Step A7.

If necessary, the desired product (Ic) of Step A2 can be isolated and purified by conventional procedures, for example, recrystallization or reprecipitation or by conventional purification procedures in organic chemistry, for example, an appropriate combination of various chromatographic techniques and elution using an appropriate solvent.

Step A3

Step A3 is a process for the preparation of compounds of general formula (Id). Step A3 is accomplished by a reduction reaction (preferably catalytic reduction under an atmosphere of hydrogen) of a compound of general formula (Ic) in an inert solvent, followed by removal, if necessary, of one or more protecting groups of the hydroxyl, amino and/or carboxyl group. The removal of said protecting group is carried out by the same procedure as that indicated hereinafter in the removal of the protecting group in Step A7.

The inert solvent employed in the above reaction is not particularly restricted provided that it has no adverse effect on the reaction and, for example, is an aliphatic hydrocarbon such as hexane, heptane, ligroin, or petroleum ether; an aromatic hydrocarbon such as benzene, toluene, or xylene; a halogenated hydrocarbon such as dichloromethane, chloroform, carbon tetrachloride, dichloroethane, chlorobenzene, or dichlorobenzene; an ester such as methyl acetate, ethyl acetate, propyl acetate, butyl acetate, or diethyl carbonate; an ether such as diethyl ether, diisopropyl ether, tetrahydrofuran, dioxane, dimethoxyethane, or di(ethylene glycol) dimethyl ether; an alcohol such as methanol, ethanol, n-propanol, isopropanol, n-butanol, isobutanol, tert-butanol, isoamyl alcohol, di(ethylene glycol), glycerin, octanol, cyclohexanol, or methyl cellosolve; an organic acid such as acetic acid or hydrochloric acid; water; or a mixture of water and a solvent indicated hereinbefore. The inert solvent is preferably an ether or alcohol (most preferably methanol).

The catalyst employed in the above catalytic reduction is not particularly restricted provided that it can generally be used for the reduction of a triple bond to a double bond, and preferably is a palladium-type catalyst such as palladium-calcium carbonate, palladium-aluminum oxide, palladium-charcoal, or palladium-barium sulfate, or a rhodium-type catalyst such as rhodium-aluminum oxide. The more preferred catalyst is palladium-calcium carbonate. In addition, the catalyst employed in the above reaction can be deactivated by the addition of a basic aromatic compound such as pyridine or quinoline; or an amine such as ammonia or triethylamine (preferably quinoline) in the solvent in order to accomplish reduction of an ethynylene group to a vinylene group and to avoid reduction of an ethynylene group to an ethylene group.

The pressure of hydrogen is not particularly restricted. It is generally between from 1 to 10 atmospheric pressures, and preferably 1 atmospheric pressure.

The reaction temperature depends on the starting material, catalyst, solvent and the like employed in the above reaction and is generally between −20° C. and 200° C., (preferably between 0° C. and 100° C.).

The reaction time depends on the starting material, catalyst, solvent, reaction temperature, and the like employed in the above reaction and is generally from 5 minutes to 96 hours (preferably from 15 minutes to 72 hours).

If necessary, the desired product (Id) of Step A3 can be isolated and purified by conventional procedures, for example recrystallization or reprecipitation, or by conventional purification procedures in organic chemistry, for example, an appropriate combination of various chromatographic techniques and elution using an appropriate solvent.

Step A4

Step A4 is a process for the preparation of compounds of general formula (Ie). Step A4 is accomplished by a reduction reaction (preferably catalytic reduction under an atmosphere of hydrogen) of a compound of general formula (Id) in an inert solvent, followed by removal, if necessary, of one or more protecting groups of the hydroxyl, amino and/or carboxyl group. The removal of said protecting group is carried out by the same procedure as that indicated hereinafter in the removal of the protecting group in Step A7.

The inert solvent employed in the above reaction is not particularly restricted provided that it has no adverse effect on the reaction and, for example, can be the same solvent as that indicated in Step A3 hereinbefore. The inert solvent is preferably an ester, ether or alcohol (most preferably ethyl acetate or methanol).

The catalyst employed in the above catalytic reduction is not particularly restricted provided that it can generally be used for catalytic reductions and, for example, can be a mixture or compound of palladium such as palladium-charcoal, palladium black, palladium hydroxide, or palladium-barium sulfate; a platinum compound such as platinum oxide or platinum black; a mixture of a rhodium compound such as rhodium-aluminum oxide or triphenylphosphine-rhodium chloride; or a type of nickel such as Raney nickel.

The pressure of hydrogen is not particularly restricted. It is generally between from 1 to 10 atmospheric pressures, and preferably 1 atmospheric pressure.

The reaction temperature depends on the starting material, catalyst, solvent and the like employed in the above reaction and is generally between −20° C. and 200° C., (preferably between 0° C. and 100° C.).

The reaction time depends on the starting material, catalyst, solvent, reaction temperature, and the like employed in the above reaction and is generally from 5 minutes to 96 hours (preferably from 15 minutes to 72 hours).

If necessary, the desired product (Ie) of Step A4 can be isolated and purified by conventional procedures, for example recrystallization or reprecipitation, or by conventional purification procedures in organic chemistry, for example, an appropriate combination of various chromatographic techniques and elution using an appropriate solvent.

Step A3a

Step A3a is a process for the preparation of compounds of general formula (Ie) without employing the two steps of Step A3 and Step A4. Step A3a is accomplished by a reduction reaction (preferably catalytic reduction under an atmosphere of hydrogen) of a compound of general formula (Ic) in an inert solvent, followed by removal, if necessary, of one or more protecting groups of the hydroxyl, amino and/or carboxyl group.

The inert solvent and catalyst employed in the above reduction reaction are not particularly restricted provided that they can be generally used in catalytic reduction reactions, and they can be the same solvent and catalyst as those indicated in Step A4.

The pressure of hydrogen is not particularly restricted. It is generally between from 1 to 10 atmospheric pressures, and preferably 1 atmospheric pressure.

The reaction temperature depends on the starting material, catalyst, solvent and the like employed in the above reaction and is generally between −20° C. and 200° C., (preferably between 0° C. and 100° C.)

The reaction time depends on the starting material, catalyst, solvent, reaction temperature, and the like employed in the above reaction and is generally from 5 minutes to 96 hours (preferably from 15 minutes to 72 hours).

Step A5

Step A5 is a process for the preparation of compounds of general formula (If). Step A5 is accomplished by an addition reaction of water to a compound of general formula (Ic) in an inert solvent using an acid catalyst, followed by removal, if necessary, of one or more protecting groups of the hydroxyl, amino and/or carboxyl group. The removal of said protecting group is carried out by the same procedure as that indicated hereinafter in the removal of the protecting group in Step A7.

The inert solvent employed in the above reaction is not particularly restricted provided that it has no adverse effect on the reaction and, for example, is an aliphatic hydrocarbon such as hexane, heptane, ligroin, or petroleum ether; an aromatic hydrocarbon such as benzene, toluene, or xylene; a halogenated hydrocarbon such as dichloromethane, chloroform, carbon tetrachloride, dichloroethane, chlorobenzene, or dichlorobenzene; an ester such as ethyl formate, ethylacetate, propyl acetate, butyl acetate, or diethyl carbonate; an ether such as diethyl ether, diisopropyl ether, tetrahydrofuran, dioxane, dimethoxyethane, or di(ethylene glycol) dimethyl ether; an alcohol such as methanol, ethanol, n-propanol, isopropanol, n-butanol, isobutanol, tert-butanol, isoamyl alcohol, di(ethylene glycol), glycerin, octanol, cyclohexanol, or methyl cellosolve; a ketone such as acetone, methyl ethyl ketone, methyl isobutyl ketone, isophorone, or cyclohexanone; water; or a mixture of the solvents indicated hereinbefore. The inert solvent is preferably an alcohol.

The acid catalyst employed in the above reaction is not particularly restricted provided that it can generally be used as an acid catalyst and can be a Brφnsted acid, for example, an inorganic acid such as hydrochloric acid, hydrobromic acid, sulfuric acid, perchloric acid, or phosphoric acid; or an organic acid such as acetic acid, formic acid, oxalic acid, methanesulfonic acid, p-toluenesulfonic acid, camphorsulfonic acid, trifluoroacetic acid, or trifluoromethanesulfonic acid; or, for example, a Lewis acid such as zinc chloride, tin tetrachloride, boron trichloride, boron trifluoride, or boron tribromide; or an acidic ion-exchange resin. The acid catalyst is preferably an inorganic acid.

The reaction temperature depends on the starting material, catalyst, solvent and the like employed in the above reaction and is generally between −20° C. and 200° C., (preferably between 0° C. and 100° C.).

The reaction time depends on the starting material, catalyst, solvent, reaction temperature, and the like employed in the above reaction and is generally from 5 minutes to 96 hours (preferably from 15 minutes to 72-hours).

Step A6

Step A6 is a process for the preparation of compounds of general formula (Ig). Step A6 is accomplished by reduction of the CO group of a compound of general formula (If) to a —CH(OH) group in an inert solvent, followed by removal, if necessary, of one or more protecting groups of the hydroxyl, amino and/or carboxyl group. The removal of said protecting group is carried out by the same procedure as that indicated hereinafter in the removal of the protecting group in Step A7.

The inert solvent employed in the above reaction is not particularly restricted provided that it has no adverse effect on the reaction and, for example, is an aliphatic hydrocarbon such as hexane, heptane, ligroin, or petroleum ether; an aromatic hydrocarbon such as benzene, toluene, or xylene; a halogenated hydrocarbon such as chloroform, dichloromethane, 1,2-dichloroethane, or carbon tetrachloride; an ether such as diethyl ether, diisopropyl ether, tetrahydrofuran, dioxane, dimethoxyethane, or di(ethylene glycol) dimethyl ether; an alcohol such as methanol, ethanol, n-propanol, isopropanol, n-butanol, isobutanol, tert-butanol, isoamyl alcohol, di(ethylene glycol), glycerin, octanol, cyclohexanol, or methyl cellosolve. The inert solvent is preferably an ether or alcohol (most preferably methanol or ethanol).

The reducing agent employed in the above reaction is not particularly restricted provided that it can reduce a CO group to a CH(OH) group and, for example, is an alkali metal borohydride such as sodium borohydride, lithium borohydride, or sodium cyanoborohydride; or an aluminum hydride compound such as diisobutylaluminum hydride, lithium aluminum hydride, or lithium triethoxyaluminum hydride. The reducing agent is preferably an alkali metal borohydride (most preferably sodium borohydride).

The reaction temperature depends on the starting material, reducing agent, solvent and the like employed in the above reaction and is generally between −10° C. and 100° C., (preferably between −20° C. and 20° C.).

The reaction time depends on the starting material, reducing agent, solvent, reaction temperature, and the like employed in the above reaction and is generally from 10 minutes to 48 hours (preferably from 30 minutes to 12 hours).

Step A7

Step A7 is a process for the preparation of compounds of general formula (Ih). Step A7 is accomplished by the Suzuki coupling reaction of a compound of general formula (V) with a compound of general formula (VIIa) or (VIIb), followed by removal, if necessary, of one or more protecting groups of the hydroxyl, amino and/or carboxyl group.

The reaction temperature depends on the starting material, solvent and the like employed in the above reaction and is generally between 0° C. and 150° C. (preferably between 10° C. and 100° C.).

The reaction time depends on the starting material, solvent, reaction temperature, and the like employed in the above reaction and is generally from 15 minutes to 24 hours (preferably from 30 minutes to 12 hours).

The solvent, base and palladium catalyst employed in the above reaction are the same as those indicated for the Sonogashira coupling reaction in Step A2 hereinbefore.

If necessary, the desired product (Ih) of Step A7 can be isolated and purified by conventional-procedures, for example recrystallization or reprecipitation, or by conventional purification procedures in organic chemistry, for example, an appropriate combination of various chromatographic techniques and elution using an appropriate solvent.

The reaction conditions for removing the protecting group depend on the protecting group of the hydroxyl, amino and/or carboxyl group. The removal reaction of these protecting groups can be carried out by procedures known to those skilled in organic chemistry, for example, indicated by T. W. Green (Protective groups in Organic Synthesis, John Wiley & Sons) and J.F.W.McOmis (Protective groups in Organic Chemistry, Plenum Press) and, for example, can be accomplished by the following procedures.

When the protecting group of the amino group is a silyl group, said protecting group can be usually removed by treatment with a compound which can produce fluoride ions, such as tetrabutylammonium fluoride, hydrofluoric acid, hydrofluoric acid-pyridine, or potassium fluoride.

The inert solvent employed in the above reaction is not particularly restricted provided that it has no adverse effect on the reaction and, for example, is preferably an ether such as diethyl ether, diisopropyl ether, tetrahydrofuran, dioxane, dimethoxyethane, or di(ethylene glycol) dimethyl ether.

The reaction temperature and reaction time are not particularly restricted and are generally between 0° C. and 50° C. and from 10 minutes to 18 hours.

When the protecting group of the amino group is an aliphatic acyl, aromatic acyl, or alkoxycarbonyl group or a substituted methylene group which can form a Schiff base, said protecting group can be removed by treatment with a base or acid in the presence of a solvent containing water.

The acid employed in the above reaction is not particularly restricted provided that it has no adverse effect on the reaction and can generally be used as an acid, and, for example, is an inorganic acid such as hydrobromic acid, hydrochloric acid, sulfuric acid, perchloric acid, phosphoric acid or nitric acid and preferably hydrochloric acid.

The base employed in the above reaction is not particularly restricted provided that it has no adverse effect on the reaction and can generally be used as a base, and, for example, is an alkali metal carbonate such as lithium carbonate, sodium carbonate, or potassium carbonate; an alkali metal hydroxide such as lithium hydroxide, sodium hydroxide, or potassium hydroxide; a metal alkoxide such as lithium methoxide, sodium ethoxide, or potassium tert-butoxide; or a form of ammonia such as aqueous ammonia solution, or concentrated ammonia in methanol; and is preferably an alkali metal hydroxide.

The inert solvent employed in the above reaction is not particularly restricted provided that it can generally be used in hydrolysis reactions and, for example, is an alcohol such as methanol, ethanol, n-propanol, isopropanol, n-butanol, isobutanol, tert-butanol, isoamyl alcohol, di(ethylene glycol), glycerin, octanol, cyclohexanol, or methyl cellosolve; an ether such as diethyl ether, diisopropyl ether, tetrahydrofuran, dioxane, dimethoxyethane, or di(ethylene glycol) dimethyl ether; water; or a mixture of water and a solvent indicated hereinbefore. The inert solvent is preferably a mixture of an ether or alcohol and water (most preferably a mixture of tetrahydrofuran, dioxane, ethanol or methanol and water).

The reaction temperature and reaction time depend on the starting material, solvent, acid or base and the like employed in the above reaction and are not particularly restricted. They are generally between 0° C. and 150° C. and from 1 hour to 10 hours respectively in order to avoid side reactions.

When the protecting group of the amino group is an aralkyl or aralkyloxycarbonyl group, said protecting group can usually be removed by treatment with a reducing agent (preferably by catalytic reduction in the presence of a catalyst at room temperature) or an oxidizing agent in an inert solvent.

The inert solvent employed in the above catalytic reduction is not particularly restricted provided that it has no adverse effect on the reaction and, for example, is an aliphatic hydrocarbon such as hexane, heptane, tigroin, or petroleum ether; an aromatic hydrocarbon such as toluene, benzene, or xylene; an ester such as methyl acetate, ethyl acetate, propyl acetate, butyl acetate, or diethyl carbonate; an ether such as diethyl ether, diisopropyl ether, tetrahydrofuran, dioxane, dimethoxyethane, or di(ethylene glycol) dimethyl ether; an alcohol such as methanol, ethanol, n-propanol, isopropanol, n-butanol, isobutanol, tert-butanol, isoamyl alcohol, di(ethylene glycol), glycerin, octanol, cyclohexanol, or methyl cellosolve; an organic acid such as acetic acid; water; or a mixture of water and a solvent indicated hereinbefore. The inert solvent is preferably an alcohol, ether, organic acid or water (most preferably an alcohol or organic acid).

The catalyst employed in the above catalytic reduction is not particularly restricted provided that it can generally be used for catalytic reductions, and is preferably palladium-charcoal, Raney nickel, platinum oxide, platinum black, rhodium-aluminum oxide, triphenylphosphine-rhodium chloride or palladium-barium sulfate.

The pressure of hydrogen is not particularly restricted. It is generally between from 1 to 10 atmospheric pressures.

The reaction temperature and reaction time depend on the starting material, catalyst, solvent and the like employed in the above reaction and are generally between 0° C. and 100° C. and from 5 minutes to 24 hours respectively.

The inert solvent in the removal reaction using an oxidizing agent is not particularly restricted provided that it has no adverse effect on the reaction and, for example, is a halogenated hydrocarbon such as chloroform, dichloromethane, 1,2-dichloroethane, or carbon tetrachloride; a nitrile such as acetonitrile; an ether such as diethyl ether, diisopropyl ether, tetrahydrofuran, dioxane, dimethoxyethane, or di(ethylene glycol) dimethyl ether; a ketone such as acetone; an amide such as formamide, dimethylformamide, dimethylacetamide, or hexamethylphosphoric triamide; a sulfoxide such as dimethyl sulfoxide; or sulfolane. The inert solvent is preferably a halogenated hydrocarbon, ether or sulfoxide (most preferably a halogenated hydrocarbon or sulfoxide).

The oxidizing agent employed in the above reaction is not particularly restricted provided that it can usually be used as an oxidizing agent and has no adverse effect on the reaction, and is preferably potassium persulfate, sodium persulfate, ceric ammonium nitrate (CAN), or 2,3-dichloro-5,6-dicyano-p-benzoquinone (DDQ).

The reaction temperature and reaction time depend on the starting material, catalyst, solvent and the like employed in the above reaction and are generally between 0° C. and 150° C. and from 10 minutes to 24 hours respectively.

In addition, when the protecting group of the amino group is an aralkyl group, said protecting group can be also removed by treatment with an acid in an inert solvent.

The acid employed in the above reaction is not particularly restricted provided that it can generally be used as an acid catalyst and is, for example, a Brønsted acid (for example, an inorganic acid such as hydrochloric acid, hydrobromic acid, sulfuric acid, perchloric acid, or phosphoric acid; or an organic acid such as acetic acid, formic acid, oxalic acid, methanesulfonic acid, p-toluenesulfonic acid, camphorsulfonic acid, trifluoroacetic acid, or trifluoromethanesulfonic acid); or a Lewis acid such as zinc chloride, tin-tetrachloride, boron trichloride, boron trifluoride, or boron tribromide; or an acidic ion-exchange resin. The acid is preferably an inorganic or organic acid (most preferably hydrochloric acid, acetic acid or trifluoroacetic acid).

The inert solvent employed in the above reaction is not particularly restricted provided that it has no adverse effect on the reaction and, for example, is an aliphatic hydrocarbon such as hexane, heptane, ligroin, or petroleum ether; an aromatic hydrocarbon such as benzene, toluene, or xylene; a halogenated hydrocarbon such as chloroform, dichloromethane, 1,2-dichloroethane, or carbon tetrachloride; an ester such as methyl acetate, ethyl acetate, propyl acetate, butyl acetate, or diethyl carbonate; an ether such as diethyl ether, diisopropyl ether, tetrahydrofuran, dioxane, dimethoxyethane, or di(ethylene glycol) dimethyl ether; an alcohol such as methanol, ethanol, n-propanol, isopropanol, n-butanol, isobutanol, tert-butanol, isoamyl alcohol, di(ethylene glycol), glycerin, octanol, cyclohexanol, or methyl cellosolve; an amide such as formamide, dimethylformamide, dimethylacetamide, or hexamethylphosphoric triamide; water; or a mixture of the solvents indicated hereinbefore. The inert solvent is preferably an ether, alcohol, or water (most preferably dioxane, tetrahydrofuran, ethanol or water).

The reaction temperature depends on the starting material, acid, solvent and the like employed in the above reaction and is generally between −20° C. and the boiling point of the solvent (preferably between 0° C. and 100° C.).

The reaction time depends on the starting material, acid, solvent, reaction temperature, and the like employed in the above reaction and is generally from 15 minutes to 48 hours (preferably from 30 minutes to 20 hours).

When the protecting group of the amino group is an alkenyloxycarbonyl group, said protecting group can usually be removed using a base by the same procedure as indicated hereinbefore for the aliphatic acyl, aromatic acyl, or alkoxycarbonyl group or substituted methylene group which can form a Schiff base, all of which are protecting groups for the amino group.

In addition, when the protecting group of the amino group is allyloxycarbonyl group, the reaction to remove said protecting group can easily be carried out with fewer side-reactions using palladium and triphenylphosphine or nickel tetracarbonyl.

When the protecting group of the hydroxyl group is a silyl group, said protecting group can be usually removed by treatment with a compound which can produce fluoride ions, such as tetrabutylammonium fluoride, hydrofluoric acid, hydrofluoric acid-pyridine, or potassium fluoride; an inorganic acid such as hydrochloric acid, hydrobromic acid, sulfuric acid, perchloric acid, or phosphoric acid; or an organic acid such as acetic acid, formic acid, oxalic acid, methanesulfonic acid, p-toluenesulfonic acid, camphorsulfonic acid, trifluoroacetic acid, or trifluoromethanesulfonic acid (preferably hydrochloric acid).

The inert solvent employed in the removal of the protecting group with fluoride ions is not particularly restricted provided that it has no adverse effect on the reaction, and is preferably an ether such as diethyl ether, diisopropyl ether, tetrahydrofuran, dioxane, dimethoxyethane, or di(ethylene glycol) dimethyl ether; a nitrile such as acetonitrile or isobutyronitrile; an organic acid such as acetic acid; water; or a mixture of the solvents indicated hereinbefore. The solvent is preferably tetrahydrofuran.

In addition, when the protecting group is removed with fluoride ions, the addition of an organic acid such as formic acid, acetic acid, or propionic acid increases the rate of the reaction and avoids decomposition of the desired product and can give good yields of the product.

In the removal reaction of the protecting group with fluoride ions, the reaction temperature and reaction time depend on the starting material, catalyst, solvent and the like employed in the above reaction and are generally between 0° C. and 100° C. (preferably 10° C. and 50° C.) and from 1 hour to 24 hours respectively.

In the removal reaction of the protecting group with an inorganic or organic acid, the removal reaction can be accomplished using an inorganic or organic acid using the same conditions as those indicated for the case where the protecting group of the amino or amino group is an aralkyl group.

When the protecting group of the hydroxyl group is an aralkyl or aralkyloxycarbonyl group, the removal of the protecting group is preferably accomplished by treatment with a reducing agent (preferably by catalytic reduction in the presence of a catalyst at room temperature) or an oxidizing agent in an inert solvent.

In the removal reaction of the protecting group by catalytic reduction, the inert solvent is not particularly restricted provided that it has no adverse effect on the reaction and, for example, is the same inert solvent as that indicated in the case that the protecting group of the amino or imino group is an aralkyl or aralkyloxycarbonyl group and can be removed by catalytic reduction. The solvent is preferably an alcohol (most preferably methanol).

In the removal reaction of the protecting group by catalytic reduction, the catalyst is not particularly restricted provided that it can usually be used for catalytic reductions, and, for example, is the same catalyst as that indicated in the case that the protecting group of the amino or imino group is an aralkyl or aralkyloxycarbonyl group and can be removed by catalytic reduction. The preferred catalyst is palladium-charcoal.

The pressure is not particularly restricted. It is generally between from 1 to 10 atmospheric pressures.

The reaction temperature and reaction time depend on the starting material, catalyst, solvent and the like employed in the above reaction and are generally between 0° C. and 100° C. (preferably 20° C. and 70° C.) and from 5 minutes to 48 hours (preferably from 1 hour to 24 hours) respectively.

In the removal reaction of the protecting group with an oxidizing agent, the solvent is not particularly restricted provided that it has no adverse effect on the reaction and, for example, is the same inert solvent as that indicated in the case that the protecting group of the amino group is an aralkyl or aralkyloxycarbonyl group and can be removed by treatment with an oxidizing reagent.

In the removal reaction of the protecting group with an oxidizing agent, the oxidizing agent is not particularly restricted provided that it can usually be used for oxidation reactions and, for example, is the same reagent as that indicated in the case that the protecting group of the amino group is an aralkyl or aralkyloxycarbonyl group and can be removed by treatment with an oxidizing agent.

The reaction temperature and reaction time depend on the starting material, catalyst, solvent and the like employed in the above reaction and are generally between 0° C. and 150° C. and from 10 minutes to 24 hours respectively.

When the protecting group of the hydroxyl group is an aralkyl or aralkyloxycarbonyl group, the removal of the protecting group can be also accomplished by treatment with an alkali metal such as metallic lithium or sodium in liquid ammonia or in an alcohol such as methanol, ethanol, n-propanol, isopropanol, n-butanol, isobutanol, tert-butanol, isoamyl alcohol, di(ethylene glycol), glycerin, octanol, cyclohexanol, or methyl cellosolve at between −78° C. and 0° C.

In addition, when the protecting group of the hydroxyl group is an aralkyl or aralkyloxycarbonyl group, the removal of the protecting group can be accomplished by treatment with aluminium chloride-sodium iodide or an alkylsilyl halide such as trimethylsilyl iodide in a solvent.

In the removal reaction of the protecting group with aluminum chloride-sodium iodide or an alkylsilyl halide, the solvent employed in the reaction is not particularly restricted provided that it has no adverse effect on the reaction, and preferably includes an halogenated hydrocarbon such as dichloromethane, chloroform, or carbon tetrachloride; a nitrile such as acetonitrile or a mixture of the solvents indicated hereinbefore.

The reaction temperature and reaction time of the removal reaction using aluminum chloride-sodium iodide or an alkylsilyl halide depend on the starting material, solvent and the like employed in the reaction and are generally between 0° C. and 50° C. and from 5 minutes to 72 hours respectively.

In addition, when a substrate contains one or more sulfur atoms, aluminum chloride-sodium iodide is preferably used.

When the protecting group of the hydroxyl group is an aliphatic acyl, aromatic acyl or alkyoxycarbonyl group, the removal of the protecting group can be accomplished by treatment with a base in a solvent.

The base employed in the above reaction is not particularly restricted provided that it can be usually used as a base and has no adverse effect on the reaction, and is, for example, an alkali metal carbonate such as lithium carbonate, sodium carbonate, or potassium carbonate; an alkali metal hydrogencarbonate such as lithium hydrogencarbonate, sodium hydrogencarbonate, or potassium hydrogencarbonate; an alkali metal hydroxide such as lithium hydroxide, sodium hydroxide or potassium hydroxide; a metal alkoxide such as lithium methoxide, sodium methoxide, sodium ethoxide, or potassium tert-butoxide; or an ammonia solution such as aqueous ammonia or concentrated ammonia in methanol. The base is preferably an alkali metal hydroxide, a metal alkoxide or an ammonia solution (most preferably an alkali metal hydroxide or a metal alkoxide).

The solvent employed in the above reaction is not particularly restricted provided that it can be usually used for hydrolysis reactions and, for example, is preferably an ether such as diethyl ether, diisopropyl ether, tetrahydrofuran, dioxane, dimethoxyethane, or di(ethylene glycol) dimethyl ether; an alcohol such as methanol, ethanol, n-propanol, isopropanol, n-butanol, isobutanol, tert-butanol, isoamyl alcohol, di(ethylene glycol), glycerin, octanol, cyclohexanol, or methyl cellosolve; water; or a mixture of the solvents indicated hereinbefore.

The reaction temperature and reaction time depend on the starting material, base, solvent and the like employed in the reaction and are generally between −20° C. and 150° C. and from 1 hour to 10 hours respectively in order to avoid side reactions.

When the protecting group of the hydroxyl group is an alkoxymethyl, tetrahydropyranyl, tetrahydrothiopyranyl, tetrahydrofuranyl, tetrahydrothiofuranyl, or substituted ethyl group, the removal of the protecting group is accomplished by treatment with an acid in an inert solvent.

The acid employed in the above reaction is not particularly restricted provided that it can be usually used as a Brønsted or Lewis acid and is preferably a Brønsted acid, for example, an inorganic acid such as hydrogen chloride, hydrochloric acid, sulfuric acid, nitric acid; or an organic acid such as acetic acid, trifluoroacetic acid, methanesulfonic acid, or p-toluenesulfonic acid; or a Lewis acid such as boron trifluoride. The acid is more preferably hydrochloric acid or acetic acid. In the above reaction a strong-acidic cation ion-exchange resin such as Dowex 50W can be also used.

The inert solvent employed in the above reaction is not particularly restricted provided that it has no adverse effect on the reaction and, for example, is an aliphatic hydrocarbon such as hexane, heptane, ligroin, or petroleum ether; an aromatic hydrocarbon such as benzene, toluene, or xylene; a halogenated hydrocarbon such as dichloromethane, chloroform, carbon tetrachloride, dichloroethane, chlorobenzene, or dichlorobenzene; an ester such as ethyl formate, ethyl acetate, propyl acetate, butyl acetate, or diethyl carbonate; an ether such as diethyl ether, diisopropyl ether, tetrahydrofuran, dioxane, dimethoxyethane; or di(ethylene glycol) dimethyl ether; an alcohol such as methanol, ethanol, n-propanol, isopropanol, n-butanol, isobutanol, tert-butanol, isoamyl alcohol, di(ethylene glycol), glycerin, octanol, cyclohexanol, or methyl cellosolve; a ketone such as acetone, methyl ethyl ketone, methyl isobutyl ketone, isophorone, or cyclohexanone; water; or a mixture of the solvents indicated hereinbefore. The solvent is preferably an ether (most preferably tetrahydrofuran) or an alcohol (most preferably methanol).

The reaction temperature and reaction time depend on the starting material, acid, solvent and the like employed in the reaction and are generally between −10° C. and 200° C. (preferably between 0° C. and 150° C.) and from 5 minutes to 48 hours (preferably from 30 minutes to 10 hours) respectively.

When the protecting group of the hydroxyl group is an alkenyloxycarbonyl group, the removal of the protecting group can usually be accomplished by treatment with a base according to the same conditions as those indicated hereinbefore in the case that the protecting group of the hydroxyl group is an aliphatic acyl, aromatic acyl or alkoxycarbonyl group.

In addition, when protecting group of the hydroxyl group is an allyloxycarbonyl group, the protecting group can easily be removed with fewer side reactions by using palladium and triphenylphosphine or bis(methyldiphenylphosphine)(1,5-cyclooctadiene)iridium (I) hexafluorophosphate.

When the protecting group of the carboxyl group is a lower alkyl group, or a lower alkyl group substituted with from 1 to 3 aryl groups wherein the aryl group may optionally be substituted with one or more lower alkyl, lower alkoxy, nitro group(s), halogen atom(s), or cyano group(s), the removal of the protecting group can usually be accomplished by treatment with a base according to the same conditions as those indicated hereinbefore in the case that the protecting group of the hydroxyl group is an aliphatic acyl, aromatic acyl or alkoxycarbonyl group.

When there are protecting groups of the amino, hydroxyl and/or carboxyl groups in the compounds indicated in the method A, the order of the removal reactions of the protecting groups of the amino, hydroxyl and/or carboxyl groups can be arbitrarily selected and the removal reaction's can be carried out in order of precedence.

In addition, if it is necessary to separate isomers, which are obtained in each step of method A, each isomer can be isolated according to the isolation or purification procedures indicated hereinbefore after the reaction of each step in method A, or after removal of the protecting group in each step in method A.

The starting materials of formula (VI) and (VII) are known or can be prepared according to similar procedures to those known to those skilled in the art.

(Method B)

Method B is a process for the preparation of compounds of formula (IV), which are intermediates for the preparation of compounds of formula (I) of the present invention.

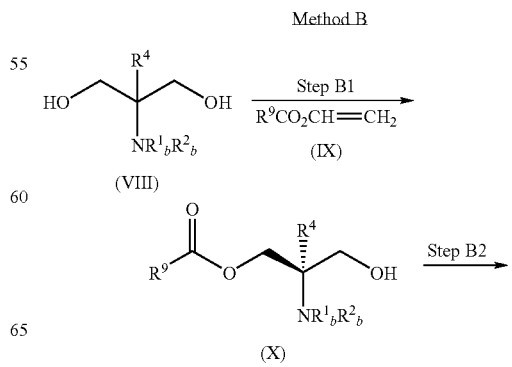

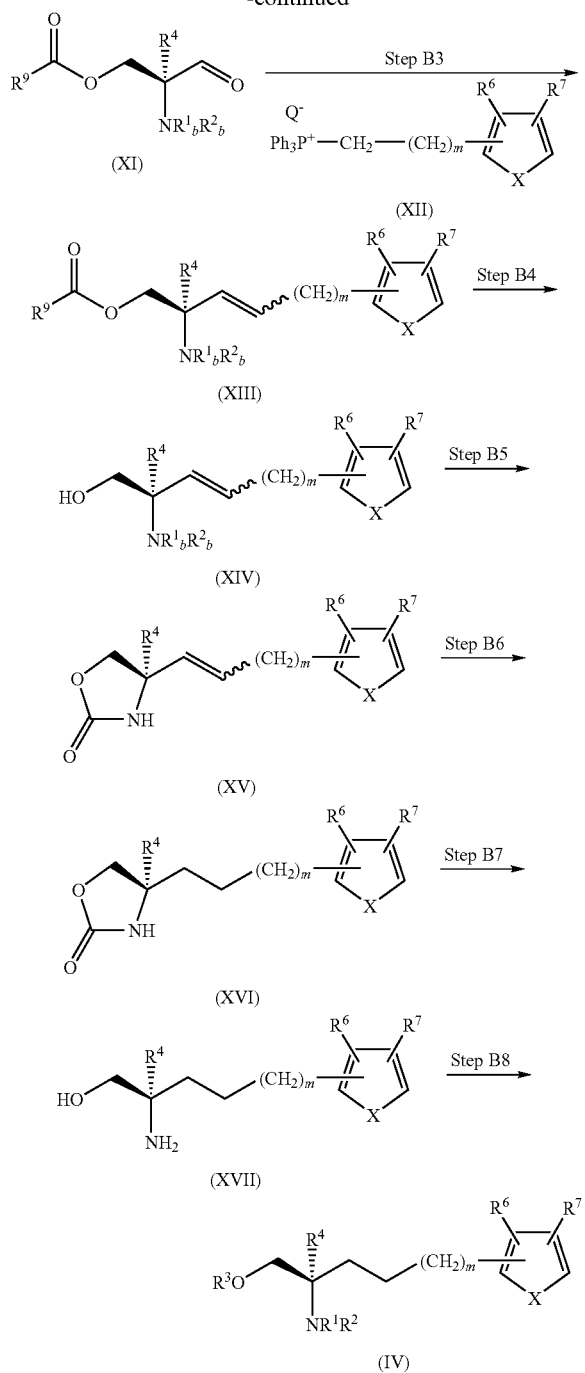

In the above reaction scheme $R^1$, $R^2$, $R^3$, $R^4$, $R^6$, $R^7$, and X have the same meanings as those indicated hereinbefore. The group of formula —$NR^1{}_bR^2{}_b$ represents an amino group protected with a protecting group having a carbonyl group. $R^9$ represents a $C_1$-$C_{20}$ alkyl group, a $C_2$-$C_{20}$ alkyl group interrupted with one or more heteroatoms, a $C_1$-$C_{20}$ alkyl group substituted with one or more aryl groups or aromatic heterocyclic groups, a $C_2$-$C_{20}$ alkynyl group, a $C_3$-$C_{20}$ alkynyl group interrupted with one or more heteroatoms, a $C_2$-$C_{20}$ alkynyl group substituted with one or more aryl groups or aromatic heterocyclic groups, a $C_2$-$C_{20}$ alkenyl group, a $C_3$-$C_{20}$ alkenyl group interrupted with one or more heteroatoms, a $C_2$-$C_{20}$ alkenyl group substituted with one or more aryl groups or aromatic heterocyclic groups, a $C_2$-$C_{20}$ alkyl group interrupted with one or more heteroatoms substituted with one or more aryl groups or aromatic heterocyclic groups, or a $C_3$-$C_{10}$ cycloalkyl group. m represents an integer of from 0 to 4. Ph represents a phenyl group. Q represents a halogen atom (preferably a chlorine, bromine or iodine atom).

The "$C_1$-$C_{20}$ alkyl group" in the above definition of $R^9$ is, for example, a straight or branched chain alkyl group having from one to twenty carbon atoms such as a "lower alkyl group" indicated hereinbefore, heptyl, 1-methylhexyl, 2-methylhexyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-dimethylhexyl, nonyl, 3-methyloctyl, 4-methyloctyl, 5-methyloctyl, 6-methyloctyl, 1-propylhexyl, 2-ethylheptyl, 6,6-dimethylheptyl, decyl, 1-methylnonyl, 3-methylnonyl, 8-methylnonyl, 3-ethyloctyl, 3,7-dimethyloctyl, 7,7-dimethyloctyl, undecyl, 4,8-dimethylnonyl, dodecyl, tridecyl, tetradecyl, pentadecyl, 3,7,11-trimethyldodecyl, hexadecyl, 4,8,12-trimethyltridecyl, 1-methylpentadecyl, 14-methylpentadecyl, 13,13-dimethyltetradecyl, heptadecyl, 15-methylhexadecyl, octadecyl, 1-methylheptadecyl, nonadecyl, icosyl, or 3,7,11,15-tetramethylhexadecyl; and is preferably a $C_1$-$C_{10}$ alkyl group.

The "$C_2$-$C_{20}$ alkyl group interrupted with one or more heteroatoms" in the above definition of $R^9$ represents a $C_2$-$C_{20}$ alkyl group interrupted with one or more heteroatoms, wherein the "$C_2$-$C_{20}$ alkyl group" is included in the "$C_1$-$C_{20}$ alkyl group" indicated hereinbefore and the alkyl group is interrupted with the same or different one or two sulfur, oxygen or nitrogen atoms, and is, for example, a $C_2$-$C_{20}$ alkyl group interrupted with one or two sulfur atoms such as methylthiomethyl, 1-methylthioethyl, 2-methylthioethyl, ethylthiomethyl, 1-methylthiopropyl, 2-methylthiopropyl, 3-methylthiopropyl, 2-ethylthioethyl, 2-methyl-2-methylthioethyl, 1-methylthiobutyl, 2-methylthiobutyl, 3-methylthiobutyl, 2-ethylthiopropyl, 3-methyl-3-methylthiopropyl, 4-methylthiopentyl, 3-methylthiopentyl, 2-methylthiopentyl, 1-methylthiopentyl, 3,3-dimethylthiobutyl, 2,2-dimethylthiobutyl, 1,1-dimethylthiobutyl, 1-methyl-2-methylthiobutyl, 1,3-dimethylthiobutyl, 2,3,-dimethylthiobutyl,2-ethylthiobutyl, 1-methylthiohexyl, 2-methylthiohexyl, 3-methylthiohexyl, 4-methylthiohexyl, 5-methylthiohexyl, 1-propylthiobutyl, 4-methyl-4-methylthiopentyl, 1-methylthioheptyl, 2-methylthioheptyl, 3-methylthioheptyl, 4-methylthioheptyl, 5-methylthioheptyl, 6-methylthioheptyl, 1-propylthiopentyl, 2-ethylthiohexyl, 5-methyl-5-methylthiohexyl, 3-methylthiooctyl, 4-methylthiooctyl, 5-methylthiooctyl, 6-methylthiooctyl, 1-propylthiohexyl, 2-ethylthioheptyl, 6-methyl-6-methylthioheptyl, 1-methylthiononyl, 3-methylthiononyl, 8-methylthiononyl, 3-ethylthiooctyl, 3-methyl-7-methylthiooctyl, 7,7-dimethylthiooctyl, 4-methyl-8-methylthiononyl, 3,7-dimethyl-11-methylthiododecyl, 4,8-dimethyl-12-methylthiotridecyl, 1-methylthiopentadecyl, 14-methylthiopentadecyl, 13-methyl-13-methylthiotetradecyl, 15-methylthiohexadecyl, 1-methylthioheptadecyl or 3,7,11-trimethyl-15-methylthiohexadecyl;

a $C_2$-$C_{20}$ alkyl group interrupted with one or two oxygen atoms such as methyloxymethyl, 1-methyloxyethyl, 2-methyloxyethyl, ethyloxymethyl, 1-methyloxypropyl, 2-methyloxypropyl, 3-methyloxypropyl, 2-ethyloxyethyl, 2-methyl-2-methyloxyethyl, 1-methyloxybutyl, 2-methyloxybutyl, 3-methyloxybutyl, 2-ethyloxypropyl, 3-methyl 3-methyloxypropyl, 4-methyloxypentyl, 3-methyloxypentyl, 2-methyloxypentyl, 1-methyloxypentyl, 3,3-dimethyloxybutyl, 2,2-dimethyloxybutyl, 1,1-dimethyloxybutyl, 1-methyl-2- methyloxybutyl, 1,3-dimethyloxybutyl, 2,3,-dimethyloxybutyl, 2-ethyloxybutyl, 1-methyloxyhexyl, 2-methyloxyhexyl, 3-methyloxyhexyl, 4-methyloxyhexyl, 5-methyloxyhexyl, 1-propyloxybutyl, 4-methyl-4-methyloxypentyl, 1-methyloxyheptyl, 2-methyloxyheptyl, 3-methyloxyheptyl, 4-methyloxyheptyl, 5-methyloxyheptyl, 6-methyloxyheptyl, 1-propyloxypentyl, 2-ethyloxyhexyl, 5-methyl-5-methyloxyhexyl, 3-methyloxyoctyl, 4-methyloxyoctyl, 5-methyloxyoctyl, 6-methyloxyoctyl, 1-propyloxyhexyl, 2-ethyloxyheptyl, 6-methyl-6-methyloxyheptyl, 1-methyloxynonyl, 3-methyloxynonyl, 8-methyloxynonyl, 3-ethyloxyoctyl, 3-methyl-7-methyloxyoctyl, 7,7-dimethyloxyoctyl, 4-methyl-8-methyloxynonyl, 3,7-dimethyl-11-methyloxydodecyl, 4,8-dimethyl-12-methyloxytridecyl, 1-methyloxypentadecyl, 14-methyloxypentadecyl, 13-methyl-13-methyloxytetradecyl, 15-methyloxyhexadecyl, 1-methyloxyheptadecyl or 3,7,11-trimethyl-15-methyloxyhexadecyl;

a $C_2$-$C_{20}$ alkyl group interrupted with one or two nitrogen atoms such as N-methylaminomethyl, 1-(N-methylamino) ethyl, 2-(N-methylamino) ethyl, N-ethylaminomethyl, 1-(N-methylamino)propyl, 2-(N-methylamino)propyl, 3-(N-methylamino)propyl, 2-(N-ethylamino)ethyl, 2-(N,N-dimethylamino)ethyl, 1-(N-methylamino)butyl, 2-(N-methylamino)butyl, 3-(N-methylamino)butyl, 2-(N-ethylamino)propyl, 3-(N,N-dimethylamino)propyl, 4-(N-methylamino)pentyl, 3-(N-methylamino)pentyl, 2-(N-methylamino)pentyl, 1-(N-methylamino)pentyl, 3-(N,N-dimethylamino)butyl, 2-(N,N-dimethylamino)butyl, 1-(N,N-dimethylamino)butyl, 1-methyl-2-(N-methylamino)butyl, 1,3-di(N-methylamino)butyl, 2,3,-di(N-methylamino)butyl, 2-(N-ethylamino)butyl, 1-(N-methylamino)hexyl, 2-(N-methylamino)hexyl, 3-(N-methylamino)hexyl, 4-(N-methylamino)hexyl, 5-(N-methylamino)hexyl, 1-(N-propylamino)butyl, 4-methyl-4-(N-methylamino)pentyl, 1-(N-methylamino)heptyl, 2-(N-methylamino)heptyl, 3-(N-methylamino)heptyl, 4-(N-methylamino)heptyl, 5-(N-methylamino)heptyl, 6-(N-methylamino)heptyl, 1-(N-propylamino)pentyl, 2-(N-ethylamino)hexyl, 5-methyl-5-(N-methylamino)hexyl, 3-(N-methylamino)octyl, 4-(N-methylamino)octyl, 5-(N-methylamino)octyl, 6-(N-methylamino)octyl, 1-(N-propylamino)hexyl, 2-(N-ethylamino)heptyl, 6-methyl-6-(N-methylamino)heptyl, 1-(N-methylamino)nonyl, 3-(N-methylamino)nonyl, 8-(N-methylamino)nonyl, 3-(N-ethylamino)octyl, 3-methyl-7-(N-methylamino)octyl, 7,7-di(N-methylamino)octyl, 4-methyl-8-(N-methylamino)nonyl, 3,7-dimethyl-1-(N-methylamino) dodecyl, 4,8-dimethyl-12-(N-methylamino)tridecyl, 1-(N-methylamino)pentadecyl, 14-(N-methylamino)pentadecyl, 13-methyl-13-(N-methylamino)tetradecyl, 15-(N-methylamino)hexadecyl, 1-(N-methylamino)heptadecyl or 3,7,11-trimethyl-15-(N-methylamino)hexadecyl.

The alkyl group interrupted with one or more heteroatoms is preferably a $C_2$-$C_{10}$ alkyl group interrupted with one or more heteroatoms.

The "$C_1$-$C_{20}$ alkyl group substituted with one or more aryl groups or aromatic heterocyclic groups" in the above definition of $R^9$ represents the above-indicated "$C_1$-$C_{20}$ alkyl group" substituted with from 1 to 3 aryl or aromatic heterocyclic groups which are the same or different and have the same meanings as those indicated hereinbefore.

The "$C_2$-$C_{20}$ alkynyl group" in the above definition of $R^9$ is, for example, a straight or branched chain alkynyl group having from two to twenty carbon atoms such as ethynyl, 2-propynyl, 1-methyl-2-propynyl, 2-butynyl, 1-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl, 5-hexynyl, heptynyl, 3-methylhexynyl, 4-methylhexynyl, 5-methylhexynyl, 4,4-dimethylpentynyl, octynyl, 3-methylheptynyl, 4-methylheptynyl, 5-methylheptynyl, 6-methylheptynyl, 5,5-dimethylhexynyl, nonynyl, 3-methyloctynyl, 4-methyloctynyl, 5-methyloctynyl, 6-methyloctynyl, 6,6-dimethylheptynyl, decynyl, 3-methylnonynyl, 8-methylnonynyl, 3-ethyloctynyl, 3,7-dimethyloctynyl, 7,7-dimethyloctynyl, undecynyl, 4,8-dimethylnonynyl, dodecynyl, tridecynyl, tetradecynyl, pentadecynyl, 3,7,11-trimethyldodecynyl, hexadecynyl, 4,8,12-trimethyltridecynyl, 14-methylpentadecynyl, 13,13-dimethyltetradecynyl, heptadecynyl, 15-methylhexadecynyl, octadecynyl, nonadecynyl, icosynyl, or 3,7,11,15-tetramethylhexadecynyl, and is preferably a $C_1$-$C_{10}$ alkynyl group.

The "$C_3$-$C_{20}$ alkynyl group interrupted with one or more heteroatoms" in the above definition of $R^9$ represents a $C_3$-$C_{20}$ alkynyl group interrupted with one or more heteroatoms, wherein the "$C_3$-$C_{20}$ alkynyl group" is included in the "$C_3$-$C_{20}$ alkynyl group" indicated hereinbefore and the alkynyl group is interrupted with the same or different one or two sulfur, oxygen or nitrogen atoms, and is, for example, a $C_3$-$C_{20}$ alkynyl group interrupted with one or two sulfur atoms such as 2-methylthioethynyl, 3-methylthiopropynyl, 2-ethylthioethynyl, 3-methylthiobutynyl, 3-methyl-3-methylthiopropynyl, 4-methylthiopentynyl, 3-methylthiopentynyl, 3,3-dimethylthiobutynyl, 3-methylthiohexynyl, 4-methylthiohexynyl, 5-methylthiohexynyl, 4-methyl-4-methylthiopentynyl, 3-methylthioheptynyl, 4-methylthioheptynyl, 5-methylthioheptynyl, 6-methylthioheptynyl, 5-methyl-5-methylthiohexynyl, 3-methylthiooctynyl, 4-methylthiooctynyl, 5-methylthiooctynyl, 6-methylthiooctynyl, 6-methyl-6-methylthioheptynyl, 3-methylthiononynyl, 8-methylthiononynyl, 3-ethylthiooctynyl, 3-methyl-7-methylthiooctynyl, 7,7-dimethylthiooctynyl, 4-methyl-8-methylthiononynyl, 3,7-dimethyl-11-methylthiododecynyl, 4,8-dimethyl-12-methylthiotridecynyl, 14-methylthiopentadecynyl, 13-methyl-13-methylthiotetradecynyl, 15-methylthiohexadecynyl, or 3,7,11-trimethyl-15-methylthiohexadecynyl;

a $C_3$-$C_{20}$ alkynyl group interrupted with one or two oxygen atoms such as 2-methyloxyethynyl, 3-methyloxypropynyl, 2-ethyloxyethynyl, 3-methyloxybutynyl, 3-methyl-3-methyloxypropynyl, 4-methyloxypentynyl, 3-methyloxypentynyl, 3,3-dimethyloxybutynyl, 3-methyloxyhexynyl, 4-methyloxyhexynyl, 5-methyloxyhexynyl, 4-methyl-4-methyloxypentynyl, 3-methyloxyheptynyl, 4-methyloxyheptynyl, 5-methyloxyheptynyl, 6-methyloxyheptynyl, 5-methyl-5-methyloxyhexynyl, 3-methyloxyoctynyl, 4-methyloxyoctynyl, 5-methyloxyoctynyl, 6-methyloxyoctynyl, 6-methyl-6-methyloxyheptynyl, 3-methyloxynonynyl, 8-methyloxynonynyl, 3-ethyloxyoctynyl, 3-methyl-7-methyloxyoctynyl, 7,7-dimethyloxyoctynyl, 4-methyl-8-methyloxynonynyl, 3,7-dimethyl-11-ethyloxydodecynyl, 4,8-dimethyl-12-methyloxytridecynyl, 14-methyloxypentadecynyl, 13-methyl-13-methyloxytetradecynyl, 15-methyloxyhexadecynyl, or 3,7,11-trimethyl-15-methyloxyhexadecynyl; or a $C_3$-$C_{20}$ alkynyl group interrupted with one or two nitrogen atoms such as 2-(N-methylamino)ethynyl, 3-(N-methylamino)propynyl, 2-(N-ethylamino)ethynyl, 2-(N,N-dimethylamino)ethynyl, 3-(N-methylamino)butynyl, 3-(N,N-dimethylamino)propynyl, 4-(N-methylamino)pentynyl, 3-(N-methylamino)pentynyl, 3-(N,N-dimethylamino)butynyl, 3-(N-methylamino)hexynyl, 4-(N-methylamino)hexynyl, 5-(N-methylamino)hexynyl, 4-methyl-4-(N-methylamino)pentynyl, 3-(N-methylamino) heptynyl, 4-(N-methylamino)heptynyl, 5-(N-methylamino)heptynyl, 6-(N-methylamino)heptynyl, 5-methyl-5-(N-methylamino) hexynyl, 3-(N-methylamino)octynyl, 4-(N-methylamino) octynyl, 5-(N-methylamino)octynyl, 6-(N-methylamino) octynyl, 6-methyl-6-(N-methylamino)heptynyl, 3-(N-methylamino)nonynyl, 8-(N-methylamino)nonynyl, 3-(N-ethylamino)octynyl, 3-methyl-7-(N-methylamino)octynyl, 7,7-di(N-methylamino)octynyl, 4-methyl-8-(N-methylamino)nonynyl, 3,7-dimethyl-11-(N-methylamino)dodecynyl, 4,8-dimethyl-12-(N-methylamino)tridecynyl, 14-(N-methylamino)pentadecynyl, 13-methyl-13-(N-methylamino)tetradecynyl, 15-(N-methylamino) hexadecynyl, or 3,7,11-trimethyl-15-(N-methylamino) hexadecynyl; preferably a $C_3$-$C_{10}$ alkynyl group interrupted with one or more heteroatoms.

The "$C_2$-$C_{20}$ alkynyl group substituted with one or more aryl groups or aromatic heterocyclic groups" in the above definition of $R^9$ represents a $C_2$-$C_{20}$ alkynyl group indicated hereinbefore wherein the alkynyl group is substituted with from 1 to 3 "aryl" or "aromatic heterocyclic" groups which are the same or different and indicated hereinbefore.

The "$C_2$-$C_{20}$ alkenyl group" in the definition of $R^9$ includes, for example, a straight or branched chain alkenyl group having from two to twenty carbon atoms such as ethenyl, 2-propenyl, 1-methyl-2-propenyl, 2-methyl-2-propenyl, 2-ethyl-2-propenyl, 2-butenyl, 1-methyl-2-butenyl, 2-methyl-2-butenyl, 1-ethyl-2-butenyl, 3-butenyl, 1-methyl-3-butenyl, 2-methyl-3-butenyl, 1-ethyl-3-butenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 2-hexenyl, 3-hexenyl, 4-hexenyl, 5-hexenyl, heptenyl, 1-methylhexenyl, 2-methylhexenyl, 3-methylhexenyl, 4-methylhexenyl, 5-methylhexenyl, 1-propylbutenyl, 4,4-dimethylpentenyl, octenyl, 1-methylheptenyl, 2-methylheptenyl, 3-methylheptenyl, 4-methylheptenyl, 5-methylheptenyl, 6-methylheptenyl, 1-propylpentenyl, 2-ethylhexenyl, 5,5-dimethylhexenyl, nonenyl, 3-methyloctenyl, 4-methyloctenyl, 5-methyloctenyl, 6-methyloctenyl, 1-propylhexenyl, 2-ethylheptenyl, 6,6-dimethylheptenyl, decenyl, 1-methylnonenyl, 3-methylnonenyl, 8-methylnonenyl, 3-ethyloctenyl, 3,7-dimethyloctenyl, 7,7-dimethyloctenyl, undecenyl, 4,8-dimethylnonenyl, dodecenyl, tridecenyl, tetradecenyl, pentadecenyl, 3,7,11-trimethyldodecenyl, hexadecenyl, 4,8,12-trimethyltridecenyl, 1-methylpentadecenyl, 14-methylpentadecenyl, 13,13-dimethyltetradecenyl, heptadecenyl, 15-methylhexadecenyl, octadecenyl, 1-methylheptadecenyl, nonadecenyl, icosenyl, or 3,7,11,15-tetramethylhexadecenyl group; and is preferably a $C_2$-$C_{10}$ alkenyl group.

The "$C_3$-$C_{20}$ alkenyl group interrupted with one or more heteroatoms" in the above definition of $R^9$ is a "$C_3$-$C_{20}$ alkenyl group", wherein the alkenyl group is interrupted with the same or different one or two sulfur, oxygen or nitrogen atoms and is included in the "$C_2$-$C_{20}$ alkenyl group" indicated hereinbefore, and includes, for example, an alkenyl group having from three to twenty carbon atoms interrupted with one or two sulfur atoms such as 1-methylthioethenyl, 2-methylthioethenyl, 1-methylthiopropenyl, 2-methylthiopropenyl, 3-methylthiopropenyl, 2-ethylthioethenyl, 2-methyl-2-methylthioethenyl, 1-methylthiobutenyl, 2-methylthiobutenyl, 3-methylthiobutenyl, 2-ethylthiopropenyl, 3-methyl-3-methylthiopropenyl, 4-methylthiopentenyl, 3-methylthiopentenyl, 2-methylthiopentenyl, 1-methylthiopentenyl, 3,3-dimethylthiobutenyl, 1-methyl-2-methylthiobutenyl, 1,3-dimethylthiobutenyl, 2,3-dimethylthiobutenyl, 2-ethylthiobutenyl, 1-methylthiohexenyl, 2-methylthiohexenyl, 3-methylthiohexenyl, 4-methylthiohexenyl, 5-methylthiohexenyl, 1-propylthiobutenyl, 4-methyl-4-methylthiopentenyl, 1-methylthioheptenyl, 2-methylthioheptenyl, 3-methylthioheptenyl, 4-methylthioheptenyl, 5-methylthioheptenyl, 6-methylthioheptenyl, 1-propylthiopentenyl, 2-ethylthiohexenyl, 5-methyl-5-methylthiohexenyl, 3-methylthiooctenyl, 4-methylthiooctenyl, 5-methylthiooctenyl, 6-methylthiooctenyl, 1-propylthiohexenyl, 2-ethylthioheptenyl, 6-methyl-6-methylthioheptenyl, 1-methylthiononenyl, 3-methylthiononenyl, 8-methylthiononenyl, 3-ethylthiooctenyl, 3-methyl-7-methylthiooctenyl, 7,7-dimethylthiooctenyl, 4-methyl-8-methylthiononenyl, 3,7-dimethyl-11-methylthiododecenyl, 4,8-dimethyl-12-methylthiotridecenyl, 1-methylthiopentadecenyl, 14-methylthiopentadecenyl, 13-methyl-13-methylthiotetradecenyl, 15-methylthiohexadecenyl, 1-methylthioheptadecenyl, or 3,7,11-trimethyl-15-methylthiohexadecenyl group;

an alkenyl group having from three to twenty carbon atoms interrupted with one or two oxygen atoms such as 1-methyloxyethenyl, 2-methyloxyethenyl, 1-methyloxypropenyl, 2-methyloxypropenyl, 3-methyloxypropenyl, 2-ethyloxyethenyl, 2-methyl-2-methyloxyethenyl, 1-methyloxybutenyl, 2-methyloxybutenyl, 3-methyloxybutenyl, 2-ethyloxypropenyl, 3-methyl-3-methyloxypropenyl, 4-methyloxypentenyl, 3-methyloxypentenyl, 2-methyloxypentenyl, 1-methyloxypentenyl, 3,3-dimethyloxybutenyl, 1-methyl-2-methyloxybutenyl, 1,3-dimethyloxybutenyl, 2,3-dimethyloxybutenyl, 2-ethyloxybutenyl, 1-methyloxyhexenyl, 2-methyloxyhexenyl, 3-methyloxyhexenyl, 4-methyloxyhexenyl, 5-methyloxyhexenyl, 1-propyloxybutenyl, 4-methyl-4-methyloxypentenyl, 1-methyloxyheptenyl, 2-methyloxyheptenyl, 3-methyloxyheptenyl, 4-methyloxyheptenyl, 5-methyloxyheptenyl, 6-methyloxyheptenyl, 1-propyloxypentenyl, 2-ethyloxyhexenyl, 5-methyl-5-methyloxyhexenyl, 3-methyloxyoctenyl, 4-methyloxyoctenyl, 5-methyloxyoctenyl, 6-methyloxyoctenyl, 1-propyloxyhexenyl, 2-ethyloxyheptenyl, 6-methyl-6-methyloxyheptenyl, 1-methyloxynonenyl, 3-methyloxynonenyl, 8-methyloxynonenyl, 3-ethyloxyoctenyl, 3-methyl-7-methyloxyoctenyl, 7,7-dimethyloxyoctenyl, 4-methyl-8-methyloxynonenyl, 3,7-dimethyl-11-methyloxydodecenyl, 4,8-dimethyl-12-methyloxytridecenyl, 1-methyloxypentadecenyl, 14-methyloxypentadecenyl, 13-methyl-13-methyloxytetradecenyl, 15-methyloxyhexadecenyl, 1-methyloxyheptadecenyl, or 3,7,11-trimethyl-15-methyloxyhexadecenyl group; or an alkenyl group having from three to twenty carbon atoms interrupted with one or two nitrogen atoms such as 1-(N-methylamino)ethenyl, 2-(N-methylamino)ethenyl, 1-(N-methylamino)propenyl, 2-(N-methylamino)propenyl, 3-(N-methylamino)propenyl, 2-(N-ethylamino)pethenyl, 2-(N,N-dimethylamino)pethenyl, 1-(N-methylamino)butenyl, 2-(N-methylamino)butenyl, 3-(N-methylamino)butenyl, 2-(N-ethylamino)propenyl, 3-(N,N-dimethylamino)propenyl, 4-(N-methylamino)pentenyl, 3-(N-methylamino)pentenyl, 2-(N-methylamino)pentenyl, 1-(N-methylamino)pentenyl, 3-(N,N-dimethylamino)butenyl, 2-(N,N-dimethylamino)butenyl, 1-(N,N-dimethylamino)butenyl, 1-methyl-2-(N-methylamino)butenyl, 1,3-di(N-methylamino)butenyl, 2,3-di(N-methylamino)butenyl, 2-(N-ethylamino)butenyl, 1-(N-methylamino)hexenyl, 2-(N-methylamino)hexenyl, 3-(N-methylamino)hexenyl, 4-(N-methylamino)hexenyl, 5-(N-methylamino)hexenyl, 1-(N-propylamino)butenyl, 4-methyl-4-(N-methylamio)pentenyl, 1-(N-methylamino) heptenyl, 2-(N-methylamino)heptenyl, 3-(N-methylamino) heptenyl, 4-(N-methylamino)heptenyl, 5-(N-methylamino) heptenyl, 6-(N-methylamino)heptenyl, 1-(N-propylamino)

pentenyl, 2-(N-ethylamino)hexenyl, 5-methyl-5-(N-methylamino)hexenyl, 3-(N-methylamino)octenyl, 4-(N-methylamino)octenyl, 5-(N-methylamino)octenyl, 6-(N-methylamino)octenyl, 1-(N-propylamino)hexenyl, 2-(N-ethylamino)heptenyl, 6-methyl-6-(N-methylamino) heptenyl, 1-(N-methylamino)nonenyl, 3-(N-methylamino) nonenyl, 8-(N-methylamino)nonenyl, 3-(N-ethylamino) octenyl, 3-methyl-7-(N-methylamino)octenyl, 7,7-di(N-methylamino)octenyl, 4-methyl-8-(N-methylamino) nonenyl, 3,7-dimethyl-11-(N-methylamino)dodecenyl, 4,8-dimethyl-12-(N-methylamino)tridecenyl, 1-(N-methylamino)pentadecenyl, 14-(N-methylamino) pentadecenyl, 13-methyl-13-(N-methylamio)tetradecenyl, 15-(N-methylamino) hexadecenyl, 1-(N-methylamino)heptadecenyl, or 3,7,11-trimethyl-15-(N-methylamino)hexadecenyl group; preferably a $C_3$-$C_{10}$ alkenyl group interrupted with one or more heteroastoms.

The "$C_2$-$C_{20}$ alkenyl group substituted with one or more aryl groups or aromatic heterocyclic groups" in the above definition of $R^9$ represents a "$C_2$-$C_{20}$ alkenyl group" which is indicated hereinbefore substituted with the same or different from 1 to 3 "aryl" or "aromatic heterocyclic" groups indicated hereinbefore.

The "$C_2$-$C_{20}$ alkyl group which is interrupted with one or more heteroatoms and substituted with one or more aryl groups or aromatic heterocyclic groups" in the above definition of $R^9$ represents a "$C_2$-$C_{20}$ alkyl group interrupted with one or more heteroatoms" which is indicated hereinbefore substituted with the same or different from 1 to 3 "aryl" or "aromatic heterocyclic" groups indicated hereinbefore.

The "$C_3$-$C_{10}$ cycloalkyl group" in the above definition of $R^9$ has the same meaning as indicated hereinbefore for "cycloalkyl group".

Step B1

Step B1 is a process for the preparation of compounds of general formula (X). Step B1 is accomplished by the selective acylation of one hydroxyl group of a compound of formula (VIII) using a compound of formula (IX) in the presence of a lipase in the presence or absence of an inert solvent (preferably in the presence of an inert solvent).

The "lipase" employed in the above reaction is not particularly restricted, and the preferred lipase depends on the starting material. Preferred lipases are derived from *Pseudomonas sp*, *Pseudomonas fluorescens*, *Pseudomonas cepacia*, *Chromobacterium viscosum*, *Aspergillus niger*, *Aspergillus oryzae*, *Candida antarctica*, *Candida cylindracea*, *Candida lipolytica*, *Candida rugosa*, *Candida utilis*, *Penicillium roqueforti*, *Rhizopus arrhizus*, *Rhizopus delemar*, *Rhizopus javanicus*, *Rhizomucor miehei*, *Rhizopus niveus*, *Humicola lanuginosa*, *Mucor javanicus*, *Mucor miehei*, *Thermus aquaticus*, *Thermus flavus*, or *Thermus thermophilus*; or human pancreas, hog pancreas, porcine pancreas, or wheat germ. Partially purified or completely purified enzymes can be used and immobilized enzymes can be also used in the above reaction. The most preferred lipase is an immobilized *Pseudomonas* sp. (for example: immobilized lipase from *Pseudomonas* sp. (product of TOYOBO Co., Ltd.).

The preferred compound of formula (IX) employed in the above reaction depends on the starting material, and is a vinyl ester of a straight chain aliphatic carboxylic acid such as vinyl n-hexanoate, vinyl n-heptanoate, vinyl n-pentanoate, or vinyl acetate; most preferably vinyl n-hexanoate.

The inert solvent employed in the above reaction is not particularly restricted, and the compound of formula (IX) can be used as the solvent without other solvents. The preferred solvent depends on the starting material, and can be a mixture of various solvents or a solvent containing water. The preferred solvents include ethers such as diisopropyl ether, tert-butyl methyl ether, diethyl ether, or tetrahydrofuran; aliphatic hydrocarbons such as n-hexane or n-pentane; aromatic hydrocarbons such as benzene or toluene; or halogenated hydrocarbons such as dichloromethane or 1,2-dichloroethane. The more preferred solvents are ethers, and the most preferred solvents are diisopropyl ether or tert-butyl methyl ether.

The reaction temperature depends on the starting material, solvent, lipase and the like employed in the above reaction and is usually between $-50°$ C. and $50°$ C., preferably between $0°$ C. and $40°$ C.

The reaction time depends on the starting material, solvent, lipase, reaction temperature and the like employed in the above reaction and is usually from 15 minutes to 150 hours, preferably from 30 minutes to 24 hours.

Step B2

Step B2 is a process for the preparation of compounds of general formula (XI) and is accomplished by oxidation of the alcohol moiety of a compound of general formula (X) to the corresponding aldehyde moiety using an oxidizing reagent in an inert solvent.

The oxidation reaction is not particularly restricted provided that it can convert a primary alcohol into the corresponding aldehyde and, for example, is the Collins oxidation which is conducted using pyridine and chromic acid in dichloromethane; the PCC oxidation which is conducted using pyridinium chlorochromate (PPC) in dichloromethane; the PDC oxidation which is conducted using pyridinium dichromate (PDC) in dichloromethane; the DMSO oxidation such as the Swern oxidation which is conducted using an electrophilic reagent (for example acetic anhydride, trifluoroacetic anhydride, thionyl chloride, sulfuryl chloride, oxalyl chloride, dicyclohexylcarbodiimide, diphenylketene-p-tolylimine, N,N-diethylaminoacetylene, or sulfur trioxide-pyridine complex) and dimethyl sulfoxide (DMSO) in dichloromethane; or the manganese dioxide oxidation which is conducted using manganese dioxide in dichloromethane or benzene. Preferred oxidation reactions are the PCC oxidation, PDC oxidation or Swern oxidation in dichloromethane.

The reaction temperature depends on the starting material, solvent, oxidizing agent and the like employed in the above reaction and is usually between $-78°$ C. and $80°$ C., preferably between $-78°$ C. and $30°$ C.

The reaction time depends on the starting material, solvent, oxidizing agent, reaction temperature and the like employed in the above reaction and is usually from 10 minutes to 48 hours, preferably from 30 minutes to 24 hours.

Step B3

Step B3 is a process for the preparation of compounds of general formula (XIII) and is accomplished by reaction of a compound of formula (XI) with a compound of formula (XII) in the presence of a base in an inert solvent.

The inert solvent employed in the above reaction is not particularly restricted provided that it has no adverse effect on the reaction and can be, for example, an ether such as diethyl ether, diisopropyl ether, tetrahydrofuran, dioxane, dimethoxyethane, or di (ethylene glycol) dimethyl ether; an aromatic hydrocarbon such as toluene, benzene, or xylene; a halogenated hydrocarbon such as dichloromethane, chloroform, carbon tetrachloride, dichloroethane, chlorobenzene, or dichlorobenzene; a lower alkyl nitrile such as acetonitrile or propionitrile; an amide such as formamide, N,N-dimethylformamide, N,N-dimethylacetamide, or hexamethylphosphoric triamide; a lower alkyl alcohol such as methanol, ethanol, propanol or butanol; or water. The solvent is preferably an ether (most preferably tetrahydrofuran).

The base employed in the above reaction is not particularly restricted provided that it does not change groups other than the aldehyde moiety of the compound of formula (XI) and can be, for example, the same base as that indicated in Step A2. The base is preferably an alkali metal alkoxide (most preferably potassium tert-butoxide).

The reaction temperature depends on the starting material, solvent, base and the like employed in the above reaction and is usually between −78° C. and 200° C., preferably between −50° C. and 150° C. (most preferably 0° C.).

The reaction time depends on the starting material, solvent, base, reaction temperature and the like employed in the above reaction and is usually from 15 minutes to 48 hours (preferably from 30 minutes to 8 hours).

Step B4

Step B4 is a process for the preparation of compounds of general formula (XIV) and is accomplished by a hydrolysis reaction of a compound of formula (XIII) in the presence of a base in an inert solvent.

The inert solvent employed in the above reaction is not particularly restricted provided that it has no adverse effect on the reaction and can dissolve the starting material to some extent and can be, for example, an ether such as diethyl ether, diisopropyl ether, tetrahydrofuran, dioxane, dimethoxyethane, or di(ethylene glycol) dimethyl ether; an alcohol such as methanol, ethanol, n-propanol, isopropanol, n-butanol, isobutanol, tert-butanol, isoamyl alcohol, di(ethylene glycol), glycerin, octanol, cyclohexanol, or methyl-cellosolve; an amide such as formamide, N,N-dimethylformamide, N,N-dimethylacetamide, or hexamethylphosphoric triamide; water; a mixture of solvents indicated hereinbefore or a mixture of water and a solvent indicated hereinbefore. The solvent is preferably a mixture of an alcohol, ether and water or a mixture of an alcohol and water (most preferably a mixture of methanol, tetrahydrofuran and water).

The base employed in the above reaction is not particularly restricted provided that it does not change groups other than the acyl moiety of the compound of formula (XIII) and can be, for example, the same base as that indicated in Step A2. The base is preferably an alkali metal hydroxide (most preferably sodium hydroxide)

The reaction temperature depends on the starting material, solvent, base and the like employed in the above reaction and is usually between −78° C. and 150° C., preferably between −50° C. and 100° C. (most preferably near room temperature).

The reaction time depends on the starting material, base, solvent, reaction temperature and the like employed in the above reaction and is usually from 15 minutes to 48 hours (most preferably from 30 minutes to 6 hours).

Step B5

Step B5 is a process for the preparation of compounds of general formula (XV) and is accomplished by treatment of a compound of formula (XIV) with a base in an inert solvent.

The inert solvent employed in the above reaction is not particularly restricted provided that it has no adverse effect on the reaction and can be, for example, an ether such as diethyl ether, diisopropyl ether, tetrahydrofuran, dioxane, dimethoxyethane, or di (ethylene glycol) dimethyl ether; an alcohol such as methanol, ethanol, n-propanol, isopropanol, n-butanol, isobutanol, tert-butanol, isoamyl-alcohol, di(ethylene glycol), glycerin, octanol, cyclohexanol, or methyl cellosolve; an amide such as formamide, N,N-dimethylformamide, N,N-dimethylacetamide, or hexamethylphosphoric triamide; water; a mixture of solvents indicated hereinbefore; or a mixture of water and a solvent indicated hereinbefore. The solvent is preferably an ether or amide (most preferably tetrahydrofuran).

The base employed in the above reaction is not particularly restricted provided that it can be used in general reactions as a base and can be, for example, the same base as that indicated in Step A2. The base is preferably an alkali metal alkoxide (most preferably potassium tert-butoxide).

The reaction temperature depends on the starting material, solvent, base and the like employed in the above reaction and is usually between −78° C. and 150° C., preferably between −50° C. and 100° C., (most preferably between 0° C. and room temperature).

The reaction time depends on the starting material, solvent, base, reaction temperature and the like employed in the above reaction and is usually from 15 minutes to 48 hours (preferably from 30 minutes to 8 hours).

Step B5 can be also accomplished by reaction with an acylating reagent such as N,N-carbonyldiimidazole, dimethyl carbonate, or diethyl carbonate after removal of the protecting group of the amino group of the compound of general formula (XIV).

Step B6

Step B6 is a process for the preparation of compounds of general formula (XVI) and is accomplished by reduction of a compound of formula (XV) in the presence of a reducing agent (preferably by catalytic reduction under an atmosphere of hydrogen) in an inert solvent.

The inert solvent employed in the above catalytic reduction is not particularly restricted provided that it has no adverse effect on the reaction and can be, for example, an aliphatic hydrocarbon such as hexane, heptane, ligroin, or petroleum ether; an aromatic hydrocarbon such as toluene, benzene, or xylene; a halogenated hydrocarbon such as dichloromethane, chloroform, carbon tetrachloride, dichloroethane, chlorobenzene, or dichlorobenzene, an ester such as methyl acetate, ethyl acetate, propyl acetate, butyl acetate, or diethyl carbonate; an ether such as diethyl ether, dioxane, tetrahydrofuran, dimethoxyethane, or di (ethylene glycol) dimethyl ether; an amide such as formamide, N,N-dimethylformamide, N,N-dimethylacetamide, or hexamethylphosphoric triamide; an alcohol such as methanol, ethanol, n-propanol, isopropanol, n-butanol, isobutanol, tert-butanol, isoamyl-alcohol, di(ethylene glycol), glycerin, octanol, cyclohexanol, or methyl cellosolve; an organic acid such as acetic acid or hydrochloric acid; water; or a mixture of water and a solvent indicated hereinbefore. The solvent is preferably an alcohol or ether (most preferably methanol).

The reducing agent employed in the above catalytic reduction reaction is not particularly restricted provided that it can be used for general catalytic reductions and can be, for example, the same catalyst as that indicated in Step A3 or Step A4. The catalyst is preferably palladium-charcoal (most preferably 10% palladium-charcoal).

The pressure of hydrogen is not particularly restricted and is usually between 1 to 10 atmospheric pressures, preferably 1 atmospheric pressure.

The reaction temperature depends on the starting material, solvent, reducing agent and the like employed in the above reaction and is usually between −20° C. and 200° C., preferably between 0° C. and 100° C. (most preferably between 20° C. and 30° C.).

The reaction time depends on the reaction temperature, starting material, reagent, solvent, and the like employed in the above reaction and is usually from 5 minutes to 96 hours, preferably from 15 minutes to 24 hours (most preferably from 30 minutes to 2 hours).

Step B7

Step B7 is a process for the preparation of compounds of general formula (XVII), and is accomplished by a hydrolysis reaction of a compound of formula (XVI) in the presence of a base in an inert solvent.

The inert solvent employed in the above reaction is not particularly restricted and can be, for example, the same solvent as that indicated in Step B4. The solvent is preferably a mixture of an alcohol and an ether or a mixture of an alcohol and water (most preferably a mixture of methanol, tetrahydrofuran and water or a mixture of methanol and water).

The base employed in the above reaction is not particularly restricted provided that it has no adverse effect on the hydrolysis reaction, and can be, for example, the same base as that indicated in Step B4. The base is preferably an alkali metal hydroxide (most preferably potassium hydroxide or sodium hydroxide).

The reaction temperature depends on the starting material, solvent, base and the like and is usually between −78° C. and 200° C., preferably between 0° C. and 180° C. (most preferably between 20° C. and 120° C.)

The reaction time depends on the starting material, base, solvent, reaction temperature, and the like and is usually from 15 minutes to 10 days (most preferably from 2 hours to 5 days).

Step B8

If necessary, Step B8 is a process for the preparation of compounds of general formula (IV) and is accomplished by alkylation or protection of the hydroxyl and amino groups of a compound of formula (XVII) in an inert solvent.

The alkylation and protection of the hydroxyl and amino groups can be carried out according to methods known to those skilled in organic chemistry, for example the methods indicated in "Protective Groups in Organic Synthesis" (Third Edition, 1999, John Wiley & Sons, Inc.), and can be accomplished by the procedure indicated hereinafter.

The alkylation or protection of the amino group can be accomplished, for example, by reaction of a compound of formula (XVII) with a compound of formula $R^1a$-Q (XIX) [wherein $R^1a$ represents a lower alkyl group or a protecting group of the amino group (which have the same meanings as indicated hereinbefore). Q has the same meaning as indicated hereinbefore.] in the presence or absence of a base in an inert solvent.

The inert solvent employed in the above reaction is preferably an ether such as diethyl ether, diisopropyl ether, tetrahydrofuran, dioxane, dimethoxyethane, or di(ethylene glycol) dimethyl ether; or an alcohol such as methanol, ethanol, n-propanol, isopropanol, n-butanol, isobutanol, tert-butanol, isoamyl alcohol, di(ethylene glycol), glycerin, octanol, cyclohexanol, or methyl cellosolve.

The base employed in the above reaction is preferably an organic amine such as triethylamine, tributylamine, diisopropylethylamine, N-methylmorpholine, or pyridine.

The reaction temperature is between −78° C. and 150° C. (preferably between −50° C. and 100° C. and most preferably near room temperature).

The reaction time is usually from 10 minutes to 48 hours (preferably from 20 minutes to 8 hours).

The alkylation or protection of the hydroxyl group can be accomplished, for example, by reaction of a compound of formula (XVII) with a compound of formula $R^3a$-Q (XX) [wherein $R^3a$ represents a lower alkyl group or a protecting group of the hydroxyl group (which have the same meanings as indicated hereinbefore). Q has the same meaning as indicated hereinbefore.] in the presence of a base in an inert solvent.

The inert solvent employed in the above reaction is preferably a halogenated hydrocarbon such as chloroform, dichloromethane, 1,2-dichlororethane, or carbon tetrachloride; an amide such as formamide, dimethylformamide, dimethylacetamide, or hexamethylphosphoric triamide; or a sulfoxide such as dimethyl sulfoxide.

The base employed in the above reaction is preferably an alkali metal hydride such as lithium hydride, sodium hydride, or potassium hydride; or an organic amine such as triethylamine, tributylamine, diisopropylethylamine, N-methylmorpholine or pyridine.

The reaction temperature is between −78° C. and 150° C. (preferably between −50° C. and 100° C. and most preferably near room temperature).

The reaction time is usually from 10 minutes to 48 hours (preferably from 20 minutes to 8 hours).

The order of the alkylation or protection of the amino and hydroxyl groups can be arbitrarily selected and the reactions can be carried out in order of precedence.

After the reactions in Method B, the desired compound in each Step can be isolated from the reaction mixture by conventional treatments, for example, neutralization of the reaction mixture, if necessary, or filtration of the reaction mixture, when insoluble material is present in the reaction mixture, addition of a solvent immiscible with water such as ethyl acetate to the neutralized solution or the filtrate, washing the resulting organic layer with water, separation of the organic layer containing the desired product, drying of the organic layer over anhydrous magnesium sulfate, anhydrous sodium sulfate or the like, and then evaporation of the organic solvent to give the desired product. If necessary, the product thus obtained is further purified by conventional treatments, for example by recrystallization or reprecipitation, or by conventional procedures in organic chemistry, for example, absorption column chromatography using a carrier such as silica gel, alumina, or Florisil consisting of magnesium and silica gel; partition column chromatography using a synthetic absorbent such as Sephadex LH-20 (product of Pharmacia Co., Ltd), Amberlite XAD-11 (product of Rohm & Hass Co., Ltd), or Diaion HP-20 (product of Mitsubishi Chemicals Co., Ltd.); ion exchange chromatography; normal phase or reversed phase column chromatography using silica gel or alkylated silica gel (preferably high performance liquid column chromatography); or an appropriate combination of these chromatographic techniques and elution using an appropriate solvent to isolate and purify the desired product.

In addition, if it is necessary to separate isomers, which are obtained in each Step of method B, each isomer can be isolated according to the isolation or purification procedures indicated hereinbefore after the reaction of each step in method B, or after protection of the hydroxyl and/or amino groups in method B.

The starting materials of formula (VIII) and (IX) are known or can be prepared according to similar procedures to those known to those skilled in the art [starting material of formula (VIII): J. Org. Chem., 64, 8220 (1999)].

(Method C)

Method C is a process for the preparation of compounds of general formula (XII).

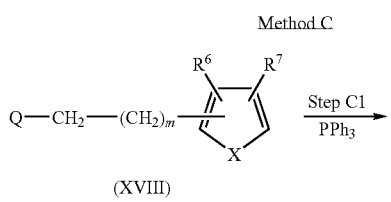

Method C

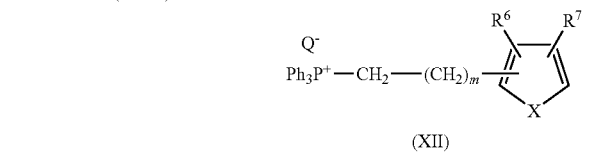

In the above reaction scheme $R^6$, $R^7$, X, m, Q and Ph have the same meanings as those indicated hereinbefore.

Step C1

Step C1 is a process for the preparation of compounds of general formula (XII) and is accomplished by reaction of a compound of general formula (XVIII) with triphenylphosphine in an inert solvent.

The inert solvent employed in the above reaction is not particularly restricted provided that it has no adverse effect on the reaction and can be, for example, an aliphatic hydrocarbon such as hexane, heptane, ligroin, or petroleum ether; an aromatic hydrocarbon such as toluene, benzene, or xylene; a halogenated hydrocarbon such as dichloromethane, chloroform, carbon tetrachloride, dichloroethane, chlorobenzene, or dichlorobenzene; an ether such as diethyl ether, diisopropyl ether, tetrahydrofuran, dioxane, dimethoxyethane, or di(ethylene glycol) dimethyl ether; a lower alkyl nitrile such as acetonitrile or propionitrile; a lower alkyl alcohol such as methanol, ethanol, propanol, or butanol; or a lower alkyl ketone such as acetone or methyl ethyl ketone. The solvent is preferably an ether or nitrile.

The reaction temperature depends on the starting material, solvent and the like and is usually between −10° C. and 200° C., preferably between 0° C. and 150° C. (most preferably between 20° C. and 120° C.).

The reaction time depends on the reaction temperature, starting material, and solvent employed in the above reaction and is usually from 5 minutes to 96 hours, preferably from 15 minutes to 48 hours (most preferably from 1 hour to 8 hours).

The desired product of formula (XII) of Step C1, if necessary, can be isolated or purified by conventional procedures, for example, recrystallization or reprecipitation, or by conventional procedures known to those skilled in organic chemistry, for example, absorption column chromatography using a carrier such as silica gel, alumina, or Florisil consisting of magnesium and silica gel; partition column chromatography using a synthetic absorbent such as Sephadex LH-20 (product of Pharmacia Co., Ltd), Amberlite XAD-11 (product of Rohm & Hass Co., Ltd), or Diaion HP-20 (product of Mitsubishi Chemicals Co.; Ltd.); ion exchange chromatography; normal phase or reversed phase column chromatography using silica gel or alkylated silica gel (preferably high performance liquid column chromatography); or an appropriate combination of these chromatographic techniques; and elution using an appropriate solvent.

In addition, if it is necessary to separate isomers, which are obtained in Step C1, each isomer can be isolated according to the isolation or purification procedures indicated hereinbefore after the reaction of Step C1.

The starting material of formula (XVIII) is known or can be prepared according to a similar procedure to those known to those skilled in the art [X=O: J. Am. Chem. Soc., 49, 1066 (1927), X=N-Me: J. Org. Chem., 52, 19-(1987)].

(Method D)

Method D is a process for increasing the optical purity of compounds of general formula (XVII).

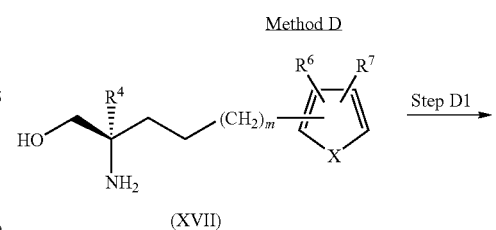

Method D

In the above reaction scheme $R^4$, $R^6$, $R^7$, X and m have the same meanings as those indicated hereinbefore.

Step D1

Step D1 is a process for increasing the optical purity of compounds of formula (XVII). Step D1 is carried out by treatment of a compound of formula (XVII) with an optically active organic acid in an inert solvent to form a salt of the compound of formula (XVII), if necessary, with recrystallization of the salt in order to increase the optical purity, followed by treatment of the salt with a base to regenerate the free form of the compound of general formula (XVII).

The inert solvent employed in the above reaction is not particularly restricted provided that it has no adverse effect on the reaction and, for example, is an aliphatic hydrocarbon such as hexane, heptane, ligroin, or petroleum ether; an aromatic hydrocarbon such as toluene, benzene, or xylene; a halogenated hydrocarbon such as dichloromethane, chloroform, carbon tetrachloride, dichloroethane, chlorobenzene, or dichlorobenzene; an ester such as methyl acetate, ethyl acetate, propyl acetate, butyl acetate, or diethyl carbonate; an ether such as diethyl ether, diisopropyl ether, tetrahydrofuran, dioxane, dimethoxyethane, or di(ethylene glycol) dimethyl ether; an alcohol such as methanol, ethanol, n-propanol, isopropanol, n-butanol, isobutanol, tert-butanol, isoamyl alcohol, di(ethylene glycol), glycerin, octanol, cyclohexanol, or methyl cellosolve; a nitrile such as acetonitrile or propionitrile; water; or a mixture of water and a solvent indicated hereinbefore. The inert solvent is preferably an alcohol (most preferably methanol or ethanol) or a mixture of water and an alcohol.

The optically active organic acid employed in the above reaction is not particularly restricted and is, for example, tartaric acid, mandelic acid or 10-camphorsulfonic acid. The preferred acid is tartaric acid.

The process for regeneration of the compound of formula (XVII) as a free form from the salt can be easily accomplished by a normal extraction procedure using an organic solvent and a base.

After the reaction, each desired compound of Method D can be isolated from the reaction mixture by conventional treatments, for example, neutralization of the reaction mixture, if necessary, or filtration of the reaction mixture when insoluble material is present in the reaction mixture, addition of a solvent immiscible with water such as ethyl acetate to the neutralized solution or the filtrate, washing the resulting organic layer with water, separation of the organic layer containing the desired product, drying of the organic layer over anhydrous magnesium sulfate, anhydrous sodium sulfate or the like, and then evaporation of the organic solvent to give the desired product. The product thus obtained, if necessary, is further purified by conventional treatments, for example by recrystallization or reprecipitation, or by conventional procedures in organic chemistry, for example, absorption column chromatography using a carrier such as silica gel, alumina, or Florisil consisting of magnesium and silica gel; partition column chromatography using a synthetic absorbent such as Sephadex LH-20 (product of Pharmacia Co., Ltd), Amberlite XAD-11 (product of Rohm & Hass Co., Ltd), or Diaion HP-20 (product of Mitsubishi Chemicals Co., Ltd.); ion exchange chromatography; normal phase or reversed phase column chromatography using silica gel or alkylated silica gel (preferably high performance liquid column chromatography); or an appropriate combination of these chromatographic techniques; and elution using an appropriate solvent to isolate and purify the desired product.

(Method E)

Method E is a process for the preparation of compounds of general formula (XXIV). Method E is a particularly useful method for the preparation of compounds of Method C, wherein X is N-D and m is 0. Method E can be accomplished according to similar procedures to those indicated in the literature (J. Org. Chem., 52, 19 (1987)).

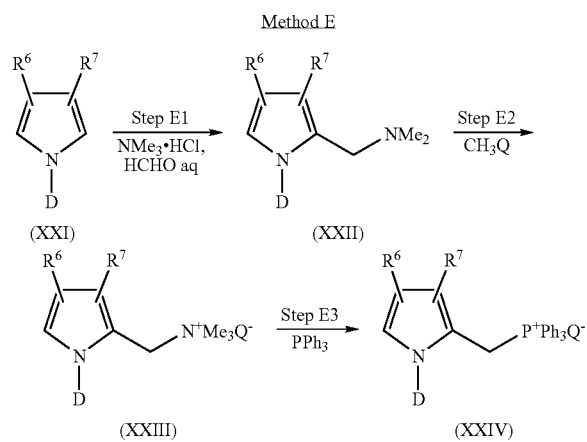

In the above reaction scheme D, $R^6$, $R^7$ and Q have the same meanings as those indicated hereinbefore.

Step E1

Step E1 is a process for the preparation of compounds of general formula (XXII). Step E1 is accomplished by reaction of a compound of formula (XXI) with formalin and dimethylamine hydrochloride according to similar-procedures to those indicated in the literature (for example, J. Am. Chem. Soc., 73, 4921 (1951) or the like).

Step E2

Step E2 is a process for the preparation of compounds of general formula (XXIII). Step E2 is accomplished by reaction of a compound of formula (XXII) with a methyl halide such as methyl iodide or the like to give a quaternary salt.

The inert solvent employed in the above reaction is not particularly restricted provided that it has no adverse effect on the reaction and, for example, can be an aliphatic hydrocarbon such as hexane, heptane, ligroin, or petroleum ether; an aromatic hydrocarbon such as toluene, benzene, or xylene; a halogenated hydrocarbon such as dichloromethane, chloroform, carbon tetrachloride, dichloroethane, chlorobenzene, or dichlorobenzene; an ether such as diethyl ether, diisopropyl ether, tetrahydrofuran, dioxane, dimethoxyethane, or di(ethylene glycol) dimethyl ether; a lower alkyl nitrile such as acetonitrile or propionitrile; a lower alkyl alcohol such as methanol, ethanol, propanol, or butanol; or a lower alkyl ketone such as acetone or methyl ethyl ketone. The inert solvent is preferably an alcohol.

The reaction temperature depends on the starting material, solvent and the like and is usually between −10° C. and 200° C., preferably between 0° C. and 50° C.

The reaction time depends on the reaction temperature, starting material and solvent employed in the above reaction and is generally from 5 minutes to 96 hours, preferably from 15 minutes to 48 hours (most preferably from 1 hour to 8 hours).

Step E3

Step E3 is a process for the preparation of compounds of general formula (XXIV). Step E3 is accomplished by reaction of a compound of general formula (XXIII) with triphenylphosphine in an inert solvent.

The inert solvent employed in the above reaction is not particularly restricted provided that it has no adverse effect on the reaction and, for example, can be an aliphatic hydrocarbon such as hexane, heptane, ligroin, or petroleum ether; an aromatic hydrocarbon such as toluene, benzene, or xylene; a halogenated hydrocarbon such as dichloromethane, chloroform, carbon tetrachloride, dichloroethane, chlorobenzene, or dichlorobenzene; an ether such as diethyl ether, diisopropyl ether, tetrahydrofuran, dioxane, dimethoxyethane, or di(ethylene glycol) dimethyl ether; a lower alkyl nitrile such as acetonitrile or propionitrile; a lower alkyl alcohol such as methanol, ethanol, propanol, or butanol; or a lower alkyl ketone such as acetone or methyl ethyl ketone. The inert solvent is preferably an ether or nitrile (most preferably acetonitrile)

The reaction temperature depends on the starting material, solvent and the like and is usually between room temperature and 200° C., preferably between 0° C. and 150° C. (most preferably between 20° C. and 100° C.).

The reaction time depends on the reaction temperature, starting material and solvent employed in the above reaction and is generally from 5 minutes to 96 hours, preferably from 15 minutes to 48 hours (most preferably from 1 hour to 8 hours).

After the reaction, each desired compound of Method E can be isolated from the reaction mixture by conventional treatments, for example, neutralization of the reaction mixture, if necessary, or filtration of the reaction mixture when insoluble material is present in the reaction mixture, addition of a solvent immiscible with water such as ethyl acetate to the neutralized solution or the filtrate, washing the resulting organic layer with water, separation of the organic layer containing the desired product, drying of the organic layer over anhydrous magnesium sulfate, anhydrous sodium sulfate or the like, and then evaporation of the organic solvent to give the desired product. The product thus obtained, if necessary, is further purified by conventional treatments, for example recrystallization or reprecipitation, or by conventional procedures in organic chemistry, for example, absorption column chromatography using a carrier such as silica gel, alumina, or Florisil consisting of magnesium and silica gel; partition column chromatography using a synthetic absorbent such as Sephadex LH-20 (product of Pharmacia Co., Ltd), Amberlite XAD-11 (product of Rohm & Hass Co., Ltd), or Diaion HP-20 (product of Mitsubishi Chemicals Co., Ltd.); ion exchange chromatography; normal phase or reversed phase column chromatography using silica gel or alkylated silica gel (preferably high performance liquid column chromatography); or an appropriate combination of these chromatographic techniques; and elution using an appropriate solvent to isolate and purify the desired product.

In addition, if it is necessary to separate isomers, which are obtained in each step of method E, each isomer can be isolated according to the isolation or purification procedures indicated hereinbefore after the reaction of each step in method E, or after removal of the protecting group in each step in method E.

The starting material of formula (XXI) is known or can be prepared according to similar procedures to those known to those skilled in the art.

(Method F)

Method F is a process for the preparation of compounds of general formula (XXVIII) from compounds of general formula (XVI) or (IV). Method F is an alternative process to Method A.

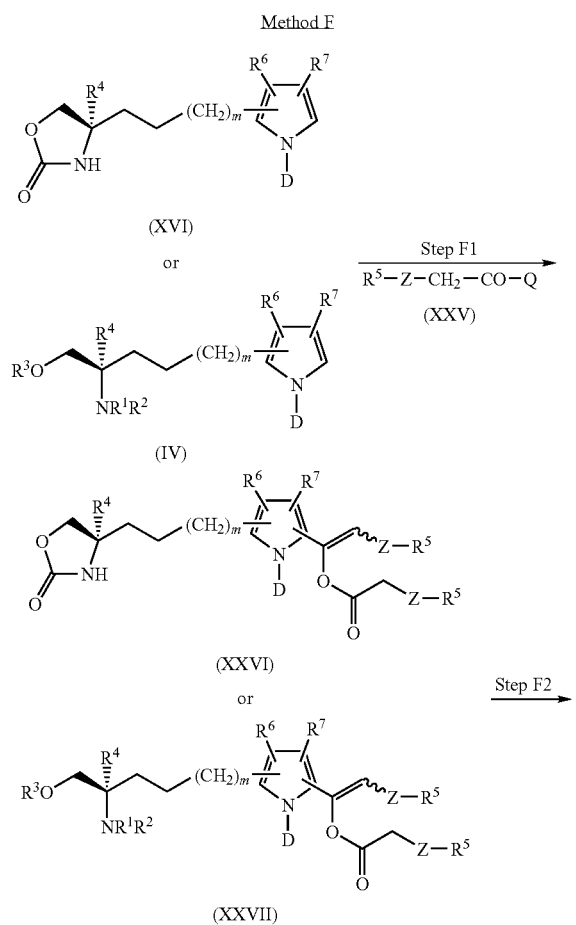

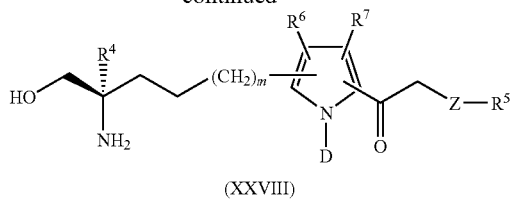

(XXVIII)

In the above reaction scheme, $R^1$, $R^2$, $R^3$, $R^4$, $R^5$, $R^6$, $R^7$, D, Q, Z, and m have the same meanings as those indicated hereinbefore.

Step F1

Step F1 is a process for the preparation of compounds of general formula (XXVI) or (XXVII). Step F1 is accomplished by reaction of a compound of general formula (XVI) or (IV) with an acyl halide of general formula (XXV) in the presence of a base in an inert solvent.

The inert solvent employed in the above reaction is not particularly restricted and can be, for example, an aliphatic hydrocarbon such as hexane, heptane, ligroin, or petroleum ether; an aromatic hydrodarbon such as toluene, benzene, or xylene; a halogenated hydrocarbon such as dichloromethane, chloroform, carbon tetrachloride, dichloroethane, chlorobenzene, or dichlorobenzene; an ether such as diethyl ether, diisopropyl ether, tetrahydrofuran, dioxane, dimethoxyethane, or di(ethylene glycol) dimethyl ether; a lower alkyl nitrile such as acetonitrile or propionitrile; a lower alkyl alcohol such as methanol, ethanol, propanol, or butanol; or a lower alkyl ketone such as acetone or methyl ethyl ketone. The solvent is preferably an aromatic hydrocarbon (particularly preferably benzene, toluene or xylene).

The base employed in the above reaction is not particularly restricted provided that it activates the compound of formula (XXV) and is, for example, 4-(N,N-dimethylaminopyridine) or 4-pyrrolidinopyridine.

The reaction temperature depends on the starting material, solvent, base and the like and is usually between 0° C. and 200° C., preferably between room temperature and 150° C.

The reaction time depends on the starting material, base, solvent, reaction temperature and the like and is usually from 15 minutes to 7 days, preferably from 6 hours to 3 days.

Step F2

Step F2 is a process for the preparation of compounds of general formula (XXVIII). Step F2 is accomplished by a hydrolysis reaction of a compound of formula (XXVI) or (XXVII) in the presence of a base in an inert solvent according to a similar procedure to that indicated in Step B7.

After the reaction, each desired compound of Method F can be isolated from the reaction mixture by conventional treatments, for example, neutralization of the reaction mixture, if necessary, or filtration of the reaction mixture when insoluble material is present in the reaction mixture, addition of a solvent immiscible with water such as ethyl acetate to the neutralized solution, washing the resulting organic layer with water, separation of the organic layer containing the desired product, drying of the organic layer over anhydrous magnesium sulfate, anhydrous sodium sulfate or the like, and then evaporation of the organic solvent to give the desired product. The product thus obtained, if necessary, is further purified by conventional treatments, for example recrystallization or reprecipitation, or by conventional procedures in organic chemistry, for example, absorption column chromatography using a carrier such as silica gel, alumina, or Florisil consisting of magnesium and silica gel; partition column chromatography using a synthetic absorbent such as Sephadex LH-20 (product of Pharmacia Co., Ltd.), Amberlite XAD-11 (product of Rohm & Hass Co., Ltd.), or Diaion HP-20 (product of Mitsubishi Chemicals Co., Ltd.); ion exchange chromatography; normal phase or reversed phase column chromatography using silica gel or alkylated silica gel (preferably high performance liquid column chromatography); or an appropriate combination of these chromatographic techniques; and elution using an appropriate solvent to isolate and purify the desired product.

In addition, if it is necessary to separate isomers, which are obtained in each step of method F, each isomer can be isolated according to the isolation or purification procedures indicated hereinbefore after the reaction of each step in method F, or after removal of the protecting group in method F.

(Method G)

Method G is a process for the preparation of compounds of general formula (XXVIII) from compounds of formula (XVI) or (IV) and is an alternative process to method F.

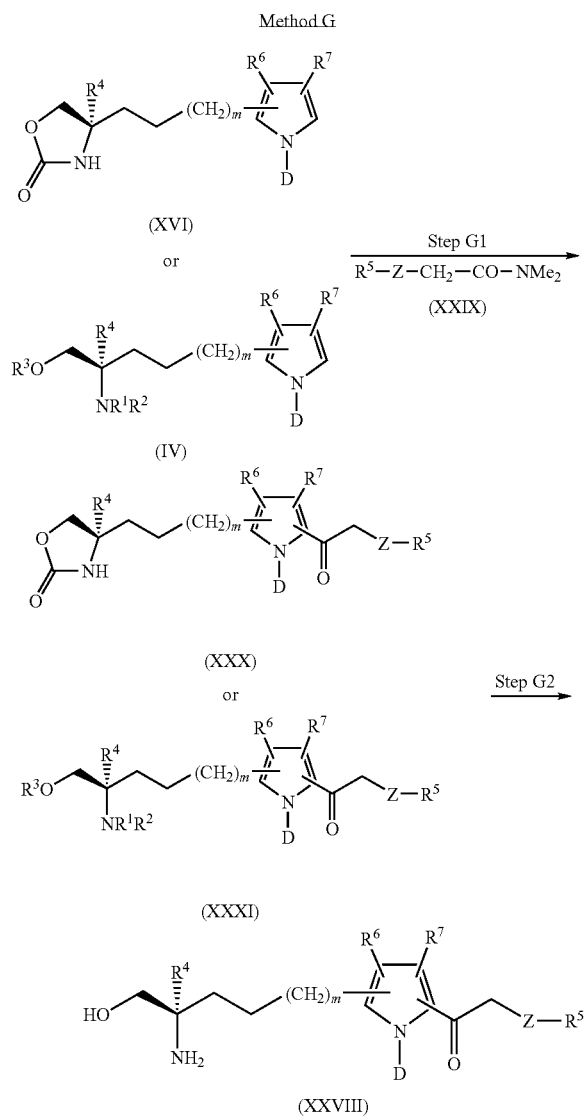

In the above reaction scheme $R^1$, $R^2$, $R^3$, $R^4$, $R^5$, $R^6$, $R^7$, D, Z and m have the same meanings as those indicated hereinbefore.

Step G1

Step G1 is a process for the preparation of compounds of general formula (XXX) or (XXXI). Step G1 is accomplished by reaction of a compound of general formula (XVI) or (IV) with an amide derivative of formula (XXIX) in the presence of phosphorous oxychloride or oxalyl chloride in an inert solvent according to similar procedures to those indicated in the literature (for example J. Med. Chem., 40, 3381 (1997)).

The inert solvent employed in the above reaction is not particularly restricted and can be an aliphatic hydrocarbon such as hexane, heptane, ligroin, or petroleum ether; an aromatic hydrocarbon such as toluene, benzene, or xylene, a halogenated hydrocarbon such as dichloromethane, chloroform, carbon tetrachloride, dichloroethane, chlorobenzene, or dichlorobenzene; an ether such as diethyl ether, diisopropyl ether, tetrahydrofuran, dioxane, dimethoxyethane, or di(ethylene glycol) dimethyl ether; a lower alkyl nitrile such as acetonitrile or propionitrile; a lower alkyl alcohol such as methanol, ethanol, propanol, or butanol; or a lower alkyl ketone such as acetone or methyl ethyl ketone. The inert solvent is preferably an aromatic hydrocarbon (particularly preferably benzene or toluene).

The reaction temperature depends on the starting material, solvent, base and the like and is usually between 0° C. and 200° C., preferably between room temperature and 150° C.

The reaction time depends on the starting material, base, solvent, reaction temperature, and the like and is generally from 1.5 minutes to 7 days, preferably from 6 hours to 3 days.

Step G2

Step G2 is a process for the preparation of compounds of general formula (XXVIII). Step G2 is accomplished by a hydrolysis reaction of a compound of formula (XXX) or (XXXI) in the presence of a base in an inert solvent according to a similar procedure to that indicated in Step B7.

After the reaction, each desired compound of Method G can be isolated from the reaction mixture by conventional treatments, for example, neutralization of the reaction mixture, if necessary, or filtration of the reaction mixture when insoluble material is present in the reaction mixture, addition of a solvent immiscible with water such as ethyl acetate to the neutralized solution or the filtrate, washing the resulting organic layer with water, separation of the organic layer containing the desired product, drying of the organic layer over anhydrous magnesium sulfate, anhydrous sodium sulfate or the like, and then evaporation of the organic solvent to give the desired product. The product thus obtained, if necessary, is further purified by conventional treatments, for example recrystallization or reprecipitation, or by conventional procedures in organic chemistry, for example, absorption column chromatography using a carrier such as silica gel, alumina, or Florisil consisting of magnesium and silica gel; partition column chromatography using a synthetic absorbent such as Sephadex LH-20 (product of Pharmacia Co., Ltd.), Amberlite XAD-11 (product of Rohm & Hass Co., Ltd.), or Diaion HP-20 (product of Mitsubishi Chemicals Co., Ltd.); ion exchange chromatography; normal-phase or reversed phase column chromatography using silica gel or alkylated silica gel (preferably high performance liquid column chromatography); or an appropriate combination of these chromatographic techniques; and elution using an appropriate solvent to isolate and purify the desired product.

In addition, if it is necessary to separate isomers, which are obtained in each step of method G, each isomer can be isolated according to the isolation or purification procedures indicated hereinbefore after the reaction of each step in method G, or after removal of the protecting group in method G.

(Method H)

Method H is a process for the preparation of compounds of general formula (XXVIII) from compounds of formula (XVI) or (IV) and is an alternative process to method F.

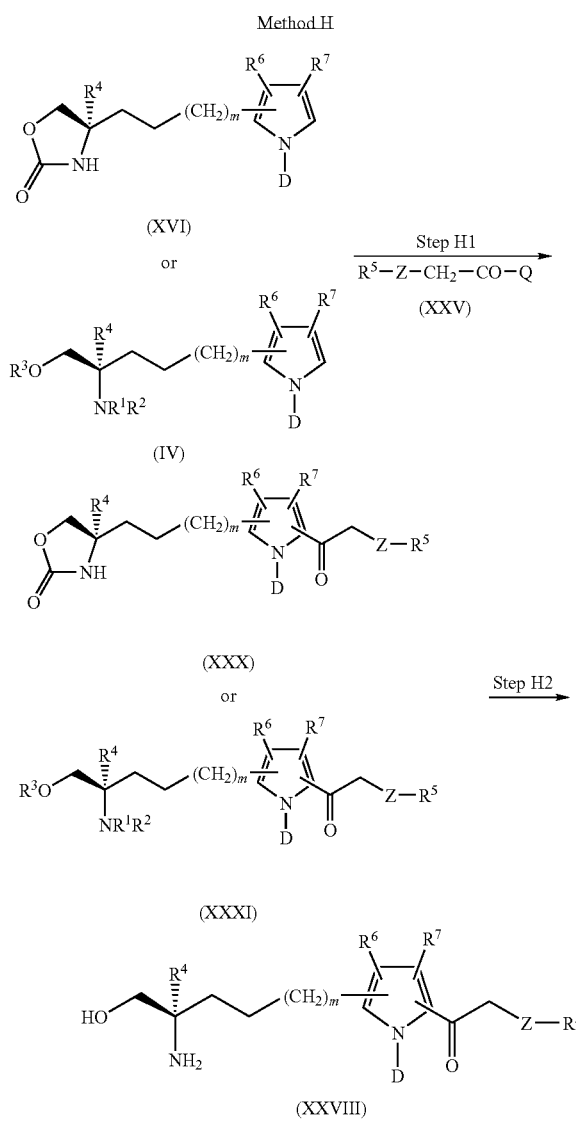

In the above reaction scheme $R^1$, $R^2$, $R^3$, $R^4$, $R^5$, $R^6$, $R^7$, D, Q, Z and m have the same meanings as those indicated hereinbefore.

Step H1

Step H1 is a process for the preparation of compounds of general formula (XXX) or (XXXI). Step H1 is accomplished by a Friedel-Crafts reaction of a compound of general formula (XVI) or (IV) with an acid halide of formula (XXV) in the presence of a Lewis acid such as aluminum chloride in an inert solvent according to similar procedures to those indicated in the literature (for example Synth. Commun., 19, 2721 (1989)). Step H1 can be also accomplished by treatment of a compound of general formula (XVI) or (IV) with a Grignard reagent, followed by reaction with an acid halide of formula (XXV) in an inert solvent according to similar procedures to those indicated in the literature (for example Bioorg. Med. Chem., 9, 621 (2001)).

The inert solvent employed in the above reaction is not particularly restricted and, for example, can be an aliphatic hydrocarbon such as hexane, heptane, ligroin, or petroleum ether; an aromatic hydrocarbon such as toluene, benzene, or xylene; a halogenated hydrocarbon such as dichloromethane, chloroform, carbon tetrachloride, dichloroethane, chlorobenzene, or dichlorobenzene; an ether such as diethyl ether, diisopropyl ether, tetrahydrofuran, dioxane, dimethoxyethane, or di(ethylene glycol) dimethyl ether; or a lower alkyl ketone such as acetone or methyl ethyl ketone. The inert solvent employed in the Friedel-Crafts reaction is preferably a halogenated hydrocarbon (particularly preferably dichloromethane or dichloroethane). The inert solvent employed in the Grignard reaction is preferably an ether (particularly preferably diethyl ether or tetrahydrofuran).

The reaction temperature depends on the starting material, solvent, reagent and the like and is usually between 0° C. and 100° C., preferably between 0° C. and 50° C.

The reaction time depends on the starting material, base, solvent, reaction temperature, and the like and is generally from 15 minutes to 24 hours, preferably from 1 hour to 12 hours.

Step H2

Step H2 is a process for the preparation of compounds of general formula (XXVIII). Step H2 is accomplished by a hydrolysis reaction of a compound of formula (XXX) or (XXXI) in the presence of a base in an inert solvent according to the same procedure as that indicated in Step G2.

After the reaction, each desired compound of Method H can be isolated from the reaction mixture by conventional treatments, for example, neutralization of the reaction mixture, if necessary, or filtration of the reaction mixture when insoluble material is present in the reaction mixture, addition of a solvent immiscible with water such as ethyl acetate to the neutralized solution or the filtrate, washing the resulting organic layer with water, separation of the organic layer containing the desired product, drying of the organic layer over anhydrous magnesium sulfate, anhydrous sodium sulfate or the like, and then evaporation of the organic solvent to give the desired product. The product thus obtained, if necessary, is further purified by conventional treatments, for example recrystallization or reprecipitation, or by conventional procedures in organic chemistry, for example, absorption column chromatography using a carrier such as silica gel, alumina, or Florisil consisting of magnesium and silica gel; partition column chromatography using a synthetic absorbent such as Sephadex LH-20 (product of Pharmacia Co., Ltd.), Amberlite XAD-11 (product of Rohm & Hass Co., Ltd.), or Diaion HP-20 (product of Mitsubishi Chemicals Co., Ltd.); ion exchange chromatography; normal phase or reversed phase column chromatography using silica gel or alkylated silica gel (preferably high performance liquid column chromatography); or an appropriate combination of these chromatographic techniques; and elution using an appropriate solvent to isolate and purify the desired product.

In addition, if it is necessary to separate isomers, which are obtained in each step of method H, each isomer can be isolated according to the isolation or purification procedures indicated hereinbefore after the reaction of each step in the method H, or after removal of the protecting group in method H.

(Method I)

Compounds of formula (II) can be prepared by methods appropriately selected from Methods A to H indicated hereinbefore, and can be also produced by Method I described hereinafter.

Method I1

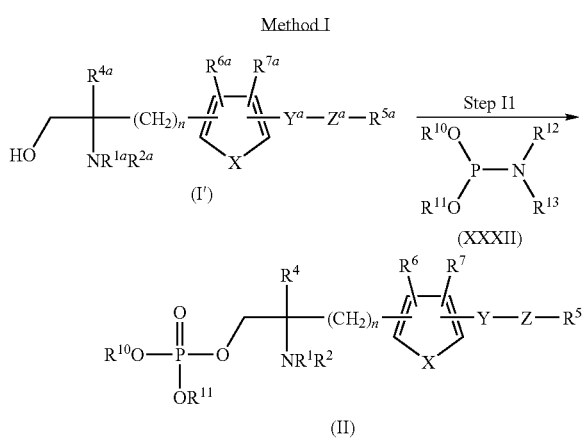

In the above reaction scheme $R^1$, $R^2$, $R^4$, $R^5$, $R^6$, $R^7$, $R^{10}$, $R^{11}$, X, Y, Z and n have the same meanings as those indicated hereinbefore. $R^{1a}$, $R^{2a}$, $R^{4a}$, $R^{5a}$, $R^{6a}$, $R^{7a}$, $Y^a$, and $Z^a$ have the same meanings as $R^1$, $R^2$, $R^4$, $R^5$, $R^6$, $R^7$, Y, and Z respectively, and when $R^{1a}$, $R^{2a}$, $R^{4a}$, $R^{5a}$, $R^{6a}$, $R^{7a}$, $Y^a$, and $Z^a$ have one or more hydroxyl, amino and/or carboxyl groups, $R^{1a}$, $R^{2a}$, $R^{4a}$, $R^{5a}$, $R^{6a}$, $R^{7a}$, $Y^a$, and $Z^a$ represent groups which may optionally contain one or more protected hydroxyl, amino and/or carboxyl groups. $R^{12}$ and $R^{13}$ are the same or different and each represents a lower alkyl group (preferably an ethyl or isopropyl group).

Step I1

Step I1 is a process for the preparation of compounds of general formula (II). Step I1 is accomplished by reaction of an alcohol derivative of formula (I'), which is a compound of formula (I) ($R^3$ is a hydrogen atom), with a compound of formula (XXXII), to afford an ester derivative of phosphorous acid, followed by reaction with an oxidizing agent and, if necessary, removal of one or more protecting groups of the amino, hydroxyl, carboxyl and/or phosphoric acid groups.

The removal of the protecting groups of the hydroxyl, amino and/or carboxyl groups of $R^1$, $R^2$, $R^4$, $R^5$, $R^6$, $R^7$, Y, and Z is accomplished according to the same procedures as those indicated in Step A7.

The order of the removal reactions of the protecting groups of the amino, hydroxyl and/or carboxyl groups can be arbitrarily selected and the removal reactions of these groups can be preferentially carried out according to the appropriate reaction conditions.

The esterification of phosphoric acid with a compound having a primary hydroxyl group can be easily accomplished by procedures known to those skilled in organic chemistry (for example, Jikken Kagaku Koza 22 (4$^{th}$ Edition) "Organic Synthesis IV" Chapter 3 "Ester of Phosphoric Acid" (published Maruzen Co., Ltd.)). The preferred procedure will be shown hereinafter.

The process is carried out by reaction of an alcohol derivative of formula (I') with a compound of formula (XXXII) in the presence of an activating reagent in an inert solvent to afford an ester of phosphorous acid, followed by reaction with an oxidizing reagent.

The inert solvent employed in the reaction of the compound of formula (I') with the compound of formula (XXXII) is, for example, an aliphatic hydrocarbon such as hexane or heptane; an aromatic hydrocarbon such as benzene, toluene, or xylene; a halogenated hydrocarbon such as dichloromethane, chloroform, 1,2-dichloroethane, or carbon tetrachloride; an ether such as diethyl ether, diisopropyl ether, or tetrahydrofuran; or a mixture of the solvents indicated hereinbefore. The inert solvent is preferably a halogenated hydrocarbon or ether (most preferably dichloromethane or tetrahydrofuran).

The activating reagent employed in the above reaction is, for example, a tetrazole derivative such as 1H-tetrazole, 5-methyl-1H-tetrazole, or 5-phenyl-1H-tetrazole (preferably 1H-tetrazole).

The compound of formula (XXXII) is preferably a phosphoramidite such as diallyl N,N-diisopropylphosphoramidite, dimethyl N,N-diisopropylphosphoramidite, diethyl N,N-diisopropylphosphoramidite, di-tert-butyl N,N-diisopropylphosphoramidite, dibenzyl N,N-diisopropylphosphoramidite, dimethyl N,N-diethylphosphoramidite, di-tert-butyl N,N-diethylphosphoramidite, dibenzyl N,N-diethylphosphoramidite, N,N-diethyl-1,5-dihydro-2,4,3-benzodioxaphtosphepin-3-amine, bis(2-cyanoethyl) N,N-diisopropylphosphoramidite, or bis(9-fluorenylmethyl) N,N-diisopropylphosphoramidite, most preferably diallyl N,N-diisopropylphosphoramidite.

The reaction temperature depends on the starting material, solvent and the like and is usually between −10° C. and 60° C. (preferably between 0° C. and 30° C.).

The reaction time depends on the starting material, solvent, reaction temperature, and the like and is generally from 10 minutes to 24 hours (preferably from 30 minutes to 2 hours).

The ester of phosphorous acid thus obtained in the above reaction can be used in next oxidation reaction without isolation or purification.

The inert solvent employed in the oxidation is the same solvent as that indicated for the reaction of the alcohol derivative of formula (I') with the compound of formula (XXXII).

The oxidizing agent is, for example, a peroxide such as tert-butyl hydroperoxide, cumene hydroperoxide, m-chloroperbenzoic acid, 3,5-dinitroperbenzoic acid, o-carboxyperbenzoic acid, dimethyloxolane, peracetic acid, trifluoroperacetic acid, perphthalic acid, or hydrogen peroxide, preferably tert-butyl hydroperoxide or m-chloroperbenzoic acid.

The reaction temperature depends on the ester of phosphorous acid, oxidizing agent, solvent and the like and is usually between −78° C. and room temperature (preferably between −78° C. and 0° C.).

The reaction time depends on the ester of phosphorous acid, oxidizing agent, solvent, reaction temperature, and the like and is generally from 5 minutes to 2 hours (preferably from 5 minutes to 30 minutes).

When the protecting group of phosphoric acid is a lower alkyl group which may be optionally substituted with one or more cyano, optionally substituted silyl, aryl, heterocyclyl, arylthio, or sulfonyl groups or halogen atoms, said protecting group can be removed by acid hydrolysis in the presence of water in an inert solvent or by reaction with a trimethylsilyl halide (for example, trimethylsilyl bromide or trimethylsilyl iodide) in an inert solvent.

The inert solvent employed in the above hydrolysis reaction is, for example, an alcohol such as methanol or ethanol; or an ether such as diethyl ether, diisopropyl ether, tetrahydrofuran, or dioxane; preferably an ether and most preferably dioxane.

The acid employed in the above reaction is, for example, an inorganic acid such as hydrochloric acid, sulfuric acid, phosphoric acid, or nitric acid; preferably hydrochloric acid.

The reaction temperature is between 0° C. and 150° C. (preferably between 20° C. and 100° C.).

The reaction time is from 1 hour to 60 hours (preferably from 1 hour to 48 hours).

The inert solvent employed in the reaction with a trimethylsilyl halide is, for example, an aliphatic hydrocarbon such as hexane or heptane; an aromatic hydrocarbon such as benzene, toluene or xylene; a halogenated hydrocarbon such as dichloromethane, chloroform, 1,2-dichloroethane, or carbon tetrachloride; a nitrile such as acetonitrile, or a mixture of the solvents indicated hereinbefore. The solvent is preferably a halogenated hydrocarbon or a nitrile (more preferably chloroform, dichloromethane or acetonitrile).

The reaction temperature depends on the starting material, solvent and the like employed in the above reaction and is generally between −78° C. and 100° C. (preferably between 0° C. and 80° C.)

The reaction time depends on the starting material, solvent, reaction temperature, and the like employed in the above reaction and is generally from 10 minutes to 24 hours (preferably from 1 hour to 6 hours).

When the protecting group of phosphoric acid is a lower alkenyl group, said protecting group can be removed by reaction with a palladium compound in the presence of an amine, formic acid, a salt of formic acid, a trialkyltin compound or a compound having an active methylene group in an inert solvent.

The inert solvent employed in the above reaction is, for example, an aliphatic hydrocarbon such as hexane or heptane; an aromatic hydrocarbon such as toluene, benzene, or xylene; a halogenated hydrocarbon such as chloroform or dichloromethane; a nitrile such as acetonitrile; an ester such as methyl acetate, ethyl acetate, or propyl acetate; an ether such as diethyl ether, diisopropyl ether, tetrahydrofuran or dioxane; an alcohol such as methanol, ethanol, n-propanol, or isopropanol; an organic acid such as acetic acid; water; or a mixture of water and a solvent indicated hereinbefore. The solvent is preferably a nitrile or an ether (particularly preferably acetonitrile or tetrahydrofuran).

The amine employed in the above reaction is, for example, a tertiary amine such as triethylamine, tributylamine, diisopropylethylamine, N-methylmorpholine, 1,4-diazabicyclo[2.2.2]octane (DABCO); a secondary amine such as diethylamine, dimethylamine, diisopropylamine, or pyrrolidine; or a primary amine such as ethylamine, propylamine, butylamine, N—N-dimethylaniline, or N,N-diethylaniline. The preferred amine is pyrrolidine.

The salt of formic acid employed in the above reaction is preferably the ammonium salt of formic acid, the triethylamine salt of formic acid, or the n-butylamine salt of formic acid.

The trialkyltin compound employed in the above reaction is preferably trimethyltin, triethyltin or tributyltin and particularly preferably tributyltin.

The compound having an active methylene group employed in the above reaction is, for example, an ester of malonic acid such as methyl malonate or ethyl malonate; an ester of cyanoacetic acid such as methyl cyanoacetate; an ester of a β-ketoacetic acid such as methyl acetoacetate, ethyl acetoacetate, or ethyl benzoate; a 1,3-diketone such as acetylacetone, benzoylacetone, dibenzoylmethane, 1,3-cyclopentanedione, 1,3-cyclohexanedione, or dimedone; or an alkali metal salt of a compound having an active methylene group indicated hereinbefore. The compound is preferably a sodium salt of a 1,3-diketone or an ester of malonic acid.

The palladium compound employed in the above reaction is, for example, a palladium compound such as tetrakis(triphenylphosphine)palladium, diacetoxypalladium, dichlorodi(triphenylphosphine)palladium, or bis(dibenzylideneacetone)palladium. The preferred palladium compound is tetrakis(triphenylphosphine)palladium.

The reaction temperature depends on the starting material, solvent and the like employed in the reaction and is generally between 0° C. and 100° C. (preferably between 20° C. and 80° C.).

The reaction time depends on the starting material, solvent, reaction temperature, and the like employed in the reaction and is generally from 10 minutes to 48 hours (preferably from 30 minutes to 24 hours).

When the protecting group of phosphoric acid is an arylmethyl group, said group is removed by the same procedure as that described in the case where the protecting group of the amino group is an aralkyl or aralkyloxycarbonyl group in Step A7 indicated hereinbefore.

When the protecting group of phosphoric acid is an aryl group, said group is removed by the same procedure as that described in the case where the protecting group of the amino group is a lower aliphatic acyl group, an aromatic acyl group, a lower alkoxycarbonyl group or a substituted methylene group which can form a Schiff base group in Step A7 indicated hereinbefore.

When the protecting group of phosphoric acid is an amide group, said group is removed by the same acid treatment as that described in the case where the protecting group of the amino group is an aliphatic acyl group, an aromatic acyl group, an alkoxycarbonyl group or a substituted methylene group which can form a Schiff base in Step A7 indicated hereinbefore.

After the reaction, the desired compound of each reaction can be isolated from the reaction mixture by conventional treatments, for example, if necessary, neutralization of the reaction mixture; or decomposition of the oxidizing agent with a reducing agent if the oxidizing agent is present in the reaction mixture, or filtration of the reaction mixture when insoluble material is present in the reaction mixture, addition of a solvent immiscible with water such as ethyl acetate to the neutralized solution or the filtrate, separation of the organic layer containing the desired compound, washing the resulting organic layer with water, drying of the organic layer over anhydrous magnesium sulfate, anhydrous sodium sulfate, anhydrous sodium hydrogencarbonate or the like, and then evaporation of the organic solvent to give the desired product. The product thus obtained, if necessary, is further purified by conventional procedures in organic chemistry, for example by recrystallization, reprecipitation, chromatography or an appropriate combination of these isolation or purification procedures.

(Method J)

Compounds of formula (III) can be produced by methods appropriately selected from Methods A to H, and also can be prepared by Method J indicated hereinafter.

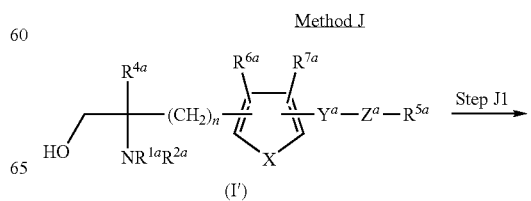

Method J

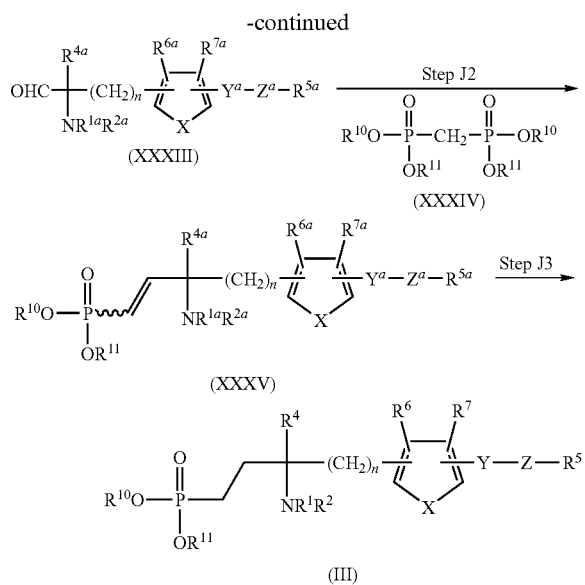

In the above reaction scheme $R^1$, $R^{1a}$, $R^2$, $R^{2a}$, $R^4$, $R^{4a}$, $R^5$, $R^{5a}$, $R^6$, $R^{6a}$, $R^7$, $R^{7a}$, $R^{10}$, $R^{11}$, Y, $Y^a$, Z, $Z^a$ and n have the same meanings as those indicated hereinbefore.

Step J1.

Step J1 is a process for the preparation of aldehyde compounds of general formula (XXXIII) and is accomplished by oxidation of an alcohol compound of general formula (I').

The oxidation reaction is not particularly restricted provided that it can convert a primary alcohol into the corresponding aldehyde and, for example, is the Collins oxidation which is conducted using pyridine and chromic acid in dichloromethane; the PCC oxidation which is conducted using pyridinium chlorochromate (PPC) in dichloromethane; the PDC oxidation which is conducted using pyridinium dichromate (PDC) in dichloromethane; the DMSO oxidation such as the Swern oxidation which is conducted using an electrophilic reagent (for example acetic anhydride, trifluoroacetic anhydride, thionyl chloride, sulfuryl chloride, oxalyl chloride, dicyclohexylcarbodiimide, diphenylketene-p-tolylimine, N,N-diethylaminoacetylene, or sulfur trioxide-pyridine complex) and dimethyl sulfoxide (DMSO) in dichloromethane; the manganese dioxide oxidation which is conducted using manganese dioxide in dichloromethane or benzene; or the Dess-Martin oxidation which is conducted using the Dess-Martin periodinane in dichloromethane. Preferred oxidation reactions are the Dess-Martin oxidation, PDC oxidation or Swern oxidation in dichloromethane.

The reaction temperature depends on the starting material, solvent, oxidizing agent and the like and is usually between −78° C. and 100° C., preferably between −78° C. and 30° C.

The reaction time depends on the starting material, solvent, oxidizing agent, reaction temperature and the like and is usually from 10 minutes to 2 days, preferably from 30 minutes to 24 hours.

Step J2

Step J2 is a process for the preparation of α,β-unsaturated esters of phosphoric acid of formula (XXXV) and is accomplished by reaction of an aldehyde compound of formula (XXXIII) with a compound of general formula (XXXIV) in the presence of a base in an inert solvent.

The inert solvent employed in the above reaction is not particularly restricted provided that it can dissolve the starting materials to some extent, and is preferably an aromatic hydrocarbon such as benzene, toluene, or xylene; a halogenated hydrocarbon such as dichloromethane, chloroform, or carbon tetrachloride; an ether such as diethyl ether, diisopropyl ether, tert-butyl methyl ether, or tetrahydrofuran; a nitrile such as acetonitrile or isobutyronitrile; an amide such as formamide; or a sulfoxide such as dimethyl sulfoxide. The solvent is more preferably an aromatic hydrocarbon or ether (most preferably benzene or tetrahydrofuran).

The base employed in the above reaction is not particularly restricted provided that a carbanion corresponding to the compound of formula (XXXIV) can be produced by the base, and is preferably an alkali metal carbonate such as sodium carbonate or potassium carbonate; an alkali metal hydrogencarbonate such as sodium hydrogencarbonate or potassium hydrogencarbonate; an alkali metal hydride such as sodium hydride or potassium hydride; an alkali metal hydroxide such as sodium hydroxide or potassium hydroxide; an alkali metal alkoxide such as sodium methoxide, sodium ethoxide, potassium methoxide or potassium ethoxide; an organic amine such as N-methylmorpholine or triethylamine; or an organometallic base such as butyllithium or lithium diisopropylamide. The base is more preferably an alkali metal alkoxide, an alkali metal hydride or an organometallic base, and most preferably sodium hydride.

The reaction temperature depends on the starting material, solvent, phosphonium salt, base, and the like and is usually between −80° C. and 100° C., preferably between −20° C. and 50° C.

The reaction time depends on the starting material, solvent, phosphonium salt, base, and the like and is usually from 10 minutes to 2 days, preferably from 10 minutes to 12 hours.

Step J3

Step J3 is a process for the preparation of compounds of general formula (III) and is accomplished by reduction of an unsaturated ester of phosphoric acid of formula (XXXV) under an atmosphere of hydrogen in the presence of a catalyst for catalytic hydrogenation in an inert solvent, followed by, if necessary, removal of the protecting group of the amino, hydroxyl, carboxyl and/or phosphoric acid groups.

The inert solvent employed in the reaction of the unsaturated ester of phosphoric acid of formula (XXXV) is not particularly restricted provided that it has no adverse effect on the reaction and can dissolve the starting materials to some extent, and is preferably an alcohol such as methanol, ethanol, or isopropanol, an ether such as diethyl ether, diisopropyl ether, tert-butyl methyl ether, tetrahydrofuran, or dioxane; an aromatic hydrocarbon such as benzene, toluene, or xylene; an aliphatic hydrocarbon such as hexane or cyclohexane; or an ester such as ethyl acetate or propyl acetate. The solvent is preferably an alcohol (most preferably methanol or ethanol).

The catalyst employed in the above catalytic hydrogenation is preferably palladium-charcoal, palladium hydroxide-charcoal, palladium black, platinum oxide, platinum black, rhodium-aluminum oxide, triphenylphosphine-rhodium chloride (Wilkinson complex), palladium-barium sulfate or Raney nickel. The more preferred catalysts are palladium-charcoal and triphenylphosphine-rhodium chloride (Wilkinson complex).

The pressure of hydrogen is not particularly restricted and is from 1 to 10 atmospheric pressures.

The reaction temperature depends on the starting material, solvent, base, and the like and is usually between 0° C. and 100° C. (preferably between 0° C. and 50° C.).

The reaction time depends on the starting material, reaction temperature, solvent, and base and is usually from 5 minutes to 48 hours (preferably from 30 minutes to 24 hours).

After the reaction, the desired compound of each reaction can be isolated from the reaction mixture by conventional treatments, for example, if necessary, neutralization of the reaction mixture, or decomposition of the oxidizing agent with a reducing agent if the oxidizing agent is present in the reaction mixture, or filtration of the reaction mixture when insoluble material is present in the reaction mixture, addition of a solvent immiscible with water such as ethyl acetate to the neutralized solution or the filtrate, separation of the organic layer containing the desired compound, washing the resulting organic layer with water, drying of the organic layer over anhydrous magnesium sulfate, anhydrous sodium sulfate, anhydrous sodium hydrogencarbonate or the like, and then evaporation of the organic solvent to give the desired product. The product thus obtained, if necessary, is further purified by conventional procedures in organic chemistry, for example by recrystallization, reprecipitation, chromatography or an appropriate combination of these isolation or purification procedures.

If necessary, the removal of the protecting group of the amino group, the removal of the protecting group of the hydroxyl group, or the removal of the protecting group of the carboxyl group can be accomplished by the same procedures as those indicated in Step A7 hereinbefore, and the removal of the protecting group of phosphoric acid can be accomplished by the same procedure as that indicated in Step I1 hereinbefore.

Amino alcohol derivatives of general formula (I), phosphate derivatives of general formula (II), phosphonic acid derivatives of general formula (III), pharmacologically acceptable salts thereof, or pharmacologically acceptable esters thereof of the present invention exhibit excellent immunosuppressive activity with low toxicity. Therefore, pharmaceutical compositions comprising, as an active ingredient, compounds of formula (I), (II), or (III), pharmacologically acceptable salts thereof, or pharmacologically acceptable esters thereof of the present invention are useful as preventive or therapeutic agents (particularly therapeutic agents) for warm-blooded animals (particularly humans) for autoimmune diseases or other immunology-related diseases such as rejection caused by transplantation of various organs or skin, systemic lupus erythematosus, rheumatoid arthritis, polymyositis, fibrositis, skeletal muscle inflammation, arthrosteitis, osteoarthritis, dermatomyositis, scleoderma, Behcet's syndrome, Crohn's disease, ulcerative colitis, autoimmune hepatitis, aplastic anemia, idiopathic thrombocytopenic purpura, autoimmune hemolytic anemia, multiple sclerosis, autoimmune bullosis, psoriasis vulgaris, vasculitis syndrome, Wegener's granuloma, uveitis, Sjögren's syndrome, idiopathic interstitial pneumonia, Goodpasture's syndrome, sarcoidosis, allergic granulomatous angitis, bronchial asthma, myocarditis, cardiomyopathy, aortitis syndrome, post myocardial infarction syndrome, primary pulmonary hypertension, minimal change nephrotic syndrome, membranous nephropathy, membranoproliferative glomerulonephritis, focal glomerular sclerosis, crescentic glomerulonephritis, myasthenia gravis, inflammatory neuropathy, atopic dermatitis, chronic actinic dermatitis, photosensitivity, pressure sores, Sydenham's chorea, sclerosis, adult-onset type diabetes mellitus, insulin dependent diabetes mellitus, juvenile diabetes mellitus, atherosclerosis, glomerular nephritis, IgA nephropathy, tubulointerstitial nephritis, primary biliary cirrhosis, primary sclerosing cholangitis, fulminant hepatitis, viral hepatitis, GVHD, contact dermatitis, and sepsis; diseases of infection by fungus, mycoplasma, virus, and protozoan and the like; cardiovascular diseases such as cardiac failure, cardiac hypertrophy, arrhythmia, angina pectoris, cardiac ischemia, arterial embolism, aneurysm, varix, and circulation disorders; brain diseases such as Alzheimer's disease, dementia, Parkinson's disease, stroke, brain infarction, brain ischemia, depression, manic-depressive illness, schizophrenia, Huntington's chorea, epilepsy, convulsion, attention deficit disorder, encephalitis, cerebral meningitis, loss of appetite, and hyperphagia; and various diseases such as lymphoma, leukemia, diuresis, pollakisuria, and diabetic retinopathy (particularly, autoimmune diseases such as rejection caused by transplantation of various organs or skin, systemic lupus erythematosus, rhematoid arthritis, multiple sclerosis, and atopic dermatitis).

The compounds of general formula (I), (II), or (III), pharmacologically acceptable salts thereof, or pharmacologically acceptable esters thereof of the present invention can be administered for the treatment or prevention of the above-mentioned diseases in a suitable dosage form, which is prepared from the compound alone or by mixing with a suitable pharmacologically acceptable carrier, i.e., excipient and/or diluent, such as tablets, capsules, granules, powders or syrups for oral administration, or injections or suppositories for parenteral administration.

Preparations are prepared by conventionally known methods using additive agents such as excipients (for instance, organic excipients including sugar derivatives such as lactose, sucrose, glucose, mannitol, and sorbitol; starch derivatives such as corn starch, potato starch, $\alpha$-starch, and dextrin; cellulose derivatives such as crystalline cellulose; gum arabic; dextran; pullulan; and inorganic excipients including silicate derivatives such as light anhydrous silicic acid, synthetic aluminum silicate, calcium silicate, and magnesium aluminometasilicate; phosphates such as calcium hydrogenphosphate; carbonates such as calcium carbonate; and sulfates such as calcium sulfate), lubricants (for instance, stearic acid, metal salts of stearic acid such as calcium stearate and magnesium stearate; talc; colloidal silica; waxes such as veegum and spermaceti; boric acid; adipic acid; sulfates such as sodium sulfate; glycol; fumaric acid; sodium benzoate; DL-leucine; sodium fatty acid; laurylsulfates such as sodium lauryl sulfate and magnesium lauryl sulfate; silicates such as silicic anhydride and silicic hydrate; and the starch derivatives described above can be listed), binders (for instance, hydroxypropylcellulose, hydroxypropylmethylcellulose, polyvinylpyrrolidone, Macrogol, and similar excipients to those described above), disintegrants (for instance, cellulose derivatives such as low-substituted hydroxypropylcellulose, carboxymethylcellulose, calcium carboxymethylcellulose, and internally crosslinked sodium carboxymethylcellulose; and chemically modified starch/cellulose derivatives such as carboxymethylstarch, sodium carboxymethylstarch, and crosslinked polyvinylpyrrolidone), stabilizers (for instance, para-oxy benzoates such as methylparaben and propylparaben; alcohols such as chlorobutanol, benzylalcohol, and phenylethylalcohol; benzalkonium chloride; phenols such as phenol and cresol; thimerosal; dehydroacetic acid; and sorbic acid), flavors (for instance, conventionally employed sweeteners, acidifiers, and flavors), diluents, and the like.

The dosage varies depending on the symptoms, age, etc. of the patient. For example, in the case of oral administration, it is desirable to administer 0.05 mg (preferably 5 mg) as a lower limit and 200 mg (preferably 40 mg) as an upper limit per one time for a human adult and one to six times per day depending on the symptoms of the patient.

In the case of intravenous administration, it is desirable to administer 0.01 mg (preferably 1 mg) as a lower limit and mg (preferably 10 mg) as an upper limit per one time for a human adult and one to six times per day depending on the symptoms of the patient.

The present invention will further be exemplified in more detail by the Examples, Reference examples, Formulation examples, and Test examples. However the scope of the present invention is not limited by these Examples.

EXAMPLES

Example 1

(2R)-2-Amino-2-methyl-4-[5-(5-phenylpent-1-ynyl)furan-2-yl]butan-1-ol oxalate (Exemplification compound number: 1-621 having formula Ia-1)

(1a) (2R)-1-Acetoxy-2-acetylamino-2-methyl-4-[5-(5-phenylpent-1-ynyl)furan-2-yl]butane To a suspension of (2R)-1-acetoxy-2-acetylamino-2-methyl-4-(5-bromofuran-2-yl)butane (0.3016 g, 0.91 mmol) obtained in Reference example 6,5-phenylpent-1-yne (0.3974 g, 2.76 mmol), dichlorobis(triphenylphosphine)palladium(II) (63.0 mg, 0.090 mmol) and copper(I) iodide (35.4 mg, 0.19 mmol) in N,N-dimethylformamide (9.0 ml) was added triethylamine (1.25 ml, 9.0 mmol) with stirring, and the resulting mixture was stirred at room temperature under a nitrogen atmosphere for 10 hours. After stirring, saturated aqueous ammonium chloride solution was added to the reaction mixture to quench the reaction, and to the resulting mixture were furthermore added water and ethyl acetate. The resulting mixture was stirred at room temperature for 30 minutes and then extracted with ethyl acetate. The extract was washed successively with water and saturated aqueous sodium chloride solution and dried over anhydrous sodium sulfate. After filtration, the solvent was removed in vacuo, and the residue was purified by chromatography on a silica gel column using a mixed solvent of ethyl acetate and hexane (1:1) as the eluent to afford the title compound (0.2841 g, yield: 79%)

$^1$H-NMR spectrum (CDCl$_3$, 400 MHz) δ: 7.31-7.27 (m, 2H), 7.22-7.18 (m, 3H), 6.38 (d, 1H, J=3.2 Hz), 5.98 (d, 1H, J=3.2 Hz), 5.36 (br s, 1H), 4.29 (d, J=11.2 Hz), 4.18 (d, 1H, J=11.2 Hz), 2.77 (t, 2H, J=7.8 Hz), 2.64 (dt, 2H, J=8.5 Hz, 17.0 Hz), 2.44 (t, 2H, J=7.1 Hz), 2.30-2.22 (m, 1H), 2.09 (s, 3H), 2.01-1.88 (m, 6H), 1.35 (s, 3H).

IR spectrum $\nu_{max}$ cm$^{-1}$ (CHCl$_3$): 3691, 3444, 2947, 1737, 1681, 1601, 1511, 1453, 1374, 1251, 1042, 812, 803.

Mass spectrum (FAB$^+$) m/z: 396 ((M+H)$^+$).

(1b) (2R)-2-Amino-2-methyl-4-[5-(5-phenylpent-1-ynyl) furan-2-yl]butan-1-ol oxalate To a solution of (2R)-1-acetoxy-2-acetylamino-2-methyl-4-[5-(5-phenylpent-1-ynyl)furan-2-yl]butane (0.2710 g, 0.69 mmol) obtained in Example (1a) in a mixed solvent of tetrahydrofuran (1.4 ml) and methanol (1.4 ml) were added successively water (1.4 ml) and lithium hydroxide monohydrate (0.2854 g, 6.80 mmol) with stirring, and the resulting mixture was stirred at 50° C. for 4 hours. After cooling, water was added to the reaction mixture, and the resulting mixture was extracted with dichloromethane. The extract was washed with saturated aqueous sodium chloride solution and dried over anhydrous sodium sulfate. After filtration, the solvent was removed in vacuo, and the residue was purified by chromatography on a basic silica gel column (NH type) using a mixed solvent of dichloromethane and methanol (100:1) as the eluent to afford the crude (2R)-2-amino-2-methyl-4-[5-(5-phenylpent-1-ynyl)furan-2-yl]butan-1-ol (0.2072 g).

Subsequently, to a solution of the crude product thus obtained in methanol was added anhydrous oxalic acid (98% pure) (59.2 mg, 0.64 mmol), and the resulting mixture was stirred at room temperature for 30 minutes. After stirring, the reaction mixture was evaporated in vacuo, and ethyl acetate was added to the residue. The crystals precipitated were collected by filtration, washed with ethyl acetate and dried in vacuo to afford the title compound (0.2344 g, yield: 91%).

$^1$H-NMR spectrum (CD$_3$OD, 400 MHz) δ: 7.29-7.25 (m, 2H), 7.21-7.14 (m, 3H), 6.40 (d, 1H, J=3.0 Hz), 6.09 (d, 1H, J=3.0 Hz), 3.59 (d, 1H, J=11.6 Hz), 3.50 (d, 1H, J=11.6 Hz), 2.77-2.65 (m, 4H), 2.41 (t, 2H, J=7.0 Hz), 2.07-1.83 (m, 4H), 1.29 (s, 3H).

IR spectrum $\nu_{max}$ cm$^{-1}$ (KBr): 3353, 3128, 2940, 1720, 1645, 1614, 1598, 1542, 1403, 1220, 1078, 789, 713, 700.

Mass spectrum (FAB$^+$) m/z: 312 ((M+H)$^+$; as free form of title compound).

Example 2

(2R)-2-Amino-2-methyl-4-[5-(5-cyclohexylpent-1-ynyl)furan-2-yl]butan-1-ol oxalate (Exemplification compound number: 1-570 having formula Ia-1)

The title compound was synthesized in a yield of 68% using (2R)-1-acetoxy-2-acetylamino-2-methyl-4-(5-bromofuran-2-yl)butane obtained in Reference example 6 and 5-cyclohexylpent-1-yne as the starting materials by conducting successively the reactions similar to those mentioned in Examples (1a) and (1b).

$^1$H-NMR spectrum (CD$_3$OD, 400 MHz) δ: 6.36 (d, 1H, J=3.1 Hz), 6.08 (d, 1H, J=3.1 Hz), 3.59 (d, 1H, J=11.5 Hz), 3.49 (d, 1H, J=11.5 Hz), 2.77-2.64 (m, 2H), 2.39 (t, 2H, J=7.2 Hz), 2.07-1.90 (m, 2H), 1.76-1.54 (m, 7H), 1.35-1.12 (m, 9H), 0.96-0.86 (m, 2H).

IR spectrum $\nu_{max}$ cm$^{-1}$ (KBr) 3362, 3124, 2923, 2850, 1720, 1611, 1597, 1542, 1467, 1403, 1279, 1220, 1067, 967, 791, 721, 700.

Mass spectrum (FAB$^+$) m/z: 318 ((M+H)$^+$; as free form of title compound).

Example 3

(2R)-2-Amino-2-methyl-4-[5-(4-cyclohexyloxybut-1-ynyl)furan-2-yl]butan-1-ol oxalate (Exemplification compound number: 1-842 having formula Ia-1)

The title compound was synthesized in a yield of 66% using (2R)-1-acetoxy-2-acetylamino-2-methyl-4-(5-iodofuran-2-yl)butane obtained in Reference example 7 and 4-cyclohexyloxybut-1-yne as the starting materials by conducting successively the reactions similar to those mentioned in Examples (1a) and (1b).

$^1$H-NMR spectrum (CD$_3$OD, 400 MHz) δ: 6.40 (d, 1H, J=3.3 Hz), 6.09 (d, 1H, J=3.3 Hz), 3.63 (t, 2H, J=6.6 Hz), 3.58 (d, 1H, J=11.7 Hz), 3.50 (d, 1H, J=11.7 Hz), 3.39-3.32 (m, 1H), 2.77-2.62 (m, 4H), 2.07-1.89 (m, 4H), 1.77-1.73 (m, 2H), 1.56-1.53 (m, 1H), 1.36-1.23 (m, 8H).

IR spectrum $\nu_{max}$ cm$^{-1}$ (KBr): 3360, 3099, 2932, 2857, 1719, 1614, 1597, 1542, 1403, 1219, 1106, 967, 785, 720, 711.

Mass spectrum (FAB$^+$) m/z: 320 ((M+H)$^+$; as free form of title compound).

Example 4

(2R)-2-Amino-2-methyl-4-{5-[3-(3,4-dimethylphenyloxy)prop-1-ynyl]furan-2-yl}butan-1-ol oxalate (Exemplification compound number: 1-1836 having formula Ia-1)

The title compound was synthesized in a yield of 46% using (2R)-1-acetoxy-2-acetylamino-2-methyl-4-(5-bromofuran-2-yl)butane obtained in Reference example 6 and 3-(3,4-dimethyl)phenyloxy-1-propyne as the starting materials by conducting successively the reactions similar to those mentioned in Examples (1a) and (1b).

$^1$H-NMR spectrum (CD$_3$OD, 400 MHz) δ: 7.02 (d, 1H, J=8.3 Hz), 6.77 (d, 1H, J=2.7 Hz), 6.71 (dd, 1H, J=8.3 Hz, 2.7 Hz), 6.55 (d, 1H, J=3.2 Hz), 6.14 (d, 1H, J=3.2 Hz), 4.88 (s, 2H), 3.58 (d, 1H, J=11.7 Hz), 3.49 (d, 1H, J=11.7 Hz), 2.79-2.66 (m, 2H), 2.23 (s, 3H), 2.19 (s, 3H), 2.07-1.90 (m, 2H), 1.28 (s, 3H).

IR spectrum ν$_{max}$ cm$^{-1}$ (KBr): 3358, 3134, 2921, 2582, 1720, 1649, 1616, 1579, 1542, 1499, 1370, 1286, 1250, 1223, 1166, 1122, 1046, 1025, 802, 712.

Mass spectrum (FAB$^+$) m/z: 328 ((M+H)$^+$; as free form of title compound).

Example 5

(2R)-2-Amino-2-methyl-4-[5-(5-phenylpentanoyl)furan-2-yl]butan-1-ol oxalate (Exemplification compound number 1-1093 having formula Ia-1)

To a solution of (2R)-2-amino-2-methyl-4-[5-(5-phenylpent-1-ynyl)furan-2-yl]butan-1-ol (0.3440 g, 1.11 mmol) obtained in Example (1b) in methanol (3.5 ml) was added a 6N aqueous sulfuric acid solution (3.5 ml) with stirring, and the resulting mixture was refluxed for 4 hours. After cooling, the reaction mixture was neutralized with saturated aqueous sodium hydrogencarbonate solution, and then water and dichloromethane were furthermore added. The resulting mixture was stirred for 30 minutes and extracted with dichloromethane. The extract was washed with saturated aqueous sodium chloride solution and dried over anhydrous sodium sulfate. After filtration, the solvent was removed in vacuo, and the residue was purified by chromatography on a basic silica gel column (NH type) using a mixed solvent of dichloromethane and methanol (100:1) as the eluent to afford the reaction product.

Subsequently, to a solution of the reaction product thus obtained in methanol was added anhydrous oxalic acid (98% pure) (91.8 mg, 1.00 mmol), and the resulting mixture was stirred at room temperature for 30 minutes. After stirring, the reaction mixture was evaporated in vacuo, and ethyl acetate was added to the residue. The crystals precipitated were collected by filtration, washed with ethyl acetate and dried in vacuo to afford the title compound (0.3687 g, yield: 90%).

$^1$H-NMR spectrum (CD$_3$OD, 400 MHz) δ: 7.31 (d, 1H, J=3.6 Hz), 7.25-7.22 (m, 2H), 7.17-7.12 (m, 3H), 6.36 (d, 1H, J=3.6 Hz), 3.61 (d, 1H, J=11.6 Hz), 3.52 (d, 1H, J=11.6 Hz), 2.89-2.76 (m, 4H), 2.64 (t, 2H, J=7.2 Hz), 2.13-1.95 (m, 2H), 1.75-1.63 (m, 4H), 1.30 (s, 3H).

IR spectrum ν$_{max}$ cm$^{-1}$ (KBr): 3108, 3027, 2981, 2935, 1718, 1698, 1661, 1604, 1542, 1516, 1202, 1093, 1082, 1047, 797, 700.

Mass spectrum (FAB$^+$) m/z: 330 ((M+H)$^+$; as free form of title compound).

Example 6

(2R)-2-Amino-2-methyl-4-[5-(5-phenylpentyl)furan-2-yl]butan-1-ol oxalate (Exemplification compound number: 1-93 having formula Ia-1)

(6a) (2R)-1-Acetoxy-2-acetylamino-2-methyl-4-[5-(5-phenylpentyl) furan-2-yl]butane To a suspension of 10% palladium-charcoal (50% wet with water) (25 mg) in methanol (1 ml) was added a solution of (2R)-1-acetoxy-2-acetylamino-2-methyl-4-[5-(5-phenylpent-1-ynyl)furan-2-yl]butane (0.1245 g, 0.32 mmol) obtained in Example (1a) in methanol (1.5 ml), and the resulting mixture was stirred at room temperature under a hydrogen atmosphere for 8 hours. After stirring, the internal atmosphere was replaced with nitrogen, and the palladium-charcoal in the reaction mixture was filtered off using celite, which was washed with ethyl acetate. The filtrate and the washings were combined and evaporated to dryness in vacuo. The residue obtained was purified by chromatography on a silica gel column using a mixed solvent of ethyl acetate and hexane (3:2) as the eluent to afford the title compound (0.1029 g, yield: 82%).

$^1$H-NMR spectrum (CDCl$_3$, 400 MHz) δ: 7.29-7.26 (m, 2H), 7.19-7.16 (m, 3H), 5.87 (d, 1H, J=3.0 Hz), 5.83 (d, 1H, J=3.0 Hz), 5.36 (br s, 1H), 4.31 (d, 1H, J=11.2 Hz), 4.17 (d, 1H, J=11.2 Hz), 2.64-2.54 (m, 4H), 2.25-2.17 (m, 1H), 2.08 (s, 3H), 2.05-1.91 (m, 1H), 1.92 (s, 3H), 1.69-1.60 (m, 4H), 1.43-1.37 (m, 2H), 1.35 (s, 3H).

Mass spectrum (FAB$^+$) m/z: 400 ((M+H)$^+$; as free form of title compound).

(6b) (2R)-2-Amino-2-methyl-4-[5-(5-phenylpentyl)furan-2-yl]butan-1-ol oxalate

To a solution of (2R)-1-acetoxy-2-acetylamino-2-methyl-4-[5-(5-phenylpentyl)furan-2-yl]butane (99.7 mg, 0.25 mmol) obtained in Example (6a) in a mixed solvent of tetrahydrofuran (0.5 ml) and methanol (0.5 ml) were added successively water (0.5 ml) and lithium hydroxide monohydrate (0.1037 g, 2.47 mmol), and the resulting mixture was stirred at 50° C. for 4 hours. After cooling, water was added to the reaction mixture, and the resulting mixture was extracted with dichloromethane. The extract was washed with saturated aqueous sodium chloride solution and dried over anhydrous sodium sulfate. After filtration, the solvent was removed in vacuo, and the residue was purified by chromatography on a basic silica gel column (NH type) using a mixed solvent of dichloromethane and methanol (100:1) as the eluent to afford (2R)-2-amino-2-methyl-4-[5-(5-phenylpentyl)furan-2-yl]butan-1-ol (74.6 mg, yield: 95%).

Subsequently, to a solution of the reaction product thus obtained in methanol (2.3 ml) was added anhydrous oxalic acid (98% pure) (21.1 mg, 0.23 mmol) with stirring, and the resulting mixture was stirred at room temperature for 1 hour. After stirring, the reaction mixture was evaporated in vacuo, and ethyl acetate was added to the residue. The crystals precipitated were collected by filtration, washed with ethyl acetate and dried in vacuo to afford the title compound (78.1 mg, yield: 85%).

$^1$H-NMR spectrum (CD$_3$OD, 400 MHz) δ: 7.25-7.21 (m, 2H), 7.15-7.11 (m, 3H), 5.94 (d, 1H, J=3.2 Hz), 5.87 (d, 1H, J=3.2 Hz), 3.58 (d, 1H, J=11.6 Hz), 3.49 (d, 1H, J=11.6 Hz), 2.69-2.53 (m, 6H), 2.04-1.88 (m, 2H), 1.67-1.59 (m, 4H), 1.40-1.32 (m, 2H), 1.28 (s, 3H).

IR spectrum $v_{max}$ cm$^{-1}$ (KBr): 3119, 3025, 2979, 2928, 2855, 1719, 1610, 1543, 1466, 1402, 1197, 1094, 1078, 1012, 786, 746, 721, 699.

Mass spectrum (FAB$^+$) m/z: 316 ((M+H)$^+$; as free form of title compound).

Example 7

(2R)-2-Amino-2-methyl-4-[5-(4-cyclohexylmethoxyphenyl)furan-2-yl]butan-1-ol oxalate (Exemplification compound number: 1-1433 having formula Ia-1)

(7a) (2R)-1-Acetoxy-2-acetylamino-2-methyl-4-[5-(4-cyclohexylmethoxyphenyl)furan-2-yl]butane (2R)-1-Acetoxy-2-acetylamino-2-methyl-4-(5-iodofuran-2-yl)butane (0.2047 g, 0.51 mmol) obtained in Reference example 7, 2-(4-cyclohexylmethoxyphenyl)-4,4,5,5-tetramethyl-1,3,2-dioxaborolane (0.2400 g, 0.76 mmol), dichlorobis(triphenylphosphine)palladium(II) (36.1 mg, 0.051 mmol) and cesium carbonate (0.6738 g, 2.03 mmol) were suspended in a mixed solvent of dimethoxyethane (4.0 ml) and water (1 ml) and stirred at 80° C. for 4 hours. After cooling, water was added to the reaction mixture, and the resulting mixture was extracted with dichloromethane. The extract was washed with saturated aqueous sodium chloride solution and dried over anhydrous sodium sulfate. After filtration, the solvent was removed in vacuo.

Subsequently, to a solution of the residue obtained in dichloromethane (5.0 ml) were added successively triethylamine (0.72 ml, 5.2 mmol), acetic anhydride (0.24 ml, 2.6 mmol) and 4-dimethylaminopyridine (6.4 mg, 0.052 mmol), and the resulting mixture was stirred at room temperature for 2 hours. After stirring, methanol (0.10 ml, 2.5 mmol) was added to quench the reaction, and to the reaction mixture were furthermore added ethyl acetate and water, and then the resulting mixture was extracted with ethyl acetate. The extract was washed successively with water, saturated aqueous sodium hydrogencarbonate solution and saturated aqueous sodium chloride solution, and dried over anhydrous sodium sulfate. After filtration, the solvent, was removed in vacuo, and the residue was purified by chromatography on a silica gel column using a mixed solvent of ethyl acetate and hexane (3:2) as the eluent to afford the title compound (45.3 mg, yield: 20%).

$^1$H-NMR spectrum (CDCl$_3$, 400 MHz) δ: 7.55-7.51 (m, 2H), 7.00-6.87 (m, 2H), 6.39 (d, 1H, J=3.1 Hz), 6.06 (d, 1H, J=3.1 Hz), 5.36 (br s, 1H), 4.34 (d, J=11.2 Hz), 4.20 (d, 1H, J=11.2 Hz), 3.76 (d, 2H, J=2.5 Hz), 2.73-2.69 (m, 2H), 2.35-2.27 (m, 1H), 2.09 (s, 3H), 2.08-1.99 (m, 1H), 1.91 (s, 3H), 1.93-1.69 (m, 6H), 1.38 (s, 3H), 1.37-1.18 (m, 3H), 1.10-1.00 (m, 2H).

Mass spectrum (FAB$^+$) m/z: 442 ((M+H)$^+$), 441 (M$^+$).

(7b) (2R)-2-Amino-2-methyl-4-[5-(4-cyclohexylmethoxyphenyl)furan-2-yl]butan-1-ol oxalate To a solution of (2R)-1-acetoxy-2-acetylamino-2-methyl-4-[5-(4-cyclohexylmethoxyphenyl)furan-2-yl]butane (44.0 mg, 0.10 mmol) obtained in Example (7a) in a mixed solvent of tetrahydrofuran (0.4 ml) and methanol (0.4 ml) were added successively water (0.4 ml) and lithium hydroxide monohydrate (43.6 mg, 1.04 mmol), and the resulting mixture was stirred at 50° C. for 4 hours. After cooling, water was added to the reaction mixture, and the resulting mixture was extracted with dichloromethane. The extract was washed with saturated aqueous sodium chloride solution and dried over anhydrous sodium sulfate. After filtration, the solvent was removed in vacuo, and the residue was purified by chromatography on a basic silica gel column (NH type) using a mixed solvent of dichloromethane and methanol (50:1) as the eluent to afford the reaction product (35.2 mg, yield: 99%).

Subsequently, to a solution of the reaction product thus obtained in methanol (2.0 ml) was added anhydrous oxalic acid (98% pure) (8.9 mg, 0.10 mmol), and the resulting mixture was stirred at room temperature for 30 minutes. After stirring, the reaction mixture was evaporated in vacuo, and acetone was added to the residue. The crystals precipitated were collected by filtration, washed with acetone and dried in vacuo to afford the title compound (28.2 mg, yield: 66%).

$^1$H-NMR spectrum (CD$_3$OD-DMSO-d$_6$, 400 MHz) δ: 7.55 (d, 2H, J=8.7 Hz), 6.93 (d, 2H, J=8.7 Hz), 7.16 (t, 1H, J=2.0 Hz), 6.53 (d, 1H, J=3.2 Hz), 6.17 (d, 1H, J=3.2 Hz), 3.79 (d, 2H, J=6.4 Hz), 3.58 (d, 1H, J=11.7 Hz), 3.50 (d, 1H, J=11.7 Hz), 3.28-3.27 (m, 2H), 2.09-1.69 (m, 8H), 1.38-1.04 (m, 8H).

IR spectrum $v_{max}$ cm$^{-1}$ (KBr): 3387, 3235, 2924, 2852, 2578, 1618, 1568, 1499, 1466, 1448, 1390, 1288, 1245, 1174, 1024, 828, 783, 765.

Mass spectrum (FAB$^+$) m/z: 358 (M+H)$^+$

Example 8

(2R)-2-Amino-2-methyl-4-{5-[3-(2-cyclohexylethoxy)phenyl]furan-2-yl}butan-1-ol oxalate (Exemplification compound number: 1-1444 having formula Ia-1)

The title compound was synthesized in a yield of 21% using (2R)-1-acetoxy-2-acetylamino-2-methyl-4-(5-iodofuran-2-yl)butane obtained in Reference example 7 and 2-[3-(2-cyclohexylethoxy)phenyl]-4,4,5,5-tetramethyl-1,3,2-dioxaborolane as the starting materials by conducting the reaction similar to that mentioned in Example 7.

$^1$H-NMR spectrum (CD$_3$OD, 400 MHz) δ: 7.27 (t, 1H, J=8.0 Hz), 7.21 (dd, 1H, J=8.0 Hz, 2.0 Hz), 7.16 (t, 1H, J=2.0 Hz), 6.80 (dd, 1H, J=8.0 Hz, 2.0 Hz), 6.69 (d, 1H, J=3.5 Hz), 6.21 (d, 1H, J=3.5 Hz), 4.04 (t, 2H, J=6.6 Hz), 3.61 (d, 1H, J=11.6 Hz), 3.52 (d, 1H, J=11.6 Hz), 2.83-2.78 (m, 2H), 2.62-2.60 (m, 1H), 2.13-1.97 (m, 2H), 1.81-1.65 (m, 6H), 1.59-1.49 (m, 1H), 1.31-1.02 (m, 6H), 1.00-0.96 (m, 2H).

IR spectrum $v_{max}$ cm$^{-1}$ (KBr): 3213, 2925, 2850, 2571, 1720, 1701, 1614, 1600, 1578, 1563, 1548, 1449, 1300, 1216, 1205, 1052, 1033, 1017, 863, 772, 721, 689.

Mass spectrum (FAB$^+$) m/z: 372 ((M+H)$^+$; as free form of title compound).

Example 9

(2R)-2-Amino-2-methyl-4-[1-methyl-5-(5-phenylpent-1-ynyl)pyrrol-2-yl]butan-1-ol oxalate (Exemplification compound number: 1-621 having formula Ia-2)

The title compound was synthesized in a yield of 57% using (2R)-1-acetoxy-2-acetylamino-2-methyl-4-(1-methyl-5-iodopyrrol-2-yl)butane obtained in Reference example 13 and 5-phenylpent-1-yne as the starting materials by conducting successively the reactions similar to those mentioned in Examples (1a) and (1b).

$^1$H-NMR spectrum (CD$_3$OD, 400 MHz) δ 7.28-7.14 (m, 5H), 6.16 (d, 1H, J=3.7 Hz), 5.80 (d, 1H, J=3.7 Hz), 3.63 (d, 1H, J=11.6 Hz), 3.57 (s, 3H), 3.54 (d, 1H, J=11.6 Hz), 2.77 (t, 2H, J=7.6 Hz), 2.66-2.61 (m, 2H), 2.43 (t, 2H, J=7.0 Hz), 2.04-1.96 (m, 1H), 1.92-1.84 (m, 3H), 1.33 (s, 3H)

IR spectrum $\nu_{max}$ cm$^{-1}$ (KBr): 3212, 3026, 2935, 2897, 2571, 1719, 1700, 1611, 1521, 1496, 1454, 1405, 1279, 1218, 1053, 767, 721, 700.

Mass spectrum (FAB$^+$) m/z: 325 ((M+H)$^+$; as free form of title compound).

Example 10

(2R)-2-Amino-2-methyl-4-[1-methyl-5-(4-cyclohexyloxybut-1-ynyl)pyrrol-2-yl]butan-1-ol 1/2-oxalate (Exemplification compound number: 1-842 having formula Ia-2)

The title compound was synthesized in a yield of 32% using (2R)-1-acetoxy-2-acetylamino-2-methyl-4-(1-methyl-5-iodopyrrol-2-yl)butane obtained in Reference example 13 and 4-cyclohexyloxybut-1-yne as the starting materials by conducting successively the reactions similar to those mentioned in Examples (1a) and (1b).

$^1$H-NMR spectrum (CD$_3$OD, 400 MHz) δ: 6.13 (d, 1H, J=3.7 Hz), 5.79 (d, 1H, J=3.7 Hz), 3.65 (t, 2H, J=6.8 Hz), 3.61 (d, 1H, J=11.5 Hz), 3.56 (s, 3H), 3.53 (d, 1H, J=11.5 Hz), 3.39-3.34 (m, 1H), 2.68-2.61 (m, 4H), 2.01-1.83 (m, 4H), 1.78-1.74 (m, 2H), 1.56-1.54 (m, 1H), 1.35-1.21 (m, 8H).

IR spectrum $\nu_{max}$ cm$^{-1}$ (KBr): 3348, 2931, 2856, 1590, 1452, 1364, 1309, 1106, 762.

Mass spectrum (FAB$^+$) m/z 333 ((M+H)$^+$; as free form of title compound).

Example 11

(2R)-2-Amino-2-methyl-4-{1-methyl-5-[3-(4-methylphenyloxy)prop-1-ynyl]pyrrol-2-yl}butan-1-ol 1/2-oxalate (Exemplification compound number: 1-833 having formula Ia-2)

The title compound was synthesized in a yield of 29% using (2R)-1-acetoxy-2-acetylamino-2-methyl-4-(1-methyl-5-iodopyrrol-2-yl)butane obtained in Reference example 13 and 3-(4-methylphenyloxy)-1-propyne as the starting materials by conducting successively the reactions similar to those mentioned in Examples (1a) and (1b).

$^1$H-NMR spectrum (CD$_3$OD, 400 MHz) δ: 7.09 (d, 1H, J=8.5 Hz), 6.90 (d, 1H, J=8.5 Hz), 6.26 (d, 1H, J=3.7 Hz), 5.83 (d, 1H, J=3.7 Hz), 4.93 (s, 2H), 3.60 (d, 1H, J=11.6 Hz), 3.53 (d, 1H, J=11.6 Hz), 3.51 (s, 3H), 2.65-2.60 (m, 2H), 2.26 (s, 3H), 2.01-1.93 (m, 1H), 1.89-1.82 (m, 1H), 1.30 (s, 3H).

IR spectrum $\nu_{max}$ cm$^{-1}$ (KBr): 3356, 2944, 2602, 2220, 1586, 1510, 1455, 1365, 1295, 1228, 1178, 1071, 1042, 1015, 815, 762.

Mass spectrum (FAB$^+$) m/z: 327 ((M+H)$^+$; as free form of title compound).

Example 12

(2R)-2-Amino-2-methyl-4-{1-methyl-5-[3-(3,4-dimethylphenyloxy)prop-1-ynyl]pyrrol-2-yl}butan-1-ol 1/2-oxalate (Exemplification compound number: 1-1836 having formula Ia-2)

The title compound was synthesized in a yield of 33% using (2R)-1-acetoxy-2-acetylamino-2-methyl-4-(1-methyl-5-iodopyrrol-2-yl)butane obtained in Reference example 13 and 3-(3,4-dimethylphenyloxy)-1-propyne as the starting materials by conducting successively the reactions similar to those mentioned in Examples (1a) and (1b).

$^1$H-NMR spectrum (CD$_3$OD, 400 MHz) δ: 7.02 (d, 1H, J=8.2 Hz), 6.81 (d, 1H, J=2.5 Hz), 6.73 (dd, 1H, J=8.2 Hz, 2.5 Hz), 6.26 (d, 1H, J=3.9 Hz), 5.83 (d, 1H, J=3.9 Hz), 4.91 (s, 2H), 3.61 (d, 1H, J=11.4 Hz), 3.53 (d, 1H, J=11.4 Hz), 3.52 (s, 3H), 2.65-2.61 (m, 2H), 2.23 (s, 3H), 2.18 (s, 3H), 1.99-1.93 (m, 1H), 1.90-1.82 (m, 1H), 1.31 (s, 3H).

IR spectrum $\nu_{max}$ cm$^{-1}$ (KBr): 3420, 2943, 2631, 2213, 1584, 1503, 1455, 1365, 1301, 1251, 1207, 1163, 1025, 806, 762.

Mass spectrum (FAB$^+$) m/z: 341 ((M+H)$^+$; as free form of title compound).

Example 13

(2R)-2-Amino-2-methyl-4-[5-(4-phenylbut-1-ynyl)furan-2-yl]butan-1-ol oxalate (Exemplification compound number: 1-559 having formula Ia-1)

The title compound was synthesized in a yield of 61% using (2R)-1-acetoxy-2-acetylamino-2-methyl-4-(5-bromofuran-2-yl)butane obtained in Reference example 6 and 4-phenylbut-1-yne as the starting materials by conducting successively the reactions similar to those mentioned in Examples (1a) and (1b)

$^1$H-NMR spectrum (CD$_3$OD, 400 MHz) δ: 7.29-7.17 (m, 5H), 6.35 (d, 1H, J=3.4 Hz), 6.07 (d, 1H, J=3.4 Hz), 3.59 (d, 1H, J=11.7 Hz), 3.50 (d, 1H, J=11.7 Hz), 2.87 (t, 2H, J=7.3 Hz), 2.77-2.64 (m, 4H), 2.06-1.89 (m, 2H), 1.29 (s, 3H).

IR spectrum $\nu_{max}$ cm$^{-1}$ (KBr): 3353, 3140, 2924, 2896, 1724, 1651, 1617, 1598, 1542, 1403, 1221, 1075, 1054, 1010, 784, 713, 501.

Mass spectrum (ESI$^+$) m/z: 298 ((M+H)$^+$; as free form of title compound).

Example 14

(2R)-2-Amino-2-methyl-4-{5-[5-(4-chlorophenyl)pent-1-ynyl]furan-2-yl}butan-1-ol oxalate (Exemplification compound number: 1-628 having formula Ia-1)

The title compound was synthesized in a yield of 60% using (2R)-1-acetoxy-2-acetylamino-2-methyl-4-(5-iodofuran-2-yl)butane obtained in Reference example 7 and 5-(4-chlorophenyl)pent-1-yne as the starting materials by conducting successively the reactions similar to those mentioned in Examples (1a) and (1b).

$^1$H-NMR spectrum (CD$_3$OD, 400 MHz) δ: 7.28-7.25 (m, 2H), 7.20 (d, 1H, J=8.3 Hz), 6.40 (d, 1H, J=3.4 Hz), 6.09 (d, 1H, J=3.4 Hz), 3.59 (d, 1H, J=11.7 Hz), 3.51 (d, 1H, J=11.7 Hz), 2.78-2.65 (m, 4H), 2.42 (t, 2H, J=6.8 Hz), 2.08-1.83 (m, 4H), 1.29 (s, 3H).

IR spectrum $\nu_{max}$ cm$^{-1}$ (KBr): 3257, 3105, 2936, 1718, 1598, 1540, 1493, 1405, 1280, 1202, 1093, 1015, 828, 792, 721, 701, 502.

Mass spectrum (FAB$^+$) m/z: 346 ((M+H)$^+$; as free form of title compound).

Example 15

(2R)-2-Amino-2-methyl-4-{5-[5-(3-trifluoromethylphenyl)pent-1-ynyl]furan-2-yl}butan-1-ol oxalate (Exemplification compound number: 1-640 having formula Ia-1)

The title compound was synthesized in a yield of 58% using (2R)-1-acetoxy-2-acetylamino-2-methyl-4-(5-iodofuran-2-yl)butane obtained in Reference example 7 and 5-(3-trifluoromethylphenyl)pent-1-yne as the starting materials by conducting successively the reactions similar to those mentioned in Examples (1a) and (1b).

$^1$H-NMR spectrum (CD$_3$OD, 400 MHz) δ: 7.51-7.48 (m, 4H), 6.41 (d, 1H, J=3.3 Hz), 6.10 (d, 1H, J=3.3 Hz), 3.59 (d, 1H, J=11.6 Hz), 3.51 (d, 1H, J=11.6 Hz), 2.85 (t, 2H, J=7.4 Hz), 2.78-2.66 (m, 2H), 2.44 (t, 2H, J=7.0 Hz), 2.08-1.87 (m, 4H), 1.29 (s, 3H).

IR spectrum $v_{max}$ cm$^{-1}$ (KBr): 3358, 3139, 2935, 1722, 1651, 1615, 1597, 1542, 1403, 1326, 1222, 1168, 1119, 1073, 797, 721, 713, 703, 503.

Mass spectrum (FAB$^+$) m/z: 380 ((M+H)$^+$; as free form of title compound).

Example 16

(2R)-2-Amino-2-methyl-4-{5-[3-(4-methylphenyloxy)prop-1-ynyl]furan-2-yl}butan-1-ol oxalate (Exemplification compound number: 1-833 having formula Ia-1)

The title compound was synthesized in a yield of 11% using (2R)-1-acetoxy-2-acetylamino-2-methyl-4-(5-bromofuran-2-yl)butane obtained in Reference example 6 and 3-(4-methylphenyloxy)-1-propyne as the starting materials by conducting successively the reactions similar to those mentioned in Examples (1a) and (1b).

$^1$H-NMR spectrum (CD$_3$OD, 400 MHz) δ: 7.13-7.06 (m, 2H), 6.92-6.84 (m, 2H), 6.55 (d, 1H, J=3.4 Hz), 6.13 (d, 1H, J=3.4 Hz), 4.90 (s, 2H), 3.59 (d, 1H, J=11.7 Hz), 3.50 (d, 1H, J=11.7 Hz), 3.34-3.28 (m, 2H), 2.80-2.64 (m, 2H), 2.27 (s, 3H), 2.07-1.87 (m, 2H), 1.28 (s, 3H).

IR spectrum $v_{max}$ cm$^{-1}$ (KBr): 3352, 3138, 2921, 2893, 1727, 1653, 1616, 1596, 1544, 1511, 1373, 1224, 1018, 713.

Mass spectrum (FAB$^+$) m/z: 314 ((M+H)$^+$; as free form of title compound).

Example 17

(2R)-2-Amino-2-methyl-4-{5-[3-(4-methylthiophenyloxy)prop-1-ynyl]furan-2-yl}butan-1-ol oxalate (Exemplification compound number: 1-838 having formula Ia-1)

The title compound was synthesized in a yield of 15% using (2R)-1-acetoxy-2-acetylamino-2-methyl-4-(5-bromofuran-2-yl)butane obtained in Reference example 6 and 3-(4-methylthiophenyloxy)-1-propyne as the starting materials by conducting successively the reactions similar to those mentioned in Examples (1a) and (1b).

$^1$H-NMR spectrum (CD$_3$OD, 400 MHz) δ: 7.30-7.25 (m, 2H), 6.99-6.94 (m, 2H), 6.57 (d, 1H, J=3.5 Hz), 6.14 (d, 1H, J=3.5 Hz), 4.94 (s, 2H), 3.59 (d, 1H, J=11.6 Hz), 3.50 (d, 1H, J=11.6 Hz), 2.80-2.65 (m, 2H), 2.42 (s, 3H), 2.08-1.88 (m, 2H), 1.28 (s, 3H).

IR spectrum $v_{max}$ cm$^{-1}$ (KBr): 3359, 3136, 3089, 2920, 2230, 1722, 1646, 1618, 1594, 1542, 1493, 1373, 1279, 1230, 1073, 1039, 1015, 820, 797, 712.

Mass spectrum (FAB$^+$) m/z: 346 ((M+H)$^+$; as free form of title compound).

Example 18

(2R)-2-Amino-2-methyl-4-[5-(4-phenyloxybut-1-ynyl)furan-2-yl]butan-1-ol oxalate (Exemplification compound number: 1-893 having formula Ia-1)

The title compound was synthesized in a yield of 42% using (2R)-1-acetoxy-2-acetylamino-2-methyl-4-(5-iodofuran-2-yl)butane obtained in Reference example 7 and 4-phenyloxybut-1-yne as the starting materials by conducting successively the reactions similar to those mentioned in Examples (1a) and (1b)

$^1$H-NMR spectrum (DMSO-d$_6$, 400 MHz) δ: 7.32-7.28 (m, 2H), 6.98-6.93 (m, 3H), 6.78 (d, 1H, J=3.2 Hz), 6.16 (d, 1H, J=3.2 Hz), 4.13 (t, 2H, J=6.4 Hz), 3.40 (dd, 2H, J=19.8 Hz, 11.4 Hz), 2.93 (t, 2H, J=6.4 Hz), 2.66 (t, 2H, J=8.5 Hz), 1.95-1.75 (m, 2H), 1.16 (s, 3H).

IR spectrum $v_{max}$ cm$^{-1}$ (KBr): 3115, 2978, 2940, 1719, 1600, 1547, 1498, 1248, 1204, 1081, 1039, 752, 700.

Mass spectrum (FAB$^+$) m/z: 314 ((M+H)$^+$; as free form of title compound),

Elemental analysis (% as C$_{19}$H$_{23}$NO$_3$—C$_2$H$_2$O$_4$)
Calculated: C, 62.52; H, 6.25; N, 3.47
Found: C, 62.47; H, 6.14; N, 3.42.

Example 19

(2R)-2-Amino-2-methyl-4-[5-(5-cyclohexylpent-1-ynyl)furan-2-yl]butan-1-ol hydrochloride (Exemplification compound number 1-570 having formula Ia-1)

(19a) (2R)-1-Acetoxy-2-acetylamino-2-methyl-4-[5-(5-cyclohexylpent-1-ynyl)furan-2-yl]butane To a suspension of (2R)-1-acetoxy-2-acetylamino-2-methyl-4-(5-iodofuran-2-yl)butane (4.1685 g, 10.99 mmol) obtained in Reference example 7, 5-cyclohexylpent-1-yne (4.48 g, 29.8 mmol), dichlorobis(triphenylphosphine)palladium(II) (0.7730 g, 1.10 mmol) and copper(I) iodide (0.4205 g, 2.21 mmol) in N,N-dimethylformamide (110 ml) was added triethylamine (15.3 ml, 110.1 mmol) with stirring, and the resulting mixture was stirred at 60° C. under a nitrogen atmosphere for 2 hours. After cooling, saturated aqueous ammonium chloride solution was added to the reaction mixture to quench the reaction, and furthermore water and ethyl acetate were added. The resulting mixture was stirred at room temperature for 30 minutes and then extracted with ethyl acetate. The extract was washed successively with water and saturated aqueous sodium chloride solution and dried over anhydrous sodium sulfate. After filtration, the solvent was removed in vacuo, and the residue was purified by chromatography on a silica gel column using a mixed solvent of ethyl acetate and hexane (3:2) as the eluent to afford the title compound (2.6576 g, yield: 60%).

$^1$H-NMR spectrum (CDCl$_3$, 400 MHz) δ: 6.36 (d, 1H, J=2.9 Hz), 5.97 (d, 1H, J=2.9 Hz), 5.36 (br s, 1H), 4.29 (d, J=11.0 Hz), 4.17 (d, 1H, J=11.0 Hz), 2.63 (t, 2H, J=8.1 Hz), 2.40 (t, 2H, J=7.3 Hz), 2.29-2.21 (m, 1H), 2.09 (s, 3H), 2.00-1.93 (m, 1H), 1.92 (s, 3H), 1.72-1.51 (m, 7H), 1.35 (s, 3H), 1.33-1.08 (m, 6H), 0.93-0.84 (m, 2H).

Mass spectrum (FAB$^+$) m/z: 402 ((M+H)$^+$).

(19b) (2R)-2-Amino-2-methyl-4-[5-(5-cyclohexylpent-1-ynyl)furan-2-yl]butan-1-ol hydrochloride To a solution of (2R)-1-acetoxy-2-acetylamino-2-methyl-4-[5-(5-cyclohexylpent-1-ynyl)furan-2-yl]butane (1.2996 g, 3.24 mmol) obtained in Example (19a) in a mixed solvent of tetrahydrofuran (6.4 ml) and methanol (6.4 ml) were added successively water (6.4 ml) and lithium hydroxide-monohydrate (1.3590 g, 32.39 mmol) with stirring, and the resulting mixture was stirred at 50° C. for 4 hours. After cooling, water was added to the reaction mixture, and the resulting mixture was extracted with dichloromethane. The extract was washed with saturated aqueous sodium chloride solution and dried over anhydrous sodium sulfate. After filtration, the solvent was removed in vacuo, and the residue was purified by chromatography on a basic silica gel column (NH type) using a mixed solvent of dichloromethane and methanol (100:1) as the eluent to afford the crude (2R)-2-amino-2-methyl-4-[5-(5-cyclohexylpent-1-ynyl)furan-2-yl]butan-1-ol (1.0048 g).

Subsequently, to a solution of the crude product obtained above in methanol (16 ml) was added a 4N hydrochloric acid-dioxane solution (0.79 ml, 3.16 mmol) with stirring, and the resulting mixture was stirred at room temperature for 10 minutes. After stirring, the reaction mixture was evaporated in vacuo, and ether was added to the residue. The crystals precipitated were collected by filtration, washed with ether and dried in vacuo to afford the title compound (1.0392 g, yield: 91%).

Melting point: 117-118° C.,
Angle of rotation: $[\alpha]_D$=+2.43 (c=1.00, MeOH),
$^1$H-NMR spectrum (CD$_3$OD, 400 MHz) δ: 6.36 (d, 1H, J=3.3 Hz), 6.08 (d, 1H, J=3.3 Hz), 3.59 (d, 1H, J=11.6 Hz), 3.49 (d, 1H, J=11.6 Hz), 2.77-2.64 (m, 2H), 2.39 (t, 2H, J=7.1 Hz), 2.07-1.89 (m, 2H), 1.76-1.54 (m, 7H), 1.35-1.12 (m, 9H), 0.96-0.86 (m, 2H).
IR spectrum $v_{max}$ cm$^{-1}$ (KBr): 3138, 2921, 2850, 2693, 2571, 1615, 1595, 1534, 1448, 1402, 1369, 1298, 1197, 1058, 788.
Mass spectrum (FAB$^+$) m/z: 318 ((M+H)$^+$; as free form of title compound).

Example 20

(2R)-2-Amino-2-methyl-4-[5-(4-cyclohexyloxybut-1-ynyl)furan-2-yl]butan-1-ol hydrochloride (Exemplification compound number: 1-842 having formula Ia-1)

The title compound was synthesized in a yield of 57% using (2R)-1-acetoxy-2-acetylamino-2-methyl-4-(5-iodofuran-2-yl)butane obtained in Reference example 7 and 4-cyclohexyloxybut-1-yne as the starting materials by conducting successively the reactions similar to those mentioned in Examples (19a) and (19b).

Melting point: 115-118° C.,
Angle of rotation: $[\alpha]_D$=+2.63 (c=1.00, MeOH),
$^1$H-NMR spectrum (CD$_3$OD, 400 MHz) δ: 6.40 (d, 1H, J=3.4 Hz), 6.09 (d, 1H, J=3.4 Hz), 3.63 (t, 2H, J=6.6 Hz), 3.58 (d, 1H, J=11.6 Hz), 3.50 (d, 1H, J=11.6 Hz), 3.39-3.32 (m, 1H), 2.76-2.62 (m, 4H), 2.07-1.87 (m, 4H), 1.78-1.73 (m, 2H), 1.56-1.53 (m, 1H), 1.35-1.19 (m, 8H).
IR spectrum $v_{max}$ cm$^{-1}$ (KBr): 3204, 2931, 2858, 2667, 2570, 1611, 1597, 1537, 1450, 1390, 1364, 1199, 1107, 1067, 1032, 1002, 967, 952, 786.
Mass spectrum (FAB$^+$) m/z: 320 ((M+H)$^+$; as free form of title compound).

Example 21

(2R)-2-Amino-2-methyl-4-[5-(4-phenyloxybutanoyl)furan-2-yl]butan-1-ol fumarate (Exemplification compound number: 1-1199 having formula Ia-1)

(21a) (2R)-1-Acetoxy-2-acetylamino-2-methyl-4-[5-(4-phenyloxybutanoyl)furan-2-yl]butane To a solution of (2R)-1-acetoxy-2-acetylamino-2-methyl-4-(furan-2-yl)butane (0.2589 g, 1.02 mmol) obtained in Reference example (5b) and 4-phenyloxybutanoyl chloride (0.2446 g, 1.23 mmol) in dichloromethane (9.0 ml) was added dropwise a solution of tin chloride (IV) in n-heptane (1.0 mmol/l) (2.05 ml, 2.05 mmol) at −78° C. over a 5-minute interval with stirring under a nitrogen atmosphere, and the resulting mixture was furthermore stirred at the same temperature for 2 hours. After stirring, saturated aqueous sodium hydrogencarbonate solution was added to the reaction mixture with stirring at the same temperature to quench the reaction, and then the temperature of the reaction mixture was raised to room temperature.

Subsequently, the reaction mixture was diluted with ethyl acetate, and insoluble materials were filtered off. The filtrate was extracted with ethyl acetate, and the extract was washed successively with water and saturated aqueous sodium chloride solution and dried over anhydrous sodium sulfate. After filtration, the solvent was removed in vacuo, and the residue was purified by chromatography on a silica gel column using a mixed solvent of ethyl acetate and hexane (2:1-1:0) as the eluent to afford the title compound (0.1483 g, yield: 35%).

$^1$H-NMR spectrum (CDCl$_3$, 400 MHz) δ: 7.29-7.25 (m, 2H), 7.13 (d, 1H, J=3.3 Hz), 7.00-6.87 (m, 3H), 6.18 (d, 1H, J=3.3 Hz), 5.42 (br s, 1H), 4.30 (d, J=11.2 Hz), 4.15 (d, 1H, J=11.2 Hz), 4.04 (t, 2H, J=6.0 Hz), 3.00 (t, 2H, J=7.2 Hz), 2.75-2.68 (m, 2H), 2.38-2.30 (m, 1H), 2.26-2.17 (m, 2H), 2.10 (s, 3H), 2.07-2.1.99 (m, 1H), 1.94 (s, 3H), 1.34 (s, 3H).
Mass spectrum (FAB$^+$) m/z: 416 ((M+H)$^+$).

(21b) (2R)-2-Amino-2-methyl-4-[5-(4-phenyloxybutanoyl)furan-2-yl]butan-1-ol fumarate To a solution of (2R)-1-acetoxy-2-acetylamino-2-methyl-4-[5-(4-phenyloxybutanoyl)furan-2-yl]butane (0.2031 g, 0.49 mmol) obtained in Example (21a) in a mixed solvent of tetrahydrofuran (1.0 ml) and methanol (1.0 ml) were added successively water (1.0 ml) and lithium hydroxide monohydrate (0.2065 g, 4.92 mmol), and the resulting mixture was stirred at 50° C. for 4 hours. After cooling, water was added to the reaction mixture, and the resulting mixture was extracted with dichloromethane. The extract was washed with saturated aqueous sodium chloride solution and dried over anhydrous sodium sulfate. After filtration, the solvent was removed in vacuo, and the residue was purified by chromatography on a basic silica gel column (NH type) using a mixed solvent of dichloromethane and methanol (100:1) as the eluent to afford the crude (2R)-2-amino-2-methyl-4-[5-(4-phenyloxybutanoyl)furan-2-yl]butan-1-ol (58.4 mg).

Subsequently, to a solution of the crude product thus obtained in methanol (1.7 ml) was added fumaric acid (20.1 mg, 0.17 mmol), and the resulting mixture was stirred at room temperature for 30 minutes. After stirring, the reaction mixture was evaporated in vacuo, and ethyl acetate was added to the residue. The crystals precipitated were collected by filtration, washed with ethyl acetate and dried in vacuo to afford the title compound (61.5 mg, yield: 29%).

$^1$H-NMR spectrum (CD$_3$OD, 400 MHz) δ: 7.33 (d, 1H, J=3.4 Hz), 7.26-7.21 (m, 2H), 6.91-6.84 (m, 3H), 6.35 (d, 1H, J=3.4 Hz), 6.25 (s, 2H), 4.03 (t, 2H, J=6.0 Hz), 3.60 (d, J=11.7 Hz), 3.51 (d, 1H, J=11.7 Hz), 3.01 (t, 2H, J=7.2 Hz), 2.88-2.75 (m, 2H), 2.18-1.95 (m, 4H), 1.30 (s, 3H).
IR spectrum $v_{max}$ cm$^{-1}$ (KBr): 3112, 3038, 2961, 1671, 1583, 1517, 1498, 1386, 1357, 1245, 1081, 1039, 869, 757, 719, 693.
Mass spectrum (FAB$^+$) m/z: 332 ((M+H)$^+$; as free form of title compound), Elemental analysis (% as $C_{19}H_{25}NO_4 \cdot C_4H_4O_4$)
Calculated: C, 61.73; H, 6.53; N, 3.13
Found: C, 61.57; H, 6.40; N, 2.93.

Example 22

(2R)-2-Amino-2-methyl-4-{5-[3-(4-chlorophenyloxy)prop-1-ynyl]furan-2-yl}butan-1-ol oxalate (Exemplification compound number: 1-1831 having formula Ia-1)

(22a) (2R)-1-Acetoxy-2-acetylamino-2-methyl-4-[5-(3-hydroxyprop-1-ynyl)furan-2-yl]-butane To a suspension of (2R)-1-acetoxy-2-acetylamino-2-methyl-4-(5-iodofuran-2-yl)butane (1.5900 g, 4.19 mmol) obtained in Reference example 7, 3-propyn-1-ol (0.73 ml, 12.54 mmol), dichlorobis(triphenylphosphine)palladium(II) (0.2940 g, 0.42 mmol) and copper(I) iodide (0.161 g, 0.85 mmol) in N,N-dimethylformamide (42 ml) was added triethylamine (5.85 ml, 42.9 mmol) with stirring, and the resulting mixture was stirred at 60° C. under a nitrogen atmosphere for 2 hours. After stirring, saturated aqueous ammonium chloride solution was added to the reaction mixture to quench the reaction, and furthermore water and ethyl acetate were added. The resulting mixture was stirred at room temperature for 30 minutes and then extracted with ethyl acetate. The extract was dried over anhydrous sodium sulfate. After filtration, the solvent was removed in vacuo, and the residue was purified by chromatography on a silica gel column using a mixed solvent of ethyl acetate and hexane (2:1-1:0) to afford the title compound (1.0748 g, yield: 83%).
$^1$H-NMR spectrum (CDCl$_3$, 400 MHz) δ: 6.50 (d, 1H, J=3.2 Hz), 6.01 (d, 1H, J=3.2 Hz), 5.39 (br s, 1H), 4.50 (s, 2H), 4.29 (d, 1H, J=11.3 Hz), 4.16 (d, 1H, J=11.3 Hz), 2.70-2.60 (m, 2H), 2.32-2.24 (m, 1H), 2.10 (s, 3H), 2.03-1.95 (m, 1H), 1.94 (s, 3H), 1.77 (br s, 1H), 1.34 (s, 3H).
Mass spectrum (FAB$^+$) m/z: 308 ((M+H)$^+$).

(22b) (2R)-1-Acetoxy-2-acetylamino-2-methyl-4-[5-(3-bromoprop-1-ynyl)furan-2-yl]butane To a solution of (2R)-1-acetoxy-2-acetylamino-2-methyl-4-[5-(3-hydroxyprop-1-ynyl)furan-2-yl]butane (0.9515 g, 3.10 mmol) obtained in Example (22a) and triphenylphosphine (1.2375 g, 3.73 mmol) in dichloromethane (15 ml) was added carbon tetrabromide (1.0545 g, 4.02 mmol) with stirring under ice-cooling, and the resulting mixture was stirred at the same temperature for 30 minutes. After stirring, methanol (0.2 ml) was added to the reaction mixture at the same temperature to quench the reaction, and then the temperature of the reaction mixture was raised to room temperature.
Subsequently, the resulting mixture was evaporated in vacuo, and the residue was purified by chromatography on a silica gel column using a mixed solvent of dichloromethane and acetone (9:1) as the eluent to afford the title compound (0.9278 g, yield: 82%).
$^1$H-NMR spectrum (CDCl$_3$, 400 MHz) δ: 6.54 (d, 1H, J=3.0 Hz), 6.02 (d, 1H, J=3.0 Hz), 5.37 (br s, 1H), 4.29 (d, 1H, J=11.0 Hz), 4.18 (s, 2H), 4.16 (d, 1H, J=11.0 Hz), 2.69-2.60 (m, 2H), 2.32-2.24 (m, 1H), 2.10 (s, 3H), 2.02-1.95 (m, 1H), 1.94 (s, 3H), 1.34 (s, 3H).

(22c) (2R)-1-Acetoxy-2-acetylamino-2-methyl-4-{5-[3-(4-chlorophenyloxy)prop-1-ynyl]furan-2-yl)}butane To a suspension of sodium hydride (content: 60%) (40.0 mg, 1.00 mmol) in N,N-dimethylformamide (4 ml) was added 4-chlorophenol (0.1302 g, 1.01 mmol) with stirring under ice-cooling, and the resulting mixture was stirred at room temperature for 30 minutes.
Subsequently, to the reaction mixture was added a solution of (2R)-1-acetoxy-2-acetylamino-2-methyl-4-[5-(3-bromoprop-1-ynyl)furan-2-yl]butane (0.3050 g, 0.82 mmol) obtained in Example (22b) in N,N-dimethylformamide (4 ml) with stirring under ice-cooling, and then the resulting mixture was stirred at room temperature for 30 minutes. After stirring, saturated aqueous ammonium chloride solution was added to the reaction mixture to quench the reaction, and then the reaction mixture was diluted with water and ethyl acetate and extracted with ethyl acetate. The extract was washed successively with water and saturated aqueous sodium chloride solution and dried over anhydrous sodium sulfate. After filtration, the solvent was removed in vacuo, and the residue was purified by chromatography on a silica gel column using a mixed solvent of dichloromethane and acetone (10:1) as the eluent to afford the title compound (0.3188 g, yield: 93%).
$^1$H-NMR spectrum (CDCl$_3$, 400 MHz) δ: 7.28-7.25 (m, 2H), 6.96-6.92 (m, 2H), 6.52 (d, 1H, J=3.4 Hz), 6.01 (d, 1H, J=3.4 Hz), 5.36 (br s, 1H), 4.90 (s, 2H), 4.29 (d, 1H, J=11.3 Hz), 4.15 (d, 1H, J=11.3 Hz), 2.67-2.59 (m, 2H), 2.31-2.24 (m, 1H), 2.09 (s, 3H), 2.02-1.94 (m, 1H), 1.93 (s, 3H), 1.34 (s, 3H).
IR spectrum ν$_{max}$ cm$^{-1}$ (CHCl$_3$): 3444, 2225, 1738, 1681, 1511, 1491, 1450, 1373, 1286, 1249, 1173, 1093, 1039, 1014, 824.
Mass spectrum (FAB$^+$) m/z: 418 ((M+H)$^+$).

(22d) (2R)-2-Amino-2-methyl-4-{5-[3-(4-chlorophenyloxy)prop-1-ynyl]furan-2-yl}butan-1-ol oxalate To a solution of (2R)-1-acetoxy-2-acetylamino-2-methyl-4-{5-[3-(4-chlorophenyloxy)prop-1-ynyl]furan-2-yl}butane (0.3083 g, 0.74 mmol) obtained in Example (22c) in a mixed solvent of tetrahydrofuran (1.5 ml) and methanol (1.5 ml) were added successively water (1.5 ml) and lithium hydroxide monohydrate (0.3096 g, 7.38 mmol), and the resulting mixture was stirred at 50° C. for 4 hours. After cooling, water was added to the reaction mixture, and the resulting mixture was extracted with dichloromethane. The extract was washed with saturated aqueous sodium chloride solution and dried over anhydrous sodium sulfate. After filtration, the solvent was removed in vacuo, and the residue was purified by chromatography on a basic silica gel column (NH type) using a mixed solvent of dichloromethane and methanol (50:1) as the eluent to afford the crude (2R)-2-amino-2-methyl-4-{5-[3-(4-chlorophenyloxy)prop-1-ynyl]furan-2-yl}butan-1-ol (0.2156 g).
Subsequently, to a solution of the crude product thus obtained in methanol (6.4 ml) was added anhydrous oxalic acid (98% pure) (59.1 mg, 0.64 mmol), and the resulting mixture was stirred at room temperature for 30 minutes. After stirring, the reaction mixture was evaporated in vacuo, and acetone was added to the residue. The crystals precipitated were collected by filtration, washed with acetone and dried in vacuo to afford the title compound (0.2307 g, yield: 75%).
$^1$H-NMR spectrum (CD$_3$OD, 400 MHz) δ: 7.30-7.26 (m, 2H), 7.01-6.97 (m, 2H), 6.57 (d, 1H, J=3.2 Hz), 6.14 (d, 1H, J=3.2 Hz), 4.96 (s, 2H), 3.58 (d, 1H, J=11.7 Hz), 3.50 (d, 1H, J=11.7 Hz), 2.79-2.66 (m, 2H), 2.07-1.89 (m, 2H), 1.28 (s, 3H).

IR spectrum ν$_{max}$ cm$^{-1}$ (KBr): 3401, 3120, 2979, 2925, 2228, 1725, 1615, 1547, 1492, 1373, 1234, 1217, 1200, 1086, 1044, 1016, 830, 795, 698, 506.

Mass spectrum (FAB$^+$) m/z: 334 ((M+H)$^+$; as free form of title compound).

Example 23

(2R)-2-Amino-2-methyl-4-{5-[3-(3-trifluoromethylphenyloxy)prop-1-ynyl]furan-2-yl}butan-1-ol oxalate (Exemplification compound number: 1-1838 having formula Ia-1)

The title compound was synthesized in a yield of 76% using (2R)-1-acetoxy-2-acetylamino-2-methyl-4-[5-(3-bromoprop-1-ynyl)furan-2-yl]butane obtained in Example (22b) and (3-trifluoromethyl)phenol as the starting materials by conducting successively the reactions similar to those mentioned in Examples (22c) and (22d).

$^1$H-NMR spectrum (DMSO-d$_6$, 400 MHz) δ: 7.60-7.55 (m, 1H), 7.36-7.53 (m, 3H), 6.77 (d, 1H, J=3.3 Hz), 6.21 (d, 1H, J=3.3 Hz), 5.21 (s, 2H), 3.43 (d, 1H, J=11.3 Hz), 3.37 (d, 1H, J=11.3 Hz), 2.67 (t, 2H, J=8.6 Hz), 1.91-1.76 (m, 2H), 1.15 (s, 3H).

IR spectrum ν$_{max}$ cm$^{-1}$ (KBr) 3126, 2980, 2220, 1719, 1614, 1593, 1546, 1455, 1328, 1207, 1167, 1130.

Mass spectrum (FAB$^+$) m/z 368 ((M+H)$^+$; as free form of title compound), 336.

Example 24

(2R)-2-Amino-2-methyl-4-{5-[3-(3,4-dimethoxyphenyloxy)prop-1-ynyl]furan-2-yl}butan-1-ol oxalate (Exemplification compound number: 1-1842 having formula Ia-1)

The title compound was synthesized in a yield of 68% using (2R)-1-acetoxy-2-acetylamino-2-methyl-4-[5-(3-bromoprop-1-ynyl)furan-2-yl]butane obtained in Example (22b) and 3,4-dimethoxyphenol as the starting materials by conducting successively the reactions similar to those mentioned in Examples (22c) and (22d).

$^1$H-NMR spectrum (CD$_3$OD, 400 MHz) δ: 6.87 (d, 1H, J=8.8 Hz), 6.66 (d, 1H, J=2.9 Hz), 6.57-6.52 (m, 2H), 6.14 (d, 1H, J=3.6 Hz), 4.90 (s, 2H), 3.81 (s, 3H), 3.78 (s, 3H), 3.59 (d, 1H, J=11.5 Hz), 3.50 (d, 1H, J=11.5 Hz), 2.79-2.66 (m, 2H), 2.08-1.88 (m, 2H), 1.29 (s, 3H).

IR spectrum ν$_{max}$ cm$^{-1}$ (KBr): 3393, 3093, 2969, 2224, 1722, 1598, 1537, 1513, 1467, 1452, 1278, 1260, 1228, 1194, 1157, 1135, 1021, 796, 721, 698.

Mass spectrum (FAB$^+$) m/z: 360 ((M+H)$^+$; as free form of title compound).

Example 25

(2R)-2-Amino-2-ethyl-4-[5-(4-cyclohexyloxybut-1-ynyl)furan-2-yl]butan-1-ol oxalate (Exemplification compound number: 1-1660 having formula Ia-1)

(25a) (2R)-1-Acetoxy-2-acetylamino-2-ethyl-4-[5-(4-cyclohexyloxybut-1-ynyl)furan-2-yl]butane To a suspension of (2R)-1-acetoxy-2-acetylamino-2-ethyl-4-(5-iodofuran-2-yl)butane (79.1 mg, 0.357 mmol) obtained in Reference example 18, 4-cyclohexyloxybut-1-yne (168.2 mg, 1.10 mmol), dichlorobis(triphenylphosphine)palladium (II) (25.1 mg, 0.036 mmol) and copper(I) iodide (13.8 mg, 0.072 mmol) in N,N-dimethylformamide (3.6 ml) was added triethylamine (0.5 ml, 0.36 mmol), and the resulting mixture was stirred at 80° C. under a nitrogen atmosphere for 4 hours. After stirring, saturated aqueous ammonium chloride solution was added to the reaction mixture to quench the reaction, and furthermore water and ethyl acetate were added. The resulting mixture was stirred at room temperature for 30 minutes. After stirring, the reaction mixture was extracted with ethyl acetate. The extract was washed successively with water and saturated aqueous sodium chloride solution and dried over anhydrous sodium sulfate. After filtration, the solvent was removed in vacuo, and the residue was purified by chromatography on a silica gel column using a mixed solvent of hexane and ethyl acetate (1:1-1:2) as the eluent to afford the crude product (68.4 mg). The crude product obtained was furthermore purified using a preparative reversed phase HPLC column [TSK-GEL ODS-80 Ts (2.0 cm×25 cm), TOSO, mobile phase: acetonitrile/water (70:30)] to afford the title compound (46.5 mg, yield: 31%).

$^1$H-NMR spectrum (CDCl$_3$, 400 MHz) δ: 6.38 (d, 1H, J=3.3 Hz), 5.96 (d, 1H, J=3.3 Hz), 5.27 (br s, 1H), 4.28 (s, 2H), 3.65 (t, 2H, J=7.3 Hz), 3.33-3.26 (m, 1H), 2.68 (t, 2H, J=7.3 Hz), 2.59 (t, 2H, J=8.4 Hz), 2.20-2.13 (m, 1H), 2.08 (s, 3H), 2.05-1.98 (m, 1H), 1.94 (s, 3H), 1.90 (m, 1H), 1.84-1.70 (m, 5H), 1.64 (m, 1H), 1.34-1.18 (m, 5H), 0.87 (t, 3H, J=7.3 Hz).

IR spectrum ν$_{max}$ cm$^{-1}$ (CDCl$_3$): 3307, 3078, 2934, 2858, 2220, 1744, 1658, 1540, 1452, 1369, 1237, 1103, 1042, 788, 756.

Mass spectrum (FAB$^+$) m/z: 418 ((M+H)$^+$).

(25b) (2R)-2-Amino-2-ethyl-4-[5-(4-cyclohexyloxybut-1-ynyl)furan-2-yl]butan-1-ol oxalate To a solution of (2R)-1-acetoxy-2-acetylamino-2-ethyl-4-[5-(4-cyclohexyloxybut-1-ynyl)furan-2-yl]butane obtained in Example (25a) in a mixed solvent of tetrahydrofuran (0.5 ml), methanol (0.5 ml) and water (0.5 ml) was added lithium hydroxide monohydrate (44.7 mg, 1.07 mmol) with stirring, and the resulting mixture was stirred at 50° C. for 4 hours. After cooling, water was added to the reaction mixture, and the resulting mixture was extracted with dichloromethane. The extract was washed with saturated aqueous sodium chloride solution and dried over anhydrous sodium sulfate. After filtration, the solvent was removed in vacuo, and the residue was purified by chromatography on a basic silica gel column (NH type) using a mixed solvent of dichloromethane and methanol (1:0-50:1) as the eluent to afford the crude (2R)-2-amino-2-ethyl-4-[5-(4-cyclohexyloxybut-1-ynyl)furan-2-yl]butan-1-ol (35.3 mg, yield: 99%).

Subsequently, to a solution of the crude product thus obtained in methanol was added anhydrous oxalic acid (98% pure) (9.5 mg, 0.106 mmol), and the resulting mixture was stirred at room temperature for 30 minutes. After stirring, the reaction mixture was evaporated in vacuo, and isopropyl ether was added to the residue. The crystals precipitated were collected by filtration, washed with isopropyl ether and dried in vacuo to afford the title compound (39.9 mg, yield: 89%).

$^1$H-NMR spectrum (DMSO-d$_6$, 400 MHz) δ: 6.56 (d, 1H, J=3.3 Hz), 6.16 (d, 1H, J=3.3 Hz), 4.19 (br s, 3H), 3.55 (t, 2H, J=6.7 Hz), 3.44 (s, 2H), 3.33-3.28 (m, 1H), 2.67-2.60 (m, 4H), 1.83-1.79 (m, 4H), 1.66-1.55 (m, 4H), 1.53-1.46 (m, 1H), 1.25-1.20 (m, 5H), 0.86 (t, 3H, J=7.5 Hz).

IR spectrum ν$_{max}$ cm$^{-1}$ (KBr): 3402, 2931, 1918, 1611, 1542, 1198, 1106, 1089, 721, 700.

Mass spectrum (FAB$^+$) m/z: 356 ((M+Na)$^+$), 334 ((M+H)$^+$; as free form of title compound).

Example 26

Mono(2R)-2-amino-2-methyl-4-[5-(4-cyclohexyloxybut-1-ynyl)furan-2-yl]-1-butyl phosphate (Exemplification compound number: 5-1072 having formula IIa-1)

(26a) (2R)-2-Allyloxycarbonylamino-2-methyl-4-[5-(4-cyclohexyloxybut-1-ynyl)furan-2-yl]butan-1-ol To a suspension of (2R)-2-amino-2-methyl-4-[5-(4-cyclohexyloxybut-1-ynyl)furan-2-yl]butan-1-ol (0.5305 g, 1.66 mmol) obtained in Example 20 in a mixed solvent of ethyl acetate (16 ml.) and water (16 ml) were added potassium hydrogencarbonate (0.1995 g, 1.99 mmol) first and then allyl chloroformate (0.21 ml, 1.98 mmol) with stirring, and the resulting mixture was stirred at room temperature for 30 minutes. After stirring, the reaction mixture was diluted with ethyl acetate and extracted with ethyl acetate. The extract was washed with saturated aqueous sodium chloride solution and dried over anhydrous sodium sulfate. After filtration, the solvent was removed in vacuo to afford the title compound (0.6202 g, yield: 93%)
$^1$H-NMR spectrum (CDCl$_3$, 400 MHz) δ: 6.38 (d, 1H, J=3.0 Hz), 5.97 (d, 1H, J=3.0 Hz), 5.96-5.86 (m, 1H), 5.30 (ddd, 1H, J=17.6 Hz, 2.9 Hz, 1.5 Hz), 5.22 (dt, 1H, J=9.5 Hz, 1.5 Hz), 4.82 (br s, 1H), 4.52 (br d, J=5.1 Hz), 3.73-3.62 (m, 4H), 3.51 (br s, 1H), 3.33-3.26 (m, 1H), 2.74-2.58 (m, 4H), 2.13 (ddd, 1H, J=13.9 Hz, 11.0 Hz, 5.1 Hz), 1.97-1.89 (m, 3H), 1.75-1.72 (m, 2H), 1.56-1.51 (m, 1H), 1.34-1.18 (m, 8H).

(26b) (2R)-2-Allyloxycarbonylamino-2-methyl-4-[5-(4-cyclohexyloxybut-1-ynyl)furan-2-yl]-1-butyl diallyl phosphate To a solution of (2R)-2-allyloxycarbonylamino-2-methyl-4-[5-(4-cyclohexyloxybut-1-ynyl)furan-2-yl]butan-1-ol (0.6202 g, 1.54 mmol) obtained in Example (26a) in dichloromethane (15 ml) were added successively 1H-tetrazole (0.7220 g, 10.31 mmol) and diallyl diisopropylphosphoramidite (0.81 ml, 3.06 mmol) with stirring under ice-cooling, and then the reaction mixture was stirred at room temperature for 2 hours. After stirring, to the reaction mixture was added m-chloroperbenzoic acid (content: 70%) (0.7556 g, 3.07 mmol) with stirring under ice cooling, and the resulting mixture was stirred at the same temperature for 10 minutes. After stirring, to the reaction mixture was added 10% aqueous sodium thiosulfate solution to quench the reaction, and the resulting mixture was extracted with dichloromethane. The extract was washed successively with saturated aqueous sodium hydrogencarbonate solution and saturated aqueous sodium chloride solution and dried over anhydrous sodium sulfate. After filtration, the solvent was removed in vacuo, and the residue was purified by chromatography on a silica gel-column using a mixed solvent of hexane and ethyl acetate (3:2) as the eluent to afford the title compound (0.7049 g, yield: 81%).
$^1$H-NMR spectrum (CDCl$_3$, 400 MHz) δ: 6.37 (d, 1H, J=3.0 Hz), 5.99-5.85 (m, 3H), 5.40-5.19 (m, 6H), 4.87 (br s, 1H), 4.16 (dd, 1H, J=10.3 Hz, 5.9 Hz), 4.03 (dd, 1H, J=10.3 Hz, 5.9 Hz), 3.65 (d, 2H, J=7.3 Hz), 3.33-3.26 (m, 1H), 2.70-2.59 (m, 4H), 2.22-2.14 (m, 1H), 1.96-1.88 (m, 3H), 1.75-1.72 (m, 2H), 1.56-1.53 (m, 1H), 1.34-1.22 (m, 8H).
Mass spectrum (FAB$^+$) m/z: 563 (M$^+$).

(26c) Mono(2R)-2-amino-2-methyl-4-[5-(4-cyclohexyloxybut-1-ynyl)furan-2-yl]-1-butyl phosphate To a suspension of (2R)-2-allyloxycarbonylamino-2-methyl-4-[5-(4-cyclohexyloxybut-1-ynyl)furan-2-yl]-1-butyl diallyl phosphate (0.7037 g, 1.25 mmol) obtained in Example (26b), triphenylphosphine (69.0 mg, 0.26 mmol) and tetrakis(triphenylphosphine)palladium(0) (75.8 mg, 0.066 mmol) in acetonitrile (13 ml) was added pyrrolidine (0.66 ml, 7.91 mmol) with stirring under a nitrogen atmosphere, and the resulting mixture was stirred at room temperature for 15 hours. After stirring, the reaction mixture was evaporated in vacuo, and the residue was diluted with 50% aqueous ethanol (40 ml) and then adjusted to pH 4 with acetic acid. The crystals precipitated were collected by filtration and washed successively with water and ethanol to afford the crude product. The crude product thus obtained was dissolved in a mixed solvent of methanol (300 ml) and water (60 ml) under heating and treated with charcoal. After filtration, the filtrate was evaporated in vacuo, and to the residue was added ethanol. The crystals precipitated were collected by filtration, washed with ethanol and dried to afford the title compound (0.2672 g, yield: 54%).
$^1$H-NMR spectrum (CD$_3$CO$_2$D, 400 MHz) δ: 6.42 (d, 1H, J=3.7 Hz), 6.09 (d, 1H, J=3.7 Hz), 4.10 (d, 2H, J=10.3 Hz), 3.70 (t, 2H, J=7.3 Hz), 3.43-3.37 (m, 1H), 2.83-2.72 (m, 2H), 2.69 (t, 2H, J=7.3 Hz), 2.18-2.06 (m, 2H), 1.94 (br d, 2H, J=10.3 Hz), 1.76-1.73 (m, 2H), 1.56-1.52 (m, 1H), 1.40 (s, 3H), 1.38-1.18 (m, 5H).
IR spectrum ν$_{max}$ cm$^{-1}$ (KBr): 3413, 2931, 2857, 1645, 1566, 1540, 1469, 1449, 1212, 1184, 1102, 1067, 1043, 949, 796, 511.
Mass spectrum (ESI$^-$) m/z: 398 ((M−H)$^-$).

Example 27

Mono(2R)-2-amino-2-methyl-4-[5-(5-cyclohexylpent-1-ynyl)furan-2-yl]-1-butyl phosphate (Exemplification compound number: 5-824 having formula IIa-1)

The title compound was synthesized in a yield of 24% using (2R)-2-amino-2-methyl-4-[5-(5-cyclohexylpent-1-ynyl)furan-2-yl]butan-1-ol oxalate obtained in Example 2 as the starting material by conducting successively the reactions similar to those mentioned in Examples (26a), (26b) and (26c).
$^1$H-NMR spectrum (CD$_3$CO$_2$D, 400 MHz) δ: 6.39 (d, 1H, J=3.7 Hz), 6.07 (d, 1H, J=3.7 Hz), 4.10 (d, 2H, J=10.3 Hz), 2.79-2.75 (m, 2H), 2.40 (t, 2H, J=7.3 Hz), 2.17-2.05 (m, 2H), 1.75-1.44 (m, 7H), 1.41 (s, 3H), 1.35-1.12 (m, 6H), 0.95-0.90 (m, 2H).
IR spectrum ν$_{max}$ cm$^{-1}$ (KBr): 3233, 2922, 2850, 2559, 1642, 1594, 1537, 1448, 1256, 1184, 1078, 1029, 942, 825, 794, 572, 514.
Mass spectrum (FAB$^-$) m/z: 396 ((M−H)$^-$).

Example 28

Mono(2R)-2-amino-2-methyl-4-{5-[3-(3,4-dimethylphenyloxy)prop-1-ynyl]furan-2-yl}-1-butyl phosphate (Exemplification compound number: 5-2278 having formula IIa-1)

The title compound was synthesized in a yield of 21% using (2R)-2-amino-2-methyl-4-{5-[3-(3,4-dimethylphenyloxy)prop-1-ynyl]furan-2-yl}butan-1-ol oxalate obtained in Example 4 as the starting material by conducting successively the reactions similar to those mentioned in Examples (26a), (26b) and (26c).

$^1$H-NMR spectrum (CD$_3$CO$_2$D, 400 MHz) δ: 7.02 (d, 1H, J=8.1 Hz), 6.78 (d, 1H, J=2.9 Hz), 6.73 (dd, 1H, J=8.1 Hz, 3.0 Hz), 6.56 (d, 1H, J=3.7 Hz), 6.13 (d, 1H, J=3.7 Hz), 4.90 (s, 2H), 4.10 (d, 2H, J=10.3 Hz), 2.84-2.72 (m, 2H), 2.22 (s, 3H), 2.17 (s, 3H), 2.15-2.05 (m, 2H), 1.40 (s, 3H).

IR spectrum $v_{max}$ cm$^{-1}$ (KBr): 3411, 2922, 2227, 1616, 1536, 1501, 1451, 1371, 1286, 1250, 1202, 1185, 1166, 1045, 1028, 931, 799, 573, 514.

Mass spectrum (FAB$^-$) m/z: 406 ((M−H)$^-$).

Example 29

(3R)-3-amino-3-methyl-5-[5-(5-phenylpentanoyl) furan-2-yl]pentylphosphonic acid (Exemplification compound number: 5-1344 having formula IIIa-1)

(29a) (2R)-2-t-Butoxycarbonylamino-2-methyl-4-[5-(5-phenylpentanoyl)furan-2-yl]butan-1-ol To a solution of (2R)-2-amino-2-methyl-4-[5-(5-phenyl-pentanoyl)furan-2-yl]butan-1-ol (97.8 mg, 0.30 mmol) obtained in Example 5 in dichloromethane (3 ml) were added successively di-t-butyl dicarbonate (77.3 mg, 0.35 mmol) and triethylamine (85 µl, 0.61 mmol) with stirring, and the resulting mixture was stirred at room temperature for 19 hours. After stirring, the reaction mixture was evaporated in vacuo, and water was added to the residue, and then the resulting mixture was extracted with ethyl acetate. The extract was washed with saturated aqueous sodium chloride solution and dried over anhydrous magnesium sulfate. After filtration, the solvent was removed in vacuo, and the residue was purified by chromatography on a silica gel column using a mixed solvent of hexane and ethyl acetate (1:1) as the eluent to afford the title compound (112.2 mg, yield: 88%).

$^1$H-NMR spectrum (CDCl$_3$, 400 MHz) δ: 7.29-7.23 (m, 2H), 7.19-7.15 (m, 3H), 7.08 (d, 1H, J=3.7 Hz), 6.18 (d, 1H, J=3.7 Hz), 4.63 (br s, 1H), 4.03 (br s, 1H), 3.66 (d, 2H, J=5.9 Hz), 2.84-2.68 (m, 4H), 2.65 (t, 2H, J=8.1 Hz), 2.18 (ddd, 1H, J=16.6 Hz, 11.0 Hz, 5.1 Hz), 1.98 (ddd, 1H, J=16.6 Hz, 11.7 Hz, 5.1 Hz), 1.81-1.65 (m, 4H), 1.43 (s, 9H), 1.19 (s, 3H).

Mass spectrum (FAB$^+$) m/z: 430 ((M+H)$^+$).

(29b) (2R)-2-t-Butoxycarbonylamino-2-methyl-4-[5-(5-phenylpentanoyl)furan-2-yl]-1-butanal To a solution of (2R)-2-t-butoxycarbonylamino-2-methyl-4-[5-(5-phenylpentanoyl)furan-2-yl]butan-1-ol (110.2 mg, 0.26 mmol) obtained in Example (29a) in dichloromethane (2.6 ml) was added Dess-Martin reagent (165.0 mg, 2.28 mmol), and the resulting mixture was stirred at room temperature under a nitrogen atmosphere for 1 hour. After stirring, the reaction mixture was evaporated in vacuo, and to the residue was added a 10% aqueous sodium thiosulfate solution to decompose the excess reagent. The resulting mixture was extracted with dichloromethane, and the extract was washed successively with saturated aqueous sodium hydrogencarbonate solution and saturated aqueous sodium chloride solution and dried over anhydrous magnesium sulfate. After filtration, the solvent was removed in vacuo, and the residue was purified by chromatography on a silica gel column using a mixed solvent of hexane and ethyl acetate (3:1) as the eluent to afford the title compound (105.9 mg, yield: 97%).

$^1$H-NMR spectrum (CDCl$_3$, 400 MHz) δ: 9.34 (s, 1H), 7.29-7.25 (m, 2H), 7.19-7.15 (m, 3H), 7.06 (d, 1H, J=3.6 Hz), 6.16 (d, 1H, J=3.6 Hz), 5.16 (br s, 1H), 2.77 (t, 2H, J=7.3 Hz), 2.74-2.56 (m, 4H), 2.40-2.36 (m, 1H), 2.22-2.14 (m, 1H), 1.80-1.65 (m, 4H), 1.44 (s, 9H), 1.37 (s, 3H).

Mass spectrum (FAB$^+$) m/z: 428 ((M+H)$^+$).

(29c) Diethyl (3R)-3-t-butoxycarbonylamino-3-methyl-5-[5-(5-phenylpentanoyl)furan-2-yl]pent-1-enylphosphonate To a suspension of sodium hydride (content: 60%)(16.0 mg, 0.40 mmol) in tetrahydrofuran (1 ml) was added tetraethyl methylenediphosphonate (0.100 ml, 0.40 mmol) with stirring under ice-cooling over a 5-minute interval, and then the resulting mixture was stirred at room temperature for 1 hour.

Subsequently, to the reaction mixture was added a solution of diethyl (2R)-2-t-butoxycarbonylamino-2-methyl-4-[5-(5-phenylpentanoyl)furan-2-yl]-1-butanal (104.5 mg, 0.24 mmol) obtained in Example (29b) in tetrahydrofuran (4 ml) with stirring under ice-cooling over a 5-minute interval, and the resulting mixture was stirred at the same temperature for 15 minutes. After stirring, the reaction mixture was neutralized with acetic acid (22 µl, 0.38 mmol) and evaporated in vacuo. Water was added to the residue obtained, and the resulting mixture was extracted with ethyl acetate. The extract was washed successively with water and saturated aqueous sodium chloride solution and dried over anhydrous magnesium sulfate. After filtration, the solvent was removed in vacuo, and the residue was purified by chromatography on a silica gel column using ethyl acetate as the eluent to afford the title compound (129.0 mg, yield: 94%).

$^1$H-NMR spectrum (CDCl$_3$, 400 MHz) δ: 7.29-7.24 (m, 2H), 7.19-7.15 (m, 3H), 7.07 (d, 1H, J=3.7 Hz), 6.75 (dd, 1H, J=22.7 Hz, 17.6 Hz), 6.16 (d, 1H, J=3.7 Hz), 5.71 (t, 1H, J=17.6 Hz), 4.60 (br s, 1H), 4.15-4.04 (m, 4H), 2.77 (t, 2H, J=8.1 Hz), 2.74-2.63 (m, 4H), 2.30-2.22 (m, 1H), 2.09-2.01 (m, 1H), 1.81-1.65 (m, 4H), 1.42 (s, 9H), 1.40 (s, 3H), 1.33 (t, 6H, J=7.3 Hz).

Mass spectrum (FAB$^+$) m/z: 562 ((M+H)$^+$).

(29d) Diethyl (3R)-3-t-butoxycarbonylamino-3-methyl-5-[5-(5-phenylpentanoyl)furan-2-yl]pentylphosphonate To a solution of diethyl (3R)-3-t-butoxycarbonylamino-3-methyl-5-[5-(5-phenylpentanoyl)furan-2-yl]pent-1-enylphosphonate (127.8 mg, 0.23 mmol) obtained in Example (29c) in ethanol (2.3 ml) was added chlorotris(triphenylphosphine) rhodium(I) (22.0 mg, 0.024 mmol), and the resulting mixture was stirred at 50° C. under a hydrogen atmosphere for 8 hours. After cooling, to the reaction mixture was furthermore added chlorotris(triphenylphosphine) rhodium(I) (21.5 mg, 0.023 mmol), and the resulting mixture was stirred at 50° C. under a hydrogen atmosphere for 8 hours. After stirring, the reaction mixture was evaporated in vacuo, and the residue was purified by chromatography on a silica gel column using ethyl acetate as the eluent to afford the crude product (142.1 mg). Furthermore, the crude product obtained was purified using a preparative reversed phase HPLC column [Inertsil ODS-3 (2.0 cm×25 cm), GL Science, mobile phase: acetonitrile/water (75:25), flow rate: 10 ml/min] to afford the title compound (109.5 mg, yield: 85%)

$^1$H-NMR spectrum (CDCl$_3$, 400 MHz) δ: 7.29-7.25 (m, 2H), 7.19-7.15 (m, 3H), 7.07 (d, 1H, J=3.7 Hz), 6.15 (d, 1H, J=3.7 Hz), 4.36 (br s, 1H), 4.15-4.10 (m, 4H), 2.77 (t, 2H, J=7.3 Hz), 2.72-2.63 (m, 4H), 2.22-2.17 (m, 2H), 1.92-1.85 (m, 1H), 1.80-1.63 (m, 7H), 1.42 (s, 9H), 1.33 (t, 6H, J=7.3 Hz), 1.19 (s, 3H).

Mass spectrum (FAB$^+$) m/z: 564 ((M+H)$^+$).

(29e) (3R)-3-Amino-3-methyl-5-[5-(5-phenylpentanoyl)furan-2-yl]pentylphosphonic acid To a solution of diethyl (3R)-3-t-butoxycarbonylamino-3-methyl-5-[5-(5-phenylpentanoyl)furan-2-yl]pentylphosphonate (108.2 mg, 0.19 mmol) obtained in Example (29d) in dichloromethane (1.9 ml) was added bromotrimethylsilane (0.255 ml, 1.93 mmol), and the resulting mixture was stirred at room temperature under a nitrogen atmosphere for 4 hours. After stirring, the reaction mixture was evaporated in vacuo, and the residue was diluted with aqueous ethanol, and then the resulting mixture was adjusted to pH 4 with aqueous ammonia and acetic acid. The crystals precipitated were collected by filtration, washed successively with water and ethanol and dried to afford the title compound (51.4 mg, yield: 66%).

$^1$H-NMR spectrum (CD$_3$CO$_2$D, 400 MHz) δ: 7.29 (d, 1H, J=3.7 Hz), 7.26-7.23 (m, 2H), 7.18-7.12 (m, 3H), 6.35 (d, 1H, J=3.7 Hz), 2.85 (t, 4H, J=7.3 Hz), 2.64 (t, 2H, J=7.3 Hz), 2.23-1.92 (m, 6H), 1.78-1.64 (m, 4H), 1.44 (s, 3H).

IR spectrum ν$_{max}$ cm$^{-1}$ (KBr): 3160, 2934, 2860, 2560, 2529, 1670, 1552, 1516, 1453, 1391, 1314, 1140, 1068, 1046, 913, 882, 804, 723, 700, 568, 525, 490, 468.

Mass spectrum (FAB$^-$) m/z: 406 ((M−H)$^-$).

Example 30

(2R)-2-Amino-2-methyl-4-[1-methyl-5-(5-phenylbut-1-ynyl)pyrrol-2-yl]butan-1-ol 1/2 oxalate (Exemplification compound number: 1-559 having formula Ia-2)

The title compound was synthesized in a yield of 58% using (2R)-1-acetoxy-2-acetylamino-2-methyl-4-(1-methyl-5-iodopyrrol-2-yl)butane obtained in Reference example 13 and 4-phenylbut-1-yne as the starting-materials by conducting successively the reactions similar to those mentioned in Examples (1a) and (1b).

$^1$H-NMR spectrum (CD$_3$OD, 400 MHz) δ: 7.30-7.26 (m, 4H); 7.21-7.16 (m, 1H), 6.09 (d, 1H, J=3.7 Hz), 5.76 (d, 1H, J=3.7 Hz), 3.59 (d, 1H, J=11.7 Hz), 3.52 (d, 1H, J=11.7 Hz), 3.41 (s, 3H), 2.88 (t, 2H, J=7.3 Hz), 2.73 (t, 2H, J=7.3 Hz), 2.62-2.58 (m, 2H), 1.98-1.80 (m, 2H), 1.29 (s, 3H).

IR spectrum ν$_{max}$ cm$^{-1}$ (KBr): 3362, 3026, 2943, 2224, 2080, 1591, 1496, 1454, 1300, 1073.

Mass spectrum (FAB$^+$) m/z: 311 ((M+H)$^+$; as free form of title compound).

Example 31

(2R)-2-Amino-2-methyl-4-[1-methyl-5-(5-phenylpentyl)pyrrol-2-yl]butan-1-ol 1/2 oxalate (Exemplification compound number 1-93 having formula Ia-2)

(31a) (2R)-1-Acetoxy-2-acetylamino-2-methyl-4-[1-methyl-5-(5-phenylpent-1-ynyl)pyrrol-2-yl]butane To a suspension of (2R)-1-acetoxy-2-acetylamino-2-methyl-4-(1-methyl-5-iodopyrrol-2-yl)butane (0.2918 g, 0.74 mmol) obtained in Reference example 13, 5-phenylpent-1-yne (0.3225 g, 2.24 mmol), dichlorobis(triphenylphopsphine)palladium(II) (52.3 mg, 0.075 mmol) and copper(I) iodide (29.0 mg, 0.15 mmol) in N,N-dimethylformamide (7.4 ml) was added triethylamine (1.04 ml, 7.5 mmol) with stirring, and the resulting mixture was stirred at room temperature under a nitrogen atmosphere for 1 hour. After stirring, saturated aqueous ammonium chloride solution was added to the reaction mixture to quench the reaction, and furthermore water and ethyl acetate were added. The resulting mixture was stirred at room temperature for 30 minutes. After stirring, the reaction mixture was extracted with ethyl acetate, and the extract was washed successively with water and saturated aqueous sodium chloride solution and dried over anhydrous sodium sulfate. After filtration, the solvent was removed in vacuo, and the residue was purified by chromatography on a silica gel column using a mixed solvent of ethyl acetate and hexane (3:2) as the eluent to afford the title compound (0.2205 g, yield: 73%).

$^1$H-NMR spectrum (CDCl$_3$, 400 MHz) δ: 7.31-7.27 (m, 2H), 7.22-7.18 (m, 3H), 6.26 (d, 1H, J=3.7 Hz), 5.81 (d, 1H, J=3.7 Hz), 5.35 (br s, 1H), 4.32 (d, 1H, J=11.3 Hz), 4.18 (d, 1H, J=11.3 Hz), 3.55 (s, 3H), 2.78 (t, 2H, J=7.7 Hz), 2.55 (t, 2H, J=8.2 Hz), 2.46 (t, 2H, J=7.0 Hz), 2.27-2.19 (m, 1H), 2.09 (s, 3H), 1.97-1.84 (m, 6H), 1.37 (s, 3H).

IR spectrum ν$_{max}$ cm$^{-1}$ (CHCl$_3$): 3443, 2944, 2861, 1736, 1679, 1603, 1512, 1454, 1374, 1251, 1042.

Mass spectrum (FAB$^+$) m/z: 409 ((M+H)$^+$), 408 (M$^+$).

(31b) (2R)-1-Acetoxy-2-acetylamino-2-methyl-4-[1-methyl-5-(5-phenylpentyl)pyrrol-2-yl]butane To a solution of (2R)-1-acetoxy-2-acetylamino-2-methyl-4-[1-methyl-5-(5-phenylpent-1-ynyl)pyrrol-2-yl]butane (77 mg, 0.19 mmol) obtained in Example (31a) in methanol (2 ml) was added 10% palladium-charcoal (50% wet with water) (4.3 mg), and the resulting mixture was stirred at room temperature under a hydrogen atmosphere for 1 hour. After stirring, the internal atmosphere was replaced with nitrogen, and the palladium-charcoal in the reaction mixture was filtered off using celite, which was washed with ethyl acetate. The filtrate and the washings were combined and evaporated to dryness in vacuo to afford the title compound (75.5 mg, yield: 97%).

$^1$H-NMR spectrum (CDCl$_3$, 400 MHz) δ: 7.28-7.25 (m, 2H), 7.18-7.15 (m, 3H), 5.79 (d, 1H, J=3.7 Hz), 5.77 (d, 1H, J=3.7 Hz), 5.36, (br s, 1H), 4.32 (d, 1H, J=11.0 Hz), 4.19 (d, 1H, J=11.0 Hz), 3.37 (s, 3H), 2.61 (t, 2H, J=7.7 Hz), 2.55-2.47 (m, 4H), 2.23-2.15 (m, 1H), 2.07 (s, 3H), 1.94-1.87 (m, 1H), 1.90 (s, 3H), 1.70-1.59 (m, 4H), 1.53 (s, 3H), 1.47-1.39 (m, 2H).

Mass spectrum (FAB$^+$) m/z: 412 ((M+H)$^+$).

(31c) (2R)-2-Amino-2-methyl-4-[1-methyl-5-(5-phenylpentyl)pyrrol-2-yl]butan-1-ol 1/2 oxalate To a solution of (2R)-1-acetoxy-2-acetylamino-2-methyl-4-[1-methyl-5-(5-phenylpentyl)pyrrol-2-yl]butane (75.0 mg, 0.18 mmol) obtained in Example (31b) in a mixed solvent of tetrahydrofuran (1 ml) and methanol (1 ml) were added successively water (1 ml) and lithium hydroxide monohydrate (76 mg, 1.81 mmol) with stirring, and the resulting mixture was stirred at 50° C. for 6 hours. After cooling, water was added to the reaction mixture, and the resulting mixture was extracted with dichloromethane. The extract was washed with saturated aqueous sodium chloride solution and dried over anhydrous sodium sulfate. After filtration, the solvent was removed in vacuo, and the residue was purified by chromatography on a basic silica gel column (NH type) using a mixed solvent of dichloromethane and methanol (1:0-50:1) as the eluent to afford (2R)-2-amino-2-methyl-4-[1-methyl-5-(5-phenylpentyl)pyrrol-2-yl]butan-1-ol (53.6 mg, yield: 90%).

Subsequently, to a solution of (2R)-2-amino-2-methyl-4-[1-methyl-5-(5-phenylpentyl)pyrrol-2-yl]butan-1-ol (53.6 mg) thus obtained in methanol (1.6 ml) was added anhydrous oxalic acid (98% pure) (7.4 mg, 0.082 mmol), and the resulting mixture was stirred at room temperature for 1 hour. After stirring, the reaction mixture was evaporated in vacuo, and ethyl acetate was added to the residue. The crystals precipitated were collected by filtration, washed with ethyl acetate and dried in vacuo to afford the title compound (49.2 mg, yield: 81%).

$^1$H-NMR spectrum (CD$_3$OD, 400 MHz) δ: 7.25-7.21 (m, 2H), 7.16-7.11 (m, 3H), 5.71 (d, 1H, J=3.7 Hz), 5.66 (d, 1H, J=3.7 Hz), 3.60 (d, 1H, J=11.7 Hz), 3.52 (d, 1H, J=11.7 Hz), 3.41 (s, 3H), 2.65-2.56 (m, 4H), 2.53-2.49 (m, 2H), 1.99-1.81 (m, 2H), 1.68-1.56 (m, 4H), 1.44-1.37 (m, 2H), 1.30 (s, 3H).

IR spectrum $v_{max}$ cm$^{-1}$ (KBr): 3315, 2930, 2092, 1632, 1591, 1549, 1455, 1304, 1073.

Mass spectrum (FAB$^+$) m/z: 329 ((M+H)$^+$; as free form of title compound).

Example 32

(2R)-2-Amino-2-methyl-4-[1-methyl-5-(4-phenylbutyl)pyrrol-2-yl]butan-1-ol 1/2 oxalate (Exemplification compound number: 1-31 having formula Ia-2)

The title compound was synthesized in a yield of 28% using (2R)-1-acetoxy-2-acetylamino-2-methyl-4-(1-methyl-5-iodopyrrol-2-yl)butane obtained in Reference example 13 and 4-phenylbut-1-yne as the starting materials by conducting successively the reactions similar to those mentioned in Examples (31a), (31b) and (31c).

$^1$H-NMR spectrum (CD$_3$OD, 400 MHz) δ: 7.25-7.21 (m, 2H), 7.16-7.11 (m, 3H), 5.71 (d, 1H, J=2.9 Hz), 5.66 (d, 1H, J=2.9 Hz), 3.60 (d, 1H, J=11.7 Hz), 3.53 (d, 1H, J=11.7 Hz), 3.39 (s, 3H), 2.66-2.53 (m, 6H), 1.98-1.81 (m, 2H), 1.72-1.55 (m, 4H), 1.30 (s, 3H).

IR spectrum $v_{max}$ cm$^{-1}$ (KBr): 3347, 3024, 2933, 2858, 1589, 1454, 1299, 1072, 763, 745, 698.

Mass spectrum (FAB$^+$) m/z: 315 ((M+H)$^+$; as free form of title compound).

Example 33

(2R)-2-Amino-2-methyl-4-[1-methyl-5-(5-phenylpentanoyl)pyrrol-2-yl]butan-1-ol hydrochloride (Exemplification compound number: 1-1093 having formula Ia-2)

(33a) (2R)-1-Acetoxy-2-acetylamino-2-methyl-4-{1-methyl-[5-phenyl-1-(5-phenylpentanoyloxy)pent-1-enyl]pyrrol-2-yl}butane To a solution of (2R)-1-acetoxy-2-acetylamino-2-methyl-4-(1-methylpyrrol-2-yl)butane (4.23 g, 15.4 mmol) obtained in Reference example (19b) in toluene (100 ml) was added a solution of 4-dimethylaminopyridine (9.41 g, 77.0 mmol) and 5-phenylvaleroyl chloride (98%) (7.92 g, 39.5 mmol) in toluene (50 ml), and the resulting mixture was stirred at 110° C. for 48 hours. After cooling to room temperature, ethyl acetate and water were added to the reaction mixture, and the resulting mixture was extracted with ethyl acetate. The extract was washed successively with water and saturated aqueous sodium chloride solution and dried over anhydrous sodium sulfate. After the solvent was removed in vacuo, and the residue was purified by chromatography on a silica gel column using a mixed solvent of ethyl acetate and hexane (3:2-2:1) as the eluent to afford the title compound (4.03 g, yield: 45%).

$^1$H-NMR spectrum (CDCl$_3$, 400 MHz) δ: 7.26-7.23 (m, 4H), 7.17-7.11 (m, 6H), 6.96 (d, 1H, J=-4.2 Hz), 5.97 (d, 1H, J=4.2 Hz), 5.41 (br s, 1H), 4.31 (d, 1H, J=11.0 Hz), 4.15 (d, 1H, J=11.0 Hz), 4.11 (t, 1H, J=8.1 Hz), 3.83 (s, 3H), 2.67-2.39 (m, 8H), 2.34-2.26 (m, 1H), 2.10 (s, 3H), 2.04-1.86 (m, 6H), 1.61-1.48 (m, 6H), 1.36 (s, 3H).

IR spectrum $v_{max}$ cm$^{-1}$ (CHCl$_3$): 3443, 2938, 2861, 1733, 1681, 1634, 1487, 1454, 1374, 1249, 1044.

Mass spectrum (FAB$^+$) m/z: 587 ((M+H)$^+$).

(33b) (2R)-2-Amino-2-methyl-4-[1-methyl-5-(5-phenylpentanoyl)pyrrol-2-yl]butan-1-ol hydrochloride To a solution of (2R)-1-acetoxy-2-acetylamino-2-methyl-4-{1-methyl-[5-phenyl-1-(5-phenylpentanoyloxy)pent-1-enyl]pyrrol-2-yl}butane (4.0270 g, 6.86 mmol) obtained in Example (33a) in a mixed solvent of tetrahydrofuran (14 ml) and methanol (14 ml) were added successively water (14 ml) and lithium hydroxide monohydrate (2.8820 g, 68.68 mmol), and the resulting mixture was stirred at 50° C. for 4 hours. After cooling, water was added to the reaction mixture, and the resulting mixture was extracted with dichloromethane. The extract was washed with saturated aqueous sodium chloride solution and dried over anhydrous sodium sulfate. After filtration, the solvent was removed in vacuo, and the residue was purified by chromatography on a basic silica gel column (NH type) using a mixed solvent of dichloromethane and methanol (100:1) as the eluent to afford the crude (2R)-2-amino-2-methyl-4-[1-methyl-5-(5-phenylpentanoyl)pyrrol-2-yl]butan-1-ol (2.1152 g).

Subsequently, to a solution of the crude product thus obtained in methanol (31 ml) was added 4N hydrochloric acid-dioxane solution (1.54 ml, 6.16 mmol), and the resulting mixture was stirred at room temperature for 10 minutes. After stirring, the reaction mixture was evaporated in vacuo, and ethyl acetate was added to the residue. The crystals precipitated were collected by filtration, washed with ethyl acetate and dried in vacuo to afford the title compound (2.0685 g, yield: 79%).

Melting point: 130-131° C.,
Angle of rotation: [α]$_D$=-4.81 (c=1.00, MeOH),
$^1$H-NMR spectrum (CD$_3$OD, 400 MHz) δ: 7.25-7.21 (m, 2H), 7.17-7.11 (m, 3H), 7.05 (d, 1H, J=4.2 Hz), 6.03 (d, 1H, J=4.2 Hz), 3.86 (s, 3H), 3.65 (d, 1H, J=11.4 Hz), 3.55 (d, 1H, J=11.4 Hz), 2.78-2.67 (m, 4H), 2.63 (t, 2H, J=7.2 Hz), 2.02 (ddd, 1H, J=13.8 Hz, 9.4 Hz, 7.6 Hz), 1.90 (ddd, 1H, J=13.8 Hz, 11.5 Hz, 6.3 Hz), 1.70-1.64 (m, 4H), 1.34 (s, 3H).

IR spectrum $v_{max}$ cm$^{-1}$ (KBr): 3215, 2937, 2883, 2691, 2571, 1646, 1525, 1482, 1457, 1380, 1294, 1228, 1182, 1055, 998, 913, 770, 751, 700.

Mass spectrum (FAB$^+$) m/z: 343 ((M+H)$^+$; as free form of title compound),

Elemental analysis (% as C$_{21}$H$_{30}$N$_2$O$_2$.HCl)
Calculated: C, 66.56; H, 8.25; N, 7.39; Cl, 9.36
Found: C, 66.51; H, 8.20; N, 7.47; Cl, 9.08.

Example 34

(2R)-2-Amino-2-methyl-4-{1-methyl-5-[5-(4-fluorophenyl)pentanoyl]pyrrol-2-yl}butan-1-ol hydrochloride (Exemplification compound number: 1-1094 having formula Ia-2)

The title compound was synthesized in a yield of 42% using (2R)-1-acetoxy-2-acetylamino-2-methyl-4-(1-methylpyrrol-2-yl)butane obtained in Reference example (19b) and 5-(4-fluorophenyl)valeroyl chloride as the starting materials by conducting successively the reactions similar to those mentioned in Examples (33a) and (33b).

$^1$H-NMR spectrum (CD$_3$OD, 400 MHz) δ: 7.20-7.13 (m, 2H), 7.05 (d, 1H, J=4.0 Hz), 6.99-6.92 (m, 2H), 6.03 (d, 1H, J=4.0 Hz), 3.86 (s, 3H), 3.65 (d, 1H, J=11.4 Hz), 3.55 (d, 1H, J=11.4 Hz), 2.76 (t, 2H, J=7.3 Hz), 2.74-2.66 (m, 2H), 2.62 (t, 2H, J=7.3 Hz), 2.08-1.8.6 (m, 2H), 1.73-1.60 (m, 4H), 1.35 (s, 3H).

IR spectrum ν$_{max}$ cm$^{-1}$ (KBr): 3352, 3210, 3153, 3035, 2930, 2863, 1634, 1601, 1509, 1480, 1464, 1371, 1349, 1222, 1175, 1067, 823, 766.

Mass spectrum (FAB$^+$) m/z: 361 ((M+H)$^+$; as free form of title compound).

Example 35

(2R)-2-Amino-2-methyl-4-[1-methyl-5-(4-phenylbutanoyl)pyrrol-2-yl]butan-1-ol hydrochloride (Exemplification compound number: 1-1082 having formula Ia-2)

The title compound was synthesized in a yield of 48% using (2R)-1-acetoxy-2-acetylamino-2-methyl-4-(1-methylpyrrol-2-yl)butane obtained in Reference example (19b) and 4-phenylbutyryl chloride as the starting materials by conducting successively the reactions similar to those mentioned in Examples (33a) and (33b).

$^1$H-NMR spectrum (CD$_3$OD, 400 MHz) δ: 7.28-7.12 (m, 5H), 6.97 (d, 1H, J=4.0 Hz), 6.02 (d, 1H, J=4.0 Hz), 3.86 (s, 3H), 3.65 (d, 1H, J=11.7 Hz), 3.55 (d, 1H, J=11.7 Hz), 2.78-2.62 (m, 6H), 2.08-1.85 (m, 4H), 1.35 (s, 3H).

IR spectrum ν$_{max}$ cm$^{-1}$ (KBr): 3203, 3025, 2941, 2572, 2029, 1649, 1518, 1482, 1457, 1382, 1297, 1179, 1140, 1057, 989, 915, 752, 699.

Mass spectrum (FAB$^+$) m/z: 329 ((M+H)$^+$; as free form of title compound).

Example 36

(2R)-2-Amino-2-methyl-4-[1-methyl-5-(3-phenylpropanoyl)pyrrol-2-yl]butan-1-ol hydrochloride (Exemplification compound number: 1-1080 having formula Ia-2)

The title compound was synthesized in a yield of 42% using (2R)-1-acetoxy-2-acetylamino-2-methyl-4-(1-methylpyrrol-2-yl)butane obtained in Reference example (19b) and 3-phenylpropionyl chloride as the starting materials by conducting successively the reactions similar to those mentioned in Examples (33a) and (33b).

$^1$H-NMR spectrum (CD$_3$OD, 400 MHz) δ: 7.27-7.11 (m, 5H), 7.03 (d, 1H, J=4.4 Hz), 6.01 (d, 1H, J=4.4 Hz), 3.86 (s, 3H), 3.65 (d, 1H, J=11.7 Hz), 3.55 (d, 1H, J=11.7 Hz), 3.09-3.02 (m, 2H), 2.99-2.92 (m, 2H), 2.76-2.62 (m, 2H), 2.08-1.85 (m, 2H), 1.34 (s, 3H).

IR spectrum ν$_{max}$ cm$^{-1}$ (KBr): 3376, 3026, 2932, 2559, 1640, 1605, 1484, 1455, 1410, 1381, 1294, 1225, 1135, 1069, 983, 924, 770, 747, 699.

Mass spectrum (FAB$^+$) m/z: 315 ((M+H)$^+$; as free form of title compound).

Example 37

(2R)-2-Amino-2-methyl-4-[1-methyl-5-(5-cyclohexylpentanoyl)pyrrol-2-yl]butan-1-ol hydrochloride (Exemplification compound number: 1-1083 having formula Ia-2)

The title compound was synthesized in a yield of 29% using (2R)-1-acetoxy-2-acetylamino-2-methyl-4-(1-methylpyrrol-2-yl)butane obtained in Reference example (19b) and 5-cyclohexylvaleroyl chloride as the starting materials by conducting successively the reactions similar to those mentioned in Examples (33a) and (33b).

$^1$H-NMR spectrum (CD$_3$OD, 400 MHz) δ: 7.05 (d, 1H, J=4.0 Hz), 6.04 (d, 1H, J=4.0 Hz), 3.87 (s, 3H), 3.65 (d, 1H, J=11.7 Hz), 3.55 (d, 1H, J=11.7 Hz), 2.78-2.64 (m, 4H), 2.09-1.86 (m, 2H), 1.76-1.58 (m, 7H), 1.40-1.10 (m, 11H), 0.95-0.80 (m, 2H).

IR spectrum ν$_{max}$ cm$^{-1}$ (KBr): 3354, 3212, 3156, 3034, 2921, 2850, 1637, 1498, 1480, 1464, 1379, 1370, 1292, 1224, 1175, 1066, 1054, 914, 762.

Mass spectrum (FAB$^+$) m/z 349 ((M+H)$^+$; as free form of title compound).

Example 38

(2R)-2-Amino-2-methyl-4-[1-methyl-4-(5-phenylpentanoyl)pyrrol-2-yl]butan-1-ol 1/2 oxalate (Exemplification compound number 2-252 having formula Ib-2)

(38a) (4R)-4-Methyl-4-{2-[1-methyl-4-(5-phenylpentanoyl)pyrrol-2-yl]ethyl}-1,3-oxazolidin-2-one To a solution of (4R)-4-methyl-4-[2-(1-methylpyrrol-2-yl) ethyl]-1,3-oxazolidin-2-one (100 mg, 0.48 mmol) obtained in Reference example 11 in benzene (4 ml) were added successively N,N-dimethyl-5-phenylpentanamide (99 mg, 0.48 mmol) and phosphoryl chloride (43 µl, 0.46 mmol), and the resulting mixture was refluxed for 6 hours. After refluxing, to the reaction mixture was added 20% aqueous sodium acetate solution (2 ml), and the resulting mixture was stirred at 80° C. for 15 minutes. After cooling to room temperature, water was added to the reaction mixture, and the resulting mixture was extracted with ethyl acetate. The extract was washed successively with water and saturated aqueous sodium chloride solution and dried over anhydrous magnesium sulfate. After filtration, the solvent was removed in vacuo, and the residue was purified by chromatography on a silica gel column using a mixed solvent of ethyl acetate and hexane (1:1-3:2-4:1) as the eluent to afford the title compound (11 mg, yield: 6%)

$^1$H-NMR spectrum (CDCl$_3$, 500 MHz) δ: 7.30-7.24 (m, 2H), 7.20-7.15 (m, 4H), 6.31 (s, 1H), 5.72 (br s, 1H), 4.17 (d, 1H, J=8.6 Hz), 4.10 (d, 1H, J=8.6 Hz), 3.57 (s, 3H), 2.70-2.55 (m, 6H), 1.94 (t, 2H, J=8.2 Hz), 1.78-1.60 (m, 4H), 1.43 (s, 3H).

Mass spectrum (FAB$^+$) m/z: 369 ((M+H)$^+$).

(38b) (2R)-2-Amino-2-methyl-4-[1-methyl-4-(5-phenylpentanoyl)pyrrol-2-yl]butan-1-ol 1/2 oxalate To a solution of (4R)-4-methyl-4-{2-[(1-methyl-4-(5-phenylpentanoyl)pyrrol-2-yl]ethyl}-1,3-oxazolidin-2-one (11 mg, 0.03 mmol) obtained in Example (38a) in a mixed solvent of tetrahydrofuran (1 ml) and methanol (1 ml) was added a 5N aqueous potassium hydroxide solution (1 ml), and the resulting mixture was refluxed for 2 days. After cooling, water was added to the reaction mixture, and the resulting mixture was extracted with dichloromethane. The extract was dried over anhydrous sodium sulfate. After filtration, the solvent was removed in vacuo to afford the crude product of (2R)-2-amino-2-methyl-4-[1-methyl-4-(5-phenylpentanoyl)pyrrol-2-yl]butan-1-ol (9 mg).

Subsequently, to a solution of the crude product (6.5 mg) thus obtained in methanol (0.5 ml) was added anhydrous oxalic acid (98% pure) (0.85 mg, 0.0095 mmol), and the resulting mixture was stirred at room temperature for 10 minutes. After stirring, the reaction mixture was concentrated to dryness to afford the title compound (7.0 mg, yield: 84%).

$^1$H-NMR spectrum (CD$_3$OD, 500 MHz) δ: 7.42 (s, 1H), 7.26-7.20 (m, 2H), 7.17-7.11 (m, 3H), 6.32 (s, 1H), 3.65-3.60 (m, 4H), 3.57 (d, 1H, J=11.7 Hz), 2.74-2.60 (m, 6H), 2.04-1.86 (m, 2H), 1.73-1.62 (m, 4H), 1.33 (s, 3H)

IR spectrum ν$_{max}$ cm$^{-1}$ (KBr): 3339, 3025, 2929, 2859, 2565, 1611, 1525, 1497, 1453, 1438, 1355, 1310, 1176, 1069, 928, 818, 774, 749, 700.

Mass spectrum (FAB$^+$) m/z: 343 ((M+H)$^+$; as free form of title compound).

Example 39

(2R)-2-Amino-2-methyl-4-[1-methyl-5-(5-phenyl-1-hydroxypentyl)pyrrol-2-yl]butan-1-ol 1/2 oxalate (Exemplification compound number: 1-1399 having formula Ia-2)

To a suspension of (2R)-2-amino-2-methyl-4-[1-methyl-5-(5-phenylpentanoyl)pyrrol-2-yl]butan-1-ol hydrochloride (185 mg, 0.49 mmol) obtained in Example (33b) in dichloromethane (10 ml) was added 1N aqueous sodium hydroxide solution, and the resulting mixture was stirred for 5 minutes. After stirring, the reaction mixture was extracted with dichloromethane, and the extract was washed with saturated aqueous sodium chloride solution and dried over anhydrous sodium sulfate. After filtration, the solvent was removed in vacuo to afford (2R)-2-amino-2-methyl-4-[1-methyl-5-(5-phenylpentanoyl)pyrrol-2-yl]butan-1-ol.

Subsequently, to a solution of (2R)-2-amino-2-methyl-4-[1-methyl-5-(5-phenylpentanoyl)pyrrol-2-yl]butan-1-ol thus obtained in methanol (5 ml) was added sodium borohydride (28 mg, 0.74 mmol) with stirring under ice-cooling, and then the resulting mixture was stirred at room temperature for 1 hour. After stirring, to the reaction mixture was furthermore added sodium borohydride (28 mg, 0.74 mmol), and the resulting mixture was stirred at room temperature for 20 hours. After stirring, to the reaction mixture was additionally added sodium borohydride (28 mg, 0.74 mmol), and the resulting mixture was stirred at room temperature for 7 hours. After stirring, water was added to the reaction mixture, and the resulting mixture was extracted with ethyl acetate. The extract was washed successively with water and saturated aqueous sodium chloride solution and dried over anhydrous sodium sulfate. After filtration, the filtrate was concentrated to dryness in vacuo, and the residue was purified using a preparative reversed phase HPLC column [Inertsil ODS-3 (2.0 cm×25 cm), GL Science, mobile phase: acetonitrile/0.1% aqueous ammonium acetate solution (70:30), flow rate: 10 ml/min] to afford (2R)-2-amino-2-methyl-4-[1-methyl-5-(5-phenyl-1-hydroxypentyl)pyrrol-2-yl]butan-1-ol (79 mg).

Subsequently, to a solution of (2R)-2-amino-2-methyl-4-[1-methyl-5-(5-phenyl-1-hydroxypentyl)pyrrol-2-yl]butan-1-ol (79 mg, 0.23 mmol) thus obtained in methanol (2 ml) was added anhydrous oxalic acid (98% pure) (9.3 mg, 0.11 mmol), and the resulting mixture was stirred at room temperature for 30 minutes. After stirring, the reaction mixture was concentrated to dryness in vacuo to afford the title compound (57 mg, yield: 30%).

$^1$H-NMR spectrum (CD$_3$OD, 400 MHz) δ: 7.25-7.20 (m, 2H), 7.17-7.09 (m, 3H), 5.91 (d, 1H, J=3.4 Hz), 5.76 (d, 1H, J=3.4 Hz), 4.57 (t, 1H, J=6.6 Hz), 3.59 (d, 1H, J=12.0 Hz), 3.54 (s, 3H), 3.53 (d, 1H, J=12.0 Hz), 2.65-2.55 μm, 4H), 2.00-1.80 (m, 4H), 1.70-1.58 (m, 2H), 1.54-1.44 (m, 1H), 1.43-1.32 (m, 1H), 1.30 (s, 3H).

IR spectrum ν$_{max}$ cm$^{-1}$ (KBr): 3212, 3026, 2935, 2897, 2571, 1719, 1700, 1611, 1521, 1496, 1454, 1405, 1279, 1218, 1053, 767, 721, 700.

Mass spectrum (FAB$^+$) m/z: 325 ((M+H)$^+$; as free form of title compound).

Example 40

(2R)-2-Amino-2-methyl-4-{5-[3-(2-cyclohexylethyloxy)phenyl]-1-methylpyrrol-2-yl}butan-1-ol 1/2 oxalate (Exemplification compound number: 1-1444 having formula Ia-2)

(40a) (4R)-4-Methyl-4-[2-(5-iodo-1-methylpyrrol-2-yl)ethyl]-1,3-oxazolidin-2-one To a solution of (4R)-4-methyl-4-[2-(1-methylpyrrol-2-yl)ethyl]-1,3-oxazolidin-2-one (0.6187 g, 2.97 mmol) obtained in Reference example 11 in tetrahydrofuran (30 ml) were added successively pyridine (1.2 ml, 14.9 mmol) and iodine (1.5060 g, 5.93 mmol) with stirring under ice-cooling, and the resulting mixture was stirred at the same temperature for 10 minutes. After stirring, to the reaction mixture was added 10% aqueous sodium thiosulfate solution to quench the reaction, and the reaction mixture was concentrated to about one-half of its initial volume, which was extracted with ethyl acetate. The extract was washed successively with saturated aqueous sodium hydrogencarbonate solution and saturated aqueous sodium chloride solution and dried over anhydrous sodium sulfate. After filtration, the filtrate was evaporated to dryness in vacuo, and the residue was purified by chromatography on a silica gel column using a mixed solvent of ethyl acetate and hexane (3:2) as the eluent to afford the title compound (0.6660 g, yield: 67%).

$^1$H-NMR spectrum (CDCl$_3$, 400 MHz) δ: 6.30 (d, 1H, J=3.7 Hz), 5.93 (d, 1H, J=3.7 Hz), 5.17 (br s, 1H), 4.15 (d, 1H, J=8.8 Hz), 4.09 (d, 1H, J=8.8 Hz), 3.50 (s, 3H) 2.76-2.63 (m, 2H), 1.96-1.85 (m, 2H), 1.42 (s, 3H).

(40b) (4R)-4-Methyl-4-[2-{2-[3-(2-cyclohexylethyloxy)phenyl]-1-methylpyrrol-2-yl}ethyl]-1,3-oxazolidin-2-one (4R)-4-Methyl-4-[2-(5-iodo-1-methylpyrrol-2-yl)ethyl]-1,3-oxazolidin-2-one (0.3101 g, 0.92 mmol) obtained in Example (40a), 2-[3-(2-cyclohexylethyloxy)phenyl]-4,4,5,5-tetramethyl-1,3,2-dioxaborolane (0.4646 g, 1.41 mmol), dichlorobis(triphenylphopsphine)palladium(II) (63.1 mg, 0.09 mmol) and cesium carbonate (0.6006 g, 1.81 mmol) were suspended in a mixed solvent of dimethoxyethane (8 ml) and water (2 ml) and stirred at 80° C. for 6 hours. After cooling, water was added to the reaction mixture, and the resulting mixture was extracted with ethyl acetate. The extract was washed successively with water and saturated aqueous sodium chloride solution and dried over anhydrous magnesium sulfate. After filtration, the solvent was removed in vacuo, and the residue was purified by chromatography on a silica gel column using a mixed solvent of ethyl acetate and hexane (3:2) as the eluent to afford the crude product. Furthermore, the crude product thus obtained was purified using a preparative reversed phase HPLC column [Inertsil ODS-3 (2.0 cm×25 cm), GL Science, mobile phase: acetonitrile/water (75:25), flow rate: 10 ml/min] to afford the title compound (41.1 mg, yield: 11%).

$^1$H-NMR spectrum (CDCl$_3$, 400 MHz) δ: 7.30-7.26 (m, 1H), 6.93-6.89 (m, 2H), 6.85-6.83 (m, 1H), 6.14 (d, 1H, J=3.7 Hz), 5.95 (d, 1H, J=3.7 Hz), 5.27 (br s, 1H), 4.18 (d, J=8.8 Hz), 4.10 (d, 1H, J=8.8 Hz), 4.01 (t, 2H, J=6.6 Hz), 3.52 (s, 3H), 2.77-2.64 (m, 2H), 2.06-1.94 (m, 2H), 1.78-1.64 (m, 6H), 1.55-1.46 (m, 1H), 1.45 (s, 3H), 1.31-1.11 (m, 4H), 1.02-0.92 (m, 2H).

Mass spectrum (FAB$^+$) m/z: 411 ((M+H)$^+$).

(40c) (2R)-2-Amino-2-methyl-4-{5-[3-(2-cyclohexylethyloxy)phenyl]-1-methylpyrrol-2-yl}butan-1-ol 1/2 oxalate To a solution of (4R)-4-methyl-4-[2-{2-[3-(2-cyclohexylethyloxy)phenyl]-1-methylpyrrol-2-yl}ethyl]-1,3-oxazolidin-2-one (41.0 g, 0.10 mmol) obtained in Example (40b) in a mixed solvent of tetrahydrofuran (1 ml) and methanol (0.5 ml) was added a 5N aqueous potassium hydroxide solution (0.5 ml), and the resulting mixture was refluxed for 4 days. After cooling, water was added to the reaction mixture, and the resulting mixture was extracted with dichloromethane. The extract was dried over anhydrous sodium sulfate. After filtration, the solvent was removed in vacuo, and the residue was purified by chromatography on a basic silica gel column (NH type) using a mixed solvent of dichloromethane and methanol (50:1) as the eluent to afford (2R)-2-amino-2-methyl-4-{5-[3-(2-cyclohexylethyloxy)phenyl]-1-methylpyrrol-2-yl}butan-1-ol (36.5 mg).

Subsequently, to a solution of (2R)-2-amino-2-methyl-4-{5-[3-(2-cyclohexylethyloxy)phenyl]-1-methylpyrrol-2-yl}butan-1-ol (36.2 mg) thus obtained in methanol (1 ml) was added anhydrous oxalic acid (98% pure) (4.4 mg, 0.05 mmol), and the resulting mixture was stirred at room temperature for 30 minutes. After stirring, the reaction mixture was evaporated in vacuo, and 2-propanol was added to the residue. The crystals precipitated were collected by filtration, washed with 2-propanol and dried in vacuo to afford the title compound (35.6 mg, yield: 86%).

$^1$H-NMR spectrum (CD$_3$OD, 400 MHz) δ: 7.27 (t, 1H, J=8.1 Hz), 6.89 (d, 1H, J=8.1 Hz), 6.85-6.81 (m, 2H), 6.03 (d, 1H, J=3.7 Hz), 5.91 (d, 1H, J=3.7 Hz), 4.02 (t, 1H, J=6.6 Hz), 3.63 (d, J=11.7 Hz), 3.56 (d, 1H, J=11.7 Hz), 3.54 (s, 3H), 2.77-2.65 (m, 2H), 2.07-1.90 (m, 2H), 1.81-1.64 (m, 7H), 1.59-1.47 (m, 1H), 1.34 (s, 3H), 1.32-1.15 (m, 3H), 1.05-0.95 (m, 2H).

IR spectrum ν$_{max}$ cm$^{-1}$ (KBr): 3354, 2923, 2851, 1595, 1579, 1509, 1463, 1301, 1211, 1066, 1049, 763, 698.

Mass spectrum (FAB$^+$) m/z: 385 ((M+H)$^+$; as free form of title compound).

Example 41

(2R)-2-Amino-2-methyl-4-[1-ethyl-5-(5-phenylpentanoyl)pyrrol-2-yl]butan-1-ol hydrochloride (Exemplification compound number: 4-12 having formula Ia-5)

(41a) (2R)-1-Acetoxy-2-acetylamino-2-methyl-4-{1-ethyl-[5-phenyl-1-(5-phenylpentanoyloxy)pent-1-enyl]pyrrol-2-yl}butane To a solution of (2R)-1-acetoxy-2-acetylamino-2-methyl-4-(1-ethylpyrrol-2-yl)butane (2.1 g, 7.49 mmol) obtained in Reference example 24 in toluene (100 ml) were added 4-dimethylaminopyridine (4.58 g, 37.5 mmol) first and then a solution of 5-phenylvaleroyl chloride (4.4 g, 22.5 mmol) in toluene (20 ml), and the resulting mixture was refluxed for 5 days. After cooling to room temperature, water was added to the reaction mixture, and the resulting mixture was extracted with ethyl acetate. The extract was washed successively with water and saturated aqueous sodium chloride solution and dried over anhydrous sodium sulfate. After filtration, the filtrate was concentrated to dryness in vacuo, and the residue was purified by chromatography on a silica gel column using a mixed solvent of hexane and ethyl acetate (4:6) as the eluent to afford the crude product. Furthermore, the crude product thus obtained was purified using a preparative reversed phase HPLC column [Inertsil ODS-3 (2.0 cm×25 cm), GL Science, mobile phase: acetonitrile/0.1% aqueous ammonium acetate solution (70/30), flow rate: 10 ml/min] to afford the title compound (2.8 g, yield: 66%).

$^1$H-NMR spectrum (CDCl$_3$, 400 MHz) δ: 7.26-7.21 (m, 4H), 7.18-7.09 (m, 6H), 6.98 (d, 1H, J=4.4 Hz), 5.97 (d, 1H, J=4.4 Hz), 5.43 (br s, 1H), 4.35-4.28 (m, 1H), 4.33 (d, 1H, J=11.0 Hz), 4.17 (d, 1H, J=11.0 Hz), 4.12 (q, 2H, J=7.3 Hz), 2.65-2.25 (m, 9H), 2.10 (s, 3H), 2.07-1.86 (m, 3H), 1.96 (s, 3H), 1.62-1.47 (m, 6H), 1.37 (s, 3H), 1.25 (t, 3H, J=7.3 Hz).

(41b) (2R)-2-Amino-2-methyl-4-[1-ethyl-5-(5-phenylpentanoyl)pyrrol-2-yl]butan-1-ol hydrochloride To a solution of (2R)-1-acetoxy-2-acetylamino-2-methyl-4-{1-ethyl-[5-phenyl-1-(5-phenylpentanoyloxy)pent-1-enyl]pyrrol-2-yl}butane (2.8 g, 4.66 mmol) obtained in Example (41a) in a mixed solvent of methanol (12 ml), tetrahydrofuran (12 ml) and water (12 ml) was added lithium hydroxide monohydrate (1.96 g, 46.6 mmol) with stirring, and the resulting mixture was stirred at 50° C. for 5 hours. After cooling to room temperature, water was added to the reaction mixture, and the resulting mixture was extracted with dichloromethane. The extract was washed with saturated aqueous sodium chloride solution and dried over anhydrous sodium sulfate. After filtration, the solvent was removed in vacuo, and the residue was purified by chromatography on a basic silica gel column (NH type) using a mixed solvent of dichloromethane and methanol (100:1) as the eluent to afford the crude product of (2R)-2-amino-2-methyl-4-[1-ethyl-5-(5-phenylpentanoyl)pyrrol-2-yl]butan-1-ol (1.53 g).

Subsequently, to a solution of the crude product (1.53 g) obtained above in ethanol (15 ml) was added 4N hydrochloric acid-dioxane solution (1.07 ml, 4.26 mmol) with stirring under ice-cooling, and the resulting mixture was stirred at the same temperature for 30 minutes. After stirring, the reaction mixture was concentrated to dryness in vacuo, and the crystals obtained were recrystallized from ethyl acetate to afford the title compound (1.46 g, yield: 80%).

$^1$H-NMR spectrum (DMSO-D$_6$, 400 MHz) δ: 7.90 (br s, 2H), 7.29-7.24 (m, 2H), 7.20-7.13 (m, 3H), 7.06 (d, 1H, J=4.0 Hz), 5.94 (d, 1H, J=4.0 Hz), 5.53 (t, 1H, J=4.8 Hz), 4.29 (q, 2H, J=7.3 Hz), 3.49 (dd, 1H, J=11.0 Hz, 4.8 Hz), 3.43 (dd, 1H, J=11.0 Hz, 4.8 Hz)., 2.79-2.70 (m, 2H), 2.69-2.55 (m, 4H), 1.94-1.88 (m, 2H), 1.64-1.53 (m, 4H), 1.22 (s, 3H), 1.17 (t, 3H, J=7.3 Hz).

IR spectrum ν$_{max}$ cm$^{-1}$ (KBr): 3377, 2936, 1639, 1479, 1393, 1068.

Mass spectrum (FAB$^+$) m/z: 357 ((M+H)$^+$; as free form of title compound).

Example 42

(2R)-2-Amino-2-methyl-4-[5-(5-phenylpentanoyl)pyrrol-2-yl]butan-1-ol (Exemplification compound number: 3-12 having formula Ia-4)

(42a) (4R)-4-Methyl-4-{2-[5-(5-phenylpentanoyl)pyrrol-2-yl]ethyl}-1,3-oxazolidin-2-one To a solution of (4R)-4-methyl-4-[2-(pyrrol-2-yl)ethyl]-1,3-oxazolidine-2-one (138 mg, 0.71 mmol) obtained in Reference example 28 in tetrahydrofuran (5 ml) was added a 3.0M solution of methylmagnesium bromide in ether (0.50 ml, 1.49 mmol), and the resulting mixture was refluxed for 30 minutes. After cooling, to the reaction mixture was added a solution of 5-phenylvaleroyl chloride (0.169 g, 22.5 mmol) in tetrahydrofuran (1 ml) at room temperature with stirring, and the resulting mixture was refluxed for 1 hour. After cooling to room temperature, water was added to the reaction mixture, and the resulting mixture was extracted with ethyl acetate. The extract was washed successively with water and saturated aqueous sodium chloride solution and dried over anhydrous sodium sulfate. After filtration, the filtrate was concentrated to dryness in vacuo, and the residue was purified by chromatography on a silica gel column using a mixed solvent of ethyl acetate and hexane (2:1) as the eluent to afford the crude product. Furthermore, the crude product obtained above was purified using a preparative-reversed phase HPLC column [Inertsil ODS-3 (2.0 cm×25 cm), GL Science, mobile phase: acetonitrile/water (70/30), flow rate: 20 ml/min] to afford the title compound (41 mg, yield: 16%).

$^1$H-NMR spectrum (CDCl$_3$, 400 MHz) δ: 9.67 (br s, 1H), 7.31-7.22 (m, 3H), 7.20-7.13 (m, 2H), 6.85-6.78 (m, 1H), 6.03-5.96 (m, 1H), 5.70 (br s, 1H), 4.16 (d, 1H, J=8.8 Hz), 4.07 (d, 1H, J=8.8 Hz), 2.80-2.67 (m, 4H), 2.67-2.58 (m, 2H), 2.01-1.88 (m, 2H), 1.81-1.61 (m, 4H), 1.37 (s, 3H).

IR spectrum $v_{max}$ cm$^{-1}$ (CHCl$_3$): 3442, 3271, 2935, 2861, 1758, 1632, 1492, 1454, 1410, 1382, 1046, 940.

Mass spectrum (FAB$^+$) m/z: 355 ((M+H)$^+$).

(42b) (2R)-2-Amino-2-methyl-4-[5-(5-phenylpentanoyl)pyrrol-2-yl]butan-1-ol

To a solution of (4R)-4-methyl-4-{2-[5-(5-phenylpentanoyl)pyrrol-2-yl]ethyl}-1,3-oxazolidin-2-one (41.0 mg, 0.12 mmol) obtained in Example (42a) in a mixed solvent of methanol (2 ml), tetrahydrofuran (2 ml) and water (2 ml) was added 10N aqueous sodium hydroxide solution (0.12 ml, 1.17 mmol), and the resulting mixture was refluxed for 4 days. After cooling to room temperature, water was added to the reaction mixture, and the resulting mixture was extracted with ethyl acetate. The extract was washed with saturated aqueous sodium chloride solution and dried over anhydrous sodium sulfate. After filtration, the solvent was removed in vacuo, and the residue was purified by chromatography on a basic silica gel column (NH type) using a mixed solvent of dichloromethane and methanol (20:1) as the eluent to afford the title compound (30.0 mg, yield: 79%).

$^1$H-NMR spectrum (CDCl$_3$, 400 MHz) δ: 9.90 (br s, 1H), 7.32-7.22 (m, 3H), 7.20-7.12 (m, 2H), 6.79 (d, 1H, J=3.7 Hz), 5.98 (d, 1H, J=3.7 Hz), 3.40 (d, 1H, J=10.3 Hz), 3.35 (d, 1H, J=10.3 Hz), 2.80-2.59 (m, 6H), 2.01-1.62 (m, 6H), 1.11 (s, 3H).

IR spectrum $v_{max}$ cm$^{-1}$ (CHCl$_3$): 3272, 2927, 2857, 1624, 1494, 1454, 1410, 1363, 1293, 1263, 1210, 1048, 915, 801, 749, 700.

Mass spectrum (FAB$^+$) m/z: 329 ((M+H)$^+$).

Example 43

Mono(2R)-2-amino-2-methyl-4-[1-methyl-5-(5-phenylpentanoyl)pyrrol-2-yl]-1-butyl phosphate (Exemplification compound number: 5-1344 having formula IIa-2)

(43a) (2R)-2-t-Butoxycarbonylamino-2-methyl-4-[1-methyl-5-(5-phenylpentanoyl)pyrrol-2-yl]butan-1-ol To a solution of (2R)-2-amino-2-methyl-4-[1-methyl-5-(5-phenylpentanoyl)pyrrol-2-yl]butan-1-ol hydrochloride (1.4647 g, 3.87 mmol) obtained in Example (33b) in dichloromethane (38 ml) were added successively di-t-butyl dicarbonate (1.0126 g, 4.64 mmol) and triethylamine (1.62 ml, 11.65 mmol) with stirring, and the resulting mixture was stirred at room temperature for 18 hours. After stirring, the reaction mixture was evaporated in vacuo, and water was added to the residue, and then the resulting mixture was extracted with ethyl acetate. The extract was washed with saturated aqueous sodium chloride solution and dried over anhydrous magnesium sulfate. After filtration, the solvent was removed in vacuo, and the residue was purified by chromatography on a silica gel column using a mixed solvent of hexane and ethyl acetate (3:2) as the eluent to afford the title compound (1.6928 g, yield: 99%).

$^1$H-NMR spectrum (CDCl$_3$, 400 MHz) δ: 7.28-7.24 (m, 2H), 7.18-7.14 (m, 3H), 6.90 (d, 1H, J=3.7 Hz), 5.95 (d, 1H, J=3.7 Hz), 4.63 (br s, 1H), 3.98 (br s, 1H), 3.87 (s, 3H), 3.68 (d, 2H, J=6.6 Hz), 2.75 (t, 2H, J=7.3 Hz), 2.70-2.62 (m, 3H), 2.55 (ddd, 1H, J=15.4 Hz, 12.4 Hz, 5.1 Hz), 2.13-2.04 (m, 1H), 1.96-1.89 (m, 1H), 1.79-1.64 (m, 4H), 1.43 (s, 9H), 1.21 (s, 3H).

Mass spectrum (FAB$^+$) m/z: 443 ((M+H)$^+$).

(43b) (2R)-2-t-Butoxycarbonylamino-2-methyl-4-[1-methyl-5-(5-phenylpentanoyl)pyrrol-2-yl]-1-butyl diallyl phosphate To a solution of (2R)-2-t-butoxycarbonylamino-2-methyl-4-[1-methyl-5-(5-phenylpentanoyl)pyrrol-2-yl]butan-1-ol (1.6928 g, 3.83 mmol) obtained in Example (43a) in dichloromethane (19 ml) were added successively 1H-tetrazole (1.7933 g, 25.60 mmol) and diallyl diisopropylphosphoramidite (2.02 ml, 7.64 mmol) with stirring under ice-cooling, and then the resulting mixture was stirred at room temperature for 2 hours. After stirring, to the reaction mixture was added a solution of t-butyl hydroperoxide in n-decane (5-6 mol/l) (2.3 ml, 11.5 mmol) with stirring under ice cooling, and the resulting mixture was stirred at the same temperature for 15 minutes. After stirring, to the reaction mixture was added an aqueous sodium sulfite solution to quench the reaction, and the resulting mixture was extracted with dichloromethane. The extract was washed successively with saturated aqueous sodium hydrogencarbonate solution and saturated aqueous sodium chloride solution and dried over anhydrous sodium sulfate. After filtration, the solvent was removed in vacuo, and the residue was purified by chromatography on a silica gel column using a mixed solvent of hexane and ethyl acetate (3:2) as the eluent to afford the title compound (1.5690 g, yield: 68%).

$^1$H-NMR spectrum (CDCl$_3$, 400 MHz) δ: 7.28-7.24 (m, 2H), 7.18-7.14 (m, 3H), 6.89 (d, 1H, J=3.7 Hz), 5.99-5.89 (m, 3H), 5.39-5.29 (m, 4H), 4.62 (br s, 1H), 4.60-4.52 (m, 4H), 4.21 (dd, 1H, J=9.5 Hz, 5.1 Hz), 4.01 (dd, 1H, J=9.5 Hz, 5.9

Hz), 3.86 (s, 3H), 2.74 (t, 2H, J=7.3 Hz), 2.64 (t, 2H, J=8.1 Hz), 2.58 (t, 2H, J=8.1 Hz), 2.22-2.12 (m, 1H), 1.90-1.81 (m, 1H), 1.79-1.64 (m, 4H), 1.43 (s, 9H), 1.26 (s, 3H).

Mass spectrum (FAB$^+$) m/z: 603 ((M+H)$^+$).

(43c) Mono(2R)-2-amino-2-methyl-4-[1-methyl-5-(5-phenylpentanoyl)pyrrol-2-yl]-1-butyl phosphate To a suspension of (2R)-2-t-butoxycarbonylamino-2-methyl-4-[1-methyl-5-(5-phenylpentanoyl)pyrrol-2-yl]-1-butyl diallyl phosphate (1.5665 g, 2.60 mmol) obtained in Example (43b), triphenylphosphine (0.1402 g, 0.54 mmol) and tetrakis(triphenylphosphine)palladium(0) (0.1503 g, 0.13 mmol) in acetonitrile (26 ml) was added pyrrolidine (1.1 ml, 13 mmol) with stirring under a nitrogen atmosphere, and the resulting mixture was stirred at room temperature for 24 hours. After stirring, the reaction mixture was evaporated in vacuo, and 1N hydrochloric acid was added to the residue, and then the resulting mixture was extracted with dichloromethane. The extract was dried over anhydrous sodium sulfate. After filtration, the filtrate was evaporated in vacuo to afford the crude product (1.4625 g).

Subsequently, to a solution of the crude product (1.4625 g) thus obtained in dichloromethane (26 ml) was added trifluoroacetic acid (8.6 ml) with stirring under ice-cooling. After the reaction temperature was raised to room temperature, the resulting mixture was furthermore stirred at room temperature for 2 hours. The reaction mixture was evaporated in vacuo, and ethanol was added to the residue. The crystals precipitated were collected by filtration to afford the crude crystals. The crude crystals obtained were dissolved in a mixed solvent of methanol (200 ml) and water (67 ml), treated with charcoal and filtered using celite. The filtrate was evaporated in vacuo, and ethanol was added to the residue. The crystals precipitated were collected by filtration, washed with ethanol and dried to afford the title compound (0.5554 g, yield: 51%).

$^1$H-NMR spectrum (CD$_3$CO$_2$D, 400 MHz) δ: 7.25-7.22 (m, 2H), 7.17-7.11 (m, 3H), 7.07 (d, 1H, J=4.4 Hz), 6.04 (d, 1H, J=4.4 Hz), 4.17 (d, 2H, J=10.3 Hz), 3.87 (s, 3H), 2.82-2.71 (m, 4H), 2.63 (t, 2H, J=7.3 Hz), 2.20-2.01 (m, 2H), 1.75-1.63 (m, 4H), 1.46 (s, 3H).

IR spectrum $v_{max}$ cm$^{-1}$ (KBr): 3429, 2934, 2857, 2717, 2603, 1639, 1557, 1480, 1455, 1378, 1182, 1056, 1041, 946, 915, 821, 748, 699, 580, 511.

Mass spectrum (FAB$^-$) m/z: 421 ((M−H)$^-$).

Example 44

(3R)-3-Amino-3-methyl-5-[1-methyl-5-(5-phenylpentanoyl)pyrrol-2-yl]pentylphosphonic acid (Exemplification compound number: 5-1344 having formula IIIa-2)

(44a) (2R)-2-t-Butoxycarbonylamino-2-methyl-4-[1-methyl-5-(5-phenylpentanoyl)pyrrol-2-yl]-1-butanal To a solution of (2R)-2-t-butoxycarbonylamino-2-methyl-4-[1-methyl-5-(5-phenylpentanoyl)pyrrol-2-yl]butan-1-ol (0.3520 g, 0.80 mmol) obtained in Example (43a) in dichloromethane (8 ml) were added successively molecular sieves 4A (0.2234 g) and pyridinium dichromate (0.4594 g, 1.22 mmol), and the resulting mixture was stirred at room temperature for 20 hours. After stirring, ether was added to the reaction mixture, and the resulting mixture was filtered. The filtrate was evaporated in vacuo, and the residue was purified by chromatography on a silica gel column using a mixed solvent of hexane and ethyl acetate (3:2) as the eluent to afford the title compound (0.2195 g, yield: 63%).

$^1$H-NMR spectrum (CDCl$_3$, 400 MHz) δ: 9.36 (s, 1H), 7.28-7.25 (m, 2H), 7.18-7.15 (m, 3H), 6.89 (d, 1H, J=3.7 Hz), 5.92 (d, 1H, J=3.7 Hz), 5.20 (br s, 1H), 3.83 (s, 3H), 2.74 (t, 2H, J=7.3 Hz), 2.64 (t, 2H, J=7.3 Hz), 2.59-2.52 (m, 1H), 2.45-2.28 (m, 2H), 2.09-2.03 (m, 1H), 1.78-1.64 (m, 4H), 1.44 (s, 9H), 1.40 (s, 3H).

(44b) Diethyl (3R)-3-t-butoxycarbonylamino-3-methyl-5-[1-methyl-5-(5-phenylpentanoyl)pyrrol-2-yl]pent-1-enylphosphonate To a suspension of sodium hydride (content: 60%) (31.0 mg, 0.78 mmol) in tetrahydrofuran (1 ml) was added tetraethyl methylenediphosphonate (0.185 ml, 0.75 mmol) with stirring under ice-cooling over a 5-minute interval, and then the resulting mixture was stirred at room temperature for 30 minutes.

Subsequently, to the reaction mixture was added a solution of (2R)-2-t-butoxycarbonylamino-2-methyl-4-[1-methyl-5-(5-phenylpentanoyl)pyrrol-2-yl]-1-butanal (0.2155 g, 0.49 mmol) obtained in Example (44a) in tetrahydrofuran (4 ml) with stirring under ice-cooling over a 5-minute interval, and the resulting mixture was stirred at the same temperature for 30 minutes. After stirring, the reaction mixture was neutralized with acetic acid (42 µl, 0.73 mmol) and evaporated in vacuo. Water was added to the residue obtained, and the resulting mixture was extracted with ethyl acetate. The extract was washed successively with water and saturated aqueous sodium chloride solution and dried over anhydrous magnesium sulfate. After filtration, the solvent was removed in vacuo, and the residue was purified by chromatography on a silica gel column using a mixed solvent of ethyl acetate and hexane (2:1-1:0) as the eluent to afford the title compound (0.2348 g, yield: 85%).

$^1$H-NMR spectrum (CDCl$_3$, 400 MHz) δ: 7.28-7.25 (m, 2H), 7.18-7.15 (m, 3H), 6.90 (d, 1H, J=4.4 Hz), 6.77 (dd, 1H, J=22.7 Hz, 17.6 Hz), 5.92 (d, 1H, J=4.4 Hz), 5.72 (t, 1H, J=17.6 Hz), 4.59 (br s, 1H), 4.12-4.05 (m, 4H), 3.84 (s, 3H), 2.74 (t, 2H, J=7.3 Hz), 2.64 (t, 2H, J=7.3 Hz), 2.59-2.50 (m, 2H), 2.26-2.18 (m, 1H), 2.01-1.93 (m, 1H), 1.78-1.64 (m, 4H), 1.42 (s, 12H), 1.32 (t, 6H, J=7.3 Hz).

Mass spectrum (FAB$^+$) m/z: 575 ((M+H)$^+$).

(44c) Diethyl (3R)-3-t-butoxycarbonylamino-3-methyl-5-[1-methyl-5-(5-phenylpentanoyl)pyrrol-2-yl]pentylphosphonate To a solution of diethyl (3R)-3-t-butoxycarbonylamino-3-methyl-5-[1-methyl-5-(5-phenylpentanoyl)pyrrol-2-yl]pent-1-enylphosphonate (145.4 mg, 0.25 mmol) obtained in Example (44b) in ethanol (2.5 ml) was added chlorotris(triphenylphosphine)rhodium(I) (23.7 mg, 0.026 mmol), and the resulting mixture was stirred at 50° C. under a hydrogen atmosphere for 5 hours. After cooling, to the reaction mixture was added furthermore chlorotris(triphenylphosphine)rhodium(I) (24.3 mg, 0.026 mmol), and the resulting mixture was stirred at 50° C. under a hydrogen atmosphere for 5 hours. After stirring, the reaction mixture was evaporated in vacuo, and the residue was purified by chromatography on a silica gel column using ethyl acetate as the eluent to afford the crude product (154.0 mg). Furthermore, the crude product obtained was purified using a preparative reversed phase HPLC column [Inertsil ODS-3 (2.0 cm×25 cm), GL Science, mobile phase: acetonitrile/water (80:20), flow rate: 10 ml/min] to afford the title compound (116.1 mg, yield: 80%).

$^1$H-NMR spectrum (CDCl$_3$, 400 MHz) δ: 7.28-7.24 (m, 2H), 7.18-7.14 (m, 3H), 6.89 (d, 1H, J=3.7 Hz), 5.92 (d, 1H, J=3.7 Hz), 4.37 (br s, 1H), 4.14-4.05 (m, 4H), 3.85 (s, 3H), 2.74 (t, 2H, J=7.3 Hz), 2.64 (t, 2H, J=7.3 Hz), 2.59-2.50 (m, 2H), 2.24-2.15 (m, 2H), 1.83-1.64 (m, 8H), 1.42 (s, 9H), 1.33 (t, 3H, J=7.3 Hz), 1.32 (t, 3H, J=7.3 Hz), 1.21 (s, 3H).

Mass spectrum (FAB$^+$) m/z: 577 ((M+H)$^+$).

(44d) (3R)-3-Amino-3-methyl-5-[1-methyl-5-(5-phenylpentanoyl)pyrrol-2-yl]pentylphosphonic acid To a solution of diethyl (3R)-3-t-butoxycarbonylamino-3-methyl-5-[1-methyl-5-(5-phenylpentanoyl)pyrrol-2-yl]pentylphosphonate (114.0 mg, 0.20 mmol) obtained in Example (44c) in dichloromethane (2.0 ml) was added bromotrimethylsilane (0.26 ml, 1.97 mmol), and the resulting mixture was stirred at room temperature under a nitrogen atmosphere for 5 hours. After stirring, the reaction mixture was evaporated in vacuo, and the residue was diluted with aqueous ethanol and then adjusted to pH 4 with aqueous ammonia and acetic acid. The crystals precipitated were collected by filtration, washed successively with water and ethanol and dried to afford the title compound (52.0 mg, yield: 63%)

$^1$H-NMR spectrum (CD$_3$CO$_2$D, 400 MHz) δ: 7.26-7.22 (m, 2H), 7.18-7.12 (m, 3H), 7.07 (d, 1H, J=4.1 Hz), 6.05 (d, 1H, J=4.1 Hz), 3.88 (s, 3H), 2.80 (t, 2H, J=7.3 Hz), 2.73 (t, 2H, J=8.8 Hz), 2.63 (t, 2H, J=7.3 Hz), 2.23-1.94 (m, 6H), 1.76-1.64 (m, 4H), 1.48 (s, 3H).

IR spectrum $v_{max}$ cm$^1$ (KBr): 3171, 3025, 2936, 2859, 2549, 1640, 1552, 1484, 1461, 1380, 1136, 1064, 1051, 914, 881, 772, 741, 699.

Mass spectrum (FAB$^-$) m/z: 419 ((M−H)$^-$).

Reference Example 1

(Furan-2-yl)methyl triphenylphosphonium bromide

To a solution of furfuryl alcohol (29.43 g, 300 mmol) in tetrahydrofuran (300 ml) was added a solution of phosphorus tribromide (10 ml, 105 mmol) in tetrahydrofuran (30 ml) with stirring under ice-cooling over a 30-minute interval, and then the resulting mixture was stirred at room temperature for 1 hour. After stirring, the reaction mixture was neutralized with aqueous sodium hydroxide solution [prepared by dissolving sodium hydroxide (30.23 g) in water (75 ml)], and the organic layer was separated by partitioning, and dried with sodium hydroxide (10 g). The organic layer was collected by decantation, and to the organic layer were added anhydrous sodium sulfate and charcoal, and then the resulting mixture was filtered.

Subsequently, to the filtrate were added tetrahydrofuran (150 ml) first and then triphenylphosphine (78.64 g, 300 mmol) with stirring, and the resulting mixture was stirred at 70° C. for 2 hours. After cooling, the crystals precipitated were collected by filtration, washed with ethyl acetate and dried in vacuo to afford the title compound (98.84 g, yield: 78%).

Reference Example 2

(2R)-2-t-Butoxycarbonylamino-1-n-hexanoyloxy-2-methyl-4-(furan-2-yl)-3-butene (2a) (2R)-2-t-Butoxycarbonylamino-3-n-hexanoyloxy-2-methyl-1-propanol To a suspension of 2-t-butoxycarbonylamino-2-methylpropane-1,3-diol (20.0 g, 97.4 mmol) in isopropyl ether (200 ml) were added successively vinyl hexanoate (16.3 ml, 0.10 mol) and lipase [Immunobilized lipase from *Pseudomonas* sp., TOYOBO, 0.67 U/mg] (0.8 g) with stirring, and the resulting mixture was stirred at room temperature for 2 hours. After stirring, the reaction mixture was filtered and evaporated in vacuo. The residue obtained was purified by chromatography on a silica gel column using a mixed solvent of hexane and ethyl acetate (10:1-2:1) as the eluent to afford the title compound (25.0 g, yield: 85%).

Furthermore, the (2R)-2-t-butoxycarbonylamino-3-n-hexanoyloxy-2-methyl-1-propanol obtained above was analyzed with a HPLC column for separating optical isomers [ChiralCel OF (0.46 cm×25 cm), Daicel Chemical Industries, Ltd., mobile phase: hexane/2-propanol (70/30), flow rate: 0.5 ml/min], and its optical purity was determined.

From the results of the HPLC analysis, it was confirmed that the compound eluted first (retention time: 8.2 min) was the 2S-isomer, and the compound eluted afterward (retention time: 10.5 min) was the 2R-isomer, and that the optical purity of the product synthesized was 85% ee.

Angle of rotation: [α]$_D$=−8.5 (c=1.86, CHCl$_3$), $^1$H-NMR spectrum (CDCl$_3$, 400 MHz) δ: 4.86 (s, 1H), 4.25 (d, 1H, J=11.2 Hz), 4.19 (d, 1H, J=11.2 Hz), 3.86 (br s, 1H), 3.70-3.55 (m, 2H), 2.36 (t, 2H, J=7.4 Hz), 1.44 (s, 9H), 1.40-1.30 (m, 4H), 1.25 (s, 3H), 0.90 (t, 3H, J=7.0 Hz).

IR spectrum $v_{max}$ cm$^{-1}$ (Liquid Film): 3415, 3380, 2961, 2935, 2874, 1721, 1505, 1458, 1392, 1368, 1293, 1248, 1168, 1076.

Mass spectrum (FAB$^+$) m/z: 304 ((M+H)$^+$).

(2b) (2S)-2-t-Butoxycarbonylamino-3-n-hexanoyloxy-2-methyl-1-propanal

To a solution of (2R)-2-t-butoxycarbonylamino-3-n-hexanoyloxy-2-methyl-1-propanol (30.70 g, 0.101 mol) obtained in Reference example (2a) in dichloromethane (600 ml) were added successively molecular sieves 4A (220 g) and pyridinium chlorochromate (43.6 g, 0.202 mol) with stirring under ice-cooling, and then the resulting mixture was stirred at room temperature for 2 hours. After stirring, ether was added to the reaction mixture, and after filtration, the filtrate was evaporated in vacuo. The residue obtained was purified by chromatography on a silica gel column using a mixed solvent of hexane and ethyl acetate (10:1-5:1) as the eluent to afford the title compound (28.81 g, yield: 95%).

$^1$H-NMR spectrum (CDCl$_3$, 400 MHz) δ: 9.45 (s, 1H), 5.26 (br s, 1H), 4.44 (d, 1H, J=11.2 Hz), 4.32 (d, 1H, J=11.2 Hz), 2.32 (t, 2H, J=7.46 Hz), 1.70-1.55 (m, 2H), 1.45 (s, 9H), 1.38 (s, 3H), 1.40-1.25 (m, 4H), 0.90 (t, 3H, J=7.0 Hz).

IR spectrum $v_{max}$ cm$^{-1}$ (Liquid Film): 3367, 2961, 2935, 2874, 1742, 1707, 1509, 1458, 1392, 1369, 1290, 1274, 1254, 1166, 1100, 1078.

Mass spectrum (FAB$^+$) m/z: 302 ((M+H)$^+$).

(2c) (2R)-2-t-Butoxycarbonylamino-1-n-hexanoyloxy-2-methyl-4-(furan-2-yl)-3-butene To a suspension of (furan-2-yl)methyl triphenylphosphonium bromide (33.65 g, 79.5 mmol) obtained in Reference example 1 in tetrahydrofuran (90 ml) was added a solution of potassium t-butoxide (8.94 g, 79.7 mmol) in tetrahydrofuran (90 ml) with stirring under ice-cooling over a 10-minute interval, and the resulting mixture was furthermore stirred under ice-cooling for 15 minutes.

Subsequently, to the reaction mixture was added a solution of (2S)-2-t-butoxycarbonylamino-3-n-hexanoyloxy-2-methyl-1-propanal (16.18 g, 53.7 mmol) obtained in Reference example (2b) in tetrahydrofuran (60 ml) with stirring under ice-cooling over a 15-minute interval, and the resulting mixture was stirred under ice-cooling for 30 minutes. After stirring, saturated aqueous ammonium chloride solution was added to the reaction mixture to quench the reaction, and then the reaction temperature was raised to room temperature. After evaporation of the reaction mixture in vacuo, ethyl acetate and water were added to the residue and then the resulting mixture was extracted with ethyl acetate. The extract was washed successively with water and saturated aqueous sodium chloride solution and dried over anhydrous sodium sulfate. After filtration, the solvent was removed in vacuo, and the residue was purified by chromatography on a silica gel column using a mixed solvent of hexane and ethyl acetate (10:1) as the eluent to afford the title compound (19.32 g, yield: 98%).

$^1$H-NMR spectrum (CDCl$_3$, 400 MHz) δ: 7.45 (d, 1H, J=1.6 Hz), 7.33 (d, 1H, J=1.5 Hz), 6.41 (dd, 1H, J=2.9 Hz, 1.6 Hz), 6.36-6.35 (m, total 2H), 6.33 (d, 1H, J=15.9 Hz), 6.26-6.22 (m, total 2H), 6.20 (d, 1H, J=15.9 Hz), 5.59 (d, 1H, J=12.7 Hz), 5.22 (br s, 1H), 4.82 (br s, 1H), 4.43 (d, 1H, J=11.0 Hz), 4.32 (d, 1H, J=11.0 Hz), 4.25 (d, 1H, J=11.0 Hz), 4.18 (d, 1H, J=11.0 Hz), 2.36-2.32 (m, total 4H), 1.67-1.22 (m, total 40H), 0.92-0.87 (s, total 6H).

IR spectrum $v_{max}$ cm$^{-1}$ (Liquid Film): 3445, 2962, 2933, 2873, 2250, 1720, 1497, 1457, 1391, 1368, 1249, 1165, 1075, 1015.

Mass spectrum (FAB$^+$) m/z: 388 ((M+Na)$^+$), 366 ((M+H)$^+$).

Reference Example 3

(4R)-4-Methyl-4-[2-(furan-2-yl)ethenyl]-1,3-oxazolidin-2-one

To a solution of (2R)-2-t-butoxycarbonylamino-1-n-hexanoyloxy-2-methyl-4-(furan-2-yl)-3-butene (19.32 g, 52.9 mmol) obtained in Reference example (2c) in a mixed solvent of tetrahydrofuran (53 ml) and methanol (53 ml) was added 2N aqueous sodium hydroxide solution (53 ml), and the resulting mixture was stirred at room temperature for 1 hour. After stirring, water and dichloromethane were added to the reaction mixture, and the resulting mixture was extracted with dichloromethane. The extract was washed with saturated aqueous sodium chloride solution and dried over anhydrous sodium sulfate. After filtration, the solvent was removed in vacuo to afford the crude product (14.84 g, yield: 100%).

Subsequently, to a solution of the crude product in tetrahydrofuran (150 ml) was added a solution of potassium t-butoxide (7.20 g, 64.2 mmol) in tetrahydrofuran (50 ml) with stirring under ice-cooling over a 10-minute interval, and the resulting mixture was stirred at the same temperature for 1 hour. After stirring, the reaction mixture was neutralized with acetic acid (3.65 ml, 63.8 mmol) and evaporated in vacuo. Water and ethyl acetate were added to the residue obtained, and the resulting mixture was extracted with ethyl acetate. The extract was washed with saturated aqueous sodium chloride solution and dried over anhydrous sodium sulfate. After filtration, the solvent was removed in vacuo, and the residue was purified by chromatography on a silica gel column using a mixed solvent of hexane and ethyl acetate (1:1) as the eluent to afford the title compound (10.04 g, yield: 98%).

$^1$H-NMR spectrum (CDCl$_3$, 400 MHz) δ: 7.49 (d, 1H, J=1.6 Hz), 7.36 (d, 1H, J=1.6 Hz), 6.46 (d, 1H, J=2.1 Hz), 6.43 (d, 1H, J=16.1 Hz), 6.04-6.37 (m, total 2H), 6.30 (br s, 1H), 6.30 (d, 1H, J=3.3 Hz), 6.21 (d, 1H, J=12.6 Hz), 6.18 (d, 1H, J=16.1 Hz), 5.88 (br s, 1H), 5.62 (d, 1H, J=12.7 Hz), 4.41 (d, 1H, J=8.5 Hz), 4.37 (d, 1H, J=8.5 Hz), 4.23 (d, 1H, J=8.3 Hz), 4.17 (d, 1H, J=8.3 Hz), 1.65 (s, 3H), 1.54 (s, 3H).

IR spectrum $v_{max}$ cm$^{-1}$ (CDCl$_3$): 3451, 2252, 1757, 1396, 1374, 1281, 1165, 1044, 1016.

Mass spectrum (EI$^+$) m/z: 193 (M$^+$), 178 (base), 163, 148, 135, 120, 107, 91, 81, 65.

Reference Example 4

(4R)-4-Methyl-4-[2-(furan-2-yl)ethyl]-1,3-oxazolidin-2-one

To a suspension of 10% palladium-charcoal (50% wet with water) (1.00 g) in methanol (20 ml) was added a solution of (4R)-4-methyl-4-[2-(furan-2-yl)ethenyl]-1,3-oxazolidin-2-one (10.04 g, 52.0 mmol) obtained in Reference example 3 in methanol (180 ml) with stirring, and the resulting mixture was stirred at room temperature under a hydrogen atmosphere for 40 minutes. After stirring, the palladium-charcoal in the reaction mixture was filtered off using celite, and the filtrate was evaporated in vacuo. The residue obtained was purified by chromatography on a silica gel column using a mixed solvent of hexane and ethyl acetate (3:2-1:1) as the eluent to afford the title compound (7.95 g, yield: 78%).

Furthermore, the (4R)-4-methyl-4-[2-(furan-2-yl)ethyl]-1,3-oxazolidin-2-one obtained was analyzed with a HPLC column for separating optical isomers [ChiralPak AD (0.46 cm×25 cm), Daicel Chemical Industries, Ltd., mobile phase: n-hexane/2-propanol (85/15), flow rate: 1.0 ml/min], and its optical purity was determined.

From the results of the HPLC analysis, it was confirmed that the compound eluted first (retention time: 13.09 min) was the 4S-isomer, and the compound eluted afterward (retention time: 15.43 min) was the 4R-isomer, and that the optical purity of the product synthesized was 84% ee.

$^1$H-NMR spectrum (CDCl$_3$, 400 MHz) δ: 7.31 (br s, 1H), 6.29 (br d, 1H, J=2.6 Hz), 6.03 (d, 1H, J=2.6 Hz), 5.92 (br s, 1H), 4.11 (d, 1H, J=8.4 Hz), 4.04 (d, 1H, J=8.4 Hz), 2.72 (t, 2H, J=8.0 Hz), 1.98-1.94 (m, 2H), 1.68-1.61 (m, 2H), 1.38 (s, 3H).

IR spectrum $v_{max}$ cm$^{-1}$ (CDCl$_3$): 3450, 2975, 2928, 2250, 1755, 1599, 1508, 1400, 1381, 1147, 1045, 1010.

Mass spectrum (EI$^+$) m/z: 195 (M$^+$), 178, 164, 134, 121, 100 (base), 96, 94, 81, 56.

Reference Example 5

(2R)-1-Acetoxy-2-acetylamino-2-methyl-4-(furan-2-yl)butane (5a) (2R)-2-Amino-2-methyl-4-(furan-2-yl)butan-1-ol 1/2 D-(−)tartrate To a solution of (4R)-4-methyl-4-[2-(furan-2-yl)ethyl]-1,3-oxazolidin-2-one (29.9 g, 153.2 mmol) obtained in Reference example 4 in a mixed solvent of tetrahydrofuran (150 ml) and methanol (150 ml) was added 5N aqueous potassium hydroxide solution (150 ml) with stirring, and the resulting mixture was refluxed for 3 days. After cooling, water was added to the reaction mixture, and the resulting mixture was extracted with dichloromethane. The extract was dried over anhydrous sodium sulfate. After filtration, the filtrate was evaporated in vacuo.

Subsequently, to a solution of the residue obtained in ethanol (250 ml) was added a solution of D-(−)-tartaric acid (11.5 g, 76.6 mmol) in ethanol (100 ml) with stirring, and the resulting mixture was stirred for 10 minutes. The crude crystals precipitated were collected by filtration and then recrystallized from a mixed solvent of ethanol (300 ml) and water (75 ml) to afford the title compound (24.4 g, yield: 65%) as colorless plate crystals.

Subsequently, to a suspension of (2R)-2-amino-2-methyl-4-(furan-2-yl)butan-1-ol 1/2 D-(−)tartrate (51.2 mg, 0.16 mmol) obtained above in dichloromethane (1.6 ml) were added successively di-t-butyl dicarbonate (0.17 g, 0.78 mmol), triethylamine (0.22 ml, 1.58 mmol) and 4-dimethylaminopyridine-(3.0 mg, 0.025 mmol) with stirring, and the resulting mixture was stirred at room temperature for 20 minutes. After stirring, water was added to the reaction mixture, and the resulting mixture was evaporated in vacuo. The residue obtained was purified by chromatography on a silica gel column using a mixed solvent of hexane and ethyl acetate (1:1) as the eluent to afford (4R)-4-methyl-4-[2-(furan-2-yl)ethyl]-1,3-oxazolidin-2-one (18.0 mg, yield: 58%).

Furthermore, the (4R)-4-methyl-4-[2-(furan-2-yl)ethyl]-1,3-oxazolidin-2-one obtained above was analyzed with a HPLC column for separating optical isomers [ChiralPak AD (0.46 cm×25 cm), Daicel Chemical Industries, Ltd., mobile phase: n-hexane/2-propanol (85/15), flow rate: 1.0 ml/min] in a similar manner to that mentioned in Reference example 4, and its optical purity was determined.

From the results of the HPLC analysis, it was confirmed that the compound eluted first (retention time: 13.09 min) was the 4S-isomer, and the compound eluted afterward (retention time: 15.43 min) was the 4R-isomer, and that the optical purity of this product was 99.3% ee.

According to the results obtained above, the optical purity of the (2R)-2-amino-2-methyl-4-(furan-2-yl)butan-1-ol 1/2 D-(−)tartrate synthesized was confirmed to be more than 99.3%.

Melting point: 225° C.,
Angle of rotation: $[\alpha]_D$=−13.43 (c=1.00, MeOH),
$^1$H-NMR spectrum (CD$_3$OD, 400 MHz) δ: 7.36 (d, 1H, J=2.0 Hz), 6.30 (dd, 1H, J=2.8 Hz, 2.0 Hz), 6.09 (d, 1H, J=2.8 Hz), 3.58 (d, 1H, J=11.6 Hz), 3.51 (d, 1H, J=11.6 Hz), 2.77-2.68 (m, 2H), 2.07-1.88 (m, 2H), 1.28 (s, 3H).
IR spectrum $v_{max}$ cm$^{-1}$ (KBr): 3405, 3226, 3135, 2943, 2597, 1598, 1528, 1401, 1299, 1228, 1124, 1079, 1003, 740.
Mass spectrum (FAB$^+$) m/z: 170 ((M+H)$^+$; as the free form of the title compound),
Elemental analysis (% as C$_9$H$_{15}$NO$_2$.1/2C$_4$H$_6$O$_6$)
Calculated: C, 54.09; H, 7.43; N, 5.73.
Found: C, 53.93; H, 7.30; N, 5.79.

(5b) (2R)-1-Acetoxy-2-acetylamino-2-methyl-4-(furan-2-yl)butane

To a suspension of (2R)-2-amino-2-methyl-4-(furan-2-yl)butan-1-ol 1/2 D-(−)tartrate (24.21 g, 99.1 mmol) obtained in Reference example (5a) in a mixed solvent of dichloromethane (400 ml) and water (100 ml) was added an aqueous sodium hydroxide solution [prepared by dissolving sodium hydroxide (97% pure) (22.34 g) in water (100 ml)] with stirring, and the resulting mixture was stirred at room temperature for 20 minutes. After stirring, the reaction mixture was extracted with dichloromethane, and the extract was dried over anhydrous sodium sulfate. After filtration, the solvent was evaporated in vacuo.

Subsequently, to a solution of the residue obtained in dichloromethane (500 ml) were added successively triethylamine (138 ml, 993 mmol), acetic anhydride (46.5 ml, 493 mmol) and 4-dimethylaminopyridine (1.21 g, 9.9 mmol), and the resulting mixture was stirred at room temperature for 1 hour. After stirring, methanol was added to the reaction mixture to quench the reaction, and the reaction mixture was evaporated in vacuo. Ethyl acetate and water were added to the residue obtained, and the resulting mixture was extracted with ethyl acetate. The extract was washed successively with water and saturated aqueous sodium chloride solution and dried over anhydrous sodium sulfate. After filtration, the solvent was removed in vacuo, and the residue was purified by chromatography on a silica gel column using a mixed solvent of ethyl acetate and hexane (2:1) as the eluent to afford the title compound (25.11 g, yield: 100%).
$^1$H-NMR spectrum (CDCl$_3$, 400 MHz) δ: 7.30 (d, 1H, J=1.8 Hz), 6.28 (dd, 1H, J=3.0 Hz, 1.8 Hz), 6.01 (d, 1H, J=3.0 Hz), 5.36 (br s, 1H), 4.30 (d, 1H, J=11.1 Hz), 4.17 (d, 1H, J=11.1 Hz), 2.66 (t, 2H, J=8.3 Hz), 2.30-2.22 (m, 1H), 2.09 (s, 3H), 2.02-1.94 (m, 1H), 1.92 (s, 3H), 1.35 (s, 3H).
Mass spectrum (EI$^+$) m/z: 253 (M$^+$), 211, 194, 180, 138, 134 (base), 121, 99, 94, 81, 74, 57, 43.

Reference Example 6

(2R)-1-Acetoxy-2-acetylamino-2-methyl-4-(5-bromofuran-2-yl)butane

To a solution of (2R)-1-acetoxy-2-acetylamino-2-methyl-4-(furan-2-yl)butane (5.85 g, 23.1 mmol) obtained in Reference example (5b) in N,N-dimethylformamide (100 ml) were added several small portions of N-bromosuccinimide (4.32 g, 24.3 mmol) with stirring under ice-cooling, and the resulting mixture was stirred at the same temperature for 30 minutes. After stirring, to the reaction mixture were added successively 10% aqueous sodium thiosulfate solution and saturated aqueous sodium hydrogencarbonate solution, and the resulting mixture was extracted with ether. The extract was washed with saturated aqueous sodium chloride solution and dried over anhydrous sodium sulfate. After filtration, the solvent was removed in vacuo, and the residue was purified by chromatography on a silica gel column using a mixed solvent of ethyl acetate and hexane (2:1) as the eluent to afford the crude product. The crude product obtained was furthermore purified using a preparative reversed phase HPLC column [TSK-GEL ODS-80 Ts (5.0 cm×30 cm), TOSO, mobile phase: acetonitrile/water (50:50), flow rate: 40 ml/min] to afford the title compound (2.95 g, yield: 38%).
$^1$H-NMR spectrum (CDCl$_3$, 400 MHz) δ: 6.18 (d, 1H, J=3.3 Hz), 5.99 (d, 1H, J=3.3 Hz), 5.37 (br s, 1H), 4.29 (d, 1H, J=11.3 Hz), 4.16 (d, 1H, J=11.3 Hz), 2.70-2.57 (m, 2H), 2.30-2.22 (m, 1H), 2.10 (s, 3H), 2.01-1.93 (m, 1H), 1.94 (s, 3H), 1.34 (s, 3H).
IR spectrum $v_{max}$ cm$^{-1}$ (Liquid Film): 3300, 3074, 2978, 2938, 1742, 1658, 1549, 1510, 1450, 1373, 1241, 1128, 1012, 945, 922, 784, 733, 605.
Mass spectrum (FAB$^+$) m/z: 332 ((M+H)$^+$).

Reference Example 7

(2R)-1-Acetoxy-2-acetylamino-2-methyl-4-(5-iodofuran-2-yl)butane

To a solution of (2R)-1-acetoxy-2-acetylamino-2-methyl-4-(furan-2-yl)butane (5.11 g, 19.8 mmol) obtained in Reference example (5b) in chloroform (100 ml) were added successively pyridine (8.0 ml, 99.1 mmol) and iodine (10.07 g, 39.7 mmol), and the resulting mixture was stirred at 60° C. for 3 hours. After cooling, 10% aqueous sodium thiosulfate solution was added to the reaction mixture to quench the reaction, and the reaction mixture was extracted with dichloromethane. The extract was washed successively with water, saturated aqueous sodium hydrogencarbonate solution and saturated aqueous sodium chloride solution and dried over anhydrous sodium sulfate. After filtration, the solvent was removed in vacuo, and the residue was purified by chromatography on a silica gel column using a mixed solvent of ethyl acetate and hexane (3:2) as the eluent to afford the crude product (5.57 g). The crude product obtained was furthermore purified using a preparative reversed phase HPLC column [TSK-GEL ODS-80 Ts (5.0 cm×30 cm), TOSO, mobile phase: acetonitrile/water (50:50), flow rate: 40 ml/min] to afford the title compound (2.9467 g, yield: 39%).

$^1$H-NMR spectrum (CDCl$_3$, 400 MHz) δ: 6.42 (d, 1H, J=3.1 Hz), 5.95 (d, 1H, J=3.1 Hz), 5.37 (br s, 1H), 4.29 (d, 1H, J=11.1 Hz), 4.16 (d, 1H, J=11.1 Hz), 2.72-2.63 (m, 2H), 2.29-2.21 (m, 1H), 2.10 (s, 3H), 2.05-1.93 (m, 1H), 1.94 (s, 3H), 1.34 (s, 3H).

IR spectrum $ν_{max}$ cm$^{-1}$ (CHCl$_3$): 3444, 2941, 1736, 1681, 1598, 1512, 1374, 1252, 1103, 1043, 1011, 947, 912.

Mass spectrum (FAB$^+$) m/z: 380 ((M+H)$^+$).

Reference Example 8

(1-Methylpyrrol-2-yl)methyl triphenylphosphonium iodide

A mixture of 35% aqueous formaldehyde solution (20.8 ml, 264.3 mmol) and dimethylamine hydrochloride (22.70 g, 278.4 mmol) was added to 1-methylpyrrole (21.42 g, 264.1 mmol) with stirring under ice-cooling over a 90-minute interval, and then the resulting mixture was stirred at room temperature for 6 hours. After stirring, 10% aqueous sodium hydroxide solution (150 ml) was added to the reaction mixture, and the reaction mixture was extracted with ether. The extract was washed with saturated aqueous sodium chloride solution and dried over anhydrous sodium sulfate. After filtration, the solvent was removed in vacuo, and the residue was purified by chromatography on a silica gel column using a mixed solvent of dichloromethane and methanol (10:1) as the eluent to afford 2-(N,N-dimethylaminomethyl)-1-methylpyrrole (31.47 g, yield: 86%).

Subsequently, to a solution of 2-(N,N-dimethylaminomethyl)-1-methylpyrrole (30.00 g, 217.5 mmol) obtained above in ethanol (220 ml) was added methyl iodide (16.2 ml, 260.2 mmol) with stirring under ice-cooling, and then the resulting mixture was stirred at room temperature for 2 hours. After stirring, ethyl acetate (220 ml) was added to the reaction mixture. The crystals precipitated were collected by filtration, washed with ethyl acetate and dried to afford (1-methylpyrrol-2-yl)methyl trimethylammonium iodide (55.34 g, yield: 91%).

Subsequently, to a suspension of (1-methylpyrrol-2-yl)methyl trimethylammonium iodide (55.34 g, 197.5 mmol) obtained above in acetonitrile (400 ml) was added triphenylphosphine (62.20 g, 237.1 mmol) with stirring, and the resulting mixture was stirred at 80° C. for 10 hours. After cooling, the reaction mixture was concentrated to about one-half of its initial volume, to which was added ethyl acetate (200 ml). The crystals precipitated were collected by filtration, washed with ethyl acetate and dried in vacuo to afford the title compound (77.14 g, yield: 81%).

Reference Example 9

(2R)-2-t-Butoxycarbonylamino-1-n-hexanoyloxy-2-methyl-4-(1-methylpyrrol-2-yl)-3-butene The title compound was synthesized in a yield of 80% using (1-methylpyrrol-2-yl)methyl triphenylphosphonium iodide obtained in Reference example 8 and (2S)-2-t-butoxycarbonylamino-3-n-hexanoyloxy-2-methyl-1-propanal obtained in Reference example (2b) as the starting materials by conducting the reaction similar to that mentioned in Reference example (2c).

$^1$H-NMR spectrum (CDCl$_3$, 400 MHz) δ: 6.60 (t, 1H, J=2.3 Hz), 6.57 (t, 1H, J=2.3 Hz), 6.38 (d, 1H, J=16.1 Hz), 6.30-6.26 (m, total 2H), 6.27 (d, 1H, J=12.5 Hz), 6.11 (t, 1H, J=3.2 Hz), 6.08 (t, 1H, J=3.2 Hz), 5.99 (d, 1H, J=16.1 Hz), 5.58 (d, 1H, J=12.5 Hz) 5.04 (br s, 1H), 4.81 (br s, 1H), 4.34-4.16 (m, total 4H), 3.60 (s, 3H), 3.54 (s, 3H), 2.36-2.30 (m, total 4H), 1.67-1.22 (m, total 4H), 0.92-0.87 (s, total 6H).

Mass spectrum (EI$^+$) m/z: 280 (M$^+$), 249, 224, 193 (base), 164; 149, 132, 108, 94, 57.

Reference Example 10

(4R)-4-Methyl-4-[2-(1-methylpyrrol-2-yl)ethenyl]-1,3-oxazolidin-2-one

The title compound was synthesized in a yield of 76% using (2R)-2-t-butoxycarbonylamino-1-n-hexanoyloxy-2-methyl-4-(1-methylpyrrol-2-yl)-3-butene obtained in Reference example 9 as the starting material by conducting the reaction similar to that mentioned in Reference example 3.

$^1$H-NMR spectrum (CDCl$_3$, 400 MHz) δ: 6.67 (t, 1H, J=2.1 Hz), 6.62 (t, 1H, J=1.5 Hz), 6.48 (d, 1H, J=15.7 Hz), 6.36 (dd, 1H, J=3.7 Hz, 1.5 Hz), 6.31 (d, 1H, J=12.2 Hz), 6.14-6.10 (m, total 2H), 6.07 (br d, 1H, J=3.6 Hz), 5.99 (d, 1H, J=15.7 Hz), 5.65 (d, 1H, J=12.2 Hz) 5.46 (br s, 1H), 5.11 (br s, 1H), 4.31 (d, 1H, J=8.2 Hz), 4.22 (d, 1H, J=8.2 Hz), 4.17 (d, 1H, J=8.2 Hz), 4.16 (d, 1H, J=8.2 Hz), 3.62 (s, 3H), 3.55 (s, 3H), 1.59 (s, 3H), 1.57 (s, 3H).

Mass spectrum (EI$^+$) m/z: 206 (M$^+$, base), 191, 176, 161, 147, 132, 120, 106, 94, 81, 77.

Reference Example 11

(4R)-4-Methyl-4-[2-(1-methylpyrrol-2-yl)ethyl]-1,3-oxazolidin-2-one

The title compound was synthesized in a yield of 78% using (4R)-4-methyl-4-[2-(1-methylpyrrol-2-yl)ethenyl]-1,3-oxazolidin-2-one obtained in Reference example 10 as the starting material by conducting the reaction similar to that mentioned in Reference example 4.

Furthermore, the (4R)-4-methyl-4-[2-(1-methylpyrrol-2-yl)ethyl]-1,3-oxazolidin-2-one obtained above was analyzed with a HPLC column for separating optical isomers [Chiral-Cel OJ (0.46 cm×25 cm), Daicel Chemical Industries, Ltd., mobile phase: n-hexane/2-propanol (70/30), flow rate: 1.0 ml/min], and its optical purity was determined.

From the results of the HPLC analysis, it was confirmed that the compound eluted first (retention time: 12.29 min) was the 4S-isomer, and the compound eluted afterward (retention time: 15.39 min) was the 4R-isomer, and that the optical purity of the product synthesized was 75% ee.

$^1$H-NMR spectrum (CDCl$_3$, 400 MHz) δ: 6.58 (t, 1H, J=2.4 Hz), 6.05 (dd, 1H, J=3.2 Hz, 2.4 Hz), 5.88 (br d, 1H, J=3.2 Hz), 5.15 (bras, 1H), 4.14 (d, 1H, J=8.3 Hz), 4.07 (d, 1H, J=8.3 Hz), 2.70-2.58 (m, 2H), 2.00-1.87 (m, 2H), 1.42 (s, 3H).

IR spectrum $ν_{max}$ cm$^{-1}$ (KBr): 3289, 3103, 2977, 2938, 1759, 1713, 1495, 1397, 1381, 1309, 1281, 1231, 1032, 945, 928, 776, 718, 706, 656.

Mass spectrum (EI$^+$) m/z: 208 (M$^+$), 108 (base), 94, 81, 56, 42.

Reference Example 12

(2R)-1-Acetoxy-2-acetylamino-2-methyl-4-(1-methylpyrrol-2-yl)butane

To a solution of (4R)-4-methyl-4-[2-(1-methylpyrrol-2-yl)ethyl]-1,3-oxazolidin-2-one (1.53 g, 7.36 mmol) obtained in Reference example 11 in a mixed solvent of tetrahydrofuran (30 ml) and methanol (15 ml) was added 5N aqueous potassium hydroxide solution (15 ml, 75 mmol), and the resulting mixture was refluxed for 5 days. After cooling, water was added to the reaction mixture, and the resulting mixture was extracted with dichloromethane. The extract was dried over anhydrous sodium sulfate. After filtration, the solvent was removed in vacuo, and the residue was purified by chromatography on a basic silica gel column (NH type) using a mixed solvent of dichloromethane and methanol (100:1) as the eluent to afford the crude product (1.32 g, yield: 98%).

Subsequently, to a solution of the crude product (1.32 g, 7.24 mmol) thus obtained in dichloromethane (36 ml) were added successively triethylamine (10.0 ml, 71.9 mmol), acetic anhydride (3.4 ml, 36.1 mmol) and 4-dimethylaminopyridine (88 mg, 0.72 mmol) with stirring, and the resulting mixture was stirred at room temperature for 40 minutes. After stirring, methanol (1.46 ml, 36.0 mmol) was added to the reaction mixture to quench the reaction, and the reaction mixture was evaporated in vacuo. Ethyl acetate and water were added to the residue obtained, and the resulting mixture was extracted with ethyl acetate. The extract was washed successively with water, saturated aqueous sodium hydrogencarbonate solution and saturated aqueous sodium chloride solution and dried over anhydrous sodium sulfate. After filtration, the filtrate was concentrated to dryness in vacuo, and the residue was purified by chromatography on a silica gel column using a mixed solvent of ethyl acetate and hexane (3:2-1:0) as the eluent to afford the title compound (1.89 g, yield: 98%).

$^1$H-NMR spectrum (CDCl$_3$, 400 MHz) δ: 6.54 (t, 1H, J=2.4 Hz), 6.04 (t, 1H, J=2.4 Hz), 5.88 (d, 1H, J=2.4 Hz), 5.39 (br s, 1H), 4.33 (d, 1H, J=11.2 Hz), 4.20 (d, 1H, J=11.2 Hz), 2.60-2.51 (m, 2H), 2.26-2.19 (m, 1H), 2.09 (s, 3H), 1.97-1.89 (m, 4H), 1.38 (s, 3H).

Mass spectrum (FAB$^+$) m/z: 267 ((M+H)$^+$), 266 (M$^+$).

Reference Example 13

(2R)-1-Acetoxy-2-acetylamino-2-methyl-4-(1-methyl-5-iodopyrrol-2-yl)butane

To a solution of (2R)-1-acetoxy-2-acetylamino-2-methyl-4-(1-methylpyrrol-2-yl)butane (1.89 g, 7.10 mmol) obtained in Reference example 12 in chloroform (35 ml) were added successively pyridine (2.9 ml, 35.9 mmol) and iodine (3.60 g, 14.17 mmol) with stirring under ice-cooling, and the resulting mixture was stirred at the same temperature for 10 minutes. After stirring, 10% aqueous sodium thiosulfate solution was added to the reaction mixture to quench the reaction, and the reaction mixture was concentrated to about one-half of its initial volume, and extracted with ethyl acetate. The extract was washed successively with saturated aqueous sodium hydrogencarbonate solution and saturated aqueous sodium chloride solution and dried over anhydrous sodium sulfate. After filtration, the filtrate was concentrated to dryness in vacuo, and the residue obtained was purified by chromatography on a silica gel column using a mixed solvent of ethyl acetate and hexane (3:2) as the eluent to afford the title compound (1.40 g, yield: 50%).

$^1$H-NMR spectrum (CDCl$_3$, 400 MHz) δ: 6.28 (d, 1H, J=3.6 Hz), 5.94 (d, 1H, J=3.6 Hz), 5.36 (br s, 1H), 4.32 (d, 1H, J=11.0 Hz), 4.17 (d, 1H, J=11.0 Hz), 3.49 (s, 3H), 2.67-2.59 (m, 2H), 2.27-2.19 (m, 1H), 2.09 (s, 3H), 1.96-1.87 (m, 4H), 1.36 (s, 3H).

Mass spectrum (FAB$^+$) m/z: 393 ((M+H)$^+$), 392 (M$^+$).

Reference Example 14

(2R)-2-t-Butoxycarbonylamino-2-ethyl-1-n-hexanoyloxy-4-(furan-2-yl)-3-butene (14a) (2R)-2-t-Butoxycarbonylamino-2-ethyl-3-n-hexanoyloxy-1-propanol To a suspension of 2-t-butoxycarbonylamino-2-ethylpropane-1,3-diol (52.9 g, 241 mmol) in isopropyl ether (1.0 l) were added successively vinyl hexanoate (41 ml, 254 mmol) and lipase [Immobilized-lipase from *Pseudomonas* sp., TOYOBO, 0.67 U/mg] (2.1 g) with stirring, and the resulting mixture was stirred at room temperature for 4 hours. After stirring, the reaction mixture was filtered and evaporated in vacuo, and the residue was purified by chromatography on a silica gel column using a mixed solvent of hexane and ethyl acetate (7:1-4:1-2:1) as the eluent to afford the title compound (66.8 g, yield: 87%).

Furthermore, the (2R)-2-t-butoxycarbonylamino-2-ethyl-3-n-hexanoyloxy-1-propanol obtained above was analyzed with a HPLC column for separating optical isomers [ChiralCel OF (0.46 cm×0.25 cm), Daicel Chemical Industries, Ltd., mobile phase: hexane/2-propanol (80/20), flow rate: 0.5 ml/min], and its optical purity was determined.

From the results of the HPLC analysis, it was confirmed that the compound eluted first (retention time: 7.35 min) was the 2S-isomer, and the compound eluted afterward (retention time: 7.86 min) was the 2R-isomer, and that the optical purity of the product synthesized was 93% ee.

$^1$H-NMR spectrum (CDCl$_3$, 400 MHz) δ: 4.76 (br s, 1H), 4.24 (d, 1H, J=11.0 Hz), 4.10 (d, 1H, J=11.0 Hz), 3.65-3.62 (m, 2H), 2.35 (t, 2H, J=7.7 Hz), 1.78-1.69 (m, 1H), 1.63-1.53 (m, 4H), 1.44 (s, 9H), 1.30-1.25 (m, 4H), 0.87-0.83 (m, 6H).

Mass spectrum (FAB$^+$) m/z: 340 ((M+Na)$^+$), 318 ((M+H)$^+$).

(14b) (2S)-2-t-Butoxycarbonylamino-2-ethyl-3-n-hexanoyloxy-1-propanal

To a solution of (2R)-2-t-butoxycarbonylamino-3-n-hexanoyloxy-2-ethyl-1-propanol (66.7 g, 210 mmol) obtained in Reference example (14a) in dichloromethane (700 ml) were added successively molecular sieves 4A (117 g) and pyridinium dichromate (117 g, 311 mmol) with stirring under ice-cooling, and then the resulting mixture was stirred at room temperature for 2 hours. After stirring, ether was added to the reaction mixture, and the resulting mixture was filtered. The filtrate was evaporated in vacuo, and the residue was purified by chromatography on a silica gel column using a mixed solvent of hexane and ethyl acetate (10:1-5:1) as the eluent to afford the title compound (45.9 g, yield: 69%).

$^1$H-NMR spectrum (CDCl$_3$, 400 MHz) δ: 9.34, (s, 1H), 5.30 (br s, 1H), 4.60 (d, 1H, J=11.4 Hz), 4.40 (d, 1H, J=11.4 Hz), 2.28 (t, 2H, J=7.3 Hz), 2.18-2.06 (m, 1H), 1.79-1.69 (m, 1H), 1.62-1.55 (m, 2H), 1.44 (s, 9H), 1.34-1.22 (m, 4H), 0.90 (t, 3H, J=7.3 Hz), 0.81 (t, 3H, J=7.3 Hz).

Mass spectrum (FAB$^+$) m/z: 338 ((M+Na)$^+$), 316 ((M+H)$^+$).

(14c) (2R)-2-t-Butoxycarbonylamino-2-ethyl-1-n-hexanoyloxy-4-(furan-2-yl)-3-butene To a suspension of (furan-2-yl)methyl triphenylphosphonium bromide (4.04 g, 9.54 mmol) obtained in Reference example 1 in tetrahydrofuran (32.4 ml) was added potassium t-butoxide (1.06 g, 9.45 mmol) with stirring under ice-cooling, and the resulting mixture was furthermore stirred under ice-cooling for 15 minutes. After stirring, to the reaction mixture was added a solution of (2S)-2-t-butoxycarbonylamino-2-ethyl-3-n-hexanoyloxy-1-propanal (2.01 g, 6.37 mmol) obtained in Reference example (14b) in tetrahydrofuran (10 ml) with stirring under ice-cooling over a 5-minute interval, and the resulting mixture was furthermore stirred under ice-cooling for 30 minutes. After stirring, saturated aqueous ammonium chloride solution was added to the reaction mixture to quench the reaction, and the reaction temperature was raised to room temperature. After evaporation of the reaction mixture in vacuo, ethyl acetate and water were added to the residue, and the resulting mixture was extracted with ethyl acetate. The extract was washed with saturated aqueous sodium chloride solution and dried over anhydrous sodium sulfate. After filtration, the solvent was removed in vacuo, and the residue was purified by chromatography on a silica gel column using a mixed solvent of hexane and ethyl acetate (5:1) as the eluent to afford the title compound (2.385 g, yield: 99%).

$^1$H-NMR spectrum (CDCl$_3$, 400 MHz) δ: 7.44 (br d, 1H, J=1.5 Hz), 7.33 (br d, 1H, J=1.5 Hz), 6.41 (dd, 1H, J=–2.9 Hz, 1.5 Hz), 6.38 (d, 1H, J=2.9 Hz), 6.36 (dd, 1H, J=2.9 Hz, 1.5 Hz), 6.29 (d, 1H, J=16.8 Hz), 6.28 (d, 1H, J=12.5 Hz), 6.22 (d, 1H, J=2.9 Hz), 6.09 (d, 1H, J=16.8 Hz), 5.47 (d, 1H, J=12.5 Hz), 5.21 (br s, 1H), 4.66 (br s, 1H), 4.50 (d, 1H, J=11.7 Hz), 4.41 (d, 1H, J=11.7 Hz), 4.33 (br s, 2H), 2.31 (q, total 4H, J=7.7 Hz), 2.08-1.88 (m, total 4H), 1.47-1.42 (m, total 10H), 1.32-1.26 (m, total 18H), 0.93-0.86 (m, total 12H).

IR spectrum ν$_{max}$ cm$^{-1}$ (CHCl$_3$): 3446, 2970, 2933, 2873, 1722, 1494, 1459, 1391, 1380, 1368, 1249, 1163.

Mass spectrum (FAB$^+$) m/z: 402 ((M+Na)$^+$), 379 (M$^+$).

Reference Example 15

(4R)-4-Ethyl-4-[2-(furan-2-yl)ethenyl]-1,3-oxazolidin-2-one

To a solution of (2R)-2-t-butoxycarbonylamino-2-ethyl-1-n-hexanoyloxy-4-(furan-2-yl)-3-butene (2.33 g, 6.14 mmol) obtained in Reference example 14 in a mixed solvent of tetrahydrofuran (7 ml) and methanol (7 ml) was added 1.8N aqueous sodium hydroxide solution (7 ml), and the resulting mixture was stirred at room temperature for 3 hours. After stirring, water and ethyl acetate were added to the reaction mixture, and the resulting mixture was extracted with ethyl acetate. The extract was washed with saturated aqueous sodium chloride solution and dried over anhydrous sodium sulfate. After filtration, the solvent was removed in vacuo to afford the crude product (1.68 g, yield: 97%).

Subsequently, to a solution of the crude product obtained above in tetrahydrofuran (30 ml) was added potassium t-butoxide (1.21 g, 10.8 mmol) with stirring, and the resulting mixture was stirred at the same temperature for 3 hours. After stirring, water and ethyl acetate were added to the reaction mixture, and the resulting mixture was extracted with ethyl acetate. The extract was washed with saturated aqueous sodium chloride solution and dried over anhydrous sodium sulfate. After filtration, the solvent was removed in vacuo, and the residue was purified by chromatography on a silica gel column using a mixed solvent of hexane and ethyl acetate (3:1-1:1) as the eluent to afford the title compound (1.24 g, quantitative yield).

$^1$H-NMR spectrum (CDCl$_3$, 400 MHz) δ: 7.43 (d, 1H, J=1.5 Hz), 7.32 (d, 1H, J=1.5 Hz), 6.45 (dd, 1H, J=3.7 Hz, 1.5 Hz), 6.44 (d, 1H, J=16.1 Hz), 6.39 (dd, 1H, J=3.7 Hz, 1.5 Hz), 6.37 (d, 1H, J=3.7 Hz), 6.29 (d, 1H, J=3.7 Hz), 6.25 (d, 1H, J=–12.5 Hz), 6.13 (d, 1H, J=16.1 Hz), 5.62 (br s, total 2H), 5.53 (d, 1H, J=12.5 Hz), 4.44 (d, 1H, J=8.8 Hz), 4.36 (d, 1H, J=8.8 Hz), 4.24 (d, 1H, J=8.8 Hz), 4.22 (d, 1H, J=8.8 Hz), 1.93 (q, 2H, J=7.3 Hz), 1.85-1.76 (m, 2H), 0.99 (t, 3H, J=7.3 Hz), 0.98 (t, 1H, J=7.3 Hz).

IR spectrum ν$_{max}$ cm$^{-1}$ (CDCl$_3$): 3453, 2975, 1757, 1396, 1373, 1053, 1015.

Mass spectrum (EI$^+$) m/z: 207 (M$^+$), 178 (base), 135, 107.

Reference Example 16

(4R)-4-Ethyl-4-[2-(furan-2-yl)ethyl]-1,3-oxazolidin-2-one

To a solution of (4R)-4-ethyl-4-[2-(furan-2-yl)ethenyl]-1,3-oxazolidin-2-one (1.24 g, 5.99 mmol) obtained in Reference example 15 in methanol (40 ml) was added 10% palladium-charcoal (50% wet with water) (124 mg), and the resulting mixture was stirred at room temperature under a hydrogen atmosphere for 2 hours. After stirring, the internal atmosphere was replaced with nitrogen, and the palladium-charcoal in the reaction mixture was filtered off using celite, which was washed with ethyl acetate. The filtrate and the washings were combined and concentrated to dryness in vacuo, and the residue was purified by chromatography on a silica gel column using a mixed solvent of hexane and ethyl acetate (1:1-1:2) as the eluent to afford the title compound (144.4 mg, yield: 12%).

$^1$H-NMR spectrum (CDCl$_3$, 400 MHz) δ: 7.32 (br d, 1H, J=2.2 Hz), 6.29 (t, 1H, J=2.2 Hz), 6.03 (br d, 1H, J=2.2 Hz), 5.40 (m, 1H), 4.11 (d, 1H, J=8.8 Hz), 4.07 (d, 1H, J=8.8 Hz), 2.74-2.67 (m, 2H), 1.97-1.93 (m, 2H), 1.72-1.64 (m, 2H), 0.96 (t, 3H, J=7.3 Hz).

IR spectrum ν$_{max}$ cm$^{-1}$ (CDCl$_3$): 3453, 2973, 229, 1757, 1601, 1397, 1380, 1052.

Mass spectrum (EI$^+$) m/z: 209 (M$^+$), 178, 114, 81 (base)

Reference Example 17

(2R)-1-Acetoxy-2-acetylamino-2-ethyl-4-(furan-2-yl)butane

To a solution of (4R)-4-ethyl-4-[2-(furan-2-yl)ethyl]-1,3-oxazolidin-2-one obtained in Reference example 16 in a mixed solvent of tetrahydrofuran (2 ml), methanol (2 ml) and water (2 ml) was added potassium hydroxide (310 mg), and the resulting mixture was refluxed for 3 days. After cooling, water was added to the reaction mixture, and the resulting mixture was extracted with dichloromethane. The extract was dried over anhydrous sodium sulfate. After filtration, the solvent was removed in vacuo, and the residue was purified by chromatography on a silica gel column using a mixed solvent of dichloromethane and methanol (1:0-50:1) as the eluent to afford (2R)-2-amino-2-ethyl-4-(furan-2-yl)butan-1-ol (104.9 mg, yield: 83%).

Subsequently, to a solution of (2R)-2-amino-2-ethyl-4-(furan-2-yl)butan-1-ol obtained above in dichloromethane (2.0 ml) were added successively triethylamine (0.64 ml, 4.59 mmol), acetic anhydride (0.32 ml, 3.39 mmol) and 4-dimethylaminopyridine (28 mg, 0.23 mmol), and the resulting mixture was stirred at room temperature for 2.5 hours. After stirring, methanol was added to the reaction mixture to quench the reaction, and the reaction mixture was evaporated in vacuo. Ethyl acetate and water were added to the residue obtained, and the resulting mixture was extracted with ethyl acetate. The extract was washed successively with water and saturated aqueous sodium chloride solution and dried-over anhydrous sodium sulfate. After filtration, the solvent was removed in vacuo, and the residue was purified by chromatography on a silica gel column using a mixed solvent of hexane and ethyl acetate (1:4) as the eluent to afford the title compound (146.5 mg, yield: 96%).

$^1$H-NMR spectrum (CDCl$_3$, 400 MHz) δ: 7.29 (d, 1H, J=2.2 Hz), 6.28 (dd, 1H, J=2.9 Hz, 2.2 Hz), 6.00 (d, 1H, J=2.9 Hz), 5.24 (br s, 1H), 4.30 (d, 1H, J=11.7 Hz), 4.28 (d, 1H, J=11.7 Hz), 2.62 (t, 2H, J=8.1 Hz), 2.21-2.13 (m, 1H), 2.08 (s, 3H), 2.08-1.99 (m, 1H), 1.94 (s, 3H), 1.86-1.72 (m, 2H), 0.87 (t, 3H, J=7.3 Hz).

IR spectrum $v_{max}$ cm$^{-1}$ (CDCl$_3$): 3442, 2975, 1739, 1680, 1600, 1510, 1462, 1383, 1368, 1248, 1043.

Mass spectrum (FAB$^+$) m/z: 290 ((M+Na)$^+$), 268 ((M+H)$^+$).

Reference Example 18

(2R)-1-Acetoxy-2-acetylamino-2-ethyl-4-(5-iodofuran-2-yl)butane

To a solution of (2R)-1-acetoxy-2-acetylamino-2-ethyl-4-(furan-2-yl)butane obtained in Reference example 17 in chloroform (5.4 ml) were added successively pyridine (0.22 ml, 2.73 mmol) and iodine (278 mg, 1.10 mmol), and the resulting mixture was stirred at 60° C. for 8 hours. After cooling, 10% aqueous sodium thiosulfate solution was added to the reaction mixture to quench the reaction, and the reaction mixture was extracted with ethyl acetate. The extract was washed successively with saturated aqueous sodium hydrogencarbonate solution and saturated aqueous sodium chloride solution and dried over anhydrous sodium sulfate. After filtration, the solvent was removed in vacuo, and the residue was purified by chromatography on a silica gel column using a mixed solvent of hexane and ethyl acetate (1:4-1:6) as the eluent to afford the crude product (151 mg). The crude product obtained was furthermore purified using a preparative reversed phase HPLC column [TSK-GEL ODS-80 Ts (2.0 cm×25 cm), TOSO, mobile phase: acetonitrile/water (60:40)] to afford the title compound (74.0 mg, yield: 35%).

$^1$H-NMR spectrum (CDCl$_3$, 400 MHz) δ: 6.42 (d, 1H, J=3.7 Hz), 5.95 (d, 1H, J=3.7 Hz), 5.23 (m, 1H), 4.27 (s, 2H), 2.64 (t, 2H, J=8.4 Hz), 2.18-2.12 (m, 1H), 2.09 (s, 3H), 2.05-1.97 (m, 1H), 1.95 (s, 3H), 1.81-1.76 (m, 2H), 0.87 (t, 3H, J=7.3 Hz).

IR spectrum $v_{max}$ cm$^{-1}$ (CDCl$_3$): 3442, 2976, 1740, 1681, 1598, 1511, 1462, 1383, 1368, 1246, 1105, 1043.

Mass spectrum (FAB$^+$) m/z: 416 ((M+Na)$^+$), 394 ((M+H)$^+$).

Reference Example 19

(2R)-1-Acetoxy-2-acetylamino-2-methyl-4-(1-methylpyrrol-2-yl)butane (19a) (2R)-2-Amino-2-methyl-4-(1-methylpyrrol-2-yl)butan-1-ol 1/2 D-(−)tartrate To a solution of (4R)-4-methyl-4-[2-(1-methylpyrrol-2-yl)ethyl]-1,3-oxazolidin-2-one (17.92 g, 86.0 mmol) obtained in Reference example 11 in a mixed solvent of tetrahydrofuran (250 ml) and methanol (125 ml) was added 5N aqueous potassium hydroxide solution (125 ml), and the resulting mixture was refluxed for 4 days. After cooling, water was added to the reaction mixture, and the resulting mixture was extracted with dichloromethane. The extract was dried over anhydrous sodium sulfate. After filtration, the solvent was removed in vacuo.

Subsequently, to a solution of the residue obtained in ethanol (260 ml) was added D-(−)-tartaric acid (6.45 g, 43.0 mmol), and the resulting mixture was stirred for 2 hours. The crystals precipitated were collected by filtration to afford the crude product (20.67 g). The crude product (18.65 g) was recrystallized repeatedly three times, firstly from a mixture of ethanol (370 ml) and water (37 ml), secondly from a mixture of ethanol (300 ml) and water (30 ml), and finally from a mixture of ethanol (240 ml) and water (24 ml), to afford the title compound (10.50 g, yield: 53%) as colorless flake crystals.

Subsequently, to a suspension of (2R)-2-amino-2-methyl-4-(1-methylpyrrol-2-yl)butan-1-ol 1/2 D-(−)tartrate (41.4 mg, 0.16 mmol) obtained above in dichloromethane (1.6 ml) was added successively di-t-butyl dicarbonate (0.1758 g, 0.81 mmol), triethylamine (0.225 ml, 1.62 mmol) and 4-dimethylaminopyridine (2.0 mg, 0.016 mmol) with stirring, and the resulting mixture was stirred at room temperature for 30 minutes. After stirring, water was added to the reaction mixture, and the resulting mixture was evaporated in vacuo. The residue obtained was purified by chromatography on a silica gel column using a mixed solvent of hexane and ethyl acetate (3:2-2:1) as the eluent to afford (4R)-4-methyl-4-[2-(1-methylpyrrol-2-yl)ethyl]-1,3-oxazolidin-2-one (17.7 mg, yield: 53%).

Furthermore, the (4R)-4-methyl-4-[2-(1-methylpyrrol-2-yl)ethyl]-1,3-oxazolidin-2-one obtained above was analyzed with a HPLC column for separating optical isomers [Chiralcel OJ (0.46 cm×25 cm), Daicel Chemical Industries, Ltd., mobile phase: n-hexane/2-propanol (70/30), flow rate: 1.0 ml/min] in a similar manner to that mentioned in Reference example 11, and its optical purity was determined.

From the results of the HPLC analysis, it was confirmed that the compound eluted first (retention time: 12.49 min) was the 4S-isomer, and the compound eluted afterward (retention time: 15.48 min) was the 4R-isomer, and that the optical purity of this product was 99.7% ee.

According to the results obtained above, the optical purity of the (2R)-2-amino-2-methyl-4-(1-methylpyrrol-2-yl)butan-1-ol 1/2 D-(−)tartrate synthesized was confirmed to be more than 99.7%.

Melting point: 198-199° C., $^1$H-NMR spectrum (CD$_3$OD, 400 MHz) δ: 6.54 (t, 1H, J=2.3 Hz), 5.91 (dd, 1H, J=3.7 Hz, 2.3 Hz), 5.82 (br d, 1H, J=3.7 Hz), 4.32 (s, 1H), 3.61 (d, 1H, J=11.3 Hz), 3.55 (s, 3H), 3.54 (d, 1H, J=11.3 Hz), 2.69-2.57 (m, 2H), 1.97 (ddd, 1H, J=13.8 Hz, 9.4 Hz, 7.6 Hz), 1.88 (ddd, 1H, J=13.8 Hz, 11.0 Hz, 6.3 Hz), 1.28 (s, 3H).

IR spectrum $v_{max}$ cm$^{-1}$ (KBr): 3480, 3430, 2926, 2634, 2545, 1586, 1516, 1389, 1359, 1309, 1291, 1105, 1039, 710, 690.

Mass spectrum (FAB$^+$) m/z: 183 ((M+H)$^+$; as the free form of the title compound), Elemental analysis (% as C$_{10}$H$_{18}$N$_2$O.1/2C$_4$H$_6$O$_6$)
Calculated: C, 56.01; H, 8.23; N, 10.89.
Found: C, 55.81; H, 8.22; N, 10.89.

(19b) (2R)-1-Acetoxy-2-acetylamino-2-methyl-4-(1-methylpyrrol-2-yl)butane

To a suspension of (2R)-2-amino-2-methyl-4-(1-methylpyrrol-2-yl)butan-1-ol 1/2 D-(−)tartrate (3.98 g, 15.5 mmol) obtained in Reference example (19a) in a mixed solvent of dichloromethane (50 ml) and water (12.5 ml) was added aqueous sodium hydroxide solution [prepared by dissolving sodium hydroxide (97% pure) (3.20 g) in water (12.5 ml)], and the resulting mixture was stirred at room temperature for 20 minutes. After stirring, the reaction mixture was extracted with dichloromethane. The extract was dried over anhydrous sodium sulfate, filtered and evaporated in vacuo.

Subsequently, to the solution of the residue obtained in dichloromethane (78 ml) were added successively triethylamine (21.5 ml, 154.7 mmol), acetic anhydride (7.3 ml, 77.4 mmol) and 4-dimethylaminopyridine (0.1893 g, 1.55 mmol) and the resulting mixture was stirred at room temperature for 1 hour. After stirring, methanol was added to the reaction mixture to quench the reaction, and the reaction mixture was evaporated in vacuo. Ethyl acetate and water were added to the residue obtained, and the resulting mixture was extracted with ethyl acetate. The extract was washed successively with water, saturated aqueous sodium hydrogencarbonate solution and saturated aqueous sodium chloride solution and dried over anhydrous sodium sulfate. After filtration, the solvent was removed in vacuo, and the residue was purified by chromatography on a silica gel column using ethyl acetate as the eluent to afford the title compound (4.23 g, quantitative yield).

$^1$H-NMR spectrum (CDCl$_3$, 400 MHz) δ: 6.54 (t, 1H, J=2.4 Hz), 6.04 (t, 1H, J=2.4 Hz), 5.88 (d, 1H, J=2.4 Hz), 5.39 (br s, 1H), 4.33 (d, 1H, J=11.2 Hz), 4.20 (d, 1H, J=11.2 Hz), 2.60-2.51 (m, 2H), 2.26-2.19 (m, 1H), 2.09 (s, 3H), 1.97-1.89 (m, 4H), 1.38 (s, 3H).

Mass spectrum (FAB$^+$) m/z: 267 ((M+H)$^+$), 266 (M$^+$).

Reference Example 20

(1-Ethylpyrrol-2-yl)methyl triphenylphosphonium iodide

A mixture of 35% aqueous formaldehyde solution (9 ml, 105 mmol) and dimethylamine hydrochloride (9.0 g, 110 mmol) was added to 1-ethylpyrrole (10.0 g, 105 mmol) with stirring under ice-cooling over a 90-minute interval, and then the resulting mixture was stirred at room temperature for 6 hours. After stirring, 10% aqueous sodium hydroxide solution (150 ml) was added to the reaction mixture, and the resulting mixture was extracted with ether. The extract was washed with saturated aqueous sodium chloride solution and dried over anhydrous sodium sulfate. After filtration, the solvent was removed in vacuo, and the residue was purified by chromatography on a silica gel column using a mixed solvent of dichloromethane and methanol (9:1) as the eluent to afford 2-(N,N-dimethylaminomethyl)-1-ethylpyrrole (15.6 g, yield: 97%).

Subsequently, to a solution of 2-(N,N-dimethylaminomethyl)-1-ethylpyrrole (15.6 g, 102 mmol) obtained above in ethanol (150 ml) was added methyl iodide (7.7 ml, 124 mmol) with stirring under ice-cooling, and then the resulting mixture was stirred at room temperature for 3 hours. After stirring, ethyl acetate (150 ml) was added to the reaction mixture. The crystals precipitated were collected by filtration, washed with ethyl acetate and dried to afford (1-ethylpyrrol-2-yl)methyl trimethylammonium iodide (20 g, yield: 66%).

Subsequently, to a suspension of (1-ethylpyrrol-2-yl)methyl trimethylammonium iodide (20 g, 68.0 mmol) obtained above in acetonitrile (200 ml) was added triphenylphosphine (22.0 g, 83.9 mmol), and the resulting mixture was stirred at 80° C. for 9 hours. After cooling, the reaction mixture was concentrated to about one-half of its initial volume, to which was added ethyl acetate (100 ml). The crystals precipitated were collected by filtration, washed with ethyl acetate and dried in vacuo to afford the title compound (27.5 g, yield: 81%).

$^1$H-NMR spectrum (CDCl$_3$, 400 MHz) δ: 7.94-7.89 (m, 3H), 7.78-7.71 (m, 6H), 7.64-7.57 (m, 6H), 6.82-6.79 (m, 1H), 5.96-5.92 (m, 1H), 5.51-5.47 (m, 1H), 5.10 (d, 2H, J=13.9 Hz), 3.35 (q, 2H, J=7.3 Hz), 0.96 (t, 3H, J=7.3 Hz).

Reference Example 21

(2R)-2-t-Butoxycarbonylamino-2-methyl-4-(1-ethylpyrrol-2-yl)-1-n-hexanoyloxy-3-butene To a suspension of (1-ethylpyrrol-2-yl)methyl triphenylphosphonium iodide (19.8 g, 39.8 mmol) obtained in Reference example 20 in tetrahydrofuran (100 ml) was added a solution of potassium t-butoxide (4.47 g, 39.8 mmol) in tetrahydrofuran (70 ml) with stirring under ice-cooling over a 30-minute interval, and the resulting mixture was stirred under ice-cooling for 1.5 hours.

Subsequently, to the reaction mixture was added a solution of (2S)-2-t-butoxycarbonylamino-3-n-hexanoyloxy-2-methyl-1-propanal (10 g, 33.2 mmol) obtained in Reference example (2b) in tetrahydrofuran (50 ml) with stirring under ice-cooling over a 30-minute interval, and the resulting mixture was stirred under ice-cooling for 1.5 hours. After stirring, saturated aqueous ammonium chloride solution was added to the reaction mixture to quench the reaction, and then the reaction temperature was raised to room temperature. After evaporation of the reaction mixture in vacuo, water and ethyl acetate were added to the residue, and then the resulting mixture was extracted with ethyl acetate. The extract was washed successively with water and saturated aqueous sodium chloride solution and dried over anhydrous sodium sulfate. After filtration, the solvent was removed in vacuo, and the residue was purified by chromatography on a silica gel column using a mixed solvent of hexane and ethyl acetate (4:1) as the eluent to afford the title compound (11.7 g, yield: 90%).

$^1$H-NMR spectrum (CDCl$_3$, 400 MHz) δ: 6.67-6.62 (m, 2H), 6.42-6.36 (m, 1H), 6.31-6.26 (m, 3H), 6.13-6.08 (m, 2H), 6.02-5.96 (m, 1H), 5.63-5.58 (m, 1H), 4.35-4.08 (m, 4H), 3.96-3.86 (m, 4H), 2.85-2.81 (m, 4H), 1.67-1.58 (m, 4H), 1.48-1.24 (m, 38H), 0.93-0.86 (m, 6H).

Reference Example 22

(4R)-4-Methyl-4-[2-(1-ethylpyrrol-2-yl)ethenyl]-1,3-oxazolidin-2-one

To a solution of (2R)-2-t-butoxycarbonylamino-2-methyl-4-(1-ethylpyrrol-2-yl)-1-n-hexanoyloxy-3-butene (11.7 g, 29.8 mmol) obtained in Reference example 21 in a mixed solvent of tetrahydrofuran (40 ml) and methanol (40 ml) was added 2N aqueous sodium hydroxide solution (40 ml), and the resulting mixture was stirred at room temperature for 1.5 hours. After stirring, acetic acid (1.5 ml) was added to the reaction mixture to quench the reaction, and then the reaction mixture was poured into water and extracted with ethyl acetate. The extract was washed successively with water and saturated aqueous sodium chloride solution and dried over anhydrous sodium sulfate. After filtration, the solvent was removed in vacuo to afford the crude product (8.7 g).

Subsequently, to a solution of the crude product obtained above in tetrahydrofuran (100 ml) was added a solution of potassium t-butoxide (4.0 g, 35.6 mmol) in tetrahydrofuran (30 ml) with stirring under ice-cooling over a 10-minute interval, and the resulting mixture was stirred at the same temperature for 1 hour. After stirring, the reaction mixture was neutralized with acetic acid (2 ml) and concentrated in vacuo. Water and ethyl acetate were added to the residue, and the resulting mixture was extracted with ethyl acetate. The extract was washed with saturated aqueous sodium chloride solution and dried over anhydrous sodium sulfate. After filtration, the solvent was removed in vacuo, and the residue was purified by chromatography on a silica gel column using a mixed solvent of hexane and ethyl acetate (3:2) as the eluent to afford the title compound (5.7 g, yield: 86%).

$^1$H-NMR spectrum (CDCl$_3$, 400 MHz) δ: 6.73-6.65 (m, 2H), 6.52-6.46 (m, 1H), 6.36-6.29 (m, 2H), 6.15-6.10 (m, 2H), 6.05-5.97 (m, 2H), 5.69-5.65 (m, 2H), 4.31-4.09 (m, 4H), 3.97-3.83 (m, 4H), 1.60-1.53 (m, 6H), 1.39-1.31 (m, 6H).

Reference Example 23

(4R)-4-Methyl-4-[2-(1-ethylpyrrol-2-yl)ethyl]-1,3-oxazolidin-2-one

To a suspension of 10% palladium-charcoal (50% wet with water) (500 mg) in ethanol (10 ml) was added a solution of (4R)-4-methyl-4-[2-(1-ethylpyrrol-2-yl)ethenyl]-1,3-oxazolidin-2-one (5.7 g, 25.9 mmol) obtained in Reference example 22 in ethanol (50 ml), and the resulting mixture was stirred at room temperature under a hydrogen atmosphere for 1 hour. After stirring, the palladium-charcoal in the reaction mixture was filtered off using celite, and the filtrate was evaporated in vacuo. The residue obtained was purified by chromatography on a silica gel column using a mixed solvent of hexane and ethyl acetate (3:7) as the eluent to afford the title compound (5.0 g, yield: 87%).

Furthermore, the (4R)-4-methyl-4-[2-(1-ethylpyrrol-2-yl)ethyl]-1,3-oxazolidin-2-one obtained above was analyzed with a HPLC column for separating optical isomers [Chiral-Pak OJ (0.46 cm×25 cm), Daicel Chemical Industries, Ltd., mobile phase: n-hexane/2-propanol (70/30), flow rate: 1.0 ml/min], and its optical purity was determined.

From the results of the HPLC analysis, it was confirmed that the compound eluted first (retention time: 7.5 min) was the 4S-isomer, and the compound eluted afterward (retention time: 8.3 min) was the 4R-isomer, and that the optical purity of the product synthesized was 83.7% ee.

$^1$H-NMR spectrum (CDCl$_3$, 400 MHz) δ: 6.66-6.63 (m, 1H), 6.10-6.07 (m, 1H), 5.89-5.86 (m, 1H), 5.00 (br s, 1H), 4.15 (d, 1H, J=8.1 Hz), 4.08 (d, 1H, J=8.1 Hz), 3.84 (q, 2H, J=7.3 Hz), 2.67-2.61 (m, 2H), 1.99-1.92 (m, 2H), 1.43 (s, 3H), 1.87 (t, 3H, J=7.3 Hz).

Reference Example 24

(2R)-1-Acetoxy-2-acetylamino-2-methyl-4-(1-ethylpyrrol-2-yl)butane (24a) (2R)-2-Amino-2-methyl-4-(1-ethylpyrrol-2-yl)butan-1-ol 1/2 D-(−)tartrate To a solution of (4R)-4-methyl-4-[2-(1-ethylpyrrol-2-yl)ethyl]-1,3-oxazolidin-2-one (4.9 g, 22.0 mmol) obtained in Reference example 23 in a mixed solvent of tetrahydrofuran (80 ml) and methanol (40 ml) was added 5.5N aqueous potassium hydroxide solution (40 ml), and the resulting mixture was refluxed for 4 days. After cooling, water was addded to the reaction mixture, and the resulting mixture was extracted with dichloromethane. The extract was dried over anhydrous sodium sulfate, and after filtration, the solvent was removed in vacuo.

Subsequently, to a solution of the residue obtained in ethanol (200 ml) was added a solution of D-(−)-tartrate (1.59 g, 10.5 mmol) in ethanol (20 ml) with stirring, and then the resulting mixture was allowed to stand at room temperature for 4 hours. The crude crystals precipitated were collected by filtration and recrystallized from a mixed solvent of ethanol (100 ml) and water (10 ml). The crystals obtained were recrystallized again from a mixed solvent of ethanol (50 ml) and water (5 ml) to afford the title compound (2.8 g, yield: 37%) as colorless plate crystals.

Subsequently, to a suspension of (2R)-2-amino-2-methyl-4-(1-ethylpyrrol-2-yl)butan-1-ol 1/2 D-(−)tartrate (55.5 mg, 0.16 mmol) in dichloromethane (1.6 ml) were added successively di-t-butyl dicarbonate (0.17 g, 0.78 mmol), triethylamine (0.22 ml, 1.58 mmol) and 4-dimethylaminopyridine (3.0 mg, 0.025 mmol) with stirring, and the resulting mixture was stirred at room temperature for 20 minutes. After stirring, water was added to the reaction mixture, and the resulting mixture was concentrated in vacuo. The residue obtained was purified by chromatography on a silica gel column using a mixed solvent of hexane and ethyl acetate (1:1) as the eluent to afford (4R)-4-methyl-4-[2-(1-ethylpyrrol-2-yl)ethyl]-1,3-oxazolidin-2-one (18.0 mg, yield: 58%).

Furthermore, the (4R)-4-methyl-4-[2-(1-ethylpyrrol-2-yl)ethyl]-1,3-oxazolidin-2-one obtained above was analyzed with a HPLC column for separating optical isomers [Chiral-Pak OJ (0.46 cm×25 cm), Daicel Chemical Industries, Ltd., mobile phase: n-hexane/2-propanol (70/30), flow rate: 1.0 ml/min], and its optical purity was confirmed to be 99.9% ee.

From the results obtained above, the optical purity of (2R)-2-methyl-2-amino-4-(1-ethylpyrrol-2-yl)butan-1-ol-1/2 D-(−)tartrate synthesized was confirmed to be more than 99.9%.

$^1$H-NMR spectrum (DMSO-d$_6$, 400 MHz) δ: 6.58-6.54 (m, 1H), 5.93-5.89 (m, 1H), 5.79-5.76 (m, 1H), 4.27 (s, 1H), 3.85 (q, 2H, J=7.3 Hz), 3.68 (d, 1H, J=11.7 Hz), 3.51 (d, 1H, J=11.7 Hz), 2.62-2.56 (m, 2H), 1.99-1.82 (m, 2H), 1.29 (t, 3H, J=7.3 Hz), 1.27 (s, 3H).

(24b) (2R)-1-Acetoxy-2-acetylamino-2-methyl-4-(1-ethylpyrrol-2-yl)butane

To a solution of (2R)-2-amino-2-methyl-4-(1-ethylpyrrol-2-yl)butan-1-ol 1/2 D-(−)tartrate (2.7 g, 7.80 mmol) obtained in Reference example (24a) in dichloromethane (30 ml) were added successively triethylamine (17.0 ml, 122 mmol), acetic anhydride (7.6 ml, 80.4 mmol) and 4-dimethylaminopyridine (20 mg, 0.16 mmol), and the resulting mixture was stirred at room temperature for 3.5 hours. After stirring, water was added to the reaction mixture, and the resulting mixture was extracted with dichloromethane. The extract was washed successively with water and saturated aqueous sodium chloride solution and dried over anhydrous sodium sulfate. After filtration, the solvent was removed in vacuo, and the residue was purified by chromatography on a silica gel column using ethyl acetate as the eluent to afford the title compound (2.2 g, yield: 96%).

$^1$H-NMR spectrum (CDCl$_3$, 400 MHz) δ: 6.62-6.59 (m, 1H), 6.09-6.06 (m, 1H), 5.89-5.87 (m, 1H), 5.4.1 (br s, 1H), 4.34 (d, 1H, J=11.0 Hz), 4.21 (d, 1H, J=11.0 Hz), 3.85 (q, 2H, J=7.3 Hz), 2.60-2.51 (m, 2H), 2.26-2.18 (m, 1H), 2.08 (s, 3H), 1.98-1.93 (m, 1H), 1.92 (s, 3H), 1.38 (s, 3H), 1.37 (t, 3H, J=7.3 Hz).

Reference Example 25

(1-t-Butoxycarbonylpyrrol-2-yl)methyl triphenylphosphonium iodide

A mixture of 35% aqueous formaldehyde solution (3.2 ml, 40.7 mmol) and dimethylamine hydrochloride (3.44 g, 42.4 mmol) was added to pyrrole (2.72 g, 40.47 mmol) at room temperature with stirring over a 20-minute interval, and the resulting mixture was stirred at room temperature for 2 hours. After stirring, 10% aqueous sodium hydroxide solution (18 ml) was added to the reaction mixture, and the reaction mixture was extracted with dichloromethane. The extract was washed with saturated aqueous sodium chloride solution and dried over anhydrous sodium sulfate. After filtration, the solvent was removed in vacuo, and the residue was purified by chromatography on a silica gel column using a mixed solvent of dichloromethane and methanol (10:1) as the eluent to afford 2-(N,N-dimethylaminomethyl)pyrrole (4.55 g, quantitative yield).

Subsequently, to a solution of 2-(N,N-dimethylaminomethyl)pyrrole (4.54 g, 40.41 mmol) obtained above in ethanol (40 ml) was added methyl iodide (3.05 ml, 49.0 mmol) with stirring under ice-cooling, and then the resulting mixture was stirred at room temperature for 7 hours. After stirring, ethyl acetate was added to the reaction mixture, and then the crystals precipitated were collected by filtration and washed with ethyl acetate and dried to afford (pyrrol-2-yl)methyl trimethylammonium iodide (7.59 g, yield: 71%).

Subsequently, to a suspension of (pyrrol-2-yl)methyl trimethylammonium iodide (7.59 g, 28.52 mmol) obtained above in acetonitrile (60 ml) was added triphenylphosphine (8.98 g, 34.2 mmol) with stirring, and the resulting mixture was stirred at 80° C. for 6 hours. After cooling, the reaction mixture was concentrated to about one-half of its initial volume, to which was added ethyl acetate (100 ml). The crystals precipitated were collected by filtration, washed with ethyl acetate and dried in vacuo to afford (pyrrol-2-yl)methyl trimethylphosphonium iodide (12.33 g, yield: 92%).

Subsequently, to a suspension of (pyrrol-2-yl)methyl trimethylphosphonium iodide (12.30 g, 26.21 mmol) obtained above in acetonitrile (115 ml) were added successively di-t-butyl dicarbonate (7.61 g, 34.87 mmol) and 4-dimethylaminopyridine (0.16 g, 1.31 mmol) with stirring, and the resulting mixture was stirred at room temperature for 24 hours. After evaporation of the reaction mixture in vacuo, ethyl acetate (50 ml) and dichloromethane (4 ml) were added to the residue with stirring, and then the crystals precipitated were collected by filtration, washed with ethyl acetate and dried in vacuo to afford the title compound (14.02 g, yield: 94%).

$^1$H-NMR spectrum (CDCl$_3$, 400 MHz) δ: 7.82-7.78 (m, 3H), 7.68-7.58 (m, 12H), 7.09-7.07 (m, 1H), 6.42-6.39 (m, 1H), 6.11 (t, 1H, J=3.7 Hz), 5.68 (d, 2H, J=13.2 Hz), 1.29 (s, 3H).

Reference Example 26

(2R)-2-t-Butoxycarbonylamino-2-methyl-4-(1-t-butoxycarbonylpyrrol-2-yl)-1-n-hexanoyloxy-3-butene To a suspension of (1-t-butoxycarbonylpyrrol-2-yl)methyl triphenylphosphonium iodide (3.30 g, 5.80 mmol) obtained in Reference example 25 in tetrahydrofuran (60 ml) was added a solution of potassium t-butoxide (0.65 g, 5.8 mmol) in tetrahydrofuran (5.8 ml) with stirring under ice-cooling, and the resulting mixture was stirred under ice-cooling for 15 minutes.

Subsequently, to the reaction mixture was added a solution of (2S)-2-t-butoxycarbonylamino-3-n-hexanoyloxy-2-methyl-1-propanal (1.46 g, 4.83 mmol) obtained in Reference example (2b) in tetrahydrofuran (3 ml) with stirring under ice-cooling, and the resulting mixture was stirred under ice-cooling for 1 hour. After stirring, saturated aqueous ammonium chloride solution was added to the reaction mixture to quench the reaction, and then the reaction temperature was raised to room temperature. To the reaction mixture were added successively water and ethyl acetate, and the resulting mixture was extracted with ethyl acetate. The extract was washed with saturated aqueous sodium chloride solution and dried over anhydrous sodium sulfate. After filtration, the solvent was removed in vacuo, and the residue was purified by chromatography on a silica gel column using a mixed solvent of hexane and ethyl acetate (5:1) as the eluent to afford the title compound (2.12 g, yield: 94%).

$^1$H-NMR spectrum (CDCl$_3$, 400 MHz) δ: 7.25-7.20 (m, total 2H), 7.11 (d, 1H, J=16.1 Hz), 6.61 (d, 1H, J=12.5 Hz), 6.39-6.24 (m, total 2H), 6.18-6.08 (m, total 2H), 6.08 (d, 1H, J=16.1 Hz), 5.64 (d, 1H, J=12.5 Hz), 4.92-4.75 (m, total 2H), 4.34-4.23 (m, total 2H), 4.22-4.16 (m, total 2H), 2.38-2.29 (m, total 4H), 1.69-1.20 (m, total 54H), 0.94-0.82 (m, total 6H).

IR spectrum $\nu_{max}$ cm$^{-1}$ (CHCl$_3$): 3445, 2981, 2934, 1734, 1495, 1457, 1393, 1370, 1333, 1252, 1163, 1123, 1066.

Mass spectrum (FAB$^+$) m/z: 465 ((M+H)$^+$).

Reference Example 27

(4R)-4-Methyl-4-[2-(pyrrol-2-yl)ethenyl]-1,3-oxazolidin-2-one

To a solution of (2R)-2-t-butoxycarbonylamino-2-methyl-4-(1-t-butoxycarbonylpyrrol-2-yl)-1-n-hexanoyloxy-3-butene (1.78 g, 3.82 mmol) obtained in Reference example 26 in a mixed solvent of tetrahydrofuran (20 ml) and methanol (20 ml) was added 1N aqueous sodium hydroxide solution (20 ml), and the resulting mixture was stirred at room temperature for 1 hour. After stirring, water was added to the reaction mixture, and the resulting mixture was extracted with ethyl acetate. The extract was washed with saturated aqueous sodium chloride solution and dried over anhydrous sodium sulfate. After filtration, the solvent was removed in vacuo to afford the crude product.

Subsequently, to a solution of the crude product obtained above in tetrahydrofuran (60 ml) was added potassium t-butoxide (0.557 g, 4.96 mmol) with stirring, and the resulting mixture was stirred at room temperature for 1 hour. After stirring, water was added to the reaction mixture, and the resulting mixture was extracted with ethyl acetate. The extract was washed with saturated aqueous sodium chloride solution and dried over anhydrous sodium sulfate. After filtration, the solvent was removed in vacuo, and the residue was purified by chromatography on a silica gel column using a mixed solvent of ethyl acetate and hexane (2:1) as the eluent to afford the title compound (0.259 g, yield: 35%).

$^1$H-NMR spectrum (CDCl$_3$, 400 MHz) δ: 8.69-8.22 (m, total 2H), 6.88-6.76 (m, total 2H), 6.48 (d, 1H, J=16.1 Hz), 6.34 (d, 1H, J=12.5 Hz), 6.39-6.18 (m, total 4H), 5.82 (d, 1H, J=16.1 Hz), 5.47 (br s, 1H), 5.37 (d, 1H, J=12.5 Hz), 5.16 (br s, 1H), 4.40 (d, total 2H, J=8.8 Hz), 4.19 (d, total 2H, J=8.8 Hz), 1.59 (s, 3H), 1.55 (s, 3H).

IR spectrum $v_{max}$ cm$^{-1}$ (CHCl$_3$): 3467, 2976, 2929, 1759, 1637, 1477, 1455, 1373, 1280, 1165, 1041, 954, 909.

Mass spectrum (FAB$^+$) m/z: 192 (M$^+$).

Reference Example 28

(4R)-4-methyl-4-[2-(pyrrol-2-yl)ethyl]-1,3-oxazolidin-2-one

To a solution of (4R)-4-methyl-4-[2-(pyrrol-2-yl)ethenyl]-1,3-oxazolidin-2-one (0.259 g, 1.35 mmol) obtained in Reference example 27 in methanol (6 ml) was added 10% palladium-charcoal (50% wet with water) (26 mg), and the resulting mixture was stirred at room temperature under a hydrogen atmosphere for 30 minutes. After stirring, the palladium-charcoal in the reaction mixture was filtered off using celite. After evaporation of the filtrate in vacuo, the residue was purified by chromatography on a silica gel column using a mixed solvent of ethyl acetate and hexane (2:1) as the eluent to afford the title compound (0.238 g, yield: 91%).

$^1$H-NMR spectrum (CDCl$_3$, 400 MHz) δ: 8.41-8.15 (m, 1H), 6.73-6.68 (m, 1H), 6.17-6.10 (m, 1H), 5.96-5.90 (m, 1H), 5.75 (br s, 1H), 4.12 (d, 1H, J=8.8 Hz), 4.05 (d, 1H, J=8.8 Hz), 2.76-2.61 (m 2H), 2.00-1.83 (m, 2H), 1.37 (s, 3H).

IR spectrum $v_{max}$ cm$^{-1}$ (CHCl$_3$): 3472, 2980, 2933, 1754, 1571, 1479, 1457, 1400, 1382, 1250, 1162, 1093, 1044, 942.

Mass spectrum (FAB$^+$) m/z: 194 (M$^+$).

Reference Example 29

5-(4-Fluorophenyl)pent-1-yne

To a suspension of sodium hydride (2.11 g, 48.4 mmol) in dry tetrahydrofuran (60 ml) was added dropwise ethyl diethylphosphonoacetate (10.84 g, 48.4 mmol) with stirring under ice-cooling, and the resulting mixture was stirred for 10 minutes.

Subsequently, to the reaction mixture was added dropwise a solution of 4-fluorobenzaldehyde (5.00 g, 40.3 mmol) in dry tetrahydrofuran (60 ml) at the same temperature with stirring, and the resulting mixture was stirred for 3 hours. After stirring, the reaction mixture was poured into ice-cold water (150 ml) with stirring and then extracted with ethyl acetate. The organic layer was dried over anhydrous magnesium sulfate. After removal of the solvent in vacuo, the residue was purified by flash chromatography on a silica gel column using a mixed solvent of hexane and ethyl acetate (10:1-3:1) as the eluent to afford ethyl 4-fluorocinnamate (6.69 g, yield: 86%) as a colorless oil.

Furthermore, to a solution of the reaction product obtained above (6.52 g, 33.6 mmol) in ethyl acetate (100 ml) was added 5% rhodium/alumina (1.30 g), and the resulting mixture was stirred at room temperature under a hydrogen atmosphere for 8 hours. After stirring, the reaction mixture was filtered using celite, and the filtrate was evaporated in vacuo.

Subsequently, to a suspension of lithium aluminum hydride (1.26 g, 33.2 mmol) in dry tetrahydrofuran (60 ml) was added dropwise a solution of the residue obtained above in dry tetrahydrofuran (30 ml) with stirring under ice-cooling, and the resulting mixture was stirred at the same temperature for 30 minutes. After stirring, saturated aqueous sodium sulfate solution was added to the reaction mixture, and the resulting mixture was furthermore stirred at room temperature for 10 minutes. After stirring, the reaction mixture was filtered using celite, and the filtrate was extracted with ethyl acetate. The organic layer was washed with saturated aqueous sodium chloride solution and dried over anhydrous magnesium sulfate. After filtration, the solvent was removed in vacuo, and the residue was purified by flash chromatography on a silica gel column using a mixed solvent of hexane and ethyl acetate (5:1-1:1) as the eluent to afford 3-(4-fluorophenyl)propan-1-ol (4.86 g, yield: 95%) as a colorless oil.

Subsequently, to a solution of 3-(4-fluorophenyl)propan-1-ol (4.83 g, 31.3 mmol) obtained above in dichloromethane (50 ml) were added successively triethylamine (6.55 ml, 47.0 mmol) and methanesulfonyl chloride (2.91 ml, 37.6 mmol) with stirring under ice-cooling, and the resulting mixture was stirred under a nitrogen atmosphere for 30 minutes. After stirring, the reaction mixture was diluted with dichloromethane (50 ml), washed successively with 10% aqueous hydrochloric acid solution and saturated aqueous sodium chloride solution, both of which were ice-chilled previously, and dried over anhydrous magnesium sulfate. After filtration, the solvent was removed in vacuo.

Subsequently, to a solution of the residue obtained in acetone (100 ml) was added sodium iodide (9.39 g, 62.6 mmol), and the resulting mixture was stirred at 50° C. under a nitrogen atmosphere for 2 hours. After stirring, the reaction mixture was diluted with ethyl acetate (250 ml), washed successively with 10% aqueous sodium thiosulfate solution and saturated aqueous sodium chloride solution and dried over anhydrous magnesium sulfate. After filtration, the solvent was removed in vacuo, and the residue was purified by flash chromatography on a silica gel column using a mixed solvent of hexane and ethyl acetate (5:1-2:1) as the eluent to afford 3-(4-fluorophenyl)-1-iodopropane (7.12 g, yield: 86%) as a pale yellow oil.

Subsequently, sodium acetylide (18% slurry in xylene) (50 ml) was added to hexamethylphosphoramide (20 ml) with stirring, and to the resulting mixture was furthermore added a solution of 3-(4-fluorophenyl)-1-iodopropane (7.00 g, 26.5 mmol) obtained above in dry dimethylformamide (20 ml) with stirring under ice-cooling, and then the resulting mixture was stirred at room temperature for 2 hours. After stirring, ice-cold water was added to the reaction mixture carefully with stirring under ice-cooling, and the resulting mixture was extracted with ethyl acetate. The organic layer was washed with saturated aqueous sodium chloride solution and dried over anhydrous magnesium sulfate. After filtration, the solvent was removed in vacuo, and the residue was purified by flash chromatography on a silica gel column using hexane as the eluent to afford the title compound (2.67 g, yield: 62%) as a colorless oil.

$^1$H-NMR spectrum (CDCl$_3$, 400 MHz) δ: 7.14 (m, 2H), 6.97 (m, 2H), 2.71 (t, 2H, J=7.5 Hz), 2.19 (m, 2H), 1.99 (t, 1H, J=2.6 Hz), 1.82 (m, 2H).

Mass spectrum (EI) m/z: 162 (M$^+$).

Reference Example 30

5-Phenylpent-1-yne

The title compound was synthesized using 3-phenyl-1-iodopropane and sodium acetylide by conducting the reactions similar to those mentioned in Reference example 29.

$^1$H-NMR spectrum (CDCl$_3$, 400 MHz) δ: 7.32-7.26 (m, 2H), 7.23-7.16 (m, 3H), 2.74 (t, 2H, J=7.6 Hz), 2.21 (dt, 2H, J=7.6 Hz, 2.8 Hz), 1.99 (t, 1H, J=2.8 Hz), 1.89-1.81 (m, 2H).

Mass spectrum (EI) m/z: 144 (M$^+$).

Reference Example 31

5-(4-Chlorophenyl)pent-1-yne

The title compound was synthesized using 3-(4-chlorophenyl)-1-iodopropane and sodium acetylide by conducting the reactions similar to those mentioned in Reference example 29.

$^1$H-NMR spectrum (CDCl$_3$, 400 MHz) δ: 7.26-7.23 (m, 2H), 7.13-7.11 (m, 2H), 2.71 (t, 2H, J=7.3 Hz), 2.19 (dt, 2H, J=7.3 Hz, 2.9 Hz), 1.99 (t, 1H, J=2.9 Hz), 1.85-1.78 (m, 2H).

Reference Example 32

5-(3-Trifluoromethylphenyl)pent-1-yne

The title compound was synthesized using 3-(3-trifluoromethylphenyl)-1-iodopropane and sodium acetylide by conducting the reactions similar to those mentioned in Reference example 29.

$^1$H-NMR spectrum (CDCl$_3$, 400 MHz) δ: 7.46-7.37 (m, 4H), 2.81 (t, 2H, J=7.3 Hz), 2.22 (dt, 2H, J=7.3 Hz, 2.9 Hz), 2.01 (t, 1H, J=2.9 Hz), 1.90-1.83 (m, 2H).

Reference Example 33

5-Cyclohexylpent-1-yne

The title compound was synthesized using 3-cyclohexyl-1-iodopropane and sodium acetylide by conducting the reactions similar to those mentioned in Reference example 29.

$^1$H-NMR spectrum (CDCl$_3$, 400 MHz) δ 2.16 (dt, 2H, J=7.2 Hz, 2.8, Hz), 1.94 (t, 1H, J=2.8 Hz), 1.59-1.48 (m, 2H), 1.38-0.75 (m, 13H).

Mass spectrum (EI) m/z: 150 (M$^+$).

Reference Example 34

4-Cyclohexyloxybut-1-yne

To a solution of cyclohexanone (32 ml, 0.31 mol) in dry dichloromethane (950 ml) were added successively 1,3-propanediol (33.5 ml, 0.46 mol), triethyl orthoformate (51.5 ml, 0.31 mol) and zirconium chloride (1.44 g, 6.18 mmol) with stirring, and the resulting mixture was stirred at room temperature under a nitrogen atmosphere for 1 hour. After stirring, ice-chilled 1N aqueous sodium hydroxide solution (1.5 l) was added to the reaction mixture with stirring, and the resulting mixture was extracted with dichloromethane. The extract was washed with water and dried over anhydrous sodium sulfate. After filtration, the solvent was removed in vacuo, and the residue was purified by reduced-pressure distillation to afford cyclohexanone trimethylene ketal (26.8 g, yield: 55%).

Subsequently, to a suspension of zirconium chloride (24.9 g, 0.11 mol) in tetrahydrofuran (500 ml) was added slowly sodium borohydride (20.5 g, 0.54 mol) in portions with stirring under a nitrogen atmosphere, and the resulting mixture was stirred at room temperature for 20 minutes. After stirring, to the reaction mixture was added dropwise a solution of cyclohexanone trimethylene ketal (16.9 g, 0.11 mol) obtained above in tetrahydrofuran (170 ml) with stirring while ice-cooling under a nitrogen atmosphere, and then the resulting mixture was stirred at room temperature for one day. After stirring, to the reaction mixture was added ice-chilled 2N hydrochloric acid (600 ml) with stirring under ice-cooling to quench the reaction, and then the tetrahydrofuran was evaporated in vacuo. The aqueous layer which remained was extracted with ethyl acetate, and the extract was washed with saturated aqueous sodium chloride solution and dried over anhydrous sodium sulfate. After filtration, the solvent was removed in vacuo, and the residue was purified by chromatography on a silica gel column using a mixed solvent of hexane and ethyl acetate (10:1-5:2) as the eluent to afford 3-cyclohexyloxypropan-1-ol (13.4 g, yield: 78%).

Subsequently, to a solution of 3-cyclohexyloxypropan-1-ol (11.5 g, 72.9 mmol) obtained above in dichloromethane (240 ml) were added successively molecular sieves 4A (58 g) and pyridinium dichromate (23.8 g, 0.11 mol) with stirring under ice-cooling, and the resulting mixture was stirred at the same temperature under a nitrogen atmosphere for 1 hour and 40 minutes. After stirring, ether was added to the reaction mixture, and the resulting mixture was filtered using celite, which was washed with ether. The filtrate and the washings were combined and evaporated in vacuo, and the residue was purified by chromatography on a silica gel column using a mixed solvent of hexane and ethyl acetate (20:1-10:1) as the eluent to afford the crude 3-cyclohexyloxypropionaldehyde (8.60 g).

Subsequently, to a solution of carbon tetrabromide (36.5 g, 0.11 mol) in dichloromethane (120 ml) was added a solution of triphenylphosphine (57.7 g, 0.22 mol) in dichloromethane (120 ml) with stirring while ice-cooling under a nitrogen atmosphere; and the resulting mixture was stirred for 5 minutes. After stirring, to the reaction mixture was added a solution of the crude 3-cyclohexyloxypropionaldehyde (8.60 g) obtained above in dichloromethane (90 ml) with stirring while ice-cooling under a nitrogen atmosphere, and the resulting mixture was stirred at the same temperature for 25 minutes. After stirring, the reaction mixture was diluted with dichloromethane and washed successively with saturated aqueous sodium hydrogencarbonate solution and saturated aqueous sodium chloride solution and dried over anhydrous sodium sulfate. After filtration, the solvent was removed in vacuo, and the residue was purified by chromatography on a silica gel column using a mixed solvent of hexane and ethyl acetate (100:1-33:1) as the eluent to afford 4-cyclohexyloxy-1,1-dibromobut-1-ene (12.6 g, overall yield in two steps: 55%).

Furthermore, to a solution of 4-cyclohexyloxy-1,1-dibromobut-1-ene (12.6 g, 40.4 mmol) obtained above in tetrahydrofuran (130 ml) was added a 1.5M solution of n-butyllithium in hexane (54 ml, 81.0 mmol) at −78° C. with stirring under a nitrogen atmosphere, and the resulting mixture was stirred at −78° C. for 1 hour. After stirring, the reaction temperature was raised slowly to room temperature with stirring, and the reaction mixture was stirred furthermore at room temperature for 50 minutes. After stirring, water was added to the reaction mixture with stirring under ice-cooling to quench the reaction, and then the resulting mixture was extracted with ether. The extract was washed with saturated aqueous sodium chloride solution and dried over anhydrous sodium sulfate. After filtration, the solvent was removed in vacuo, and the residue was purified by chromatography on a silica gel column using a mixed solvent of hexane and ethyl acetate (100:1-50:1) as the eluent to afford the title compound (4.35 g, yield: 71%).

$^1$H-NMR spectrum (CDCl$_3$, 400 MHz) δ: 3.59 (t, 2H, J=7.2 Hz), 3.32-3.23 (m, 1H), 2.45 (dt, 2H, J=7.2 Hz, 2.8 Hz), 1.97 (t, 1H, J=2.8 Hz), 1.95-1.85 (m, 2H), 1.81-1.67 (m, 2H), 1.58-1.48 (m, 1H), 1.36-1.13 (m, 5H).

Mass spectrum (E1) m/z: 153 ((M+H)$^+$).

Reference Example 35

4-(4-Fluorophenyloxy)but-1-yne

To a solution of 4-fluorophenol (5.00 g, 44.6 mmol), 3-butyn-1-ol (3.38 ml, 44.6 mmol) and triphenylphosphine (17.5 g, 66.9 mmol) in tetrahydrofuran (100 ml) was added diethyl azodicarboxylate (11.7 g, 66.9 mmol) with stirring under ice-cooling, and then the resulting mixture was stirred at room temperature for 18 hours. After stirring, the reaction mixture was evaporated in vacuo, and to the residue were added hexane (200 ml) and ethyl acetate (20 ml). The precipitate separated out was filtered off, and the filtrate was evaporated in vacuo. The residue obtained was purified by flash chromatography on a silica gel column using hexane as the eluent to afford the title compound.

$^1$H-NMR spectrum (CDCl$_3$, 400 MHz) δ: 7.02-6.94 (m, 2H), 6.90-6.82 (m, 2H), 4.07 (t, 2H, J=7.0 Hz), 2.70-2.63 (m, 2H), 2.05 (t, 1H, J=2.7 Hz).

Mass spectrum (EI) m/z: 164 (M$^+$).

Reference Example 36

4-Phenyloxybut-1-yne

The title compound was synthesized using phenol and 3-butyn-1-ol by conducting a reaction similar to that mentioned in Reference example 35.

$^1$H-NMR spectrum (CDCl$_3$, 400 MHz) δ: 7.29 (dd, 2H, J=8.8 Hz, 7.3 Hz), 6.96 (t, 1H, J=7.3 Hz), 6.92 (d, 2H, J=8.8 Hz), 4.11 (t, 2H, J=6.6 Hz), 2.68 (dt, 2H, J=6.6 Hz, 2.2 Hz), 2.04 (t, 1H, J=2.2 Hz).

Reference Example 37

3-(3,4-Dimethylphenyloxy)-1-propyne

The title compound was synthesized using 3,4-dimethylphenol and propargyl alcohol by conducting a reaction similar to that mentioned in Reference example 35.

$^1$H-NMR spectrum (CDCl$_3$, 400 MHz) δ: 7.04 (d, 1H, J=8.0 Hz), 6.78 (d, 1H, J=2.4 Hz), 6.72 (dd, 1H, J=8.0 Hz, 2.4 Hz), 4.65 (d, 2H, J=2.4 Hz), 2.49 (t, 1H, J=2.4 Hz), 2.24 (s, 3H), 2.20 (s, 3H).

Mass spectrum (EI) m/z: 160 (M$^+$).

Reference Example 38

3-(4-Methylphenyloxy)-1-propyne

The title compound was synthesized using 4-methylphenol and propargyl alcohol by conducting a reaction similar to that mentioned in Reference example 35.

$^1$H-NMR spectrum (CDCl$_3$, 400 MHz) δ: 7.10 (d, 2H, J=8.4 Hz), 6.88 (d, 2H, J=8.4 Hz), 4.67 (d, 2H, J=2.4 Hz), 2.50 (t, 1H, J=2.4 Hz), 2.29 (s, 3H).

Mass spectrum (EI) m/z: 446 (M$^+$).

Reference Example 39

3-(4-Methylthiophenyloxy)-1-propyne

The title compound was synthesized using 4-methylthiophenol and propargyl alcohol by conducting a reaction similar to that mentioned in Reference example 35.

$^1$H-NMR spectrum (CDCl$_3$, 400 MHz) δ: 7.27 (d, 2H, J=8.9 Hz), 6.93 (d, 2H, J=8.9 Hz), 4.68 (d, 2H, J=2.4 Hz), 2.52 (t, 1H, J=2.4 Hz), 2.45 (s, 3H).

Mass spectrum (EI) m/z: 178 (M$^+$).

Reference Example 40

2-[4-(Cyclohexylmethoxy)phenyl]-4,4,5,5-tetramethyl-[1,3,2]-dioxaborolane

To a solution of 4-bromophenol (6.0 g, 34.7 mmol), cyclohexylmethylphenol (4.3 ml, 34.7 mmol) and triphenylphosphine (9.1 g, 34.7 mmol) in tetrahydrofuran (100 ml) was added slowly a 40% solution of diethyl azodicarboxylate in toluene (15.1 ml, 34.7 mmol) in portions at 0° C. with stirring, and then the resulting mixture was stirred at room temperature for 3 hours. After stirring, the reaction mixture was evaporated in vacuo, and hexane was added to the residue. After filtration, the filtrate was evaporated in vacuo once again, and the residue was purified by chromatography on a silica gel column using a mixed solvent of ethyl acetate and hexane (1:20) as the eluent to afford 1-bromo-4-(cyclohexylmethoxy)benzene (5.1 g, yield: 54%).

Subsequently, 1-bromo-4-(cyclohexylmethoxy)benzene (3.0 g, 11.1 mmol) obtained above, bis(pinacolato)diborane (3.4 g, 13.3 mmol), palladium chloride-diphenylphosphinoferrocene complex (450 mg, 0.551 mmol) and potassium acetate (2.2 g, 22.2 mmol) were dissolved in dimethyl sulfoxide (50 ml) and stirred at 80° C. for 30 minutes. After stirring, the reaction mixture was diluted with ethyl acetate, and charcoal was added to the resulting mixture. The resulting mixture was stirred at room temperature for 30 minutes. After filtration, the solvent was removed in vacuo, and the residue was purified by chromatography on a silica gel column using a mixed solvent of ethyl acetate and hexane (1:100) as the eluent to afford the title compound (1.72 g, yield: 49%).

$^1$H-NMR spectrum (CDCl$_3$, 400 MHz) δ: 7.73 (d, 2H, J=8.5 Hz), 6.88 (d, 2H, J=8.5 Hz), 3.77 (d, 2H, J=5.9 Hz), 1.93-1.64 (m, 5H), 1.33 (s, 12H), 1.33-1.14 (m, 4H), 1.12-0.97 (m, 2H).

Reference Example 41

2-[3-(2-Cyclohexylethoxy)phenyl]-4,4,5,5-tetramethyl-[1,3,2]-dioxaborolane

To a solution of 3-bromophenol (15.0 g, 86.7 mmol), 2-cyclohexylethylphenol (12.0 ml, 86.7 mmol) and triphenylphosphine (23.0 g, 86.7 mmol) in tetrahydrofuran (200 ml) was added slowly a 40% solution of diethyl azodicarboxylate in toluene (38.0 ml, 86.7 mmol) in portions at 0° C. with stirring, and then the resulting mixture was stirred at room temperature for 7 hours. After stirring, the reaction mixture was evaporated in vacuo, and hexane was added to the residue. After filtration, the filtrate was evaporated in vacuo once again, and the residue was purified by chromatography on a silica gel column using a mixed solvent of ethyl acetate and hexane (1:100) as the eluent to afford 1-bromo-3-(2-cyclohexylethoxy)benzene (23.0 g, yield: 94%).

Subsequently, 1-bromo-3-(2-cyclohexylethoxy)benzene (5.0 g, 17.7 mmol) obtained above, bis(pinacolato)diborane (5.4 g, 21.2 mmol), palladium chloride-diphenylphosphinoferrocene complex (1.40 g, 1.77 mmol) and potassium acetate (3.5 g, 35.4 mmol) were dissolved in dimethyl sulfoxide (80 ml) and stirred at 80° C. for 30 minutes. After stirring, the reaction mixture was diluted with ethyl acetate, and charcoal was added to the resulting mixture, and then the resulting mixture was stirred at room temperature for 30 minutes. After filtration, the solvent was removed in vacuo, and the residue was purified by chromatography on a silica gel column using a mixed solvent of ethyl acetate and hexane (1:100) as the eluent to afford the title compound (4.70 g, yield: 80%).

$^1$H-NMR spectrum (CDCl$_3$, 400 MHz) δ: 7.38-7.24 (m, 3H), 7.00 (dd, 1H, J=8.1, 2.9 Hz); 4.02 (t, 2H, J=6.6 Hz), 1.81-1.63 (m, 8H), 1.34 (s, 12H), 1.31-1.12 (m, 3H), 1.06-0.88 (m, 2H).

Reference Example 42

4-Phenyloxybutanoyl chloride (42a) 4-Phenyloxybutanoic Acid

To a suspension of sodium hydride (content: 60%) (2.41 g, 60.3 mmol) in N,N-dimethylformamide (60 ml) was added a solution of phenol (5.70 g, 60.0 mmol) in N,N-dimethylformamide (30 ml) over a 20-minute interval with stirring while ice-cooling under a nitrogen atmosphere, and then the resulting mixture was stirred at room temperature for 1.5 hours. After stirring, to the reaction mixture was added a solution of γ-butyrolactone (5.01 g, 58.2 mmol) in N,N-dimethylformamide (30 ml), and the resulting mixture was stirred at 130° C. for 6 hours. After cooling, the reaction mixture was evaporated in vacuo.

Subsequently, water was added to the residue, and the resulting mixture was partitioned with dichloromethane to separate the aqueous layer. The dichloromethane layer was washed with water. The washings and the aqueous layer separated above were combined, and acidified with 1N hydrochloric acid (72 ml), and then extracted with ethyl acetate. The extract was washed successively with water and saturated aqueous sodium chloride solution and dried over anhydrous magnesium sulfate. After filtration, the solvent was removed in vacuo, and the residue was purified by chromatography on a silica gel column using a mixed solvent of hexane and ethyl acetate (5:1-2:1) as the eluent to afford the title compound (3.58 g, yield: 34%).

$^1$H-NMR spectrum (CDCl$_3$, 400 MHz) δ: 7.30-7.27 (m, 2H), 6.96-6.87 (m, 3H), 4.03 (t, 2H, J=5.9 Hz), 2.60 (t, 2H, J=7.3 Hz), 2.16-2.09 (m, 2H).

(42b) 4-Phenyloxybutanoyl chloride

To a solution of 4-phenyloxybutanoic acid (0.5066 g, 2.81 mmol) obtained in Reference example (42a) in benzene (5 ml) were added successively thionyl chloride (0.42 ml, 5.76 mmol) and N,N-dimethylformamide (2 μl), and the resulting mixture was stirred at 80° C. for 1 hour. After cooling, the reaction mixture was evaporated in vacuo to afford the title compound (0.5556 g, yield: 99%).

Test Example 1

Determination of Inhibitory Activities of Compounds against Host versus Graft Reaction in Rats (1) Two strains of rats [Lewis rats (male, 6 weeks of age, Charles River Japan Inc.) and WKAH/Hkm rats (male, 7 weeks of age, Japan SLC Inc.) were used. Five rats/group were used.
(2). Induction of HvGR Spleen cells were isolated from the spleens of WKAH/Hkm and Lewis rats and floated in RPMI1640 medium (Life Technologies Inc.) at a concentration of 1×10$^8$ cells/ml. 0.1 ml of the medium containing the free-floating spleen cells of WKAH/Hkm rats or Lewis rats (1×10$^7$ of the spleen cells) was then intracutaneously injected into the bilateral foot-pads of hindlimbs of Lewis rats.

(3) Administration of the Compounds

Compounds were suspended in 0.5% tragacanth solution. The suspended compounds were orally administered to rats in the drug-treated group (Lewis rats injected with spleen cells of WKAH/Hkm rats and treated with the compound) at a volume of 5 ml/kg once daily for 4 successive days starting on the day of spleen cell injection. The tragacanth solution (0.5%) was orally administered, instead of the compound-suspended solution, to rats in the "same strain group" (Lewis rats injected with spleen cells of Lewis rats) and the control group (Lewis rats injected with spleen cells of WKAH/Hkm rats and not treated with the compound).

(4) Determination of Inhibitory Activities of Compounds against HvGR

Average weight of the popliteal lymph nodes of the same strain rats was subtracted from individual weights of the popliteal lymph nodes of individual rats ("HvGR-induced changes in weight of the popliteal lymph nodes"). The inhibitory activities of compounds were calculated from the "HvGR-induced changes in weights of the popliteal lymph nodes" of individual rats in the drug-treated group versus the average "HvGR-induced changes in weights of the popliteal lymph nodes" in the control group. The inhibitory activities of compounds were expressed as ID$_{50}$ values (mg/kg) as calculated by least squares method based on the doses of compounds administered and inhibitory activities at these doses.

From the present experiments, compounds of the present invention exhibited excellent inhibitory activities.

TABLE 9

| Compound | HvGR ID$_{50}$ values (mg/kg) |
| --- | --- |
| Example 2 | 0.714 |
| Example 3 | 0.116 |
| Example 9 | 0.120 |
| Example 10 | 0.276 |
| Example 15 | 0.304 |
| Example 19 | 0.097 |
| Example 20 | 0.082 |
| Example 33 | 0.013 |

Test Example 2

Determination of Inhibitory Activities of Compounds against Adjuvant-induced Arthritis (1) Preparation of Adjuvant Adjuvant was prepared by suspension of killed Mycobacterium butyricum in mineral oil at a concentration of 2 mg/ml, followed by application of ultrasonic waves.

(2) Preparation of Test Compound

Test compounds were suspended or dissolved in 0.5% tragacanth solution.

(3) Induction of Adjuvant Arthritis 0.05 ml of adjuvant solution prepared as described in (1) was intracutaneously injected into the right foot-pad of rats (usually Lewis rats). Five rats/group were usually used. Adjuvant was not injected in one group of rats (normal group).

(4) Administration of Compound

Compounds prepared as described in (2) were orally administered to rats at a volume of 5 ml/kg once daily for 21 successive days. 0.5% tragacanth solution was similarly administered to rats in one group injected adjuvant (control group) and a group not injected adjuvant.

(5) Calculation of Inhibitory Activities of Compounds against Adjuvant Arthritis One day after the final drug administration, the foot volume of each rat was measured by an apparatus for determination of the volume. The average value in normal rats was subtracted from the individual values in the drug-treated and control groups. The difference was expressed as the swelling volume. Inhibitory rate of the compound was calculated from the ratio of the individual swelling volume of the rat treated with the compound to the average swelling volume in the control group.

Inhibitory activities of compounds were expressed as $ID_{50}$ values (mg/kg) calculated by least squares method based on the doses of the compound and their inhibitory ratios.

From the present experiments, compounds of the present invention exhibited excellent inhibitory activities.

TABLE 10

| Compound | $ID_{50}$ values (mg/kg) |
|---|---|
| Example 2 | 0.0899 |
| Example 3 | 0.0774 |
| Example 19 | 0.108 |
| Example 20 | 0.102 |
| Example 33 | 0.0941 |

Test Example 3

Determination of Inhibitory Activities of Compounds against HvGR (Host versus Graft Reaction) in Rats (1) Two strains of rats (Lewis rats (male, 6 weeks of age, Charles River Japan Inc.) and WKAH/Hkm rats (male, 7 weeks of age, Japan SLC Inc.) were used. Five rats/group were used.

(2) Induction of HvGR

Spleen cells were isolated from the spleens of WKAH/Hkm rats or Lewis rats and floated in RPMI1640 medium (Life Technologies Inc.) at a concentration of $1\times10^8$ cells/ml. 0.1 ml of the medium containing the free-floating spleen cells of WKAH/Hkm rats or 0.1 ml of the medium containing the free-floating spleen cells of Lewis rats were intracutaneously injected into the bilateral foot-pads of hindlimbs of Lewis rats.

(3) Administration of Compounds

Cyclosporin A, tacrolimus and Exemplification compound number 1-1093 having formula (Ia-3) {2-methyl-4-{5-[5-phenylpentanoyl]thiophen-2-yl}butan-1-ol}maleate (hereinafter expressed as Compound A) were suspended in 0.5% tragacanth solution at concentrations of 0.08 mg/5 ml, 0.08 mg/5 ml, and 0.008 mg/5 ml.

Cyclosporin A suspended solution and the compound suspended solution were orally co-administered to rats in the cyclosporin A plus compound group, while tacrolimus suspended solution plus compound suspended solution were orally co-administered to rats in the tacrolimus plus compound group, at a volume of 5 ml/kg once daily for 4 successive days.

Furthermore, Cyclosporin A suspended solution and 0.5% tragacanth solution, tacrolimus and 0.5% tragacanth solution, or compound A and 0.5% tragacanth solution were orally co-administered at a volume of 5 ml/kg once daily for 4 successive days, in the cyclosporin A, tacrolimus, or compound A administered groups, respectively.

In both the "same strain group" (Lewis rats treated with spleen cells of Lewis rats but not with the compounds) and "control group" (Lewis rats treated with the spleen cells of WKAH/Hkm rats but not with the compounds), 0.5% tragacanth solution was orally administered.

(4) Determination Methods of Inhibitory Activity of Compounds against HvGR

The average weight of the popliteal lymph nodes in the same strain group was subtracted from individual weights of the popliteal lymph nodes in individual rats ("HvGR-induced changes in the popliteal lymph node weights"). The inhibitory activities of the compounds were calculated from the "HvGR-induced changes in the popliteal lymph node weights" of individual rats in drug-treated group versus the average "HvGR-induced changes in the popliteal lymph node weights" in the control group.

TABLE 11

| Group | HvGR Inhibitory Rate (%) |
|---|---|
| Cyclosporin A administered group | 18.7 |
| Tacrolimus administered group | 25.8 |
| Compound A administered group | 16.0 |
| Cyclosporin A + Compound A administered group | 36.1 |
| Tacrolimus + Compound A administered group | 44.8 |

Test Example 4

Determination of Inhibitory Activities of Compounds against Mice GvHD (Graft-versus Host Disease)

(1) Two strains of mice [BDF1 mice (male, 6 weeks of age, Charles River Japan Inc.) and C57BL/6 mice (male, 7 weeks of age, Charles River Japan Inc.)] were used. Five mice/group (hosts) were used.

(2) Induction of GvHD

Spleen cells were isolated from the spleens of C57BL/6-mice or BDF1 mice and floated in RPMI1640 medium (Life Technologies Inc.) at a concentration of $2\times10^7$ cells/ml. 0.5 ml of the medium containing the free-floating spleen cells of C57BL/6 mice) was intravenously injected into the tail vein of BDF1 mice (GvHD induction group) and the same volume of the medium containing free-floating spleen cells of BDF1 mice was intravenously injected into the tail vein of BDF1 mice (the "same strain group").

(3) Administration of Compounds

Cyclosporin A, tacrolimus, and Exemplification compound number 1-1093 having formula (Ia-2) {2-amino-2-methyl-4-[1-methyl-5-(5-phenylpentanoyl)pyrrol-2-yl]butan-1-ol}hydrochloride (hereinafter expressed as Compound B) was suspended in 0.5% methylcellulose (MC) solution at concentrations of 0.1 mg/10 ml, 0.2 mg/10 ml, and 0.01 mg/10 ml.

Cyclosporin A suspended solution and compound B suspended solution were orally co-administered to mice in the cyclosporin A plus compound B group, while tacrolimus suspended solution and compound B suspended solution were orally co-administered to mice in the tacrolimus plus compound B group, at a volume of 10 ml/kg once daily for 10 successive days.

Cyclosporin A suspended solution plus 0.5% MC solution, tacrolimus plus 0.5% MC solution, and compound B plus 0.5% MC solution were orally co-administered at a volume of 10 ml/kg once daily for 10 successive days starting on the day of injection of spleen cells in the cyclosporin A, tacrolimus, and compound B administered groups, respectively.

In both the "same strain group" (BDF1 mice treated with spleen cells of BDF1 mice but not treated with the compound) and "control group" (BDF1 mice injected spleen cells of C57BL/6 mice, but not treated with the compound), 0.5% MC solution was orally administered.

(4) Determination Methods of Inhibitory Activities of Compounds against GvHD

Body weight was determined and spleens were weighed, and "spleen weight compensated for the body weight following injection of GvHD" was calculated by dividing the spleen weight by the body weight. Average "spleen weight compensated for body weight in the same strain group" was sdbtracted from the individual "spleen weight compensated for body weight following injection of GvHD". The inhibitory activities of compounds were calculated from the ratios of individual "spleen weight compensated for body weight following injection of GvHD" to the average "spleen weight compensated for body weight following injection of GvHD" in the control group.

TABLE 12

| Group | GvHD Inhibitory Rate (%) |
|---|---|
| Cyclosporin A administered group | 12.5 |
| Tacrolimus administered group | 7.6 |
| Compound B administered group | −2.9 |
| Cyclosporin A + Compound B administered group | 28.4 |
| Tacrolimus + Compound B administered group | 13.4 |

Test Example 5

Determination of Inhibitory Activities of Compounds against Rejection Response against Skin Transplantation of Mice (1) Two strains of mice [C57BL/6N mice (female, 5 weeks of age, Charles River Japan Inc.) and BALB/cAnN mice (female, 5 weeks of age, Charles River Japan Inc.)] were used. Ten mice/group (transplanted individuals) were used.

(2) Skin Transplantation Procedures

C57BL/6N mice were sacrificed by cervical dislocation and their skins removed. The skins were cut to 8-mm diameter sizes by biopsy punch (MK706, 8 mm, Kai Industries Co., Ltd.). Next, 8 mm diameter sections of the back skins of BALB/cAnN mice anaesthetized with Avertin were removed by biopsy punch. The skin was cut along the edge of the damaged area by fine ophthalmic scissors. The previously cut skins of C57BL/6N mice were transplanted to the removed areas of the skin in BALB/cAnN mice. The transplanted areas were fixed with Aron Alpha (Sankyo Co., Ltd.). Sofratulle [10.8 mg of fradiomycin was contained in one piece (10 cm×10 cm), Aventis Pharma Ltd.] and sterilized gauze were applied to the transplanted area of the skin, which was bound with a sterilized bandage (S size, Sumitomo 3M Co., Ltd.) of which both edges were fixed with SILKYTEX (Type 1, ALCARE Co., Ltd.).

(3) Administration of Compounds

Cyclosporin A, tacrolimus and Exemplification compound number 1-1093 having formula (Ia-2) {2-amino-2-methyl-4-[1-methyl-5-(5-phenylpentanoyl)pyrrol-2-yl]butan-1-ol}hydrochloride (hereinafter expressed as Compound B) was suspended in 0.5% methylcellulose (MC) solution at concentrations of 30 mg/10 ml, 3 mg/10 ml, and 0.1 mg/10 ml.

Cyclosporin A suspended solution and compound B suspended solution were orally co-administered to mice in the cyclosporin A and compound B group, while tacrolimus suspended solution and compound B suspended solution were orally co-administered to mice in the tacrolimus and compound B group, at a volume of 10 ml/kg once daily for 14 successive days starting on the day of transplantation.

(4) Determination Methods of Inhibitory Activities of Compounds against Rejection Responses to Transplanted Skin On the 6th day after transplantation (the day of transplantation was defined as day 0), the Coban, SYLKYTEX, sterilized gauze, and Sofratulle were gently removed paying attention not to damage the skin by a pair of scissors. From the next day to 20 days after transplantation, it was determined whether rejection responses occurred in the transplanted skin. This determination was carried out blind, and the median day when the rejection response occurred was calculated.

TABLE 13

| Group | Median Day of Rejection Response (Days) |
|---|---|
| 0.5% MC administered group | 10.0 |
| Cyclosporin A administered group | 12.0 |
| Tacrolimus administered group | 11.0 |
| Compound B administered group | 15.0 |
| Cyclosporin A + Compound B administered group | 17.5 |
| Tacrolimus + Compound B administered group | 16.5 |

Formulation Example 1

| Tablets | |
|---|---|
| Cyclosporin A | 50.0 mg |
| Compound A | 10.0 mg |
| Lactose | 113.0 mg |
| Corn starch | 25.0 mg |
| Magnesium stearate | 2.0 mg |
| | 200 mg |

Powders of the ingredients listed above are mixed and tableted with a tableting machine to prepare tablets containing 200 mg of the above ingredients/tablet.

Compound A in the above formulation is 2-amino-2-methyl-4-[5-[5-phenylpentanoyl]thiophen-2-yl]butan-1-ol maleate.

The compounds and the pharmaceutical compositions of the present invention exerted potent immunosuppressive activity and showed low toxicity. Since the pharmaceutical compositions of the present invention potentiated the pharmacological action of each immunosuppressant contained in the pharmaceutical composition and reduced adverse events elicited by the individual immunosuppressants, the pharmaceutical compositions of the present invention are useful as pharmaceutical agents. Thus the pharmaceutical compositions of the present invention are useful as preventive or therapeutic agents for warm-blooded animals (particularly humans) for the following autoimmune diseases or other immunology-related diseases such as rejection caused by transplantation of various organs or skin, systemic lupus erythematosus, rheumatoid arthritis, polymyositis, fibrositis, skeletal muscle inflammation, arthrosteitis, osteoarthritis, dermatomyositis, scleoderma, Behcet's syndrome, Crohn's disease, ulcerative colitis, autoimmune hepatitis, aplastic anemia, idiopathic thrombocytopenic purpura, autoimmune hemolytic anemia, multiple sclerosis, autoimmune-bullosis, psoriasis vulgaris, vasculitis syndrome, Wegener's granuloma, uveitis, Sjögren's syndrome, idiopathic interstitial pneumonia, Goodpasture's syndrome, sarcoidosis, allergic granulomatous angitis, bronchial asthma, myocarditis, cardiomyopathy, aortitis syndrome, post myocardial infarction syndrome, primary pulmonary hypertension, minimal change nephrotic syndrome, membranous nephropathy, membranoproliferative glomerulonephritis, focal glomerular sclerosis, crescentic glomerulonephritis, myasthenia gravis, inflammatory neuropathy, atopic dermatitis, chronic actinic dermatitis, photosensitivity, pressure sores, Sydenham's chorea, sclerosis, adult-onset type diabetes mellitus, insulin dependent diabetes mellitus, juvenile diabetes mellitus, atherosclerosis, glomerular nephritis, IgA nephropathy, tubulointerstitial nephritis, primary biliary cirrhosis, primary sclerosing cholangitis, fulminant hepatitis, viral hepatitis, GVHD, contact dermatitis, and sepsis.

Furthermore, the pharmaceutical compositions of the present invention are useful for diseases of infection by fungus, mycoplasma, virus, and protozoan and the like; cardiovascular diseases such as cardiac failure, cardiac hypertrophy, arrhythmia, angina pectoris, cardiac ischemia, arterial embolism, aneurysm, varix, and circulation disorders; brain diseases such as Alzheimer's disease, dementia, Parkinson's disease, stroke, brain infarction, brain ischemia, depression, manic-depressive illness, schizophrenia, Huntington's chorea, epilepsy, convulsion, attention deficit disorder, encephalitis, cerebral meningitis, loss of appetite, and hyperphagia; and various diseases such as lymphoma, leukemia, diuresis, pollakisuria, and diabetic retinopathy. Particularly, the pharmaceutical compositions of the present invention are useful as preventive or therapeutic agents for autoimmune diseases such as rejection caused by transplantation of various organs or skin, systemic lupus erythematosus, rhematoid arthritis, multiple sclerosis, and atopic dermatitis.

The doses and the ratio of (i) the at least one immunosuppressant defined hereinabove and (ii) the at least one compound selected from the group consisting of the compound of the formula (I), a pharmacologically acceptable salt thereof and a pharmacologically acceptable ester thereof, which are the active ingredients of compositions of the present invention, may vary depending on a variety of conditions, such as activity of each medicament, and the symptoms, age or weight of the patient.

The doses of both (i) the immunosuppressant and (ii) the compound of the formula (I) (or said salt or ester) may widely vary depending on the symptoms, age of the patients, and so on. In the case of oral administration, the dose of the compound of the formula (I) (or said salt or ester) is normally within the range of from 0.05 mg (preferably from 5 mg) to 200 mg (preferably to 40 mg), for an adult human and is administered one to six times per day depending on the symptoms of the patients, respectively. In the case of intravenous injection, the dose of the compound of the formula (I) (or said salt or ester) is normally within the range of from 0.01 mg (preferably from 1 mg) to 100 mg (preferably to 10 mg), for an adult human and is administered one to six times per day depending on the symptoms of the patients, respectively.

The ratio of the doses of (i) the at least one immunosuppressant and (ii) the compound of the formula (I) (or said salt or ester) can be widely varied, but the ratio is normally within the range of from 1:500 to 500:1 by weight.

In the present invention, the aforesaid active ingredients (i) and (ii) can be administered together either in a single composition, separately at the same time, i.e., simultaneously, or separately at different times, in the doses and ratio of doses described above.

When the compounds of the formula (I) (or said salt or ester) are used in conjunction with an immunosuppressant, X represents not only an oxygen atom or a group of the formula =N-D, but also a sulfur atom.

What is claimed is:
1. A method for the treatment of an immunology-related disease selected from the group consisting of systemic lupus erythematosus, polymyositis, fibrositis, skeletal muscle inflammation, arthrosteitis, osteoarthritis, dermatomyositis, scleoderma, Behcet's syndrome, autoimmune hepatitis, aplastic anemia, idiopathic thrombocytopenic purpura, autoimmune hemolytic anemia, autoimmune bullosis, psoriasis vulgaris, vasculitis syndrome, Wegener's granuloma, uveitis, Sjögren's syndrome, idiopathic interstitial pneumonia, Goodpasture's syndrome, sarcoidosis, allergic granulomatous angitis, bronchial asthma, myocarditis, cardiomyopathy, aortitis syndrome, post myocardial infarction syndrome, primary pulmonary hypertension, minimal change nephrotic syndrome, membranous nephropathy, membranoproliferative glomerulonephritis, focal glomerular sclerosis, crescentic glomerulonephritis, myasthenia gravis, inflammatory neuropathy, chronic actinic dermatitis, photosensitivity, pressure sores, Sydenham's chorea, sclerosis, adult-onset type diabetes mellitus, juvenile diabetes mellitus, atherosclerosis, IgA nephropathy, tubulointerstitial nephritis, primary biliary cirrhosis, primary sclerosing cholangitis, fulminant hepatitis, viral hepatitis, GVHD, contact dermatitis, sepsis, an infection caused by fungus, mycoplasma, virus or protozoan, cardiac failure, cardiac hypertrophy, arrhythmia, angina pectoris, cardiac ischemia, arterial embolism, aneurysm, varix, a circulation disorder, Alzheimer's disease, dementia, Parkinson's disease, stroke, brain infarction, brain ischemia, depression, manic-depressive illness, schizophrenia, Huntington's chorea, epilepsy, convulsion, attention deficit disorder, encephalitis, cerebral meningitis, loss of appetite, hyperphagia, lymphoma, leukemia, diuresis, pollakisuria and diabetic retinopathy in a mammal in need thereof, which comprises administering to said mammal a pharmaceutically effective amount of a compound, a pharmacologically acceptable salt of the compound or a pharmacologically acceptable ester of the compound, wherein the compound is a compound having a formula (Ia):

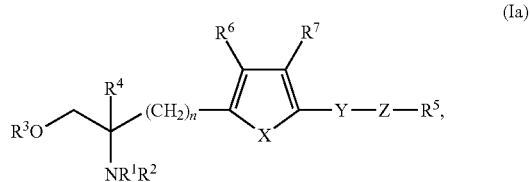

wherein $R^1$ and $R^2$ are each a hydrogen atom;
$R^3$ is a hydrogen atom;
$R^4$ is a $C_1$-$C_2$ alkyl group;
n is 2;
X is =N-D, wherein D is a hydrogen atom, a $C_1$-$C_4$ alkyl group or a phenyl group;

Y is an ethylene group, an ethynylene group, a group of a formula —CO—CH$_2$ or a phenylene group;

Z is an ethylene group or a trimethylene group;

R$^5$ is an unsubstituted C$_3$-C$_{10}$ cycloalkyl group, an unsubstituted C$_6$-C$_{10}$ aryl group, or a C$_3$-C$_{10}$ cycloalkyl group or a C$_6$-C$_{10}$ aryl group substituted with from 1 to 3 substituents selected from the group consisting of a halogen atom, a lower alkyl group, a halogeno lower alkyl group and a lower alkoxy group; and R$^6$ and R$^7$ are each a hydrogen atom.

2. The method according to claim 1, wherein the mammal is a human.

3. The method according to claim 2, wherein, in the compound, R$^4$ is a methyl group, or a pharmacologically acceptable salt thereof.

4. The method according to claim 3 or a pharmacologically acceptable salt thereof, wherein, in the compound, X is a group of a formula =N—CH$_3$, or a pharmacologically acceptable salt thereof.

5. The method according to claim 2, wherein said compound is 2-amino-2-methyl-4-{1-methyl-5-[4-(3,4-dimethylphenyl)butanoyl]pyrrol-2-yl}butan-1-ol, or a pharmacologically acceptable salt thereof.

6. The method according to claim 2, wherein said compound is 2-amino-2-methyl-4-{1-methyl-5-[4-(3,5-dimethylphenyl)butanoyl]pyrrol-2-yl}butan-1-ol, or a pharmacologically acceptable salt thereof.

7. The method according to claim 2, wherein said compound is 2-amino-2-methyl-4-{1-methyl-5-[4-(3-trifluoromethylphenyl)butanoyl]pyrrol-2-yl}butan-1-ol, or a pharmacologically acceptable salt thereof.

8. The method according to claim 2, wherein said compound is 2-amino-2-methyl-4-{1-methyl-5-[4-(4-trifluoromethylphenyl)butanoyl]pyrrol-2-yl}butan-1-ol.

9. The method according to claim 2, wherein said compound is 2-amino-2-methyl-4-{1-methyl-5-[4-(4-methylphenyl)butanoyl]pyrrol-2-yl}butan-1-ol.

10. The method according to claim 2, wherein said compound is 2-amino-2-methyl-4-{1-methyl-5-[4-(4-methoxyphenyl)butanoyl]pyrrol-2-yl}butan-1-ol.

11. The method according to claim 2, wherein said compound is 2-amino-2-methyl-4-{1-methyl-5-[4-(3-methylphenyl)butyl]pyrrol-2-yl}butan-1-ol.

12. The method according to claim 2, wherein said compound is 2-amino-2-methyl-4-{1-methyl-5-[4-(3,4-dimethylphenyl)butyl]pyrrol-2-yl}butan-1-ol.

13. The method according to claim 2, wherein said compound is 2-amino-2-methyl-4-{1-methyl-5-[4-(3,5-dimethylphenyl)butyl]pyrrol-2-yl}butan-1-ol.

14. The method according to claim 2, wherein said compound is 2-amino-2-methyl-4-{1-methyl-5-[4-(3-trifluoromethylphenyl)butyl]pyrrol-2-yl}butan-1-ol.

15. The method according to claim 2, wherein R$^1$, R$^2$ and R$^3$ are each a hydrogen atom, R$^4$ is a methyl group, n is 2 and Y—Z—R$^5$ is —(O—(CH$_2$)$_3$-(4-F-phenyl).

16. The method according to claim 5, wherein the configuration at the carbon atom to which the group of the formula —NR$^1$R$^2$ attaches is the R configuration, or a pharmacologically acceptable salt thereof.

17. The method according to claim 6, wherein the configuration at the carbon atom to which the group of the formula —NR$^1$R$^2$ attaches is the R configuration, or a pharmacologically acceptable salt thereof.

18. The method according to claim 7, wherein the configuration at the carbon atom to which the group of the formula —NR$^1$R$^2$ attaches is the R configuration, or a pharmacologically acceptable salt thereof.

19. The method according to claim 8, wherein the configuration at the carbon atom to which the group of the formula —NR$^1$R$^2$ attaches is the R configuration, or a pharmacologically acceptable salt thereof.

20. The method according to claim 9, wherein the configuration at the carbon atom to which the group of the formula —NR$^1$R$^2$ attaches is the R configuration, or a pharmacologically acceptable salt thereof.

21. The method according to claim 10, wherein the configuration at the carbon atom to which the group of the formula —NR$^1$R$^2$ attaches is the R configuration, or a pharmacologically acceptable salt thereof.

22. The method according to claim 11, wherein the configuration at the carbon atom to which the group of the formula —NR$^1$R$^2$ attaches is the R configuration, or a pharmacologically acceptable salt thereof.

23. The method according to claim 12, wherein the configuration at the carbon atom to which the group of the formula —NR$^1$R$^2$ attaches is the R configuration, or a pharmacologically acceptable salt thereof.

24. The method according to claim 13, wherein the configuration at the carbon atom to which the group of the formula —NR$^1$R$^2$ attaches is the R configuration, or a pharmacologically acceptable salt thereof.

25. The method according to claim 14, wherein the configuration at the carbon atom to which the group of the formula —NR$^1$R$^2$ attaches is the R configuration, or a pharmacologically acceptable salt thereof.

26. The method according to claim 15, wherein the configuration at the carbon atom to which the group of the formula —NR$^1$R$^2$ attaches is the R configuration, or a pharmacologically acceptable salt thereof.

* * * * *